United States Patent
Rajeev et al.

(10) Patent No.: US 12,024,484 B2
(45) Date of Patent: Jul. 2, 2024

(54) LIPID FORMULATIONS FOR GENE EDITING

(71) Applicant: Verve Therapeutics, Inc., Boston, MA (US)

(72) Inventors: Kallanthottathil G. Rajeev, Wayland, MA (US); Souvik Biswas, Woburn, MA (US)

(73) Assignee: VERVE THERAPEUTICS, INC., Boston, MA (US)

(*) Notice: Subject to any disclaimer, the term of this patent is extended or adjusted under 35 U.S.C. 154(b) by 0 days.

(21) Appl. No.: 18/180,306

(22) Filed: Mar. 8, 2023

(65) Prior Publication Data

US 2024/0010609 A1    Jan. 11, 2024

Related U.S. Application Data

(63) Continuation of application No. PCT/US2021/050511, filed on Sep. 15, 2021.

(60) Provisional application No. 63/078,738, filed on Sep. 15, 2020, provisional application No. 63/220,340, filed on Jul. 9, 2021.

(51) Int. Cl.
  *C07C 229/12* (2006.01)
  *A61K 47/54* (2017.01)
  *C07C 229/24* (2006.01)

(52) U.S. Cl.
  CPC .................. *C07C 229/12* (2013.01)

(58) Field of Classification Search
  CPC .... C07C 229/12; C07C 229/24; A61K 47/543
  See application file for complete search history.

(56) References Cited

U.S. PATENT DOCUMENTS

| | | |
|---|---|---|
| 5,885,613 A | 3/1999 | Holland et al. |
| 7,371,404 B2 | 5/2008 | Panzner et al. |
| 7,780,983 B2 | 8/2010 | Panzner et al. |
| 7,858,117 B2 | 12/2010 | Panzner et al. |
| 8,021,686 B2 | 9/2011 | Semple et al. |
| 8,236,770 B2 | 8/2012 | Endert et al. |
| 8,492,359 B2 | 7/2013 | Yaworski et al. |
| 9,186,325 B2 | 11/2015 | Manoharan et al. |
| 9,404,127 B2 | 8/2016 | Yaworski et al. |
| 9,415,109 B2 | 8/2016 | Kumar et al. |
| 9,504,651 B2 | 11/2016 | MacLachlan et al. |
| 9,512,073 B2 | 12/2016 | Dong et al. |
| 9,687,448 B2 | 6/2017 | Akinc et al. |
| 9,867,888 B2 | 1/2018 | Benenato |
| 9,868,692 B2 | 1/2018 | Benenato |
| 9,878,042 B2 | 1/2018 | Yaworski et al. |
| 10,059,655 B2 | 8/2018 | Brito et al. |
| 2005/0222064 A1 | 10/2005 | Vargeese et al. |
| 2007/0087045 A1 | 4/2007 | Li et al. |
| 2009/0053142 A1 | 2/2009 | Wynn et al. |
| 2012/0178858 A1 | 7/2012 | Wnuk et al. |
| 2015/0050295 A9 | 2/2015 | Constien et al. |
| 2016/0375134 A1 | 12/2016 | Bancel et al. |
| 2017/0273907 A1 | 9/2017 | Haas et al. |
| 2018/0092848 A1 | 4/2018 | Yaworski et al. |
| 2018/0147298 A1 | 5/2018 | Besin et al. |
| 2018/0148719 A1 | 5/2018 | Lee et al. |
| 2018/0200186 A1 | 7/2018 | Chen et al. |
| 2018/0290965 A1 | 10/2018 | Brito et al. |
| 2018/0353434 A1 | 12/2018 | Hatanaka et al. |
| 2019/0336452 A1 | 11/2019 | Brader |

FOREIGN PATENT DOCUMENTS

| | | |
|---|---|---|
| CN | 101724210 A | 6/2010 |
| CN | 102617364 A | 8/2012 |
| WO | WO-2006007712 A1 | 1/2006 |
| WO | WO-2009122044 A2 | 10/2009 |
| WO | WO-2010006282 A2 | 1/2010 |
| WO | WO-2010054401 A1 | 5/2010 |
| WO | WO-2013063468 A1 | 5/2013 |
| WO | WO-2014136086 A1 | 9/2014 |
| WO | WO-2015095340 A1 | 6/2015 |
| WO | WO-2015096982 A1 | 7/2015 |
| WO | WO-2016126941 A1 | 8/2016 |
| WO | WO-2016153012 A1 | 9/2016 |
| WO | WO-2016197133 A1 | 12/2016 |
| WO | WO-2016207098 A1 | 12/2016 |
| WO | WO-2017173054 A1 | 10/2017 |
| WO | WO-2017196969 A1 | 11/2017 |
| WO | WO-2018062413 A1 | 4/2018 |
| WO | WO-2018119514 A1 | 7/2018 |
| WO | WO-2018170306 A1 | 9/2018 |
| WO | WO-2018185241 A1 | 10/2018 |
| WO | WO-2018191750 A2 | 10/2018 |
| WO | WO-2019027055 A1 | 2/2019 |
| WO | WO-2019046809 A1 | 3/2019 |
| WO | WO-2019067992 A1 | 4/2019 |

(Continued)

OTHER PUBLICATIONS

Annenkov, V.V. et al., "Synthesis of biomimetic polyamines," ARKIVOC, 2009;13:116-130.
Dekmezian, A.H., et al., "An Efficient and Unambiguous Synthesis of 2-Hydroxymethyl-1, 3-Propanediol," Synthetic Communications, 1979;9(5):431-435.
Doherty, D.G. et al., "Synthesis of Aminoalkylisothiuronium Salts and their Conversion to Mercaptoalkylguanidines and Thiazolines2," Journal of the American Chemical Society, 1957;79(21):5667-5671.
Forse, A.C. et al., "Elucidating CO2 Chemisorption in Diamine-Appended Metal-Organic Frameworks," Journal of the American Chemical Society, 2018;140:18016-18031.

(Continued)

*Primary Examiner* — Sikarl A Witherspoon
(74) *Attorney, Agent, or Firm* — Wilson Sonsoni Goodrich & Rosati

(57) ABSTRACT

The present disclosure relates to PEG-lipids, cationic and/or ionizable lipids and nucleic acid-lipid particle compositions comprising the same. The present disclosure also relates to methods of making, using and delivering the described lipids and lipid-containing particles.

30 Claims, 19 Drawing Sheets

Specification includes a Sequence Listing.

(56) References Cited

FOREIGN PATENT DOCUMENTS

| WO | WO-2019067999 A1 | 4/2019 |
|---|---|---|
| WO | WO-2022060871 A1 | 3/2022 |

OTHER PUBLICATIONS

Morris-Natschke, S.L. et al., "Synthesis of phosphocholine and quaternary amine ether lipids and evaluation of in vitro antineoplastic activity," Journal of Medicinal Chemistry, 1993;36(14):2018-2025.

Nasiri, M. et al., "Sustainable glucose-based block copolymers exhibit elastomeric and adhesive behavior," Polymer Chemistry, 2016;7(33):5233-5240.

Nemeth, C. et al., "Effect of side groups on the properties of cationic polyaspartamides," European Polymer Journal, 2017;93.

Popr, M. et al., "A complete series of 6-deoxy-monosubstituted tetraalkylammonium derivatives of α-, β-, and γ-cyclodextrin with 1, 2, and 3 permanent positive charges," Beilstein Journal of Organic Chemistry, 2014;10:1390-1396.

Tazarki, H. et al., "New pyrido[3,4-g]quinazoline derivatives as CLK1 and DYRK1A inhibitors: synthesis, biological evaluation and binding mode analysis," European Journal of Medicinal Chemistry, 2019;166:304-317.

Ye, B. et al., "Thiophene-Anthranilamides as Highly Potent and Orally Available Factor Xa Inhibitors1," Journal of Medicinal Chemistry, 2007;50(13):2967-2980.

De Costa, B.R. et al., "Synthesis, characterization, and biological evaluation of a novel class of N-(arylethyl)-N-alkyl-2-(1-pyrrolidinyl)ethylamines: structural requirements and binding affinity at the sigma receptor," J Med Chem., 1992;35(1):38-47.

De Costa, B.R. et al., "A new approach to the design of sigma-2-selective ligands: synthesis and evaluation of N-[2-(3,4-dichlorophenyl)ethyl]-N-methyl-2-(1-pyrrolidinyl)ethylamine-related polyamines at sigma-1 and sigma-2 receptor subtypes," J Med Chem., 1994;37(2):314-321.

Moffett, R. et al., "Antispasmodics. III.2 Tertiary Aminoalkyl Esters of Cyclopentyl and Δ2-Cyclopentenyl Substituted Acetic Acids," The Journal of Organic Chemistry, 1950;15(2):343-353.

Gribble, G.W. et al., "A biomimetic approach to the Elaeocarpus alkaloids. Syntheses of (.+-.)-elaeokanine A, (.+-.)-elaeokanine C, (.+-.)-elaeocarpidine, and (.+-.)-tarennine," The Journal of Organic Chemistry, 1988;53(14):3164-3170.

Affini, A. et al., "Novel indanone derivatives as MAO B/H3R dual-targeting ligands for treatment of Parkinson's disease," Eur J Med Chem., 2018;148:487-497.

Mielanczyk, A. et al., "Functional (mikto)stars and star-comb copolymers from D-gluconolactone derivative: An efficient route for tuning the architecture and responsiveness to stimuli," Polymer, 2018;146:331-343.

Batzer, M.A. et al., "Enhanced evolutionary PCR using oligonucleotides with inosine at the 3'-terminus," Nucleic Acid Res., 1991;19:5081.

Chadwick, A.C. et al., "In Vivo Base Editing of PCSK9 (Proprotein Convertase Subtilisin/Kexin Type 9) as a Therapeutic Alternative to Genome Editing," Arterioscler. Thromb. Vasc. Biol., 2017;37(9):1741-1747.

Clement, K. et al., CRISPResso2 provides accurate and rapid genome editing sequence analysis. Nat Biotechnol., 2019;37(3):224-226.

Ding, Q. et al., "Permanent Alteration of PCSK9 With In Vivo CRISPR-Cas9 Genome Editing," Circ Res., 2014;115(5):488-492.

International Preliminary Report on Patentability issued in PCTUS2021050511, dated May 1, 2023.

International Search Report and Written Opinion issued in PCTUS2021050511, dated Jan. 31, 2022.

Jayaraman, M. et al., "Maximizing the potency of siRNA lipid nanoparticles for hepatic gene silencing in vivo," Angew. Chem. Int. Ed., 2012;51(34):8529-8533.

Miller, J.B. et al., "Non-viral CRISPR/Cas gene editing in vitro and in vivo enabled by synthetic nanoparticle co-delivery of Cas9 mRNA and sgRNA," Angew. Chem. Int. Ed. Engl., 2017;56(4):1059-1063.

Moss, K.H. et al., "Lipid nanoparticles for delivery of therapeutic RNA oligonucleotides," Molecular Pharmaceutics, 2019;16(6):2265-2277.

Ohtsuka, E. et al., "An alternative approach to Deoxyoligonucleotides as Hybridization probes by insertion of Deoxyinosine at ambiguous codon positions," J Biol. Chem., 1985;260:2605-2608.

Rejman, J. et al., "Characterization and transfection properties of lipoplexes stabilized with novel exchangeable polyethylene glycol-lipid conjugates," Biochimica et Biophysica Acta, 2004;1660:41-52.

Romberg, B. et al., "Sheddable coatings for long-circulating nanoparticles," Pharmaceutical Research, 2008;25(1):55-71.

Rossidis, A.C. et al., "In utero CRISPR-mediated therapeutic editing of metabolic genes," Nat. Med., 2018;24(10):1513-1518.

Rossolini, G.M. et al., "Use of deoxyinosine-containing primers vs degenerate primers for polymerase chain reaction based on ambiguous sequence information," Mal. Cell. Probes, 1994;8:91-98.

Sabnis, S. et al., "A Novel Amino Lipid Series for mRNA Delivery: Improved Endosomal Escape and Sustained Pharmacology and Safety in Non-human Primates," Molecular Therapy, 2018;26(6):1509-1519.

Yin, H. et al., "Therapeutic genome editing by combined viral and non-viral delivery of CRISPR system components in vivo," Nature Biotechnology, 2016;34(3):328-333.

Affini, A. et al.: Novel indanone derivatives as MAO B/H3R dual-targeting ligands for treatment of Parkinson's disease. Eur. J. Med. Chem. 148:487-497n(2018).

De Costa, B.R. et al.: A new approach to the design of sigma-2-selective ligands: synthesis and evaluation of N-[2-(3,4-dichlorophenyl)ethyl]-N-methyl-2-(1-pyrrolidinyl)ethylamine-related polyamines at sigma-1 and sigma-2 receptor subtypes. J. Med. Chem. 37(2):314-321 (1994).

De Costa, B.R. et al.: Synthesis, characterization, and biological evaluation of a novel class of N-(arylethyl)-N-alkyl-2-(1-pyrrolidinyl)ethylamines: structural requirements and binding affinity at the sigma receptor. J. Med. Chem. 35(1):38-47 (1992).

Gribble, G.W. et al.: A biomimetic approach to the Elaeocarpus alkaloids. Syntheses of (.+-.)-elaeokanine A, (.+-.)-elaeokanine C, (.+-.)-elaeocarpidine, and (.+-.)-tarennine. The Journal of Organic Chemistry 53(14):3164-3170 (1988).

Mielanczyk, A. et al.: Functional (mikto)stars and star-comb copolymers from D-gluconolactone derivative: An efficient route for tuning the architecture and responsiveness to stimuli, Polymer 146:331-343 (2018).

Moffett, R. et al.: Antispasmodics. III.2 Tertiary Aminoalkyl Esters of Cyclopentyl and Δ2-Cyclopentenyl Substituted Acetic Acids. The Journal of Organic Chemistry. 15(2):343-353 (1950).

Shimada; K.: Determination of the Thickness of the Fixed Aqueous Layer Around Polyethyleneglycol-coated Liposomes. Journal of Drug Targeting 3(4):1029-2330 (1995). https://www.tandfonline.com/loi/idrt20.

(A)

(B)

(A)

(B)

(A)

(B)

LIPID FORMULATIONS FOR GENE EDITING

CROSS-REFERENCE

This application is a continuation of International Application No. PCT/US2021/050511, filed Sep. 15, 2021, which claims the benefit of U.S. Provisional Application No. 63/078,738, filed Sep. 15, 2020, and U.S. Provisional Application No. 63/220,340, filed Jul. 9, 2021, each of which is incorporated herein by reference in its entirety.

SEQUENCE LISTING

The instant application contains a Sequence Listing which has been submitted electronically in XML format and is hereby incorporated by reference in its entirety. Said XML copy, created on Jul. 14, 2023, is named 53989-703_301_US_SL.xml and is 1,069,846 bytes in size.

BACKGROUND

Lipid-containing particles have been used to encapsulate, and as transport vehicles for therapeutic agents such as nucleic acids, small molecules compounds, and proteins into cells and other intracellular compartments. There remains an ongoing need to develop new lipids to encapsulate therapeutic agents and improve the safety, efficacy, and specificity of such nanoparticle-based transport vehicles.

SUMMARY

Described herein are novel lipids and lipid nanoparticles comprised thereof. In one aspect, novel amino lipids are described. In another aspect novel PEG-lipids are described. In yet another aspects, novel lipid nanoparticles are described comprising one or more of the novel amino lipids and/or novel PEG-lipids. The nanoparticles, as described herein, in one aspect, are comprised of one or more of the following: an amino lipid, a neutral lipid, a PEG-lipid, a sterol or a derivative thereof, and optionally one or more of a nucleic acid molecular entity, a nucleic acid stabilizer, a surfactant, and an antioxidant. Further described herein are methods of using and making the same.

In one aspect, disclosed herein is an amino lipid having a structure of Formula (I), or a pharmaceutically acceptable salt or solvate thereof,

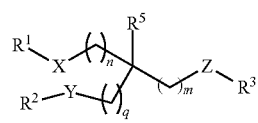

Formula (I)

wherein each of $R^1$ and $R^2$ is independently $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, $-C_0$-$C_{10}$ alkylene-L-$R^6$, or $-C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently $-C(=O)NR^4-$, $-NR^4C(=O)-$, $-C(=O)O-$, $-OC(=O)-$, $-OC(=O)O-$, $-NR^4C(=O)O-$, $-OC(=O)NR^4-$, $-NR^4C(=O)NR^4-$, $-NRC(=NR^4)NR^4-$, $-C(=S)NR^4-$, $-NR^4C(=S)-$, $-C(=S)O-$, $-OC(=S)-$, $OC(=S)O-$, $-NR^4C(=S)O-$, $-OC(=S)NR^4-$, $-NR^4C(=S)NR^4-$, $-C(=O)S-$, $-SC(=O)-$, $-OC(=O)S-$, $-NR^4C(=O)S-$, $-SC(=O)NR^4-$, $-C(=S)S-$, $-SC(=S)-$, $-SC(=S)O-$, $-NR^4C(=S)S-$, $-SC(=S)NR^4-$, $-C(=S)S-$, $-SC(=S)-$, $-SC(=O)S-$, $-SC(=S)S-$, $-NR^4C(=S)S-$, $-SC(=S)NR^4-$, $-O-$, $-S-$, or a bond;

each of L is independently $-C(=O)NR^4-$, $-NR^4C(=O)-$, $-C(=O)O-$, $-OC(=O)-$, $-OC(=O)O-$, $-NR^4C(=O)O-$, $-OC(=O)NR^4-$, $-NR^4C(=O)NR^4-$, $-NR^4C(=NR^4)NR^4-$, $-C(=S)NR^4-$, $-NR^4C(=S)-$, $-C(=S)O-$, $-OC(=S)-$, $OC(=S)O-$, $-NR^4C(=S)O-$, $-OC(=S)NR^4-$, $-NR^4C(=S)NR^4-$, $-C(=O)S-$, $-SC(=O)-$, $-OC(=O)S-$, $-NR^4C(=O)S-$, $-SC(=O)NR^4-$, $-C(=S)S-$, $-SC(=S)-$, $-SC(=S)O-$, $-NR^4C(=S)S-$, $-SC(=S)NR^4-$, $-C(=S)S-$, $-SC(=S)-$, $-SC(=O)S-$, $-SC(=S)S-$, $-NR^4C(=S)S-$, $-SC(=S)NR^4-$, $-O-N=CR^4-$, $-CR^4=N-O-$, $-O-$, $-S-$, $-C_1$-$C_{10}$ alkylene-O-, $-C_1$-$C_{10}$ alkylene-C(=O)O-, $-C_1$-$C_{10}$ alkylene-OC(=O)-, or a bond, wherein the alkylene is substituted or unsubstituted;

$R^3$ is $-C_0$-$C_{10}$ alkylene-$NR^7R^8$, $-C_0$-$C_{10}$ alkylene-heterocycloalkyl, or $-C_0$-$C_{10}$ alkylene-heterocycloaryl, wherein the alkylene, heterocycloalkyl and heterocycloaryl is independently substituted or unsubstituted;

each of $R^4$ is independently hydrogen or substituted or unsubstituted $C_1$-$C_6$ alkyl;

$R^5$ is hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl; and each of n, m, and q is independently 0, 1, 2, 3, 4, or 5.

In one aspect, disclosed herein is an amino lipid having a structure of Formula (I*), or a pharmaceutically acceptable salt or solvate thereof,

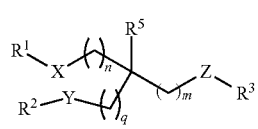

Formula (I*)

wherein $R^1$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, $-C_0$-$C_{10}$ alkylene-L-$R^6$, or $-C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

$R^2$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)N$R^4$—, —N$R^4$C(=O)—, —C(=O)O—, —OC(=O)—, —OC(=O)O—, —N$R^4$C(=O)O—, —OC(=O)N$R^4$—, —N$R^4$C(=O)N$R^4$—, —N$R^4$C(=N$R^4$)N$R^4$—, —C(=S)N$R^4$—, —N$R^4$C(=S)—, —C(=S)O—, —OC(=S)—, OC(=S)O—, —N$R^4$C(=S)O—, —OC(=S)N$R^4$—, —N$R^4$C(=S)N$R^4$—, —C(=O)S—, —SC(=O)—, —OC(=O)S—, —N$R^4$C(=O)S—, —SC(=O)N$R^4$—, —C(=S)S—, —SC(=S)—, —SC(=S)O—, —N$R^4$C(=S)S—, —SC(=S)N$R^4$—, —C(=S)S—, —SC(=S)—, —SC(=O)S—, —SC(=S)S—, —N$R^4$C(=S)S—, —SC(=S)N$R^4$—, —$R^{11}$C(=O)N($R^4$)$R^9$—, —N$R^7$C(=O)$R^9$—, —C(=O)O—, —OC(=O)—, —$R^{11}$C(=O)O$R^9$—, —$R^{11}$OC(=O)$R^9$—, —$R^{11}$OC(=O)O$R^9$—, —$R^{11}$N($R^4$)C(=O)O$R^9$—, —$R^{11}$OC(=O)N($R^4$)$R^9$—, —$R^{11}$(N$R^4$)C(=O)N($R^4$)$R^9$—, —$R^{11}$N($R^4$)C(=N$R^4$)$R^9$—, —$R^{11}$C(=S)N($R^4$)$R^9$—, —$R^{11}$N($R^4$)C(=S)$R^9$—, —$R^{11}$C(=S)O$R^9$—, —$R^{11}$OC(=S)$R^9$—, —$R^{11}$OC(=S)O$R^9$—, —$R^{11}$N($R^4$)C(=S)O$R^9$—, —$R^{11}$OC(=S)N($R^4$)$R^9$—, —$R^{11}$N($R^4$)C(=S)N($R^4$)$R^9$—, —$R^{11}$C(=O)S$R^9$—, —$R^{11}$SC(=O)$R^9$—, —$R^{11}$OC(=O)S$R^9$—, —$R^{11}$N($R^4$)C(=O)S$R^9$—, —$R^{11}$SC(=O)N($R^4$)$R^9$—, —$R^{11}$C(=S)S$R^9$—, —$R^{11}$SC(=S)$R^9$—, —$R^{11}$SC(=S)O$R^9$—, —$R^{11}$N($R^4$)C(=S)S$R^9$—, —$R^{11}$SC(=S)N($R^4$)$R^9$—, —$R^{11}$C(=S)S$R^9$—, —$R^{11}$SC(=S)$R^9$—, —$R^{11}$SC(=O)S$R^9$—, —$R^{11}$SC(=S)S$R^9$—, —$R^{11}$N($R^4$)C(=S)S$R^9$—, —$R^{11}$SC(=S)N($R^4$)$R^9$—, —$R^{11}$O$R^9$—, —$R^{11}$S$R^9$—, —O—, —S—, or a bond;

each of L is independently —C(=O)N$R^4$—, —N$R^4$C(=O)—, —C(=O)O—, —OC(=O)—, —C(=O)—, —OC(=O)O—, —N$R^4$C(=O)O—, —OC(=O)N$R^4$—, —N$R^4$C(=O)N$R^4$—, —N$R^4$C(=N$R^4$)N$R^4$—, —C(=S)N$R^4$—, —N$R^4$C(=S)—, —C(=S)O—, —OC(=S)—, OC(=S)O—, —N$R^4$C(=S)O—, —OC(=S)N$R^4$—, —N$R^4$C(=S)N$R^4$—, —C(=O)S—, —SC(=O)—, —OC(=O)S—, —N$R^4$C(=O)S—, —SC(=O)N$R^4$—, —C(=S)S—, —SC(=S)—, —SC(=S)O—, —N$R^4$C(=S)S—, —SC(=S)N$R^4$—, —C(=S)S—, —SC(=S)—, —SC(=O)S—, —SC(=S)S—, —N$R^4$C(=S)S—, —SC(=S)N$R^4$—, —O—N=C$R^4$—, —C$R^4$=N—O—, —O—, —S—, —$R^{11}$C(=O)N($R^4$)$R^9$—, —$R^{11}$N($R^4$)C(=O)$R^9$—, —$R^{11}$C(=O)O$R^9$—, —$R^{11}$OC(=O)$R^9$—, —$R^{11}$OC(=O)O$R^9$—, —$R^{11}$N($R^4$)C(=O)O$R^9$—, —$R^{11}$OC(=O)N($R^4$)$R^9$—, —$R^{11}$N($R^4$)C(=O)N($R^4$)$R^9$—, —$R^{11}$N($R^4$)C(=N$R^4$)N($R^4$)$R^9$—, —$R^{11}$C(=S)N($R^4$)$R^9$—, —$R^{11}$N($R^4$)C(=S)$R^9$—, —$R^{11}$C(=S)O$R^9$—, —$R^{11}$OC(=S)$R^9$—, —$R^{11}$OC(=S)O$R^9$—, —$R^{11}$N($R^4$)C(=S)O$R^9$—, —$R^{11}$OC(=S)N($R^4$)$R^9$—, —$R^{11}$N($R^4$)C(=S)N($R^4$)$R^9$—, —$R^{11}$C(=O)S$R^9$—, —$R^{11}$SC(=O)$R^9$—, —$R^{11}$OC(=O)S$R^9$—, —$R^{11}$N($R^4$)C(=O)S$R^9$—, —$R^{11}$SC(=O)N($R^4$)$R^9$—, —$R^{11}$C(=S)S$R^9$—, —$R^{11}$SC(=S)$R^9$—, —$R^{11}$SC(=S)O$R^9$—, —$R^{11}$N($R^4$)C(=S)S$R^9$—, —$R^{11}$SC(=S)N($R^4$)$R^9$—, —$R^{11}$C(=S)S$R^9$—, —$R^{11}$SC(=S)$R^9$—, —$R^{11}$SC(=O)S$R^9$—, —$R^{11}$SC(=S)S$R^9$—, —$R^{11}$N($R^4$)C(=S)S$R^9$—, —$R^{11}$SC(=S)N($R^4$)$R^9$—, —$R^{11}$O$R^9$—, —$R^{11}$C($R^{10}$)=N—O$R^9$—, —$R^{11}$O$R^9$—, —$R^{11}$S$R^9$—, —$C_1$-$C_{10}$ alkylene-C(=O)O—, —$C_1$-$C_{10}$ alkylene-OC(=O)—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-N$R^7R^8$, —$C_0$-$C_{10}$ alkylene-heterocycloalkyl, or —$C_0$-$C_{10}$ alkylene-heterocycloaryl, wherein the alkylene, heterocycloalkyl and heterocycloaryl is independently substituted or unsubstituted;

each of $R^4$ is independently hydrogen, substituted or unsubstituted $C_1$-$C_{16}$ alkyl or substituted or unsubstituted $C_1$-$C_{16}$ heteroalkyl;

$R^5$ is hydrogen, substituted or unsubstituted —$C_0$-$C_{10}$ alkylene-L-$R^4$;

each of $R^6$ is independently hydrogen, $C_3$-$C_{30}$ alkyl, $C_3$-$C_{30}$ alkenyl, $C_3$-$C_{30}$ alkynyl, Cy-$C_{3\text{-}30}$ alkyl, Cy-$C_{3\text{-}30}$ alkenyl, or Cy-$C_{3\text{-}30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_{16}$ alkyl, substituted or unsubstituted $C_1$-$C_{16}$ heteroalkyl, or $R^7$ and $R^8$ taken together with the nitrogen to which they are attached form a substituted or unsubstituted $C_2$-$C_6$ heterocyclyl; and each of $R^9$ is independently hydrogen or substituted or unsubstituted $C_1$-$C_{16}$ alkylene, or unsubstituted $C_1$-$C_{16}$ heteroalkylene;

each of $R^{10}$ is independently hydrogen or substituted or unsubstituted $C_1$-$C_{16}$ alkylene, or unsubstituted $C_1$-$C_{16}$ heteroalkylene; and each of $R^{10}$ is independently substituted or unsubstituted $C_1$-$C_{16}$ alkylene, or unsubstituted $C_1$-$C_{16}$ heteroalkylene.

each of n, m, and q is independently 0, 1, 2, 3, 4, or 5.

In some embodiments, the amino lipid of Formula (I) or (I*) has a structure of Formula (Ia), or a pharmaceutically acceptable salt or solvate thereof,

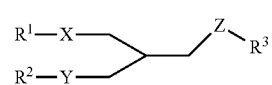

Formula (Ia)

wherein each of $R^1$ and $R^2$ is independently $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently C(=O)N$R^4$—, —N$R^4$C(=O)—, —C(=O)O—, —OC(=O)—, —OC(=O)O—, —N$R^4$C(=O)O—, —OC(=O)N$R^4$—, —N$R^4$C(=O)N$R^4$—, —N$R^4$C(=N$R^4$)N$R^4$—, —C(=S)N$R^4$—, —N$R^4$C(=S)—, —C(=S)

O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, —C$_1$-C$_{10}$ alkylene-O—, or a bond, wherein the alkylene is substituted or unsubstituted;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is —C$_0$-C$_{10}$ alkylene-NR$^7$R$^8$ or —C$_0$-C$_{10}$ alkylene-heterocycloalkyl, wherein the alkylene and heterocycloalkyl are each independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl; and each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl.

In another aspect, disclosed herein is an amino lipid having structure of Formula (Ib), or a pharmaceutically acceptable salt thereof,

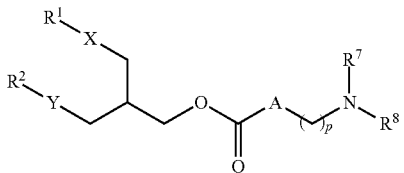

Formula (Ib)

wherein
each of X and Y are the same and are selected from the group consisting of: —OC(=O)—, —OC(=O)O—, —OC(=O)NR$^4$—, —C(=S)O—, —OC(=S)—, OC(=S)O—, —NR$^4$C(=S)O—, —OC(=S)NR$^4$—, —SC(=O)—, —OC(=O)S—, —SC(=S)O—, —O—, —C$_1$-C$_{10}$ alkylene-O—, and a bond, wherein the alkylene is substituted or unsubstituted R$^1$ and R$^2$ are the same and are selected from the group consisting of: hydrogen, C$_1$-C$_{30}$ alkyl, C$_1$-C$_{30}$ heteroalkyl, and Cy-C$_{3-30}$ alkyl, wherein the alkyl and heteroalkyl are each independently substituted or unsubstituted;

each of R$^4$ is independently hydrogen or substituted or unsubstituted C$_1$-C$_6$ alkyl;

each of Cy is substituted or unsubstituted cycloalkyl, substituted or unsubstituted heterocycloalkyl, substituted or unsubstituted aryl, substituted or unsubstituted heteroaryl; and each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl.

A is —O—, —CH$_2$—, —S—, or —NR$^{12}$—;
R$^{12}$ is hydrogen, C$_1$-C$_{10}$ alkyl, or C$_1$-C$_{10}$ heteroalkyl, wherein the alkyl and heteroalkyl are each independently substituted or unsubstituted; and Cy is substituted or unsubstituted cycloalkyl, substituted or unsubstituted heterocycloalkyl, substituted or unsubstituted aryl, or substituted or unsubstituted heteroaryl.

p is 1, 2, 3, 4, 5 or 6

In some embodiments, R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

In one aspect, disclosed herein is an amino lipid having a structure of Formula (II), or a pharmaceutically acceptable salt or solvate thereof,

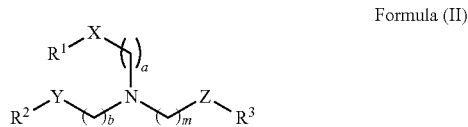

Formula (II)

wherein
each of R$^1$ and R$^2$ is independently C$_3$-C$_{30}$ alkyl, C$_3$-C$_{30}$ alkenyl, C$_3$-C$_{30}$ alkynyl, C$_3$-C$_{30}$ heteroalkyl, C$_3$-C$_{30}$ heteroalkenyl, C$_3$-C$_{30}$ heteroalkynyl, C$_3$-C$_{10}$ cycloalkyl, —C$_0$-C$_{10}$ alkylene-L-R$^6$, or —C$_1$-C$_{10}$ alkenylene-L-R$^6$, wherein each of the alkyl, alkylene, alkenyl, alkenylene, alkynyl, heteroalkyl, heteroalkenyl, and cycloalkyl is independently substituted or unsubstituted;

each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)

NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is —C$_0$-C$_{10}$ alkylene-NR$^7$R$^8$, —C$_0$-C$_{10}$ alkylene-heterocycloalkyl, or —C$_0$-C$_{10}$ alkylene-heterocycloaryl, wherein the alkylene, heterocycloalkyl and heterocycloaryl is independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl;

each of a and b is independently 1, 2, 3, 4, 5, 6, 7, 8, 9, or 10; and m is 0, 1, 2, 3, 4, or 5.

In one aspect, disclosed herein is an amino lipid having a structure of Formula (II*), or a pharmaceutically acceptable salt or solvate thereof,

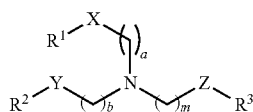

Formula (II*)

wherein each of R$^1$ and R$^2$ is independently hydrogen, C$_3$-C$_{30}$ alkyl, C$_3$-C$_{30}$ alkenyl, C$_3$-C$_{30}$ alkynyl, C$_3$-C$_{30}$ heteroalkyl, C$_3$-C$_{30}$ heteroalkenyl, C$_3$-C$_{30}$ heteroalkynyl, C$_3$-C$_{10}$ cycloalkyl, —C$_0$-C$_{10}$ alkylene-L-R$^6$, or —C$_1$-C$_{10}$ alkenylene-L-R$^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —C(=O)—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is hydrogen, —C$_1$-C$_6$ alkyl, —C$_0$-C$_{10}$ alkylene-NR$^7$R$^8$, —C$_0$-C$_{10}$ alkylene-heterocycloalkyl, or —C$_0$-C$_{10}$ alkylene-heterocycloaryl, wherein the alkyl, alkylene, heterocycloalkyl and heterocycloaryl is independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl;

each of a and b is independently 1, 2, 3, 4, 5, 6, 7, 8, 9, or 10; and m is 0, 1, 2, 3, 4, or 5.

In one aspect, disclosed herein is a nanoparticle composition that comprises an amino lipid described herein or a pharmaceutically acceptable salt or solvate thereof. In one aspect, disclosed herein is an amino lipid having a structure selected from Table 1A, or a pharmaceutically acceptable salt or solvate thereof. In one aspect, disclosed herein is a nanoparticle composition that comprises an amino lipid having a structure selected from Table 1A, or a pharmaceutically acceptable salt or solvate thereof. In some embodiments, said amino lipid or a pharmaceutically acceptable salt or solvate thereof, comprises from 20 mol % to 80 mol % of a total lipid content present in said nanoparticle composition. In some embodiments, said amino lipid or a pharmaceutically acceptable salt or solvate thereof, comprises from 40 mol % to 60 mol % of a total lipid content present in said nanoparticle composition. In some embodiments, said amino lipid or a pharmaceutically acceptable salt or solvate thereof, comprises from 50 mol % to 60 mol % of a total lipid content present in said nanoparticle composition. In some embodiments, said amino lipid or a salt or solvate thereof, comprises one or more ionizable nitrogen atoms. In some embodiments, the nanoparticle composition comprises one or more ionizable nitrogen atoms that are from the one or more amino lipids. In some embodiments, said nanoparticle composition comprises only one amino lipid or a salt or solvate thereof. In some embodiments, said nanoparticle composition comprises one or more nucleic acid molecular entities. In some embodiments, a molar ratio of said ionizable nitrogen atoms to phosphate groups present in said nucleic acid molecular entities (the N to P or N/P ratio) is from about 2 to about 20. In some embodiments, said N/P ratio is from about 2 to about 15, from about 2 to about 10, from about 2 to about 8, from about 2 to about 6, from about 3 to about 15, from about 3 to about 10, from about 3 to about 8, from about 3 to about 6, from about 4 to about 15, from about 4 to about 10, from about 4 to about 8, or from about 4 to about 6. In some embodiments, said N/P ratio is from about 3.5 to about 10. In some embodiments, said nanoparticle composition comprises a neutral lipid. In some embodiments, said neutral lipid comprises from about 1 mol % to about 20 mol % of a total lipid content present in said nanoparticle composition. In some embodiments, said neutral lipid comprises from about 2 mol % to about 25 mol % of a total lipid content present in said nanoparticle composition. In some embodiments, said neutral lipid comprises from about 5 mol % to about 10 mol % of a total lipid content present in said nanoparticle composition. In some embodiments, said neutral lipid is selected from 1,2-distearoyl-sn-glycero-3-phosphocholine (DSPC), 1,2-dipalmitoyl-sn-glycero-3-phosphocholine (DPPC), 1,2-dimyristoyl-sn-glycero-phosphocholine (DMPC), 2-oleoyl-1-palmitoyl-sn-glycero-3-phosphocholine (POPC), 1,2-dioleoyl-sn-glycero-3-phosphoethanolamine (DOPE), and sphingomyelin. In some embodiments, said neutral lipid is DSPC. In some embodiments, said nanoparticle composition comprises a structural lipid. In some embodiments, said structural lipid is sterol or a derivative thereof. In some embodiments, said sterol or said derivative thereof is cholesterol or cholesterol derivative. In some embodiments, said structural lipid comprises from about 15 mol % to about 65 mol % of a total lipid content present in the nanoparticle composition. In some embodiments, said structural lipid comprises from about 30 mol % to about 60 mol % of a total lipid content present in the nanoparticle composition. In some embodiments, said structural lipid comprises from about 30 mol % to about 40 mol % of a total lipid content present in the nanoparticle composition. In some embodiments, said nanoparticle composition comprises a PEG-lipid. In some embodiments, said PEG-lipid is a PEG-lipid of Table 2. In some embodiments, said PEG-lipid comprises from about 0.1 mol % to about 6 mol % of a total lipid content present in said nanoparticle composition. In some embodiments, said PEG-lipid comprises about 2.0 mol % to about 2.5 mol % of a total lipid content present in said nanoparticle composition. In some embodiments, a number average molecular weight of said PEG-lipid is from about 200 Da to about 5000 Da. In some embodiments, said one or more nucleic acid molecular entities comprise a guide RNA (gRNA) targeting a disease causing gene of interest. In some embodiments, the guide RNA is a single guide RNA (sgRNA). In some embodiments, the disease causing gene of interest is produced in hepatocytes. In some embodiments, said one or more nucleic acid molecular entities comprise an mRNA encoding SpCas9, CBE, and/or ABE proteins. In some embodiments, the composition comprises a nucleic acid stabilizer.

In one aspect, disclosed herein is a nanoparticle composition comprising: (a) one or more nucleic acid molecular entities; (b) an amino lipid described herein, or a salt or solvate thereof, wherein said amino lipid or a salt thereof, comprises from 20 mol % to 80 mol % of a total lipid content present in said nanoparticle composition, wherein said amino lipid or a salt thereof, comprises one or more ionizable nitrogen atoms, and wherein a molar ratio of said ionizable nitrogen atoms to phosphate groups present in said nucleic acid molecular entity is from 2 to 12; (c) a neutral lipid, comprising from 2 mol % to 25 mol % of said total lipid content present in said nanoparticle composition; (d) a structural lipid, comprising from 30 mol % to 60 mol % of said total lipid content present in said nanoparticle composition; and (e) a PEG-lipid, comprising from 0.1 mol % to 6 mol % of said total lipid content present in said nanoparticle composition. In some embodiments, the composition further comprises a nucleic acid stabilizer. In some embodiments, the nucleic acid stabilizer comprises polyethylene glycol, cetrimonium bromide, or chitosan. In some embodiments, the nucleic acid stabilizer comprises polyethylene glycol that has a number average molecular weight of about 120 to about 2000 Da.

In one aspect, disclosed herein is a nanoparticle composition comprising: (a) one or more nucleic acid molecular entities; (b) an amino lipid or a salt thereof, wherein said amino lipid or a salt thereof, comprises from 20 mol % to 80 mol % of a total lipid content present in said nanoparticle composition, wherein said amino lipid or a salt thereof, comprises one or more ionizable nitrogen atoms, and wherein a molar ratio of said ionizable nitrogen atoms to phosphate groups present in said nucleic acid molecular entity is from 2 to 12; (c) a neutral lipid, comprising from 2 mol %/c to 25 mol % of said total lipid content present in said nanoparticle composition; (d) a structural lipid, comprising from 30 mol %/c to 60 mol % of said total lipid content present in said nanoparticle composition; (e) a PEG-lipid, comprising from 0.1 mol % to 6 mol % of said total lipid content present in said nanoparticle composition; and (f) a nucleic acid stabilizer, wherein the nucleic acid stabilizer comprises chitosan, cetrimonium bromide, polyethylene glycol that has a number average molecular weight of about 120 to about 2000 Da, or a combination thereof. In some embodiments, the nucleic acid stabilizer comprises PEG 200, PEG 400, or PEG 600. In some embodiments, the nucleic acid stabilizer is PEG 400. In some embodiments, the nucleic acid stabilizer is present in the nanoparticle composition in an amount of about 0.01% to about 20% by total weight. In some embodiments, the nucleic acid stabilizer is present in the nanoparticle composition in an amount of about 0.5% to about 5% by total weight. In some embodiments, said one or more nucleic acid molecular entities comprise a PCSK9 gRNA. In some embodiments, said one or more nucleic acid molecular entities comprise an mRNA encoding a Cas nuclease. In some embodiments, said one or more nucleic acid molecular entities comprise an mRNA, a gRNA, a siRNA, an antisense oligonucleotide, a microRNA, an anti-microRNA, an RNA activator, an aptamer, or a combination thereof. In some embodiments, said nanoparticle composition comprises an antioxidant. In some embodiments, said antioxidant comprise EDTA. In some embodiments, the composition comprises a surfactant. In some embodiments, the surfactant is a fatty acid or a fatty alcohol. In some embodiments, the surfactant is a $C_{12}$-$C_{24}$ fatty alcohol. In some embodiments, the $C_{12}$-$C_{24}$ fatty alcohol is lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, or a combination thereof. In some embodiments, the $C_{12}$-$C_{24}$ fatty alcohol is oleyl alcohol, stearyl alcohol, or a mixture thereof. In some embodiments, the surfactant comprises about 1.0 mol % to about 10 mol % of a total lipid content present in said nanoparticle composition. In some embodiments, a median diameter of the nanoparticle is from about 50 nm to about 150 nm. In some embodiments, a polydispersity index of the nanoparticle is from 0 to 0.15. In some embodiments, a polydispersity index of the nanoparticle is from 0 to 0.05. In some embodiments, a nucleic acid entrapment efficiency of the nanoparticle composition is at least 80%, at least 85%, at least 90%, at least 91%, at least 92%, at least 93%, at least 94%, at least 95%, at least 96%, at least 97%, at least 98%, or at least 99%.

In one aspect, disclosed herein is a PEG-lipid having the structure of Formula (III), or a pharmaceutically acceptable salt or solvate thereof, Formula (III)

[chemical structure]

wherein
- each of $R^{21}$ and $R^{22}$ is independently substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;
- each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;
- each of $R^4$ is independently hydrogen or substituted or unsubstituted $C_1$-$C_6$ alkyl;
- $R^{23}$ is —C$_0$-C$_{10}$ alkylene-(CH$_2$—CH$_2$—O)$_{k4}$—R$^{24}$ or —C$_1$-C$_{10}$ heteroalkylene-(CH$_2$—CH$_2$—O)$_{k4}$—R$^{24}$, wherein the alkylene and heteroalkylene are each independently substituted or unsubstituted;
- $R^{24}$ is independently hydrogen or substituted or unsubstituted $C_1$-$C_3$ alkyl;
- $R^{25}$ is hydrogen or substituted or unsubstituted $C_1$-$C_6$ alkyl;
- each of k1, k2, and k3 is independently 0, 1, 2, 3, 4, or 5; and
- k4 is an integer selected from 1 to 100.

In one aspect, disclosed herein is a PEG-lipid having the structure of Formula (III*), or a pharmaceutically acceptable salt or solvate thereof, Formula (III*)

[chemical structure]

wherein
- $R^{21}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;
- $R^{22}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;
- each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —N(Ac)—, —OC(O)OCH$_2$C(O)O—, —OC(O)OCH$_2$C(O)NH—, —OC(O)NHCH$_2$C(O)O—, —OC(O)NHCH$_2$C(O)NH—, —OC(O)O(CH$_2$)$_2$C(O)O—, —OC(O)O(CH$_2$)$_2$C(O)NH—, —OC(O)NH(CH$_2$)$_2$C(O)O—, —OC(O)NH(CH$_2$)$_2$C(O)NH—, —OC(O)O(CH$_2$)$_3$C(O)O—, —OC(O)O(CH$_2$)$_3$C(O)NH—, —OC(O)NH(CH$_2$)$_3$C(O)O—, —OC(O)NH(CH$_2$)$_3$C(O)NH—, —C(O)OCH$_2$C(O)NH—, —C(O)NHCH$_2$C(O)O—, —C(O)NHCH$_2$C(O)NH—, —C(O)O(CH$_2$)$_2$C(O)O—, —C(O)O(CH$_2$)$_2$C(O)NH—, —C(O)NH(CH$_2$)$_2$C(O)O—, —C(O)NH(CH$_2$)$_2$C(O)NH—, —C(O)O(CH$_2$)$_3$C(O)O—, —C(O)O(CH$_2$)$_3$C(O)NH—, —C(O)NH(CH$_2$)$_3$C(O)O—, —C(O)NH(CH$_2$)$_3$C(O)NH—, —OC(=O)NR$^4$(CH$_2$)$_{1-3}$C(=O)NH—, —OC(=O)NR$^4$(CH$_2$)$_{1-3}$C(=O)O—, —C(=O)NR$^4$(CH$_2$)$_{1-3}$C(=O)NH—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;
- each of $R^4$ is independently hydrogen or substituted or unsubstituted $C_1$-$C_6$ alkyl;
- $R^{23}$ is —C$_0$-C$_{10}$ alkylene-(CH$_2$—CH$_2$—O)$_{k4}$—R$^{24}$, —C$_1$-C$_{10}$ heteroalkylene-(CH$_2$—CH$_2$—O)$_{k4}$—R$^{24}$, —C$_0$-C$_{10}$ alkylene-(O—CH$_2$—CH$_2$)$_{k4}$—R$^{24}$ or —C$_1$-C$_{10}$ heteroalkylene-(O—CH$_2$—CH$_2$)$_{k4}$—R$^{24}$, wherein the alkylene and heteroalkylene are each independently substituted or unsubstituted;
- $R^{24}$ is independently hydrogen, substituted or unsubstituted $C_1$-$C_3$ alkyl, —O—R$^4$, —C(=O)OH, or —C(=O)R$^4$;

$R^{25}$ is hydrogen or substituted or unsubstituted $C_1$-$C_{22}$ alkyl;

each of k1, k2, and k3 is independently 0, 1, 2, 3, 4, or 5; and k4 is an integer selected from 1 to 100.

In some embodiments, the PEG-lipid of Formula (III) or (III*), or a pharmaceutically acceptable salt or solvate thereof, wherein $R^{21}$ is substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;

$R^{22}$ is hydrogen, substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;

each of $R^{26}$, $R^{27}$ and $R^{28}$ is independently —C(═O) $NR^4$—, —$NR^4$C(═O)—, —C(═O)O—, —OC(═O)—, —OC(═O)O—, —$NR^4$C(═O)O—, —OC(═O)$NR^4$—, —$NR^4$C(═O)$NR^4$—, —$NR^4$C(═N$R^4$)$NR^4$—, —C(═S)$NR^4$—, —$NR^4$C(═S)—, —C(═S)O—, —OC(═S)—, OC(═S)O—, —$NR^4$C(═S)O—, —OC(═S)$NR^4$—, —$NR^4$C(═S)$NR^4$—, —C(═O)S—, —SC(═O)—, —OC(═O)S—, —$NR^4$C(═O)S—, —OC(═O)$NR^4$(CH$_2$)$_{1-3}$C(═O)NH—, —OC(═O)$NR^4$(CH$_2$)$_{1-3}$C(═O)O—, —C(═O)$NR^4$(CH$_2$)$_{1-3}$C(═O)NH—, —SC(═O)$NR^4$—, —C(═S)S—, —SC(═S)—, —SC(═S)O—, —$NR^4$C(═S)S—, —SC(═S)$NR^4$—, —C(═S)S—, —SC(═S)—, —SC(═O)S—, —SC(═S)S—, —$NR^4$C(═S)S—, —SC(═S)$NR^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH—, —O—, —S—, or a bond;

each of $R^4$ is independently hydrogen or substituted or unsubstituted $C_1$-$C_6$ alkyl;

$R^{23}$ is —$C_0$-$C_{10}$ alkylene-(CH$_2$—CH$_2$—O)$_{k4}$—$R^{24}$ or —$C_1$-$C_{10}$ heteroalkylene-(CH$_2$—CH$_2$—O)$_{k4}$—$R^{24}$, wherein the alkylene and heteroalkylene are each independently substituted or unsubstituted;

$R^{24}$ is independently hydrogen, substituted or unsubstituted $C_1$-$C_3$ alkyl, —O—$R^4$, —C(═O)O$R^4$, or —C(═O)$R^4$;

$R^{25}$ is hydrogen or substituted or unsubstituted $C_1$-$C_6$ alkyl;

each of k1, k2, and k3 is independently 0, 1, 2, 3, 4, or 5; and k4 is an integer selected from 1 to 100.

In one aspect, disclosed herein is a PEG-lipid having the structure selected from Table 2, or a pharmaceutically acceptable salt or solvate thereof. In one aspect, disclosed herein is a pharmaceutical composition comprising a described nanoparticle composition, and an excipient or carrier. In some embodiments, said pharmaceutical composition comprises an mRNA encoding a gene editor nuclease. In some embodiments, said pharmaceutical composition comprises one or more guide RNA molecules. In some embodiments, said pharmaceutical composition comprises a PCSK9 guide RNA. In some embodiments, said pharmaceutical composition comprises two or more guide RNA molecules. In some embodiments, said two or more guide RNA molecules target two or more genes of interest. In some embodiments, said mRNA encodes Cas9 nuclease. In some embodiments, said mRNA encodes a base editor nuclease. In some embodiments, said mRNA and said one or more guide RNA molecules are present in a same nanoparticle composition. In some embodiments, said mRNA and said one or more guide RNA molecules are present in different nanoparticle compositions. In some embodiments, a ratio of said gRNA molecules to said mRNA in said pharmaceutical composition is from about 0.01 to about 100 by weight or by mole. In some embodiments, a ratio of said gRNA molecules to said mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole. In one aspect, disclosed herein is a pharmaceutical composition comprising: a first nanoparticle composition as described herein, and a second nanoparticle composition as described herein. In some embodiments, said first nanoparticle composition comprises a gene editor mRNA, and said second nanoparticle composition comprises one or more guide RNA molecules. In some embodiments, a ratio of guide RNA molecules to mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole. In some embodiments, a ratio of guide RNA to mRNA in said pharmaceutical composition is about 1:1 by weight or by mole.

In one aspect, disclosed herein is a method of delivering a nucleic acid molecular entity to a cell, the method comprising contacting said cell with a nanoparticle composition or a pharmaceutical composition as described herein, whereby said nucleic acid molecular entity is delivered to said cell. In some embodiments, said cell is contacted in vivo, ex vivo, or in intro. In one aspect, disclosed herein is a method of producing a polypeptide of interest in a cell, the method comprising contacting said cell with a nanoparticle composition or a pharmaceutical composition described herein, wherein said nanoparticle composition or said pharmaceutical composition comprises a nucleic acid molecular entity, and wherein said nucleic acid molecular entity is translated in the cell thereby producing the polypeptide. In one aspect, disclosed herein is a method of making a pharmaceutical composition, comprising combining a first nanoparticle composition and a second nanoparticle composition described herein. In one aspect, disclosed herein is a method of treating a disease or condition in a mammal, the method comprising administering to a mammal a therapeutically effective amount of a pharmaceutical composition described herein. In one aspect, disclosed herein is a method of editing PCSK9 gene in a cell comprising contacting said cell with a nanoparticle composition or a pharmaceutical composition described herein, wherein said nanoparticle composition or said pharmaceutical composition comprises a PCSK9 guide RNA. In one aspect, disclosed herein is a method of producing a stabilized nanoparticle composition described herein, comprising combining a nucleic acid stabilizer with a nanoparticle composition that lacks the nucleic acid stabilizer. In some embodiments, the nucleic acid stabilizer is combined with the nanoparticle composition before freezing or storage. In some embodiments, the nucleic acid stabilizer is combined with the nanoparticle composition before, concurrently, or after the addition of the one or more nucleic acid entities. In some embodiments, the combining comprises mixing the nucleic acid stabilizer with the one or more nucleic acid entities in an aqueous buffer.

In one aspect, disclosed herein is a method of producing a stabilized nanoparticle composition, comprising (a) combining a nucleic acid stabilizer with one or more nucleic acid molecular entities thereby producing a solution comprising the stabilized one or more nucleic acid molecular entities; and (b) combining the solution of (a) with a nanoparticle composition that comprises one or more of an amino lipid, a neutral lipid, a structural lipid, and a PEG-lipid. In some embodiments, the combining in (a) comprises mixing the nucleic acid stabilizer with the one or more nucleic acid entities in an aqueous buffer. In some embodiments, the method comprising collecting and dialyzing the nanoparticle composition against a buffer with a pH of about 6.5 to about 8.0. In some embodiments, the nucleic acid stabilizer is polyethylene glycol that has a number average molecular weight of about 120 to about 1000.

In one aspect, disclosed herein is a method of preparing a formulation comprising lipid nanoparticles, wherein the nanoparticles comprise (i) one or more nucleic acid molecular entities, (ii) an amino lipid, and (iii) one or more lipids selected from a structural lipid, a neutral lipid, and a PEG-lipid, the method comprising, (a) combining a first faction of the amino lipid with the one or more nucleic acid molecular entities in a first solution, wherein the first fraction comprises 0.1 mol % to 99 mol % of the total amino lipid; (b) combining the remaining of the amino lipid with the one or more lipids selected from a structural lipid, a neutral lipid, and a PEG-lipid in a second solution; (c) mixing the first solution and the second solution, thereby producing the lipid nanoparticles. In some embodiments, the first fraction of the amino lipid is configured to neutralize between 0.1-99% of the phosphate (on an N:P basis) in the one or more nucleic acid molecular entities. In some embodiments, the first fraction of the amino lipid is configured to neutralize between 0.5-90% of the phosphate (on an N:P basis) in the one or more nucleic acid molecular entities. In some embodiments, the first fraction of the amino lipid is configured to neutralize about 10%, 15%, 25%, 50%, or 75% of the phosphate (on an N:P basis) in the one or more nucleic acid molecular entities. In some embodiments, the first solution is an aqueous buffer solution. In some embodiments, the first solution further comprises a nucleic acid stabilizer. In some embodiments, the first solution and the second solution are mixed in an inline mixer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 22 (B) illustrates the percentage of PCSK9 gene editing in wild type C57BL/6 female mice liver after single dose administration of LNPs F151B, F193A-F193C (n=5) at 0.1 mg/kg dose of total RNA, Table 20. F151B is the reference LNP constituted using amino lipid 502. The commercially available PEG-Lipid 507 was replaced with PEG-Lipid VP177 in LNPs F19B and F193C and formulated with amino lipid VL422.

FIG. 23 (B) illustrates the percentage of ANGPTL3 gene editing in the livers of cynomolgus monkeys (n=3) after single dose administration of LNPs F190A and F190B as described in Example 25, Table 23. F190A and F190B were dosed at 2 mg/kg total RNA dose. The PEG-Lipid 507 of F190A is replaced with PEG-Lipid VP159 in F190B.

DETAILED DESCRIPTION

Figure 1:
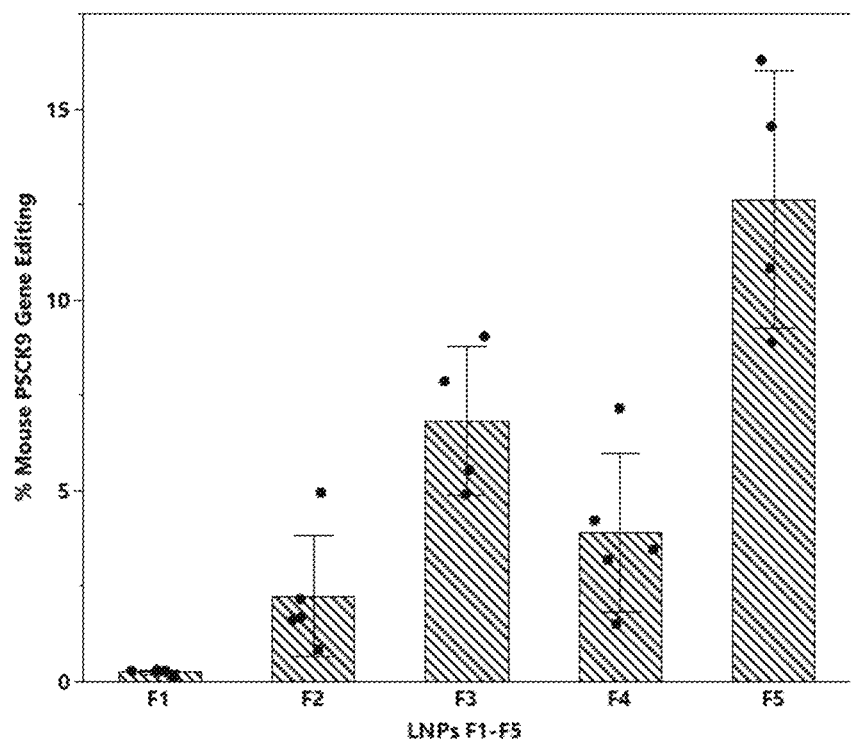
FIG. 1 illustrates PCSK9 gene editing in wild type C57BL/6 female mice (n=5) at 0.5 mg/kg total RNA dose for LNPs except F1. Total RNA dose F1: 0.75 mg/kg. LNPs F1-F5 were constituting by using SpCas9 mRNA and PCSK9 gRNA.
Figure 2A:
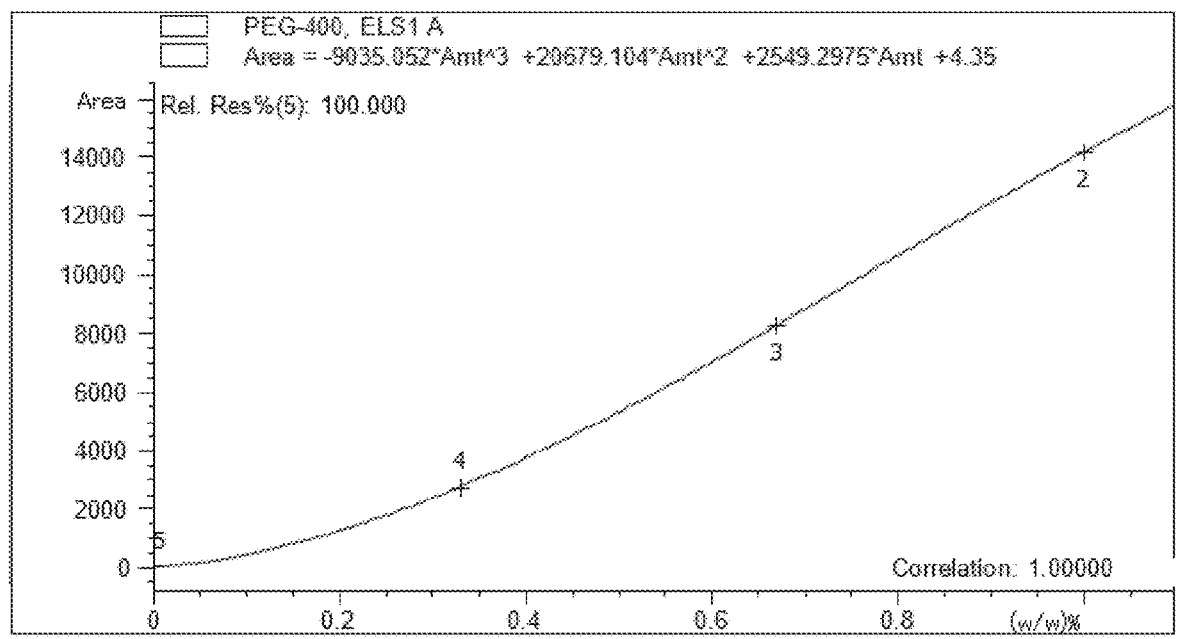
FIGS. 2A and 2B illustrate the calibration curve and example chromatogram from the IP-RPLC-HPLC-ELSD method used to determine PEG400 (w/w) %. The calibration curve is fit to a cubic fit, as the ELSD detection has a non-linear response.
Figure 2B:
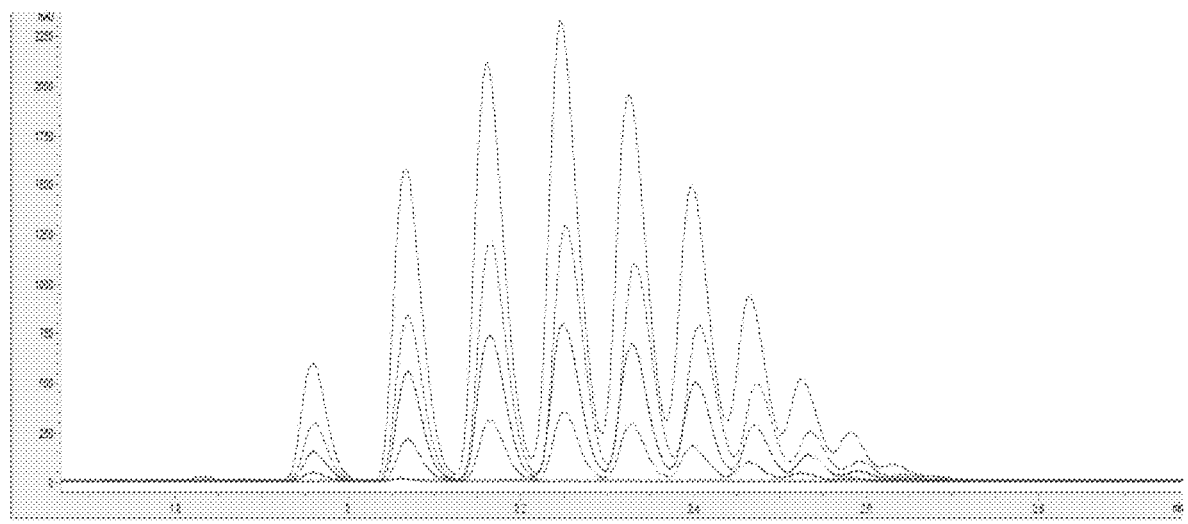

The present disclosure relates to cationic and/or ionizable lipids and lipid-containing particles comprising the same.

The disclosure also relates to methods of delivering a therapeutic agent (such as a nucleic acid) to a mammalian cell, methods of producing a polypeptide of interest in a mammalian cell, and methods of treating a disease or disorder in a mammal in need thereof. For example, a method of producing a polypeptide of interest in a cell can comprise a step of contacting a herein described lipid-containing particle with the cell, thereby delivering an mRNA that encodes the polypeptide of interest into the cell, and thereby the mRNA can be translated to produce the polypeptide of interest. For another example, a method of delivering a therapeutic agent to a mammalian cell or organ may involve administration of a herein described lipid-containing particle comprising the therapeutic agent to a subject, in which the administration comprises contacting the cell or organ with the lipid-containing particle, whereby the therapeutic agent is delivered to the cell or organ.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The section headings used herein are for organizational purposes only and are not to be construed as limiting the subject matter described.

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

1. Definitions

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

The term "derivative" as used herein indicates a chemical or biological substance that is related structurally to a second substance and derivable from the second substance through a modification of the second substance. In particular, if a first compound is a derivative of a second compound and the second compound is associated with a chemical and/or biological activity, the first compound differs from the second compound for at least one structural feature, while retaining (at least to a certain extent) the chemical and/or biological activity of the second compound and at least one structural feature (e.g. a sequence, a fragment, a functional group and others) associated thereto. A skilled person will be able to identify, on a case by case basis and upon reading of the present disclosure, structural features of the second compound that have to be maintained in the first compound to retain the second compound chemical and/or biological activity as well as assays that can be used to prove retention of the chemical and/or biological activity. Exemplary "derivatives" can include a prodrug, a metabolite, an enantiomer, a diastereomer, esters (e.g. acyloxyalkyl esters, alkoxycarbonyloxyalkyl esters, alkyl esters, aryl esters, phosphate esters, sulfonate esters, sulfate esters and disulfide containing esters), ethers, amides, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, sulfonate esters, and the like. In some cases, a derivative may include trivial substitutions (i.e. additional alkyl/ akylene groups) to a parent compound that retains the chemical and/or biological activity of the parent compound.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)$n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the term "therapeutically effective amount" means an amount of an agent to be delivered (e.g., nucleic acid, drug, payload, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the LNP composition to a subject after the onset, or suspected onset, of a disease or condition. "Treating" includes the concepts of "alleviating", which refers to lessening the frequency of occurrence or recurrence, or the severity, of any symptoms or other ill effects related to a disease or condition and/or the side effects associated with the disease or condition. The term "treating" also encompasses the concept of "managing" which refers to reducing the severity of a particular disease or disorder in a patient or delaying its recurrence, e.g., lengthening the period of remission in a patient who had suffered from the disease. The term "treating" further encompasses the concept of "prevent," "preventing," and "prevention," as previously stated. It is appreciated that, although not precluded, treating a disorder or condition does not require that the disorder, condition, or symptoms associated therewith be completely eliminated.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, and the like.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I), Formula (I*), Formula (Ia), Formula (II), Formula (II*), Formula (III) or Formula (III*). A person of ordinary skill in the art would understand that, while only a single bond is shown, a double bond is intended for those substituents.

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (1-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

The term "aryl" refers to a radical derived from a hydrocarbon ring system comprising at least one aromatic ring. In some embodiments, an aryl comprises hydrogens and 6 to 30 carbon atoms. The aryl radical can be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, indane, indene, naphthalene, phenalene, phenanthrene, pleiadene, pyrene, and triphenylene. In some embodiments, the aryl is phenyl. Unless stated otherwise specifically in the specification, an aryl can be optionally substituted, for example, with halogen, amino, alkylamino, aminoalkyl, nitrile, nitro, hydroxyl, alkyl, alkenyl, alkynyl, haloalkyl, heteroalkyl, alkoxy, aryl, cycloalkyl, heterocycloalkyl, heteroaryl, —S(O)$_2$NH—C$_1$-C$_6$alkyl, and the like. In some embodiments, an aryl is optionally substituted with halogen, methyl, ethyl, —CN, —CF$_3$, —OH, —OMe, —NH$_2$, —NO$_2$, —S(O)$_2$NH$_2$, —S(O)$_2$NHCH$_3$, —S(O)$_2$NHCH$_2$CH$_3$, —S(O)$_2$NHCH(CH$_3$)$_2$, —S(O)$_2$N(CH$_3$)$_2$, or —S(O)$_2$NHC(CH$_3$)$_3$. In some embodiments, an aryl is optionally substituted with halogen, methyl, ethyl, —CN, —CF$_3$, —OH, or —OMe. In some embodiments, the aryl is optionally substituted with halogen. In some embodiments, the aryl is substituted with alkyl, alkenyl, alkynyl, haloalkyl, or heteroalkyl, wherein each alkyl, alkenyl, alkynyl, haloalkyl, heteroalkyl is independently unsubstituted, or substituted with halogen, methyl, ethyl, —CN, —CF$_3$, —OH, —OMe, —NH$_2$, or —NO$_2$.

The term "alkenyl" refers to a type of alkyl group in which at least one carbon-carbon double bond is present. In one embodiment, an alkenyl group has the formula —C(R$^a$)=CR$^a_2$, wherein R$^a$ refers to the remaining portions of the alkenyl group, which may be the same or different. In some embodiments, R$^a$ is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$. "Alkenylene" or "alkenylene chain" refers to a alkylene group in which at least one carbon-carbon double bond is present. In some embodiments, the alkenylene is —CH=CH—, —CH$_2$CH$_2$CH=CH—, or —CH=CHCH$_2$CH$_2$—. In some embodiments, the alkenylene is —CH=CH—. In some embodiments, the alkenylene is —CH$_2$CH$_2$CH=CH—. In some embodiments, the alkenylene is —CH=CHCH$_2$CH$_2$—.

The term "alkynyl" refers to a type of alkyl group in which at least one carbon-carbon triple bond is present. In one embodiment, an alkynyl group has the formula —C≡CR$^a$, wherein R$^a$ refers to the remaining portions of the alkynyl group. In some embodiments, R$^a$ is H or an alkyl. In some embodiments, an alkynyl is selected from ethynyl (i.e., acetylenyl), propynyl (i.e., propargyl), butynyl, pentynyl, and the like. Non-limiting examples of an alkynyl group include —C≡CH, —C≡CCH$_3$, and —CH$_2$C≡CH. "Alkynylene" or "alkynylene chain" refers to a alkylene group in which at least one carbon-carbon triple bond is present. In some embodiments, the alkynylene is —C≡C—, —CH$_2$CH$_2$C≡C—, or —C≡CCH$_2$CH$_2$—. In some embodiments, the alkynylene is —C≡C—. In some embodiments, the alkynylene is —CH$_2$CH$_2$C≡C—. In some embodiments, the alkynylene is —C≡CCH$_2$CH$_2$—.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted. Depending on the structure, a cycloalkyl group can be monovalent or divalent (i.e., a cycloalkylene group).

The term "heterocycle" or "heterocyclic" refers to heteroaromatic rings (also known as heteroaryls) and heterocycloalkyl rings (also known as heteroalicyclic groups) that includes at least one heteroatom selected from nitrogen, oxygen and sulfur, wherein each heterocyclic group has from 3 to 12 atoms in its ring system, and with the proviso that any ring does not contain two adjacent O or S atoms. A "heterocyclyl" is a univalent group formed by removing a hydrogen atom from any ring atoms of a heterocyclic compound. In some embodiments, heterocycles are monocyclic, bicyclic, polycyclic, spirocyclic or bridged compounds. Non-aromatic heterocyclic groups (also known as heterocycloalkyls) include rings having 3 to 12 atoms in its ring system and aromatic heterocyclic groups include rings having 5 to 12 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, ₃ h-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The term "heterocycloalkyl" refers to a cycloalkyl group that includes at least one ring heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted. As used herein, the term "heterocycloalkylene" can refer to a divalent heterocycloalkyl group.

The term "heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group is partially reduced to form a heterocycloalkyl group defined herein. In some embodiments, a heteroaryl group is fully reduced to form a heterocycloalkyl group defined herein.

The term "heteroalkyl" refers to an alkyl group in which one or more skeletal atoms of the alkyl are selected from an atom other than carbon, e.g., oxygen, nitrogen (e.g. —NH—, —N(alkyl)-, or —N(aryl)-), sulfur (e.g. —S—, —S(=O)—, or —S(=O)$_2$—), or combinations thereof. In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_6$ heteroalkyl. Representative heteroalkyl groups include, but are not limited to —OCH$_2$OMe, —OCH$_2$CH$_2$OH, —OCH$_2$CH$_2$OMe, or —OCH$_2$CH$_2$OCH$_2$CH$_2$NH$_2$. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "heteroalkenyl" refers to an alkenyl group in which one or more skeletal atoms of the alkenyl are selected from an atom other than carbon, e.g., oxygen, nitrogen (e.g. —NH—, —N(alkyl)-, or —N(aryl)-), sulfur (e.g. —S—, —S(=O)—, or —S(=O)$_2$—), or combinations thereof. In some embodiments, a heteroalkenyl is attached to the rest of the molecule at a carbon atom of the heteroalkenyl. In some embodiments, a heteroalkenyl is attached to the rest of the molecule at a heteroatom of the heteroalkenyl. In some embodiments, a heteroalkyl is a C$_1$-C$_6$ heteroalkenyl.

The term "heteroalkynyl" refers to an alkynyl group in which one or more skeletal atoms of the alkynyl are selected from an atom other than carbon, e.g., oxygen, nitrogen (e.g. —NH—, —N(alkyl)-, or —N(aryl)-), sulfur (e.g. —S—, —S(=O)—, or —S(=O)$_2$—), or combinations thereof. In some embodiments, a heteroalkynyl is attached to the rest of the molecule at a carbon atom of the heteroalkynyl. In some embodiments, a heteroalkynyl is attached to the rest of the molecule at a heteroatom of the heteroalkynyl. In some embodiments, a heteroalkyl is a C$_1$-C$_6$ heteroalkynyl.

As used herein, the "N/P ratio" is the molar ratio of ionizable (e.g., within a pH range close to the pKa of the lipid nanoparticle) nitrogen atoms in an amino lipid (or lipids) to phosphate groups in a nucleic acid molecular entity (or nucleic acid molecular entities), e.g., in a nanoparticle composition comprising a lipid component and an RNA. Ionizable nitrogen atoms can include, for example, nitrogen atoms that can be protonated at about pH 1, about pH 2, about pH 3, about pH 4, about pH5, about pH 6, about pH 7, about pH 7.5, or about pH 8 or higher. The physiological pH range can include, for example, the pH range of different cellular compartments (such as organs, tissues, and cells) and bodily fluids (such as blood, CSF, gastric juice, milk, bile, saliva, tears, and urine). In certain specific embodiments, the physiological pH range refers to the pH range of blood in a mammal, for example, from about 7.35 to about 7.45. In some embodiments, ionizable nitrogen atoms refer to those nitrogen atoms that are ionizable within a pH range between 5 and 14.

For the payload that does not contain a phosphate group, the N/P ratio can refer to a molar ratio of ionizable nitrogen atoms in a lipid to the total negative charge in the payload. For example, the N/P ratio of an LNP composition can refer to a molar ratio of the total ionizable nitrogen atoms in the LNP composition to the total negative charge in the payload that is present in the composition.

As used herein, amino lipids can contain at least one primary, secondary or tertiary amine moiety that is protonatable (or ionizable) between pH range 4 and 14. In some embodiments, and the amine moiety/moieties function as the hydrophilic headgroup of the amino lipids described in Tables 1A and 1B. When most of the amine moiety(ies) of an amino lipid (or amino lipids) in a nucleic acid-lipid nanoparticle formulation is protonated at physiological pH, then the nanoparticles can be termed as cationic lipid nanoparticle (cLNP). When most of the amine moiety(ies) of an amino lipid (or amino lipids) in a nucleic acid-lipid nanoparticle formulation is not protonated at physiological pH but can be protonated at acidic pH, endosomal pH for example, can be termed as ionizable lipid nanoparticle (iLNP). The amino lipids that constitute cLNPs can be generally called cationic amino lipids (cLipids). The amino lipids that constitute iLNPs can be called ionizable amino lipids (iLipids). The amino lipids described in Tables 1A and 1B can be an iLipid or a cLipid at physiological pH.

As used herein, a "lipid nanoparticle (LNP) composition" or a "nanoparticle composition" is a composition comprising one or more described lipids. LNP compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less. The LNPs described herein can have a mean diameter of from about 1 nm to about 2500 nm, from about 10 nm to about 1500 nm, from about 20 nm to about 1000 nm, from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, or from about 70 nm to about 80 nm. The LNPs described herein can have a mean diameter of about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, or greater. The LNPs described herein can be substantially non-toxic.

As used herein, a "PEG-lipid" or "PEG-lipid" refers to a lipid comprising a polyethylene glycol component.

As used herein, a "phospholipid" can refer to a lipid that includes a phosphate moiety and one or more carbon chains, such as unsaturated fatty acid chains. A phospholipid may include one or more multiple (e.g., double or triple) bonds. In some embodiments, a phospholipid may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of an LNP to pass through the membrane, i.e., delivery of the one or more elements to a cell.

The term "therapeutic agent" can refer to any agent that, when administered to a subject, has a therapeutic, diagnostic, and/or prophylactic effect and/or elicits a desired biological and/or pharmacological effect. Therapeutic agents can also be referred to as "actives" or "active agents." Such agents include, but are not limited to, cytotoxins, radioactive ions, chemotherapeutic agents, small molecule drugs, proteins, and nucleic acids.

The term "nucleic acid molecular entity" is used interchangeably with "nucleic acid." The term "nucleic acid" as used herein generally refers to one or more nucleobases, nucleosides, or nucleotides, and the term includes polynucleobases, polynucleosides, and polynucleotides. A nucleic acid can include polynucleotides, mononucleotides, and oligonucleoitdes. A nucleic acid can include DNA, RNA, or a mixture thereof, and can be single stranded, double stranded, or partially single or double stranded, and can form secondary structures. In some embodiments, a nucleic acid has multiple double-stranded segments and single stranded segments. For example, a nucleic acid may comprise a polynucleotide, e.g. a mRNA, with multiple double stranded segments within it. DNA may be in the form of, e.g., antisense molecules, plasmid DNA, pre-condensed DNA, a PCR product, vectors, expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, viral RNA (vRNA), CRISPR RNA, base editor RNA and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2', 3', 4' and 5' substituted ribonucleotide, 2', 3', 4' and 5' substituted 2'-ribonucleotide, substituted and unsubstituted carbocyclic nucleotides, substituted and unsubstituted acyclic nucleotides and peptide-nucleic acids (PNAs). Examples of nucleic acids also include acyclic and carbocyclic nucleotide, such as Glycol nucleic acid. Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs. SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al, Nucleic Acid Res., 19:5081 (1991), Ohtsuka et al., J Biol. Chem., 260: 2605-2608 (1985); Rossolini et al., Mal. Cell. Probes, 8:91-98 (1994)). "Nucleotides" contain a substituted and/or unsubstituted sugar deoxyribose (DNA), or a substituted and/or unsubstituted sugar ribose (RNA), or a substituted and/or unsubstituted carbocyclic, or a substituted and/or unsubstituted acyclic moiety (e.g., glycol nucleic), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. The term "gene" refers to a nucleic acid (e.g., DNA or RNA) sequence that comprises partial length or entire length coding sequences necessary for the production of a polypeptide or precursor polypeptide.

Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260: 2605-2608 (1985); Rossolini et al., Mol. Cell. Probes, 8:91-98 (1994)).

The present disclosure encompasses isolated or substantially purified nucleic acid molecules and compositions containing those molecules. As used herein, an "isolated" or "purified" DNA molecule or RNA molecule is a DNA molecule or RNA molecule that exists apart from its native environment. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in some embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

II. Lipid Nanoparticle (LNP) Composition

Amino Lipid

Described herein are LNP compositions comprising an amino lipid, a phospholipid, a PEG-lipid, a cholesterol or a derivative thereof, a payload, or any combination thereof. In some embodiments, the LNP composition comprises an amino lipid. Exemplary amino lipids include, but are not limited to, the lipids in Table 1A. In some embodiments, the LNP composition comprises an amino lipid having the structure of Formula (I), Formula (I*), Formula (Ia), Formula (II), Formula (II*), or a pharmaceutically acceptable salt or solvate thereof. In some embodiments, the LNP composition comprises an amino lipid of having the structure of Formula (Ia), or a pharmaceutically acceptable salt or solvate thereof. In some embodiments, the LNP comprises a plurality of amino lipids. For example, the LNP composition can comprise 2, 3, 4, 5, 6, 7, 8, 9, 10, or more amino lipids. For another example, the LNP composition can comprise at least 2, at least 3, at least 4, at least 5, at least 6, at least 7, at least 9, at least 10, or at least 20 amino lipids. For yet another example, the LNP composition can comprise at most 2, at most 3, at most 4, at most 5, at most 6, at most 7, at most 9, at most 10, at most 20, or at most 30 amino lipids.

In some embodiments, the LNP composition comprises one or more amino lipids. In some embodiments, the one or more amino lipids comprise from about 40 mol % to about 65 mol % of the total lipid present in the particle. In some embodiments, the one or more amino lipids comprise about 40 mol %, about 41 mol %, about 42 mol %, about 43 mol %, about 44 mol %, about 45 mol %, about 46 mol %, about 47 mol %, about 48 mol %, about 49 mol %, about 50 mol %, about 51 mol %, about 52 mol %, about 53 mol %, about 54 mol %, about 55 mol %, about 56 mol %, about 57 mol %, about 58 mol %, about 59 mol %, about 60 mol %, about 61 mol %, about 62 mol %, about 63 mol %, about 64 mol %, or about 65 mol % of the total lipid present in the particle.

In some embodiments, the amino lipid is an ionizable lipid. An ionizable lipid can comprise one or more ionizable nitrogen atoms. In some embodiments, at least one of the one or more ionizable nitrogen atoms is positively charged. In some embodiments, at least 10 mol %, 20 mol %, 30 mol %, 40 mol %, 50 mol %, 60 mol %, 70 mol %, 80 mol %, 90 mol %, 95 mol %, or 99 mol % of the ionizable nitrogen atoms in the LNP composition are positively charged. In some embodiments, the amino lipid comprises a primary amine, a secondary amine, a tertiary amine, an imine, an amide, a guanidine moiety, a histidine residue, a lysine residue, an arginine residue, or any combination thereof. In some embodiments, the amino lipid comprises a primary amine, a secondary amine, a tertiary amine, a guanidine moiety, or any combination thereof. In some embodiments, the amino lipid comprises a tertiary amine.

In some embodiments, the amino lipid is a cationic lipid. In some embodiments, the amino lipid is an ionizable lipid. In some embodiments, the amino lipid comprises one or more nitrogen atoms. In some embodiments, the amino lipid comprises one or more ionizable nitrogen atoms. Exemplary cationic and/or ionizable lipids include, but are not limited to, 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3p)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In some embodiments, the amino lipid is symmetric, which may result in fewer metabolites and make the molecule achiral. In some embodiments, the amino lipid contains more number of hydrolysable bonds, which results in a faster metabolic clearance of the nanoparticles comprising the lipid. In some embodiments the symmetric achiral amino lipid helps yield tighter and/or smaller lipid nanoparticle than unsymmetric amino lipid after LNP formation wherein small particles translate efficient delivery to livers of mammalian subject compared to LNP particle of larger size In one aspect, disclosed herein is an amino lipid having the structure of Formula (I), or a pharmaceutically acceptable salt or solvate thereof,

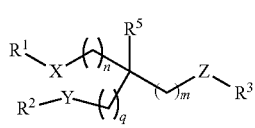

Formula (I)

wherein each of $R^1$ and $R^2$ is independently $C_3$-$C_{30}$ alkyl, $C_3$-$C_{30}$ alkenyl, $C_3$-$C_{30}$ alkynyl, $C_3$-$C_{10}$ cycloalkyl, $C_3$-$C_{30}$ heteroalkyl, $C_3$-$C_{30}$ heteroalkenyl, $C_3$-$C_{30}$ heteroalkynyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —C(=NR$^4$)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-NR$^7$R$^8$, —$C_0$-$C_{10}$ alkylene-heterocycloalkyl, or —$C_0$-$C_{10}$ alkylene-heterocycloaryl, wherein the alkylene, heterocycloalkyl and heterocycloaryl is independently substituted or unsubstituted;

each of $R^4$ is independently hydrogen or substituted or unsubstituted $C_1$-$C_6$ alkyl;

$R^5$ is hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl; and each of n, m, and q is independently 0, 1, 2, 3, 4, or 5.

In some embodiments of Formula (I), each of X, Y, and Z is independently —R$^{11}$C(=O)N(R$^9$)R$^4$—, —NR$^7$C(=O)R$^4$—, —C(=O)O—, —OC(=O)—, —R$^{11}$C(=O)OR$^4$—, —R$^{11}$OC(=O)R$^4$—, —R$^{11}$OC(=O)OR$^4$—, —R$^{11}$N(R$^9$)C(=O)OR$^4$—, —R$^{11}$OC(=O)N(R$^9$)R$^4$—, —R$^{11}$(NR$^9$)C(=O)N(R$^9$)R$^4$—, —R$^{11}$N(R$^9$)C(=NR$^9$)R$^4$—, —R$^{11}$C(=S)N(R$^9$)R$^4$—, —R$^{11}$N(R$^9$)C(=S)R$^4$—, —R$^{11}$C(=S)OR$^4$—, —R$^{11}$OC(=S)R$^4$—, —R$^{11}$OC(=S)OR$^4$—, —R$^{11}$N(R$^9$)C(=S)OR$^4$—, —R$^{11}$OC(=S)N(R$^9$)R$^4$—, —R$^{11}$N(R$^9$)C(=S)N(R$^9$)R$^4$—, —R$^{11}$C(=O)SR$^4$—, —R$^{11}$SC(=O)R$^4$—, —R$^{11}$OC(=O)SR$^4$—, —R$^{11}$N(R$^9$)C(=O)SR$^4$—, —R$^{11}$SC(=O)N(R$^9$)R$^4$—, —R$^{11}$C(=S)SR$^4$—, —R$^{11}$SC(=S)R$^4$—, —R$^{11}$SC(=S)OR$^4$—, —R$^{11}$N(R$^9$)C(=S)SR$^4$—, —R$^{11}$SC(=S)N(R$^9$)R$^4$—, —R$^{11}$C(=S)SR$^4$—, —R$^{11}$SC(=S)R$^4$—, —R$^{11}$SC(=O)SR$^4$—, —R$^{11}$SC(=S)SR$^4$—, —R$^{11}$N(R$^9$)C(=S)SR$^4$—, —R$^{11}$SC(=S)N(R$^9$)R$^4$—, —R$^{11}$OR$^4$—, —R$^{11}$SR$^4$—, or a bond;

each of L is independently —R$^{11}$C(=O)N(R$^9$)R$^4$—, —R$^{11}$N(R$^9$)C(=O)R$^4$—, —R$^{11}$C(=O)OR$^4$—, —R$^{11}$OC(=O)R$^4$—, —R$^{11}$OC(=O)OR$^4$—, —R$^{11}$N(R$^9$)C(=O)OR$^4$—, —R$^{11}$OC(=O)N(R$^9$)R$^4$—, —R$^{11}$N(R$^9$)C(=O)N(R$^9$)R$^4$—, —R$^{11}$N(R$^9$)C(=NR$^9$)N(R$^9$)R$^4$—, —R$^{11}$C(=S)N(R$^9$)R$^4$—, —R$^{11}$N(R$^9$)C(=S)R$^4$—, —R$^{11}$C(=S)OR$^4$—, —R$^{11}$OC(=S)R$^4$—, —R$^{11}$OC(=S)OR$^4$—, —R$^{11}$N(R$^9$)C(=S)OR$^4$—, —R$^{11}$OC(=S)N(R$^9$)R$^4$—, —R$^{11}$N(R$^9$)C(=S)N(R$^9$)R$^4$—, —R$^{11}$C(=O)SR$^4$—, —R$^{11}$SC(=O)R$^4$—, —R$^{11}$OC(=O)SR$^4$—, —R$^{11}$N(R$^9$)C(=O)SR$^4$—, —R$^{11}$SC(=O)N(R$^9$)R$^4$—, —R$^{11}$C(=S)SR$^4$—, —R$^{11}$SC(=S)R$^4$—, —R$^{11}$SC(=S)OR$^4$—, —R$^{11}$N(R$^9$)C(=S)SR$^4$—, —R$^{11}$SC(=S)N(R$^9$)R$^4$—, —R$^{11}$C(=S)SR$^4$—, —R$^{11}$SC(=S)R$^4$—, —R$^{11}$SC(=O)SR$^4$—, —R$^{11}$SC(=S)SR$^4$—, —R$^{11}$N(R$^9$)C(=S)SR$^4$—, —R$^{11}$SC(=S)N(R$^9$)R$^4$—, —R$^{11}$O—N=CR$^4$—, —R$^{11}$C(R$^{10}$)=N—OR$^4$—, —R$^{11}$OR$^4$—, —R$^{11}$SR$^4$—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

each of R$^4$ is independently substituted or unsubstituted C$_1$-C$_{16}$ alkyl, or unsubstituted C$_1$-C$_{16}$ heteroalkyl or absent;

R$^5$ is hydrogen or substituted or unsubstituted C$_1$-C$_{16}$ alkyl;

each of R$^6$ is independently hydrogen, C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each R$^7$ is independently substituted or unsubstituted C$_1$-C$_{16}$ alkyl, substituted or unsubstituted C$_1$-C$_{16}$ heteroalkyl or absent;

each of R$^9$ is independently hydrogen or substituted or unsubstituted C$_1$-C$_{16}$ alkyl, or unsubstituted C$_1$-C$_{16}$ heteroalkyl;

each of R$^{10}$ s independently hydrogen or substituted or unsubstituted C$_1$-C$_{16}$ alkyl, or unsubstituted C$_1$-C$_{16}$ heteroalkyl; and each of R$^{11}$ is independently substituted or unsubstituted C$_1$-C$_{16}$ alkyl, or unsubstituted C$_1$-C$_{16}$ heteroalkyl.

In one aspect, disclosed herein is an amino lipid having a structure of Formula (I*), or a pharmaceutically acceptable salt or solvate thereof, Formula (I*)

wherein

R$^1$ is hydrogen, C$_3$-C$_{30}$ alkyl, C$_3$-C$_{30}$ alkenyl, C$_3$-C$_{30}$ alkynyl, C$_3$-C$_{30}$ heteroalkyl, C$_3$-C$_{30}$ heteroalkenyl, C$_3$-C$_{30}$ heteroalkynyl, C$_3$-C$_{10}$ cycloalkyl, —C$_0$-C$_{10}$ alkylene-L-R$^6$, or —C$_2$-C$_{10}$ alkylene-L-R$^6$, wherein each of the alkyl, alkylene, alkenyl, alkenylene, alkynyl, heteroalkyl, heteroalkenyl, heteroalkynyl, and cycloalkyl is independently substituted or unsubstituted;

R$^2$ is hydrogen, C$_3$-C$_{30}$ alkyl, C$_3$-C$_{30}$ alkenyl, C$_3$-C$_{30}$ alkynyl, C$_3$-C$_{30}$ heteroalkyl, C$_3$-C$_{30}$ heteroalkenyl, C$_3$-C$_{30}$ heteroalkynyl, C$_3$-C$_{10}$ cycloalkyl, —C$_0$-C$_{10}$ alkylene-L-R$^6$, or —C$_2$-C$_{10}$ alkylene-L-R$^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —R$^{11}$C(=O)N(R$^4$)R$^9$—, —NR$^7$C(=O)R$^9$—, —C(=O)O—, —OC(=O)—, —R$^{11}$C(=O)OR$^9$—, —R$^{11}$OC(=O)R$^9$—, —R$^{11}$OC(=O)OR$^9$—, —R$^{11}$N(R$^4$)C(=O)OR$^9$—, —R$^{11}$OC(=O)N(R$^4$)R$^9$—, —R$^{11}$(NR$^4$)C(=O)N(R$^4$)R$^9$—, —R$^{11}$N(R$^4$)C(=NR$^4$)R$^9$—, —R$^{11}$C(=S)N(R$^4$)R$^9$—, —R$^{11}$N(R$^4$)C(=S)R$^9$—, —R$^{11}$C(=S)OR$^9$—, —R$^{11}$OC(=S)R$^9$—, —R$^{11}$OC(=S)OR$^9$—, —R$^{11}$N(R$^4$)C(=S)OR$^9$—, —R$^{11}$OC(=S)N(R$^4$)R$^9$—, —R$^{11}$N(R$^4$)C(=S)N(R$^4$)R$^9$—, —R$^{11}$C(=O)SR$^9$—, —R$^{11}$SC(=O)R$^9$—, —R$^{11}$OC(=O)SR$^9$—, —R$^{11}$N(R$^4$)C(=O)SR$^9$—, —R$^{11}$SC(=O)N(R$^4$)R$^9$—, —R$^{11}$C(=S)SR$^9$—, —R$^{11}$SC(=S)R$^9$—, —R$^{11}$SC(=S)OR$^9$—, —R$^{11}$N(R$^4$)C(=S)SR$^9$—, —R$^{11}$SC(=S)N(R$^4$)R$^9$—, —R$^{11}$C(=S)SR$^9$—, —R$^{11}$SC(=S)R$^9$—, —R$^{11}$SC(=O)SR$^9$—, —R$^{11}$SC(=S)SR$^9$—, —R$^{11}$N(R$^4$)C(=S)SR$^9$—, —R$^{11}$SC(=S)N(R$^4$)R$^9$—, —R$^{11}$OR$^9$—, —R$^{11}$SR$^9$—, —O—, —S—, or a bond;

each of L is independently —C(=O)NR$^4$—, —NR$^4$C(=O)—, —C(=O)O—, —OC(=O)—, —C(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —R$^{11}$C(=O)N(R$^4$)R$^9$—, —R$^{11}$N(R$^4$)C(=O)R$^9$—, —R$^{11}$C(=O)OR$^9$—, —R$^{11}$OC(=O)R$^9$—, —R$^{11}$OC(=O)OR$^9$—, —R$^{11}$N(R$^4$)C(=O)OR$^9$—, —R$^{11}$OC(=O)N(R$^4$)R$^9$—, —R$^{11}$N(R$^4$)C(=O)N(R$^4$)R$^9$—, —R$^{11}$N(R$^4$)C(=NR$^4$)N(R$^4$)R$^9$—, —R$^{11}$C(=S)N(R$^4$)R$^9$—, —R$^{11}$N(R$^4$)C(=S)R$^9$—, —R$^{11}$C(=S)OR$^9$—, —R$^{11}$OC(=S)R$^9$—, —R$^{11}$OC(=S)OR$^9$—, —R$^{11}$N(R$^4$)C(=S)OR$^9$—, —R$^{11}$OC(=S)N(R$^4$)R$^9$—, —R$^{11}$N(R$^4$)C(=S)N(R$^4$)R$^9$—, —R$^{11}$C(=O)SR$^9$—, —R$^{11}$SC(=O)R$^9$—, —R$^{11}$OC(=O)SR$^9$—, —R$^{11}$N(R$^4$)C(=O)SR$^9$—, —R$^{11}$SC(=O)N(R$^4$)R$^9$—, —R$^{11}$C(=S)SR$^9$—, —R$^{11}$SC(=S)R$^9$—, —R$^{11}$SC(=S)OR$^9$—, —R$^{11}$N(R$^4$)C(=S)SR$^9$—, —R$^{11}$SC(=S)N(R$^4$)R$^9$—, —R$^{11}$C(=S)SR$^9$—, —R$^{11}$SC(=S)R$^9$—, —R$^{11}$SC(=O)SR$^9$—, —R$^{11}$SC(=S)SR$^9$—, —R$^{11}$N(R$^4$)C(=S)SR$^9$—, —R$^{11}$SC(=S)N(R$^4$)R$^9$—, —R$^{11}$O—N=CR$^9$—, —R$^{11}$C(R$^{10}$)=N—OR$^9$—, —R$^{11}$OR$^9$—, —R$^{11}$SR$^9$—, —C$_1$-C$_{10}$ alkylene-C(=O)O—, —C$_1$-C$_{10}$ alkylene-OC(=O)—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is —C$_0$-C$_{10}$ alkylene-NR$^7$R$^8$, —C$_0$-C$_{10}$ alkylene-heterocycloalkyl, or —C$_0$-C$_{10}$ alkylene-heterocycloaryl, wherein the alkylene, heterocycloalkyl and heterocycloaryl is independently substituted or unsubstituted;

each of R$^4$ is independently hydrogen, substituted or unsubstituted C$_1$-C$_{16}$ alkyl or substituted or unsubstituted C$_1$-C$_{16}$ heteroalkyl;

R$^5$ is hydrogen or substituted or unsubstituted —C$_0$-C$_{10}$ alkylene-L-R$^4$;

each of R$^6$ is independently hydrogen, C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R$^7$ and R$^8$ is independently hydrogen or substituted or unsubstituted C$_1$-C$_{16}$ alkyl, substituted or unsubstituted C$_1$-C$_{16}$ heteroalkyl, or R$^7$ and R$^8$ taken together with the nitrogen to which they are attached form a substituted or unsubstituted C$_2$-C$_6$ heterocyclyl; and each of R$^9$ is independently hydrogen or substituted or unsubstituted C$_1$-C$_{16}$ alkylene, or unsubstituted C$_1$-C$_{16}$ heteroalkylene;

each of R$^{10}$ is independently hydrogen or substituted or unsubstituted C$_1$-C$_{16}$ alkylene, or unsubstituted C$_1$-C$_{16}$ heteroalkylene; and each of R$^{11}$ is independently substituted or unsubstituted C$_1$-C$_{16}$ alkylene, or unsubstituted C$_1$-C$_{16}$ heteroalkylene.

each of n, m, and q is independently 0, 1, 2, 3, 4, or 5.

In some embodiments, R$^5$ of Formula (I*) is hydrogen or substituted or unsubstituted C$_1$-C$_{16}$ alkyl. In some embodiments, R$^5$ of Formula (I*) is substituted or unsubstituted C$_1$-C$_{16}$ alkyl.

In some embodiments of Formula (I) or (I*), if the structure carries more than one asymmetric C-atom, each asymmetric C-atom independently represents racemic, chirally pure R and/or chirally pure S isomer, or a combination thereof.

In some embodiments, each of n, m, and q in Formula (I) or (I*) is independently 0, 1, 2, or 3. In some embodiments, each of n and m in Formula (I) or (I*) is 1. In some embodiments, n is 0. In some embodiments, n is 1. In some embodiments, n is 2. In some embodiments, n is 3. In some embodiments, m is 0. In some embodiments, m is 1. In some embodiments, m is 2. In some embodiments, m is 3. In some embodiments, q is 0. In some embodiments, q is 1. In some embodiments, q is 2. In some embodiments, q is 3.

In some embodiments, the compound of Formula (I) or (I*) has a structure of Formula (Ia), or a pharmaceutically acceptable salt or pharmaceutically acceptable solvate thereof:

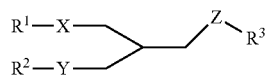

Formula (Ia)

wherein each of R$^1$ and R$^2$ is independently C$_3$-C$_{30}$ alkyl, C$_3$-C$_{30}$ alkenyl, C$_3$-C$_{30}$ alkynyl, C$_3$-C$_{10}$ cycloalkyl, C$_3$-C$_{30}$ heteroalkyl, C$_3$-C$_{30}$ heteroalkenyl, C$_3$-C$_{30}$ heteroalkynyl, —C$_0$-C$_{10}$ alkylene-L-R$^6$, or —C$_2$-C$_{10}$ alkenylene-L-R$^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, —C$_1$-C$_{10}$ alkylene-O—, or a bond, wherein the alkylene is substituted or unsubstituted;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is —C$_0$-C$_{10}$ alkylene-NR$^7$R$^8$, or —C$_0$-C$_{10}$ alkylene-heterocycloalkyl, wherein the alkylene and heterocycloalkyl are each independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl; and each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl.

In some embodiments of Formula (Ia), if the structure carries more than one asymmetric C-atom, each asymmetric C-atom independently represents racemic, chirally pure R and/or chirally pure S isomer, or a combination thereof.

In some embodiments, a compound of Formula (I), Formula (I*), Formula (Ia), or Formula (Ib) comprises an unsymmetrical heteroatom on R$^1$ and/or R$^2$.

In some embodiments, each R$^1$ and R$^2$ in Formula (I), Formula (I*) or Formula (Ia) is independently C$_5$-C$_{30}$ alkyl, C$_5$-C$_{30}$ alkenyl, C$_5$-C$_{30}$ alkynyl, C$_3$-C$_{10}$ cycloalkyl, —C$_0$-

$C_{10}$ alkylene-L-$R^6$, or —$C_2$-$C_{10}$ alkenylene-L-$R^6$, wherein each of the alkyl, alkylene, alkenyl, alkenylene, alkynyl, and cycloalkyl is independently substituted or unsubstituted. In some embodiments, each $R^1$ and $R^2$ in Formula (I), Formula (I*), Formula (Ia), or Formula (Ib) is independently $C_7$-$C_{28}$ alkyl, $C_7$-$C_{28}$ alkenyl, $C_7$-$C_{28}$ alkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, and cycloalkyl is independently substituted or unsubstituted. In some embodiments, each $R^1$ and $R^2$ in Formula (I), Formula (I*), Formula (Ia), or Formula (Ib) is independently $C_7$-$C_{25}$ alkyl, $C_7$-$C_{25}$ alkenyl, $C_7$-$C_{25}$ alkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, and cycloalkyl is independently substituted or unsubstituted. In some embodiments, each $R^1$ and $R^2$ in Formula (I), Formula (I*), Formula (Ia), or Formula (Ib) is independently $C_7$-$C_{22}$ alkyl, $C_7$-$C_{22}$ alkenyl, $C_7$-$C_{22}$ alkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, and cycloalkyl is independently substituted or unsubstituted. In some embodiments, each $R^1$ and $R^2$ in Formula (I), Formula (I*), Formula (Ia), or Formula (Ib) is independently $C_{10}$-$C_{20}$ alkyl, $C_{10}$-$C_{20}$ alkenyl, —$C_4$-$C_8$ alkylene-L-$R^6$, or —$C_4$-$C_8$ alkylene-L-$R^6$, wherein each of the alkyl, alkylene, alkenyl, and cycloalkyl is independently substituted or unsubstituted. In some embodiments, each $R^1$ and $R^2$ in Formula (I), Formula (I*), Formula (Ia), or Formula (Ib) is —$C_0$-$C_{10}$ alkylene-L-$R^6$. In some embodiments, each $R^1$ and $R^2$ in Formula (I), Formula (I*), Formula (Ia), or Formula (Ib) is $C_7$-$C_{30}$ alkenyl. In some embodiments, each $R^1$ and $R^2$ in Formula (I), Formula (I*), Formula (Ia), or Formula (Ib) is $C_7$-$C_{28}$ alkenyl. In some embodiments, each $R^1$ and $R^2$ in Formula (I), Formula (I*), Formula (Ia), or Formula (Ib) is $C_7$-$C_{25}$ alkenyl. In some embodiments, each $R^1$ and $R^2$ in Formula (I), Formula (I*), Formula (Ia), or Formula (Ib) is $C_7$-$C_{22}$ alkenyl.

In some embodiments, each $R^1$ and $R^2$ in Formula (I), Formula (I*), Formula (Ia), or Formula (Ib) is independently substituted or unsubstituted linear or branched $C_3$-$C_{30}$ alkyl or substituted or unsubstituted linear or branched $C_3$-$C_{30}$ alkenyl. In some embodiments, each $R^1$ and $R^2$ in Formula (I), Formula (I*), Formula (Ia), or Formula (Ib) is independently substituted or unsubstituted linear or branched $C_3$-$C_{28}$ alkyl or substituted or unsubstituted linear or branched $C_3$-$C_{28}$ alkenyl. In some embodiments, each $R^1$ and $R^2$ in Formula (I), Formula (I*), Formula (Ia), or Formula (Ib) is independently substituted or unsubstituted $C_3$-$C_{25}$ alkyl or substituted or unsubstituted $C_3$-$C_{25}$ alkenyl. In some embodiments, each $R^1$ and $R^2$ in Formula (I), Formula (I*), Formula (Ia), or Formula (Ib) is independently substituted or unsubstituted $C_3$-$C_{25}$ alkyl. In some embodiments, each $R^1$ and $R^2$ in Formula (I), Formula (I*), Formula (Ia), or Formula (Ib) is independently $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl, $C_{21}$ alkyl, $C_{22}$ alkyl, $C_{23}$ alkyl, $C_{24}$ alkyl, or $C_{25}$ alkyl. In some embodiments, each $R^1$ and $R^2$ in Formula (I), Formula (I*), Formula (Ia), or Formula (Ib) is independently at least $C_3$ alkyl, at least $C_4$ alkyl, at least $C_5$ alkyl, at least $C_6$ alkyl, at least $C_7$ alkyl, at least $C_8$ alkyl, at least $C_9$ alkyl, at least $C_{10}$ alkyl, at least $C_{11}$ alkyl, at least $C_{12}$ alkyl, at least $C_{13}$ alkyl, at least $C_{14}$ alkyl, at least $C_{15}$ alkyl, at least $C_{16}$ alkyl, at least $C_{17}$ alkyl, at least $C_{18}$ alkyl, at least $C_{19}$ alkyl, at least $C_{20}$ alkyl, at least $C_{21}$ alkyl, at least $C_{22}$ alkyl, at least $C_{23}$ alkyl, at least $C_{24}$ alkyl, or at least $C_{25}$ alkyl. In some embodiments, each $R^1$ and $R^2$ in Formula (I), Formula (I*), Formula (Ia), or Formula (Ib) is independently at most $C_3$ alkyl, at most $C_4$ alkyl, at most $C_5$ alkyl, at most $C_6$ alkyl, at most $C_7$ alkyl, at most $C_8$ alkyl, at most $C_9$ alkyl, at most $C_{10}$ alkyl, at most $C_{11}$ alkyl, at most $C_{12}$ alkyl, at most $C_{13}$ alkyl, at most $C_{14}$ alkyl, at most $C_{15}$ alkyl, at most $C_{16}$ alkyl, at most $C_{17}$ alkyl, at most $C_{18}$ alkyl, at most $C_{19}$ alkyl, at most $C_{20}$ alkyl, at most $C_{21}$ alkyl, at most $C_{22}$ alkyl, at most $C_{23}$ alkyl, at most $C_{24}$ alkyl, or at most $C_{25}$ alkyl. In some embodiments, each $R^1$ and $R^2$ in Formula (I), Formula (I*), Formula (Ia), or Formula (Ib) is independently $C_8$-$C_{24}$ alkyl. In some embodiments, each $R^1$ and $R^2$ in Formula (I), Formula (I*), Formula (Ia), or Formula (Ib) is independently $C_{12}$-$C_{24}$ alkyl. In some embodiments, each $R^1$ and $R^2$ in Formula (I), Formula (I*), Formula (Ia), or Formula (Ib) is independently $C_6$-$C_{15}$ alkyl. In some embodiments, each $R^1$ and $R^2$ in Formula (I), Formula (I*), Formula (Ia), or Formula (Ib) is independently substituted or unsubstituted $C_3$-$C_{25}$ alkenyl. In some embodiments, each $R^1$ and $R^2$ in Formula (I), Formula (I*), Formula (Ia), or Formula (Ib) is independently $C_3$ alkenyl, $C_4$ alkenyl, $C_5$ alkenyl, $C_6$ alkenyl, $C_7$ alkenyl, $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, $C_{16}$ alkenyl, $C_{17}$ alkenyl, $C_{18}$ alkenyl, $C_{19}$ alkenyl, $C_{20}$ alkenyl, $C_{21}$ alkenyl, $C_{22}$ alkenyl, $C_{23}$ alkenyl, $C_{24}$ alkenyl, or $C_{25}$ alkenyl. In some embodiments, each $R^1$ and $R^2$ in Formula (I), Formula (I*), Formula (Ia), or Formula (Ib) is independently at least $C_3$ alkenyl, at least $C_4$ alkenyl, at least $C_5$ alkenyl, at least $C_6$ alkenyl, at least $C_7$ alkenyl, at least $C_8$ alkenyl, at least $C_9$ alkenyl, at least $C_{10}$ alkenyl, at least $C_{11}$ alkenyl, at least $C_{12}$ alkenyl, at least $C_{13}$ alkenyl, at least $C_{14}$ alkenyl, at least $C_{15}$ alkenyl, at least $C_{16}$ alkenyl, at least $C_{17}$ alkenyl, at least $C_{18}$ alkenyl, at least $C_{19}$ alkenyl, at least $C_{20}$ alkenyl, at least $C_{21}$ alkenyl, at least $C_{22}$ alkenyl, at least $C_{23}$ alkenyl, at least $C_{24}$ alkenyl, or at least $C_{25}$ alkenyl. In some embodiments, each $R^1$ and $R^2$ in Formula (I), Formula (I*), Formula (Ia), or Formula (Ib) is independently at most $C_3$ alkenyl, at most $C_4$ alkenyl, at most $C_5$ alkenyl, at most $C_6$ alkenyl, at most $C_7$ alkenyl, at most $C_8$ alkenyl, at most $C_9$ alkenyl, at most $C_{10}$ alkenyl, at most $C_{11}$ alkenyl, at most $C_{12}$ alkenyl, at most $C_{13}$ alkenyl, at most $C_{14}$ alkenyl, at most $C_{15}$ alkenyl, at most $C_{16}$ alkenyl, at most $C_{17}$ alkenyl, at most $C_{18}$ alkenyl, at most $C_{19}$ alkenyl, at most $C_{20}$ alkenyl, at most $C_{21}$ alkenyl, at most $C_{22}$ alkenyl, at most $C_{23}$ alkenyl, at most $C_{24}$ alkenyl, or at most $C_{25}$ alkenyl.

In some embodiments of a compound of Formula (I), Formula (I*), Formula (Ia), or Formula (Ib), $R^1$ and $R^2$ are each substituted or unsubstituted Cy-$C_{3-30}$ alkyl. In some embodiments, Cy is a bicyclic. In some embodiments, Cy is a monocylic. In some embodiments, Cy is bicyclic heteroaryl with 0-2 Nitrongen and 0-1 oxygen. In some embodiments, Cy is bicyclic heteroalkyl with 0-2 Nitrongen and 0-1 oxygen.

In some embodiments, $R^1$ and/or $R^2$ in Formula (I), Formula (I*), Formula (Ia), or Formula (Ib) is independently

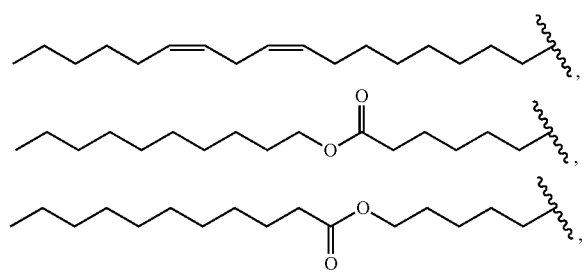

-continued

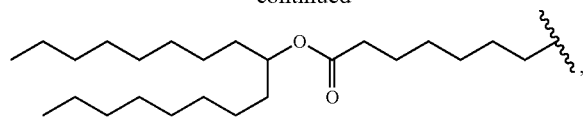

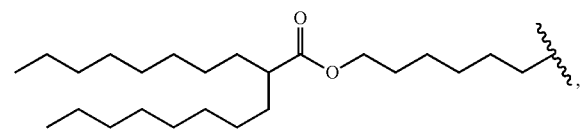

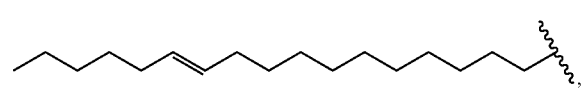

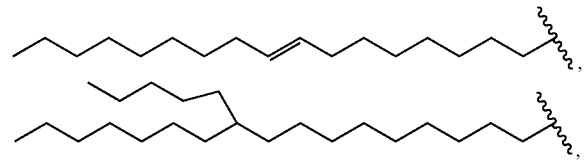

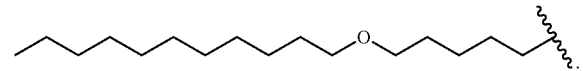, or

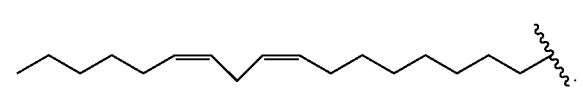

In some embodiments, R¹ and/or R² in Formula (I), Formula (I*), Formula (Ia), or Formula (Ib) is

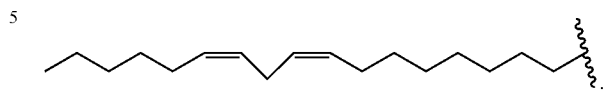

In some embodiments, R¹ and/or R² in Formula (I), Formula (I*), Formula (Ia), or Formula (Ib) is

In some embodiments, R¹ and/or R² in Formula (I), Formula (I*), Formula (Ia), or Formula (Ib) is

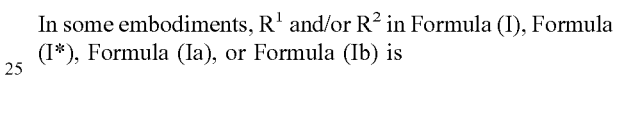

In some embodiments, R¹ and/or R² in Formula (I), Formula (I*), Formula (Ia), or Formula (Ib) is

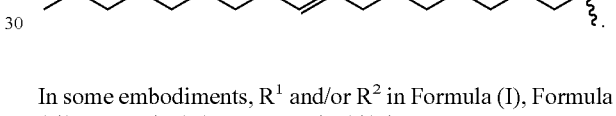

In some embodiments, R¹ and/or R² in Formula (I), Formula (I*), Formula (Ia), or Formula (Ib) is

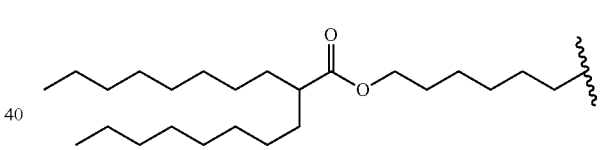

In some embodiments, R¹ and/or R² in Formula (I), Formula (I*), Formula (Ia), or Formula (Ib) is

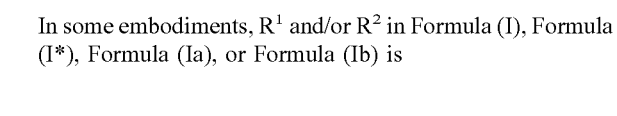

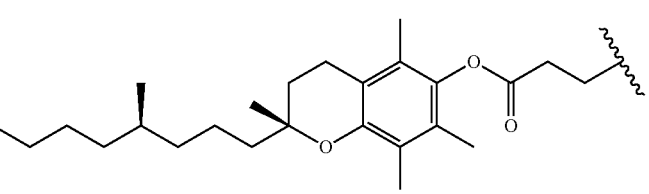

In some embodiments, $R^1$ and/or $R^2$ in Formula (I), Formula (I*), Formula (Ia), or Formula (Ib) is

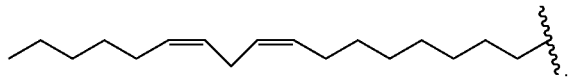 [SMILES: *CCCCCCC/C=C\C/C=C\CCCCC]

In some embodiments, $R^1$ and/or $R^2$ in Formula (I), Formula (I*), Formula (Ia), or Formula (Ib) is

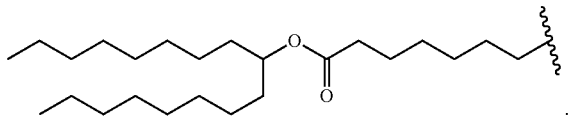 [SMILES: *CCCCCCC(=O)OC(CCCCCCCC)CCCCCCCC]

In some embodiments, L in Formula (I), Formula (I*), Formula (Ia), or Formula (Ib) is independently —O—, —S—, —$C_1$-$C_{10}$ alkylene-O—, —$C_1$-$C_{10}$ alkylene-C(=O)O—, —$C_1$-$C_{10}$ alkylene-OC(=O)—, —C(=O)O—, —OC(=O)—, —C(=O)$NR^4$—, —$NR^4$C(=O)—, or a bond, wherein the alkylene is substituted or unsubstituted. In some embodiments, at least one L in Formula (I), Formula (I*), Formula (Ia), or Formula (Ib) is independently —O—, —S—, —$C_1$-$C_3$ alkylene-O—, —$C_1$-$C_3$ alkylene-C(=O)O—, —$C_1$-$C_3$ alkylene-OC(=O)—, —C(=O)O—, —OC(=O)—, —C(=O)$NR^4$—, —$NR^4$C(=O)—, or a bond, wherein the alkylene is substituted or unsubstituted. In some embodiments, at least one L in Formula (I), Formula (I*), Formula (Ia), or Formula (Ib) is independently —O—, —S—, —$C_1$-$C_3$ alkylene-O—, —$C_1$-$C_3$ alkylene-C(=O)O—, —$C_1$-$C_3$ alkylene-OC(=O)—, or a bond, wherein the alkylene is linear or branched unsubstituted alkylene. In some embodiments, at least one L in Formula (I), Formula (I*), Formula (Ia), or Formula (Ib) is —C(=O)O—, —OC(=O)—, —C(=O)$NR^4$—, —$NR^4$C(=O)—. In some embodiments, at least one L in Formula (I), Formula (I*), Formula (Ia), or Formula (Ib) is —C(=O)O—. In some embodiments, at least one L in Formula (I), Formula (I*), Formula (Ia), or Formula (Ib) is —OC(=O)—. In some embodiments, at least one L in Formula (I), Formula (I*), Formula (Ia), or Formula (Ib) is —C(=O)$NR^4$—. In some embodiments, at least one L in Formula (I), Formula (I*), Formula (Ia), or Formula (Ib) is —C(=O)NH—. In some embodiments, at least one L in Formula (I), Formula (I*), Formula (Ia), or Formula (Ib) is —C(=O)N($CH_3$)—. In some embodiments, at least one L in Formula (I), Formula (I*), Formula (Ia), or Formula (Ib) is —$NR^4$C(=O)—. In some embodiments, at least one L in Formula (I), Formula (I*), Formula (Ia), or Formula (Ib) is —NHC(=O)—. In some embodiments, at least one L in Formula (I), Formula (I*), Formula (Ia), or Formula (Ib) is —N($CH_3$)C(=O)—. In some embodiments, at least one L in Formula (I), Formula (I*), Formula (Ia), or Formula (Ib) is —O—N=$CR^4$— or —$CR^4$=N—O—. In some embodiments, at least one L in Formula (I), Formula (I*), Formula (Ia), or Formula (Ib) Formula (I), Formula (I*), Formula (Ia), or Formula (Ib), $R^1$ and $R^2$ are the same. In some embodiments, at least one L in Formula (I), Formula (I*), Formula (Ia), or Formula (Ib) Formula (I), Formula (I*), Formula (Ia), or Formula (Ib), $R^1$ and $R^2$ are different.

In some embodiments of Formula (I), Formula (I*), Formula (Ia), or Formula (Ib), $R^1$ is —$C_0$-$C_{10}$ alkylene-L-$R^6$. In some embodiments of Formula (I), Formula (I*), Formula (Ia), or Formula (Ib), R2 is —$C_0$-$C_{10}$ alkylene-L-$R^6$. In some embodiments of Formula (I), Formula (I*), Formula (Ia), or Formula (Ib), X is —C(=O)O—. In some embodiments of Formula (I), Formula (I*), Formula (Ia), or Formula (Ib), X is —OC(=O)—. In some embodiments of Formula (I), Formula (I*), Formula (Ia), or Formula (Ib), X is —OC(=O)$NR^4$—. In some embodiments of Formula (I), Formula (I*), Formula (Ia), or Formula (Ib), Y is —C(=O)O—. In some embodiments of Formula (I), Formula (I*), Formula (Ia), or Formula (Ib), Y is —OC(=O)—. In some embodiments of Formula (I), Formula (I*), Formula (Ia), or Formula (Ib), Y is —OC(=O)$NR^4$—. In some embodiments of Formula (I), Formula (I*), Formula (Ia), or Formula (Ib), L is —OC(=O)—. In some embodiments of Formula (I), Formula (I*), Formula (Ia), or Formula (Ib), L is —C(=O)—. In some embodiments of Formula (I), Formula (I*), Formula (Ia), or Formula (Ib), $R^1$ is —$C_4$-$C_8$ alkylene-L-$R^6$. In some embodiments of Formula (I), Formula (I*), Formula (Ia), or Formula (Ib), $R^2$ is —$C_4$-$C_8$ alkylene-L-$R^6$.

In some embodiments of Formula (I), Formula (I*), Formula (Ia), or Formula (Ib), $R^1$ is optionally substituted by oxo. In some embodiments of Formula (I), Formula (I*), Formula (Ia), or Formula (Ib), $R^1$ or $R^2$ does not contain any hydrylozable bonds. In some embodiments of Formula (I), Formula (I*), Formula (Ia), or Formula (Ib), $R^1$ or $R^2$ does not contain any C=C bonds. In some embodiments of Formula (I), Formula (I*), Formula (Ia), or Formula (Ib), $R^1$ or $R^2$ does not contain any carbon-carbon triple bonds.

In some embodiments, p in Formula (Ib) is 1 to 6. In some embodiments, p in Formula (Ib) is 1 to 2, 1 to 3, 1 to 4, 1 to 5, 1 to 6, 2 to 3, 2 to 4, 2 to 5, 2 to 6, 3 to 4, 3 to 5, 3 to 6, 4 to 5, 4 to 6, or 5 to 6. In some embodiments, p in Formula (Ib) is 1, 2, 3, 4, 5, or 6. In some embodiments, p in Formula (Ib) is at least 1, 2, 3, 4, or 5. In some embodiments, p in Formula (Ib) is at most 2, 3, 4, 5, or 6. In some embodiments, p in Formula (Ib) is 1-3. In some embodiments, p in Formula (Ib) is 1. In some embodiments, p in Formula (Ib) is 2. In some embodiments, p in Formula (Ib) is 3. In some embodiments, p in Formula (Ib) is 4. In some embodiments, p in Formula (Ib) is 5. In some embodiments, p in Formula (Ib) is 6.

In some embodiments, at least one $R^6$ in Formula (I), Formula (I*), Formula (Ia), or Formula (Ib) is independently substituted or unsubstituted linear or branched $C_3$-$C_{30}$ alkyl or substituted or unsubstituted linear or branched $C_3$-$C_{30}$ alkenyl. In some embodiments, at least one $R^6$ in Formula (I), Formula (I*), Formula (Ia), or Formula (Ib) is independently substituted or unsubstituted linear or branched $C_3$-$C_{28}$ alkyl or substituted or unsubstituted linear or branched $C_3$-$C_{28}$ alkenyl. In some embodiments, at least one $R^6$ in Formula (I), Formula (I*), Formula (Ia), or Formula (Ib) is independently substituted or unsubstituted $C_3$-$C_{25}$ alkyl or substituted or unsubstituted $C_3$-$C_{25}$ alkenyl. In some embodiments, at least one $R^6$ in Formula (I), Formula (I*), Formula (Ia), or Formula (Ib) is independently substituted or unsubstituted $C_3$-$C_{25}$ alkyl. In some embodiments, at least one $R^6$ in Formula (I), Formula (I*), Formula (Ia), or Formula (Ib) is independently $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl, $C_{21}$ alkyl, $C_{22}$ alkyl, $C_{23}$ alkyl, $C_{24}$ alkyl, or $C_{25}$ alkyl. In some embodiments, at least one $R^6$ in Formula (I), Formula (I*), Formula (Ia), or Formula (Ib) is independently at least $C_3$ alkyl, at least $C_4$ alkyl, at least $C_5$ alkyl, at least $C_6$ alkyl, at least $C_7$ alkyl, at least $C_8$ alkyl, at least $C_9$ alkyl, at least $C_{10}$ alkyl, at least $C_{11}$ alkyl, at least $C_{12}$ alkyl, at least $C_{13}$ alkyl, at least $C_{14}$ alkyl, at least $C_{15}$ alkyl, at least $C_{16}$ alkyl, at least $C_{17}$ alkyl, at least $C_{18}$ alkyl, at least $C_{19}$ alkyl, at least $C_{20}$ alkyl, at least $C_{21}$ alkyl, at least $C_{22}$ alkyl, at least $C_{23}$ alkyl, at least $C_{24}$ alkyl, or at least $C_{25}$ alkyl. In some embodiments, at least one $R^6$ in Formula (I), Formula (I*), Formula (Ia), or Formula (Ib) is independently at most $C_3$ alkyl, at most $C_4$ alkyl, at most $C_5$ alkyl, at most $C_6$ alkyl, at most $C_7$ alkyl, at most $C_8$ alkyl, at most $C_9$ alkyl, at most $C_{10}$ alkyl, at most $C_{11}$ alkyl, at most $C_{12}$ alkyl, at most $C_{13}$ alkyl, at most $C_{14}$ alkyl, at most $C_{15}$ alkyl, at most $C_{16}$ alkyl, at most $C_{17}$ alkyl, at most $C_{18}$ alkyl, at most $C_{19}$ alkyl, at most $C_{20}$ alkyl, at most $C_{21}$ alkyl, at most $C_{22}$ alkyl, at most $C_{23}$ alkyl, at most $C_{24}$ alkyl, or at most $C_{25}$ alkyl. In some embodiments, at least one R in Formula (I), Formula (I*), Formula (Ia), or Formula (Ib) is independently substituted or unsubstituted $C_3$-$C_{25}$ alkenyl. In some embodiments, at least one $R^6$ in Formula (I), Formula (I*), Formula (Ia), or Formula (Ib) is independently $C_3$ alkenyl, $C_4$ alkenyl, $C_5$ alkenyl, $C_6$ alkenyl, $C_7$ alkenyl, $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, $C_{16}$ alkenyl, $C_{17}$ alkenyl, $C_{18}$ alkenyl, $C_{19}$ alkenyl, $C_{20}$ alkenyl, $C_{21}$ alkenyl, $C_{22}$ alkenyl, $C_{23}$ alkenyl, $C_{24}$ alkenyl, or $C_{25}$ alkenyl. In some embodiments, at least one $R^6$ in Formula (I), Formula (I*), Formula (Ia), or Formula (Ib) is independently at least $C_3$ alkenyl, at least $C_4$ alkenyl, at least $C_5$ alkenyl, at least $C_6$ alkenyl, at least $C_7$ alkenyl, at least $C_8$ alkenyl, at least $C_9$ alkenyl, at least $C_{10}$ alkenyl, at least $C_{11}$ alkenyl, at least $C_{12}$ alkenyl, at least $C_{13}$ alkenyl, at least $C_{14}$ alkenyl, at least Cis alkenyl, at least $C_{16}$ alkenyl, at least $C_{17}$ alkenyl, at least $C_{15}$ alkenyl, at least $C_{19}$ alkenyl, at least $C_{20}$ alkenyl, at least $C_{21}$ alkenyl, at least $C_{22}$ alkenyl, at least $C_{23}$ alkenyl, at least $C_{24}$ alkenyl, or at least $C_{25}$ alkenyl. In some embodiments, at least one $R^6$ in Formula (I), Formula (I*), Formula (Ia), or Formula (Ib) is independently at most $C_3$ alkenyl, at most $C_4$ alkenyl, at most $C_5$ alkenyl, at most $C_6$ alkenyl, at most $C_7$ alkenyl, at most $C_8$ alkenyl, at most $C_9$ alkenyl, at most $C_{10}$ alkenyl, at most $C_{11}$ alkenyl, at most $C_{12}$ alkenyl, at most $C_{13}$ alkenyl, at most $C_{14}$ alkenyl, at most $C_{15}$ alkenyl, at most $C_{16}$ alkenyl, at most $C_{17}$ alkenyl, at most $C_{18}$ alkenyl, at most $C_{19}$ alkenyl, at most $C_{20}$ alkenyl, at most $C_{21}$ alkenyl, at most Cn alkenyl, at most $C_{23}$ alkenyl, at most $C_{24}$ alkenyl, or at most $C_{25}$ alkenyl. In some embodiments, at least one $R^6$ in Formula (I), Formula (I*), Formula (Ia), or Formula (Ib) is independently substituted or unsubstituted $C_3$-$C_{30}$ alkynyl. In some embodiments, at least one $R^6$ in Formula (I), Formula (I*), Formula (Ia), or Formula (Ib) is independently Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted. In some embodiments, $R^6$ in Cy-$C_{3-30}$ alkyl, wherein the Cy is substituted or unsubstituted cycloalkyl, substituted or unsubstituted heterocycloalkyl, substituted or unsubstituted aryl, substituted or unsubstituted heteroaryl. In some embodiments, Cy is a bicyclic. In some embodiments, Cy is a monocylic. In some embodiments, Cy is bicyclic heteroaryl with 0-2 Nitrongen and 0-1 oxygen. In some embodiments, Cy is bicyclic heteroalkyl with 0-2 Nitrongen and 0-1 oxygen.

In some embodiments, $R^6$ in Formula (I), Formula (I*), Formula (Ia), or Formula (Ib) is independently

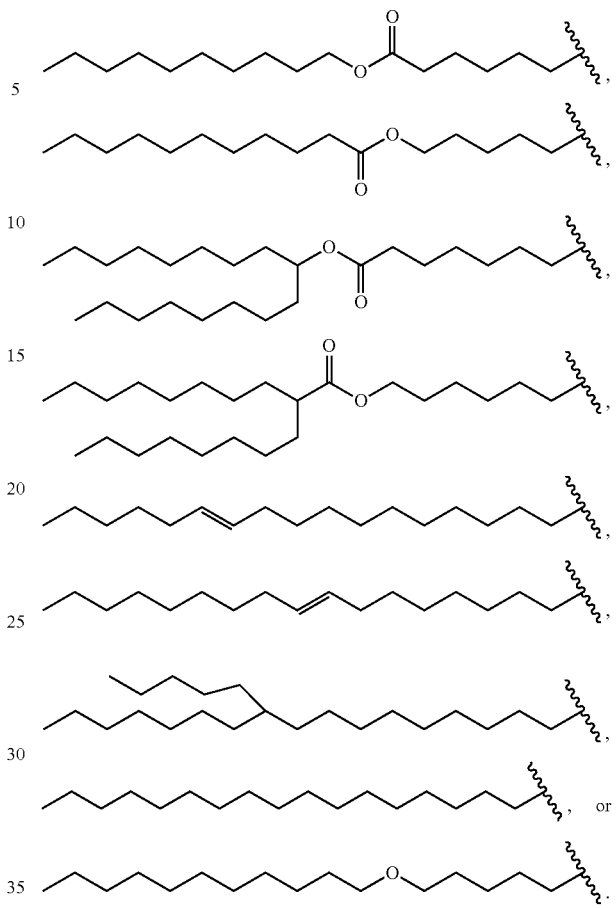

In some embodiments, at least one $R^6$ in Formula (I), Formula (I*), Formula (Ia), or Formula (Ib) is

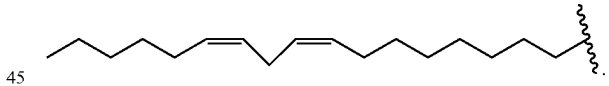

In some embodiments, at least one $R^6$ in Formula (I), Formula (I*), Formula (Ia), or Formula (Ib) is

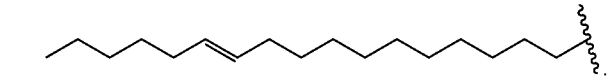 [SMILES: *CCCCCCCCCC/C=C/CCCCC]

In some embodiments, at least one $R^6$ in Formula (I), Formula (I*), Formula (Ia), or Formula (Ib) is

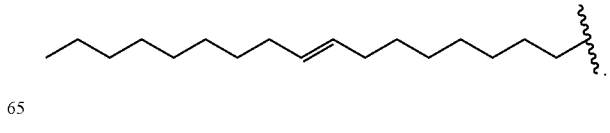

In some embodiments, at least one $R^6$ in Formula (I), Formula (I*), Formula (Ia), or Formula (Ib) is

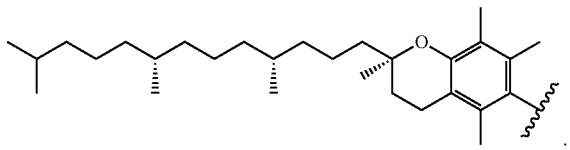 [SMILES: *c1c(C)c(C)c2c(c1C)CC[C@@](C)(CCC[C@H](C)CCC[C@H](C)CCCC(C)C)O2]

In some embodiments, at least one $R^6$ in Formula (I), Formula (I*), Formula (Ia), or Formula (Ib) is

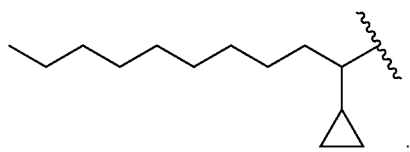 [SMILES: *C(CCCCCCCCC)C1CC1]

In some embodiments, at least one $R^6$ in Formula (I), Formula (I*), Formula (Ia), or Formula (Ib) is

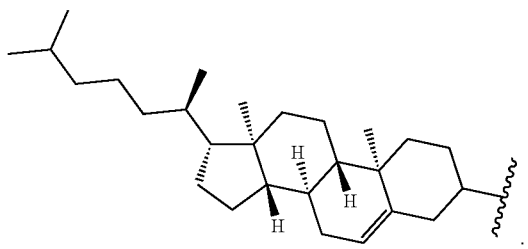

In some embodiments, $R^4$ in Formula (I), Formula (I*), Formula (Ia), or Formula (Ib) is independently H or substituted or unsubstituted $C_1$-$C_4$ alkyl. In some embodiments, at least one $R^4$ in Formula (I), Formula (I*), Formula (Ia), or Formula (Ib) is independently substituted or unsubstituted linear or branched $C_1$-$C_4$ alkyl. In some embodiments, at least one $R^4$ in Formula (I), Formula (I*), Formula (Ia), or Formula (Ib) is H. In some embodiments, at least one $R^4$ in Formula (I), Formula (I*), Formula (Ia), or Formula (Ib) is independently H, —$CH_3$, —$CH_2CH_3$, —$CH_2CH_2CH_3$, or —$CH(CH_3)_2$. In some embodiments, at least one $R^4$ in Formula (I), Formula (I*), Formula (Ia), or Formula (Ib) is independently H or —$CH_3$. In some embodiments, at least one $R^4$ in Formula (I), Formula (I*), Formula (Ia), or Formula (Ib) is —$CH_3$.

In some embodiments, W, X, and Y in Formula (I), Formula (I*), Formula (Ia), or Formula (Ib) is independently —C(=O)O— or —OC(=O)—. In some embodiments, at least one W, X, and Y in Formula (I), Formula (I*), Formula (Ia), or Formula (Ib) is —C(=O)O—. In some embodiments, at least one W, X, and Y in Formula (I), Formula (I*), Formula (Ia), or Formula (Ib) is —OC(=O)—. In some embodiments, at least one W, X, and Y in Formula (I), Formula (I*), Formula (Ia), or Formula (Ib) is independently —C(=O)$NR^4$— or —$NR^4$C(=O)—. In some embodiments, at least one W, X, and Y in Formula (I), Formula (I*), Formula (Ia), or Formula (Ib) is independently —C(=O)N($CH_3$)—, —N($CH_3$)C(=O)—, —C(=O)NH—, or —NHC(=O)—. In some embodiments, at least one W, X, and Y in Formula (I), Formula (I*), Formula (Ia), or Formula (Ib) is independently —C(=O)NH—, —C(=O)N($CH_3$)—, —OC(=O)—, —NHC(=O)—, —N($CH_3$)C(=O)—, —C(=O)O—, —OC(=O)O—, —NHC(=O)O—, —N($CH_3$)C(=O)O—, —OC(=O)NH—, —OC(=O)N($CH_3$)—, —NHC(=O)NH—, —N($CH_3$)C(=O)NH—, —NHC(=O)N($CH_3$)—, —N($CH_3$)C(=O)N($CH_3$)—, NHC(=NH)NH—, —N($CH_3$)C(=NH)NH—, —NHC(=NH)N($CH_3$)—, —N($CH_3$)C(=NH)N($CH_3$)—, NHC(=NMe)NH—, —N($CH_3$)C(=NMe)NH—, —NHC(=NMe)N($CH_3$)—, or —N($CH_3$)C(=NMe)N($CH_3$)—. In some embodiments, at least one W, X, and Y in Formula (I), Formula (I*), Formula (Ia), or Formula (Ib) is independently —OC(=O)O—, —$NR^4$C(=O)O—, —OC(=O)$NR^4$—, or —$NR^4$C(=O)$NR^4$—. In some embodiments, at least one W, X, and Y in Formula (I), Formula (I*), Formula (Ia), or Formula (Ib) is independently —OC(=O)O—, —NHC(=O)O—, —OC(=O)NH—, —NHC(=O)NH—, —N($CH_3$)C(=O)O—, —OC(=O)N($CH_3$)—, —N($CH_3$)C(=O)N($CH_3$)— or —N($CH_3$)C(=O)NH—. In some embodiments, at least one W, X, and Y in Formula (I), Formula (I*), Formula (Ia), or Formula (Ib) is independently —OC(=O)O—, —NHC(=O)O—, —OC(=O)NH—, or —NHC(=O)NH—.

In some embodiments, $R^3$ in Formula (I), Formula (I*), Formula (Ia), or Formula (Ib) is —$C_0$-$C_{10}$ alkylene-$NR^7R^8$ or —$C_0$-$C_{10}$ alkylene-heterocycloalkyl, wherein the alkylene and heterocycloalkyl is independently substituted or unsubstituted. In some embodiments, $R^3$ in Formula (I), Formula (I*), Formula (Ia), or Formula (Ib) is —$C_0$-$C_{10}$ alkylene-$NR^7R^8$. In some embodiments, $R^3$ in Formula (I), Formula (I*), Formula (Ia), or Formula (Ib) is —$C_1$-$C_6$ alkylene-$NR^7R^8$. In some embodiments, $R^3$ in Formula (I), Formula (I*), Formula (Ia), or Formula (Ib) is —$C_1$-$C_4$ alkylene-$NR^7R^8$. In some embodiments, $R^3$ in Formula (I), Formula (I*), Formula (Ia), or Formula (Ib) is —$C_1$-alkylene-$NR^7R^8$ In some embodiments, $R^3$ in Formula (I), Formula (I*), Formula (Ia), or Formula (Ib) is —$C_2$-alkylene-$NR^7R^8$. In some embodiments, $R^3$ in Formula (I), Formula (I*), Formula (Ia), or Formula (Ib) is —$C_3$-alkylene-$NR^7R^8$. In some embodiments, $R^3$ in Formula (I), Formula (I*), Formula (Ia), or Formula (Ib) is —$C_4$-alkylene-$NR^7R^8$. In some embodiments, $R^3$ in Formula (I), Formula (I*), Formula (Ia), or Formula (Ib) is —$C_5$-alkylene-$NR^7R^8$. In some embodiments, $R^3$ in Formula (I), Formula (I*), Formula (Ia), or Formula (Ib) is —$C_0$-$C_{10}$ alkylene-heterocycloalkyl. In some embodiments, $R^3$ in Formula (I), Formula (I*), Formula (Ia), or Formula (Ib) is —$C_1$-$C_6$ alkylene-heterocycloalkyl, wherein the heterocycloalkyl comprises 1 to 3 nitrogen and 0-2 oxygen. In some embodiments, $R^3$ in Formula (I), Formula (I*), Formula (Ia), or Formula (Ib) is quaternized.

In some embodiments, $R^7$ and $R^8$ in Formula (I), Formula (I*), Formula (Ia), or Formula (Ib) is independently hydrogen or substituted or unsubstituted $C_1$-$C_6$ alkyl. In some embodiments, $R^7$ and $R^8$ in Formula (I), Formula (I*), Formula (Ia), or Formula (Ib) is independently substituted or unsubstituted $C_1$-$C_6$ alkyl. In some embodiments, $R^7$ and $R^8$ is independently hydrogen or substituted or unsubstituted $C_1$-$C_3$ alkyl. In some embodiments, at least one $R^7$ and $R^8$ is independently substituted or unsubstituted $C_1$-$C_3$ alkyl. In some embodiments, at least one $R^7$ and $R^8$ is independently —$CH_3$, —$CH_2CH_3$, —$CH_2CH_2CH_3$, or —$CH(CH_3)_2$. In some embodiments, at least one $R^7$ and $R^8$ is $CH_3$. In some embodiments, at least one $R^7$ and $R^8$ is —$CH_2CH_3$.

In some embodiments, $R^7$ and $R^8$ in Formula (I), Formula (I*), Formula (Ia), or Formula (Ib) Formula (I), Formula (I*), Formula (Ia), or Formula (Ib), taken together with the nitrogen to which they are attached, form a substituted or unsubstituted $C_2$-$C_6$ heterocyclyl. In some embodiments, $R^7$ and $R^8$ taken together with the nitrogen to which they are attached form a substituted or unsubstituted $C_2$-$C_6$ heterocycloalkyl. In some embodiments, $R^7$ and $R^8$ taken together with the nitrogen to which they are attached form a substituted or unsubstituted 3-7 membered heterocycloalkyl.

In some embodiments, $R^3$ in Formula (I), Formula (I*), Formula (Ia), or Formula (Ib) is

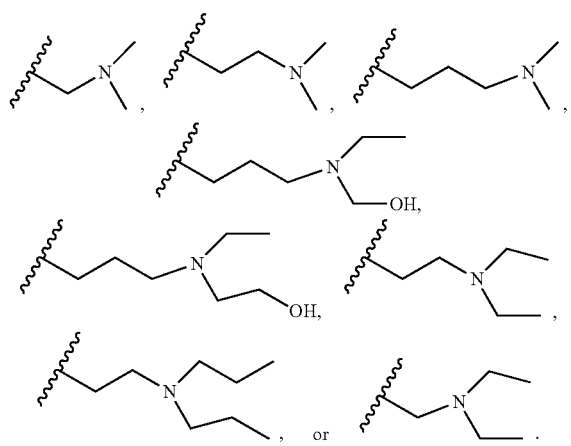

In some embodiments, $R^3$ in Formula (I), Formula (I*), Formula (Ia), or Formula (Ib) is

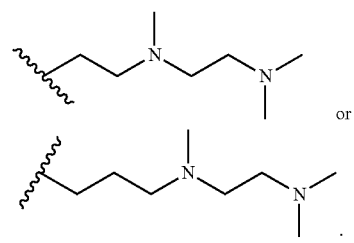

In some embodiments, $R^3$ in Formula (I), Formula (I*), Formula (Ia), or Formula (Ib) is

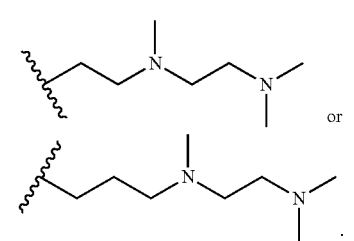

In some embodiments, $R^3$ in Formula (I), Formula (I*), Formula (Ia), or Formula (Ib) is

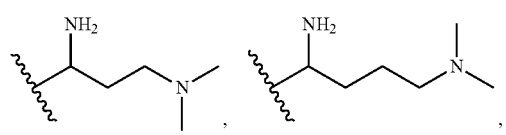

-continued

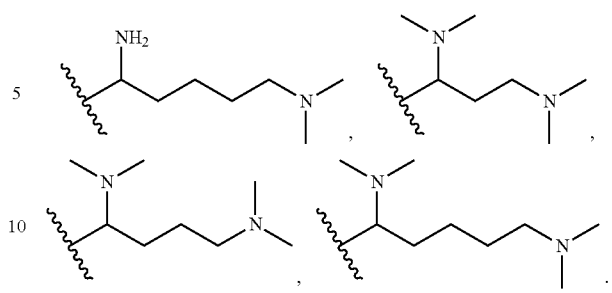

In some embodiments, $R^3$ in Formula (I), Formula (I*), Formula (Ia), or Formula (Ib) is

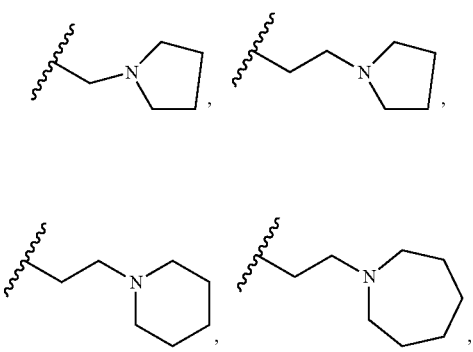

In some embodiments, $R^3$ in Formula (I), Formula (I*), Formula (Ia), or Formula (Ib) is

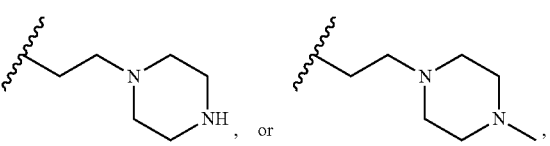

In some embodiments, $R^3$ in Formula (I), Formula (I*), Formula (Ia), or Formula (Ib) is

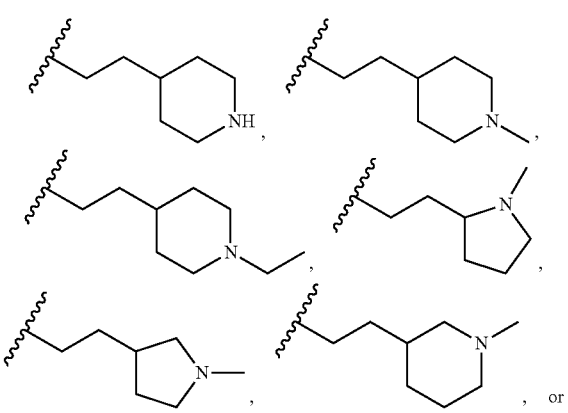

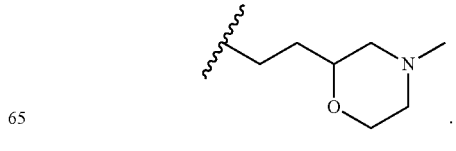

In some embodiments, $R^3$ in Formula (I), Formula (I*), Formula (Ia), or Formula (Ib) is

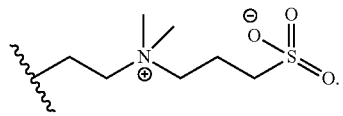 [SMILES: *CC[N+](C)(C)CCCS(=O)(=O)[O-]]

In some embodiments, Z in Formula (I), Formula (I*), Formula (Ia), or Formula (Ib) is —C(=O)O— or —OC(=O)—. In some embodiments, Z in Formula (I), Formula (I*), Formula (Ia), or Formula (Ib) is —C(=O)O—. In some embodiments, Z in Formula (I), Formula (I*), Formula (Ia), or Formula (Ib) is —OC(=O)—. In some embodiments, Z in Formula (I), Formula (I*), Formula (Ia), or Formula (Ib) is —C(=O)NR$^4$— or —NR$^4$C(=O)—. In some embodiments, Z in Formula (I), Formula (I*), Formula (Ia), or Formula (Ib) is —C(=O)NR$^4$—. In some embodiments, Z in Formula (I), Formula (I*), Formula (Ia), or Formula (Ib) is —NR$^4$C(=O)—. In some embodiments, $R^4$ in Z is hydrogen or $C_1$-$C_4$ alkyl. In some embodiments, $R^4$ in Z is hydrogen. In some embodiments, $R^4$ in Z is $C_1$-$C_4$ alkyl. In some embodiments, Z in Formula (I), Formula (I*), Formula (Ia), or Formula (Ib) is —C(=O)N(CH$_3$)—, —N(CH$_3$)C(=O)—, —C(=O)NH—, or —NHC(=O)—. In some embodiments, Z in Formula (I), Formula (I*), Formula (Ia), or Formula (Ib) is —OC(=O)O—, —NR$^4$C(=O)O—, —OC(=O)NR$^4$—, or —NR$^4$C(=O)NR$^4$—. In some embodiments, Z in Formula (I), Formula (I*), Formula (Ia), or Formula (Ib) is —OC(=O)O—, —NHC(=O)O—, —OC(=O)NH—, —NHC(=O)NH—, —N(CH$_3$)C(=O)O—, —OC(=O)N(CH$_3$)—, —N(CH$_3$)C(=O)N(CH$_3$)—, —NHC(=O)N(CH$_3$)— or —N(CH$_3$)C(=O)NH—. In some embodiments, Z in Formula (I), Formula (I*), Formula (Ia), or Formula (Ib) is —OC(=O)O—, —NHC(=O)O—, —OC(=O)NH—, or —NHC(=O)NH—. In some embodiments, Z in Formula (I), Formula (I*), Formula (Ia), or Formula (Ib) is a bond.

In some embodiments, $R^5$ in Formula (I), Formula (I*), Formula (Ia), or Formula (Ib) is hydrogen or substituted or unsubstituted $C_1$-$C_3$ alkyl. In some embodiments, $R^5$ in Formula (I), Formula (I*), Formula (Ia), or Formula (Ib) is H, —CH$_3$, —CH$_2$CH$_3$, —CH$_2$CH$_2$CH$_3$, or —CH(CH$_3$)$_2$. In some embodiments, $R^5$ in Formula (I), Formula (I*), Formula (Ia), or Formula (Ib) is H. In some embodiments, $R^5$ is substituted or unsubstituted —C$_0$-C$_{10}$ alkylene-L-R$^4$. In some embodiments, $R^5$ is substituted or unsubstituted $C_1$-$C_{16}$ alkyl.

In another aspect, disclosed herein is an amino lipid having structure of Formula (Ib), or a pharmaceutically acceptable salt thereof,

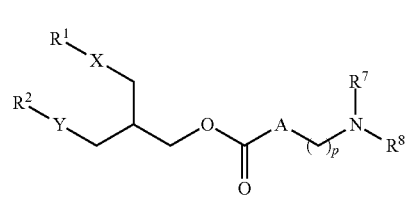

Formula (Ib)

wherein
each of X and Y are the same as in Formulas (I), (I*) and (Ia) and are selected from the group consisting of: —OC(=O)—, —OC(=O)O—, —OC(=O)NR$^4$—, —C(=S)O—, —OC(=S)—, OC(=S)O—, —NR$^4$C(=S)O—, —OC(=S)NR$^4$—, SC(=O)—, —OC(=O)S—, —SC(=S)O—, —O—, —C$_1$-C$_{10}$ alkylene-O—, and a bond, wherein the alkylene is substituted or unsubstituted $R^1$ and $R^2$ are the same as in Formulas (I), (I*) and (Ia) and are selected from the group consisting of: hydrogen, $C_1$-$C_{30}$ alkyl, $C_1$-$C_{30}$ heteroalkyl, and Cy-$C_{3-30}$ alkyl, wherein the alkyl and heteroalkyl are each independently substituted or unsubstituted;

each of $R^4$ is independently hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl; and each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl.

A is —O—, —CH$_2$—, —S—, or —NR$^{12}$—;

$R^{12}$ is hydrogen, $C_1$-$C_{10}$ alkyl, or $C_1$-$C_{10}$ heteroalkyl, wherein the alkyl and heteroalkyl are each independently substituted or unsubstituted; and Cy is substituted or unsubstituted cycloalkyl, substituted or unsubstituted heterocycloalkyl, substituted or unsubstituted aryl, or substituted or unsubstituted heteroaryl.

p is 1, 2, 3, 4, 5 or 6

In some embodiments, the amino lipid of Formula (I), Formula (I*), Formula (Ia), or Formula (Ib) is a

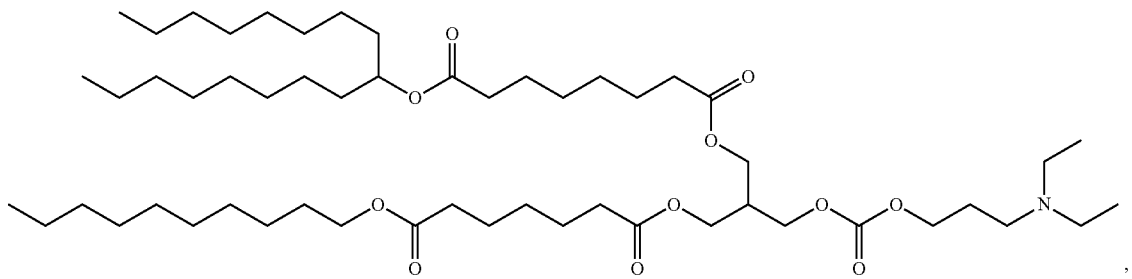

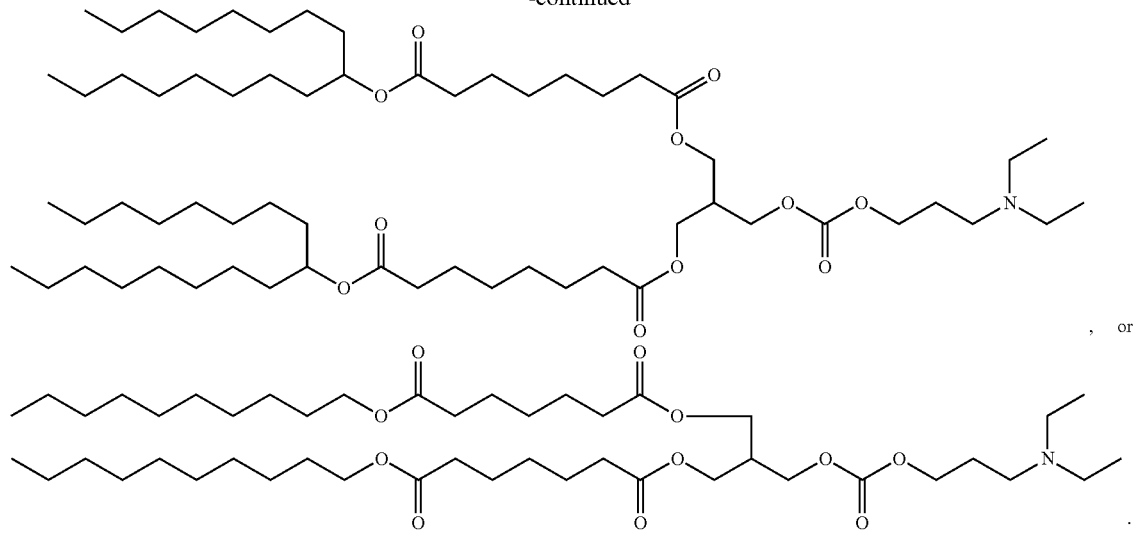

, or

In another aspect, disclosed herein is an amino lipid having the structure of Formula (II), or a pharmaceutically acceptable salt or solvate thereof,

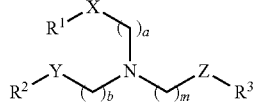

Formula (II)

wherein
- each of $R^1$ and $R^2$ is independently $C_3$-$C_{30}$ alkyl, $C_3$-$C_{30}$ alkenyl, $C_3$-$C_{30}$ alkynyl, $C_3$-$C_{10}$ cycloalkyl, —$C_0$-$C_{10}$ alkylene-L-$R^6$, or —$C_1$-$C_{10}$ alkenylene-L-$R^6$, wherein each of the alkyl, alkylene, alkenyl, alkenylene, alkynyl, and cycloalkyl is independently substituted or unsubstituted;
- each of X, Y, and Z is independently —C(=O)$NR^4$—, —$NR^4$C(=O)—, —C(=O)O—, —OC(=O)—, —OC(=O)O—, —$NR^4$C(=O)O—, —OC(=O) $NR^4$—, —$NR^4$C(=O)$NR^4$—, —$NR^4$C(=$NR^4$) $NR^4$—, —C(=S)$NR^4$—, —$NR^4$C(=S)—, —C(=S) O—, —OC(=S)—, OC(=S)O—, —$NR^4$C(=S)O—, —OC(=S)$NR^4$—, —$NR^4$C(=S)$NR^4$—, —C(=O) S—, —SC(=O)—, —OC(=O)S—, —$NR^4$C(=O) S—, —SC(=O)$NR^4$—, —C(=S)S—, —SC(=S)—, —SC(=S)O—, —$NR^4$C(=S)S—, —SC(=S)$NR^4$—, —C(=S)S—, —SC(=S)—, —SC(=O)S—, —SC (=S)S—, —$NR^4$C(=S)S—, —SC(=S)$NR^4$—, —O—, —S—, or a bond;
- each of L is independently —C(=O)$NR^4$—, —$NR^4$C (=O)—, —C(=O)O—, —OC(=O)—, —OC(=O) O—, —$NR^4$C(=O)O—, —OC(=O)$NR^4$—, —$NR^4$C (=O)$NR^4$—, —$NR^4$C(=$NR^4$)$NR^4$—, —C(=S) $NR^4$—, —$NR^4$C(=S)—, —C(=S)O—, —OC (=S)—, OC(=S)O—, —$NR^4$C(=S)O—, —OC(=S) $NR^4$—, —$NR^4$C(=S)$NR^4$—, —C(=O)S—, —SC (=O)—, —OC(=O)S—, —$NR^4$C(=O)S—, —SC (=O)$NR^4$—, —C(=S)S—, —SC(=S)—, —SC(=S) O—, —$NR^4$C(=S)S—, —SC(=S)$NR^4$—, —C(=S) S—, —SC(=S)—, —SC(=O)S—, —SC(=S)S—, —$NR^4$C(=S)S—, —SC(=S)$NR^4$—,
- —O—N=$CR^4$—, —$CR^4$=N—O—, —O—, —S—, —$C_1$-$C_{10}$ alkylene-O—, —$C_1$-$C_{10}$ alkylene-C(=O) O—, —$C_1$-$C_{10}$ alkylene-OC(=O)—, or a bond, wherein the alkylene is substituted or unsubstituted;
- $R^3$ is —$C_0$-$C_{10}$ alkylene-$NR^7R^8$, —$C_0$-$C_{10}$ alkylene-heterocycloalkyl, or —$C_0$-$C_{10}$ alkylene-heterocycloaryl, wherein the alkylene, heterocycloalkyl and heterocycloaryl is independently substituted or unsubstituted;
- each of $R^4$ is independently hydrogen or substituted or unsubstituted $C_1$-$C_6$ alkyl;
- each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;
- each of Cy is substituted or unsubstituted cycloalkyl, substituted or unsubstituted heterocycloalkyl, substituted or unsubstituted aryl, substituted or unsubstituted heteroaryl;
- each of $R^7$ and $R^8$ is independently hydrogen or substituted or unsubstituted $C_1$-$C_6$ alkyl, or $R^7$ and R taken together with the nitrogen to which they are attached form a substituted or unsubstituted $C_2$-$C_6$ heterocyclyl;
- each of a and b is independently 1, 2, 3, 4, 5, 6, 7, 8, 9, or 10; and
- m is 0, 1, 2, 3, 4, or 5.

In one aspect, disclosed herein is an amino lipid having a structure of Formula (II*), or a pharmaceutically acceptable salt or solvate thereof,

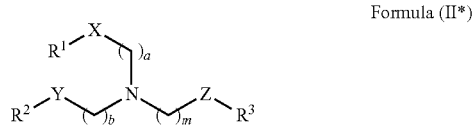

Formula (II*)

wherein
- each of $R^1$ and $R^2$ is independently hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_1$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —C(=O)—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is hydrogen, —C$_1$-C$_6$ alkyl, —C$_0$-C$_{10}$ alkylene-NR$^7$R$^8$, —C$_0$-C$_{10}$ alkylene-heterocycloalkyl, or —C$_0$-C$_{10}$ alkylene-heterocycloaryl, wherein the alkyl, alkylene, heterocycloalkyl and heterocycloaryl is independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl;

each of a and b is independently 1, 2, 3, 4, 5, 6, 7, 8, 9, or 10; and m is 0, 1, 2, 3, 4, or 5.

In some embodiments of Formula (II) or (II*), if the structure carries more than one asymmetric C-atom, each asymmetric C-atom independently represents racemic, chirally pure R and/or chirally pure S isomer, or a combination thereof.

In some embodiments, each of a and b in Formula (II) or (II*) is independently 3, 4, 5, 6, 7, 8, 9, or 10. In some embodiments, a is 1. In some embodiments, a is 2. In some embodiments, a is 3. In some embodiments, a is 4. In some embodiments, a is 5. In some embodiments, b is 1. In some embodiments, b is 2. In some embodiments, b is 3. In some embodiments, b is 4. In some embodiments, b is 5.

In some embodiments, m in Formula (II) or (II*) is 1, 2, 3, 4, or 5. In some embodiments, m is 1. In some embodiments, m is 2. In some embodiments, m is 3. In some embodiments, m is 4. In some embodiments, m is 5.

In some embodiments, each R$^1$ and R$^2$ in Formula (II) or (II*) is independently C$_5$-C$_{28}$ alkyl, C$_5$-C$_{28}$ alkenyl, C$_5$-C$_{28}$ alkynyl, C$_3$-C$_{10}$ cycloalkyl, —C$_1$-C$_{10}$ alkylene-L-R$^6$, or —C$_1$-C$_{10}$ alkenylene-L-R$^6$, wherein each of the alkyl, alkylene, alkenyl, alkenylene, alkynyl, and cycloalkyl is independently substituted or unsubstituted. In some embodiments, each R$^1$ and R$^2$ in Formula (II) or (II*) is independently C$_7$-C$_{25}$ alkyl, C$_7$-C$_{25}$ alkenyl, C$_7$-C$_{25}$ alkynyl, C$_3$-C$_{10}$ cycloalkyl, —C$_1$-C$_{10}$ alkylene-L-R$^6$, or —C$_1$-C$_{10}$ alkenylene-L-R$^6$, wherein each of the alkyl, alkylene, alkenyl, alkenylene, alkynyl, and cycloalkyl is independently substituted or unsubstituted. In some embodiments, each R$^1$ and R$^2$ in Formula (II) or (II*) is independently C$_7$-C$_{22}$ alkyl, C$_7$-C$_{22}$ alkenyl, C$_7$-C$_{22}$ alkynyl, C$_3$-C$_{10}$ cycloalkyl, —C$_1$-C$_{10}$ alkylene-L-R$^6$, or —C$_1$-C$_{10}$ alkenylene-L-R$^6$, wherein each of the alkyl, alkylene, alkenyl, alkenylene, alkynyl, and cycloalkyl is independently substituted or unsubstituted. In some embodiments, each R$^1$ and R$^2$ in Formula (II) or (II*) is independently C$_{10}$-C$_{20}$ alkyl, C$_{10}$-C$_{20}$ alkenyl, —C$_4$-C$_8$ alkylene-L-R$^6$, or —C$_4$-C$_8$ alkylene-L-R$^6$, wherein each of the alkyl, alkylene, alkenyl, and cycloalkyl is independently substituted or unsubstituted. In some embodiments, each R$^1$ and R$^2$ in Formula (II) or (II*) is —C$_1$-C$_{10}$ alkylene-L-R$^6$. In some embodiments, each R$^1$ and R$^2$ in Formula (II) or (II*) is C$_7$-C$_{30}$ alkenyl. In some embodiments, each R$^1$ and R$^2$ in Formula (II) or (II*) is C$_7$-C$_{28}$ alkenyl. In some embodiments, each R$^1$ and R$^2$ in Formula (II) or (II*) is C$_7$-C$_{25}$ alkenyl. In some embodiments, each R$^1$ and R$^2$ in Formula (II) or (II*) is C$_7$-C$_{22}$ alkenyl.

In some embodiments, each R$^1$ and R$^2$ in Formula (II) or (II*) is independently substituted or unsubstituted linear or branched C$_3$-C$_{30}$ alkyl or substituted or unsubstituted linear or branched C$_3$-C$_{30}$ alkenyl. In some embodiments, each R$^1$ and R$^2$ in Formula (I) or (II*) is independently substituted or unsubstituted linear or branched C$_3$-C$_{25}$ alkyl or substituted or unsubstituted linear or branched C$_3$-C$_{28}$ alkenyl. In some embodiments, each R$^1$ and R$^2$ in Formula (I) or (II*) is independently substituted or unsubstituted C$_3$-C$_{25}$ alkyl or substituted or unsubstituted C$_3$-C$_{25}$ alkenyl. In some embodiments, each R$^1$ and R$^2$ in Formula (II) or (II*) is independently substituted or unsubstituted C$_3$-C$_{22}$ alkyl or substituted or unsubstituted C$_3$-C$_{22}$ alkenyl. In some embodiments, each R$^1$ and R$^2$ in Formula (II) or (II*) is independently substituted or unsubstituted C$_3$-C$_{25}$ alkyl. In some embodiments, each R$^1$ and R$^2$ in Formula (II) or (II*) is independently C$_3$ alkyl, C$_4$ alkyl, C$_5$ alkyl, C$_6$ alkyl, C$_7$ alkyl, C$_8$ alkyl, C$_9$ alkyl, C$_{10}$ alkyl, C$_{11}$ alkyl, C$_{12}$ alkyl, C$_{13}$ alkyl, C$_{14}$ alkyl, C$_{15}$ alkyl, C$_{16}$ alkyl, C$_{17}$ alkyl, C$_{15}$ alkyl, C$_{19}$ alkyl, C$_{20}$ alkyl, C$_{21}$ alkyl, C$_{22}$ alkyl, C$_{23}$ alkyl, C$_{24}$ alkyl, or C$_{25}$ alkyl. In some embodiments, each R$^1$ and R$^2$ in Formula (II) or (II*) is independently at least C$_3$ alkyl, at least C$_4$ alkyl, at least C$_5$ alkyl, at least C$_6$ alkyl, at least C$_7$ alkyl, at least C$_8$ alkyl, at least C$_9$ alkyl, at least C$_{10}$ alkyl, at least C$_{11}$ alkyl, at least C$_{12}$ alkyl, at least C$_{13}$ alkyl, at least C$_{14}$ alkyl, at least C$_{15}$ alkyl, at least C$_{16}$ alkyl, at least C$_{17}$ alkyl, at least C$_{15}$ alkyl, at least C$_{19}$ alkyl, at least C$_{20}$ alkyl, at least C$_{21}$ alkyl, at least C$_{22}$ alkyl, at least C$_{23}$ alkyl, at least C$_{24}$ alkyl, or at least C$_{25}$ alkyl. In some embodiments, each R$^1$ and R$^2$ in Formula (II) or (II*) is independently at most C$_3$ alkyl, at most C$_4$ alkyl, at most C$_5$ alkyl, at most C$_6$ alkyl, at most C$_7$ alkyl, at most C$_8$ alkyl, at most C$_9$ alkyl, at most C$_{10}$ alkyl, at most C$_{11}$ alkyl, at most C$_{12}$ alkyl, at most C$_{13}$ alkyl, at most C$_{14}$ alkyl, at most C$_{15}$ alkyl, at most C$_{16}$ alkyl, at most $C_{17}$ alkyl, at most $C_{18}$ alkyl, at most $C_{19}$ alkyl, at most $C_{20}$ alkyl, at most $C_{21}$ alkyl, at most $C_{22}$ alkyl, at most $C_{23}$ alkyl, at most $C_{24}$ alkyl, or at most $C_{25}$ alkyl. In some embodiments, each $R^1$ and $R^2$ in Formula (II) or (II*) is independently substituted or unsubstituted $C_3$-$C_{25}$ alkenyl. In some embodiments, each $R^1$ and $R^2$ in Formula (II) or (II*) is independently $C_3$ alkenyl, $C_4$ alkenyl, $C_5$ alkenyl, $C_6$ alkenyl, $C_7$ alkenyl, $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, $C_{16}$ alkenyl, $C_{17}$ alkenyl, $C_{18}$ alkenyl, $C_{19}$ alkenyl, $C_{20}$ alkenyl, $C_{21}$ alkenyl, $C_{22}$ alkenyl, $C_{23}$ alkenyl, $C_{24}$ alkenyl, or $C_{25}$ alkenyl. In some embodiments, each $R^1$ and $R^2$ in Formula (II) or (II*) is independently at least $C_3$ alkenyl, at least $C_4$ alkenyl, at least $C_5$ alkenyl, at least $C_6$ alkenyl, at least $C_7$ alkenyl, at least $C_8$ alkenyl, at least $C_9$ alkenyl, at least $C_{10}$ alkenyl, at least $C_{11}$ alkenyl, at least $C_{12}$ alkenyl, at least $C_{13}$ alkenyl, at least $C_{14}$ alkenyl, at least $C_{15}$ alkenyl, at least $C_{16}$ alkenyl, at least $C_{17}$ alkenyl, at least $C_{18}$ alkenyl, at least $C_{19}$ alkenyl, at least $C_{20}$ alkenyl, at least $C_{21}$ alkenyl, at least $C_{22}$ alkenyl, at least $C_{23}$ alkenyl, at least $C_{24}$ alkenyl, or at least $C_{25}$ alkenyl. In some embodiments, each $R^1$ and $R^2$ in Formula (II) or (II*) is independently at most $C_3$ alkenyl, at most $C_4$ alkenyl, at most $C_5$ alkenyl, at most $C_6$ alkenyl, at most $C_7$ alkenyl, at most $C_8$ alkenyl, at most $C_9$ alkenyl, at most $C_{10}$ alkenyl, at most $C_{11}$ alkenyl, at most $C_{12}$ alkenyl, at most $C_{13}$ alkenyl, at most $C_{14}$ alkenyl, at most $C_{15}$ alkenyl, at most $C_{16}$ alkenyl, at most $C_{17}$ alkenyl, at most $C_{18}$ alkenyl, at most $C_{19}$ alkenyl, at most $C_{20}$ alkenyl, at most $C_{21}$ alkenyl, at most $C_{22}$ alkenyl, at most $C_{23}$; alkenyl, at most $C_{24}$ alkenyl, or at most $C_{25}$ alkenyl.

In some embodiments, $R^1$ and/or $R^2$ in Formula (II) or (II*) is independently

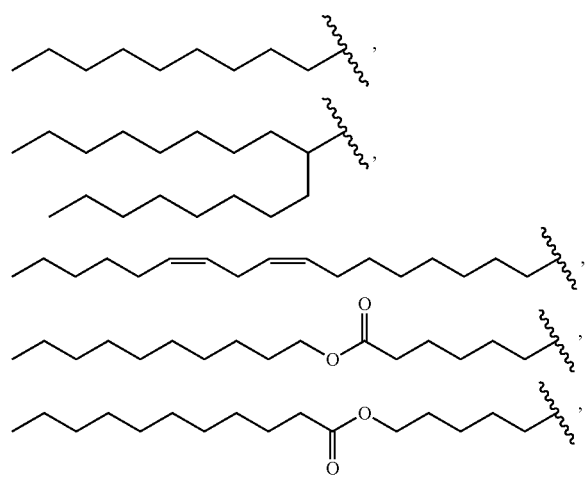

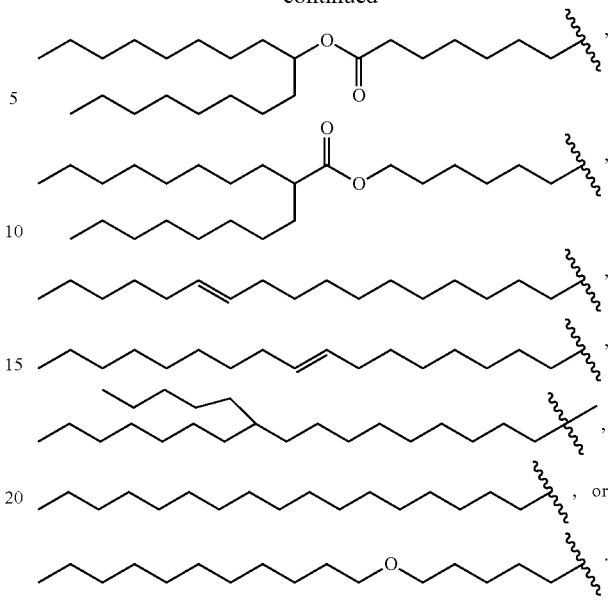

In some embodiments, $R^1$ and/or $R^2$ in Formula (II) or (II*) is

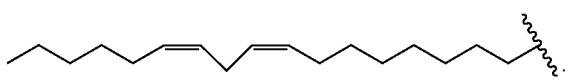 [SMILES: *CCCCCCC/C=C\C/C=C\CCCCC]

In some embodiments, $R^1$ and/or $R^2$ in Formula (II) or (II*) is

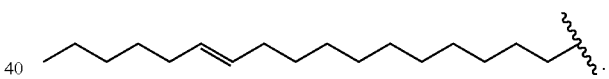

In some embodiments, $R^1$ and/or $R^2$ in Formula (II) or (II*) is

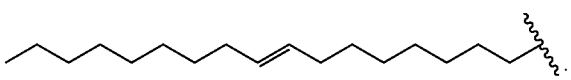 [SMILES: *CCCCCCC/C=C/CCCCCCCC]

In some embodiments, $R^1$ and/or $R^2$ in Formula (II) or (II*) is

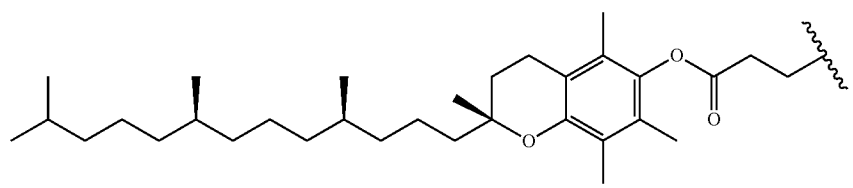

In some embodiments, $R^1$ in Formula (II) or (II*) is

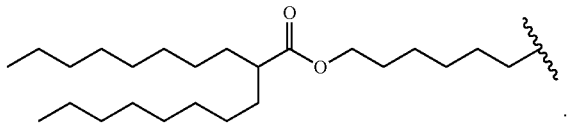 [SMILES: *CCCCCCOC(=O)C(CCCCCCCC)CCCCCCCC]

In some embodiments, $R^2$ in Formula (II) or (II*) is

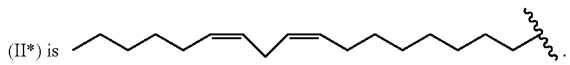

In some embodiments, $R^1$ in Formula (II) or (II*) is

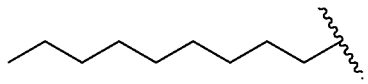

In some embodiments, $R^2$ in Formula (II) or (II*) is

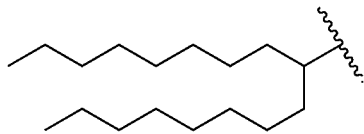

In some embodiments, each of L in Formula (II) or (II*) is independently —O—, —S—, —$C_1$-$C_{10}$ alkylene-O—, —$C_1$-$C_{10}$ alkylene-C(=O)O—, —$C_1$-$C_{10}$ alkylene-OC(=O)—, —C(=O)O—, —OC(=O)—, —C(=O)$NR^4$—, —$NR^4$C(=O)—, or a bond, wherein the alkylene is substituted or unsubstituted. In some embodiments, at least one L in Formula (II) or (II*) is independently —O—, —S—, —$C_1$-$C_3$ alkylene-O—, —$C_1$-$C_3$ alkylene-C(=O)O—, —$C_1$-$C_3$ alkylene-OC(=O)—, —C(=O)O—, —OC(=O)—, —C(=O)$NR^4$—, —$NR^4$C(=O)—, or a bond, wherein the alkylene is substituted or unsubstituted. In some embodiments, at least one L in Formula (II) or (II*) is independently —O—, —S—, —$C_1$-$C_3$ alkylene-O—, —$C_1$-$C_3$ alkylene-C(=O)O—, —$C_1$-$C_3$ alkylene-OC(=O)—, or a bond, wherein the alkylene is linear or branched unsubstituted alkylene. In some embodiments, at least one L in Formula (II) or (II*) is —C(=O)O—, —OC(=O)—, —C(=O)$NR^4$—, —$NR^4$C(=O)—. In some embodiments, at least one L in Formula (II) or (II*) is —C(=O)O—. In some embodiments, at least one L in Formula (II) or (II*) is —OC(=O)—. In some embodiments, at least one L in Formula (II) or (II*) is —C(=O)$NR^4$—. In some embodiments, at least one L in Formula (II) or (II*) is —C(=O)NH—. In some embodiments, at least one L in Formula (II) or (II*) is —C(=O)N($CH_3$)—. In some embodiments, at least one L in Formula (II) or (II*) is —$NR^4$C(=O)—. In some embodiments, at least one L in Formula (II) or (II*) is —NHC(=O)—. In some embodiments, at least one L in Formula (II) or (II*) is —N($CH_3$)C(=O)—.

In some embodiments, at least one $R^6$ in Formula (II) or (II*) is independently substituted or unsubstituted linear or branched $C_3$-$C_{30}$ alkyl or substituted or unsubstituted linear or branched $C_3$-$C_{30}$ alkenyl. In some embodiments, each of $R^6$ in Formula (II) or (II*) is independently substituted or unsubstituted linear or branched $C_3$-$C_{28}$ alkyl or substituted or unsubstituted linear or branched $C_3$-$C_{28}$ alkenyl. In some embodiments, each of $R^6$ in Formula (II) or (II*) is independently substituted or unsubstituted $C_3$-$C_{25}$ alkyl or substituted or unsubstituted $C_3$-$C_{25}$ alkenyl. In some embodiments, at least one $R^6$ in Formula (II) or (II*) is independently substituted or unsubstituted $C_3$-$C_{25}$ alkyl. In some embodiments, at least one $R^6$ in Formula (II) or (II*) is independently $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl, $C_{21}$ alkyl, $C_{22}$ alkyl, $C_{23}$ alkyl, $C_{24}$ alkyl, or $C_{25}$ alkyl. In some embodiments, at least one $R^6$ in Formula (II) or (II*) is independently at least $C_3$ alkyl, at least $C_4$ alkyl, at least $C_5$ alkyl, at least $C_6$ alkyl, at least $C_7$ alkyl, at least $C_8$ alkyl, at least $C_9$ alkyl, at least $C_{10}$ alkyl, at least $C_{11}$ alkyl, at least $C_{12}$ alkyl, at least $C_{13}$ alkyl, at least $C_{14}$ alkyl, at least $C_{15}$ alkyl, at least $C_{16}$ alkyl, at least $C_{17}$ alkyl, at least $C_{18}$ alkyl, at least $C_{19}$ alkyl, at least $C_{20}$ alkyl, at least $C_{21}$ alkyl, at least $C_{22}$ alkyl, at least $C_{23}$ alkyl, at least $C_{24}$ alkyl, or at least $C_{25}$ alkyl. In some embodiments, at least one $R^6$ in Formula (II) or (II*) is independently at most $C_3$ alkyl, at most $C_4$ alkyl, at most $C_5$ alkyl, at most $C_6$ alkyl, at most $C_7$ alkyl, at most $C_8$ alkyl, at most $C_9$ alkyl, at most $C_{10}$ alkyl, at most $C_{11}$ alkyl, at most $C_{12}$ alkyl, at most $C_{13}$ alkyl, at most $C_{14}$ alkyl, at most $C_{15}$ alkyl, at most $C_{16}$ alkyl, at most $C_{17}$ alkyl, at most $C_{18}$ alkyl, at most $C_{19}$ alkyl, at most $C_{20}$ alkyl, at most $C_{21}$ alkyl, at most $C_{22}$ alkyl, at most $C_{23}$ alkyl, at most $C_{24}$ alkyl, or at most $C_{25}$ alkyl. In some embodiments, at least one $R^6$ in Formula (II) or (II*) is independently substituted or unsubstituted $C_3$-$C_{25}$ alkenyl. In some embodiments, at least one $R^6$ in Formula (II) or (II*) is independently $C_3$ alkenyl, $C_4$ alkenyl, $C_5$ alkenyl, $C_6$ alkenyl, $C_7$ alkenyl, $C_8$ alkenyl, $C_9$ alkenyl, $C_{10}$ alkenyl, $C_{11}$ alkenyl, $C_{12}$ alkenyl, $C_{13}$ alkenyl, $C_{14}$ alkenyl, $C_{15}$ alkenyl, $C_{16}$ alkenyl, $C_{17}$ alkenyl, $C_{18}$ alkenyl, $C_{19}$ alkenyl, $C_{20}$ alkenyl, $C_{21}$ alkenyl, $C_{22}$ alkenyl, $C_{23}$ alkenyl, $C_{24}$ alkenyl, or $C_{25}$ alkenyl. In some embodiments, at least one $R^6$ in Formula (II) or (II*) is independently at least $C_3$ alkenyl, at least $C_4$ alkenyl, at least $C_5$ alkenyl, at least $C_6$ alkenyl, at least $C_7$ alkenyl, at least $C_8$ alkenyl, at least $C_9$ alkenyl, at least $C_{10}$ alkenyl, at least $C_{11}$ alkenyl, at least $C_{12}$ alkenyl, at least $C_{13}$ alkenyl, at least $C_{14}$ alkenyl, at least $C_{15}$ alkenyl, at least $C_{16}$ alkenyl, at least $C_{17}$ alkenyl, at least $C_{18}$ alkenyl, at least $C_{19}$ alkenyl, at least $C_{20}$ alkenyl, at least $C_{21}$ alkenyl, at least $C_{22}$ alkenyl, at least $C_{23}$ alkenyl, at least $C_{24}$ alkenyl, or at least $C_{25}$ alkenyl. In some embodiments, at least one $R^6$ in Formula (II) or (II*) is independently at most $C_3$ alkenyl, at most $C_4$ alkenyl, at most $C_5$ alkenyl, at most $C_6$ alkenyl, at most $C_7$ alkenyl, at most $C_8$ alkenyl, at most $C_9$ alkenyl, at most $C_{10}$ alkenyl, at most $C_{11}$ alkenyl, at most $C_{12}$ alkenyl, at most $C_{13}$ alkenyl, at most $C_{14}$ alkenyl, at most $C_{15}$ alkenyl, at most $C_{16}$ alkenyl, at most $C_{17}$ alkenyl, at most $C_{18}$ alkenyl, at most $C_{19}$ alkenyl, at most $C_{20}$ alkenyl, at most $C_{21}$ alkenyl, at most $C_{22}$ alkenyl, at most $C_{23}$ alkenyl, at most $C_{24}$ alkenyl, or at most $C_{25}$ alkenyl.

In some embodiments, each $R^6$ in Formula (II) or (II*) is independently

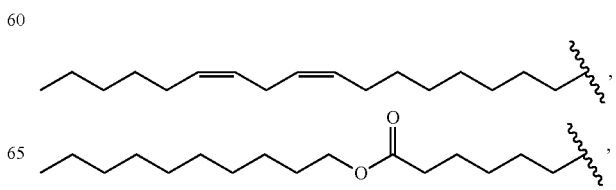

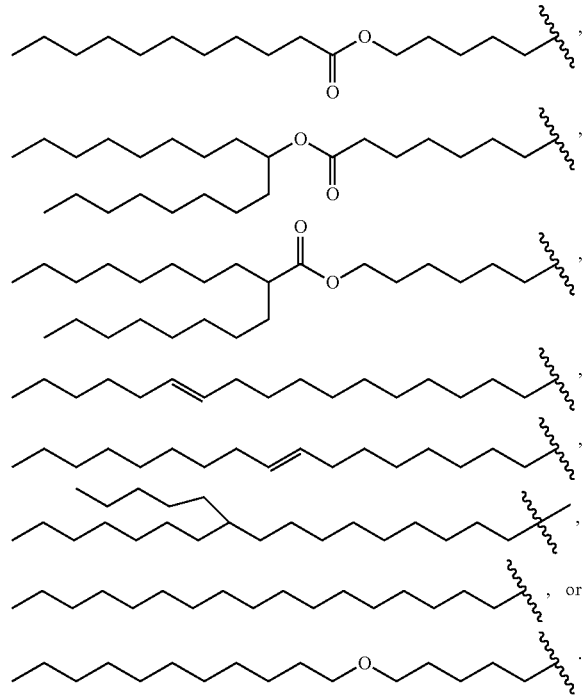

In some embodiments, each $R^6$ in Formula (II) or (II*) is

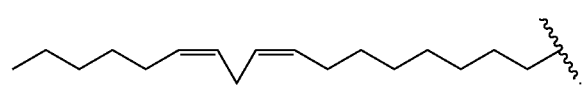

In some embodiments, each $R^6$ in Formula (II) or (II*) is

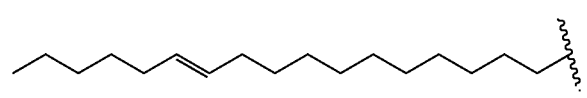

In some embodiments, each $R^6$ in Formula (II) or (II*) is

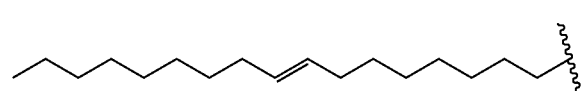

In some embodiments, $R^4$ in Formula (II) or (II*) is independently H or substituted or unsubstituted $C_1$-$C_4$ alkyl. In some embodiments, at least one $R^4$ in Formula (II) or (II*) is independently substituted or unsubstituted linear $C_1$-$C_4$ alkyl. In some embodiments, at least one $R^4$ in Formula (II) or (II*) is H. In some embodiments, at least one $R^4$ in Formula (II) or (II*) is independently H, —$CH_3$, —$CH_2CH_3$, —$CH_2CH_2CH_3$, or —$CH(CH_3)_2$. In some embodiments, at least one $R^4$ in Formula (II) or (II*) is independently H or —$CH_3$. In some embodiments, at least one $R^4$ in Formula (II) or (II*) is —$CH_3$.

In some embodiments, each X and Y in Formula (II) or (II*) is independently —C(=O)O— or —OC(=O)—. In some embodiments, each X and Y in Formula (II) or (II*) is —C(=O)O—. In some embodiments, each X and Y in Formula (II) or (II*) is —OC(=O)—. In some embodiments, Y in Formula (II) or (II*) is —C(=O)O—. In some embodiments, Y in Formula (II) or (II*) is —OC(=O)—. In some embodiments, each X and Y in Formula (II) or (II*) is independently —C(=O)NR$^4$— or —NR$^4$C(=O)—. In some embodiments, X in Formula (II) or (II*) is —C(=O)NR$^4$— or —NR$^4$C(=O)—. In some embodiments, X in Formula (II) or (II*) is —C(=O)NR$^4$—. In some embodiments, X in Formula (II) or (II*) is —NR$^4$C(=O)—. In some embodiments, each X and Y in Formula (II) or (II*) is independently —C(=O)N(CH$_3$)—, —N(CH$_3$)C(=O)—, —C(=O)NH—, or —NHC(=O)—. In some embodiments, each X and Y in Formula (II) or (II*) is independently —C(=O)NH—, —C(=O)N(CH$_3$)—, —OC(=O)—, —NHC(=O)—, —N(CH$_3$)C(=O)—, —C(=O)O—, —OC(=O)O—, —NHC(=O)O—, —N(CH$_3$)C(=O)O—, —OC(=O)NH—, —OC(=O)N(CH$_3$)—, —NHC(=O)NH—, —N(CH$_3$)C(=O)NH—, —NHC(=O)N(CH$_3$)—, —N(CH$_3$)C(=O)N(CH$_3$)—, NHC(=NH)NH—, —N(CH$_3$)C(=NH)NH—, —NHC(=NH)N(CH$_3$)—, —N(CH$_3$)C(=NH)N(CH$_3$)—, NHC(=NMe)NH—, —N(CH$_3$)C(=NMe)NH—, —NHC(=NMe)N(CH$_3$)—, or —N(CH$_3$)C(=NMe)N(CH$_3$)—. In some embodiments, each X and Y in Formula (II) or (*) is independently —OC(=O)O—, —NR$^4$C(=O)O—, —OC(=O)NR$^4$—, or —NR$^4$C(=O)NR$^4$—. In some embodiments, each X and Y in Formula (II) or (II*) is independently —OC(=O)O—, —NHC(=O)O—, —OC(=O)NH—, —NHC(=O)NH—, —N(CH$_3$)C(=O)O—, —OC(=O)N(CH$_3$)—, —N(CH$_3$)C(=O)N(CH$_3$)— or —N(CH$_3$)C(=O)NH—. In some embodiments, each X and Y in Formula (II) or (II*) is independently —OC(=O)O—, —NHC(=O)O—, —OC(=O)NH—, or —NHC(=O)NH—.

In some embodiments, $R^3$ in Formula (II) or (II*) is —$C_0$-$C_{10}$ alkylene-NR$^7$R$^8$ or —$C_0$-$C_{10}$ alkylene-heterocycloalkyl, wherein the alkylene and heterocycloalkyl is independently substituted or unsubstituted. In some embodiments, $R^3$ in Formula (II) or (II*) is —$C_0$-$C_{10}$ alkylene-NR$^7$R$^8$. In some embodiments, $R^3$ in Formula (II) or (II*) is —$C_1$-$C_6$ alkylene-NR$^7$R$^8$. In some embodiments, $R^3$ in Formula (II) or (II*) is —$C_1$-$C_4$ alkylene-NR$^7$R$^8$ In some embodiments, $R^3$ in Formula (II) or (II*) is —$C_1$-alkylene-NR$^7$R$^8$. In some embodiments, $R^3$ in Formula (II) or (II*) is —$C_2$-alkylene-NR$^7$R$^8$. In some embodiments, $R^3$ in Formula (II) or (II*) is —$C_3$-alkylene-NR$^7$R$^8$ In some embodiments, $R^3$ in Formula (II) or (II*) is —$C_4$-alkylene-NR$^7$R$^8$. In some embodiments, $R^3$ in Formula (II) or (II*) is —$C_5$-alkylene-NR$^7$R$^8$. In some embodiments, $R^3$ in Formula (II) or (II*) is —$C_0$-$C_{10}$ alkylene-heterocycloalkyl. In some embodiments, $R^3$ in Formula (II) or (II*) is —$C_1$-$C_6$ alkylene-heterocycloalkyl, wherein the heterocycloalkyl comprises 1 to 3 nitrogen and 0-2 oxygen. In some embodiments, $R^3$ in Formula (II) or (II*) is quaternized.

In some embodiments, $R^7$ and $R^8$ in Formula (II) or (II*) is independently hydrogen or substituted or unsubstituted $C_1$-$C_6$ alkyl. In some embodiments, at least one $R^7$ and $R^8$ in Formula (II) or (II*) is independently substituted or unsubstituted $C_1$-$C_6$ alkyl. In some embodiments, at least one $R^7$ and $R^8$ is independently hydrogen or substituted or unsubstituted $C_1$-$C_3$ alkyl. In some embodiments, at least one $R^7$ and $R^8$ is independently substituted or unsubstituted $C_1$-$C_3$ alkyl. In some embodiments, at least one $R^7$ and $R^8$ is independently —$CH_3$, —$CH_2CH_3$, —$CH_2CH_2CH_3$, or —$CH(CH_3)_2$. In some embodiments, at least one $R^7$ and $R^8$ is $CH_3$. In some embodiments, at least one $R^7$ and $R^8$ is —$CH_2CH_3$.

In some embodiments, $R^7$ and $R^8$ in Formula (II) or (II*), taken together with the nitrogen to which they are attached, form a substituted or unsubstituted $C_2$-$C_6$ heterocyclyl. In some embodiments, $R^7$ and $R^8$ taken together with the nitrogen to which they are attached form a substituted or unsubstituted $C_2$-$C_6$ heterocycloalkyl. In some embodiments, $R^7$ and $R^8$ taken together with the nitrogen to which they are attached form a substituted or unsubstituted 3-7 membered heterocycloalkyl.

In some embodiments, $R^3$ in Formula (II) or (II*) is

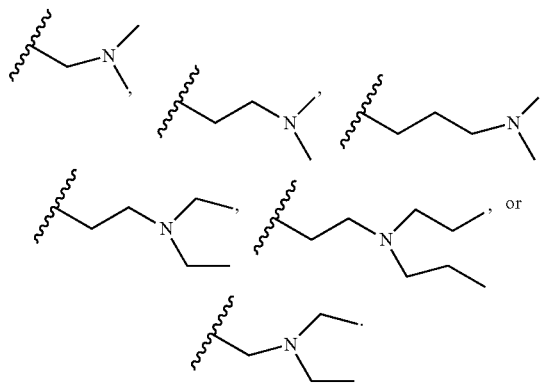

In some embodiments, $R^3$ in Formula (II) or (II*) is

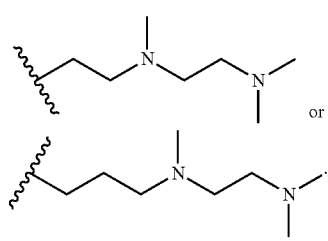

In some embodiments, $R^3$ in Formula (II) or (II*) is

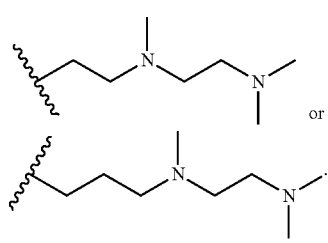

In some embodiments, $R^3$ in Formula (II) or (II*) is

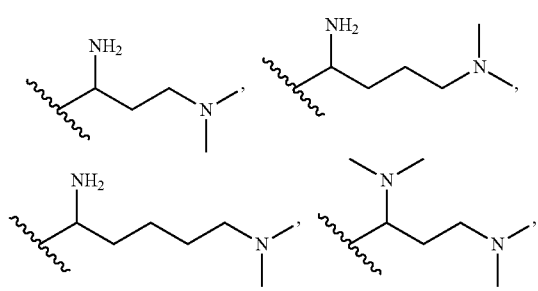

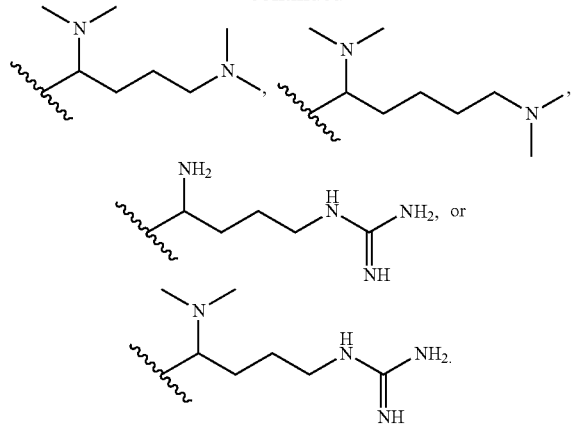

In some embodiments, $R^3$ in Formula (II) or (II*) is

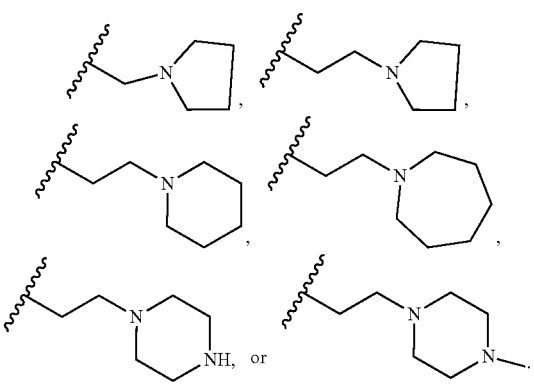

In some embodiments, $R^3$ in Formula (II) or (II*) is

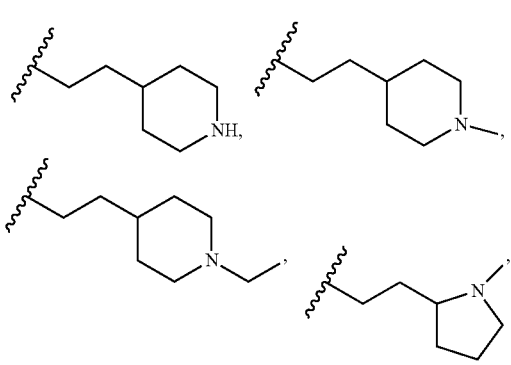

In some embodiments, $R^3$ in Formula (II) or (II*) is

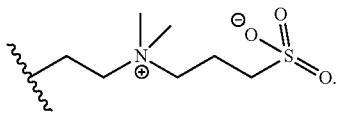 [SMILES: *CC[N+](C)(C)CCCS(=O)(=O)[O-]]

In some embodiments, Z in Formula (II) or (II*) is —C(=O)O— or —OC(=O)—. In some embodiments, Z in Formula (II) or (II*) is —C(=O)O—. In some embodiments, Z in Formula (II) or (II*) is —OC(=O)—. In some embodiments, Z in Formula (II) or (II*) is —C(=O)NR$^4$— or —NR$^4$C(=O)—. In some embodiments, Z in Formula (II) or (II*) is —C(=O)NR$^4$—. In some embodiments, Z in Formula (II) or (II*) is —NR$^4$C(=O)—. In some embodiments, $R^4$ in Z is hydrogen or $C_1$-$C_4$ alkyl. In some embodiments, $R^4$ in Z is hydrogen. In some embodiments, $R^4$ in Z is $C_1$-$C_4$ alkyl. In some embodiments, Z in Formula (II) or (II*) is —C(=O)N(CH$_3$)—, —N(CH$_3$)C(=O)—, —C(=O)NH—, or —NHC(=O)—. In some embodiments, Z in Formula (II) or (II*) is —OC(=O)O—, —NR$^4$C(=O)O—, —OC(=O)NR$^4$—, or —NR$^4$C(=O)NR$^4$—. In some embodiments, Z in Formula (II) or (II*) is —OC(=O)O—, —NHC(=O)O—, —OC(=O)NH—, —NHC(=O)NH—, —N(CH$_3$)C(=O)O—, —OC(=O)N(CH$_3$)—, —N(CH$_3$)C(=O)N(CH$_3$)—, —NHC(=O)N(CH$_3$)— or —N(CH$_3$)C(=O)NH—. In some embodiments, Z in Formula (II) or (II*) is —OC(=O)O—, —NHC(=O)O—, —OC(=O)NH—, or —NHC(=O)NH—.

In one aspect, disclosed herein is an amino lipid of Table 1A, or a salt or solvate thereof.

TABLE 1A
Amino lipids for constituting lipid nanoparticles. The chiral carbon atom(s) in any of the structures indicate(s) racemic, and/or chirally pure R and S stereoisomers.
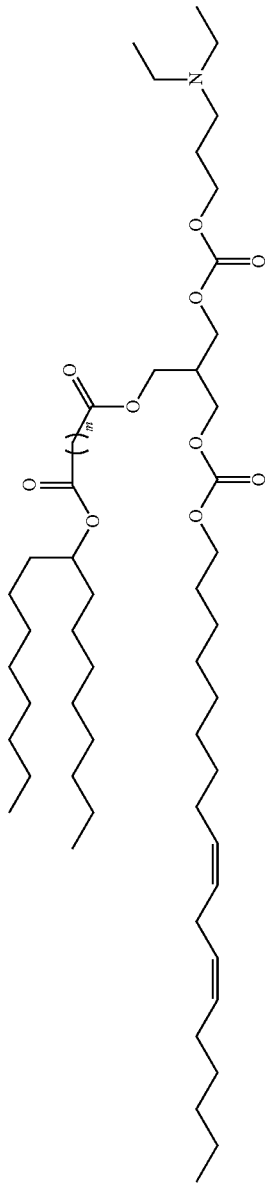
m = 1-10
VL011-VL020
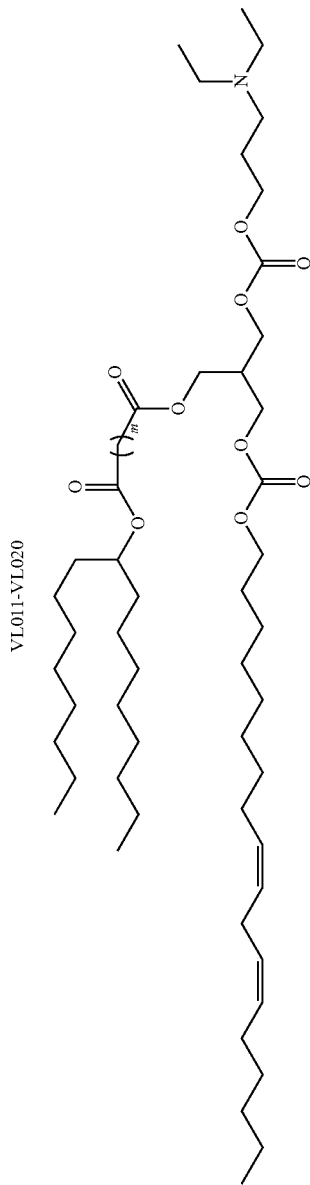
m = 1-10
VL021-VL030
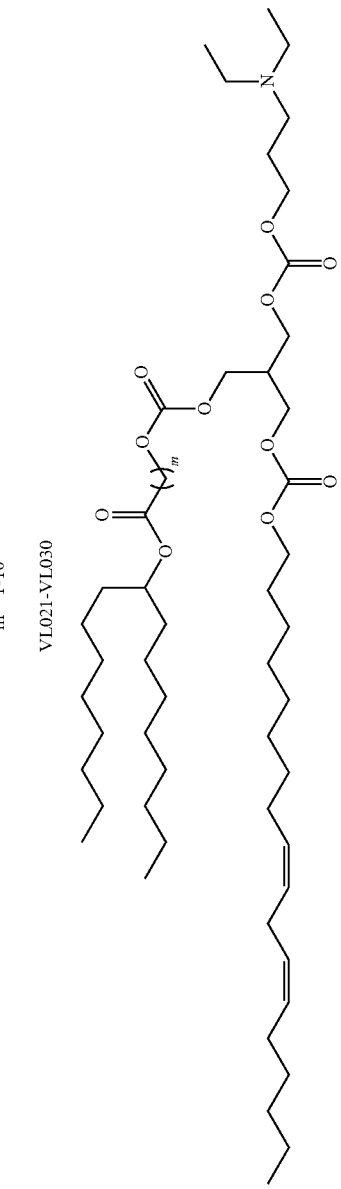
m = 1-10

TABLE 1A-continued
Amino lipids for constituting lipid nanoparticles. The chiral carbon atom(s) in any of the structures indicate(s) racemic, and/or chirally pure R and S stereoisomers.
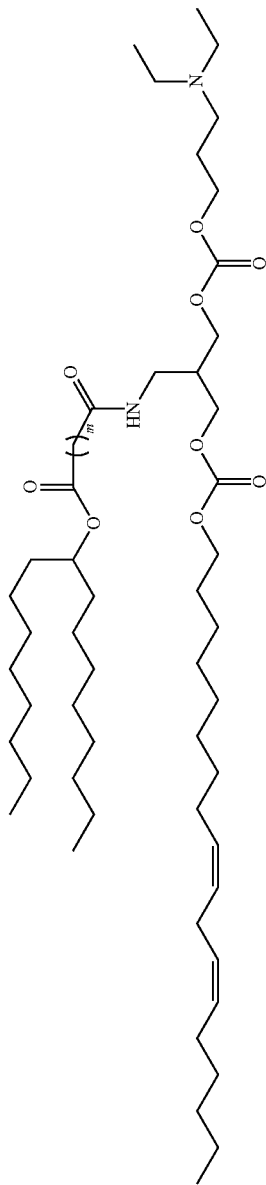
VL031-VL040
VL041-VL050
m = 1-10
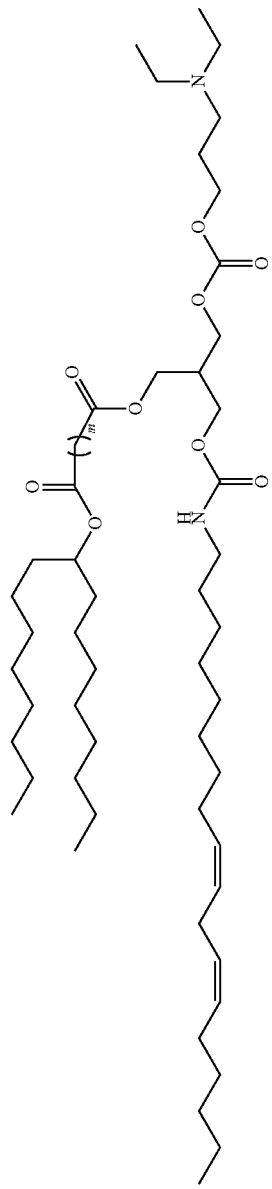
VL051-VL060
m = 1-10

TABLE 1A-continued
Amino lipids for constituting lipid nanoparticles. The chiral carbon atom(s) in any of the structures indicate(s) racemic, and/or chirally pure R and S stereoisomers.
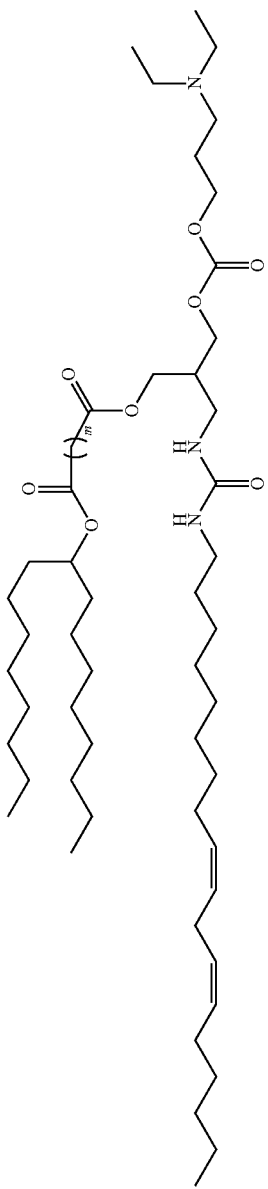
m = 1-10
VL061-VL070
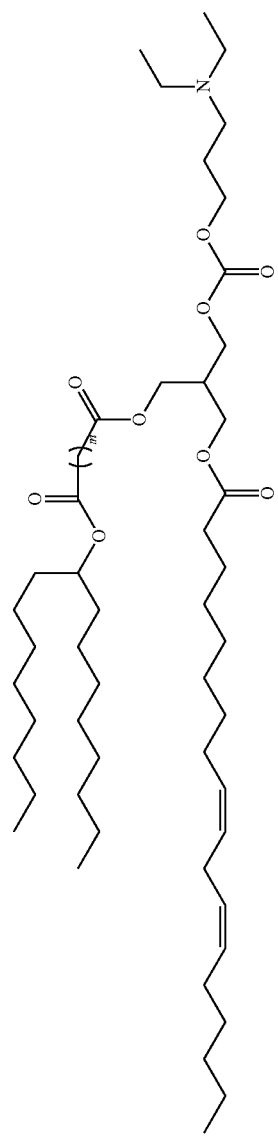
m = 1-10
VL071-VL080
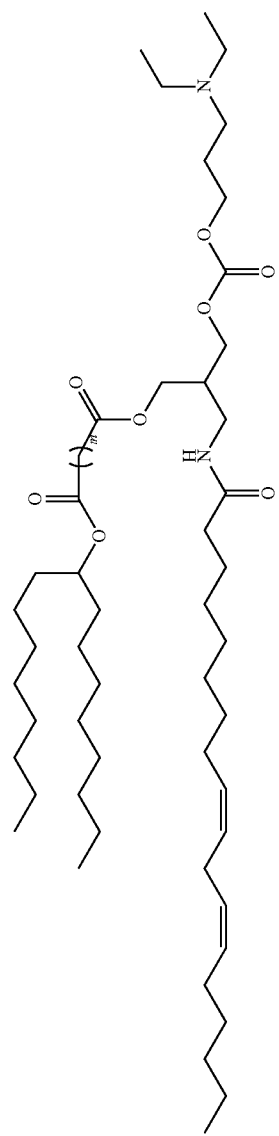
m = 1-10

TABLE 1A-continued
Amino lipids for constituting lipid nanoparticles. The chiral carbon atom(s) in any of the structures indicate(s) racemic, and/or chirally pure R and S stereoisomers.
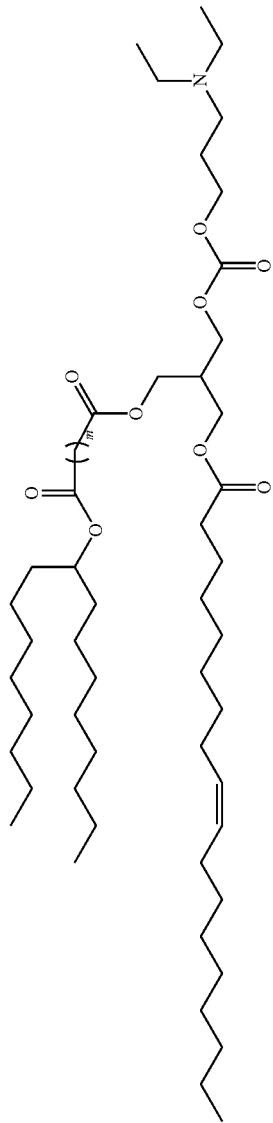
VL081-VL090
m = 1-10
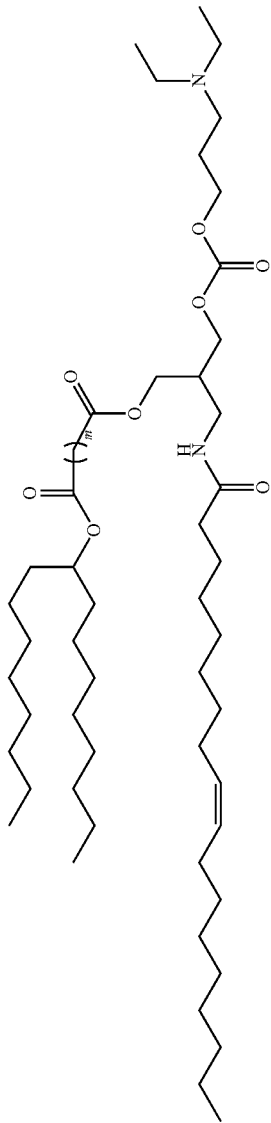
VL091-VL10
m = 1-10
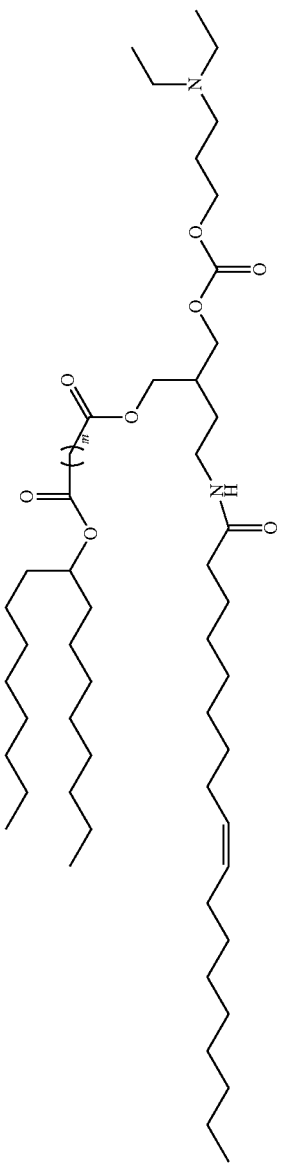
VL101-VL110
m = 1-10

TABLE 1A-continued
Amino lipids for constituting lipid nanoparticles. The chiral carbon atom(s) in any of the structures indicate(s) racemic, and/or chirally pure R and S stereoisomers.
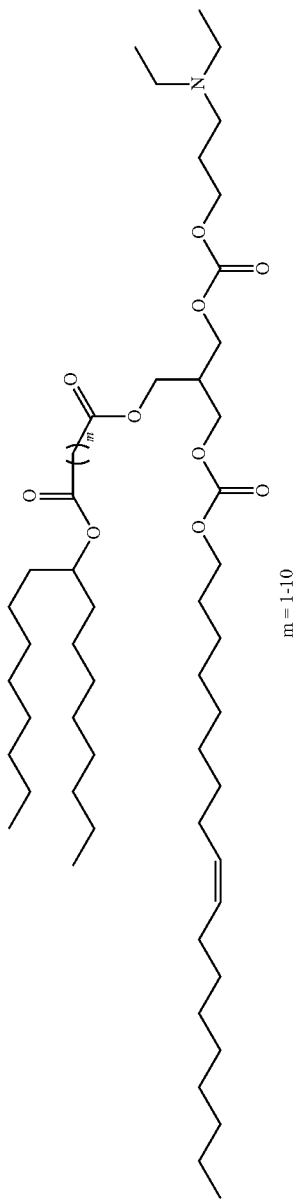
VL111-VL120
m = 1-10
VL121-VL130
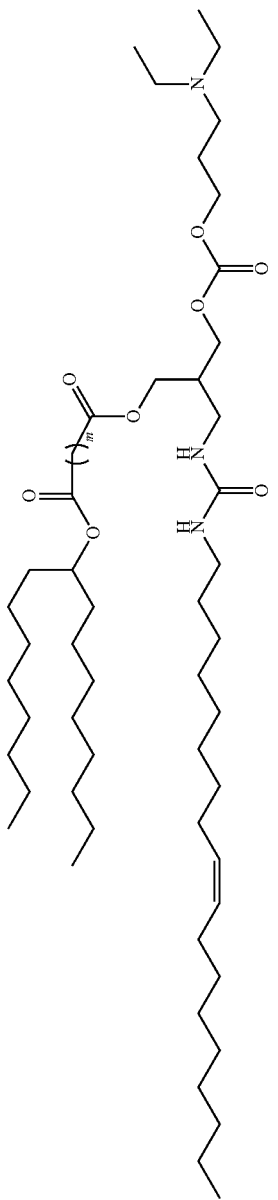
m = 1-10
VL131-VL140

TABLE 1A-continued
Amino lipids for constituting lipid nanoparticles. The chiral carbon atom(s) in any of the structures indicate(s) racemic, and/or chirally pure R and S stereoisomers.
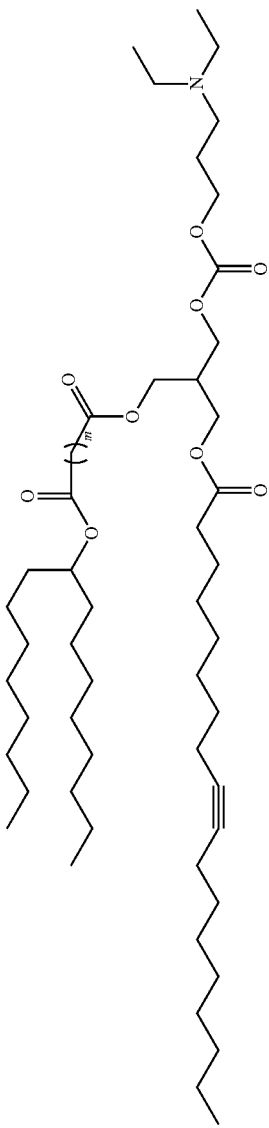
m = 1-10
VL141-VL150
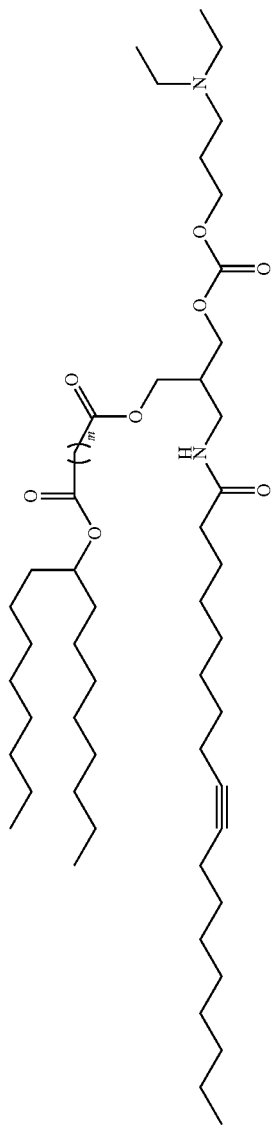
m = 1-10
VL151-VL160
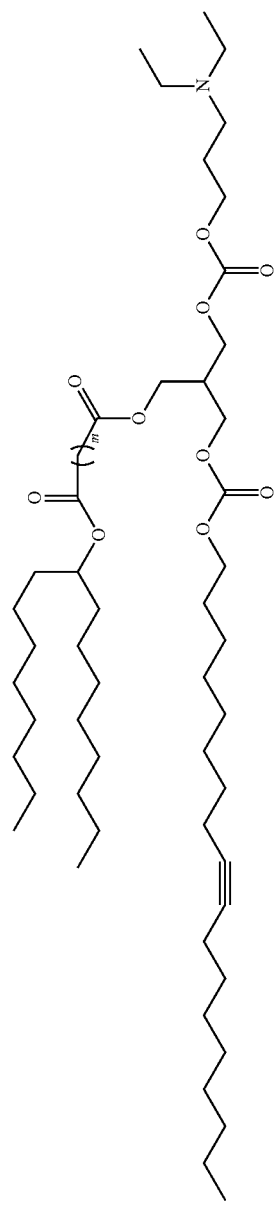
m = 1-10
VL161-VL170

TABLE 1A-continued
Amino lipids for constituting lipid nanoparticles. The chiral carbon atom(s) in any of the structures indicate(s) racemic, and/or chirally pure R and S stereoisomers.
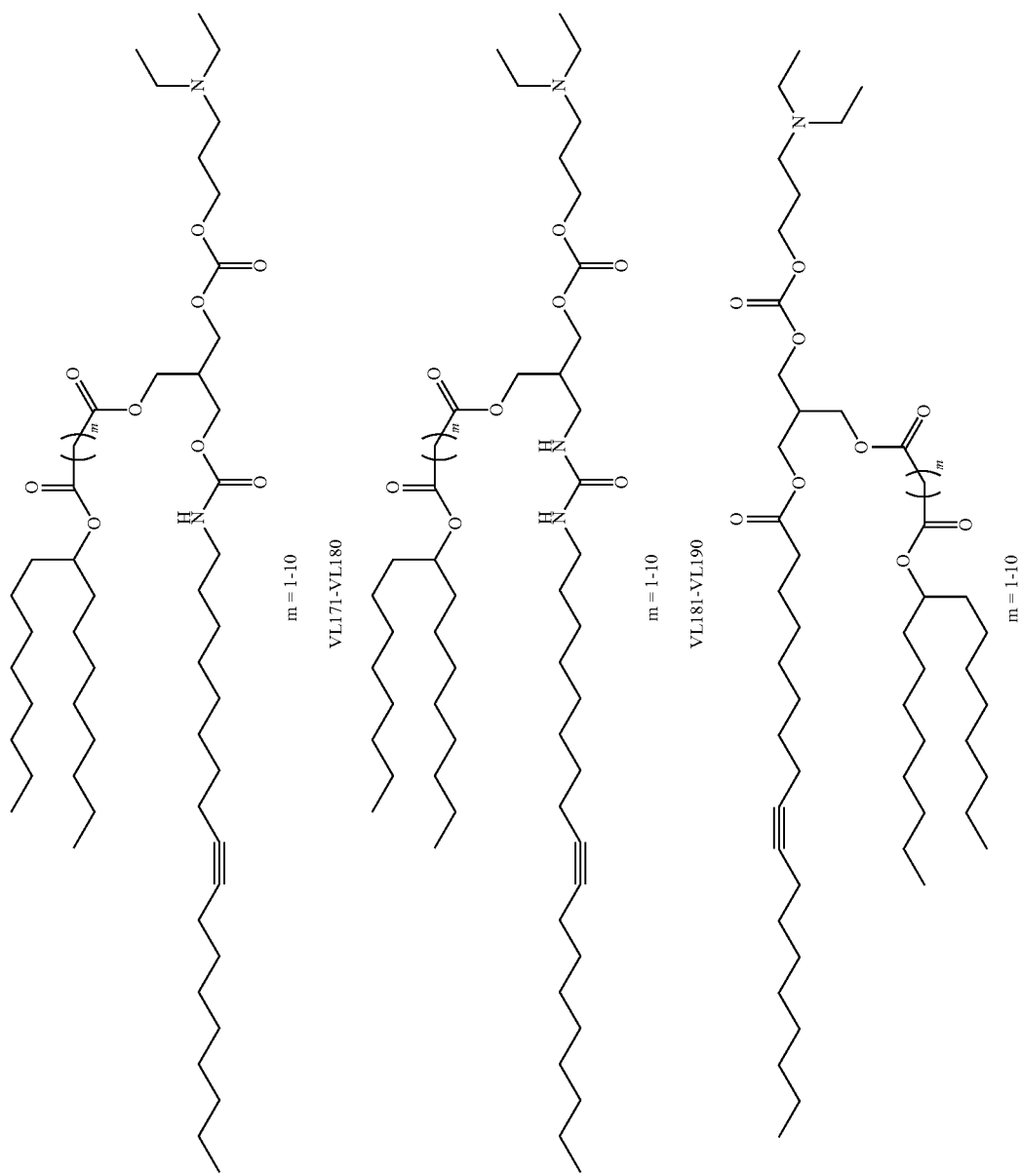
m = 1-10
VL171-VL180
m = 1-10
VL181-VL190
m = 1-10

TABLE 1A-continued
Amino lipids for constituting lipid nanoparticles. The chiral carbon atom(s) in any of the structures indicate(s) racemic, and/or chirally pure R and S stereoisomers.
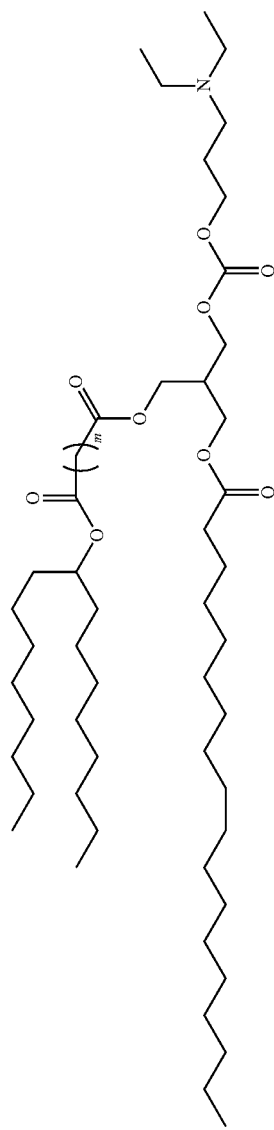
VL191-VL200
m = 1-10
VL201-VL210
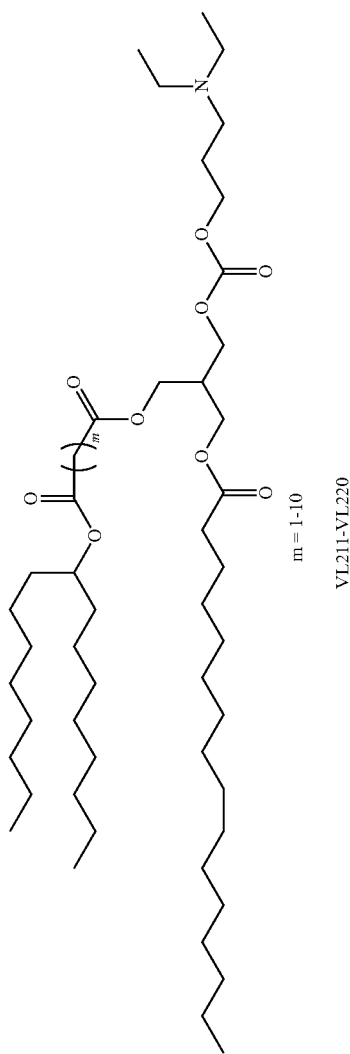
m = 1-10
VL211-VL220

TABLE 1A-continued
Amino lipids for constituting lipid nanoparticles. The chiral carbon atom(s) in any of the structures indicate(s) racemic, and/or chirally pure R and S stereoisomers.
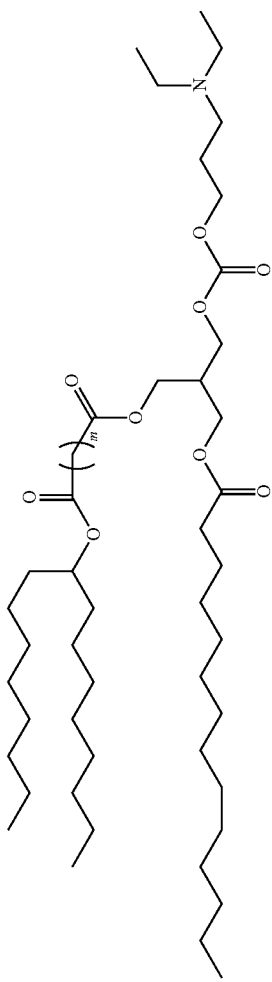
m = 1-10
VL221-VL230
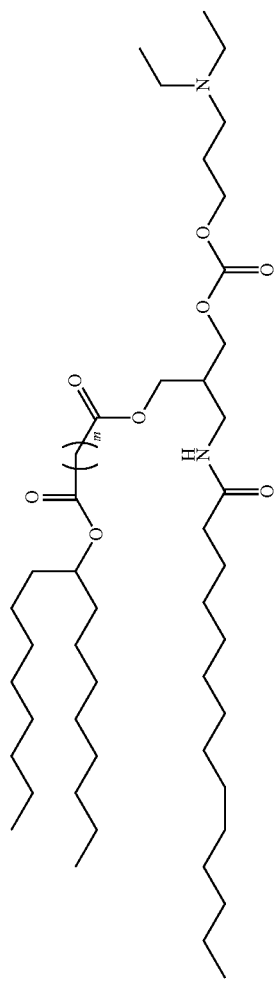
m = 1-10
VL251-260
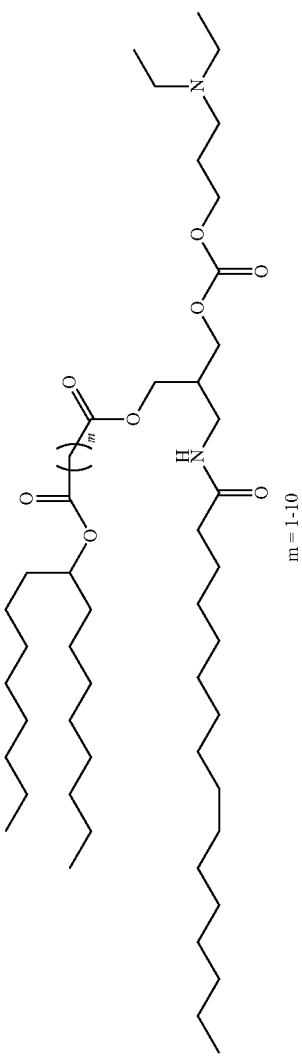
m = 1-10

TABLE 1A-continued
Amino lipids for constituting lipid nanoparticles. The chiral carbon atom(s) in any of the structures indicate(s) racemic, and/or chirally pure R and S stereoisomers.
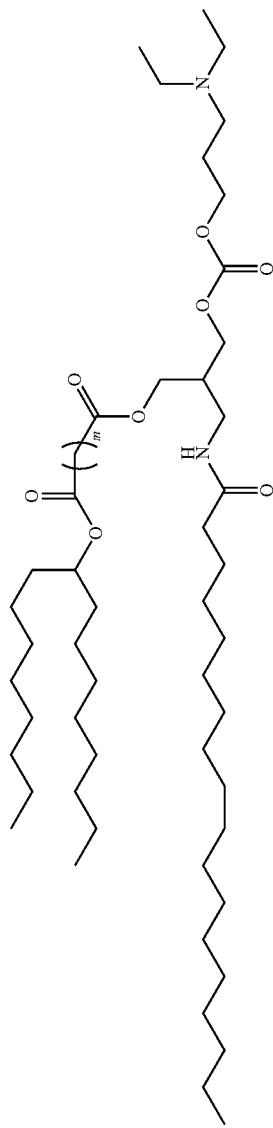
VL261-270
m = 1-10
VL271-280
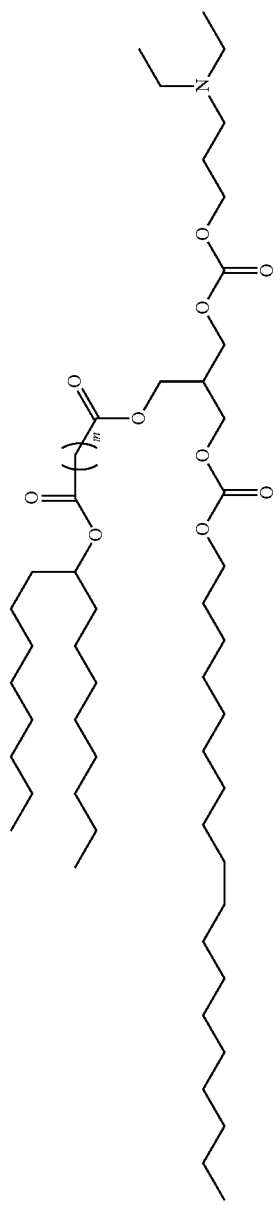
m = 1-10
VL281-290

TABLE 1A-continued
Amino lipids for constituting lipid nanoparticles. The chiral carbon atom(s) in any of the structures indicate(s) racemic, and/or chirally pure R and S stereoisomers.
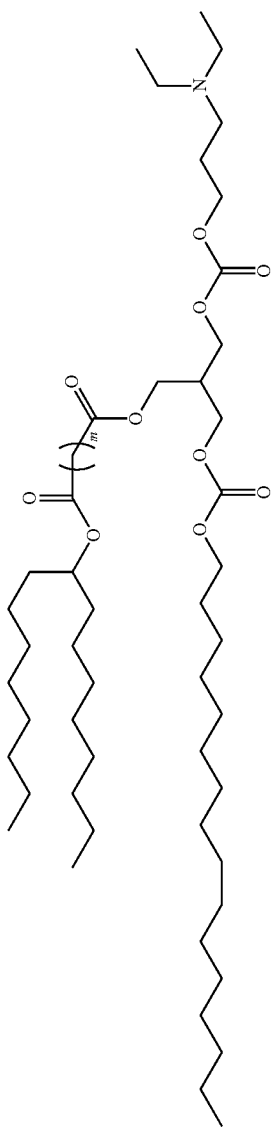
m = 1-10
VL291-VL300
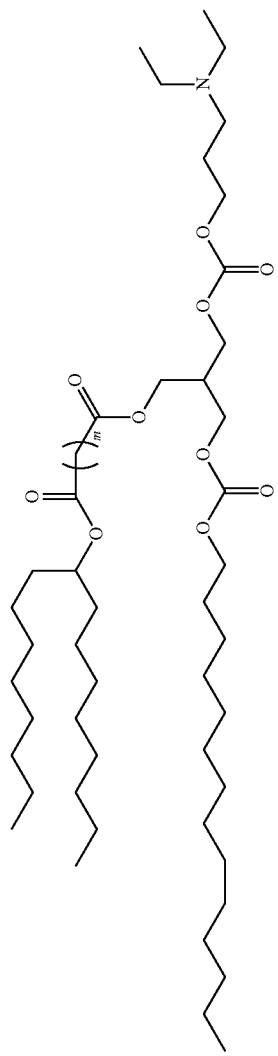
m = 1-10
VL301-VL310
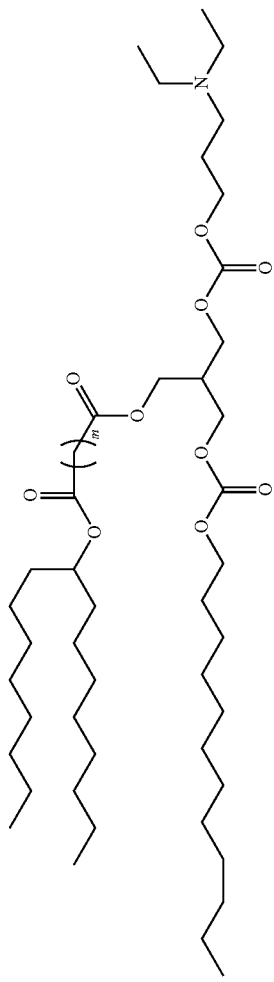
m = 1-10

TABLE 1A-continued

Amino lipids for constituting lipid nanoparticles. The chiral carbon atom(s) in any of the structures indicate(s) racemic, and/or chirally pure R and S stereoisomers.

VL311-VL320 m = 1-10

VL321-VL330

VL331-VL340 m = 1-10

TABLE 1A-continued
Amino lipids for constituting lipid nanoparticles. The chiral carbon atom(s) in any of the structures indicate(s) racemic, and/or chirally pure R and S stereoisomers.
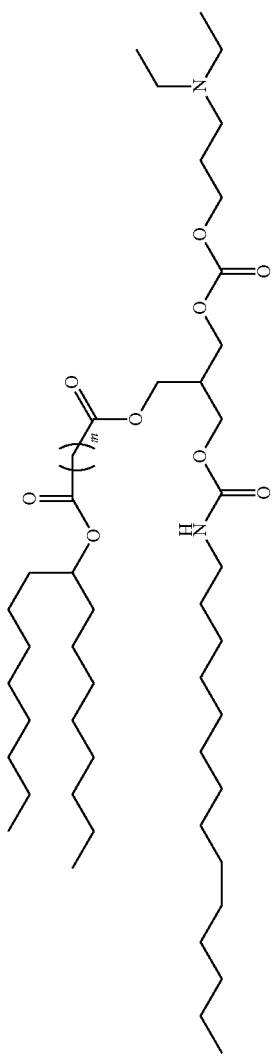
m = 1-10
VL341-VL350
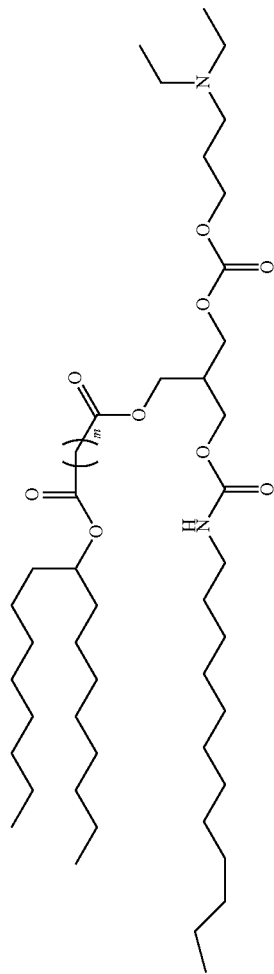
m = 1-10
VL351-VL360
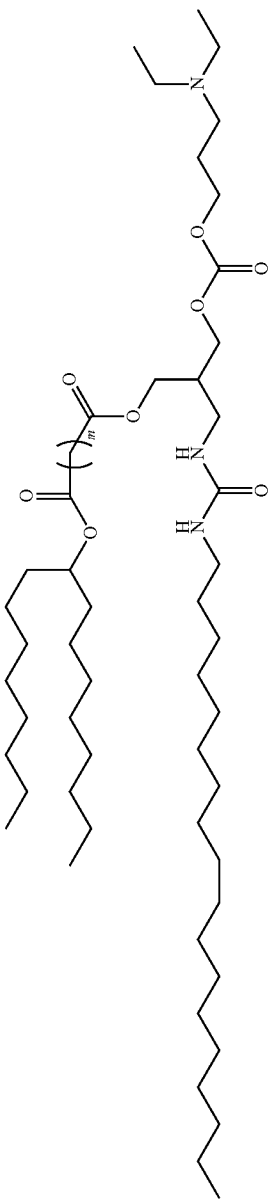
m = 1-10

TABLE 1A-continued
Amino lipids for constituting lipid nanoparticles. The chiral carbon atom(s) in any of the structures indicate(s) racemic, and/or chirally pure R and S stereoisomers.
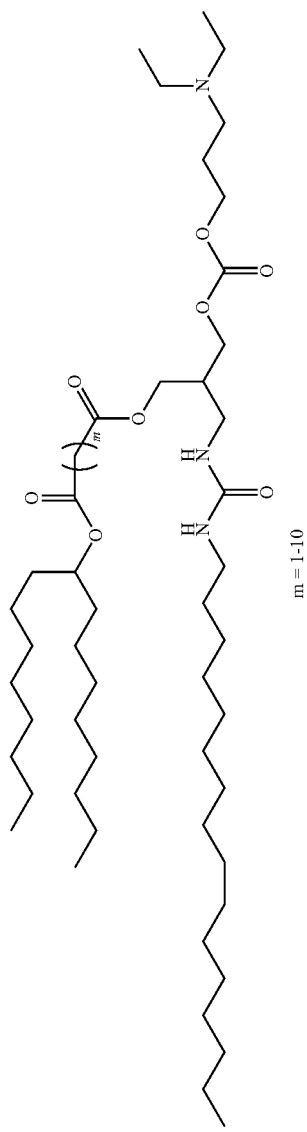
VL361-VL370
m = 1-10
VL371-VL380
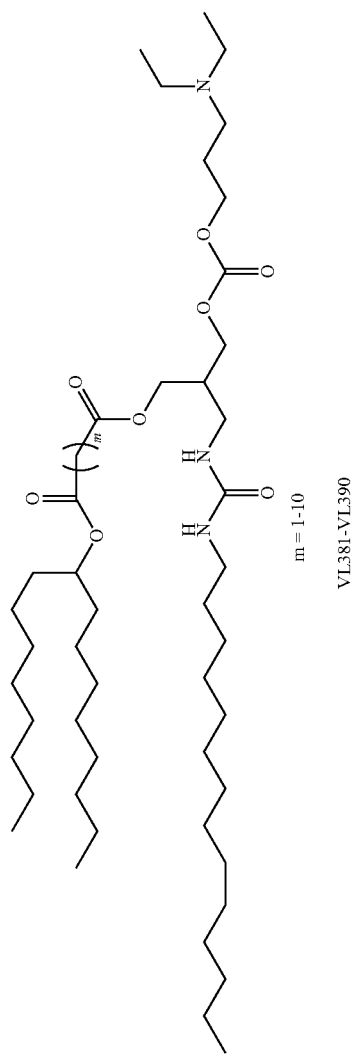
m = 1-10
VL381-VL390

TABLE 1A-continued
Amino lipids for constituting lipid nanoparticles. The chiral carbon atom(s) in any of the structures indicate(s) racemic, and/or chirally pure R and S stereoisomers.
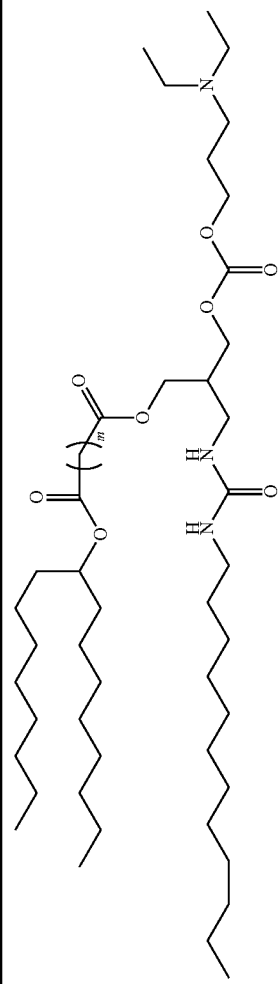
m = 1-10
VL391-VL400
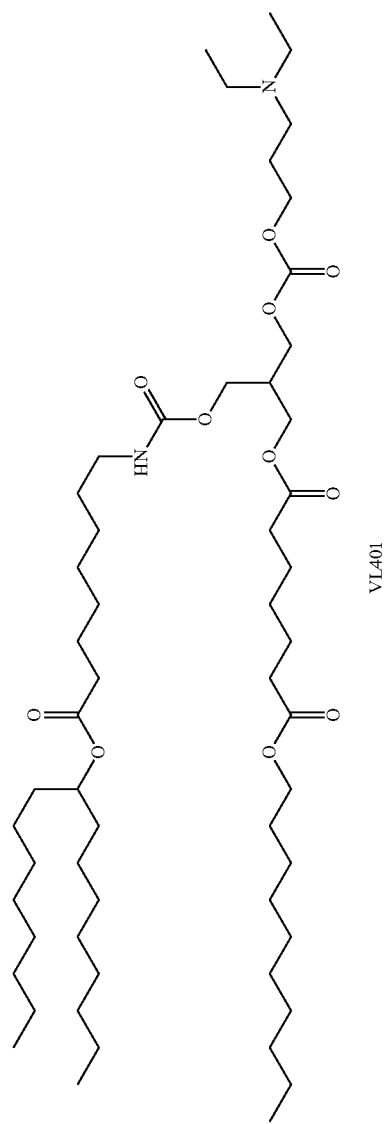
VL401

TABLE 1A-continued
Amino lipids for constituting lipid nanoparticles. The chiral carbon atom(s) in any of the structures indicate(s) racemic, and/or chirally pure R and S stereoisomers.
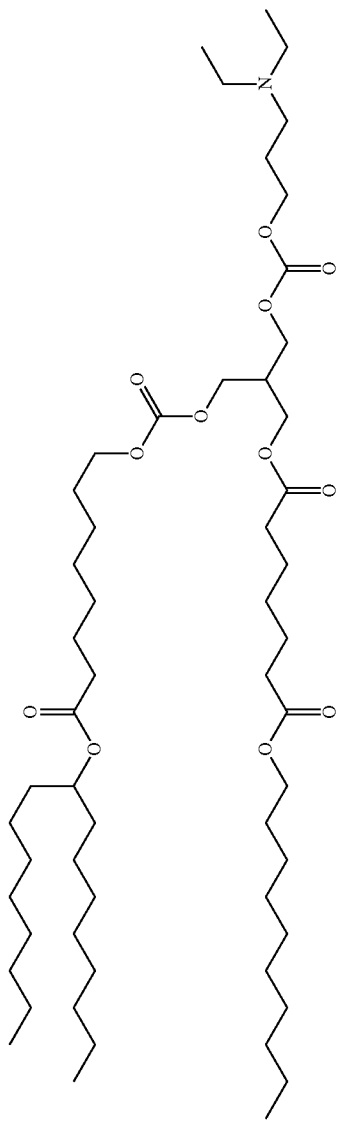
VL402
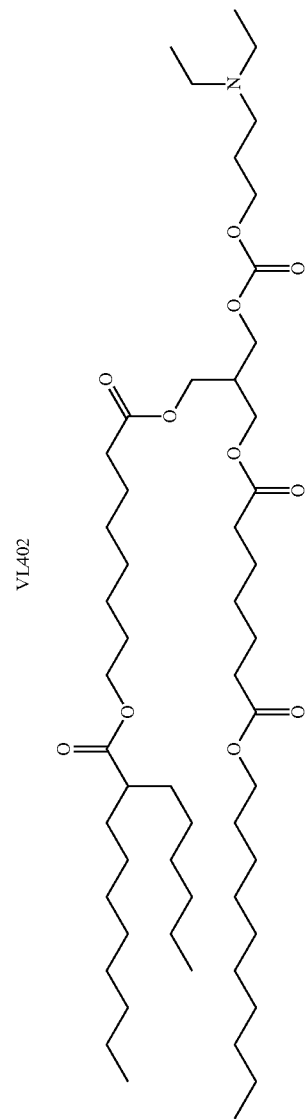
VL403
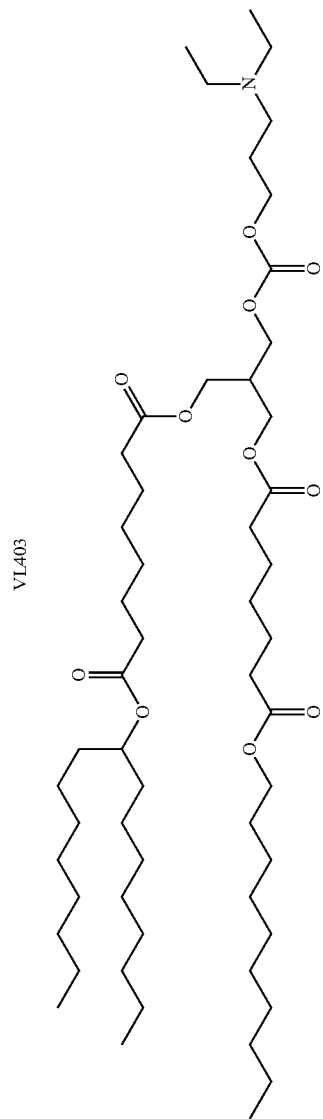
VL404

TABLE 1A-continued
Amino lipids for constituting lipid nanoparticles. The chiral carbon atom(s) in any of the structures indicate(s) racemic, and/or chirally pure R and S stereoisomers.
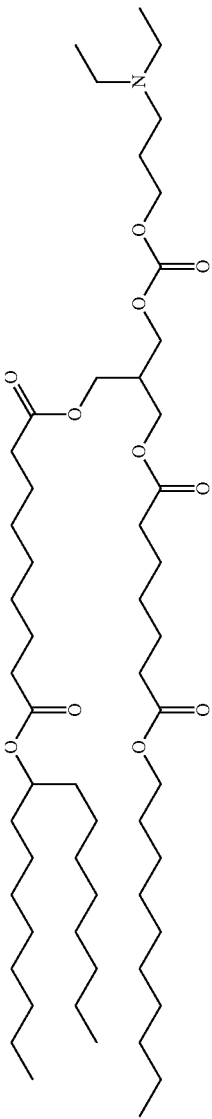
VL405
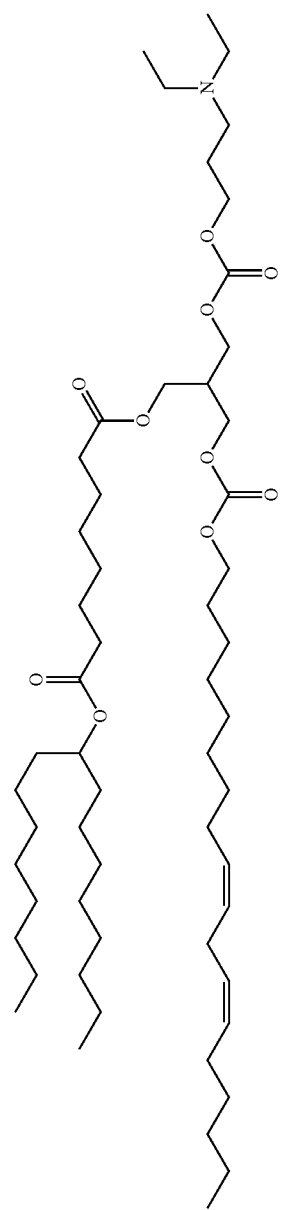
VL406
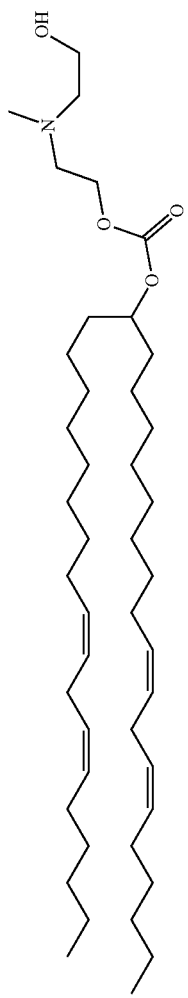
VL407

TABLE 1A-continued
Amino lipids for constituting lipid nanoparticles. The chiral carbon atom(s) in any of the structures indicate(s) racemic, and/or chirally pure R and S stereoisomers.
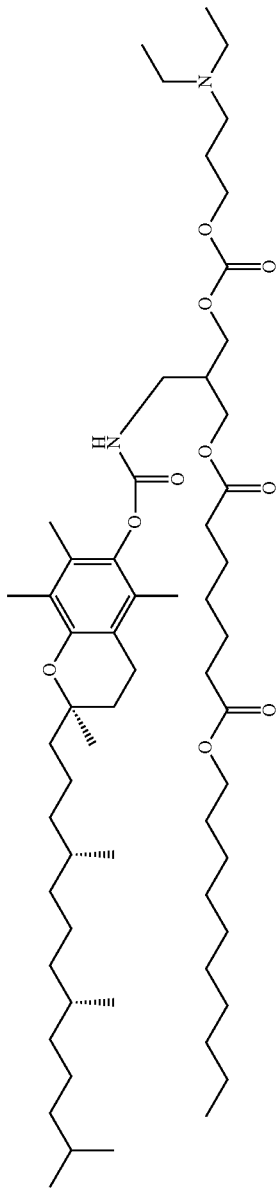
VL408
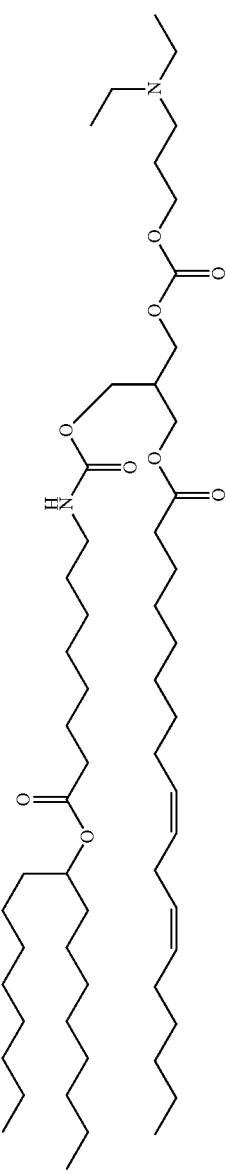
VL409
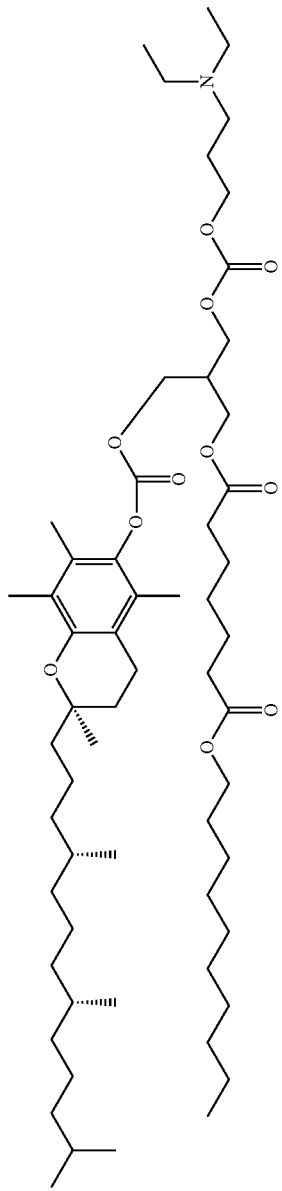
VL410

TABLE 1A-continued
Amino lipids for constituting lipid nanoparticles. The chiral carbon atom(s) in any of the structures indicate(s) racemic, and/or chirally pure R and S stereoisomers.
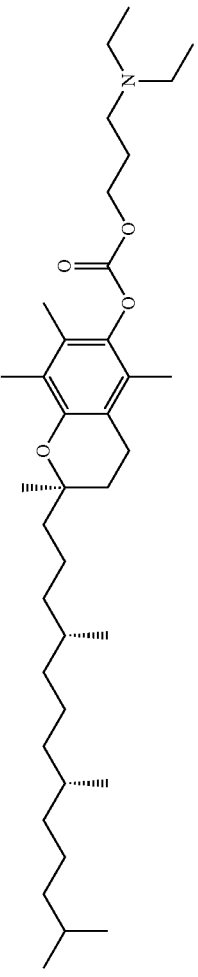
VL411
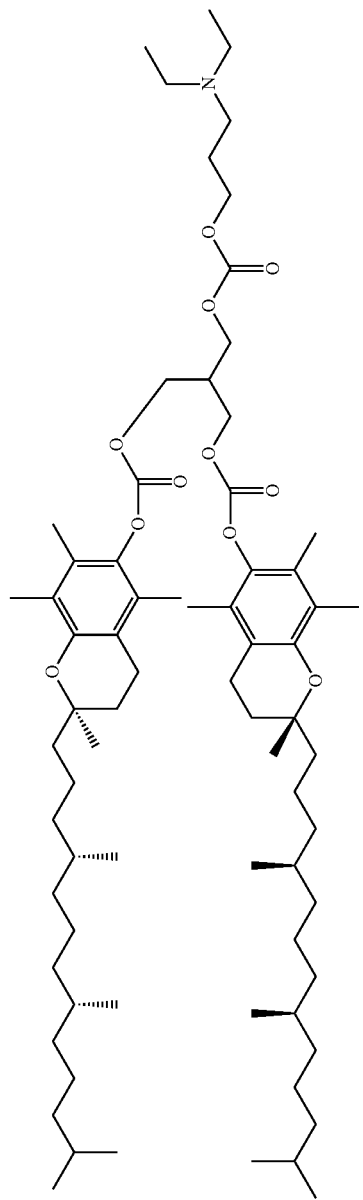
VL412
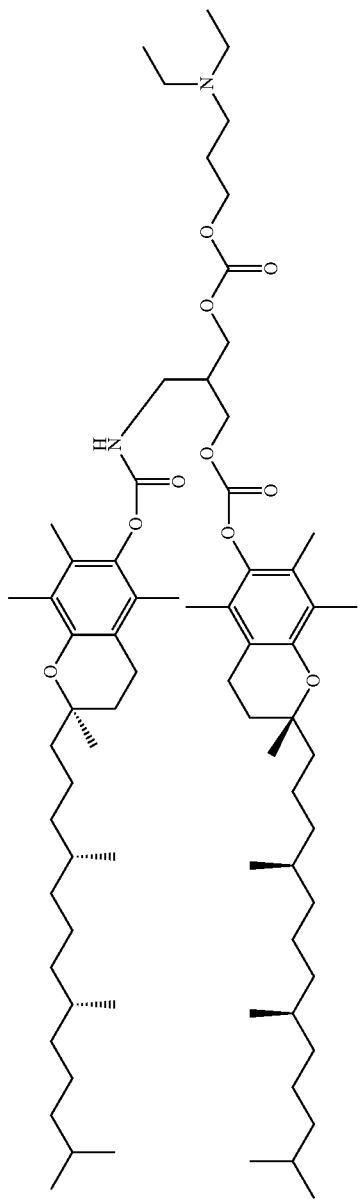
VL413

TABLE 1A-continued
Amino lipids for constituting lipid nanoparticles. The chiral carbon atom(s) in any of the structures indicate(s) racemic, and/or chirally pure R and S stereoisomers.
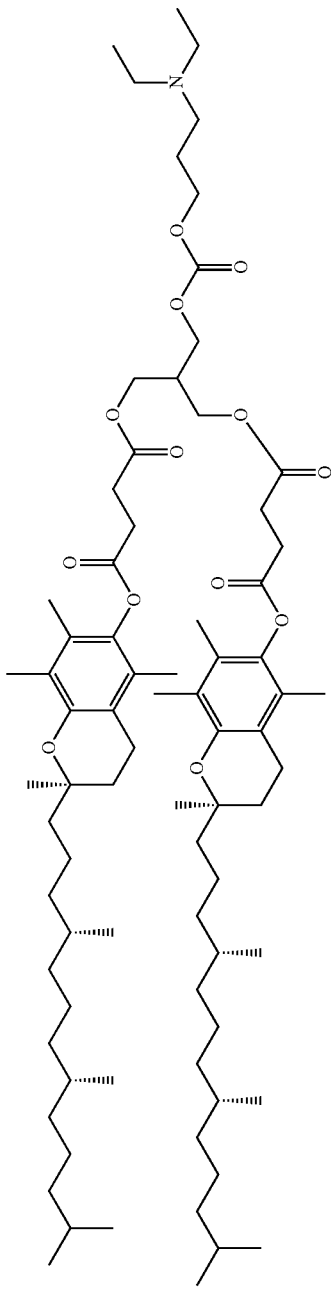
VL414
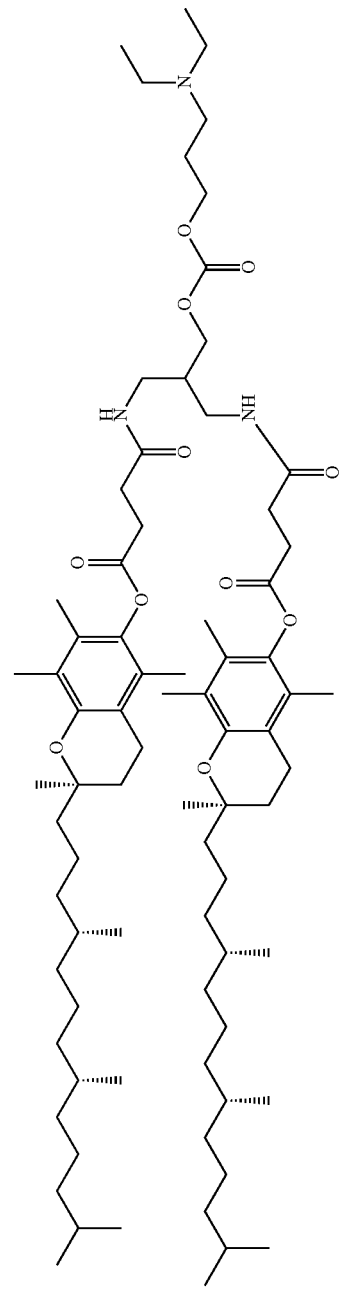
VL415

TABLE 1A-continued
Amino lipids for constituting lipid nanoparticles. The chiral carbon atom(s) in any of the structures indicate(s) racemic, and/or chirally pure R and S stereoisomers.
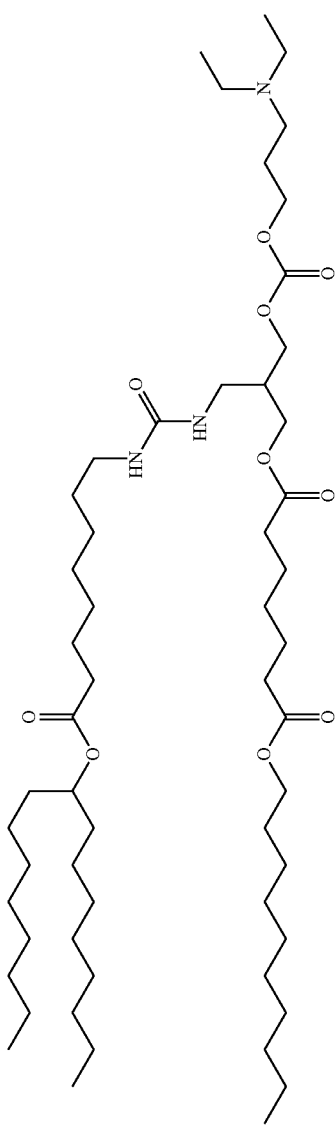
VL416
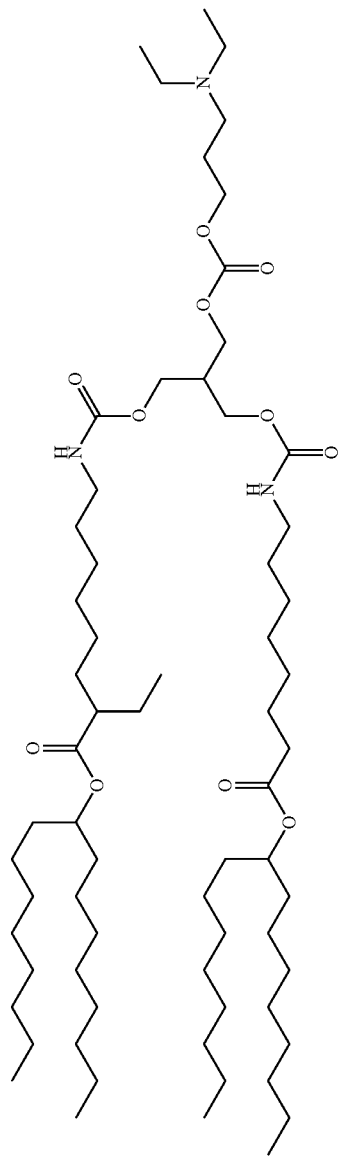
VL417

TABLE 1A-continued
Amino lipids for constituting lipid nanoparticles. The chiral carbon atom(s) in any of the structures indicate(s) racemic, and/or chirally pure R and S stereoisomers.
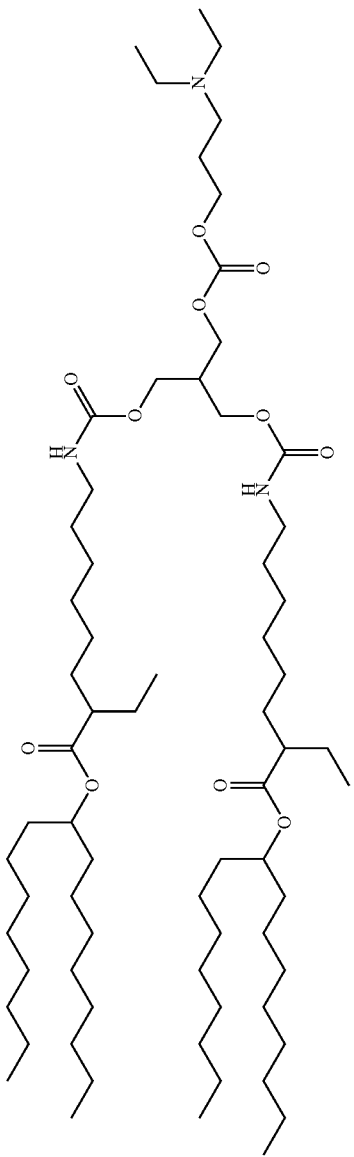
VL418
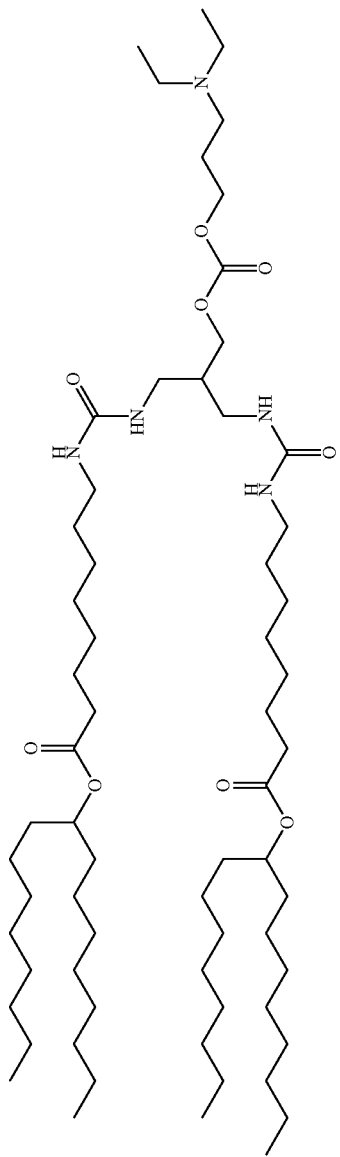
VL419

TABLE 1A-continued
Amino lipids for constituting lipid nanoparticles. The chiral carbon atom(s) in any of the structures indicate(s) racemic, and/or chirally pure R and S stereoisomers.
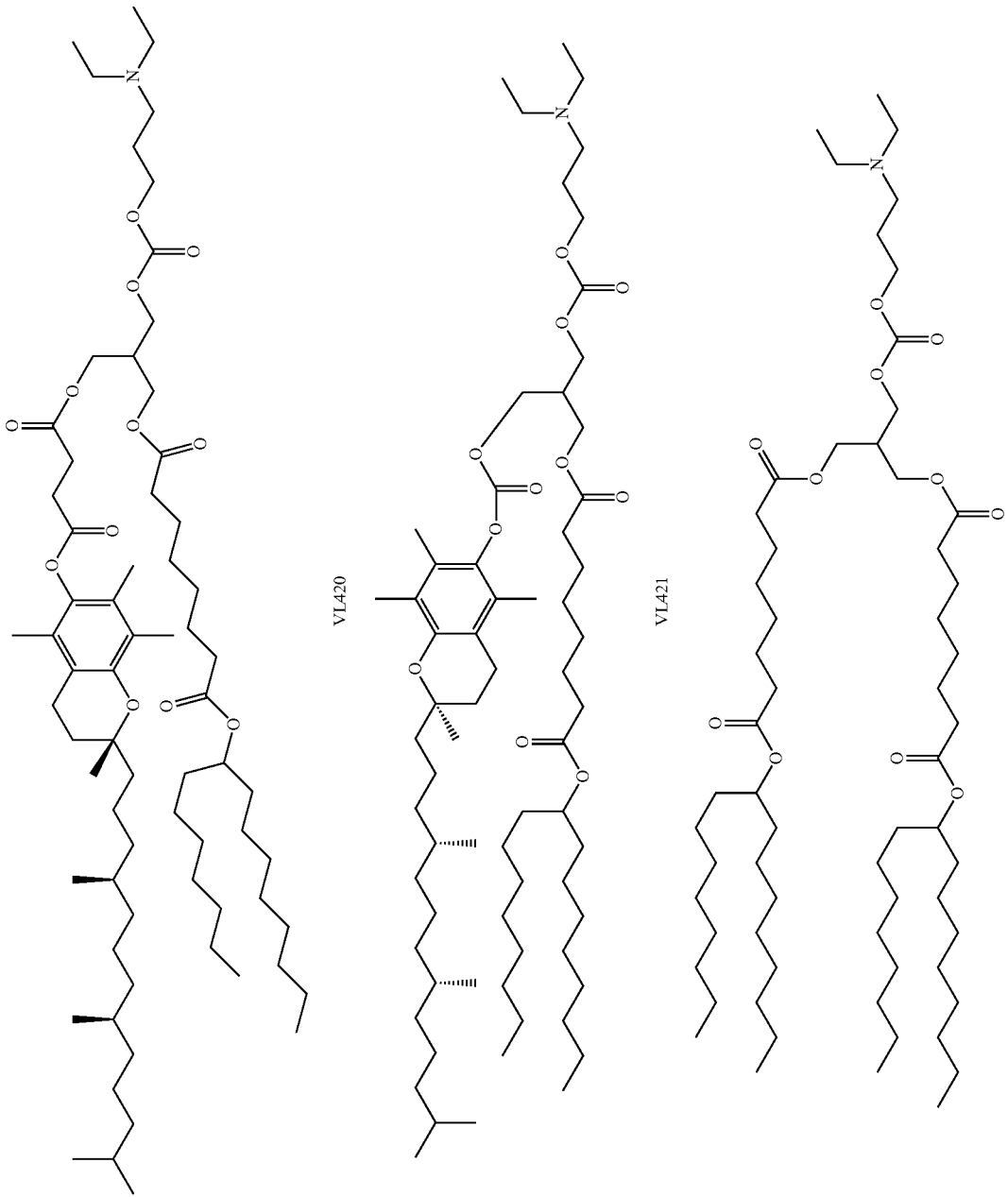

TABLE 1A-continued
Amino lipids for constituting lipid nanoparticles. The chiral carbon atom(s) in any of the structures indicate(s) racemic, and/or chirally pure R and S stereoisomers.
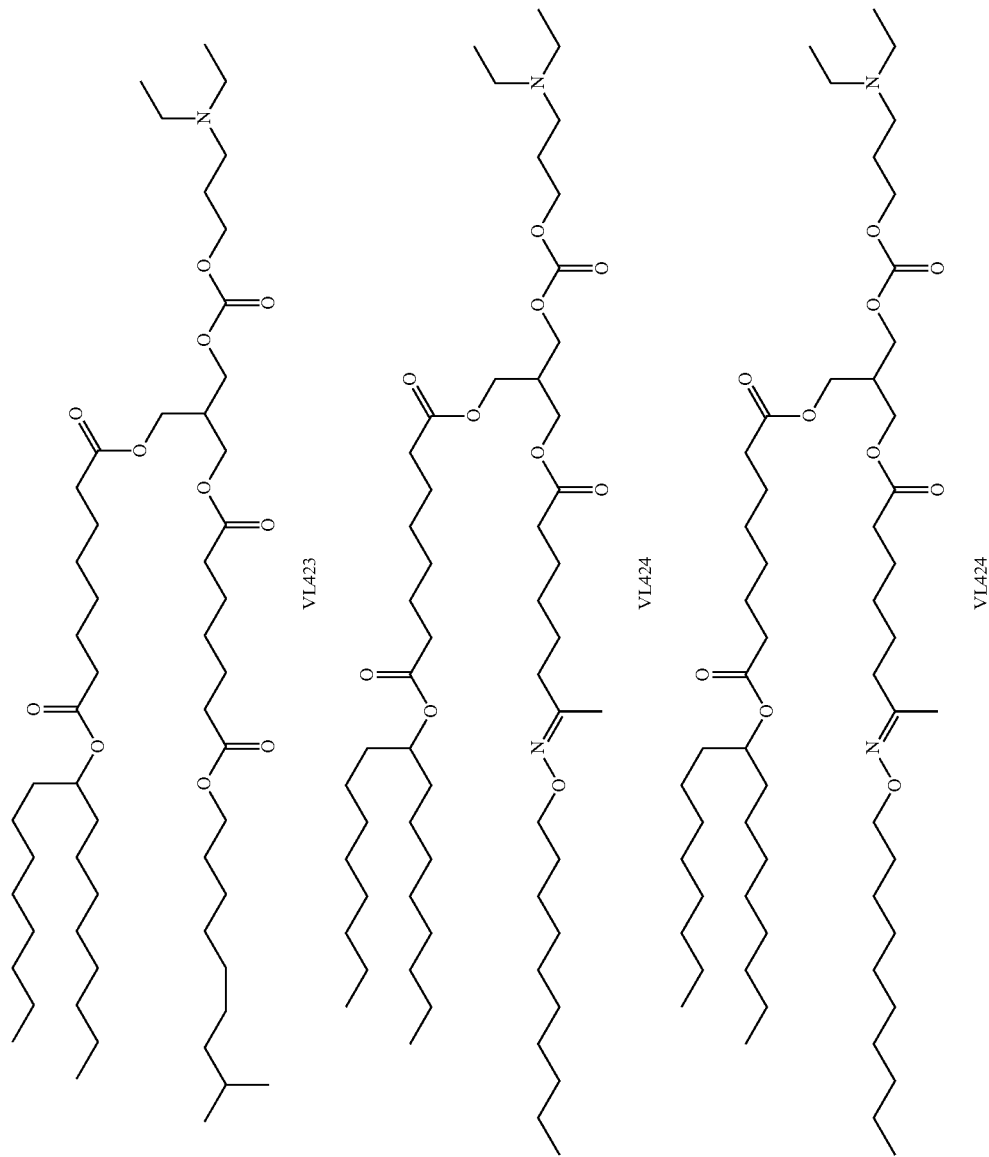

TABLE 1A-continued
Amino lipids for constituting lipid nanoparticles. The chiral carbon atom(s) in any of the structures indicate(s) racemic, and/or chirally pure R and S stereoisomers.
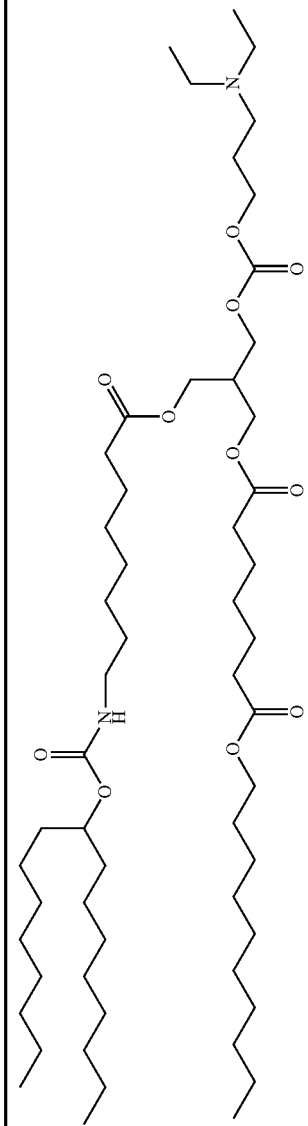
VL425
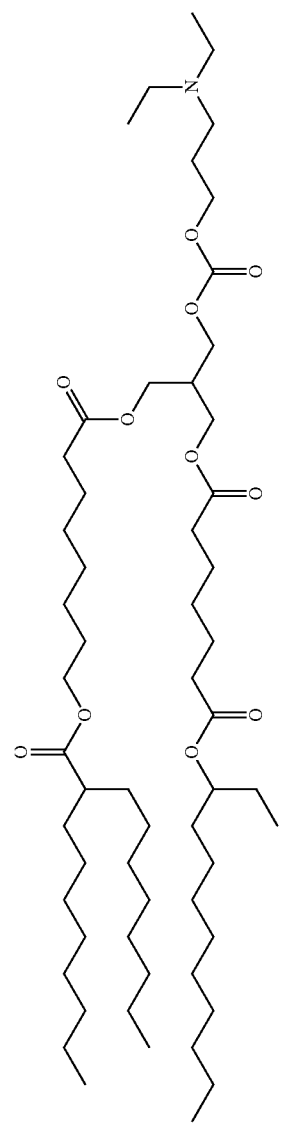
VL426
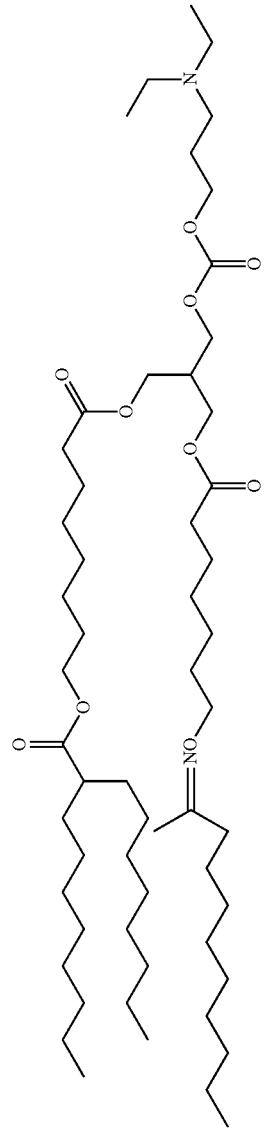
VL427

TABLE 1A-continued
Amino lipids for constituting lipid nanoparticles. The chiral carbon atom(s) in any of the structures indicate(s) racemic, and/or chirally pure R and S stereoisomers.
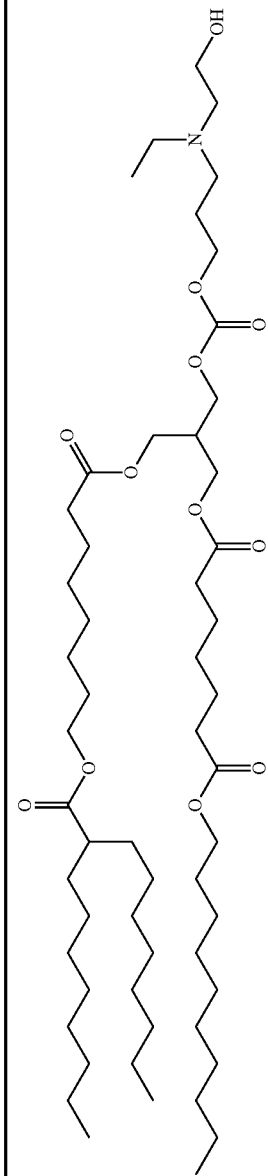
VL428
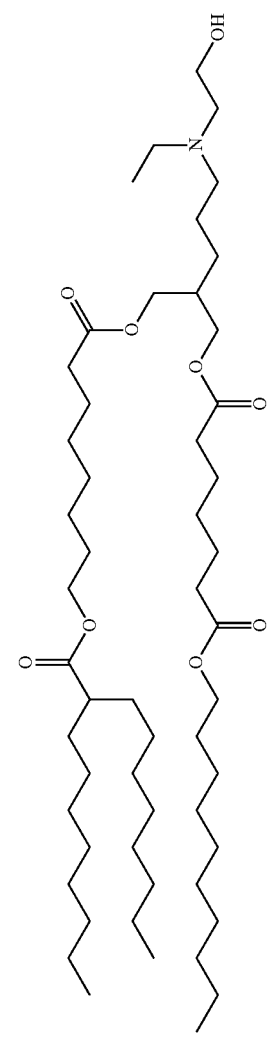
VL429
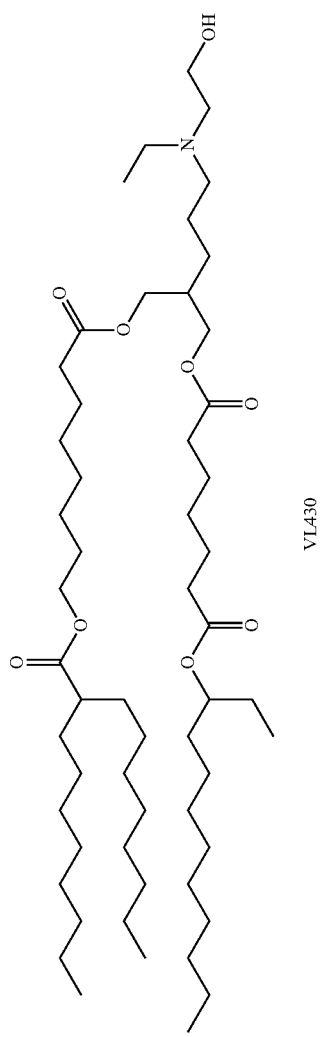
VL430

TABLE 1A-continued
Amino lipids for constituting lipid nanoparticles. The chiral carbon atom(s) in any of the structures indicate(s) racemic, and/or chirally pure R and S stereoisomers.
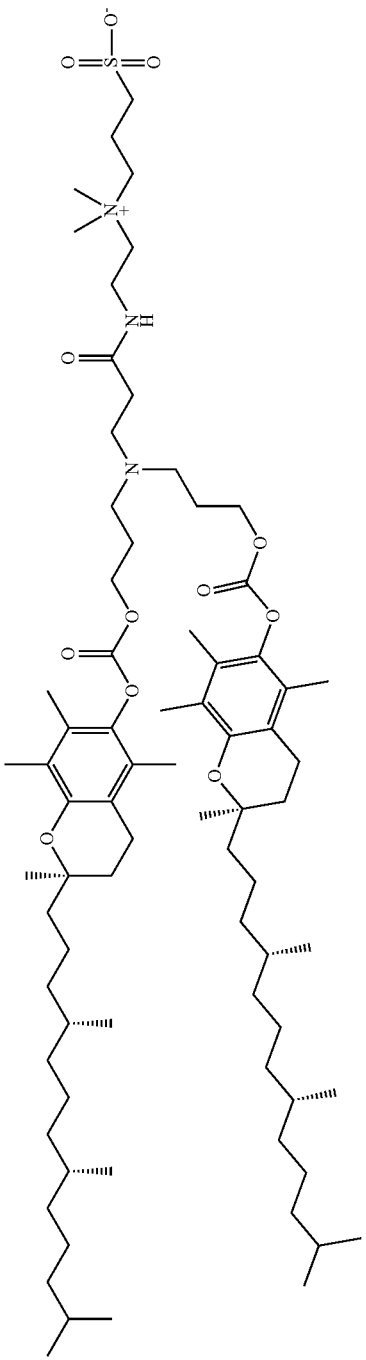
VL431
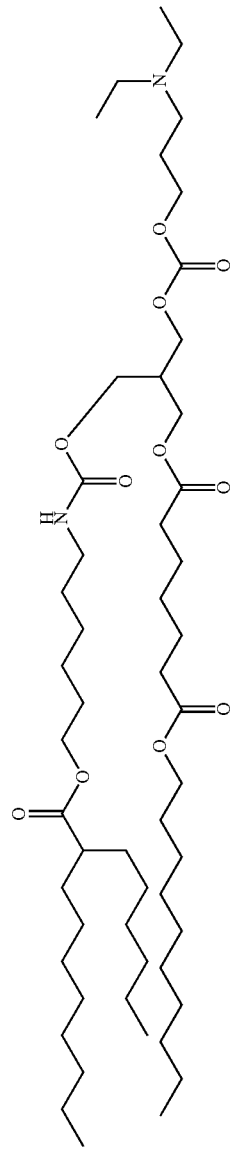
VL432
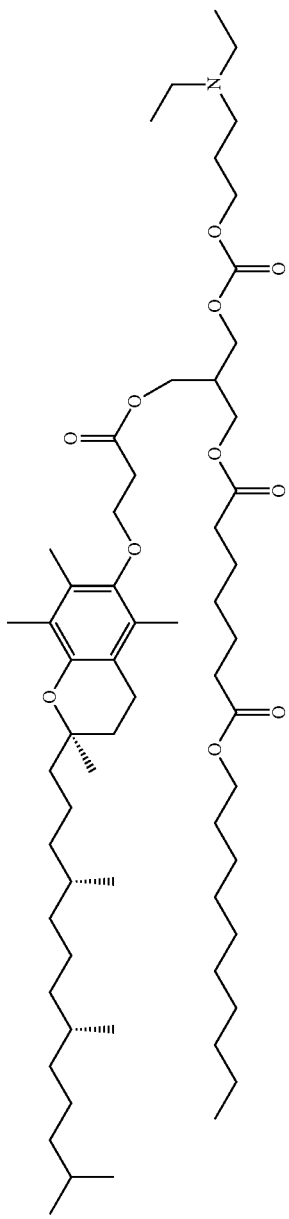
VL433

TABLE 1A-continued
Amino lipids for constituting lipid nanoparticles. The chiral carbon atom(s) in any of the structures indicate(s) racemic, and/or chirally pure R and S stereoisomers.
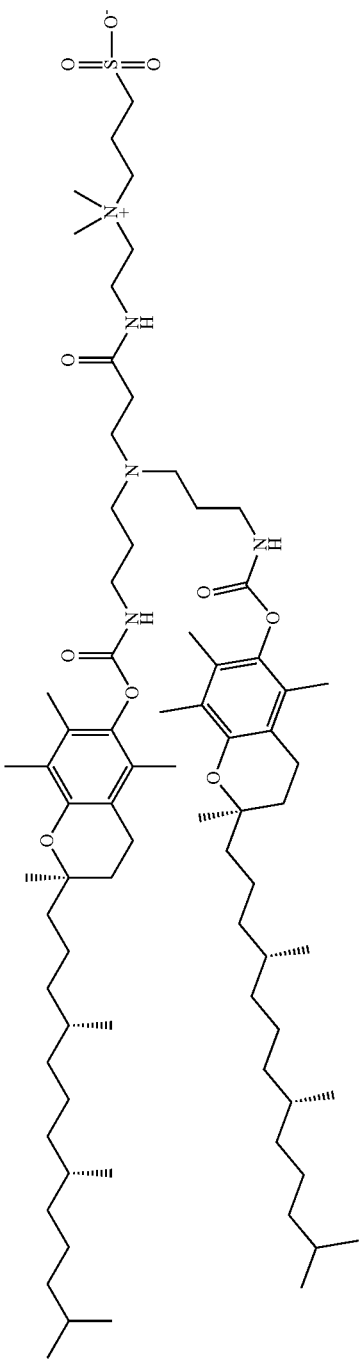
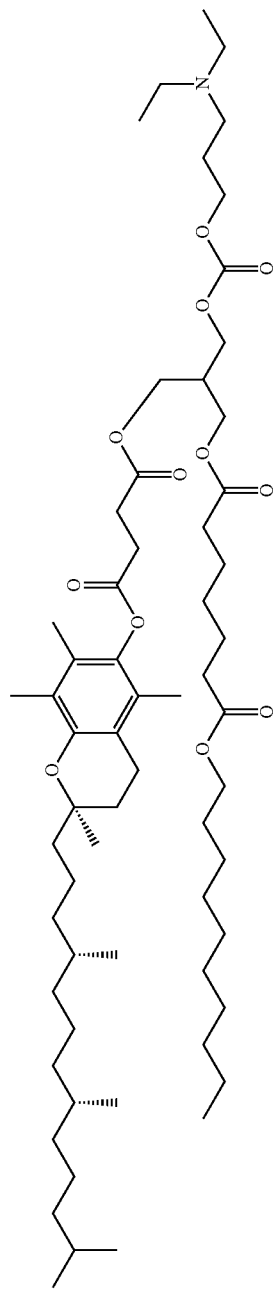
VL434
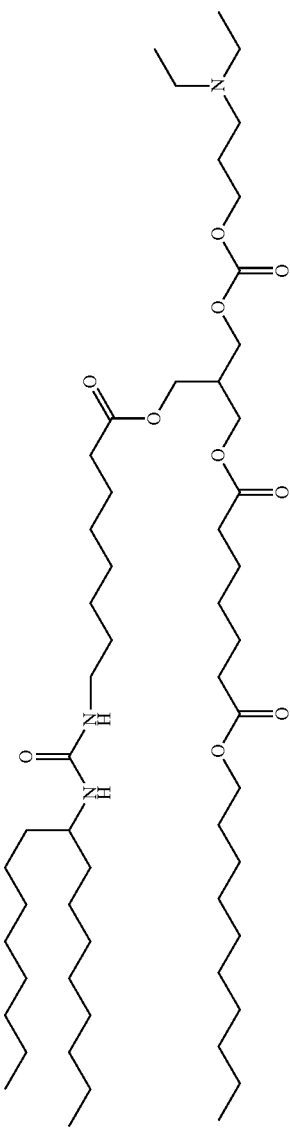
VL435

TABLE 1A-continued
Amino lipids for constituting lipid nanoparticles. The chiral carbon atom(s) in any of the structures indicate(s) racemic, and/or chirally pure R and S stereoisomers.
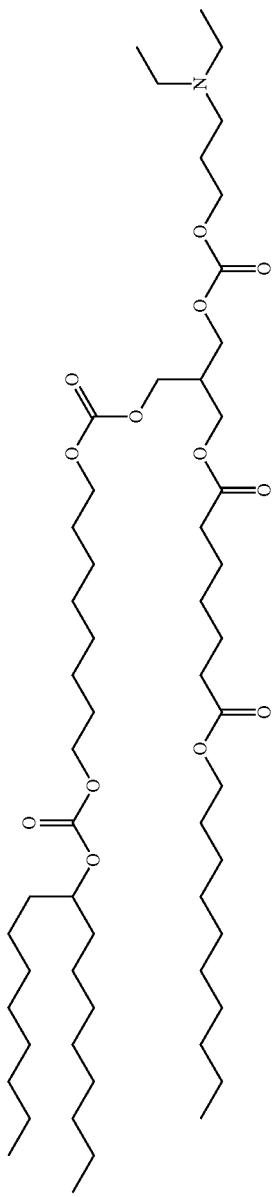
VL436
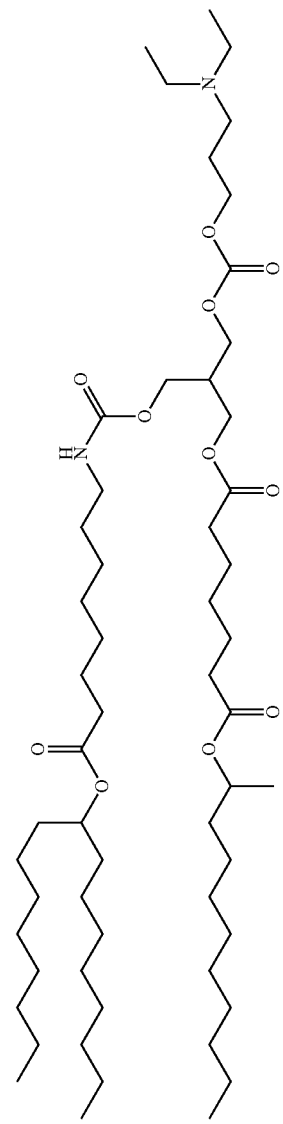
VL437
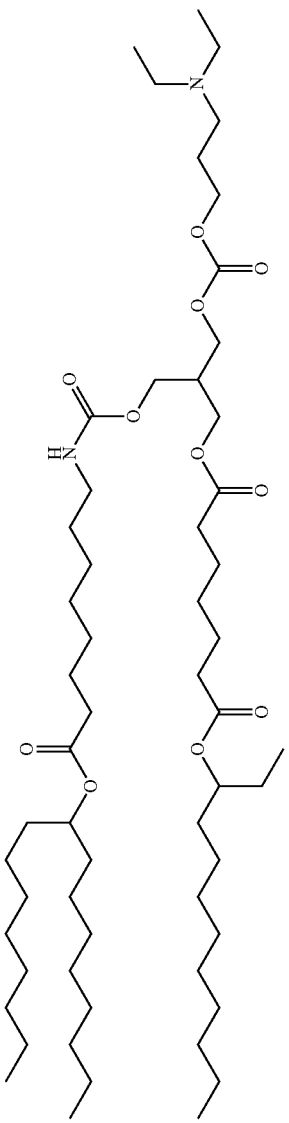
VL438
VL439

TABLE 1A-continued
Amino lipids for constituting lipid nanoparticles. The chiral carbon atom(s) in any of the structures indicate(s) racemic, and/or chirally pure R and S stereoisomers.
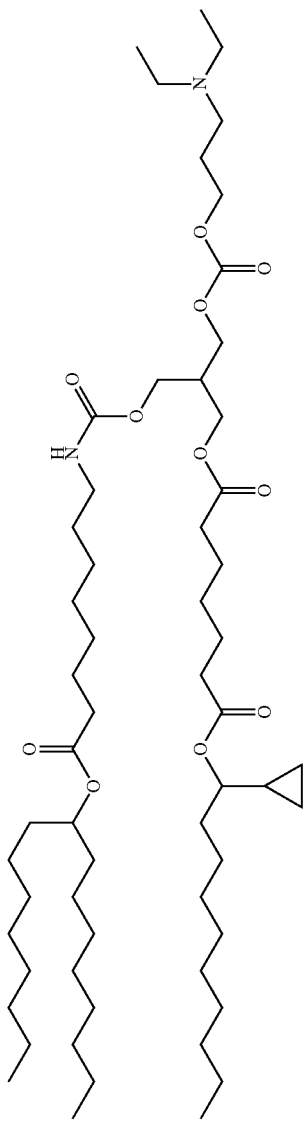
VL440
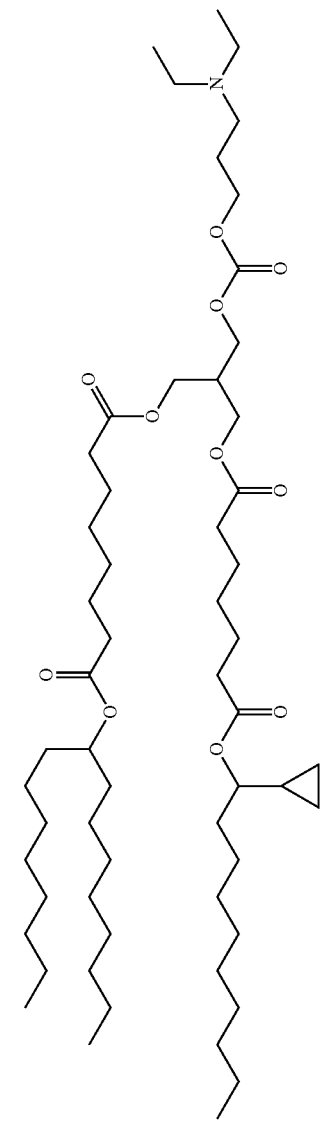
VL441
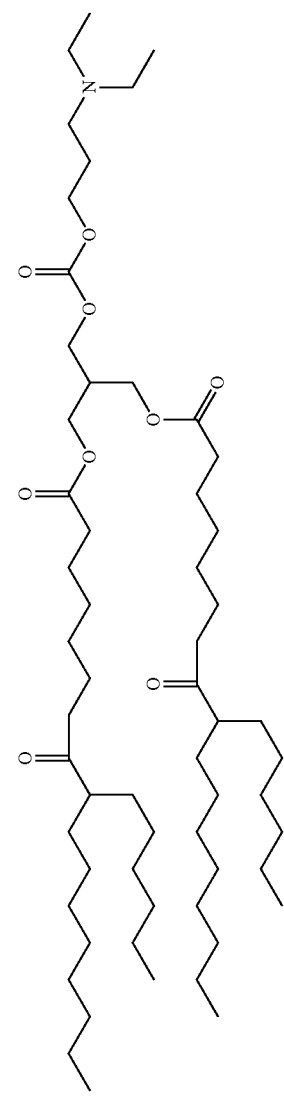
VL442

TABLE 1A-continued
Amino lipids for constituting lipid nanoparticles. The chiral carbon atom(s) in any of the structures indicate(s) racemic, and/or chirally pure R and S stereoisomers.
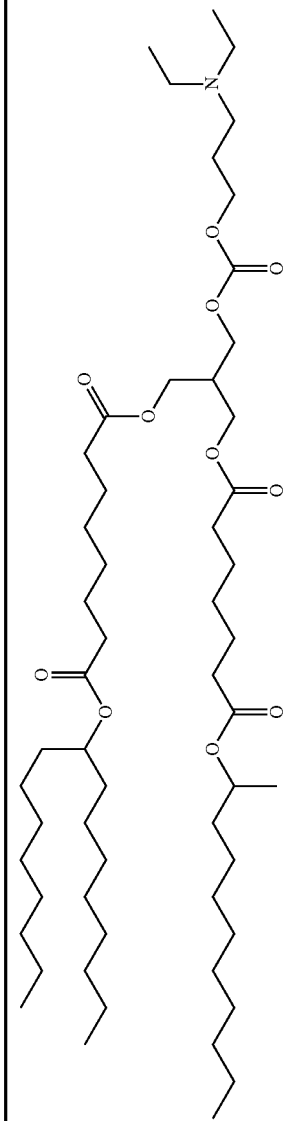
VL443
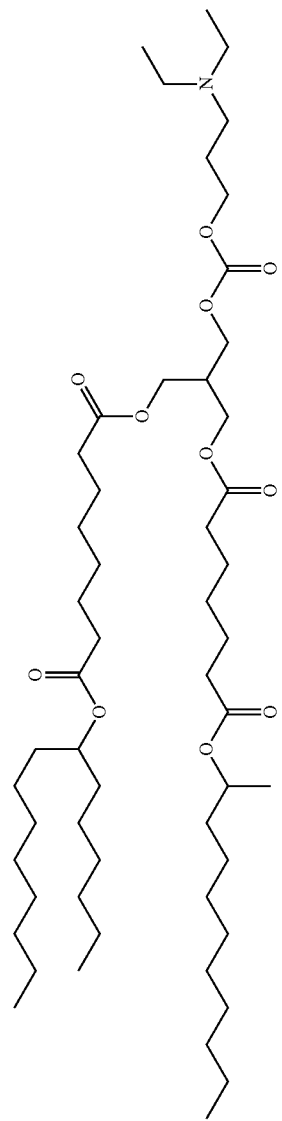
VL444
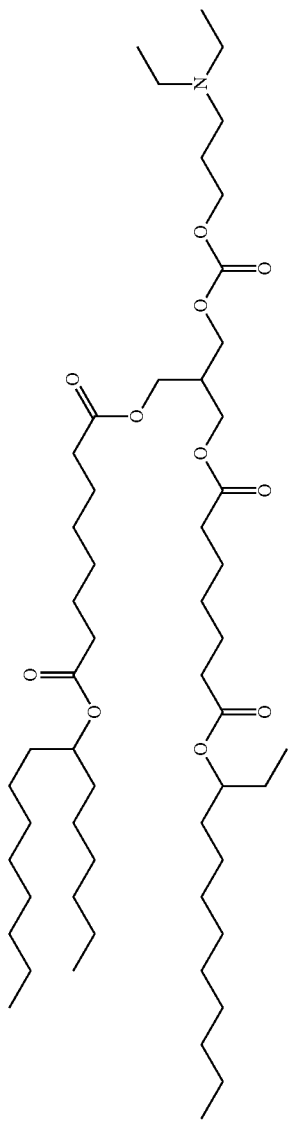
VL445

TABLE 1A-continued
Amino lipids for constituting lipid nanoparticles. The chiral carbon atom(s) in any of the structures indicate(s) racemic, and/or chirally pure R and S stereoisomers.
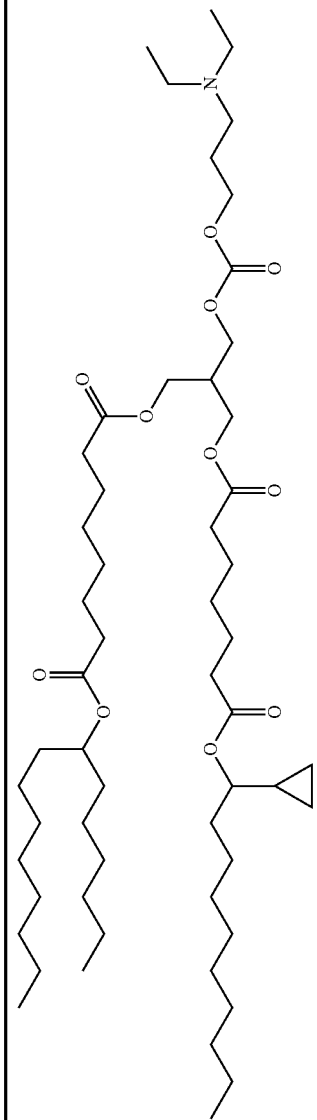
VL446
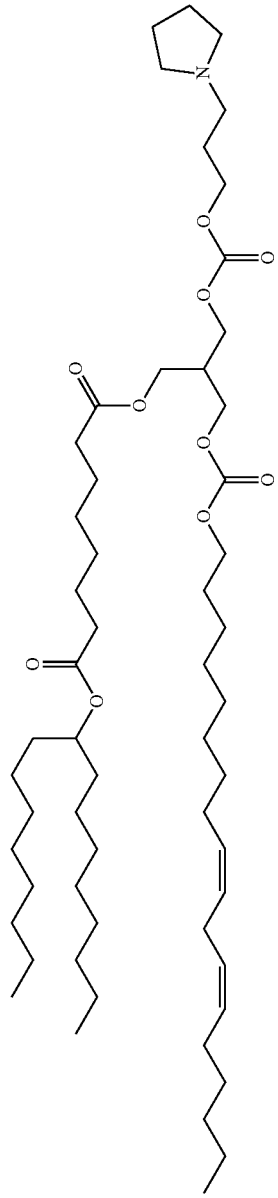
VL447
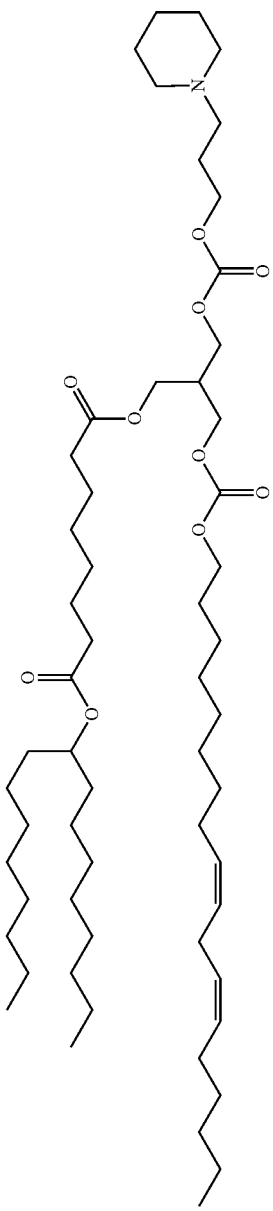
VL448

TABLE 1A-continued
Amino lipids for constituting lipid nanoparticles. The chiral carbon atom(s) in any of the structures indicate(s) racemic, and/or chirally pure R and S stereoisomers.
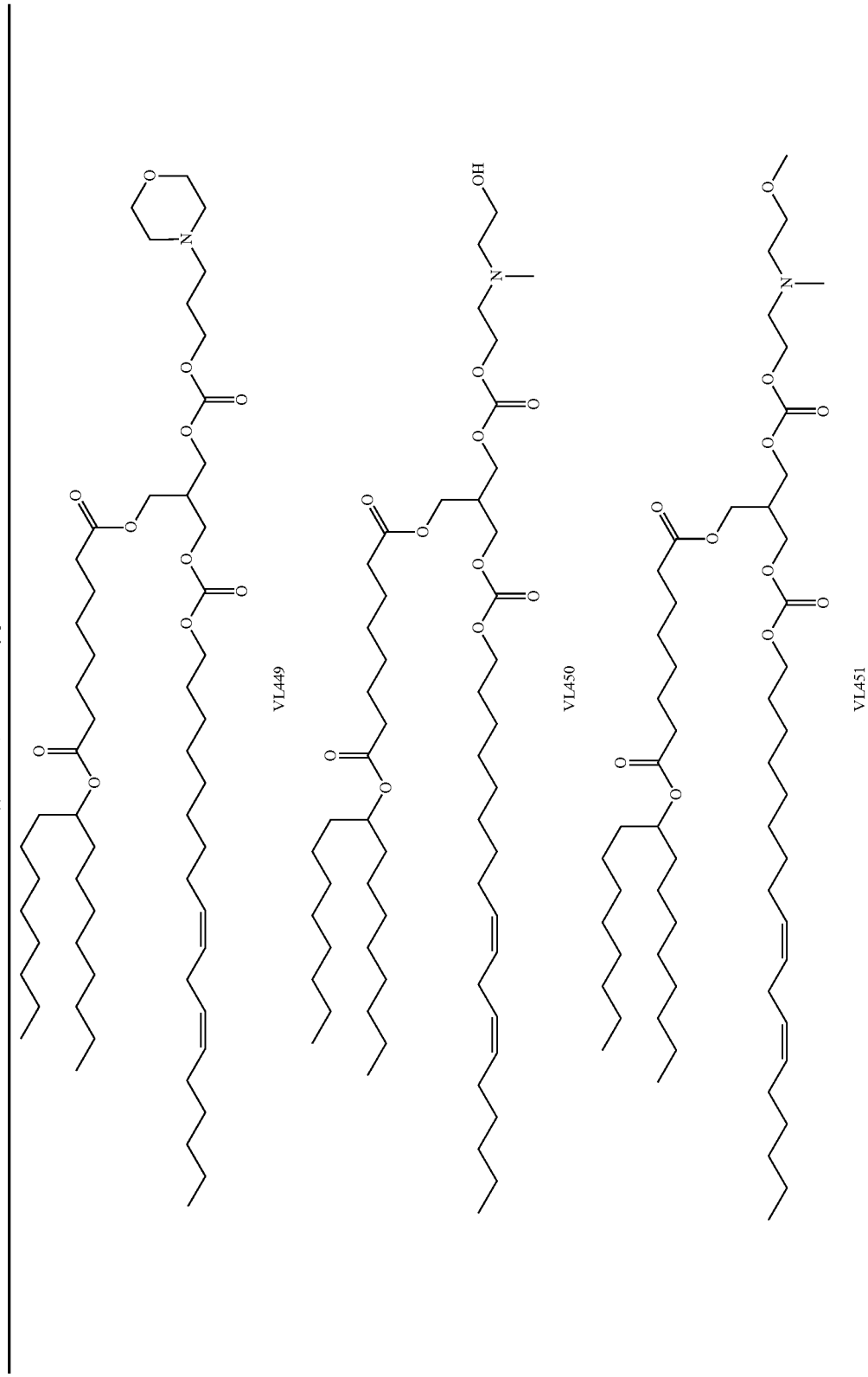

TABLE 1A-continued
Amino lipids for constituting lipid nanoparticles. The chiral carbon atom(s) in any of the structures indicate(s) racemic, and/or chirally pure R and S stereoisomers.
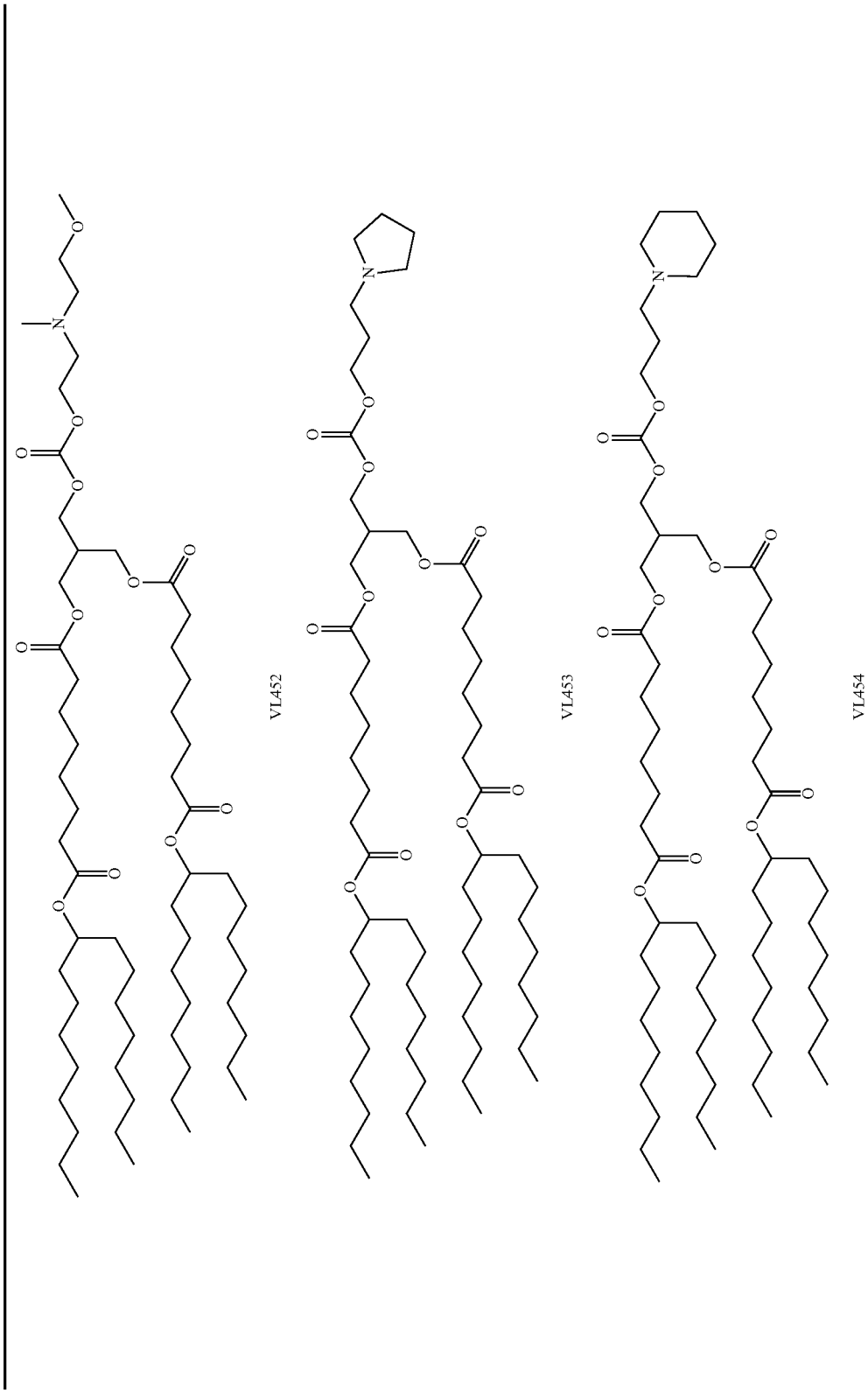
VL452
VL453
VL454

TABLE 1A-continued
Amino lipids for constituting lipid nanoparticles. The chiral carbon atom(s) in any of the structures indicate(s) racemic, and/or chirally pure R and S stereoisomers.
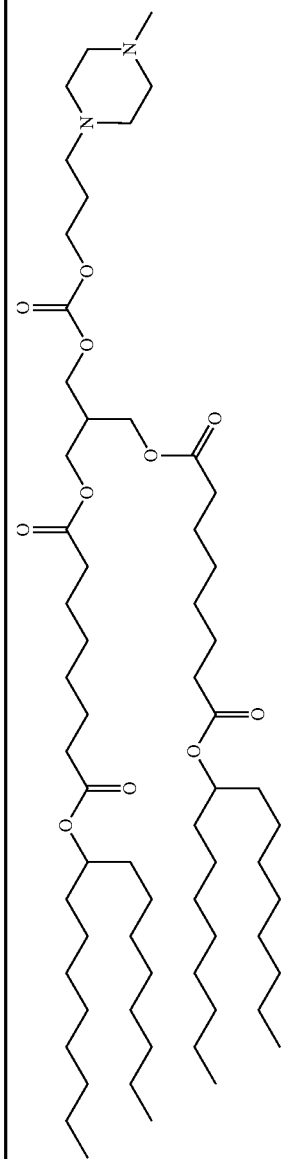
VL455
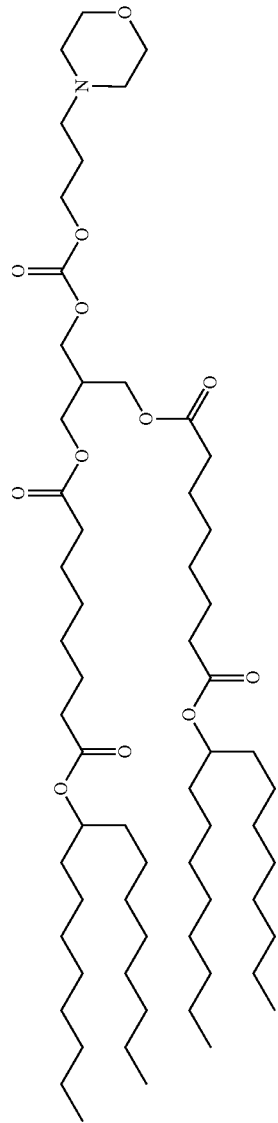
VL456
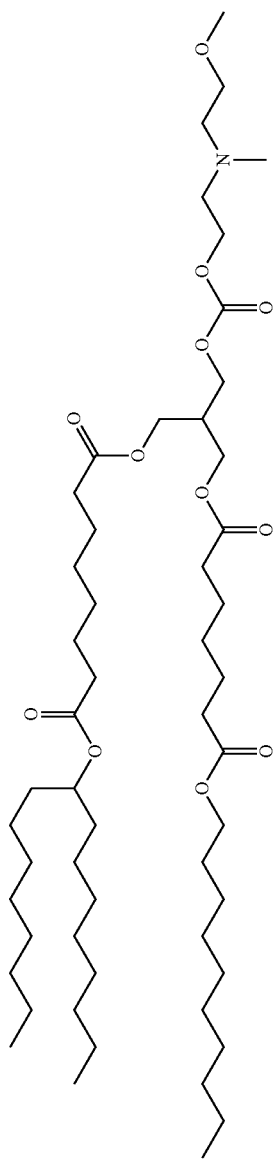
VL457

TABLE 1A-continued
Amino lipids for constituting lipid nanoparticles. The chiral carbon atom(s) in any of the structures indicate(s) racemic, and/or chirally pure R and S stereoisomers.
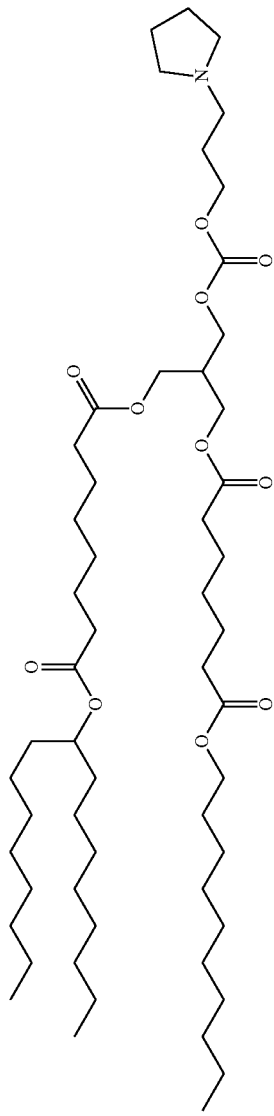
VL458
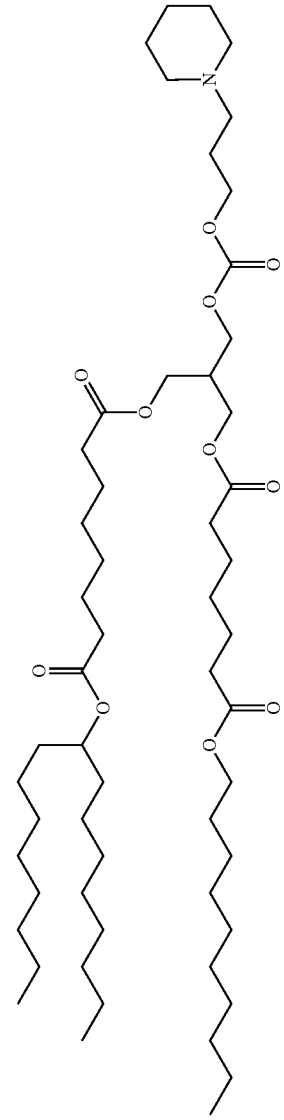
VL459
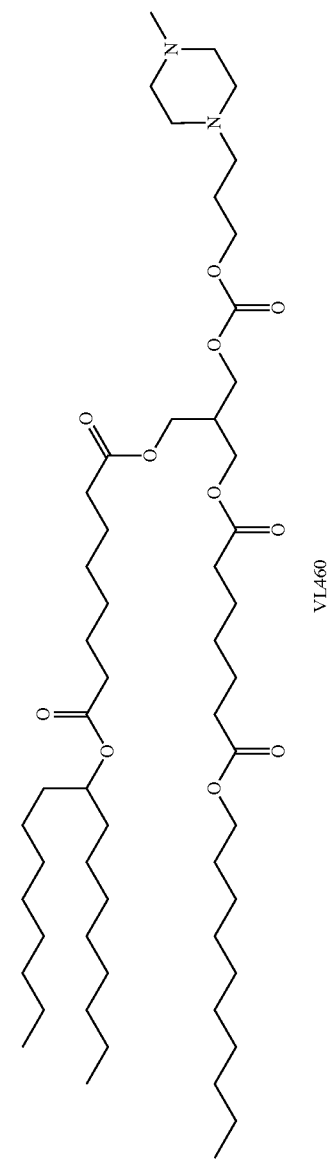
VL460

TABLE 1A-continued
Amino lipids for constituting lipid nanoparticles. The chiral carbon atom(s) in any of the structures indicate(s) racemic, and/or chirally pure R and S stereoisomers.
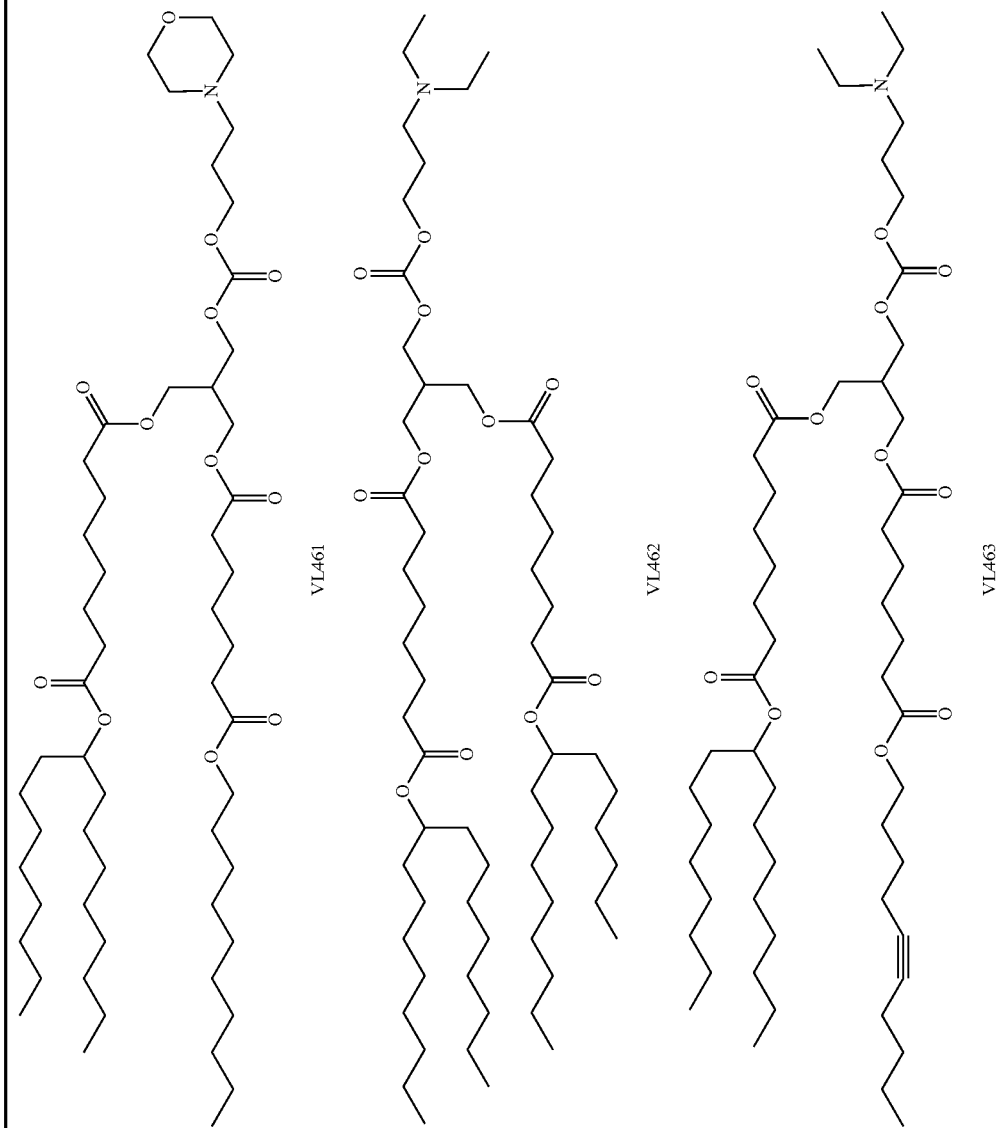

TABLE 1A-continued
Amino lipids for constituting lipid nanoparticles. The chiral carbon atom(s) in any of the structures indicate(s) racemic, and/or chirally pure R and S stereoisomers.
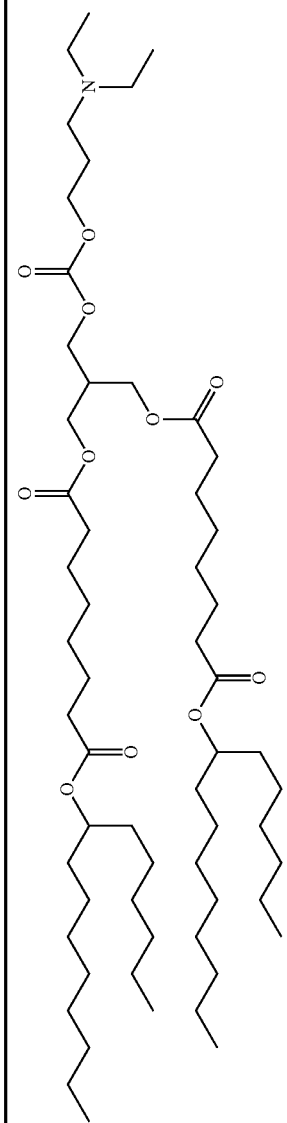
VL464
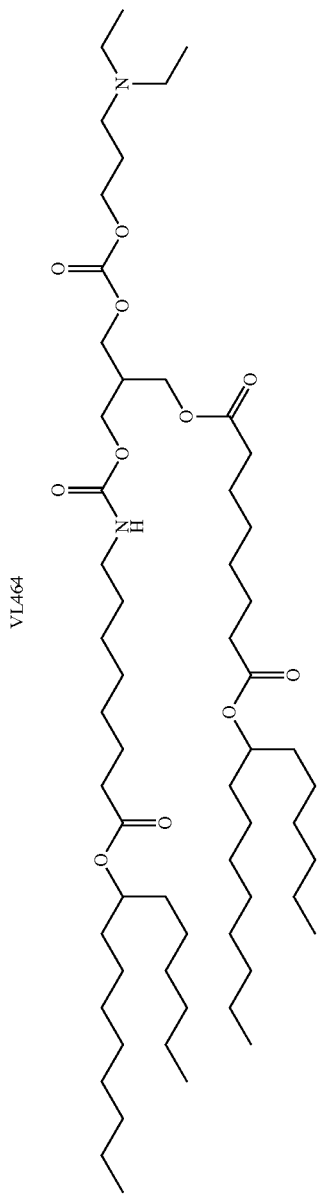
VL465
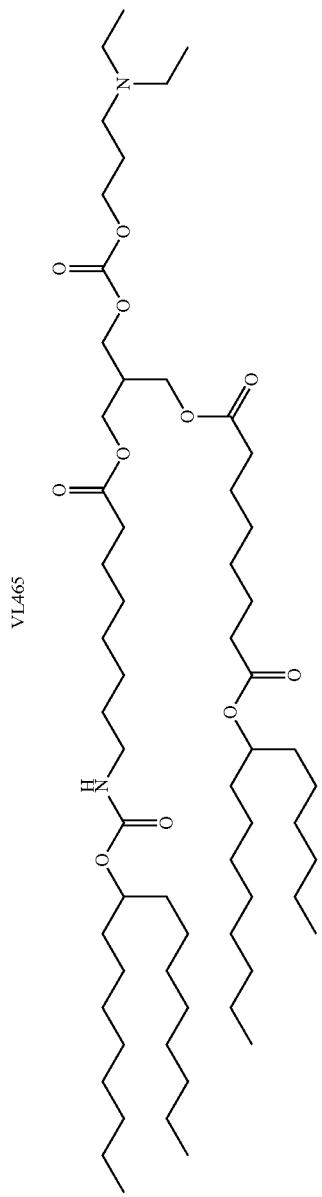
VL466

TABLE 1A-continued
Amino lipids for constituting lipid nanoparticles. The chiral carbon atom(s) in any of the structures indicate(s) racemic, and/or chirally pure R and S stereoisomers.
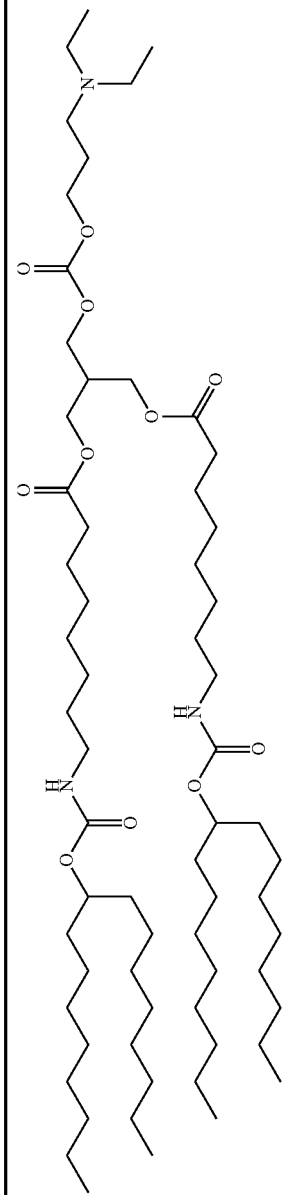
VL467
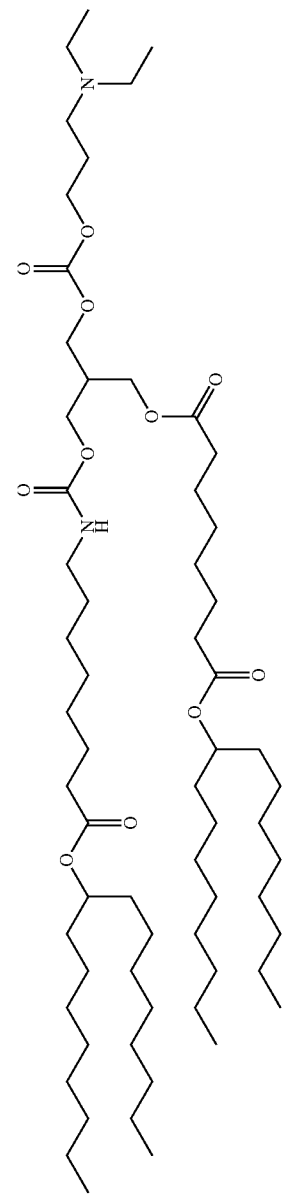
VL468
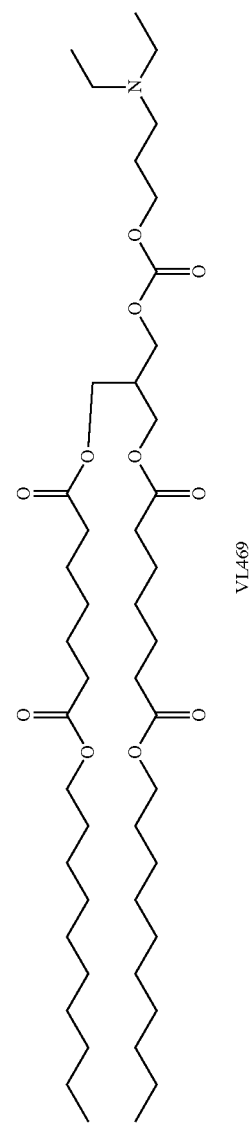
VL469

TABLE 1A-continued
Amino lipids for constituting lipid nanoparticles. The chiral carbon atom(s) in any of the structures indicate(s) racemic, and/or chirally pure R and S stereoisomers.
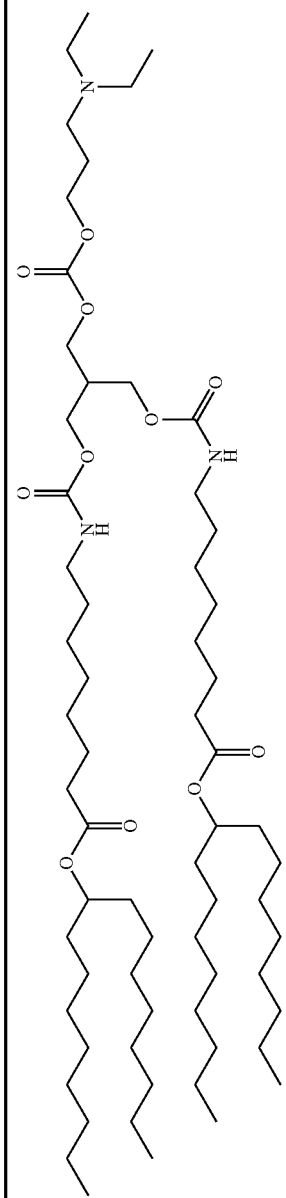
VL470
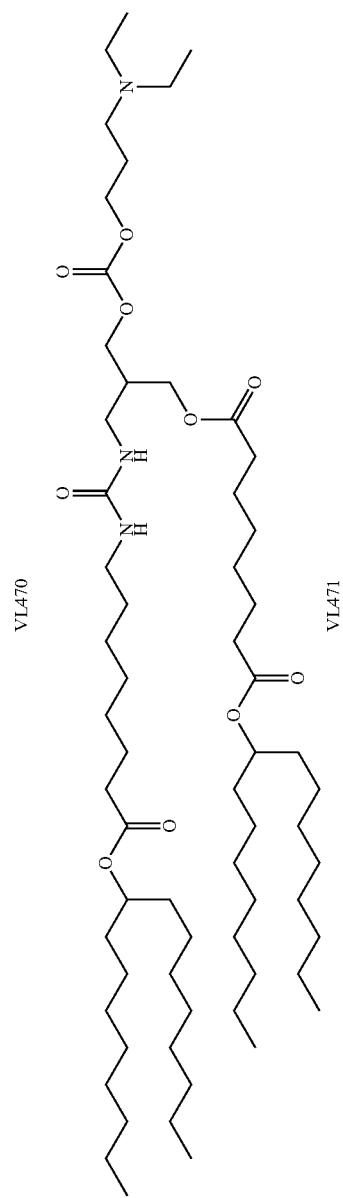
VL471
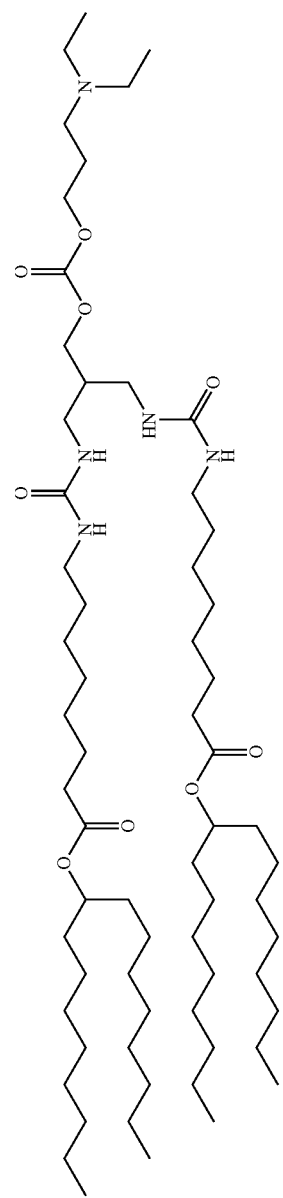
VL472

TABLE 1A-continued
Amino lipids for constituting lipid nanoparticles. The chiral carbon atom(s) in any of the structures indicate(s) racemic, and/or chirally pure R and S stereoisomers.
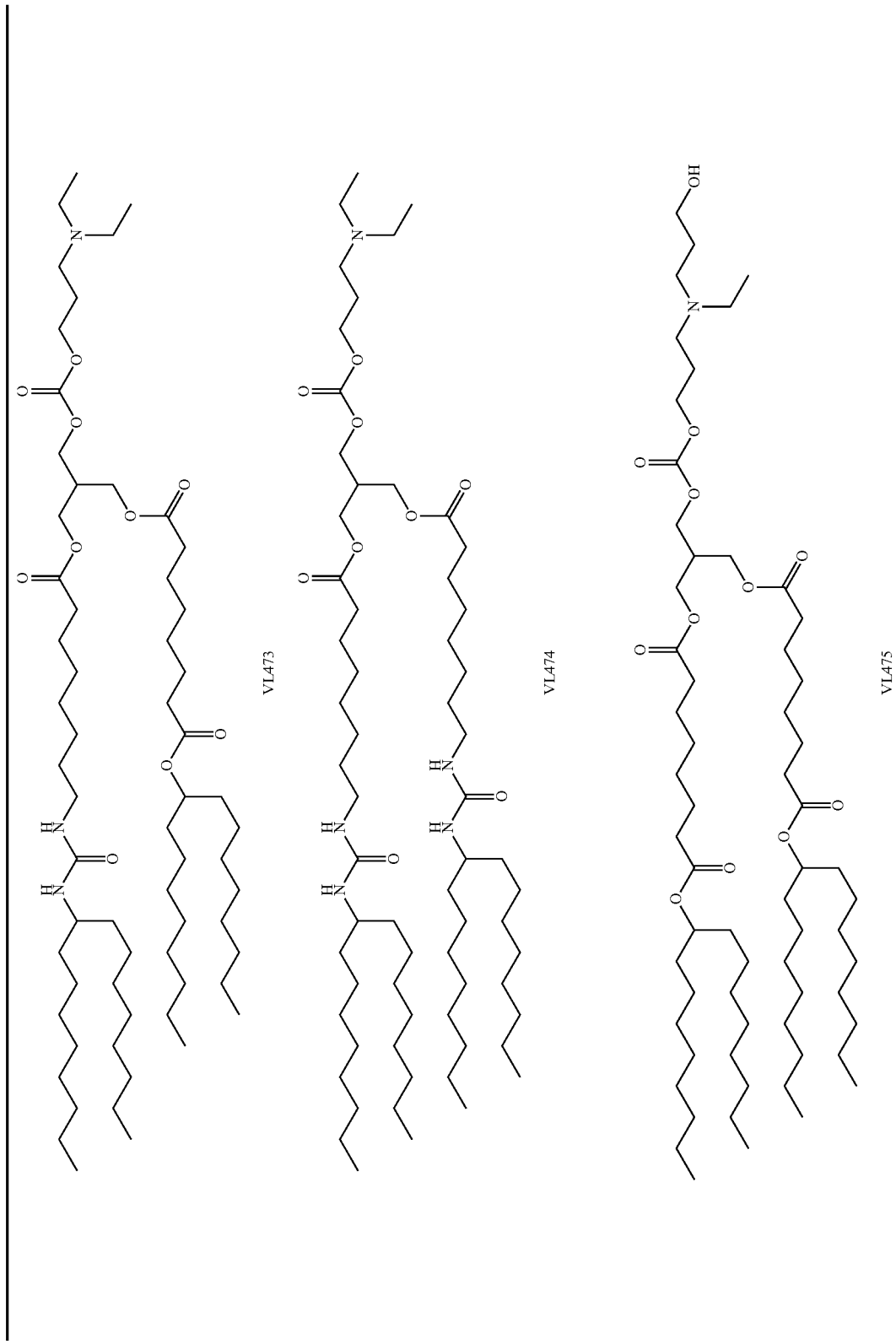

TABLE 1A-continued
Amino lipids for constituting lipid nanoparticles. The chiral carbon atom(s) in any of the structures indicate(s) racemic, and/or chirally pure R and S stereoisomers.
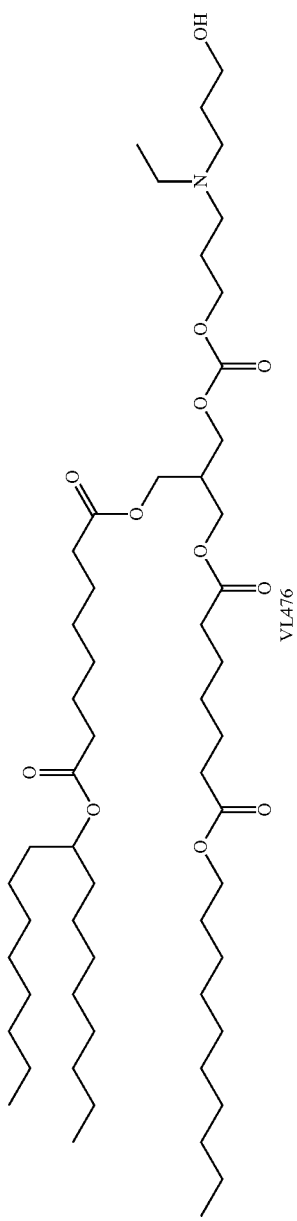
VL476
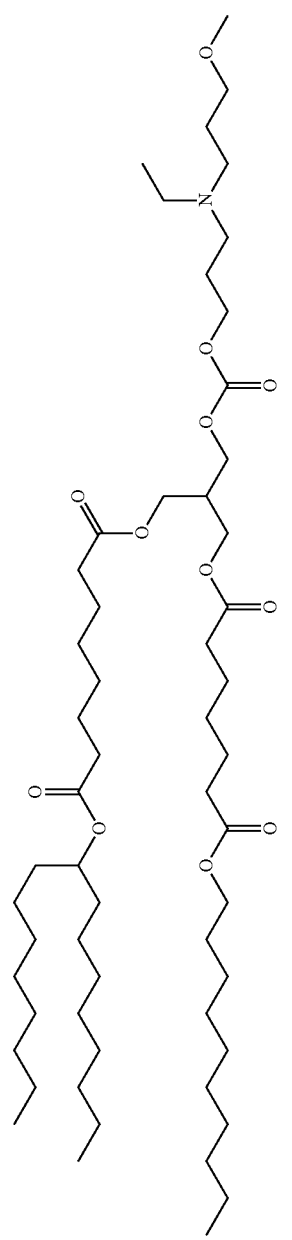
VL477
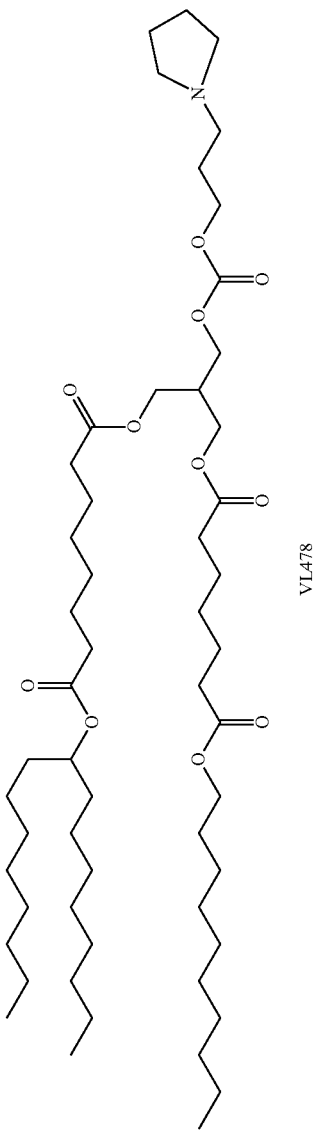
VL478

TABLE 1A-continued
Amino lipids for constituting lipid nanoparticles. The chiral carbon atom(s) in any of the structures indicate(s) racemic, and/or chirally pure R and S stereoisomers.
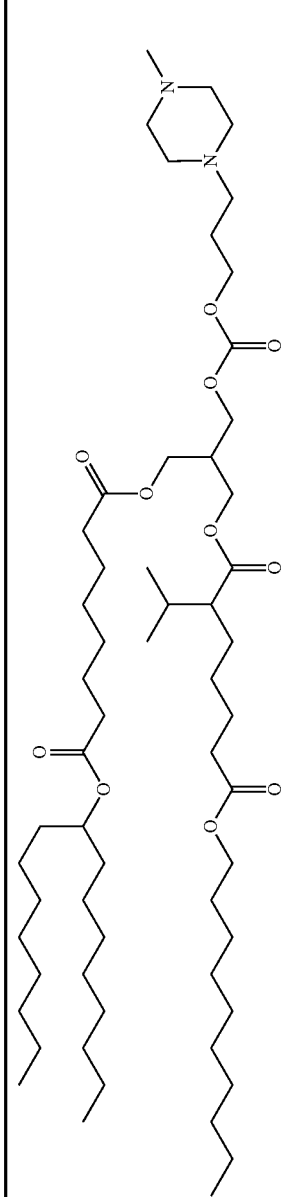
VL479
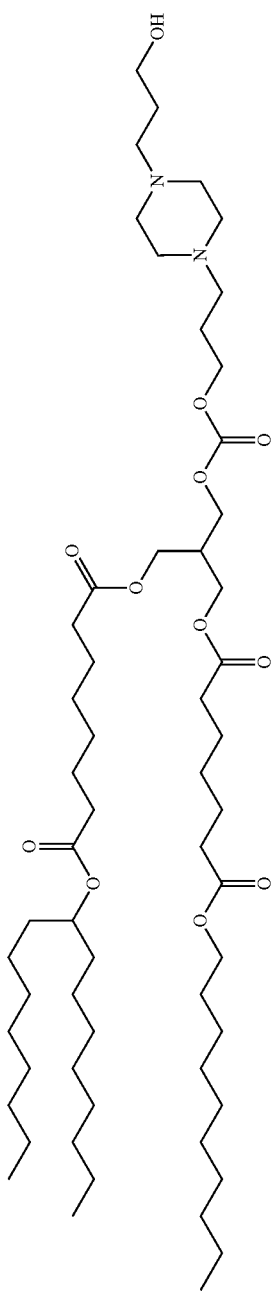
VL480
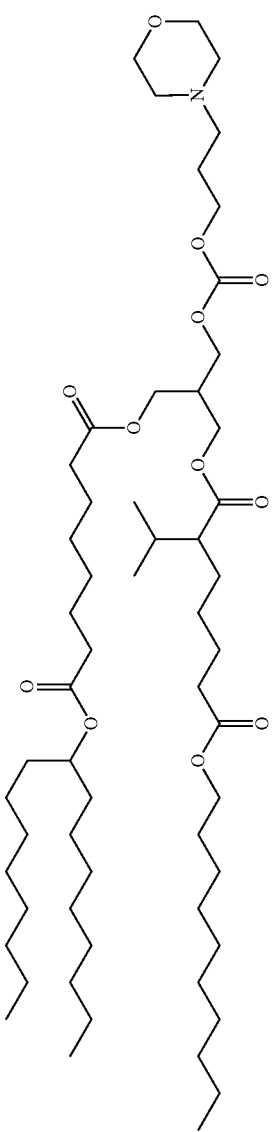
VL481

TABLE 1A-continued
Amino lipids for constituting lipid nanoparticles. The chiral carbon atom(s) in any of the structures indicate(s) racemic, and/or chirally pure R and S stereoisomers.
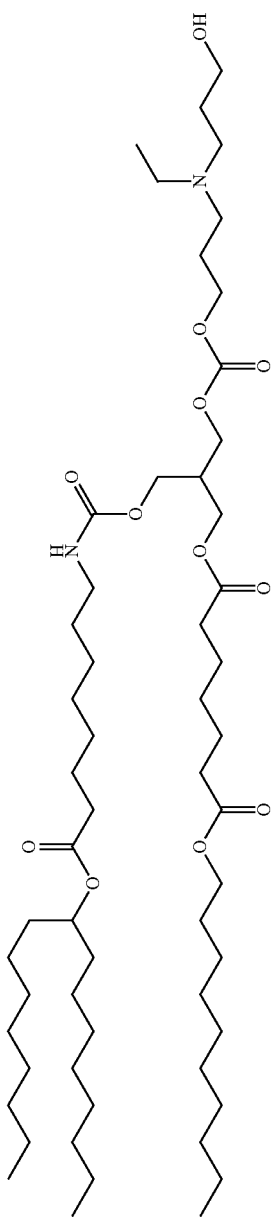
VL482
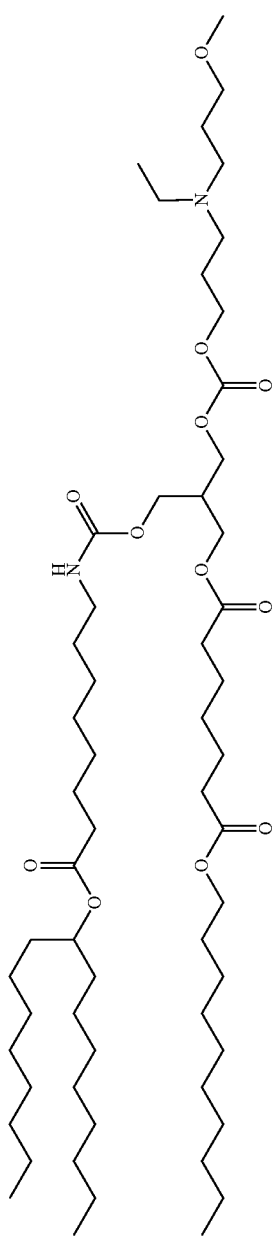
VL483
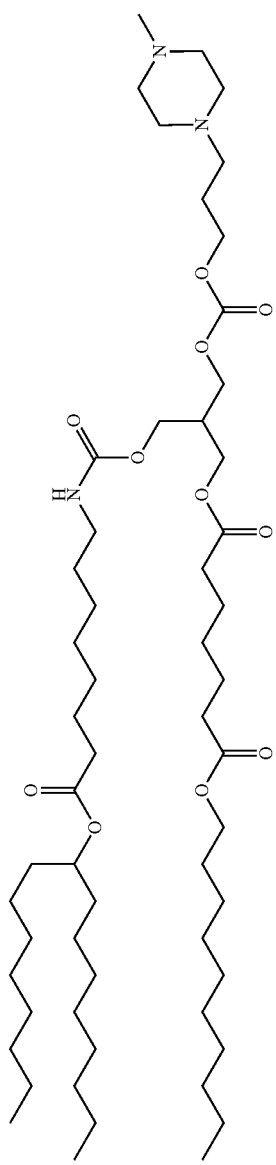
VL484

TABLE 1A-continued
Amino lipids for constituting lipid nanoparticles. The chiral carbon atom(s) in any of the structures indicate(s) racemic, and/or chirally pure R and S stereoisomers.
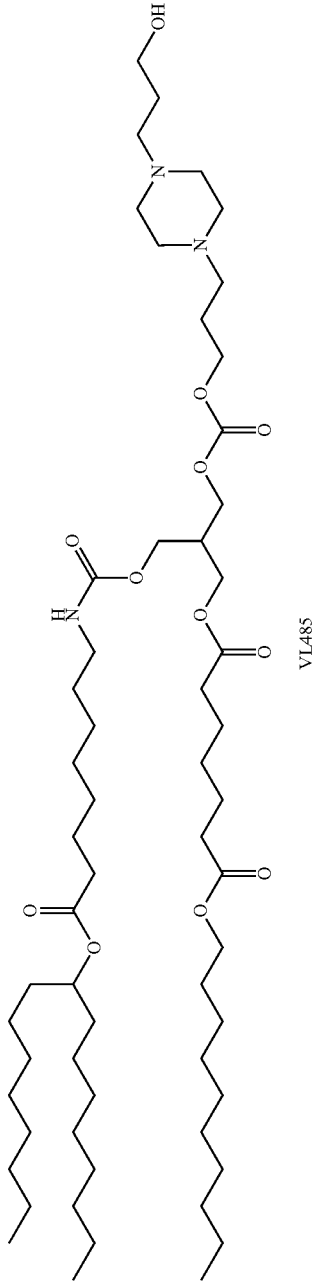
VL485
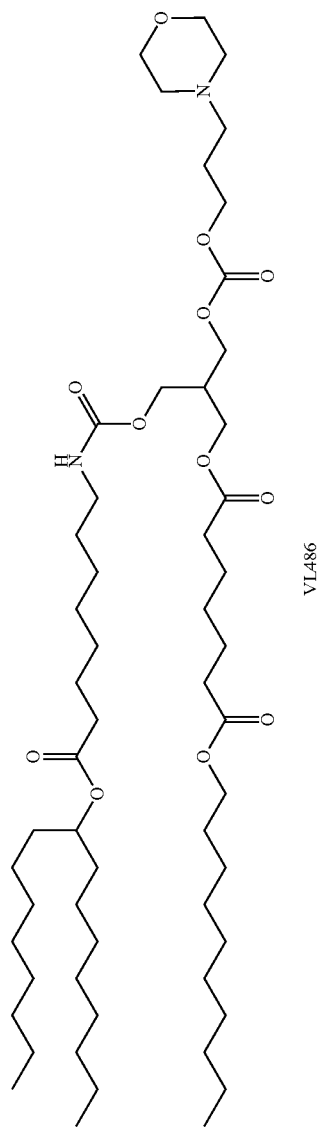
VL486

TABLE 1A-continued
Amino lipids for constituting lipid nanoparticles. The chiral carbon atom(s) in any of the structures indicate(s) racemic, and/or chirally pure R and S stereoisomers.
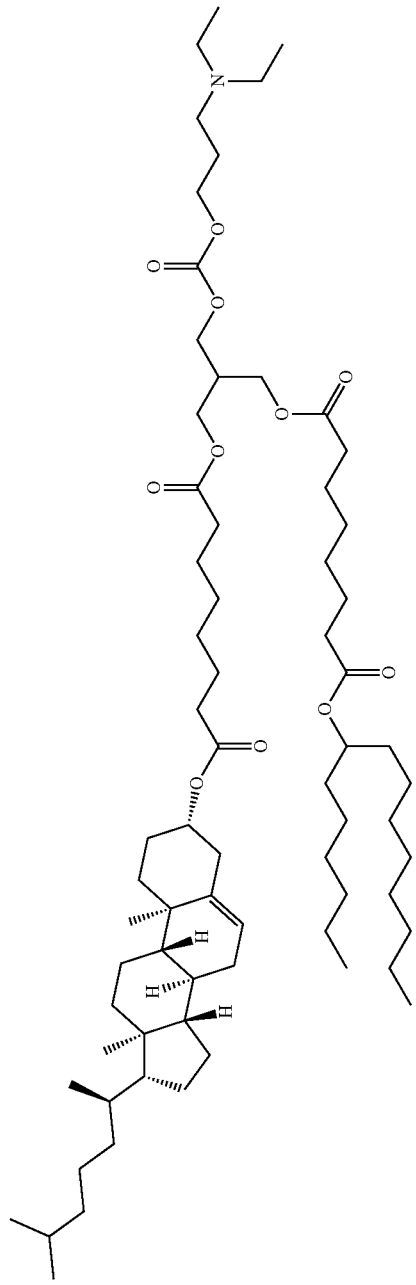
VL487
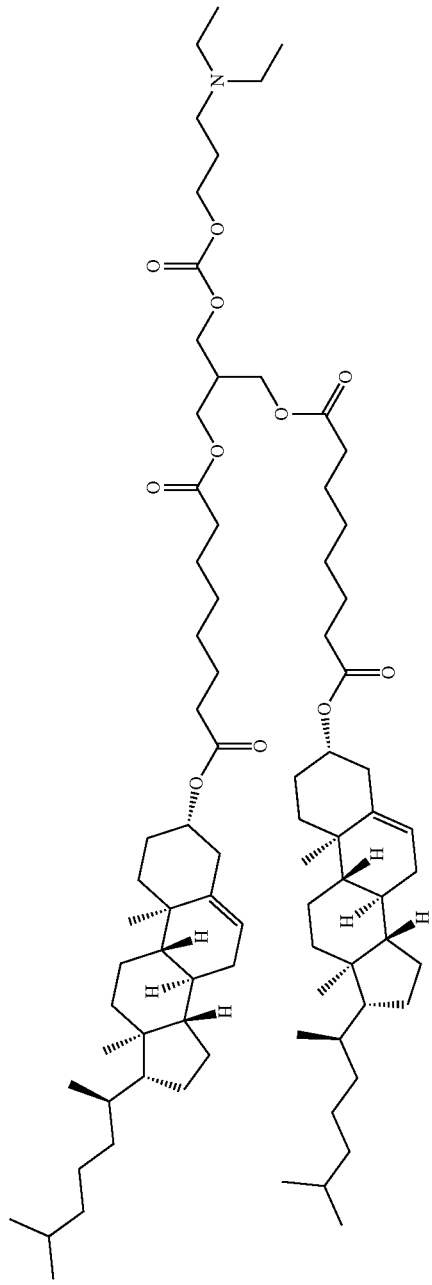
VL488

TABLE 1A-continued
Amino lipids for constituting lipid nanoparticles. The chiral carbon atom(s) in any of the structures indicate(s) racemic, and/or chirally pure R and S stereoisomers.
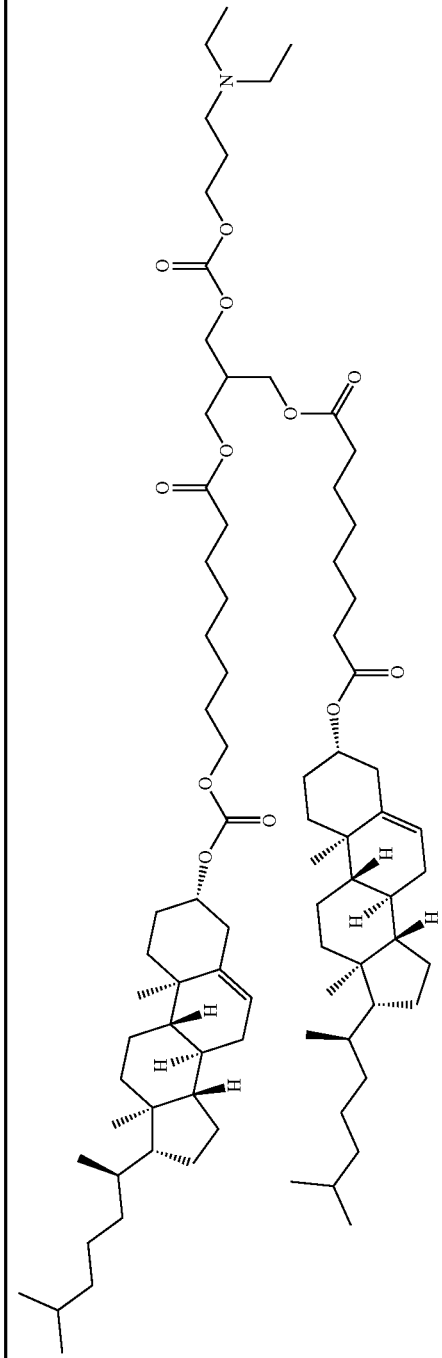
VL489
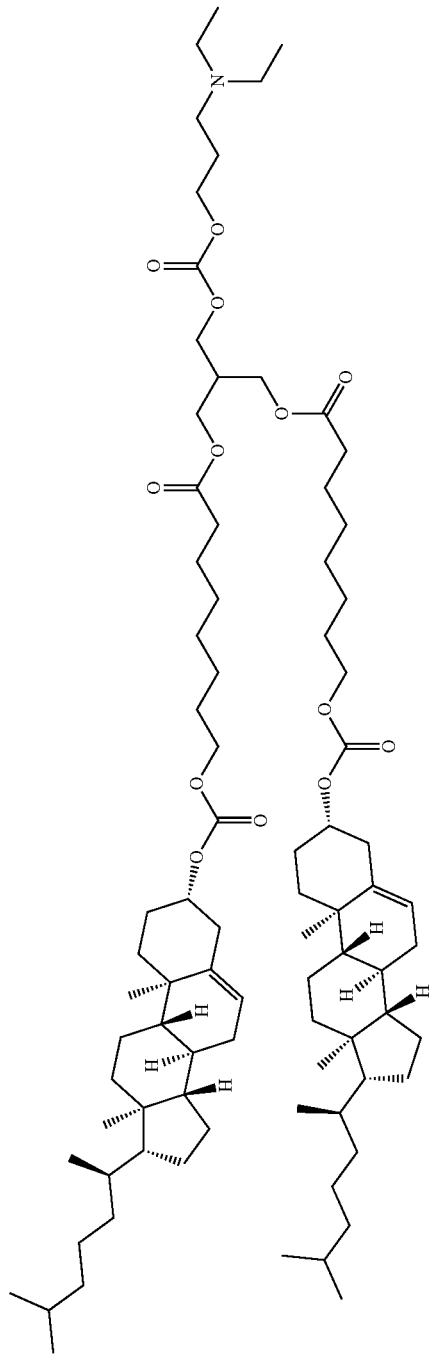
VL490

TABLE 1A-continued
Amino lipids for constituting lipid nanoparticles. The chiral carbon atom(s) in any of the structures indicate(s) racemic, and/or chirally pure R and S stereoisomers.
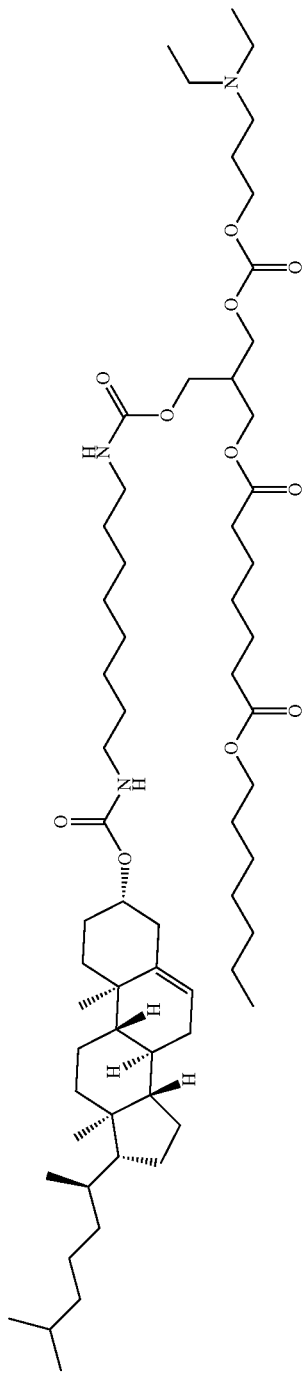
VL491
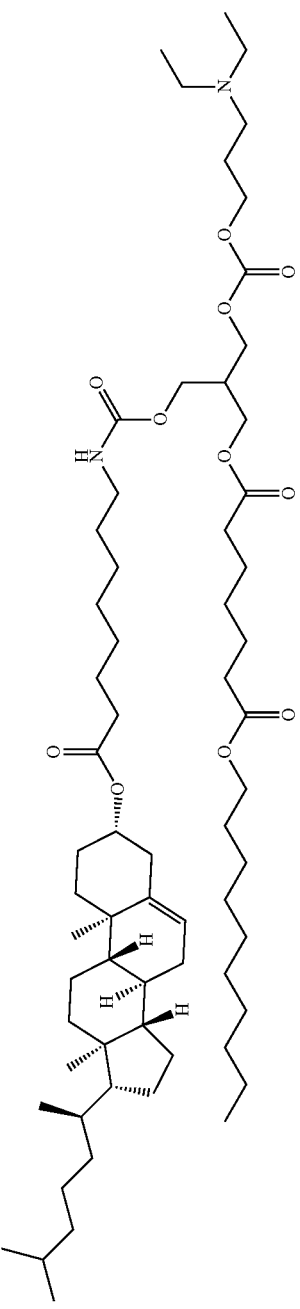
VL492
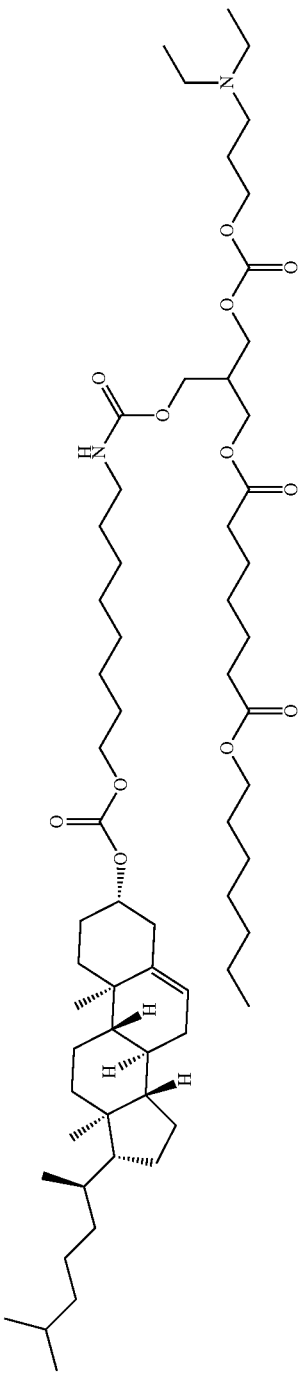
VL493

TABLE 1A-continued
Amino lipids for constituting lipid nanoparticles. The chiral carbon atom(s) in any of the structures indicate(s) racemic, and/or chirally pure R and S stereoisomers.
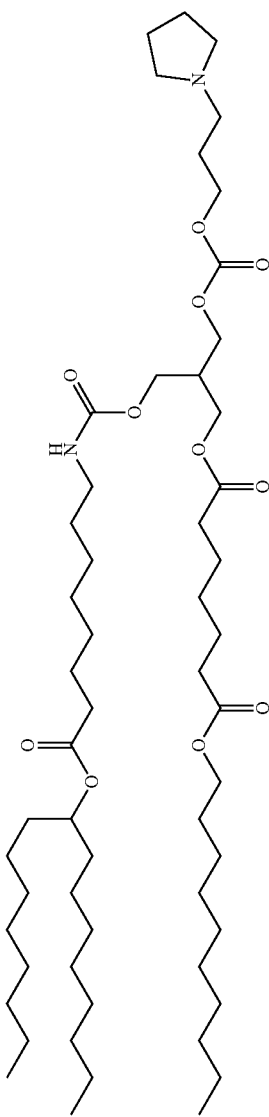
VL494
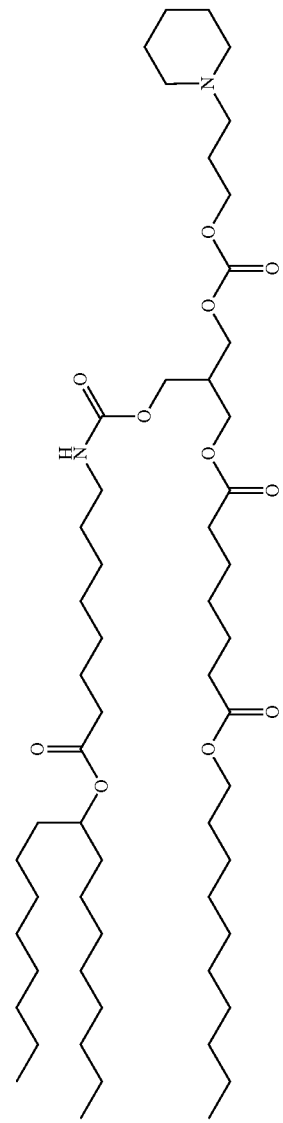
VL495
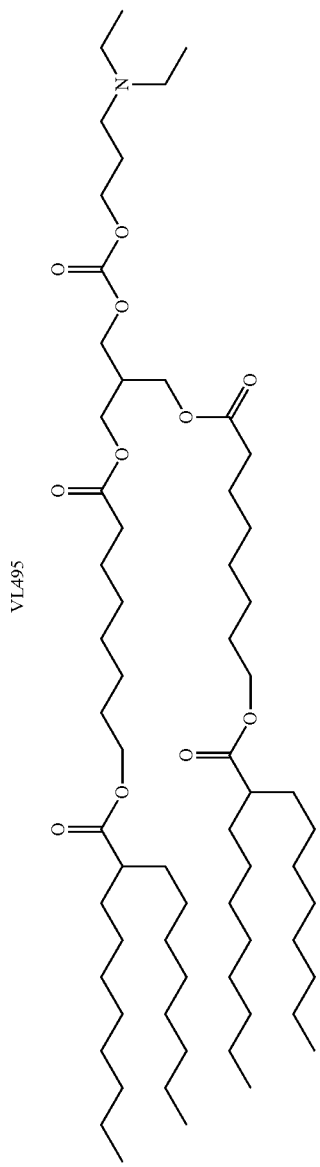
VL496

TABLE 1A-continued
Amino lipids for constituting lipid nanoparticles. The chiral carbon atom(s) in any of the structures indicate(s) racemic, and/or chirally pure R and S stereoisomers.
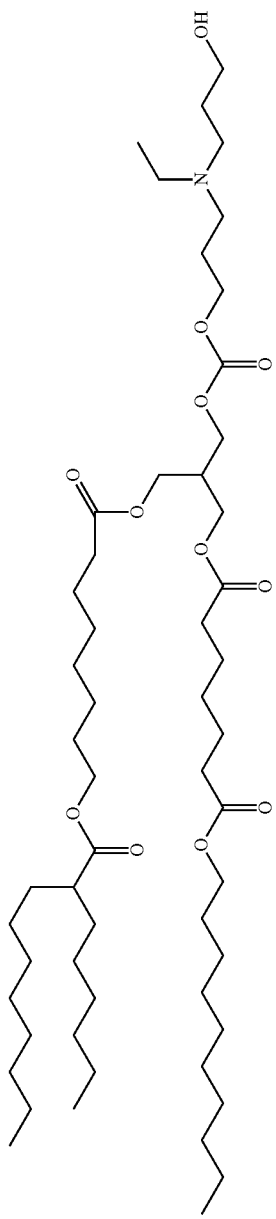
VL497
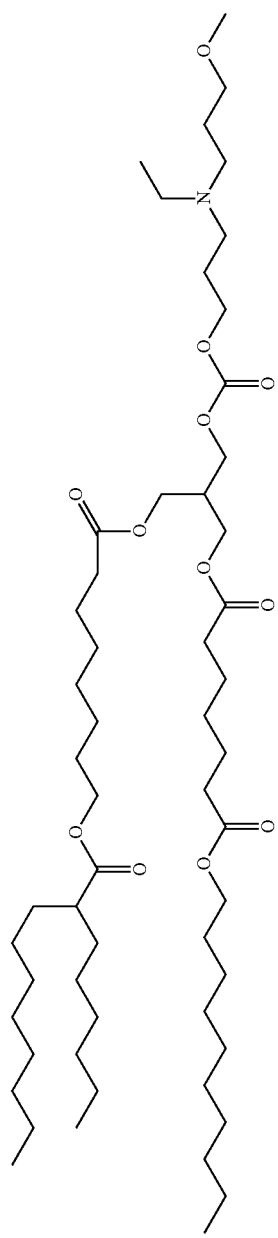
VL498
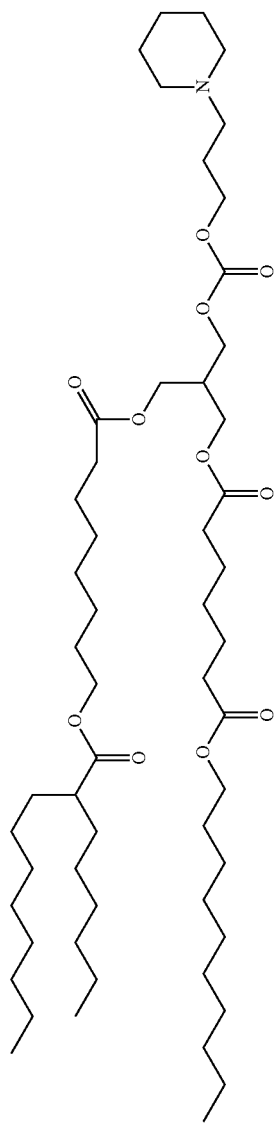
VL499

TABLE 1A-continued
Amino lipids for constituting lipid nanoparticles. The chiral carbon atom(s) in any of the structures indicate(s) racemic, and/or chirally pure R and S stereoisomers.
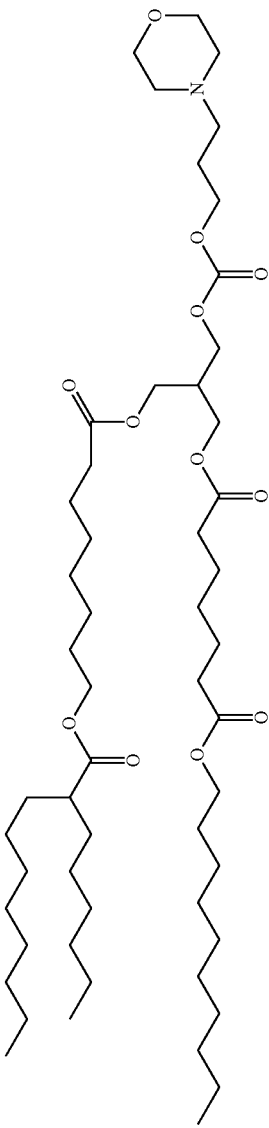
VL500
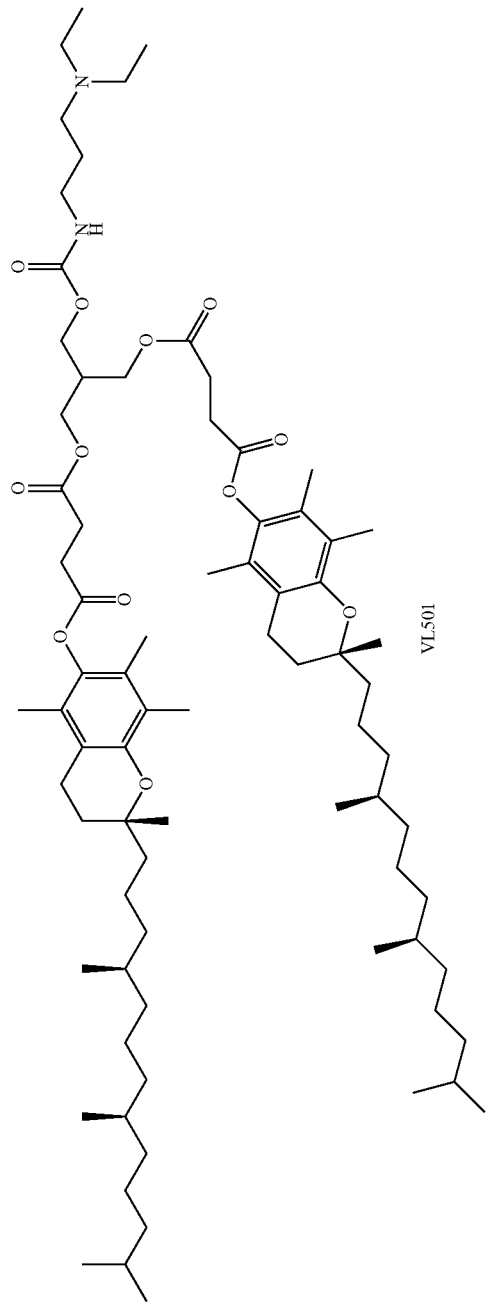
VL501

TABLE 1A-continued
Amino lipids for constituting lipid nanoparticles. The chiral carbon atom(s) in any of the structures indicate(s) racemic, and/or chirally pure R and S stereoisomers.
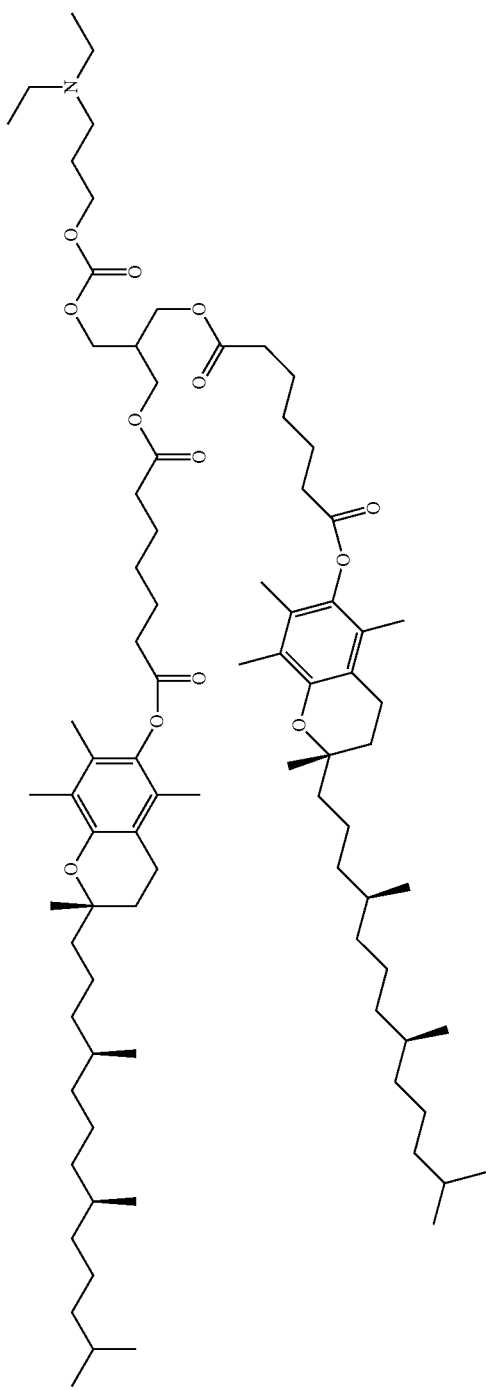
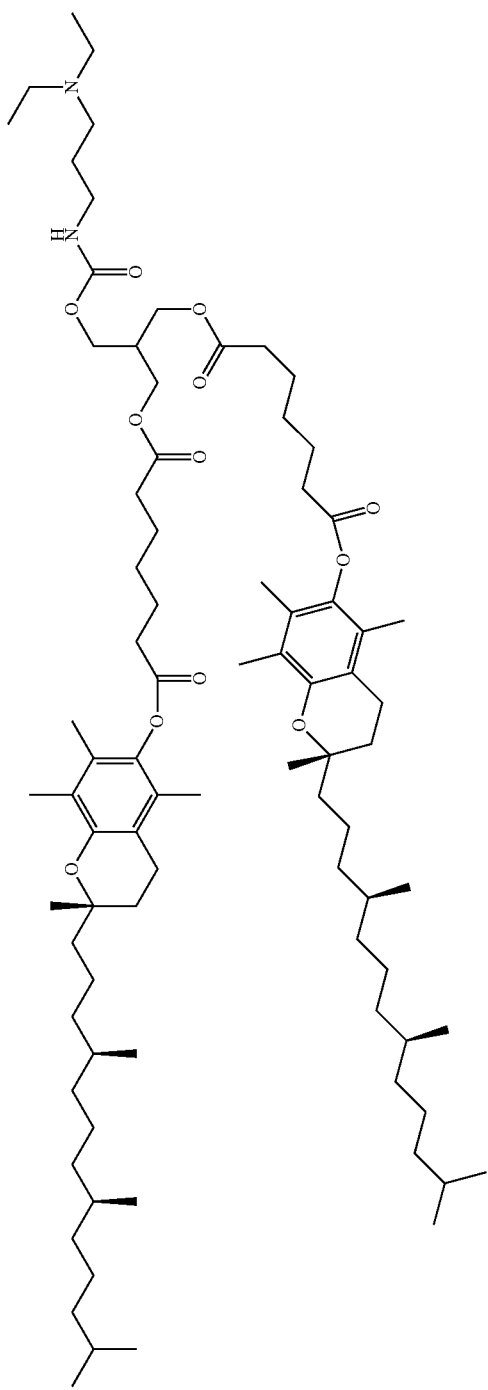
VL502

TABLE 1A-continued
Amino lipids for constituting lipid nanoparticles. The chiral carbon atom(s) in any of the structures indicate(s) racemic, and/or chirally pure R and S stereoisomers.
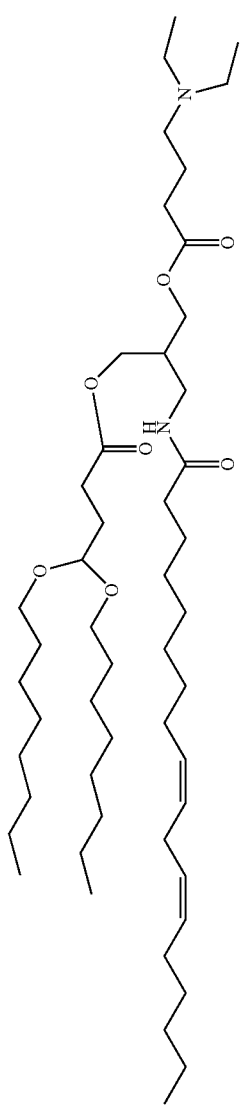
VL503
VL506
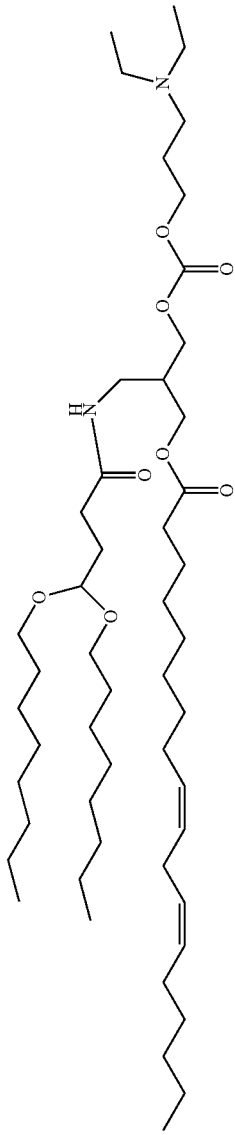
VL507
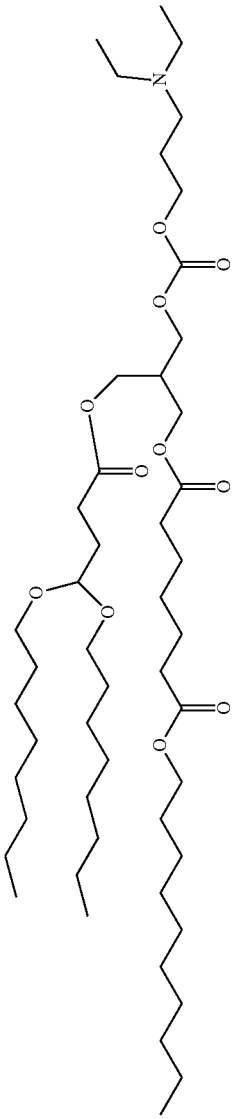
VL508

TABLE 1A-continued
Amino lipids for constituting lipid nanoparticles. The chiral carbon atom(s) in any of the structures indicate(s) racemic, and/or chirally pure R and S stereoisomers.
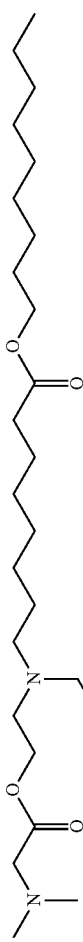
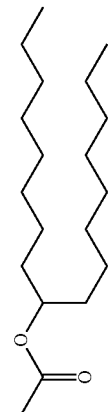
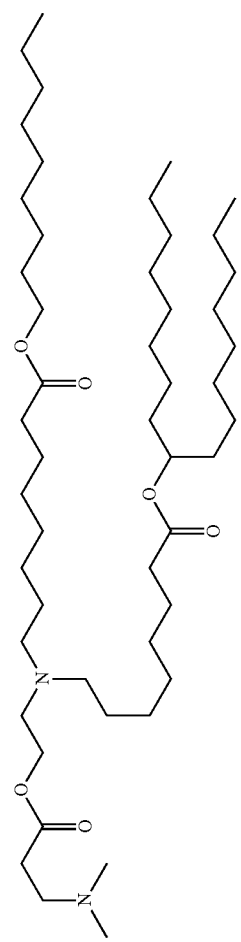
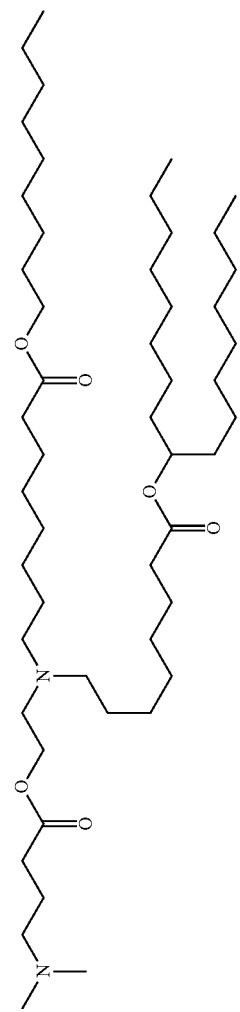
VL509
VL510
VL511

TABLE 1A-continued
Amino lipids for constituting lipid nanoparticles. The chiral carbon atom(s) in any of the structures indicate(s) racemic, and/or chirally pure R and S stereoisomers.
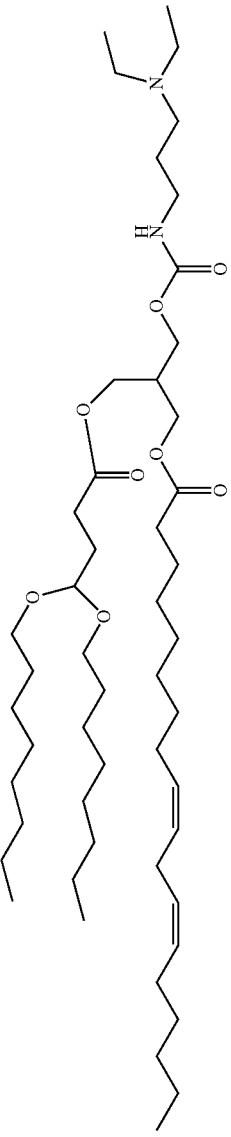
VL512
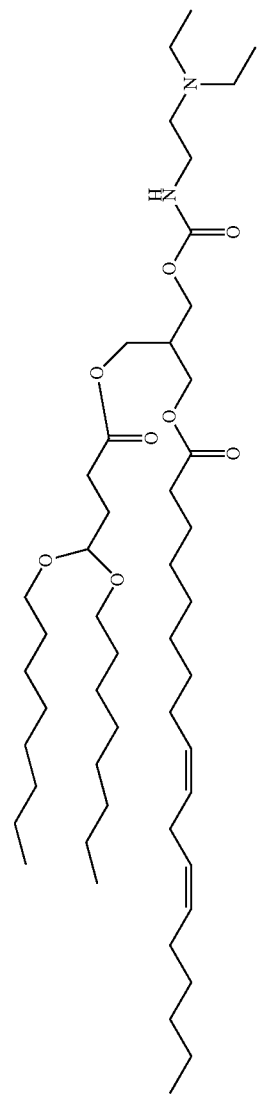
VL513
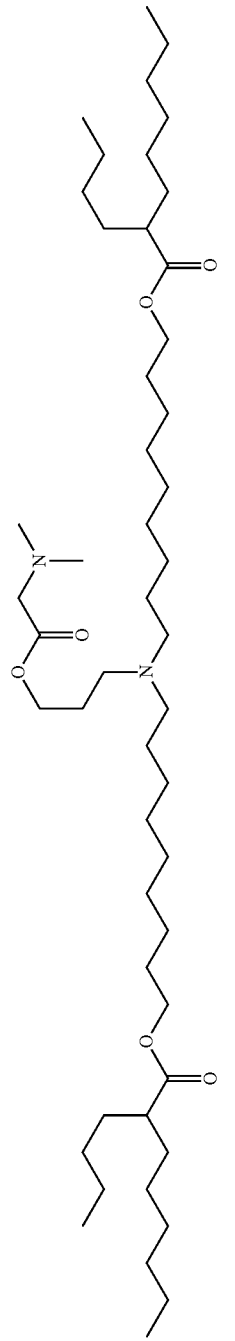
VL514

TABLE 1A-continued
Amino lipids for constituting lipid nanoparticles. The chiral carbon atom(s) in any of the structures indicate(s) racemic, and/or chirally pure R and S stereoisomers.
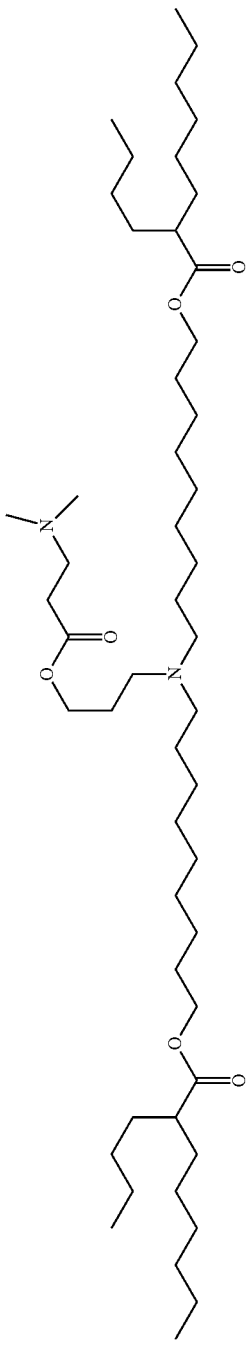
VL515
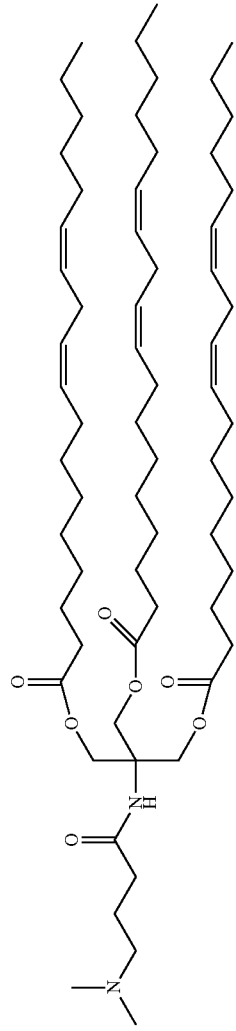
VL516
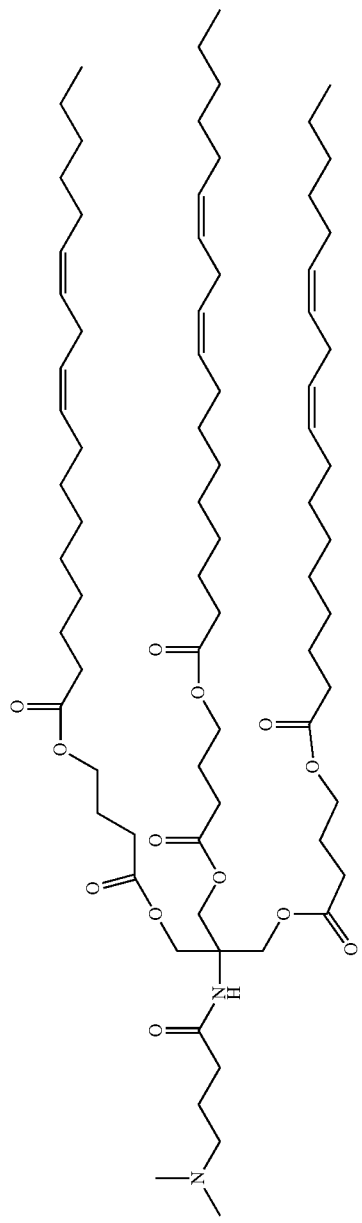
VL517

TABLE 1A-continued
Amino lipids for constituting lipid nanoparticles. The chiral carbon atom(s) in any of the structures indicate(s) racemic, and/or chirally pure R and S stereoisomers.
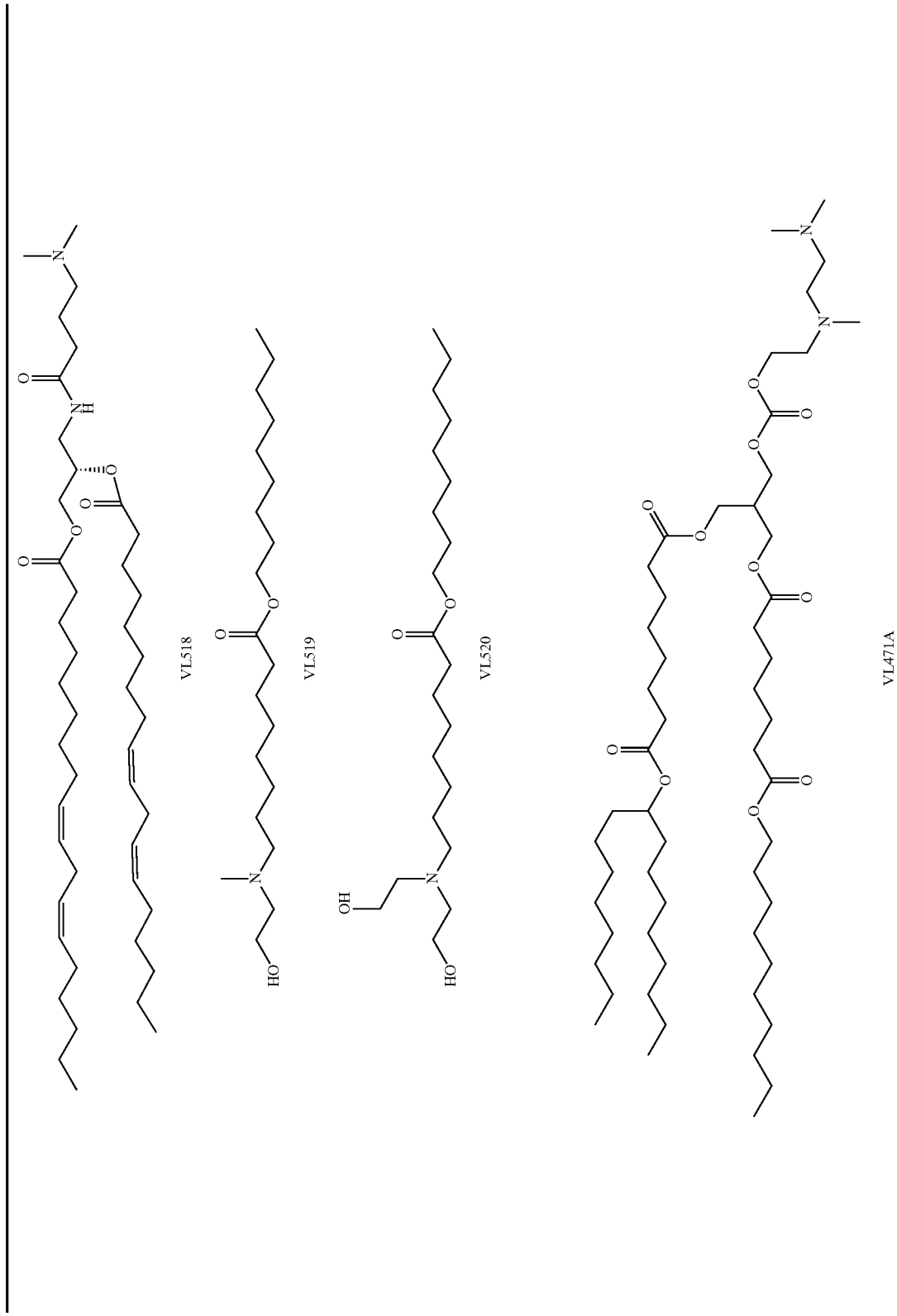

TABLE 1A-continued
Amino lipids for constituting lipid nanoparticles. The chiral carbon atom(s) in any of the structures indicate(s) racemic, and/or chirally pure R and S stereoisomers.
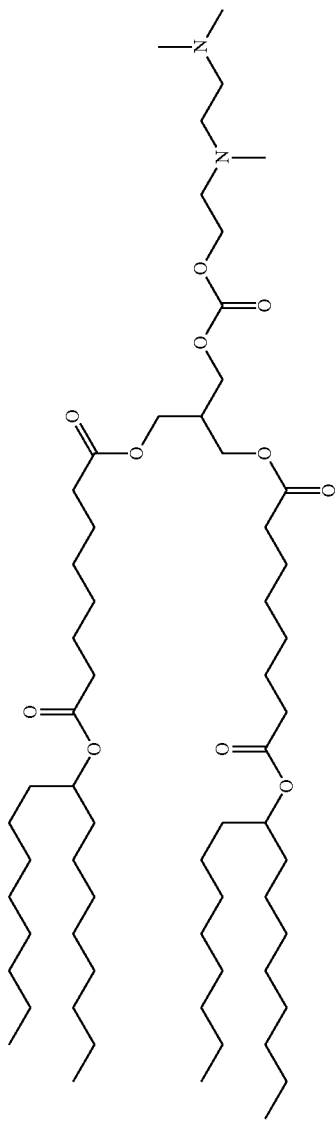
VL472A
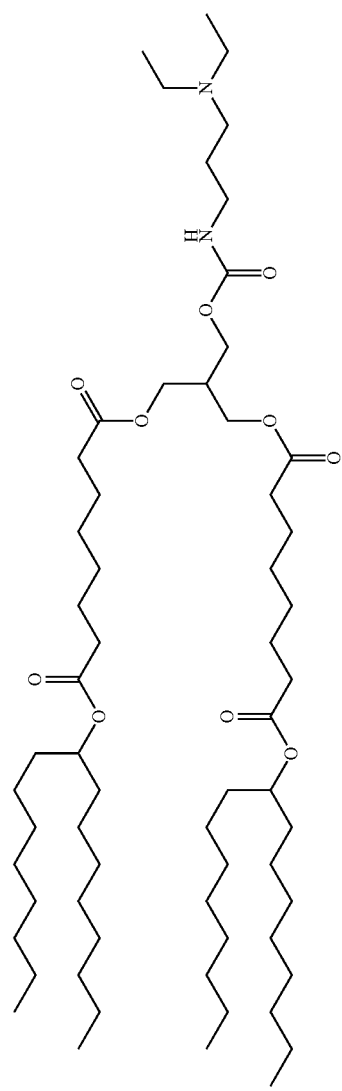
VL473A TABLE 1A-continued
Amino lipids for constituting lipid nanoparticles. The chiral carbon atom(s) in any of the structures indicate(s) racemic, and/or chirally pure R and S stereoisomers.
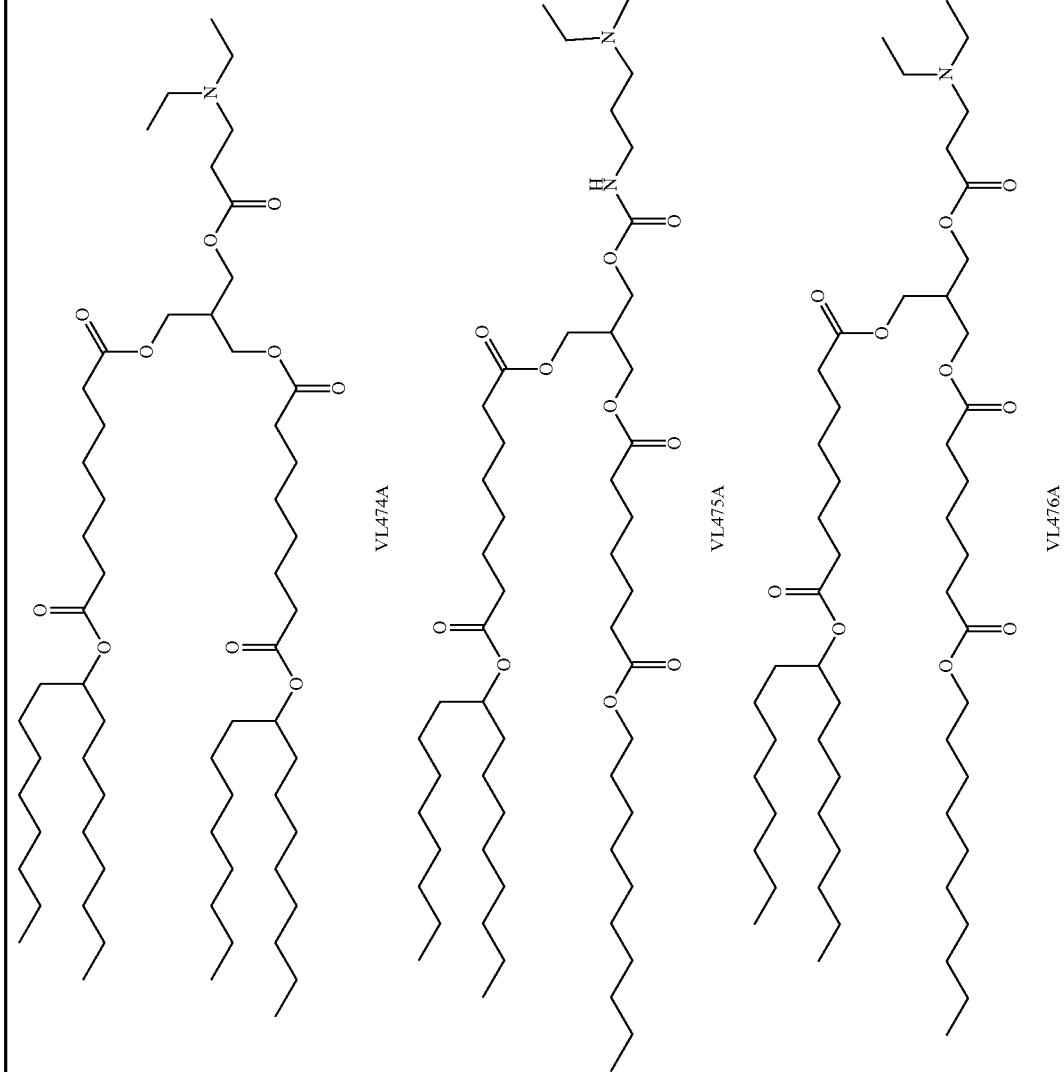
VL474A
VL475A
VL476A TABLE 1A-continued
Amino lipids for constituting lipid nanoparticles. The chiral carbon atom(s) in any of the structures indicate(s) racemic, and/or chirally pure R and S stereoisomers.
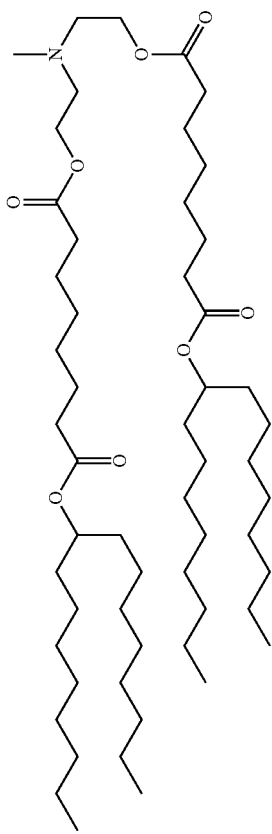
VL529
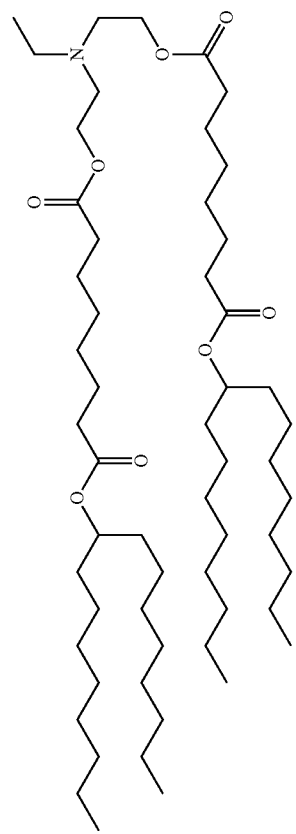

TABLE 1A-continued
Amino lipids for constituting lipid nanoparticles. The chiral carbon atom(s) in any of the structures indicate(s) racemic, and/or chirally pure R and S stereoisomers.
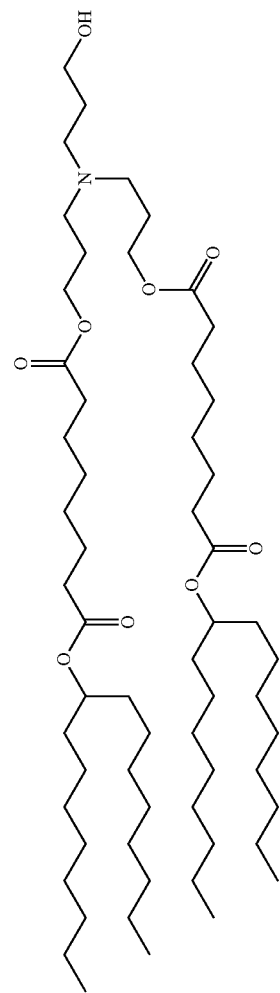
VL530
VL522
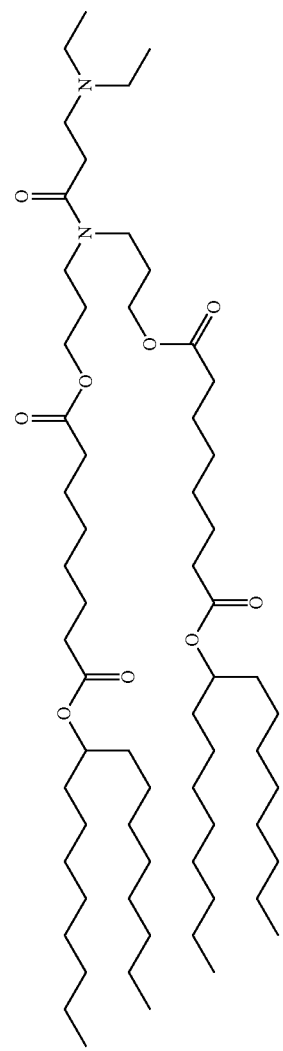
VL531

In some embodiments of a compound of Table 1A, m is 1-10. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, an asymmetric carbon atom in Table 1A represents racemic, chirally pure R or chirally S. In some embodiments, if a compound of Table 1A contains two or more chiral centers, all the combinations of the stereochemistries for each of the chiral centers are encompassed by the disclosure.

In some embodiments, the disclosed amino lipids can be converted to N-oxides. In some embodiments, N-oxides are formed by a treatment with an oxidizing agent (e.g., 3-chloroperoxybenzoic acid and/or hydrogen peroxides). Accordingly, disclosed herein are N-oxide compounds of the described amino lipids, when allowed by valency and structure, which can be designated as N→0 or N$^+$-0$^-$. In some embodiments, the nitrogen in the compounds of the disclosure can be converted to N-hydroxy or N-alkoxy. For example, N-hydroxy compounds can be prepared by oxidation of the parent amine by an oxidizing agent such as ra-CPBA. All shown and claimed nitrogen-containing compounds are also considered. Accordingly, also disclosed herein are N-hydroxy and N-alkoxy (e.g., N—OR, wherein R is substituted or unsubstituted C1-C6 alkyl, C2-C6 alkenyl, C2-C6 alkynyl, 3-14-membered carbocycle or 3-14-membered heterocycle) derivatives of the described amino lipids.

In some embodiments, an amino lipid described herein can take the form of a salt, such as a pharmaceutically acceptable salt. All pharmaceutically acceptable salts of the amino lipid are encompassed by this disclosure. As used herein, the term "amino lipid" also includes its pharmaceutically acceptable salts, and its diastereomeric, enantiomeric, and epimeric forms.

In some embodiments, an amino lipid described herein, possesses one or more stereocenters and each stereocenter exists independently in either the R or S configuration. The lipids presented herein include all diastereomeric, enantiomeric, and epimeric forms as well as the appropriate mixtures thereof. The lipids provided herein include all cis, trans, syn, anti, entgegen (E), and zusammen (Z) isomers as well as the appropriate mixtures thereof. In certain embodiments, lipids described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, the lipids such as the amino lipids are substituted based on the structures disclosed herein. In some embodiments, the amino lipid is a lipid of Table 1A with one or more substituents. In some embodiments, the lipids such as the amino lipids are unsubstituted. In another embodiment, the lipids described herein are labeled isotopically (e.g. with a radioisotope) or by another other means, including, but not limited to, the use of chromophores or fluorescent moieties, bioluminescent labels, or chemiluminescent labels.

Lipids described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present lipids include isotopes of hydrogen, carbon, nitrogen, oxygen, sulfur, fluorine and chlorine, such as, for example, $^2$H, $_3$h, $^{13}$C, $^{14}$C, $^{15}$N, $^{18}$O, $^{17}$O, $^{35}$S, $^{18}$F, $^3_6$cl. In one aspect, isotopically-labeled lipids described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the asymmetric carbon atom of the amino lipid is present in enantiomerically enriched form. In certain embodiments, the asymmetric carbon atom of the amino lipid has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (S)- or (R)-configuration.

Also disclosed herein is a lipid of Table 1B, or a salt or solvate thereof.

TABLE 1B

Amino lipids and excipients for constituting lipid nanoparticles

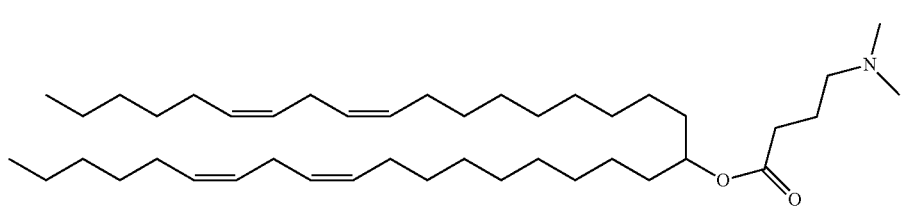 [SMILES: CCCCC/C=C\C/C=C\CCCCCCCCC(CCCCCCCC/C=C\C/C=C\CCCCC)OC(=O)CCCN(C)C]

501

TABLE 1B-continued
Amino lipids and excipients for constituting lipid nanoparticles
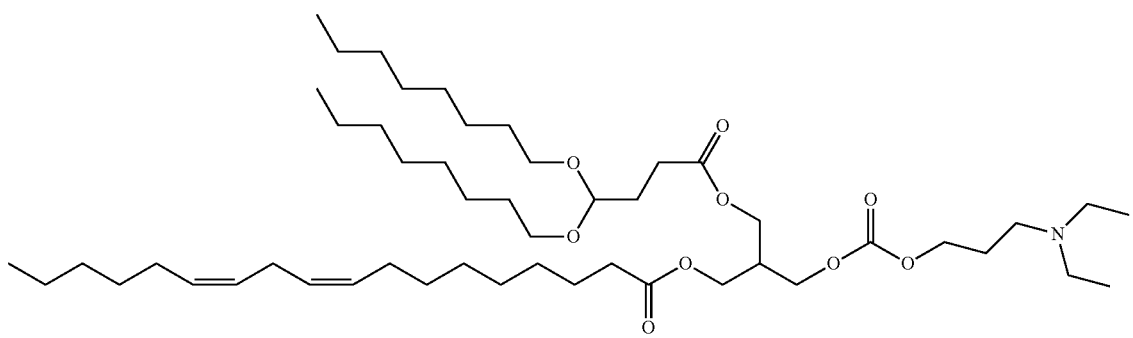 [SMILES: CCCCC/C=C\C/C=C\CCCCCCCC(=O)OCC(COC(=O)CCC(OCCCCCCCC)OCCCCCCCC)COC(=O)OCCCN(CC)CC]
502
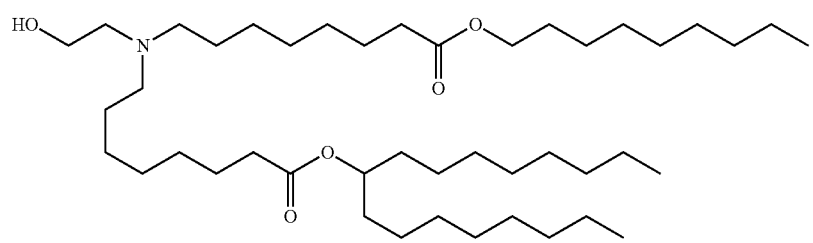 [SMILES: CCCCCCCCCOC(=O)CCCCCCCN(CCO)CCCCCCCC(=O)OC(CCCCCCCC)CCCCCCCC]
503
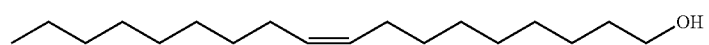 [SMILES: CCCCCCCC/C=C\CCCCCCCCO]
504
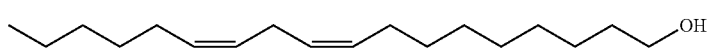
505
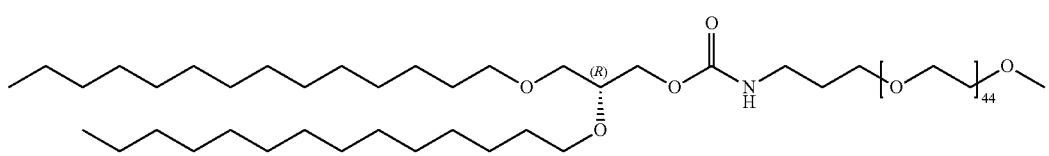
506
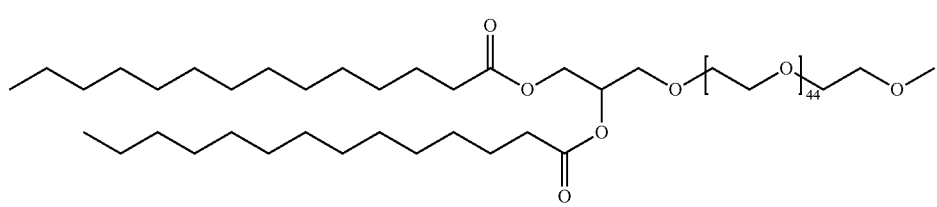
507
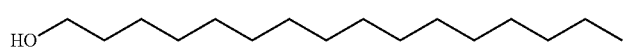 [SMILES: CCCCCCCCCCCCCCCCO]
508
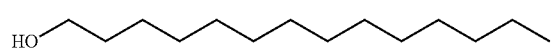
509
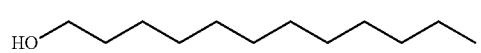
510
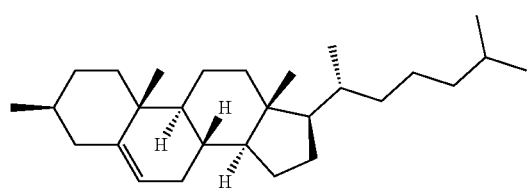
511

TABLE 1B-continued
Amino lipids and excipients for constituting lipid nanoparticles
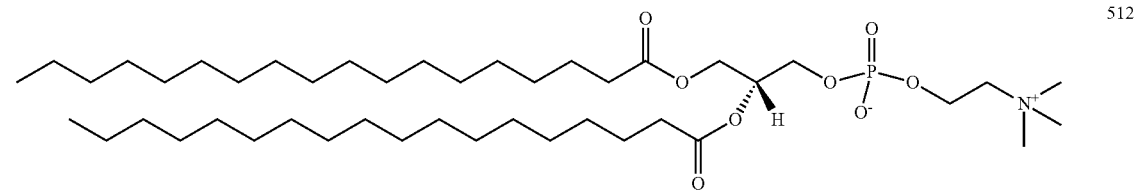 512
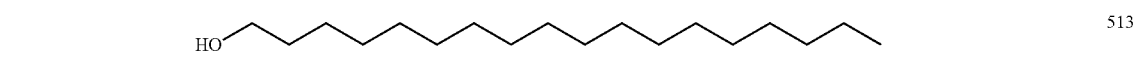 513
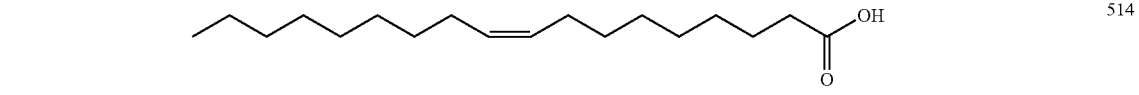 514
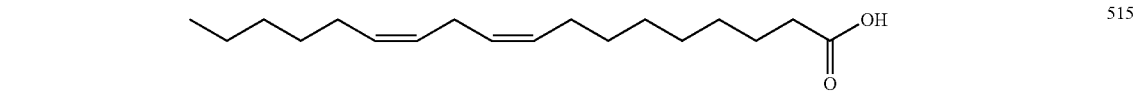 515
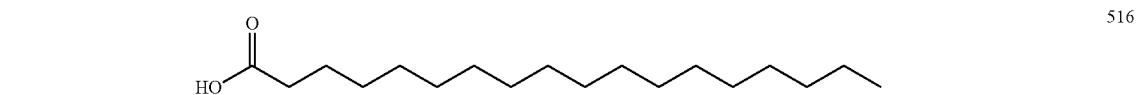 516
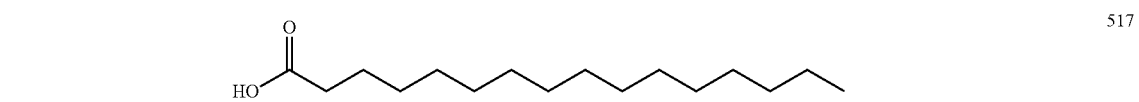 517
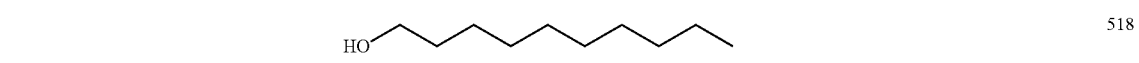 518
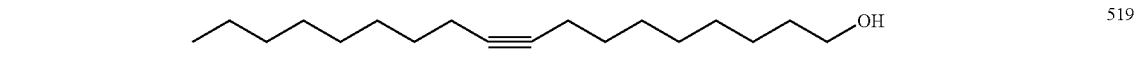 519
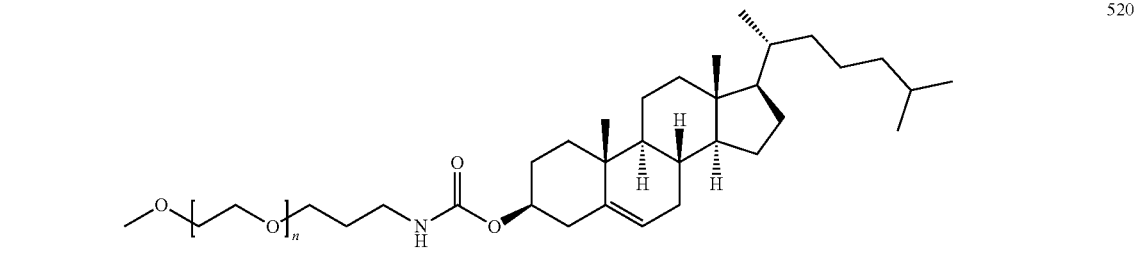 520
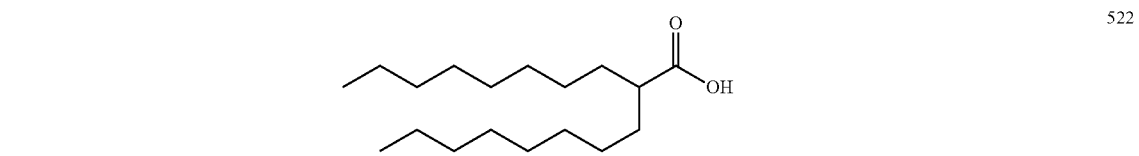 522
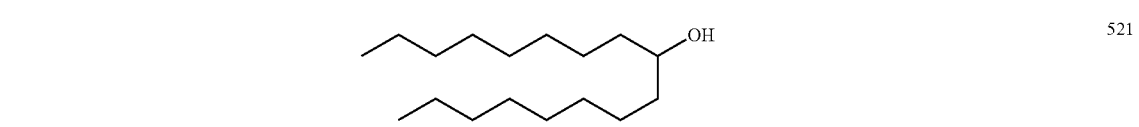 521

TABLE 1B-continued

Amino lipids and excipients for constituting lipid nanoparticles

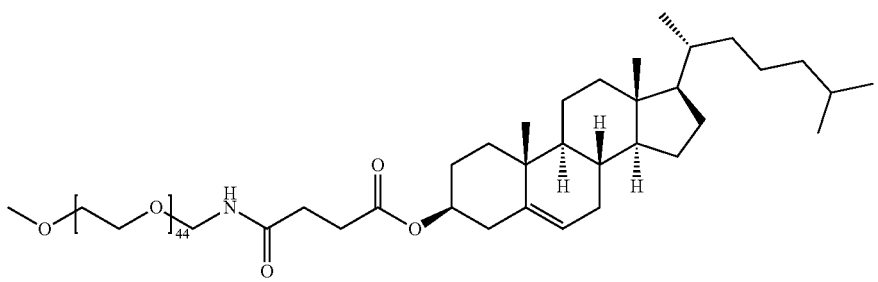
523

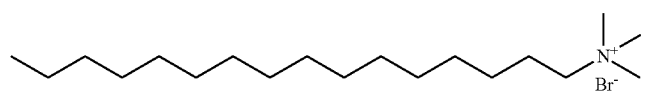 [SMILES: CCCCCCCCCCCCCCCC[N+](C)(C)C ; [Br-]]
524

In some embodiments, an amino lipid (or other lipids) provided herein can be designated by more than one compound ID number in different parts of the disclosure.

PEG-Lipid

In some embodiments, the described LNP composition comprises a PEG-lipid. In some embodiments, the described LNP composition comprises two or more PEG-lipids. Exemplary PEG-lipids include, but are not limited to, the lipids in Table 2. Exemplary PEG-lipids also include, but are not limited to, PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, the one or more PEG-lipids can comprise PEG-c-DOMG, PEG-DMG, PEG-DLPE, PEG-DMPE, PEG-DPPC, a PEG-DSPE lipid, or a combination thereof. In some embodiments, PEG moiety is an optionally substituted linear or branched polymer of ethylene glycol or ethylene oxide. In some embodiments, the PEG moiety is substituted, e.g., by one or more alkyl, alkoxy, acyl, hydroxy, or aryl groups. In some embodiments, the PEG moiety includes PEG copolymer such as PEG-polyurethane or PEG-polypropylene (see, e.g., j. Milton Harris, Poly(ethylene glycol) chemistry: biotechnical and biomedical applications (1992)). In some embodiments, the PEG moiety does not include PEG copolymers, e.g., it may be a PEG monopolymer. Exemplary PEG-lipids include, but are not limited to, PEG-dilauroylglycerol, PEG-dimyristoylglycerol (PEG-DMG), PEG-dipalmitoylglycerol, PEG-distearoylglycerol (PEG-DSPE), PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol, and PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000]).

In some embodiments, a PEG-lipid is a PEG-lipid conjugate, for example, PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG-lipids, polyoxazoline (POZ)-lipid conjugates (e.g., POZ-DAA conjugates; see, e.g., WO 2010/006282), polyamide oligomers (e.g., ATTA-lipid conjugates), and mixtures thereof.

In one aspect, disclosed herein is a PEG-lipid having the structure of Formula (III), or a pharmaceutically acceptable salt or solvate thereof, Formula (III)

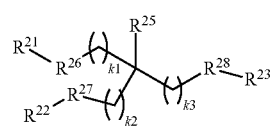

wherein each of $R^{21}$ and $R^{22}$ is independently substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;

each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$ C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH—, —O—, —S—, or a bond;

each of $R^4$ is independently hydrogen or substituted or unsubstituted $C_1$-$C_6$ alkyl;

$R^{23}$ is —C$_0$-C$_{10}$ alkylene-(CH$_2$—CH$_2$—O)$_{k4}$—R$^{24}$ or —C$_1$-C$_{10}$ heteroalkylene-(CH$_2$—CH$_2$—O)$_{k4}$—R$^{24}$, wherein the alkylene and heteroalkylene are each independently substituted or unsubstituted;

$R^{24}$ is independently hydrogen or substituted or unsubstituted $C_1$-$C_3$ alkyl;

$R^{25}$ is hydrogen or substituted or unsubstituted $C_1$-$C_6$ alkyl;

each of k1, k2, and k3 is independently 0, 1, 2, 3, 4, or 5; and k4 is an integer selected from 1 to 100.

In one aspect, disclosed herein is a PEG-lipid having the structure of Formula (III*), or a pharmaceutically acceptable salt or solvate thereof,

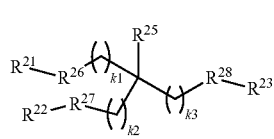

Formula (III*)

wherein $R^{21}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;

$R^{22}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;

each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —N(Ac)—, —OC(O)OCH$_2$C(O)O—, —OC(O)OCH$_2$C(O)NH—, —OC(O)NHCH$_2$C(O)O—, —OC(O)NHCH$_2$C(O)NH—, —OC(O)O(CH$_2$)$_2$C(O)O—, —OC(O)O(CH$_2$)$_2$C(O)NH—, —OC(O)NH(CH$_2$)$_2$C(O)O—, —OC(O)NH(CH$_2$)$_2$C(O)NH—, —OC(O)O(CH$_2$)$_3$C(O)O—, —OC(O)O(CH$_2$)$_3$C(O)NH—, —OC(O)NH(CH$_2$)$_3$C(O)O—, —OC(O)NH(CH$_2$)$_3$C(O)NH—, —C(O)OCH$_2$C(O)NH—, —C(O)NHCH$_2$C(O)O—, —C(O)NHCH$_2$C(O)NH—, —C(O)O(CH$_2$)$_2$C(O)O—, —C(O)O(CH$_2$)$_2$C(O)NH—, —C(O)NH(CH$_2$)$_2$C(O)O—, —C(O)NH(CH$_2$)$_2$C(O)NH—, —C(O)O(CH$_2$)$_3$C(O)O—, —C(O)O(CH$_2$)$_3$C(O)NH—, —C(O)NH(CH$_2$)$_3$C(O)O—, —C(O)NH(CH$_2$)$_3$C(O)NH—, —OC(=O)NR$^4$(CH$_2$)$_{1-3}$C(=O)NH—, —OC(=O)NR$^4$(CH$_2$)$_{1-3}$C(=O)O—, —C(=O)NR$^4$(CH$_2$)$_{1-3}$C(=O)NH—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, —NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;

each of $R^4$ is independently hydrogen or substituted or unsubstituted $C_1$-$C_6$ alkyl;

$R^{23}$ is —C$_0$-C$_{10}$ alkylene-(CH$_2$—CH$_2$—O)$_{k4}$—R$^{24}$, —C$_1$-C$_{10}$ heteroalkylene-(CH$_2$—CH$_2$—O)$_{k4}$—R$^{24}$, —C$_0$-C$_{10}$ alkylene-(O—CH$_2$—CH$_2$)$_{k4}$—R$^{24}$ or —C$_1$-C$_{10}$ heteroalkylene-(O—CH$_2$—CH$_2$)$_{k4}$—R$^{24}$, wherein the alkylene and heteroalkylene are each independently substituted or unsubstituted;

$R^{24}$ is independently hydrogen, substituted or unsubstituted $C_1$-$C_3$ alkyl, —O—R$^4$, —C(=O)OH, or —C(=O)R$^4$;

$R^{25}$ is hydrogen or substituted or unsubstituted $C_1$-$C_{22}$ alkyl;

each of k1, k2, and k3 is independently 0, 1, 2, 3, 4, or 5; and k4 is an integer selected from 1 to 100.

In some embodiments, the PEG-lipid of Formula (III) or (II*), or a pharmaceutically acceptable salt or solvate thereof, wherein $R^{21}$ is substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;

$R^{22}$ is hydrogen, substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;

each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —OC(=O)NR$^4$C(=O)NH—, —OC(=O)NR$^4$C(=O)O—, —C(=O)NR$^4$C(=O)NH—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH—, —O—, —S—, or a bond;

each of $R^4$ is independently hydrogen or substituted or unsubstituted $C_1$-$C_6$ alkyl;

$R^{23}$ is —C$_0$-C$_{10}$ alkylene-(CH$_2$—CH$_2$—O)$_{k4}$—R$^{24}$ or —C$_1$-C$_{10}$ heteroalkylene-(CH$_2$—CH$_2$—O)$_{k4}$—R$^{24}$, wherein the alkylene and heteroalkylene are each independently substituted or unsubstituted;

$R^{24}$ is independently hydrogen, substituted or unsubstituted $C_1$-$C_3$ alkyl, —O—R$^4$, —C(=O)OR$^4$, or —C(=O)R$^4$;

$R^{25}$ is hydrogen or substituted or unsubstituted $C_1$-$C_6$ alkyl;

each of k1, k2, and k3 is independently 0, 1, 2, 3, 4, or 5; and k4 is an integer selected from 1 to 100.

In some embodiments of a compound of Formula (III) or (III*), or a pharmaceutically acceptable salt or solvate thereof, each of $R^{21}$ and $R^{22}$ is independently unsubstituted or substituted, linear or branched $C_{12}$-$C_{30}$ alkyl. In some embodiments, each of $R^{21}$ and $R^{12}$ is independently unsubstituted, linear $C_{12}$-$C_{25}$ alkyl. In some embodiments of a compound of Formula (III), or a pharmaceutically acceptable salt or solvate thereof, each of $R^{21}$ and $R^{22}$ is independently unsubstituted or substituted, linear or branched $C_{12}$-$C_{30}$ alkenyl. In some embodiments, each of $R^{21}$ and $R^{22}$ is independently unsubstituted, linear $C_{12}$-$C_{25}$ alkenyl.

In some embodiments of a compound of Formula (III) or (III*), or a pharmaceutically acceptable salt or solvate thereof, each of $R^{26}$ and $R^{27}$ is —O—, —C(=O)O—, or —OC(=O)—. In some embodiments, each of $R^{26}$ and $R^{21}$ is —O—. In some embodiments, each of $R^{26}$ and $R^{27}$ is a bond.

In some embodiments of a compound of Formula (III) or (III*), or a pharmaceutically acceptable salt or solvate thereof, $R^{28}$ is —O—, —C(=O)O—, —OC(=O)—, or —OC(=O)NR$^4$. In some embodiments of a compound of Formula (III*), $R^{28}$ is —OC(=O)NR$^4$. In some embodiments of a compound of Formula (III) or (III*), or a pharmaceutically acceptable salt or solvate thereof, $R^{28}$ is —C(=O)O— or —OC(=O)—.

In some embodiments of a compound of Formula (III*), or a pharmaceutically acceptable salt or solvate thereof, $R^{26}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$ C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH, —N(Ac)—, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(O)(NH)(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)O—, —C(O)O(CH$_2$)$_3$C(O)(NH)—, —C(O)(NH)(CH$_2$)$_3$C(O)O—, —C(O)(NH)(CH$_2$)$_3$C(O)(NH)— or a bond.

In some embodiments of a compound of Formula (III) or (III*), or a pharmaceutically acceptable salt or solvate thereof, $R^{26}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —C(O)NH(CH$_2$)$_2$O—, —C(O)N(Me)(CH$_2$)$_2$NH—, —O$_2$C(NH)(CH$_2$)N(CH$_3$)—, or —O(CH$_2$)$_2$C(NH)NH—.

In some embodiments of a compound of Formula (III*), or a pharmaceutically acceptable salt or solvate thereof, $R^{27}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)— —O C(NH)(CH$_2$)$_2$O—, —OC(NMe)(CH$_2$)$_2$NH—, —O$_2$C(NH)(CH$_2$)N(CH$_3$)—, or —O(CH$_2$)$_2$C(NH)NH—.

In some embodiments of a compound of Formula (II*), or a pharmaceutically acceptable salt or solvate thereof, $R^{28}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$ C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH, —N(Ac)—, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(O)(NH)(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)O—, —C(O)O(CH$_2$)$_3$C(O)(NH)—, —C(O)(NH)(CH$_2$)$_3$C(O)O—, or —C(O)(NH)(CH$_2$)$_3$C(O)(NH)—.

In some embodiments of a compound of Formula (III) or (III*), or a pharmaceutically acceptable salt or solvate thereof, $R^{28}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C (O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)(CH$_2$)$_2$NH—, —O$_2$C(NH)(CH$_2$)N(CH$_3$)—, or —O(CH$_2$)$_2$C(NH)NH—.

In some embodiments of a compound of Formula (III) or (III*), or a pharmaceutically acceptable salt or solvate thereof, k1 is 0, 1, or 2. In some embodiment, k1 is 0. In some embodiment, k1 is 1. In some embodiment, k1 is 2.

In some embodiments of a compound of Formula (III) or (III*), or a pharmaceutically acceptable salt or solvate thereof, k2 is 0, 1, or 2. In some embodiment, k2 is 0. In some embodiment, k2 is 1. In some embodiment, k2 is 2.

In some embodiments of a compound of Formula (III) or (III*), or a pharmaceutically acceptable salt or solvate thereof, k3 is 0, 1, or 2. In some embodiment, k3 is 0. In some embodiment, k3 is 1. In some embodiment, k3 is 2.

In some embodiments of a compound of Formula (III) or (III*), or a pharmaceutically acceptable salt or solvate thereof, $R^{23}$ is —C$_0$-C$_3$ alkylene-(CH$_2$—CH$_2$—O)$_{k4}$—R$^{24}$, wherein $R^{24}$ is H, ethyl or methyl. In some embodiments of a compound of Formula (III) or (III*), or a pharmaceutically acceptable salt or solvate thereof, $R^{23}$ is —C$_1$-C$_5$ heteroalkylene-(CH$_2$—CH$_2$—O)$_{k4}$—R$^{24}$, wherein $R^{14}$ is H or methyl. In some embodiments of a compound of Formula (III) or (III*), or a pharmaceutically acceptable salt or solvate thereof, $R^{23}$ is —C$_2$ alkylene-(CH$_2$—CH$_2$—O)$_{k4}$—R$^{24}$; wherein $R^{24}$ is —O—CH$_3$ In some embodiments of a compound of Formula (III) or (III*), or a pharmaceutically acceptable salt or solvate thereof, $R^{23}$ is —C$_3$ alkylene-(CH$_2$—CH$_2$—O)$_{k4}$—R$^{24}$; wherein $R^{24}$ is —O—CH$_3$.

In some embodiments of a compound of Formula (III) or (III*), or a pharmaceutically acceptable salt or solvate thereof, k4 is 1 to 75. In some embodiments, k4 is 1 to 50, 1 to 30, 1 to 25, 1 to 20, 1 to 15, 1 to 10, 1 to 5, 20 to 50, or 5 to 50. In some embodiments, k4 is 30 to 50. In some embodiments, k4 is 35 to 45. In some embodiments, k4 is 40 to 50. In some embodiments, k4 is 36 to 48.

In some embodiments of a compound of Formula (III) or (III*), or a pharmaceutically acceptable salt or solvate thereof, $R^{25}$ is hydrogen.

In some embodiments of a compound of Formula (III*), $R^{22}$ is the unsubstituted C$_{28}$ alkenyl:

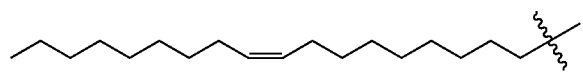 [SMILES: *CCCCCCCC/C=C\CCCCCCCC]

In some embodiments of a compound of Formula (III*), or a pharmaceutically acceptable salt or solvate thereof, $R^{21}$ is C$_{12-22}$ substituted or unsubstituted alkyl; $R^{22}$ is C$_{12-22}$ substituted or unsubstituted alkyl; $R^{25}$ is H; $R^{26}$ is —O—; $R^{27}$ is —O—; $R^{28}$ is —N(Ac)—, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(O)(NH)(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)O—, —C(O)O(CH$_2$)$_3$C(O)(NH)—, —C(O)(NH)(CH$_2$)$_3$C(O)O—, or —C(O)(NH)(CH$_2$)$_3$C(O)(NH)—; k1 is 1, k2 is zero and k3 is 1

In some embodiments of a compound of Formula (III*), or a pharmaceutically acceptable salt or solvate thereof, $R^{25}$ is C$_{10-22}$ substituted or unsubstituted alkyl, $R^{28}$ is —O(CH$_2$)$_2$ C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$ C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH, —N(Ac)—, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(O)(NH)(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)O—, —C(O)O(CH$_2$)$_3$C(O)(NH)—, —C(O)(NH)(CH$_2$)$_3$C(O)O—, or —C(O)(NH)(CH$_2$)$_3$C(O)(NH)— and k3 is 1, wherein $R^{21}$ is hydrogen, $R^{22}$ is hydrogen, $R^{26}$ is a bond, $R^{27}$ is a bond, k1 is 0, and k2 is 0.

In some embodiments of a compound of Formula (III*), or a pharmaceutically acceptable salt or solvate thereof, $R^2$ is C$_{10-22}$ alkyl; $R^{28}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$ C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH, —N(Ac)-, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(OX)NH(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)O—, —C(O)O(CH$_2$)$_3$C(O)(NH)—, —C(O)(NH)(CH$_2$)$_3$C(O)O—, or —C(O)(NH)(CH$_2$)$_3$C(O)(NH)— and k3 is 1; wherein $R^{21}$ is a hydrogen, $R^{22}$ is hydrogen, $R^{26}$ is a bond, $R^{27}$ is a bond, k1 is 0, and k2 is 0.

In some embodiments of a compound of Formula (III*), or a pharmaceutically acceptable salt or solvate thereof, $R^{21}$ is C$_{14-18}$ substituted or unsubstituted alkyl; $R^{22}$ is C$_{14-18}$ substituted or unsubstituted alkyl; $R^{25}$ is H; $R^{26}$ is —O—; $R^{27}$ is —O—; $R^{28}$ is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)CH$_2$)$_2$NH—, —O$_2$C(NH)(CH$_2$)N(CH$_3$)—, —O(CH$_2$)$_2$C(NH)NH, —N(Ac)—, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(O)(NH)(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)(NH)(CH$_2$)$_2$C(O)(NH)—, —C(O)O(CH$_2$)$_3$C(O)(NH)—, —C(O)O(CH$_2$)$_3$C(O)(NH)—, —C(O)(NH)(CH$_2$)$_3$C(O)O—, or —C(O)(NH)(CH$_2$)$_3$C(O)(NH)—; k1 is 1, k2 is zero and k3 is 1

In some embodiments of a compound of Formula (III*), or a pharmaceutically acceptable salt or solvate thereof, $R^{21}$ is C$_{14}$ substituted or unsubstituted alkyl; $R^{22}$ is C$_{14}$ substituted or unsubstituted alkyl; $R^{25}$ is H; $R^{26}$ is —O—; $R^{27}$ is —O—; R'S is —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —O C(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH, —N(Ac)-, —OC(O)O(CH$_2$)C(O)O—, —OC(O)O(CH$_2$)C(O)(NH)— —OC(O)(NH)(CH$_2$)C(O)O—, —OC(O)(NH)(CH$_2$)C(O)(NH)—, —OC(O)O(CH$_2$)$_2$C(O)O—, —OC(O)O(CH$_2$)$_2$C(O)(NH)—, —OC(O)(NH)(CH$_2$)$_2$C(O)O—, —OC(O)(NH)(CH$_2$)$_2$C(O)(NH)—, —OC(O)O(CH$_2$)$_3$C(O)O—, —OC(O)O(CH$_2$)$_3$C(O)(NH)—, —OC(O)(NH)(CH$_2$)$_3$C(O)O—, —OC(O)(NH)(CH$_2$)$_3$C(O)(NH)—, —C(O)O(CH$_2$)C(O)(NH)— —C(O)(NH)(CH$_2$)C(O)O—, —C(OX)NH(CH$_2$)C(O)(NH)—, —C(O)O(CH$_2$)$_2$C(O)O—, —C(O)O(CH$_2$)$_2$C(O)(NH)—, —C(O)(NH)(CH$_2$)$_2$C(O)O—, —C(O)NH(CH$_2$)$_2$C(O)(NH)—, —C(O)O(CH$_2$)$_3$C(O)(NH)—, —C(O)O(CH$_2$)$_3$C(O)(NH)—, —C(O)(NH)(CH$_2$)$_3$C(O)(NH)—; k1 is 1, k2 is zero and k3 is 1.

In some embodiments, disclosed herein is a PEG-lipid comprising a structure of —O(CH$_2$)$_2$C(O)O— or —O(CH$_2$)$_2$ C(O)NH—.

In one aspect, disclosed herein is a PEG-lipid of Table 2.

TABLE 2

Exemplary PEG-Lipids for constituting LNP

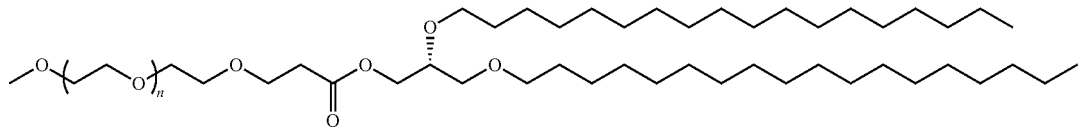

VP101

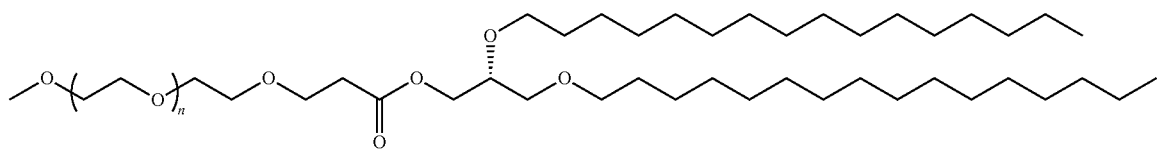

VP102

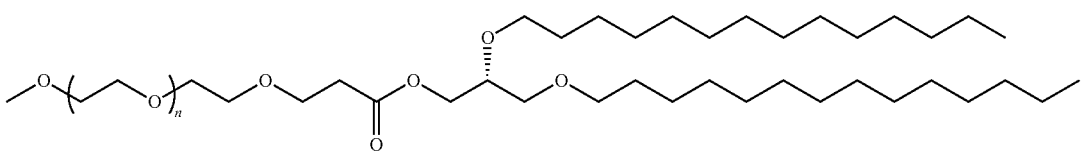

VP103

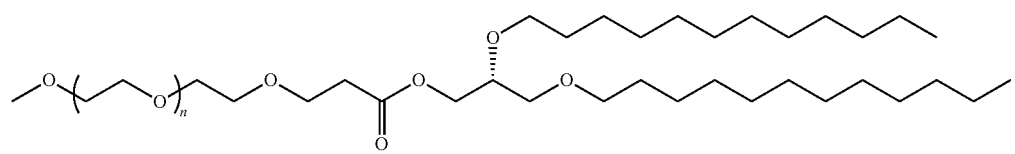

VP104

TABLE 2-continued
Exemplary PEG-Lipids for constituting LNP
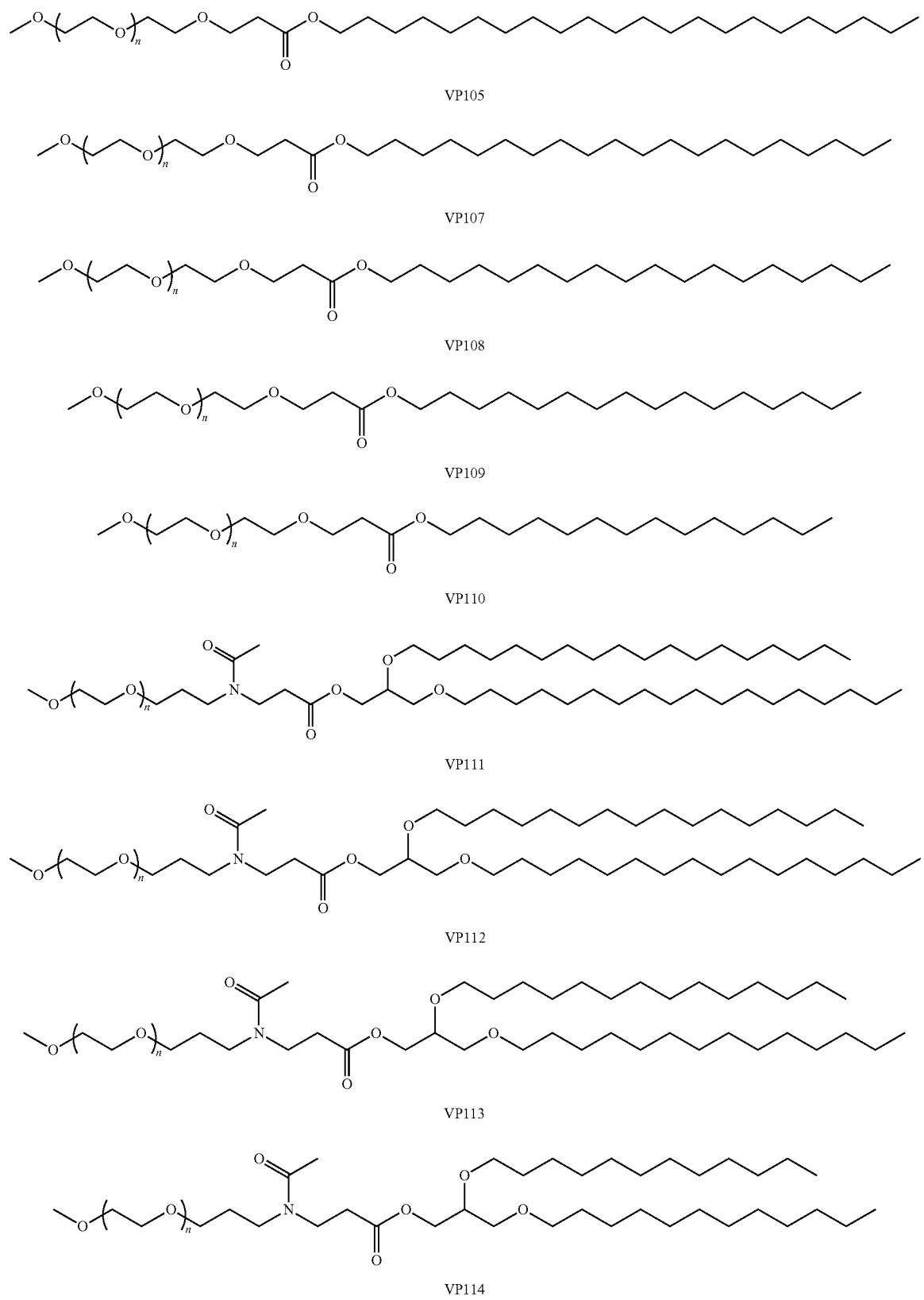

TABLE 2-continued
Exemplary PEG-Lipids for constituting LNP
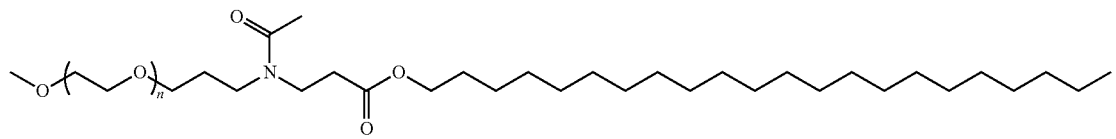
VP115
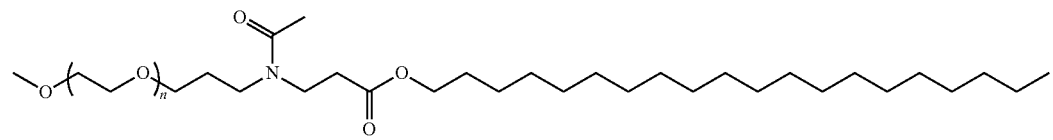
VP116
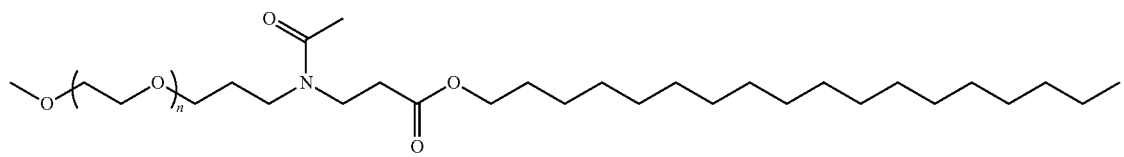
VP117
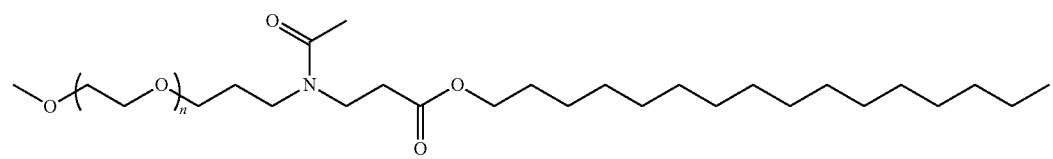
VP118
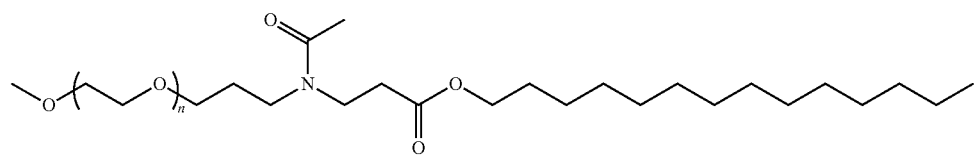
VP119
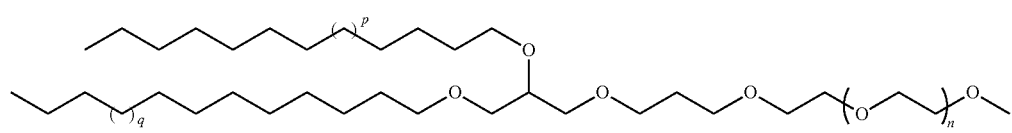
VP120 (p, q = 7)
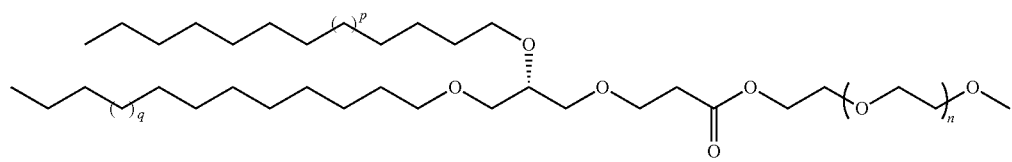
VP121 (p, q = 7)

TABLE 2-continued
Exemplary PEG-Lipids for constituting LNP
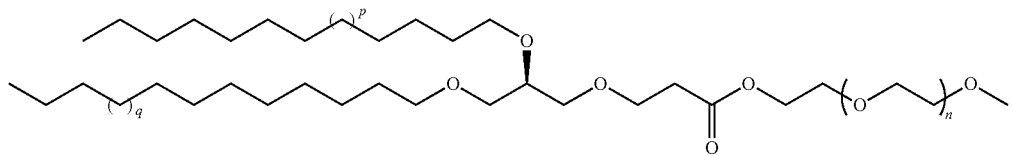
VP122 (p, q = 7)
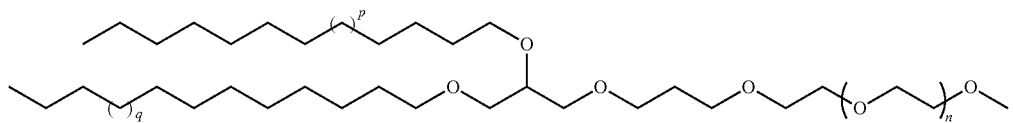
VP123 (p, q = 5)
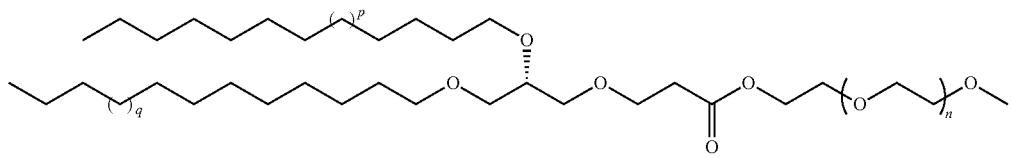
VP124 (p, q = 5)
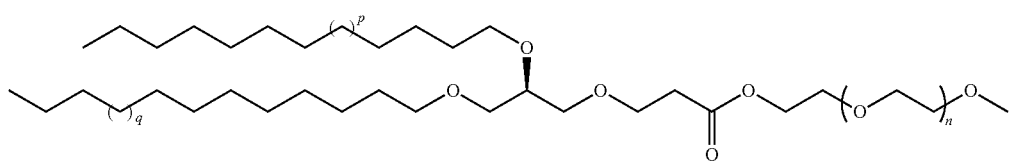
VP125 (p, q = 5)
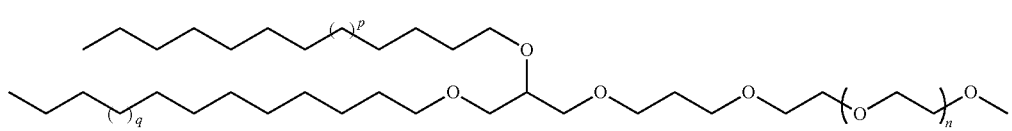
VP126 (p, q = 3)
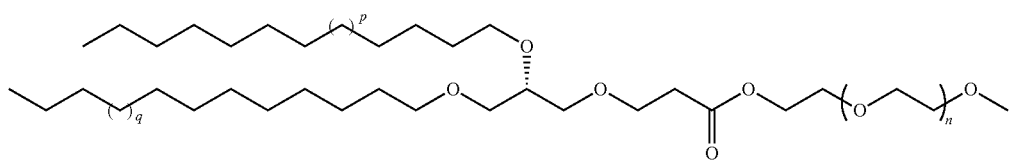
VP127 (p, q = 3)
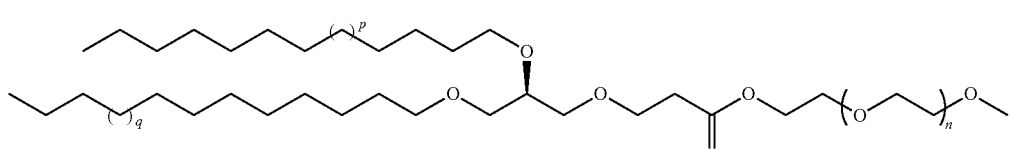
VP128 (p, q = 3)

TABLE 2-continued
Exemplary PEG-Lipids for constituting LNP
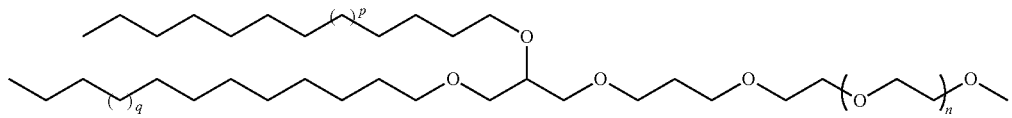
VP129 (p, q = 1)
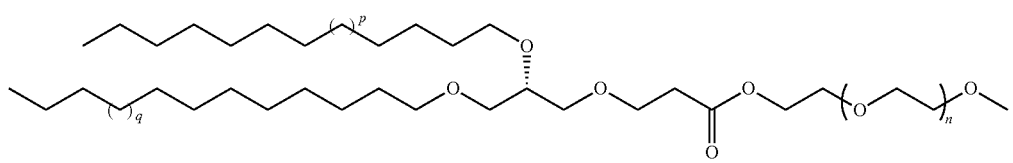
VP130 (p, q = 1)
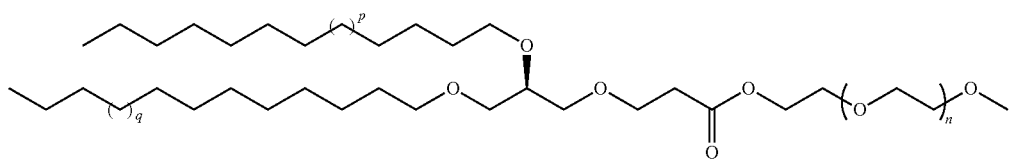
VP131 (p, q = 1)
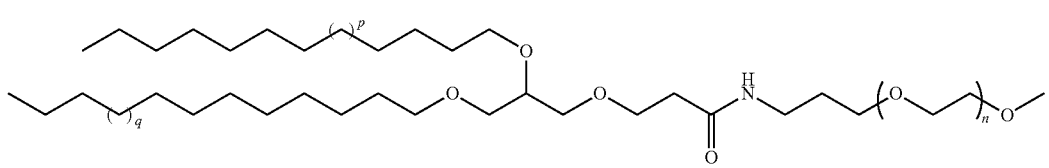
VP132 (p, q = 7)
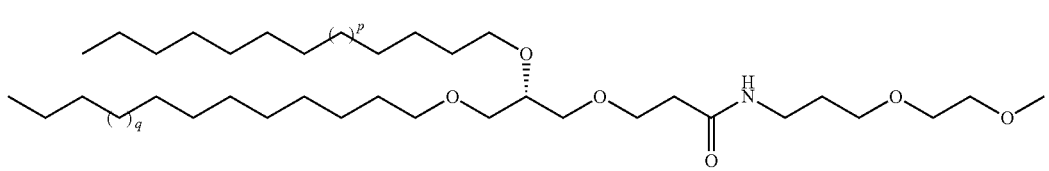
VP133 (p, q = 7)
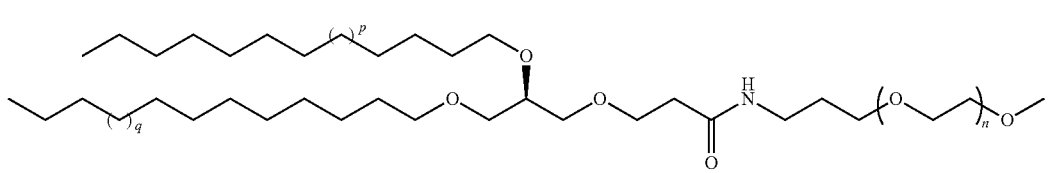
VP134 (p, q = 7)
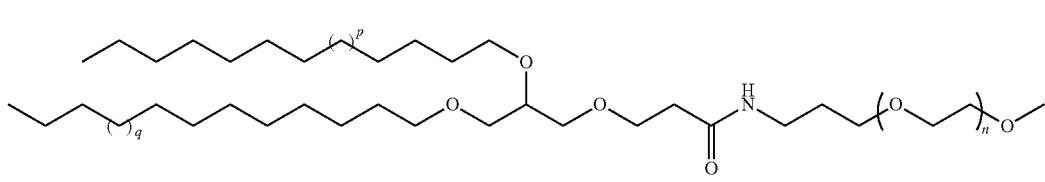
VP135 (p, q = 5)

TABLE 2-continued
Exemplary PEG-Lipids for constituting LNP
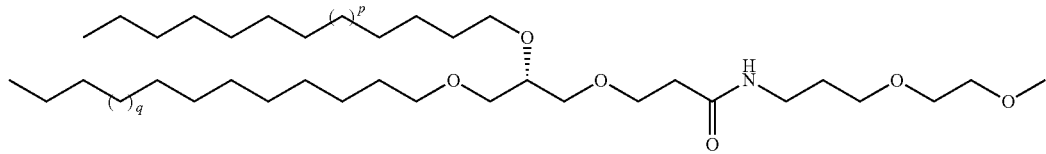
VP136 (p, q = 5)
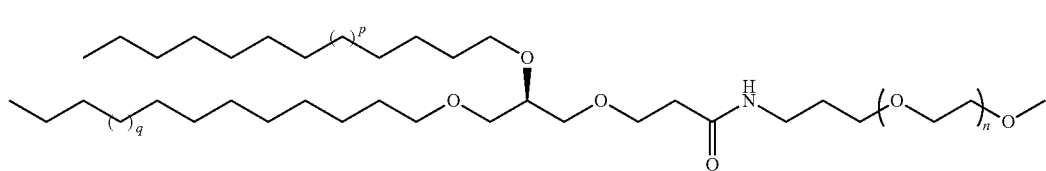
VP137 (p, q = 5)
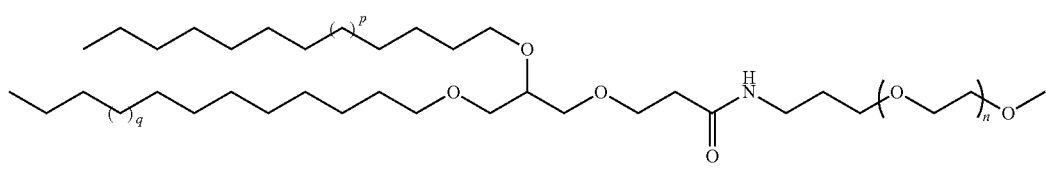
VP138 (p, q = 3)
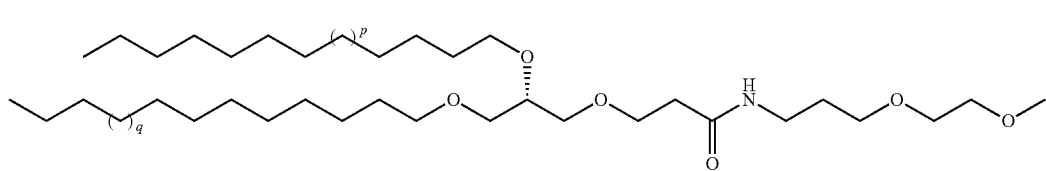
VP139 (p, q = 3)
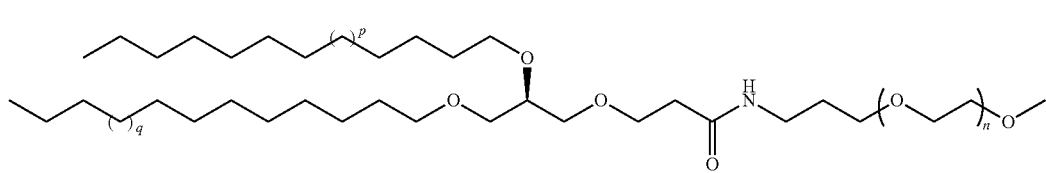
VP140 (p, q = 3)
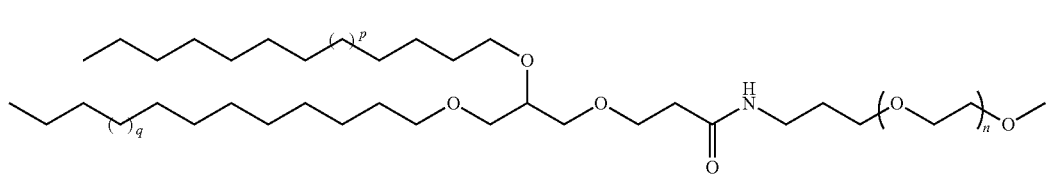
VP141 (p, q = 1)

TABLE 2-continued
Exemplary PEG-Lipids for constituting LNP
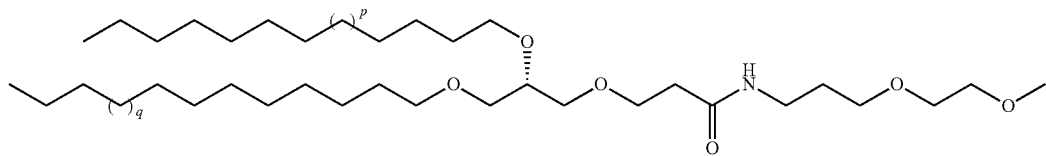
VP142 (p, q = 1)
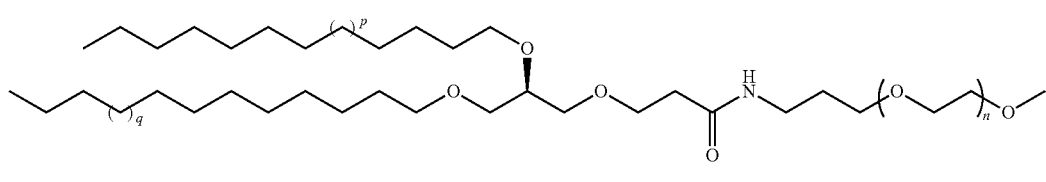
VP143 (p, q = 1)
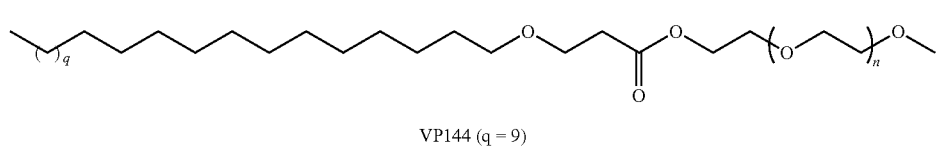
VP144 (q = 9)
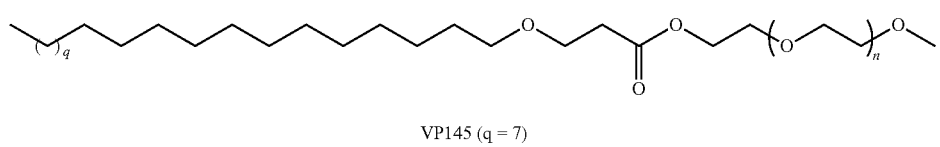
VP145 (q = 7)
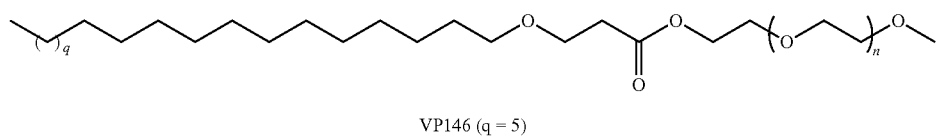
VP146 (q = 5)
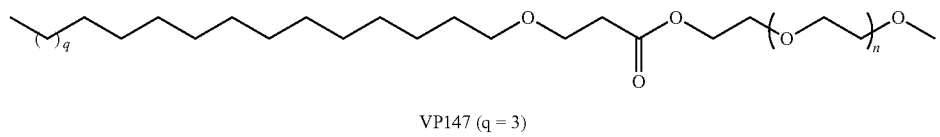
VP147 (q = 3)
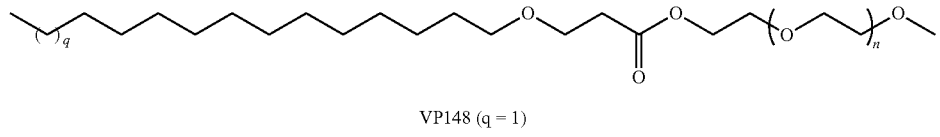
VP148 (q = 1)
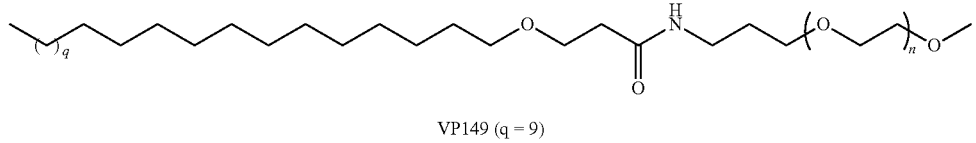
VP149 (q = 9)
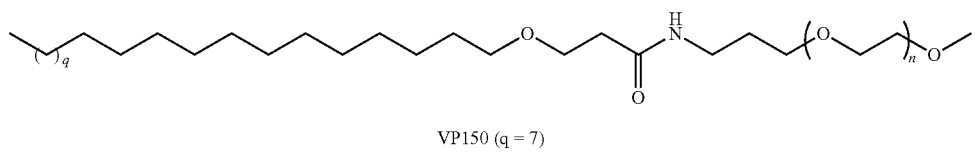
VP150 (q = 7)

TABLE 2-continued
Exemplary PEG-Lipids for constituting LNP
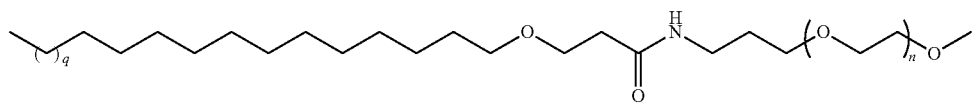
VP151 (q = 5)
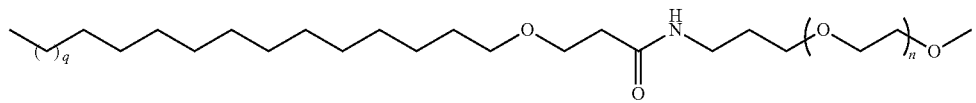
VP152 (q = 3)
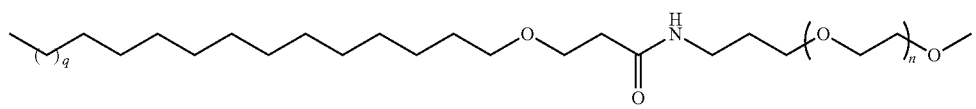
VP153 (q = 1)
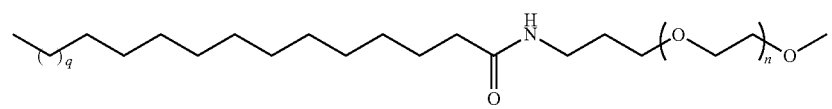
VP154 (q = 5)
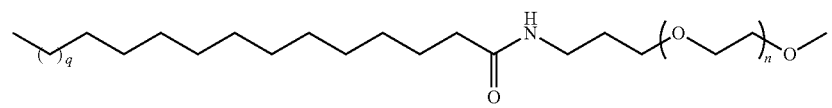
VP155 (q = 3)
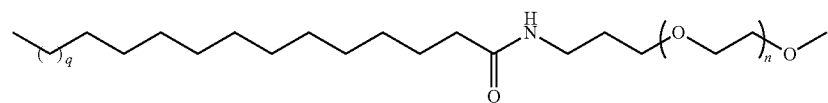
VP156 (q = 1)
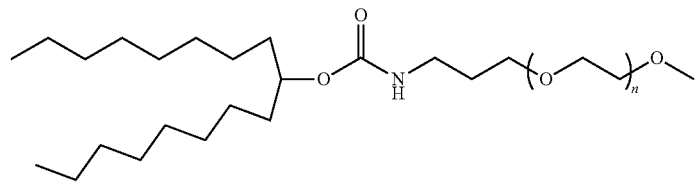
VP157
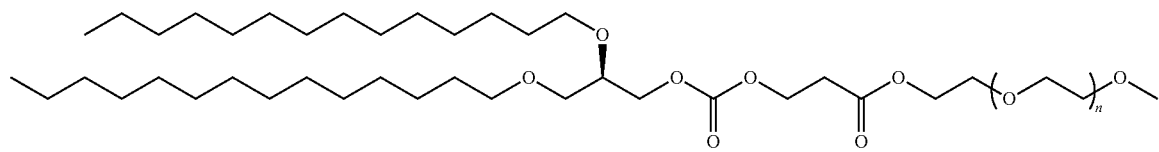
VP158, n = 36-48

TABLE 2-continued
Exemplary PEG-Lipids for constituting LNP
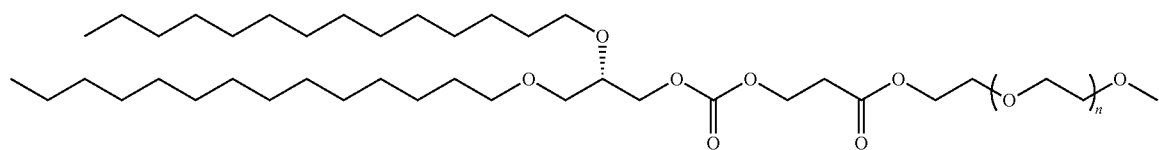
VP158A, n = 36-48
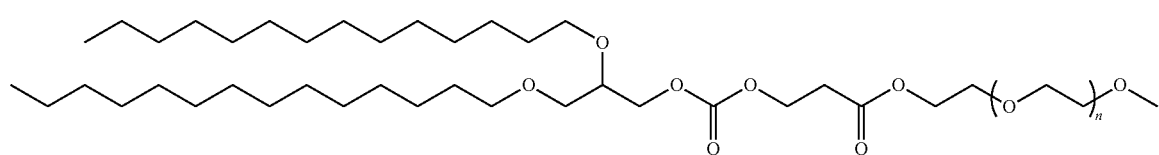
VP158B, n = 36-48
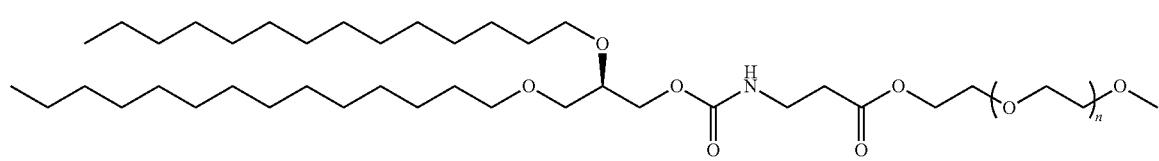
VP159, n = 36-48
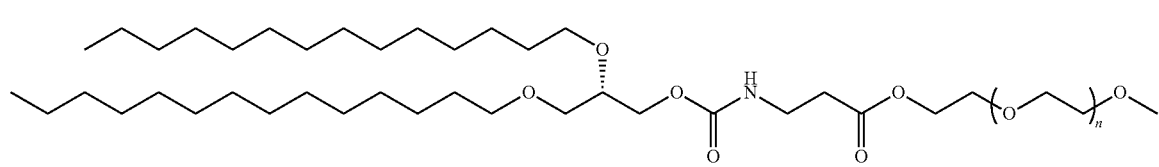
VP159A, n = 36-48
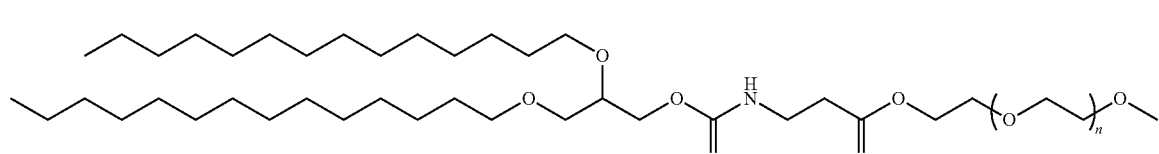
VP159B, n = 36-48
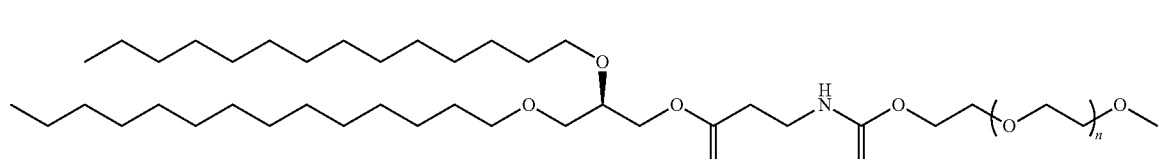
VP160, n = 36-48
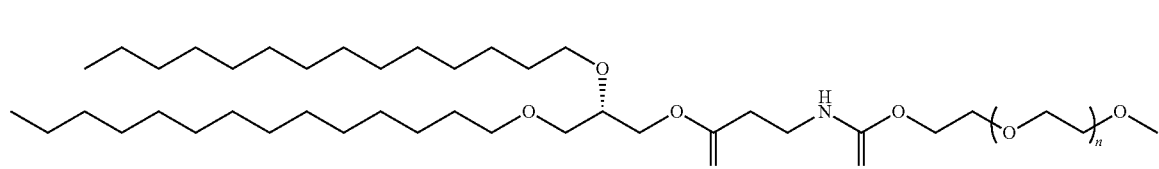
VP160A, n = 36-48

TABLE 2-continued
Exemplary PEG-Lipids for constituting LNP
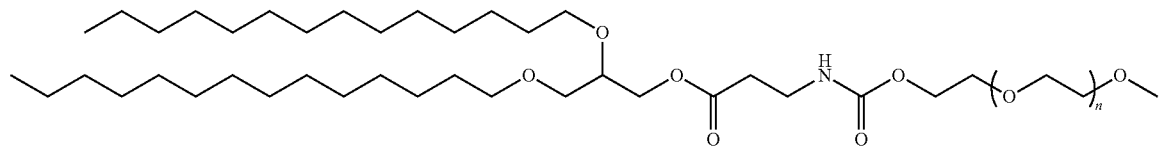
VP160B, n = 36-48
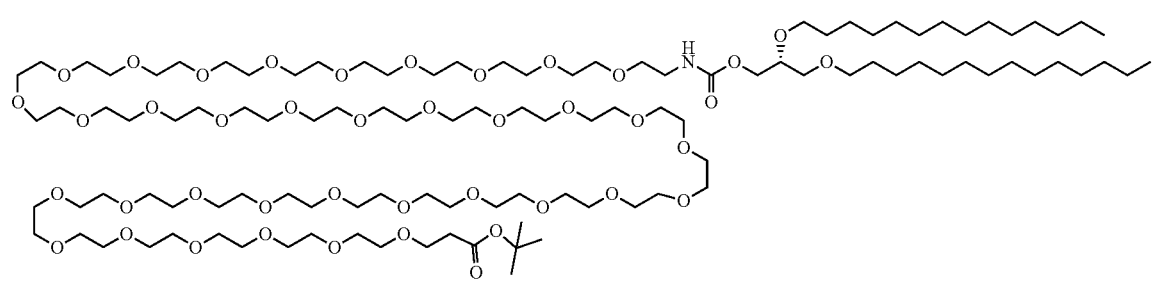
VP161
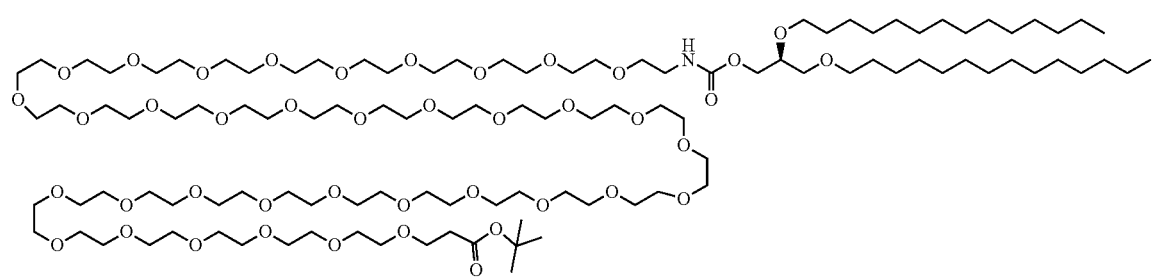
VP161A
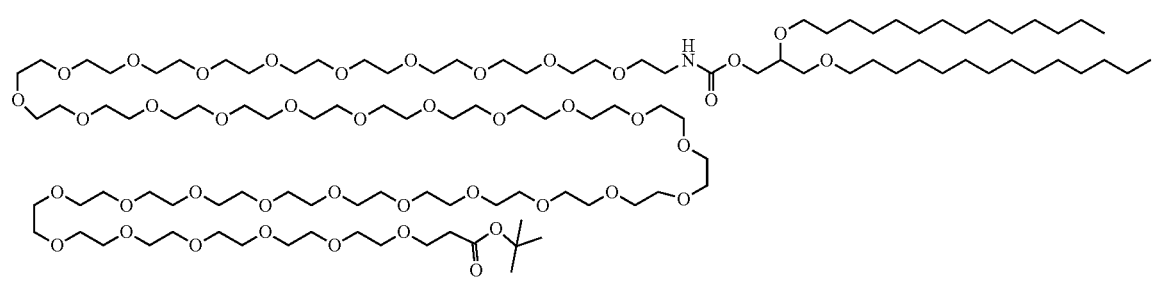
VP161B
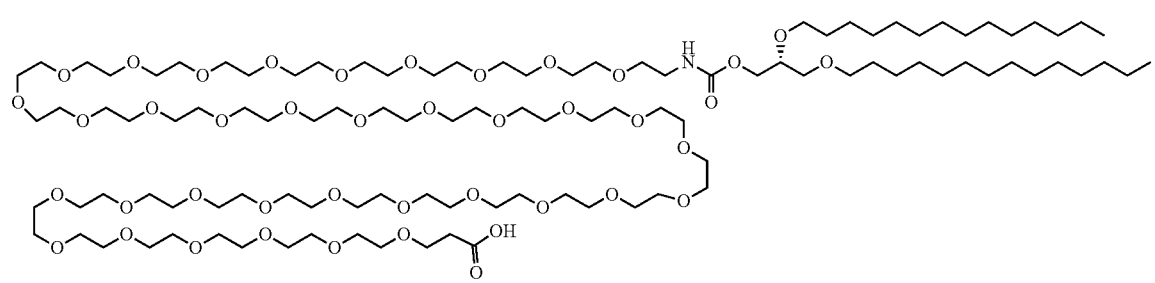
VP162

TABLE 2-continued
Exemplary PEG-Lipids for constituting LNP
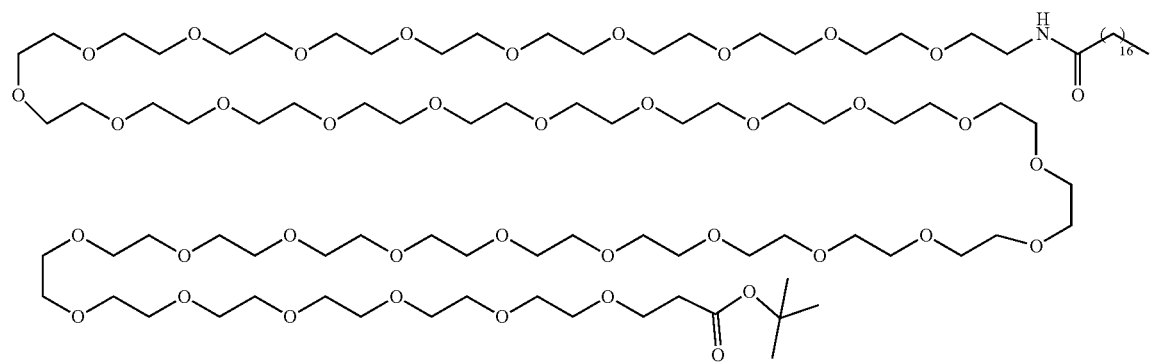
VP163
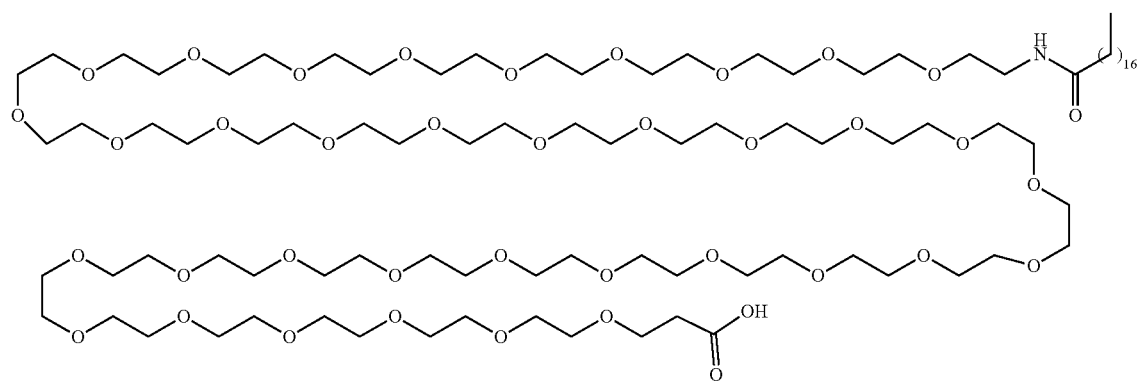
VP164
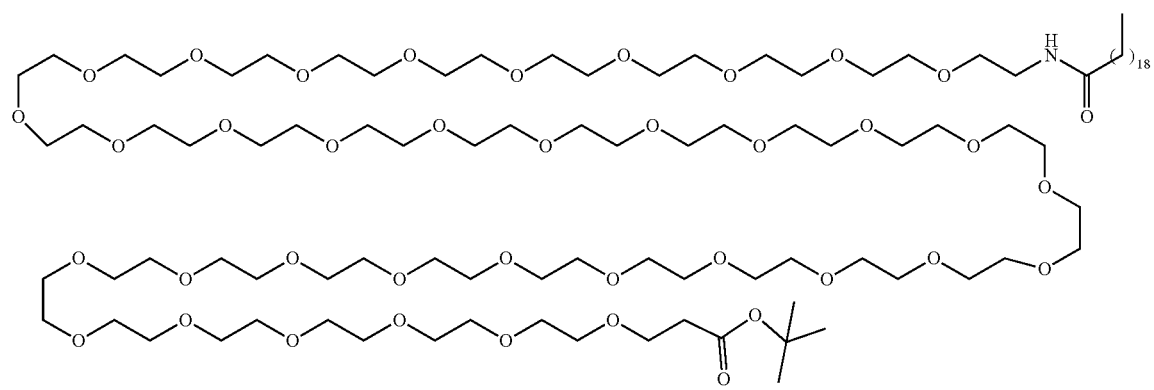
VP165

TABLE 2-continued
Exemplary PEG-Lipids for constituting LNP
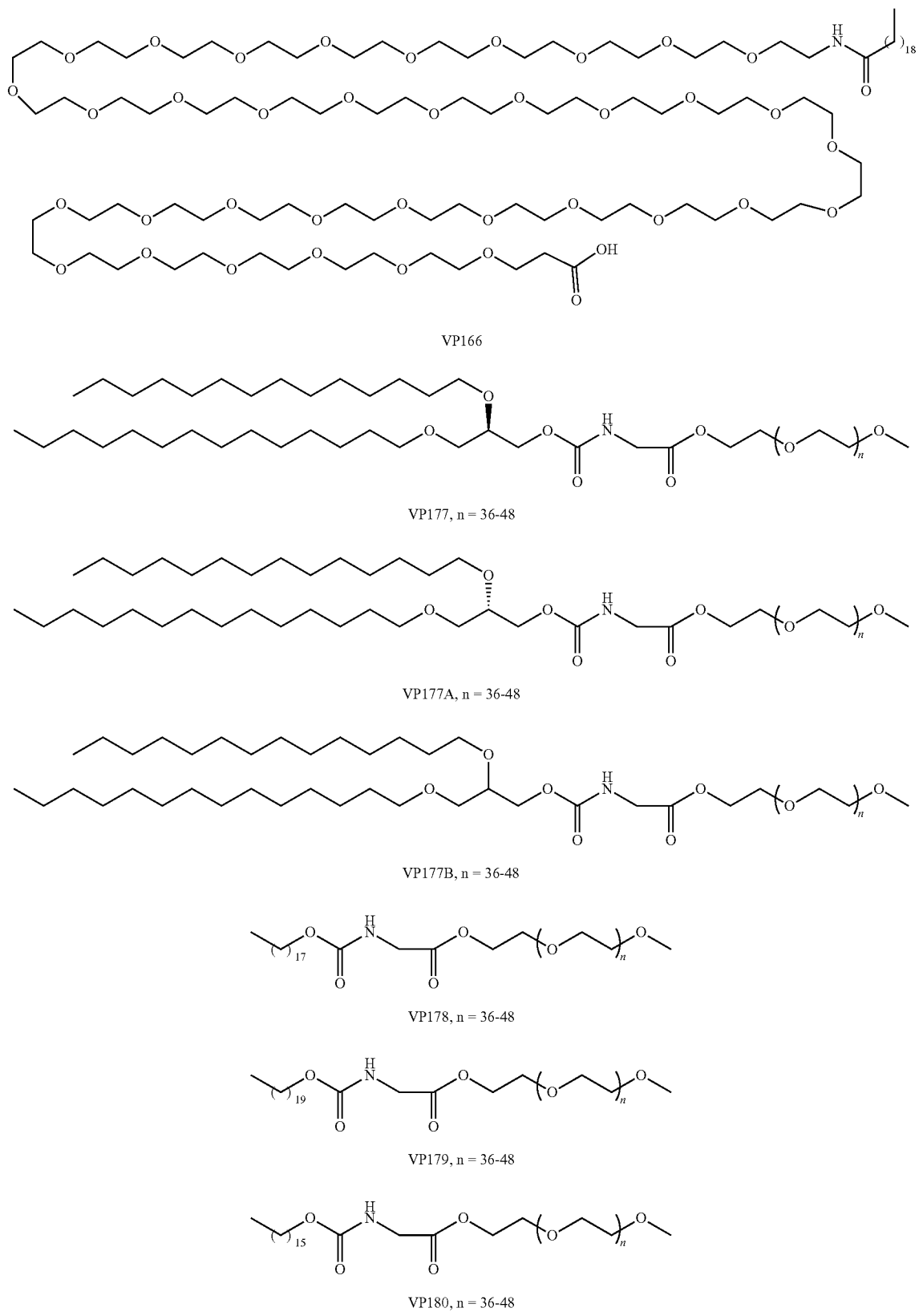
VP166
VP177, n = 36-48
VP177A, n = 36-48
VP177B, n = 36-48
VP178, n = 36-48
VP179, n = 36-48
VP180, n = 36-48

TABLE 2-continued
Exemplary PEG-Lipids for constituting LNP
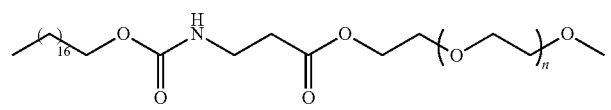
VP181, n = 36-48
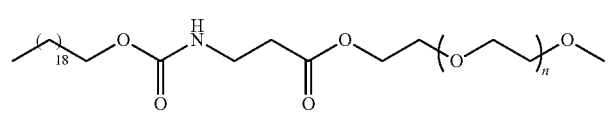
VP182, n = 36-48
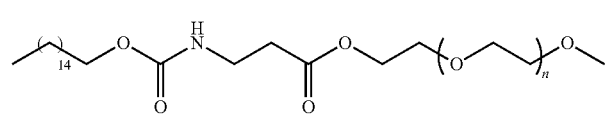
VP183, n = 32-48
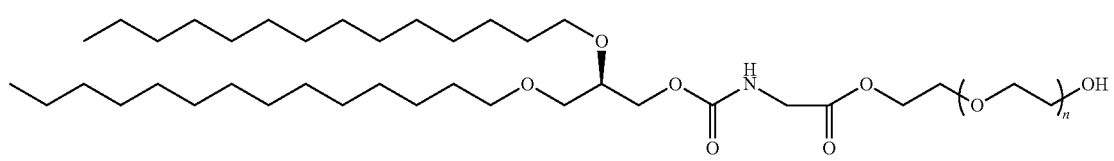
VP184, n = 36-48
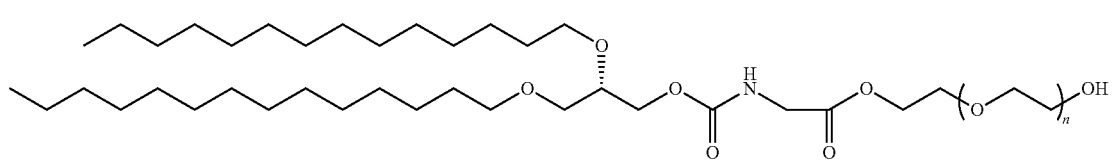
VP184A, n = 36-48
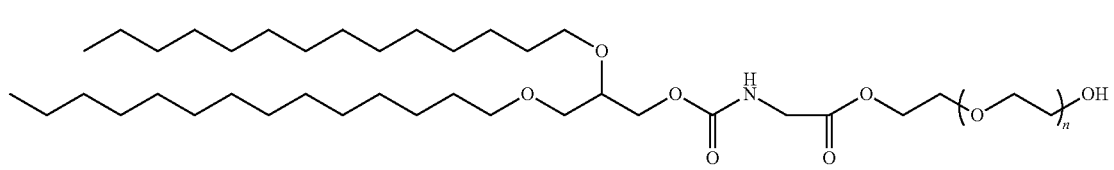
VP184B, n = 36-48
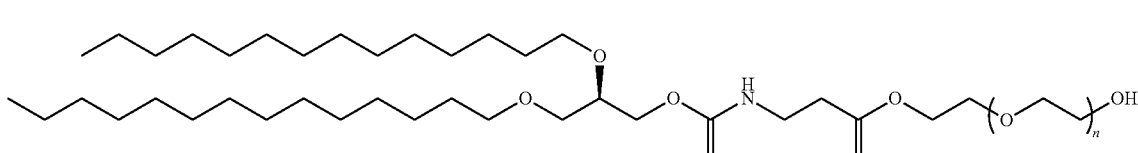
VP185, n = 32-48
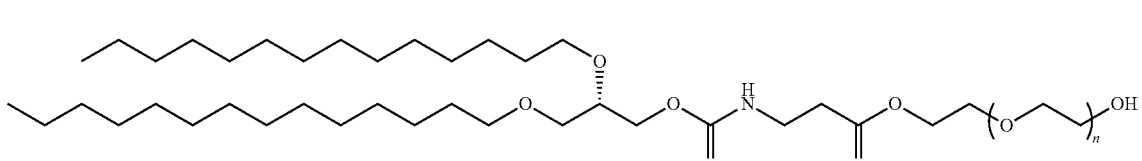
VP185A, n = 36-48

TABLE 2-continued
Exemplary PEG-Lipids for constituting LNP
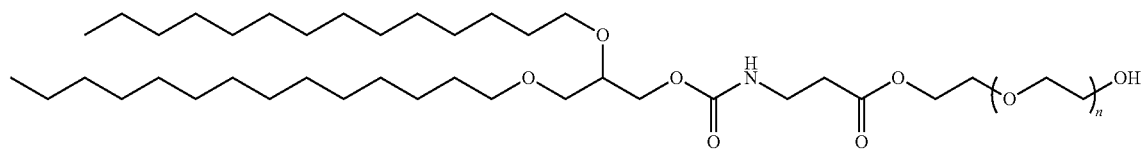
VP185B, n = 36-48
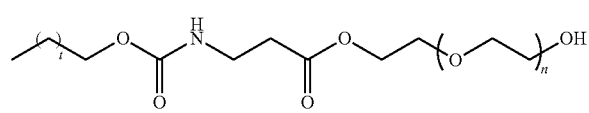
t = 14, VP186
t = 16, VP187
t = 18, VP188
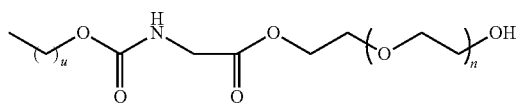
u = 15, VP189
u = 17, VP190
u = 19, VP191
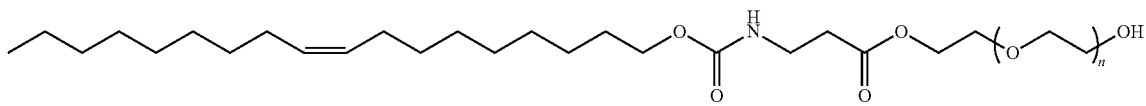
VP192
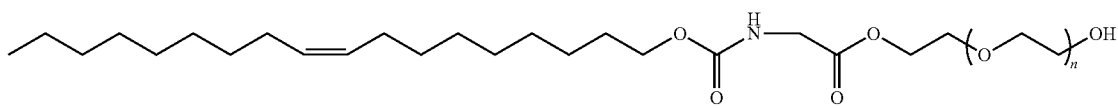
VP193
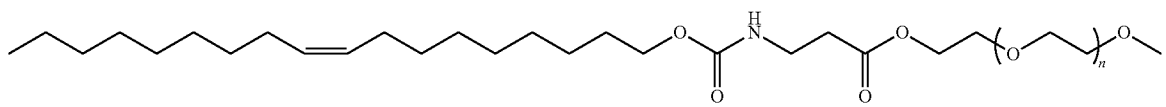
VP194
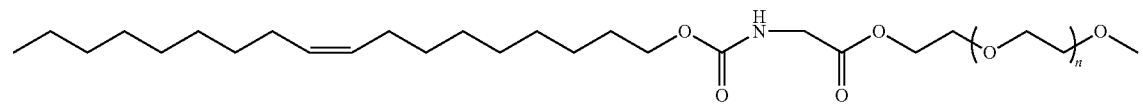
VP195
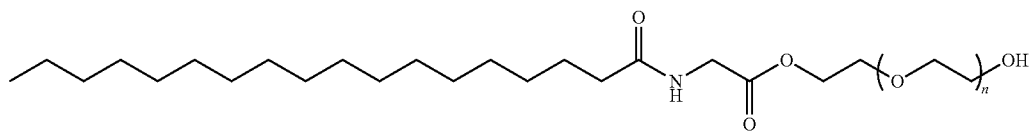
VP196

TABLE 2-continued
Exemplary PEG-Lipids for constituting LNP
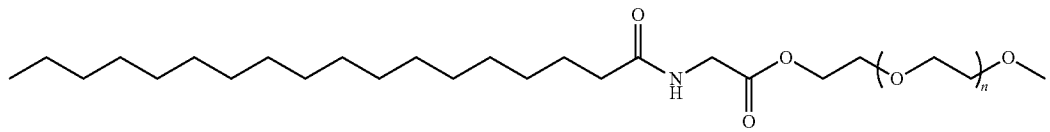
VP197
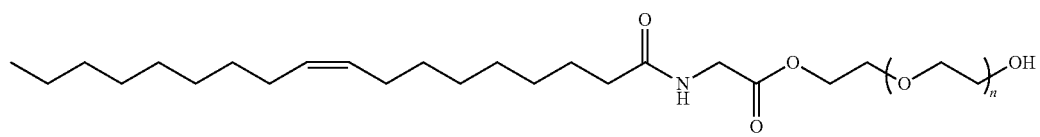
VP198
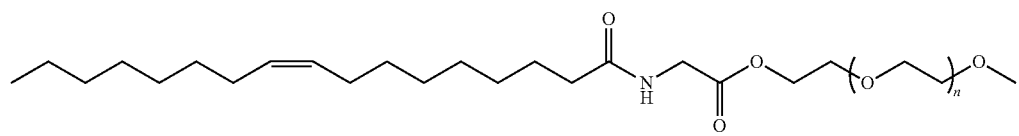
VP199
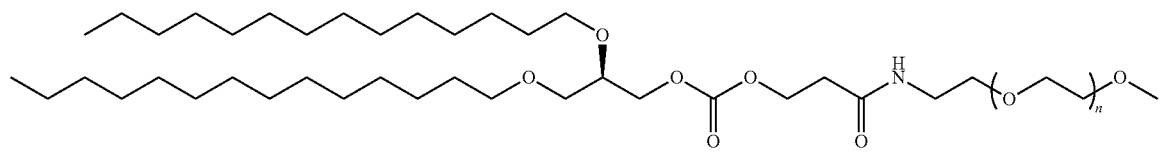
VP200, n = 36-48
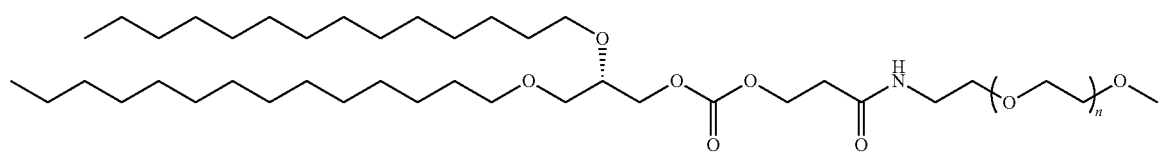
VP200A, n = 36-48
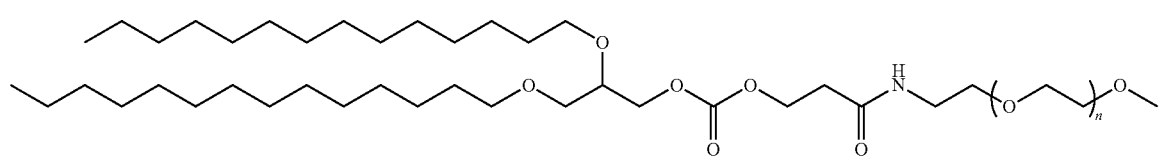
VP200B, n = 36-48
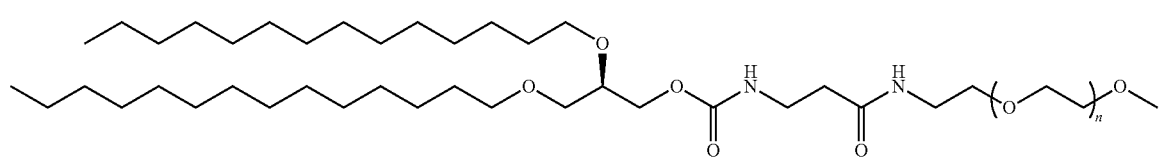
VP201, n = 36-48

TABLE 2-continued
Exemplary PEG-Lipids for constituting LNP
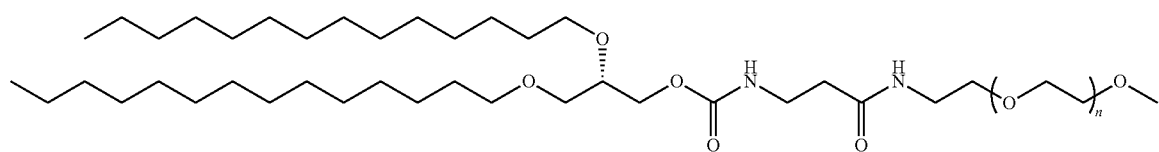
VP201A, n = 36-48
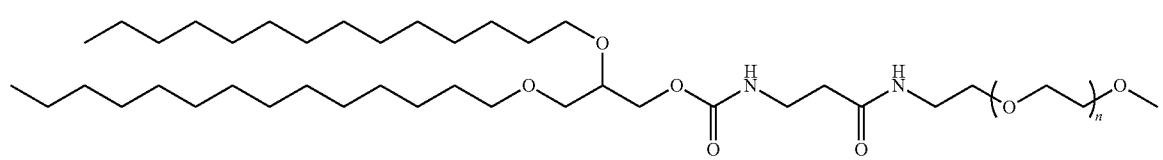
VP201B, n = 36-48
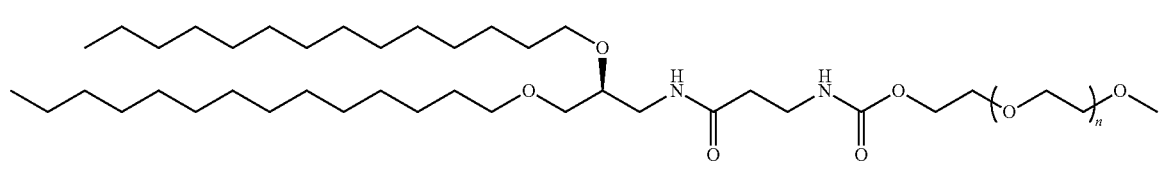
VP202, n = 36-48
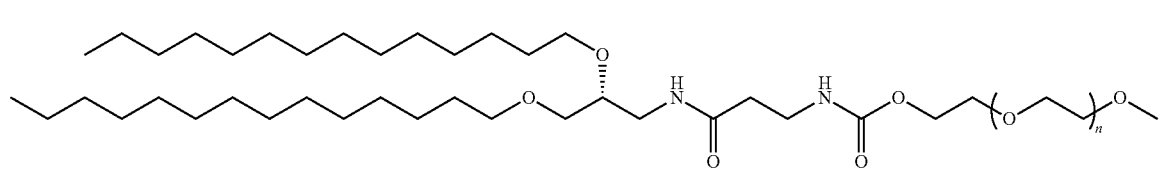
VP202A, n = 36-48
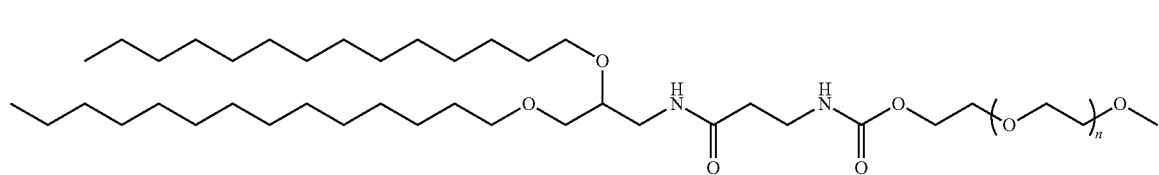
VP202B, n = 36-48
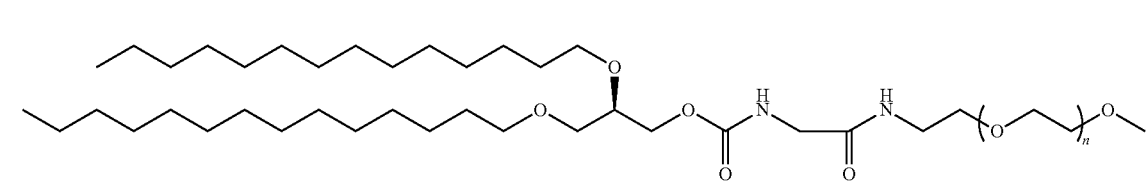
VP203, n = 36-48
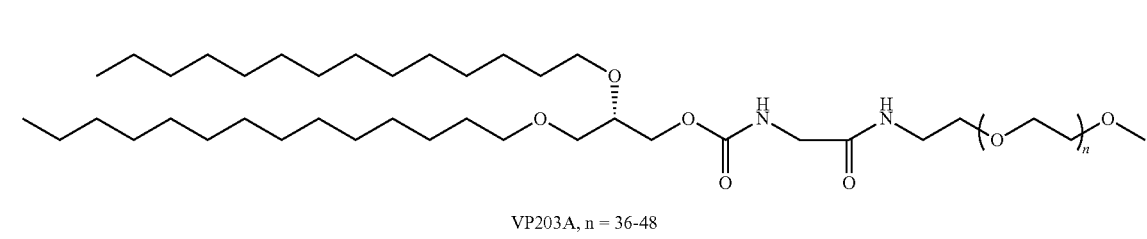
VP203A, n = 36-48

TABLE 2-continued
Exemplary PEG-Lipids for constituting LNP
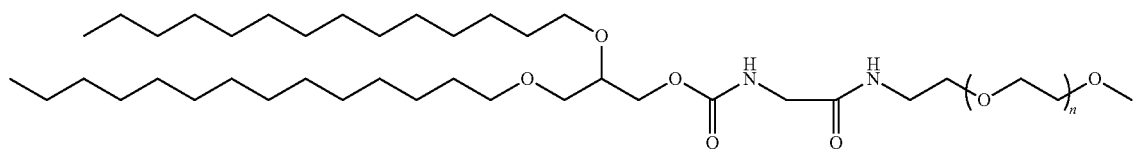
VP203B, n = 36-48
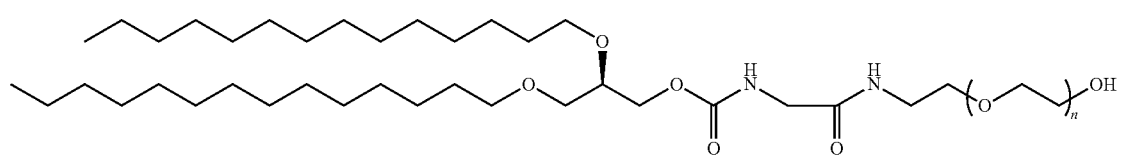
VP204, n = 36-48
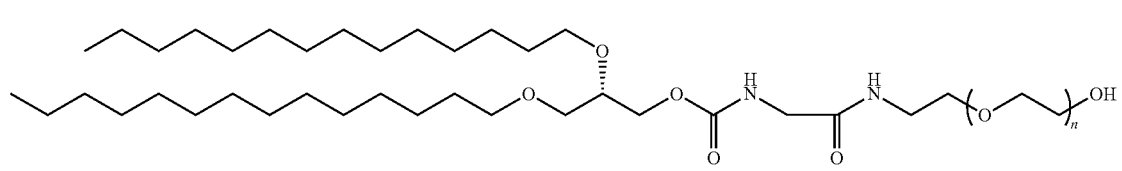
VP204A, n = 36-48
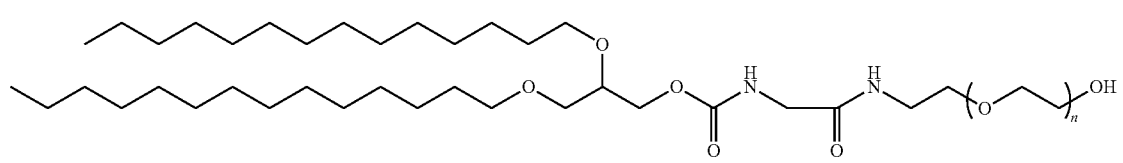
VP204B, n = 36-48
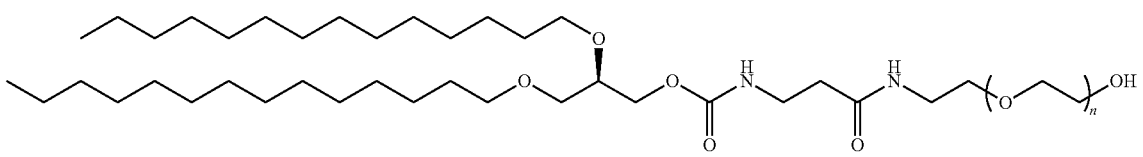
VP205, n = 36-48
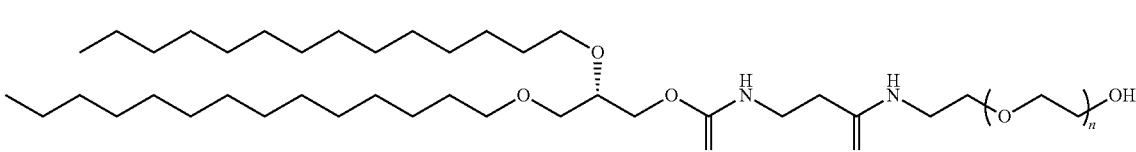
VP205A, n = 36-48
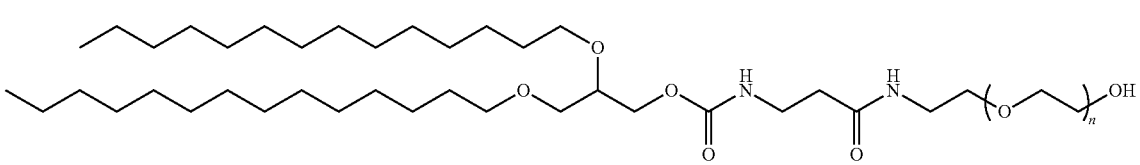
VP205B, n = 36-48

In some embodiments, the n in Table 2 is an integer from 2 to 200, from 10 to 100, from 25 to 50, or from 42 to 48. In some embodiments, the n in Table 2 is 25, 26, 27, 28, 29, 30, 31, 32, 33, 34, 35, 36, 37, 38, 39, 40, 41, 42, 43, 44, 45, 46, 47, 48, 49, 50, or more.

A PEG-lipid can comprise one or more ethylene glycol units, for example, at least 1, at least 2, at least 5, at least 10, at least 20, at least 30, at least 40, at least 50, at least 60, at least 70, at least 80, at least 90, at least 100, at least 120, or at least 150 ethylene glycol units. In some embodiments, a number average molecular weight of the PEG-lipids is from about 200 Da to about 5000 Da. In some embodiments, a number average molecular weight of the PEG-lipids is from about 500 Da to about 3000 Da. In some embodiments, a number average molecular weight of the PEG-lipids is from about 750 Da to about 2500 Da. In some embodiments, a number average molecular weight of the PEG-lipids is from about 750 Da to about 2500 Da. In some embodiments, a number average molecular weight of the PEG-lipids is about 500 Da, about 750 Da, about 1000 Da, about 1250 Da, about 1500 Da, about 1750 Da, or about 2000 Da. In some embodiments, a polydispersity index (PDI) of the one or more PEG-lipids is smaller than 2. In some embodiments, a PDI of the one or more PEG-lipids is at most 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In some embodiments, a PDI of the one or more PEG-lipids is at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

In some embodiments, the PEG-lipid comprises from about 0.1 mol % to about 10 mol % of the total lipid present in the particle. In some embodiments, the PEG-lipid comprises from about 0.1 mol % to about 6 mol % of the total lipid present in the particle. In some embodiments, the PEG-lipid comprises from about 0.5 mol % to about 5 mol % of the total lipid present in the particle. In some embodiments, the PEG-lipid comprises from about 1 mol % to about 3 mol % of the total lipid present in the particle. In some embodiments, the PEG-lipid comprises about 2.0 mol % to about 2.5 mol % of the total lipid present in the particle. In some embodiments, the PEG-lipid comprises about 1 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, or about 3.0 mol % of the total lipid present in the particle.

In some embodiments, the LNP composition comprises a plurality of PEG-lipids, for example, at least 2, 3, 4, 5, 6, 7, 8, 9, 10, or more distinct PEG-lipids. In some embodiments, at least one of the plurality of PEG-lipids is selected from Table 2.

Phospholipid

In some embodiments, the described LNP composition comprises a phospholipid. In some embodiments, the phospholipid comprises a lipid selected from the group consisting of: phosphatidylcholine (PC), phosphatidylethanolamine amine, glycerophospholipid, sphingophospholipids, Guriserohosuhono, sphingolipids phosphono lipids, natural lecithins, and hydrogenated phospholipid. In some embodiments, the phospholipid comprises a phosphatidylcholine. Exemplary phosphatidylcholines include, but are not limited to, soybean phosphatidylcholine, egg yolk phosphatidylcholine (EPC), distearoylphosphatidylcholine, 1,2-distearoyl-sn-glycero-3-phosphocholine (DSPC), dipalmitoyl phosphatidylcholine, dipalmitoyl-sn-glycero-3-phosphocholine (DPPC), palmitoyl oleoyl phosphatidylcholine (POPC), dimyristoyl phosphatidylcholine (DMPC), and dioleoyl phosphatidylcholine (DOPC). In certain specific embodiments, the phospholipid is DSPC.

In some embodiments, the phospholipid comprises a phosphatidylethanolamine amine. In some embodiments, the phosphatidylethanolamine amine is distearoyl phosphatidylethanolamine (DSPE), dipalmitoyl phosphatidyl ethanolamine (DPPE), dioleoyl phosphatidylethanolamine (DOPE), dimyristoyl phosphoethanolamine (DMPE), 16-O-Monome Le PE, 16-0-dimethyl PE, 18-1-trans PE, palmitoyl oleoyl-phosphatidylethanolamine (POPE), or 1-stearoyl-2-oleoyl-phosphatidyl ethanolamine (SOPE). In some embodiments, the phospholipid comprises a glycerophospholipid. In some embodiments, the glycerophospholipid is plasmalogen, phosphatidate, or phosphatidylcholine. In some embodiments, the glycerophospholipid is phosphatidylserine, phosphatidic acid, phosphatidylglycerol, phosphatidylinositol, palmitoyl oleoyl phosphatidylglycerol (POPG), or lysophosphatidylcholine. In some embodiments, the phospholipid comprises a sphingophospholipid. In some embodiments, the sphingophospholipid is sphingomyelin, ceramide phosphoethanolamine, ceramide phosphoglycerol, or ceramide phosphoglycerophosphoric acid. In some embodiments, the phospholipid comprises a natural lecithin. In some embodiments, the natural lecithin is egg yolk lecithin or soybean lecithin. In some embodiments, the phospholipid comprises a hydrogenated phospholipid. In some embodiments, the hydrogenated phospholipid is hydrogenated soybean phosphatidylcholine. In some embodiments, the phospholipid is selected from the group consisting of: phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine.

In some embodiments, the phospholipid comprises a lipid selected from: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

A phospholipid can comprise a phospholipid moiety and one or more fatty acid moieties. A phospholipid moiety can comprise phosphatidyl choline, phosphatidyl ethanolamine, phosphatidyl glycerol, phosphatidyl serine, phosphatidic acid, 2-lysophosphatidyl choline, or a sphingomyelin. A fatty acid moiety can comprise lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, or docosahexaenoic acid. In some specific embodiments, a phospholipid can be functionalized with or cross-linked to one or more alkynes, which may undergo a copper-catalyzed cycloaddition upon exposure to an azide.

In some embodiments, the LNP composition comprises a plurality of phospholipids, for example, at least 2, 3, 4, 5, or more distinct phospholipids. In some embodiments, the phospholipid comprises from 1 mol % to 20 mol % of the total lipid present in the particle. In some embodiments, the phospholipid comprises from about 5 mol % to about 15 mol % of the total lipid present in the particle. In some embodiments, the phospholipid comprises from about 8 mol % to about 12 mol % of the total lipid present in the particle. In some embodiments, the phospholipid comprises from about 9 mol %, 10 mol %, or 11 mol % of the total lipid present in the particle.

Cholesterol

In some embodiments, the LNP composition comprises a cholesterol or a derivative thereof. In some embodiments, the LNP composition comprises a structural lipid. The structural lipid can be selected from steroid, sterol, alkyl resoreinol, cholesterol or derivative thereof, fecosterol, sitosterol, ergosterol, campesterol, stigmasterol, brassicasterol, tomatidine, tomatine, ursolic acid, alpha-tocopherol, and a combination thereof. In some embodiments, the structural lipid is a corticosteroid such as prednisolone, dexamethasone, prednisone, and hydrocortisone. In some embodiments, the cholesterol or derivative thereof is cholesterol, 5-heptadecylresorcinol, or cholesterol hemisuccinate. In some embodiments, the cholesterol or derivative thereof is cholesterol.

In some embodiments, the cholesterol or derivative thereof is a cholesterol derivative. In some embodiments, the cholesterol derivative is a polar cholesterol analogue. In some embodiments, the polar cholesterol analogue is 5α-cholestanol, 5β-coprostanol, cholesteryl-(2'-hydroxy)-ethyl ether, cholesteryl-(4'-hydroxy)-butyl ether, or 6-ketocholestanol. In some embodiments, the polar cholesterol analogue is cholesteryl-(4'-hydroxy)-butyl ether. In some embodiments, the cholesterol derivative is a non-polar cholesterol analogue. In some embodiments, the non-polar cholesterol analogue is 5α-cholestane, cholestenone, 5α-cholestanone, 5β-cholestanone, or cholesteryl decanoate.

In some embodiments, the cholesterol or the derivative thereof comprises from 20 mol % to 50 mol % of the total lipid present in the particle. In some embodiments, the cholesterol or the derivative thereof comprises about 20 mol %, about 21 mol %, about 22 mol %, about 23 mol %, about 24 mol %, about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, about 37 mol %, about 38 mol %, about 39 mol %, about 40 mol %, about 41 mol %, about 42 mol %, about 43 mol %, about 44 mol %, about 45 mol %, about 46 mol %, about 47 mol %, about 48 mol %, or about 50 mol % of the total lipid present in the particle.

Antioxidants

In some embodiments, the LNP described herein comprises one or more antioxidants. In some embodiments, the one or more antioxidants function to reduce a degradation of the cationic lipids, the payload, or both. In some embodiments, the one or more antioxidants comprise a hydrophilic antioxidant. In some embodiments, the one or more antioxidants is a chelating agent such as ethylenediaminetetraacetic acid (EDTA) and citrate. In some embodiments, the one or more antioxidants is EDTA. In some embodiments, the one or more antioxidants comprise a lipophilic antioxidant. In some embodiments, the lipophilic antioxidant comprises a vitamin E isomer or a polyphenol. In some embodiments, the one or more antioxidants are present in the LNP composition at a concentration of at least 1 mM, at least 10 mM, at least 20 mM, at least 50 mM, or at least 100 mM. In some embodiments, the one or more antioxidants are present in the particle at a concentration of about 20 mM.

Payload

The LNPs described herein can be designed to deliver a payload, such as a therapeutic agent, or a target of interest. Exemplary therapeutic agents include, but are not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siRNA), messenger ribonucleic acid (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), siRNA (small internally segmented interfering RNA), aiRNA (asymmetric interfering RNA), and siRNA with 1, 2 or more mismatches between the sense and anti-sense strand to relevant cells and/or tissues, such as in a cell culture, subject or organism. Therapeutic agents can be purified or partially purified, and can be naturally occurring or synthetic, or chemically modified. In some embodiments, the therapeutic agent is an RNAi agent, short interfering nucleic acid (siNA), short interfering RNA (siRNA), double-stranded RNA (dsRNA), micro-RNA (miRNA), or a short hairpin RNA (shRNA) molecule. In some embodiments, the therapeutic agent is an mRNA.

In some embodiments, the payload comprises one or more nucleic acid(s) (i.e., one or more nucleic acid molecular entities). In some embodiments, the nucleic acid is a single-stranded nucleic acid. In some embodiments, single-stranded nucleic acid is a DNA. In some embodiments, single-stranded nucleic acid is an RNA. In some embodiments, the nucleic acid is a double-stranded nucleic acid. In some embodiments, the double-stranded nucleic acid is a DNA. In some embodiments, the double-stranded nucleic acid is an RNA. In some embodiments, the double-stranded nucleic acid is a DNA-RNA hybrid. In some embodiments, the nucleic acid is a messenger RNA (mRNA), a microRNA, an asymmetrical interfering RNA (aiRNA), a small hairpin RNA (shRNA), or a Dicer-Substrate dsRNA.

In some embodiments, the payload comprises an mRNA. In some embodiments, the payload comprises an mRNA molecule encoding a Cas nuclease, i.e., a Cas nuclease mRNA. In some embodiments, the payload comprises one or more guide RNAs or nucleic acids encoding guide RNAs. In some embodiments, the payload comprises a template nucleic acid for repair or recombination. In some embodiments, the payload comprises an mRNA encoding a gene editor nuclease. In some embodiments, the payload comprises an mRNA encoding a base editor nuclease. In some embodiments, the payload comprises an mRNA encoding a restriction enzyme. In some embodiments, the payload comprises zinc-finger nuclease or TALEN nuclease.

In some embodiments, the mRNA payload, such as a Cas nuclease mRNA, can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. Additional modifications to improve stability, expression, and immunogenicity can also be made. The mRNA encoding a Cas nuclease can be codon optimized for expression in a particular cell type, such as a eukaryotic cell, a mammalian cell, or more specifically, a human cell. In some embodiments, the mRNA encodes a human codon optimized Cas9 nuclease or human codon optimized Cpf nuclease as the Cas nuclease. In some embodiments, the mRNA encodes a gene editor (i.e., genome editor) nuclease and is called a gene editor mRNA. In some embodiments, the gene editor is a Cas protein, such as the ones described herein. In some embodiments, the gene editor is an engineered nuclease. In some embodiments, the gene editor introduces a double stranded break in a gene of interest. In some embodiments, the gene editor introduces a double stranded break at a targeted point within a gene of interest. In some embodiments, the gene editor introduces a single stranded break in a gene of interest. In some embodiments, the gene editor is a base editor. In some embodiments, the gene editor inserts a nucleic acid sequence into a gene of interest. In some embodiments, the gene editor deletes a targeted sequence from a gene of interest. In some embodiments, the gene editor mRNA encodes Cas9 nuclease. In some embodiments, the gene editor mRNA encodes base editor nuclease. In some embodiments, the gene editor mRNA encodes a restriction enzyme. In some embodiments, the gene editor mRNA encodes zinc-finger nuclease. In some embodiments, the gene editor mRNA encodes transcription activator-like effector-based nucleases (TALEN). In some embodiments, the gene editor mRNA encodes a meganuclease. In some embodiments, the gene editor mRNA encodes an Argonaute protein. In some embodiments, the mRNA is purified. In some embodiments, the mRNA is purified using a precipitation method (e.g., LiCl precipitation, alcohol precipitation, or an equivalent method, e.g., as described herein) or a chromatography-based method (e.g., an HPLC-based method or an equivalent method).

In some embodiments, the Cas nuclease mRNA comprises a 3' or 5' untranslated region (UTR). In some embodiments, the 3' or 5' UTR can be derived from a human gene sequence. Exemplary 3' and 5' UTRs include a- and β-globin, albumin, HSD17B4, and eukaryotic elongation factor 1a. In addition, viral-derived 5' and 3' UTRs can also be used and include orthopoxvirus and cytomegalovirus UTR sequences. In certain embodiments, the mRNA includes a 5' cap, such as m7G(5')ppp(5')N. In certain embodiments, this cap can be a cap-0 where nucleotide N does not contain 2'OMe, or cap-1 where nucleotide N contains 2'OMe, or cap-2 where nucleotides N and N+1 contain 2'OMe. In some embodiments, the 5' cap can regulate nuclear export; prevent degradation by exonucleases; promote translation; and promote 5' proximal intron excision. In addition, caps can also contain a non-nucleic acid entity that acts as the binding element for eukaryotic translation initiation factor 4E, eIF4E. In certain embodiments, the mRNA includes a poly(A) tail. This tail can be about 40 to about 300 nucleotides in length. In some embodiments, the tail is about 40 to about 100 nucleotides in length. In some embodiments, the tail is about 100 to about 300 nucleotides in length. In some embodiments, the tail is about 100 to about 300 nucleotides in length. In some embodiments, the tail is about 50 to about 200 nucleotides in length. In some embodiments, the tail is about 50 to about 250 nucleotides in length. In certain embodiments, the tail is about 100, 150, or 200 nucleotides in length. The poly(A) tail can contain modifications to prevent exonuclease degradation including phosphorotioate linkages and modifications to the nucleobase. In some embodiments, the poly(A) tail contains a 3' "cap" which could include modified or non-natural nucleobases or other synthetic moieties. In some embodiments, the mRNA comprises at least one element that is capable of modifying the intracellular half-life of the RNA. The half-life of the RNA can be increased or decreased. In some embodiments, the element is capable of increasing or decreasing the stability of the RNA. In some embodiments the element may promote RNA decay. In some embodiments, the element can activate translation. In some embodiments, the element may be within the 3' UTR of the RNA. For example, the element may be an mRNA decay signal or may include a polyadenylation signal (PA).

In some embodiments, the Cas nuclease mRNA encodes a Cas protein from a CRISPR/Cas system. In some embodiments, the Cas protein comprises at least one domain that interacts with a guide RNA ("gRNA"). In some embodiments, the Cas protein is directed to a target sequence by a guide RNA. The guide RNA can interact with the Cas protein as well as the target sequence such that, it can direct binding to the target sequence. In some embodiments, the guide RNA provides the specificity for the targeted cleavage, and the Cas protein may be universal and paired with different guide RNAs to cleave different target sequences. In certain embodiments, the Cas protein may cleave single or double-stranded DNA. In certain embodiments, the Cas protein may cleave RNA. In certain embodiments, the Cas protein may nick RNA. In some embodiments, the Cas protein comprises at least one DNA binding domain and at least one nuclease domain. In some embodiments, the nuclease domain may be heterologous to the DNA binding domain. In certain embodiments, the Cas protein may be modified to reduce or eliminate nuclease activity. The Cas protein may be used to bind to and modulate the expression or activity of a DNA sequence.

In some embodiments, the CRISPR/Cas system comprises Class 1 or Class 2 system components, including ribonucleic acid protein complexes. The Class 2 Cas nuclease families of proteins are enzymes with DNA endonuclease activity, and they can be directed to cleave a desired nucleic acid target by designing an appropriate guide RNA, as described further herein. A Class 2 CRISPR/Cas system component may be from a Type-IIA, Type-IIB, Type-IIC, Type V, or Type VI system. Class 2 Cas nucleases include, for example, Cas9, Cpf1, C2c1, C2c2, and C2c3 proteins. In some embodiments, the Cas protein is from a Type-II CRISPR/Cas system, i.e., a Cas9 protein from a CRISPR/Cas9 system, or a Type-V CRISPR/Cas system, e.g., a Cpf1 protein. In some embodiments, the Cas protein is from a Class 2 CRISPR/Cas system, i.e., a single-protein Cas nuclease such as a Cas9 protein or a Cpf1 protein.

Exemplary species that the Cas9 protein or other components can be from include, but are not limited to, *Streptococcus pyogenes, Streptococcus thermophilus, Streptococcus* sp., *Staphylococcus aureus, Listeria innocua,*

*Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polar omonas naphthalenivorans, Polar omonas sp., Crocosphaera watsonii, Cyanothece sp., Microcystis aeruginosa, Synechococcus sp., Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionium, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodular ia spumigena, Nostoc sp., Arthrospira maxima, Arthrospira platensis, Arthrospira sp., Lyngbya sp., Microcoleus chthonoplastes, Oscillator ia sp., Petrotoga mobilis, Thermosipho africanus, Streptococcus pasteurianus, Neisseria cinerea, Campylobacter lari, Parvibaculum lavamentivorans, Coryne bacterium diphtheria,* or *Acaryochloris marina*. In some embodiments, the Cas9 protein is from *Streptococcus pyogenes*. In some embodiments, the Cas9 protein may be from *Streptococcus thermophilus*. In some embodiments, the Cas9 protein is from *Staphylococcus aureus*.

In some embodiments, the payload comprises at least one guide RNA. The guide RNA may guide the Class 2 Cas nuclease to a target sequence on a target nucleic acid molecule, where the guide RNA hybridizes with and the Cas nuclease cleaves or modulates the target sequence. In some embodiments, a guide RNA binds with and provides specificity of cleavage by a Class 2 nuclease. In some embodiments, the guide RNA and the Cas protein may form a ribonucleoprotein (RNP), e.g., a CRISPR/Cas complex. In some embodiments, the CRISPR complex may be a Type-II CRISPR/Cas9 complex. In some embodiments, the CRISPR/Cas complex may be a Type-V CRISPR/Cas complex, such as a Cpf1/guide RNA complex. In some embodiments, the Cas nuclease may be a single-protein Cas nuclease, e.g. a Cas9 protein or a Cpf 1 protein. In some embodiments, the guide RNA targets cleavage by a Cas9 protein. In some embodiments, the payload comprises two or more guide RNA molecules. In some embodiments, the two or more guide RNA molecules target the same disease-causing gene. In some embodiments, the two or more guide RNA molecules target different genes. In some specific embodiments, the two guide RNA molecules target two separate disease-causing genes of interest.

A guide RNA for a CRISPR/Cas9 nuclease system comprises a CRISPR RNA (crRNA) and a tracr RNA (tracr). In some embodiments, the crRNA may comprise a targeting sequence that is complementary to and hybridizes with the target sequence on the target nucleic acid molecule. The crRNA may also comprise a flagpole that is complementary to and hybridizes with a portion of the tracrRNA. In some embodiments, the crRNA may parallel the structure of a naturally occurring crRNA transcribed from a CRISPR locus of a bacteria, where the targeting sequence acts as the spacer of the CRISPR/Cas9 system, and the flagpole corresponds to a portion of a repeat sequence flanking the spacers on the CRISPR locus. The guide RNA may target any sequence of interest via the targeting sequence of the crRNA. In some embodiments, the degree of complementarity between the targeting sequence of the guide RNA and the target sequence on the target nucleic acid molecule is at least about 60%, 65%, 70%, 75%, 80%, 85%, 90%, 95%, 97%, 98%, 99%, or 100%. In some embodiments, the targeting sequence of the guide RNA and the target sequence on the target nucleic acid molecule may be 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches.

In some embodiments, the length of the targeting sequence depends on the CRISPR/Cas system and components used. For example, different Cas proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence comprised 18-24 nucleotides in length. In some embodiments, the targeting sequence comprises 19-21 nucleotides in length. In some embodiments, the targeting sequence comprises 20 nucleotides in length.

In some embodiments, the guide RNA is a "dual guide RNA" or "dgRNA". In some embodiments, the dgRNA comprises a first RNA molecule comprising a crRNA, and a second RNA molecule comprising a tracr RNA. The first and second RNA molecules may form a RNA duplex via the base pairing between the flagpole on the crRNA and the tracr RNA. In some embodiments, the guide RNA is a "single guide RNA" or "sgRNA". In some embodiments, the sgRNA may comprise a crRNA covalently linked to a tracr RNA. In some embodiments, the crRNA and the tracr RNA may be covalently linked via a linker. In some embodiments, the single-molecule guide RNA may comprise a stem-loop structure via the base pairing between the flagpole on the crRNA and the tracr RNA. In some embodiments, the sgRNA is a "Cas9 sgRNA" capable of mediating RNA-guided DNA cleavage by a Cas9 protein. In certain embodiments, the guide RNA comprises a crRNA and tracr RNA sufficient for forming an active complex with a Cas9 protein and mediating RNA-guided DNA cleavage. In some embodiments, the payload comprises more than one guide RNAs; each guide RNA contains a different targeting sequence, such that the CRISPR/Cas system cleaves more than one target sequence. In some embodiments, one or more guide RNAs may have the same or differing properties such as activity or stability within a CRISPR/Cas complex. Where more than one guide RNA is used, each guide RNA can be encoded on the same or on different expression cassettes. The promoters used to drive expression of the more than one guide RNA may be the same or different.

In some embodiments, the nucleic acid payload, such as RNAs, is modified. Modified nucleosides or nucleotides can be present in a guide RNA or mRNA. A guide RNA or Cas nuclease encoding mRNA comprising one or more modified nucleosides or nucleotides is called a "modified" RNA to describe the presence of one or more non-naturally and/or naturally occurring components or configurations that are used instead of or in addition to the canonical A, G, C, and U residues. In some embodiments, a modified RNA is synthesized with a non-canonical nucleoside or nucleotide. Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

In some embodiments, the payload can include a template nucleic acid. The template can be used to alter or insert a nucleic acid sequence at or near a target site for a Cas nuclease. In some embodiments, the template is used in homologous recombination. In some embodiments, the homologous recombination may result in the integration of the template sequence or a portion of the template sequence into the target nucleic acid molecule. In some embodiments, a single template is provided. In other embodiments, two or more templates are provided such that homologous recombination may occur at two or more target sites.

In some embodiments, the payload, such as one or more RNAs, are fully encapsulated within the lipid portion of the particle, thereby protecting the RNAs from nuclease degradation. Fully encapsulated can indicate that the RNA in the nucleic acid-lipid particle is not significantly degraded after exposure to serum or a nuclease assay that would significantly degrade free DNA or RNA. In some embodiments, the nucleic acid-lipid particle composition comprises a RNA molecule that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the RNA encapsulated therein.

In some embodiments, the payload comprises an mRNA and one or more guide RNA. In some embodiments, the mRNA encodes a gene editor nuclease and is called a gene editor mRNA. In some embodiments, the gene editor mRNA encodes Cas9 nuclease. In some embodiments, the mRNA encodes base editor nuclease. In some embodiments, the gene editor mRNA encodes zinc-finger nuclease. In some embodiments, the gene editor mRNA encodes TALEN nuclease.

Surfactants and Other Components

Nanoparticles described herein can comprise one or more surfactants. In some embodiments, the one or more surfactants comprise one or more anionic surfactants. Exemplary anionic surfactants include but are not limited to 2-acrylamido-2-methylpropane sulfonic acid, ammonium lauryl sulfate, ammonium perfluorononanoate, docusate, disodium cocoamphodiacetate, magnesium laureth sulfate, perfluorobutanesulfonic acid, perfluorononanoic acid, perfluorooctanesulfonic acid, perfluorooctanoic acid, potassium lauryl sulfate, sodium alkyl sulfate, sodium dodecyl sulfate, sodium dodecylbenzenesulfonate, sodium laurate, sodium laureth sulfate, sodium lauroyl sarcosinate, sodium myreth sulfate, sodium nonanoyloxybenzenesulfonate, sodium pareth sulfate, sodium stearate, and sulfolipid. In some embodiments, the one or more surfactants comprise one or more cationic surfactants. Exemplary cationic surfactants include but are not limited to behentrimonium chloride, benzalkonium chloride, benzethonium chloride, benzododecinium bromide, bronidox, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, domiphen bromide, lauryl methyl gluceth-10 hydroxypropyl dimonium chloride, octenidine dihydrochloride, olaflur, n-oleyl-1,3-propanediamine, pahutoxin, stearalkonium chloride, tetramethylammonium hydroxide, and thonzonium bromide. In some embodiments, the one or more surfactants comprise one or more zwitterionic surfactants. Exemplary zwitterionic surfactants include but are not limited to cocamidopropyl betaine, cocamidopropyl hydroxysultaine, dipalmitoylphosphatidylcholine, egg lecithin, hydroxysultaine, lecithin, myristamine oxide, peptitergents, and sodium lauroamphoacetate.

In some embodiments, the one or more surfactants comprise one or more non-ionic surfactants. Exemplary non-ionic surfactants include but are not limited to alkyl polyglycoside, cetomacrogol 1000, cetostearyl alcohol, cetyl alcohol, cocamide dea, cocamide mea, decyl glucoside, decyl polyglucose, glycerol monostearate, igepal ca-630, isoceteth-20, lauryl glucoside, maltosides, monolaurin, mycosubtilin, narrow-range ethoxylate, nonidet p-40, nonoxynol-9, nonoxynols, np-40, octaethylene glycol monododecyl ether, n-octyl beta-d-thioglucopyranoside, octyl glucoside, oleyl alcohol, peg-10 sunflower glycerides, pentaethylene glycol monododecyl ether, polidocanol, poloxamer (e.g., poloxamer 188 an dpoloxamer 407), polyethoxylated tallow amine, polyglycerol polyricinoleate, polysorbate (e.g., polysorbate 20, polysorbate 40, polysorbate 60, or polysorbate 80), sorbitan, sorbitan monolaurate, sorbitan monostearate, sorbitan tristearate, stearyl alcohol, surfactin, triton x-100.

In some embodiments, a nanoparticle described herein comprises one or more non-ionic surfactants. In some embodiments, the one or more non-ionic surfactants comprise a fatty alcohol, a fatty acid, or both. In some embodiments, the fatty alcohol is a $C_{12}$-$C_{24}$ fatty alcohol. In some embodiments, the fatty alcohol is lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, or a combination thereof. In some embodiments, the $C_{12}$-$C_{24}$ fatty alcohol is oleyl alcohol, stearyl alcohol, or a mixture thereof. In some embodiments, the nanoparticle comprises oleyl alcohol. In some embodiments, the nanoparticle comprises stearyl alcohol.

In some embodiments, the one or more surfactants (such as fatty alcohol) are present in a herein described nanoparticle composition in an amount of about 0.5 mol % to about 20 mol % of a total lipid content present in the nanoparticle composition, or any ranges therebetween. In some embodiments, the one or more surfactants (such as fatty alcohol) are present in the nanoparticle composition in an amount of about 1 mol % to about 10 mol % of a total lipid content present in the nanoparticle composition. In some embodiments, the one or more surfactants (such as fatty alcohol) are present in the nanoparticle composition in an amount of about 3 mol % to about 8 mol % of a total lipid content present in the nanoparticle composition. In some embodiments, the one or more surfactants (such as fatty alcohol) are present in the nanoparticle composition at about 3 mol %, about 4 mol %, about 5 mol %, about 6 mol %, about 7 mol %, about 8 mol %, about 9 mol %, or about 10 mol % of a total lipid content present in the nanoparticle composition. In some embodiments, the one or more surfactants (such as fatty alcohol) are present in the nanoparticle composition in a range from about 0.5 mol %, 1 mol %, 1.5 mol %, 2 mol %, 2.5 mol %, 3 mol %, or 3.5 mol % to about 4 mol %, 4.5 mol %, 5 mol %, 5.5 mol %, 6 mol %, 7 mol %, 8 mol %, 9 mol %, or 10 mol % of a total lipid content present in the nanoparticle composition. In some embodiments, the one or more surfactants (such as fatty alcohol) are present in the nanoparticle composition in a range from about 1 mol %, 2 mol %, 3 mol %, 4 mol %, 5 mol %, 6 mol %, or 7 mol % to about 8 mol %, 9 mol %, 10 mol %, 11 mol %, 12 mol %, 13 mol %, 14 mol %, 15 mol %, or 20 mol % of a total lipid content present in the nanoparticle composition.

Nanoparticle compositions described herein can comprise one or more permeability enhancer molecules, carbohydrates, polymers, or other components. A permeability enhancer molecule can be, e.g., a molecule described by U.S. patent application publication No. 2005/0222064. The carbohydrates can be simple sugars (e.g., glucose) and polysaccharides (e.g., glycogen and derivatives and analogs thereof).

In some embodiments, a nanoparticle composition described herein comprises a polymer. The polymer can be biodegradable and/or biocompatible. Exemplary polymers include but are not limited to polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. In some embodiments, a nanoparticle composition described herein comprises poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide)(PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone (PVP), polysiloxanes, polystyrene, polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poloxamines, poly(ortho)esters, poly(butyric acid), poly(valeric acid), poly(lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), polyglycerol, or a combination thereof.

Nucleic Acid Stabilizer

In some embodiments, nanoparticle compositions described herein comprise excipients that stabilize lipid nanoparticles encapsulating nucleic acid payload (e.g., nucleic acid therapeutics). For example, the nucleic acid therapeutics can be mRNA to modulate disease causing proteins; mRNA and guide RNA to edit therapeutic genes of interest; RNA-editing nucleic acid payloads; siRNA; antisense oligonucleotides such as those to elicit RNase H-mediated gene silencing; microRNA and anti-microRNA; RNA activators; aptamers and the like.

Lipid nanoparticles (LNPs) represent an efficacious non-viral delivery system for nucleic acid therapeutics. Efficacy of an LNP treatment can be determined by numerous variables, including the stability and functionality of the encapsulated RNA cargo. If the RNA cargo experiences nicking, degradation, or a structural change during long-term storage or freeze/thaw, a partial or complete loss in therapeutic potency may occur. As such, the herein disclosed nanoparticle compositions are advantageous in the delivering of nucleic acid payloads, at least partially due to the enhanced stability of the nanoparticle compositions and/or encapsulated compositions including e.g. nucleic acid therapeutics. In some embodiments, the enhanced stability can prolong the shelf-storage life and improve the freeze-thaw resistance of a pharmaceutical composition comprising the nanoparticle. In some embodiments, the enhanced stability is achieved, at least partially, by the selection of the type, the pH, the osmolarity, and the counter ions of the buffer used to solubilize the nucleic acid payload. In some embodiments, the enhanced stability is achieved, at least partially, by the addition of a nucleic acid stabilizer. The nucleic acid stabilizer can be selected from excipients that are designated by the FDA as generally recognized as safe (GRAS). Accordingly, in one aspect, the present disclosure describes the innovative use of commonly used GRAS excipients to improve RNA stability and delivery by LNPs Nanoparticle compositions described herein can comprise a nucleic acid stabilizer. In some embodiments, the nucleic acid stabilizer is polyethylene glycol. In some embodiments, the nucleic acid stabilizer is a cationic surfactant such as cetrimonium bromide and cetrimonium chloride. In some embodiments, the nucleic acid stabilizer is cetrimonium bromide (i.e., cetyltrimethylammonium bromide or CTAB).

In some embodiments, the nucleic acid stabilizer is polysaccharide or oligosaccharide such as low molecular weight chitosan. Exemplary low molecular weight chitosan can have a molecular weight of 50,000 to 190,000 Da, or lower than 50,000 Da. In some embodiments, the nucleic acid stabilizer is a cryoprotectant. Exemplary cryoprotectants include, but are not limited to, a polyol (e.g., a diol or a triol such as propylene glycol (i.e., 1,2-propanediol), 1,3-propanediol, glycerol, 2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a water soluble polymer (e.g., polyethylene glycol, polyethylene glycol monomethyl ether (mPEG) such as mPEG 550, mPEG 600, mPEG 2000, mPEG 3350, mPEG 4000, and mPEG 5000, polyvinylpyrrolidone, pentaerythritol propoxylate, and a block polymer of polyethylene glycol and polypropylene glycol), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the nanoparticle composition comprises two or more nucleic acid stabilizers.

In some embodiments, the nucleic acid stabilizer is polyethylene glycol (PEG). In some embodiments, the polyethylene glycol is PEG 200, PEG 400, PEG 600, PEG 1000, PEG 3350, PEG 4000, PEG 8000, PEG 10000, PEG 20000, or a combination thereof. In some embodiments, the polyethylene glycol is PEG 200, PEG 400, PEG 600, or a combination thereof. In some embodiments, the polyethylene glycol has a number average molecular weight (Mn) of from about 120 to about 5000 Da, or any numbers or ranges therebetween. In some embodiments, the polyethylene glycol has a Mn of about 120 to about 200 Da, about 200 to about 800 Da, about 200 to about 600 Da, about 120 to about 1000 Da, or about 40 to about 1200 Da. In some embodiments, the polyethylene glycol has a number average molecular weight of about 120, about 160, or about 200 to about 300, 400, about 500, about 600, about 700, or about 800 Da. In some embodiments, the nucleic acid stabilizer comprise PEG 400. In some embodiments, a herein described nanoparticle composition comprises a polyethylene glycol (such as PEG400) and a nucleic acid payload (such as mRNA, guide RNA, and/or siRNA).

In one aspect, disclosed herein is a method of making a nanoparticle composition that comprises a nucleic acid stabilizer. The nucleic acid stabilizer (e.g., polyethylene glycol) can be added into the nanoparticle composition before, concurrently, or after with addition of nucleic acid payload. In some embodiments, the nucleic acid stabilizer is added to the nanoparticle composition concurrently with the nucleic acid. In some embodiments, the nucleic acid stabilizer is pre-mixed with the nucleic acid payload. In some embodiments, the nucleic acid stabilizer is combined with the nucleic acid payload in a buffer solution. In some embodiments, the nucleic acid stabilizer (such as PEG400) is combined with a nucleic acid payload (such as mRNA, guide RNA, and/or siRNA) in a buffer solution. In some embodiments, the nucleic acid stabilizer (such as PEG400) is mixed with a nucleic acid payload in a buffer solution. In some embodiments, the nucleic acid stabilizer (such as PEG400) is added into a buffer that comprises the nucleic acid payload. In some embodiments, adding the nucleic acid stabilizer such as PEG-400 along with the RNA cargo to the drug substance buffer before lipid mixing can allow it to incorporate into the core of the LNP, where it is expected to confer several advantages: 1) increase long-term stability both at 2-8° C. and at freezing temperature such as −20, −40 and −80° C. by providing cushion to the RNA core, 2) improve RNA encapsulation (also known to those skilled in the art as "entrapment") efficiency, and 3) preserve RNA potency and prevent nicking/degradation. In some embodiments, the nucleic acid stabilizer (such as PEG400) is added into the nanoparticle composition after the addition of the lipids and the nucleic acid payload. In some embodiments, the nucleic acid stabilizer (such as PEG400) is added into the nanoparticle composition after formulation and before freezing. In some embodiments, the method of making a nanoparticle composition comprises collecting or buffer exchanging LNPs into a drug product or freezing buffer solution containing the target amount of a nucleic acid stabilizer such as PEG400. In some embodiments, adding a nucleic acid stabilizer such as PEG400 in the freezing buffer solution as well as in the drug substance buffer can increase long-term stability both at 2-8° C. and at freezing temperature such as −20, −40 and −80° C. by providing cushion to the RNA core and preserve RNA potency and prevent nicking/degradation.

In some embodiments, the nucleic acid stabilizer (such as PEG400) is present in the described nanoparticle composition in an amount of about 0.001% to about 50% by total weight. In some embodiments, the nucleic acid stabilizer (such as PEG400) is present in the nanoparticle composition in an amount of about 0.01% to about 20% by total weight. In some embodiments, the nucleic acid stabilizer (such as PEG400) is present in the nanoparticle composition in an amount of about 0.01% to about 5% by total weight. In some embodiments, the nucleic acid stabilizer (such as PEG400) is present in the nanoparticle composition in an amount up to about 15% by total weight. In some embodiments, the nucleic acid stabilizer is present in the nanoparticle composition at about 0.01%, about 0.05%, about 0.1%, about 0.15%, or about 0.2% to about 0.3%, about 0.4%, about 0.5%, about 0.6%, about 0.7%, about 0.8%, about 0.9%, about 1.0% or about 2.0% by total weight. In some embodiments, the nucleic acid stabilizer is present in the nanoparticle composition within a range of about 0.01%, 0.25%, about 0.5%, about 0.75%, about 1%, or about 5% to about 7.5%, about 10%, about 15%, or about 20% by total weight. In some embodiments, the nucleic acid stabilizer is present in the nanoparticle composition in an amount of about 0.01% to about 0.5%, 0.01% to about 2%, 0.01% to about 3%, about 0.2% to about 0.8%, about 0.4% to about 0.6%, about 0.6% to about 0.8%, about 0.5% to about 1.0%, about 0.5% to about 2.0%, about 1% to about 2%, about 1% to about 5%, about 5% to about 10%, about 10% to about 15%, about 15% to about 20%, about 2.5% to about 7.5%, about 7.5% to about 12.5%, about 12.5% to about 17.5%, or about 15% to about 25% by total weight. In some embodiments, the nucleic acid stabilizer is present in the nanoparticle composition in an amount of at least 0.1%, at least 0.2%, at least 0.25%, at least 0.5%, at least 0.75%, at least 1%, at least 2%, at least 5%, at least 10%, or at least 15% by total weight. In some embodiments, the nucleic acid stabilizer is present in the nanoparticle composition in an amount of at most 0.25%, at most 0.5%, at most 0.75%, at most 1%, at most 2%, at most 5%, at most 7.5%, at most 10%, at most 15%, at most 20%, at most 25%, or at most 30% by total weight. In some embodiments, the nucleic acid stabilizer is present in the nanoparticle composition in an amount of about 0.25%, about 0.5%, about 0.75%, about 5%, about 10%, or about 15% by total weight.

In some embodiments, adding the nucleic acid stabilizer (such as PEG-400) to the drug substance buffer prior to or co-mixed with nucleic acid payload, the w/w % in the non-RNA containing drug substance buffer is higher than the target w/w % in the final RNA containing drug substance buffer, such that eventual dilution with RNA dilutes the nucleic acid stabilizer % to the target w/w %. In some embodiments, the nucleic acid stabilizer (e.g., PEG-400) is trapped within the core of the particle at an amount proportional to its weight percentage in the drug substance buffer.

Other Lipids

In some embodiments, the disclosed LNP compositions comprise a helper lipid. In some embodiments, the disclosed LNP compositions comprise a neutral lipid. In some embodiments, the disclosed LNP compositions comprise a stealth lipid. In some embodiments, the disclosed LNP compositions comprises additional lipids.

As used herein, "neutral lipids" suitable for use in a lipid composition of the disclosure include, for example, a variety of neutral, uncharged or zwitterionic lipids. Examples of neutral phospholipids suitable for use in the present disclosure include, but are not limited to, 5-heptadecylbenzene-1, 3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), I-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In some embodiments, the neutral phospholipid may be selected from the group consisting of SPC and dimyristoyl phosphatidyl ethanolamine (DMPE). In some embodiments, the neutral phospholipid is DSPC. Neutral lipids can function to stabilize and improve processing of the LNPs.

"Helper lipids" can refer to lipids that enhance transfection (e.g. transfection of the nanoparticle including the biologically active agent). The mechanism by which the helper lipid enhances transfection includes enhancing particle stability. In some embodiments, the helper lipid enhances membrane fusogenicity. In some embodiments, the helper lipid is a neutral lipid.

"Stealth lipids" can refer to lipids that alter the length of time the nanoparticles can exist in vivo {e.g., in the blood). Stealth lipids can assist in the formulation process by, for example, reducing particle aggregation and controlling particle size. Stealth lipids used herein may modulate pharmacokinetic properties of the LNP. Stealth lipids suitable for use in a lipid composition of the disclosure can include, but are not limited to, stealth lipids having a hydrophilic head group linked to a lipid moiety. Stealth lipids suitable for use in a lipid composition of the present disclosure and information about the biochemistry of such lipids can be found in Romberg et al, Pharmaceutical Research, Vol. 25, No. 1, 2008, pg. 55-71 and Hoekstra et al, Biochimica et Biophysica Acta 1660 (2004) 41-52. Additional suitable PEG-lipids are disclosed, e.g., in WO 2006/007712.

In some embodiments, the stealth lipid is a PEG-lipid. In one embodiment, the hydrophilic head group of stealth lipid comprises a polymer moiety selected from polymers based on PEG (sometimes referred to as poly(ethylene oxide)), poly(oxazoline), poly(vinyl alcohol), poly(glycerol), poly (N-vinylpyrrolidone), polyaminoacids and poly N-(2-hydroxypropyl)methacrylamide]. Stealth lipids can comprise a lipid moiety. In some embodiments, the lipid moiety of the stealth lipid may be derived from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

The structures and properties of helper lipids, neutral lipids, stealth lipids, and/or other lipids are further described in WO2017173054A1, WO2019067999A1, US20180290965A1, US20180147298A1, US20160375134A1, U.S. Pat. Nos. 8,236,770, 8,021,686, 8,236,770B2, 7,371,404B2, 7,780,983B2, 7,858,117B2, US20180200186A1, US20070087045A1, WO2018119514A1, and WO2019067992A1, all of which are hereby incorporated by reference in their entirety.

LNP Formulations

The LNPs described herein can be designed for one or more specific applications or targets. The elements of a nanoparticle composition can be selected based on a particular application or target, and/or based on the efficacy, toxicity, expense, ease of use, and availability. Similarly, the particular formulation of a nanoparticle composition may be selected for the particular application or target. Exemplary LNP formulations include, but are not limited to, the formulations described in Tables 4-6, 8-15 and 17. Exemplary LNP formulations also include compositions comprising an amino lipid of Formula (I), (I*), (Ia) (Ib), (II), (II*) and a PEG lipid of Formula (III) and (III*).

The described LNP formulations can be designed for one or more specific applications or targets. For example, a nanoparticle composition may be designed to deliver a therapeutic agent such as an RNA to a particular cell, tissue, organ, or system or group thereof in a mammal's body. Physiochemical properties of nanoparticle compositions may be altered in order to increase selectivity for particular bodily targets. For instance, particle sizes may be adjusted based on the fenestration sizes of different organs. The therapeutic agent included in a nanoparticle composition may also be selected based on the desired delivery target or targets. For example, a therapeutic agent may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ.

The amount of a therapeutic agent in an LNP composition may depend on the size, composition, desired target and/or application, or other properties of the nanoparticle composition. For example, the amount of an RNA comprised in a nanoparticle composition may depend on the size, sequence, and other characteristics of the RNA. The relative amounts of a therapeutic agent and other elements (e.g., lipids) in a nanoparticle composition may also vary. In some embodiments, the wt/wt ratio of the lipid component to a therapeutic agent in a nanoparticle composition may be from about 5:1 to about 60:1, such as about 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic agent may be from about 10:1 to about 40:1. In certain embodiments, the wt/wt ratio is about 20:1. The amount of a therapeutic agent in a nanoparticle composition can be measured using absorption spectroscopy (e.g., ultraviolet-visible spectroscopy).

In some embodiments, an LNP composition comprises one or more nucleic acids such as RNAs. In some embodiments, the one or more RNAs, lipids, and amounts thereof may be selected to provide a specific N/P ratio. The N/P ratio can be selected from about 1 to about 30. The N/P ratio can be selected from about 2 to about 10. In some embodiments, the N/P ratio is from about 0.1 to about 50. In some embodiments, the N/P ratio is from about 2 to about 8. In some embodiments, the N/P ratio is from about 2 to about 15, from about 2 to about 10, from about 2 to about 8, from about 2 to about 6, from about 3 to about 15, from about 3 to about 10, from about 3 to about 8, from about 3 to about 6, from about 4 to about 15, from about 4 to about 10, from about 4 to about 8, or from about 4 to about 6. In some embodiments, the N/P ratio is from about 2 to about 8. In some embodiments, the N/P ratio is about 2, about 2.5, about 3, about 3.5, about 4, about 4.5, about 5, about 5.5, about 6, or about 6.5. In some embodiments, the N/P ratio is from about 4 to about 6. In some embodiments, the N/P ratio is about 4, about 4.5, about 5, about 5.5, or about 6.

In some embodiments, the LNPs are formed with an average encapsulation efficiency ranging from about 50% to about 70%, from about 70% to about 90%, or from about 90% to about 100%. In some embodiments, the LNPs are formed with an average encapsulation efficiency ranging from about 75% to about 95%. In some embodiments, a nucleic acid (e.g., RNA) entrapment efficiency of a nanoparticle described herein is at least 80%, at least 85%, at least 90%, at least 91%, at least 92%, at least 93%, at least 94%, at least 95%, at least 96%, at least 97%, at least 98%, or at least 99%. In some embodiments, a nucleic acid entrapment efficiency of a nanoparticle described herein is from about 80% to about 100%, from about 85% to about 100%, from about 90% to about 100%, from about 95% to about 100%, from about 90% to about 99%, or from about 95% to about 99%. In some embodiments, a nucleic acid entrapment efficiency of a nanoparticle described herein is from about 90% to about 99%, In some embodiments, nanoparticles described herein have a median diameter of about 10 nm to about 500 nm. In some embodiments, the median diameter of the nanoparticles described herein is from about 50 nm to about 150 nm, from about 60 nm to about 140 nm, from about 70 nm to about 130 nm, from about 80 nm to about 120 nm, or from about 90 nm to about 110 nm. In some embodiments, the median diameter of the nanoparticles described herein is about 60 nm, about 65 nm, about 70 nm, about 75 nm, about 80 nm, about 85 nm, about 90 nm, about 95 nm, about 100 nm, about 105 nm, about 110 nm, about 115 nm, or about 120 nm. Particle size and particle size distribution of the nanoparticles can be measured by light scattering using, for example, a Zetasizer Ultra ZSU 5700 (Malvern, USA). In some embodiments, the particle size distribution is unimodal.

Preparation of LNP Formulation

In one aspect, described in the present disclosure are processes for making LNP compositions.

A process for making lipid nanoparticles can comprise several general steps: (i) providing a first solution, such as citrate or phosphate buffer, comprising one or more nucleic acid molecular entities in a first reservoir; (ii) providing a second solution comprising one or more lipids and an organic solvent, such as an alcohol (e.g., ethanol) in a second reservoir; and (iii) mixing the first solution with the second solution. The first reservoir is optionally in fluid communication with the second reservoir.

In some embodiments, disclosed herein is a method of preparing a formulation comprising lipid nanoparticles, wherein the nanoparticles comprise (i) one or more nucleic acid molecular entities, (ii) an amino lipid, and (iii) one or more lipids selected from a structural lipid, a neutral lipid, and a PEG-lipid. In some embodiments, the method comprises (a) combining a first faction of the amino lipid with the one or more nucleic acid molecular entities in a first solution, wherein the first fraction comprises 0.1 mol % to 99 mol % of the total amino lipid; (a) combining the remaining of the amino lipid with the one or more lipids selected from a structural lipid, a neutral lipid, and a PEG-lipid in a second solution; (c) mixing the first solution and the second solution, thereby producing the lipid nanoparticles. In some embodiments, the first fraction of the amino lipid is configured to neutralize between 0.1-99% of the phosphate (on an N:P basis) in the one or more nucleic acid molecular entities, or any numbers or ranges therebetween. In some embodiments, the first fraction of the amino lipid is configured to neutralize between 0.5-90% of the phosphate (on an N:P basis) in the one or more nucleic acid molecular entities. In some embodiments, the first fraction of the amino lipid is configured to neutralize about 5 to 90%, 10 to 75%, 25 to 50%, 25 to 75%, 50 to 75%, or 50 to 90% of the phosphate (on an N:P basis) in the one or more nucleic acid molecular entities. In some embodiments, the first fraction of the amino lipid is configured to neutralize about 10%, 15%, 25%, 50%, or 75% of the phosphate (on an N:P basis) in the one or more nucleic acid molecular entities. In some embodiments, the first solution is an aqueous buffer solution, e.g., a citrate buffer. In some embodiments, the first solution further comprises a nucleic acid stabilizer, e.g., PEG 400. In some embodiments, the first solution and the second solution are mixed in an inline mixer.

The process can optionally comprise one or more dilution steps, one or more incubation steps, one or more buffer exchange steps, one or more concentration steps, and/or one or more filtrations steps. In some embodiments, the dilution step involves dilution by adding a dilution buffer. In some embodiments, the dilution step involves dilution with aqueous buffer (e.g. citrate buffer or pure water) e.g., using a pumping apparatus (e.g. a peristaltic pump). In some embodiments, the dilution buffer is an organic solution such as alcohol. The dilution step can comprise a dilution that is 1 to 20 times of the initial volume, or any numbers or ranges therebetween. In some embodiments, the dilution step comprises a dilution that is 1 to 10 times of the initial volume. In some embodiments, the dilution step is followed by the buffer exchange step or the incubation step.

The incubation step comprises allowing a solution from the mixing step to stand in a vessel for about 0 to about 100 hours at about room temperature and optionally protected from light. In some embodiments, the incubation step runs from 0 to 24 hours, 1 minute to 2 hours, or 1 minute to 60 minutes. In some embodiments, the incubation step runs from 1 minutes to 120 minutes. In some embodiments, the incubation step is followed by the buffer exchange step. In some embodiments, the incubation step follows the buffer exchange step.

In some embodiments, the buffer exchange step comprises a solvent exchange that results in a higher concentration of phosphate buffered saline (PBS) buffer. In some embodiments, the buffer exchange step comprises removing all or a portion of organic solvent. In some embodiments, the buffer exchange step comprises dialysis through a suitable membrane (e.g. 10,000 mwc snakeskin membrane). In some embodiments, the buffer exchange step comprises filtration such as tangential flow filtration (TFF)). In some embodiments, the buffer exchange step comprises chromatography such as using a desalting column, e.g., PD10 column. In some embodiments, the buffer exchange step comprises ultrafiltration. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent).

In some embodiments, the mixing step provides a clear single phase. In some embodiments, after the mixing step, the organic solvent is removed to provide a suspension of particles, wherein the one or more nucleic acid molecular entities are encapsulated by the lipid(s). The selection of an organic solvent can involve consideration of solvent polarity and the ease with which the solvent can be removed at the later stages of particle formation. The organic solvent, which can serve as a solubilizing agent, can be in an amount sufficient to provide a clear single phase mixture of the one or more nucleic acid molecular entities and lipid(s). The organic solvent may be selected from one or more (e.g., two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, iso-butanol, pentanol and hexanol. The methods used to remove the organic solvent can involve diafiltration or dialysis or evaporation at reduced pressures or blowing a stream of inert gas (e.g. nitrogen or argon) across the mixture.

In some embodiments, the method further comprises adding nonlipid polycations which are useful to effect the transformation of cells using the present compositions. Examples of suitable nonlipid polycations include, but are limited to, hexadimethrine bromide (sold under the brand name POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine. In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticles can be formed in a mono- or a bi-phase system. In some embodiments, in a mono-phase system, the amino lipid(s) and one or more nucleic acid molecular entities are each dissolved in a volume of the mono-phase mixture. Combining the two solutions provides a single mixture in which the complexes form. In some embodiments, in a bi-phase system, the amino lipids bind to the one or more nucleic acid molecular entities (which is present in the aqueous phase), and thus increasing the solubility in organic phase.

In some embodiments, the lipid nanoparticles are prepared in an apparatus comprising a first reservoir for holding an aqueous solution and a second reservoir for holding an organic lipid solution. In some embodiments, the apparatus comprises additional reservoirs for holding an aqueous solution (such as for a portion of the one or more nucleic acid molecular entities) and/or an organic solution. The apparatus can include a pump mechanism configured to pump the aqueous and the organic lipid solutions into a mixing region or mixing chamber at substantially equal flow rates. In some embodiments, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.

In some embodiments, the first solution comprises an aqueous buffer. In some embodiments, the first solution comprises a mixture of an aqueous buffer mixed with an organic solvent. In some embodiments, the organic solvent present in the aqueous buffer is ethanol. In some embodiments, the second solution comprises a mixture of an aqueous buffer mixed with an organic solvent. In some embodiments, the second solution comprises ethanol. In some embodiments, the second solution comprises ethanol and water. In some embodiments, the ethanol percentage in the aqueous buffer ranges from 0.1% to 50%, or any numbers or ranges therebetween. In some embodiments, the dilution buffer comprises an aqueous buffer. In some embodiments, the dilution buffer comprises an organic solvent. In some embodiments, the dilution buffer comprises ethanol and water. In some embodiments, the dilution buffer comprises 10% to 20% of ethanol in PBS buffer.

In some embodiments, the mixing comprises laminar mixing, vortex mixing, turbulent mixing, or a combination thereof. In some embodiments, the mixing comprises cross-mixing. In some embodiments, the mixing comprises inline mixing. In some embodiments, the mixing comprises introducing at least a portion of the first solution through a first inlet channel and at least a portion of the second solution through a second inlet channel, and wherein an angle between the first inlet channel and the second inlet channel is from about 0 to 180 degrees. In some embodiments, the angle between the first inlet channel and the second inlet channel is from about 15 to 180 degrees, from about 30 to 180 degrees, from about 45 to 180 degrees, from about 60 to 180 degrees, from about 90 to 180 degrees, or any numbers or ranges therebetween. In some embodiments, the mixing comprises introducing a portion of the first solution through a third inlet channel. The mixing step can take place by any number of methods, e.g., by mechanical means such as a vortex mixer. In some embodiments, the mixing step comprises inline mixing.

In some embodiments, a method of making a formulation comprising the herein-described nanoparticles comprises a filtration step. In some embodiments, a method of making a formulation comprising the herein-described nanoparticles comprises buffer exchange. In some embodiments, the buffer exchange comprises dialysis, chromatography, or tangential flow filtration (TFF).

III. Pharmaceutical Compositions

In one aspect, disclosed herein are pharmaceutical compositions comprising one or more described particle compositions. For example, a pharmaceutical composition can include one or more LNP compositions including one or more different payloads. Pharmaceutical compositions can further include one or more pharmaceutically acceptable excipients, carrier, or accessory ingredients such as those described herein. General guidelines for the formulation and manufacture of pharmaceutical compositions and agents are available, for example, in Remington's The Science and Practice of Pharmacy, 21st Edition, A. R. Gennaro; Lippincott, Williams & Wilkins, Baltimore, Md., 2006. Excipients or carriers can include any ingredient other than the compound(s) of the disclosure, the other lipid component(s) and the payload. An excipient may impart either a functional (e.g. drug release rate controlling) and/or a nonfunctional (e.g. processing aid or diluent) characteristic to the formulations. The choice of excipient and carrier can depend on factors such as the particular mode of administration, the effect of the excipient on solubility and stability, and the nature of the dosage form. Parenteral formulations are typically aqueous or oily solutions or suspensions. Excipients or carrier such as sugars (including but not restricted to glucose, mannitol, sorbitol, etc.), salts, carbohydrates and buffering agents (preferably to a pH of from 3 to 9) can be used. In some embodiments, the LNP compositions can be formulated with a sterile non-aqueous solution or as a dried form to be used in conjunction with a suitable vehicle such as sterile, pyrogen-free water (WFI).

In some embodiments, the excipient or carrier can make up greater than 50% of the total mass or volume of a pharmaceutical composition comprising a nanoparticle composition. For example, the excipient or carrier can make up 50%, 60%, 70%, 80%, 90%, or more of a pharmaceutical composition. In some embodiments, a pharmaceutically acceptable excipient or carrier is at least 95%, at least 96%, at least 97%, at least 98%, at least 99%, or 100% pure. In some embodiments, a pharmaceutical composition can comprise between 0.1% and 100% (wt/wt) of one or more nanoparticle compositions. In certain embodiments, the nanoparticle compositions and/or pharmaceutical compositions are refrigerated or frozen for storage and/or shipment (e.g., being stored at a temperature of 4° C. or lower, such as a temperature between about −150° C. and about 0° C. or between about −80° C. and about −20° C. In some embodiments, the nanoparticle compositions and/or pharmaceutical compositions are refrigerated or frozen at about −5° C., −10° C., −15° C., −20° C., −25° C., −30° C., −40° C., −50° C., −60° C., −70° C., −80° C., −90° C., −130° C., or −150° C.

The described LNP compositions and/or pharmaceutical compositions can be administered to any patient or subject, including those patients or subjects that may benefit from a therapeutic effect provided by the delivery of the payload to one or more particular cells, tissues, organs, or systems or groups thereof. In some embodiments, the subject is a mammal such as human. In some embodiments, the subject is non-human primates or mammals, including commercially relevant mammals such as cattle, pigs, hoses, sheep, cats, dogs, mice, and/or rats.

A pharmaceutical composition including one or more nanoparticle compositions may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage. Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

In some embodiments, the pharmaceutical composition comprises 1, 2, 3, 4, 5, 6, 7, 8, 9, 10 or more payloads. In some embodiments, the pharmaceutical composition comprises two distinct payloads, such guide RNA and mRNA. The guide RNA and mRNA can be located in the same LNP composition, or they can be located at separate LNP compositions. For example, a pharmaceutical composition can comprise two distinct LNP compositions, one comprising a guide RNA payload and the other comprising an mRNA payload. For another example, a pharmaceutical composition can comprise two distinct LNP compositions, one comprising a guide RNA (or mRNA) payload and the other comprising both an mRNA payload and a guide RNA payload. For yet another example, a pharmaceutical composition can comprise one LNP composition, which comprising an mRNA payload and a guide RNA payload. In some embodiments, the pharmaceutical composition comprises two or more distinct LNP compositions. In some embodiments, the two or more distinct LNP compositions are present in the pharmaceutical composition such that the mRNA molecule(s) and the guide RNA molecule(s) are at a mole or weight ratio described herein.

The gRNA and mRNA payloads can be present in the pharmaceutical composition at various molar or weight ratios. For example, the gRNA to mRNA ratio in the pharmaceutical composition can be from 0.01 to 100 by weight, and/or any value therebetween. For example, the gRNA to mRNA ratio in the pharmaceutical composition can be from 0.01 to 100 by mole, and/or any value therebetween. In some embodiments, the ratio of gRNA to mRNA in the pharmaceutical composition is from about 1 to about 50 by weight or by mole, and/or any value therebetween. In some embodiments, the ratio of gRNA to mRNA in the pharmaceutical composition is from about 0.1 to about 10 by weight or by mole, and/or any value therebetween. In some embodiments, the ratio of gRNA to mRNA in the pharmaceutical composition is from about 0.2 to about 5, from about 0.25 to about 4, from about 0.3 to about 3, or from about 0.5 to about 2 by weight. In some embodiments, the ratio of gRNA to mRNA in the pharmaceutical composition is from about 0.2 to about 5, from about 0.25 to about 4, from about 0.3 to about 3, or from about 0.5 to about 2 by mole. In some embodiments, the gRNA to mRNA ratio in the pharmaceutical composition is about 1:1, about 1:2, about 1:3, about 1:4, about 1:5, about 1:6, about 1:7, about 1:8, about 1:9, or about 1:10 by weight. In some embodiments, the gRNA to mRNA ratio in the pharmaceutical composition is about 1:1, about 1:2, about 1:3, about 1:4, about 1:5, about 1:6, about 1:7, about 1:8, about 1:9, or about 1:10 by mole. In some embodiments, the mRNA to gRNA ratio in the pharmaceutical composition is about 1:1, about 1:2, about 1:3, about 1:4, about 1:5, about 1.6, about 1:7, about 1:8, about 1:9, or about 1:10 by weight. In some embodiments, the mRNA to gRNA ratio in the pharmaceutical composition is about 1:1, about 1:2, about 1:3, about 1:4, about 1:5, about 1:6, about 1:7, about 1:8, about 1:9, or about 1:10 by mole. In some embodiments, the gRNA to mRNA ratio in the pharmaceutical composition is about 1:1 by weight. In some embodiments, the gRNA to mRNA ratio in the pharmaceutical composition is about 1:1 by mole.

In some embodiments, the gRNA in the pharmaceutical composition targets a disease-causing gene that is produced in the hepatocytes. In some embodiments, the target cells of the disclosed compositions are selected from hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells. In some embodiments, the pharmaceutical composition comprises more than one guide RNA. For example, the pharmaceutical composition can comprise 2, 3, 4, 5, or more distinct guide RNAs. In some embodiments, the pharmaceutical composition comprises two guide RNA molecules. In some embodiments, the pharmaceutical composition comprises one mRNA and two or more guide RNA molecules. In some embodiments, the two or more guide RNA molecules target the same disease-causing gene. In some embodiments, the two or more guide RNA molecules target different genes. In some specific embodiments, the two or more guide RNA molecules target two separate disease-causing genes of interest produced in the hepatocytes. In some embodiments, the gRNA is a sgRNA. In some embodiments, the gRNA is a dgRNA.

IV. Method of Use

The LNP compositions and pharmaceutical compositions disclosed herein can be used in methods for gene editing, both in vivo and in vitro. In some embodiments, the methods comprise contacting a cell with an LNP composition or a pharmaceutical composition described herein. In some embodiments, the cell is a mammalian cell. In some embodiments, the cell is a rodent cell. In some embodiments, the cell is a human cell. In some embodiments, the cell is a liver cell. In certain embodiments, the cell is a human liver cell. In some embodiments, the liver cell is a hepatocyte. In some embodiments, the hepatocyte is a human hepatocyte. In some embodiments, the liver cell is a stem cell. In some embodiments, the human liver cell is a liver sinusoidal endothelial cell (LSEC). In some embodiments, the human liver cell is a Kupffer cell. In some embodiments, the human liver cell is a hepatic stellate cell. In some embodiments, the human liver cell is a tumor cell. In some embodiments, the human liver cell is a liver stem cell. In some embodiments, the cell comprises ApoE-binding receptors. In some embodiments, engineered cells are provided; for example an engineered cell can be derived from any one of the cell types as described herein. Such engineered cells can be produced according to the methods described herein. In some embodiments, the engineered cell resides within a tissue or organ, e.g., a liver within a subject.

In some embodiments, the cell comprises a modification, for example an insertion or deletion ("indel") or substitution of nucleotides in a target sequence. In some embodiments, the modification comprises an insertion of 1, 2, 3, 4 or 5 or more nucleotides in a target sequence. In some embodiments, the modification comprises an insertion of either 1 or 2 nucleotides in a target sequence. In other embodiments, the modification comprises a deletion of 1, 2, 3, 4, 5, 6, 7, 8, 9, 10, 15, 20 or 25 or more nucleotides in a target sequence. In some embodiments, the modification comprises a deletion of either 1 or 2 nucleotides in a target sequence. In some embodiments, the modification comprises an indel which results in a frameshift mutation in a target sequence. In some embodiments, the modification comprises a substitution of 1, 2, 3, 4, 5, 6, 7, 8, 9, 10, 15, 20 or 25 or more nucleotides in a target sequence. In some embodiments, the modification comprises a substitution of either 1 or 2 nucleotides in a target sequence. In some embodiments, the modification comprises one or more of an insertion, deletion, or substitution of nucleotides resulting from the incorporation of a template nucleic acid, for example any of the template nucleic acids described herein.

In some embodiments, the method comprises contacting a population of cells, such as a population of engineered cells. In some embodiments, the population of cells comprises engineered cells cultured in vitro. In some embodiments, the population resides within a tissue or organ, e.g., a liver within a subject. In some embodiments, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% or more of the cells within the population is engineered. In certain embodiments, a method disclosed herein results in at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% editing efficiency (or "percent editing"), defined by detection of indels. In other embodiments, a method disclosed herein, results in at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% DNA modification efficiency, defined by detecting a change in sequence, whether by insertion, deletion, substitution or otherwise. In certain embodiments, a method disclosed herein results in an editing efficiency level or a DNA modification efficiency level of between about 5% to about 100%, about 10% to about 50%, about 20 to about 100%, about 20 to about 80%, about 40 to about 100%, or about 40 to about 80%.

In some embodiments, cells within the population comprise a modification. In some embodiments, the modification comprises an insertion of 1, 2, 3, 4 or 5 or more nucleotides in a target sequence. In some embodiments, the modification comprises an insertion of either 1 or 2 nucleotides in a target sequence. In other embodiments, the modification comprises a deletion of 1, 2, 3, 4, 5, 6, 7, 8, 9, 10, 15, 20 or 25 or more nucleotides in a target sequence. In some embodiments, the modification comprises a deletion of either 1 or 2 nucleotides in a target sequence. In some embodiments, the modification comprises an indel which results in a frameshift mutation in a target sequence. In some embodiments, at least 80%, at least 85%, at least 90%, at least 91%, at least 92%, at least 93%, at least 94%, at least 95%, at least 96%, at least 97%, at least 98%, or at least 99% or more of the engineered cells in the population comprise a frameshift mutation.

In some embodiments, the LNP compositions can be used to edit a gene resulting in a gene knockout. In some embodiments, the LNP compositions can be used to edit a gene resulting in a gene correction. In some embodiments, the LNP compositions can be used to edit a cell resulting in gene insertion. In some embodiments, disclosed are methods for silencing expression of a target gene in a cell. In some embodiments, the method comprises contacting a cell comprising an expressed target gene with an LNP composition or a pharmaceutical composition described herein under conditions whereby the gRNA enters the cell and silences the expression of the target gene within the cell. In certain embodiments, the cell is in a mammal, such as a human. In some embodiments, the method for silencing expression of a target gene comprises administering to the mammal a therapeutically effective amount of an LNP composition or pharmaceutical composition comprising one or more gRNAs described herein. In some embodiments, the administration of the LNP composition or pharmaceutical composition comprising one or more gRNAs described herein reduces target RNA levels by at least about 5%, 100%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to RNA levels detected in the absence of the gRNA (e.g., buffer control or irrelevant gRNA control). In some embodiments, the administration of the LNP composition or pharmaceutical composition comprising one or more gRNAs reduces target RNA levels for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant non-targeting gRNA control.

In some embodiments, administration of the LNP composition or pharmaceutical composition may result in gene editing which results in persistent response. For example, administration can result in a duration of response of a day, a month, a year, or longer. As used herein, "duration of response" means that, after cells have been edited using an LNP composition or pharmaceutical composition disclosed herein, the resulting modification is still present for a certain period of time after the administration. The modification can be detected by measuring target protein levels. The modification can be detected by detecting the target DNA. In some embodiments, the duration of response can be at least 1 week, at least 2 weeks, at least 1 month, at least 2 months, at least 4 months, at least 6 months, or at least 1 year. In certain embodiments, the duration of response may be about 26 weeks. In some embodiments, the duration of response can be at least 5 years or at least 10 years. A persistent response is detectable after at least 6 months, either by measuring target protein levels or by detection of the target DNA.

In one aspect, disclosed herein are methods for treating a disease or condition, including raising an immune response to an immunogen, in a subject. In one embodiment, the disease or condition is treatable by administering the payload. In some embodiments, the disease or condition is characterized by missing or aberrant protein or polypeptide activity. For example, an LNP composition comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. A payload included in an LNP composition may also be capable of altering the rate of transcription of a given species, thereby affecting gene expression.

Diseases and/or conditions characterized by dysfunctional or aberrant protein or polypeptide activity can include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene. In some embodiments, the present disclosure provides a method for treating such diseases and/or conditions in a subject by administering an LNP composition or pharmaceutical composition comprising an RNA payload, wherein the RNA can be an mRNA encoding a polypeptide that antagonizes or otherwise overcomes an aberrant protein activity present in the cell of the subject.

Although the present invention and its advantages have been described in detail, it should be understood that various changes, substitutions and alterations can be made herein without departing from the spirit and scope of the invention as defined in the appended claims.

Further embodiments of the present disclosure, for example, the LNP compositions (including the various components of the LNP composition), the pharmaceutical compositions, the methods of preparing the compositions, the methods of gene editing, the methods of treatment, and other methods of using the compositions, can be found in various WO and US patent/patent application publications, including U.S. Pat. No. 9,868,692B2, US20180353434A1, U.S. Pat. Nos. 8,492,359B2, 9,878,042B2, US20180148719, U.S. Pat. Nos. 9,687,448B2, 9,415,109B2, 7,858,117B2, 9,404,127B2, 9,504,651, US20070087045A1, US20180092848A1, US20170273907A1, US20180147298A1, WO2019067992A1, WO2019067999A1, WO2018185241, WO 2018170306A1, WO 2019046809A1, WO2017173054A1, WO2015095340, WO2016197133A1, and WO2018191750, all of which are hereby incorporated by reference in their entirety. Further description about the LNP compositions, the pharmaceutical compositions, and the methods are described in WO2016153012 A1, WO2018062413 A1, WO2019027055 A1, WO2017/173054A1, WO2015/095340A1, WO2013063468A1, WO2010054401A1, and WO 2018/170306, all of which are hereby incorporated by reference in their entirety.

The present invention is further illustrated in the following Examples which are given for illustration purposes only and are not intended to limit the invention in any way.

EXAMPLES

Example 1. Synthesis of VL401 and VL469

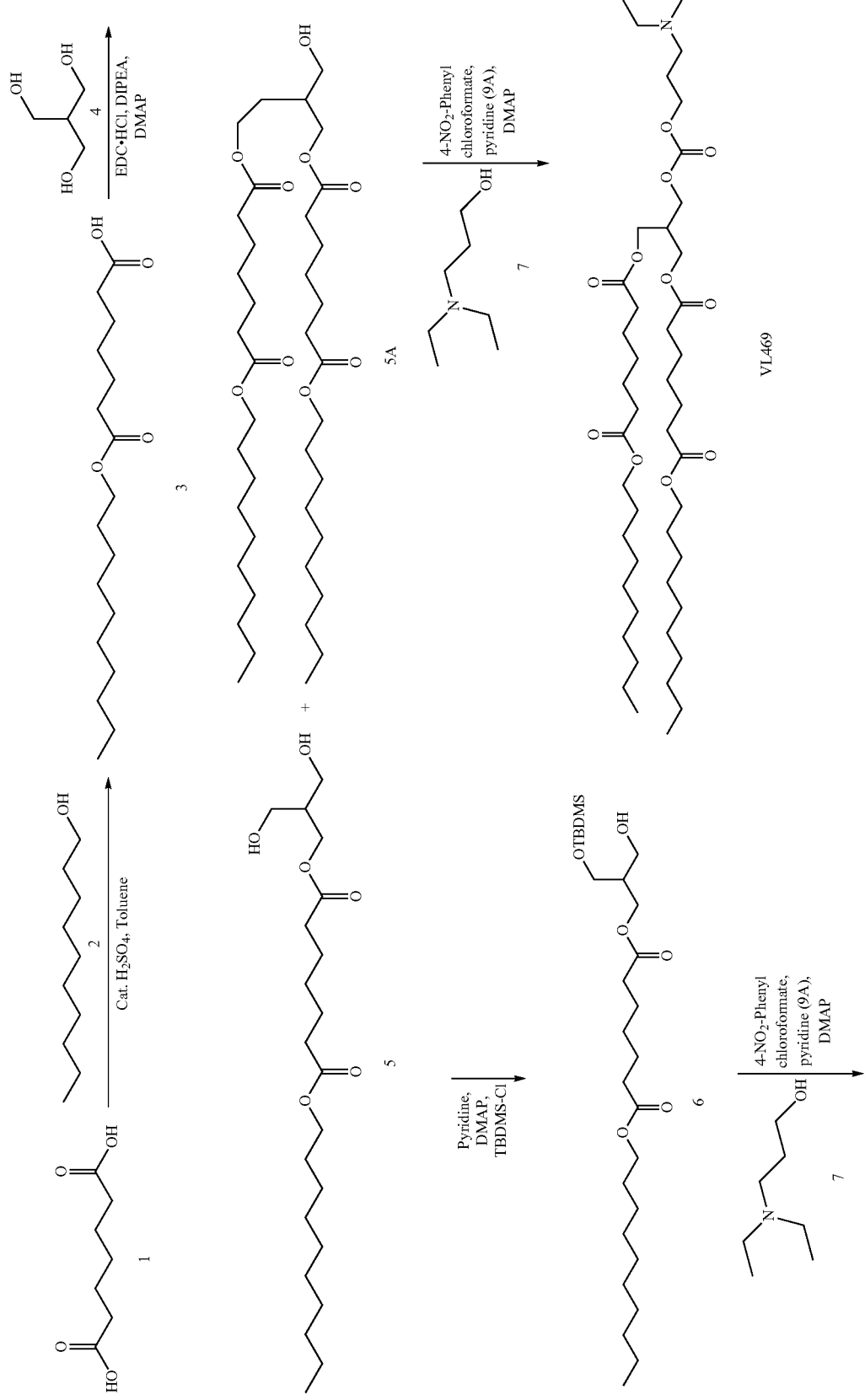

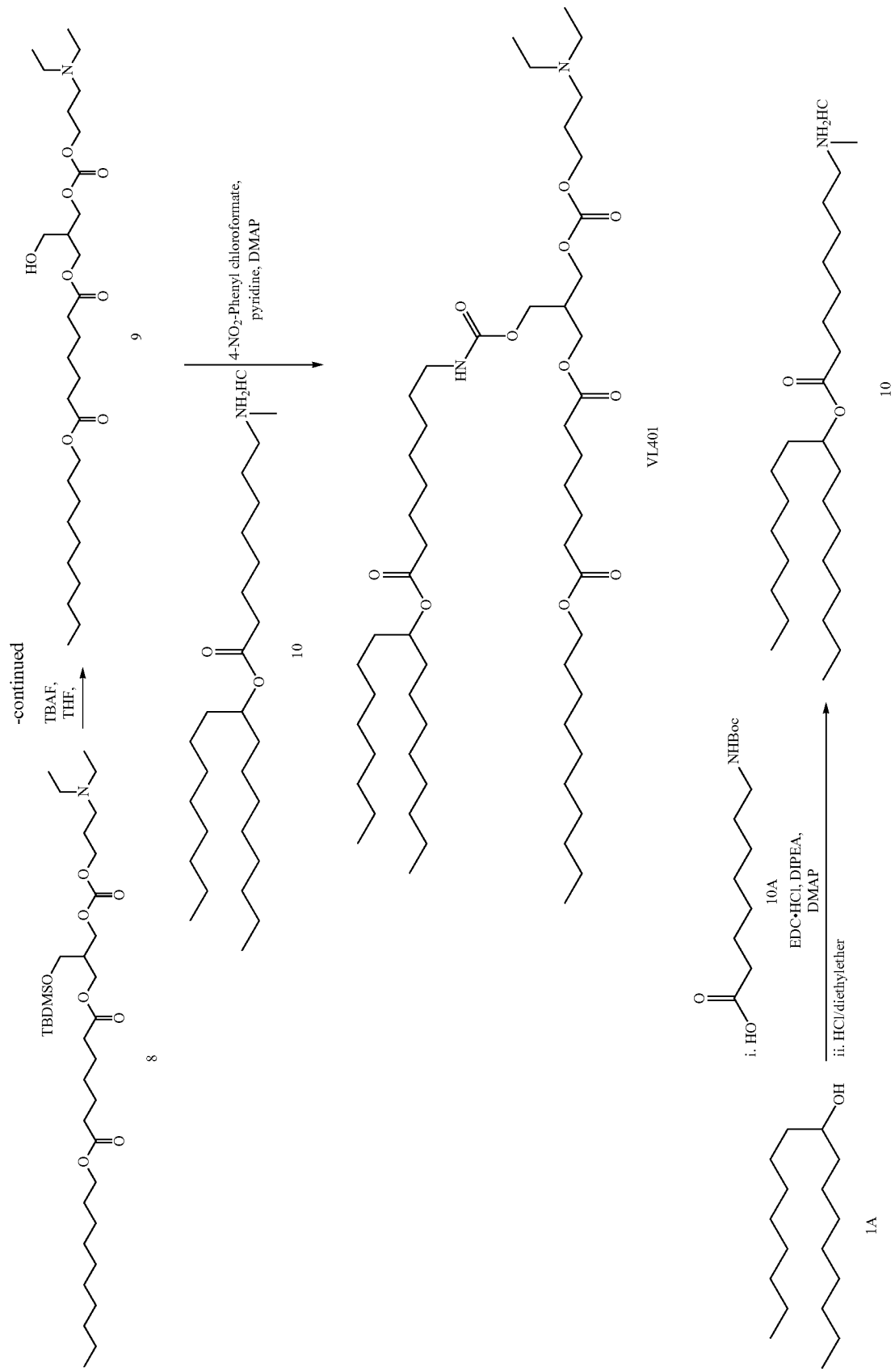

To a solution of compound 1 (16.0 g, 100 mmol) in toluene (90 mL) was added compound 2 (4 mL, 100 mmol) followed by H$_2$SO$_4$ (0.1 mL) as catalytic amount and refluxed for 6 h. After 6 h, TLC showed completion of compound 1 and the reaction mixture was quenched with a solution of Na$_2$CO$_3$ (100 mL) and the product was extracted into EtOAc (3×200 mL). The organic layer was separated and evaporated to get the crude. The crude mass was then purified by silica gel (60-120 mesh) column chromatography by eluting with 20% EtOAc in pet-ether to afford compound 3 (8.0 g, 27%) as white solid. $^1$H NMR (400 MHz, DMSO-d$_6$): δ ppm 11.97 (s, 1H), 3.98 (t, J=6.4 Hz, 2H), 2.26 (t, J=7.6 Hz, 2H), 2.18 (t, J=7.6 Hz, 2H), 1.70-1.50 (m, 6H), 1.40-1.20 (m, 16H), 0.88 (t, J=6.4 Hz, 3H).

To a solution of compound 3 (6.0 g, 20 mmol) in CH$_2$Cl$_2$ (60 mL) was added 2-(hydroxymethyl)propane-1,3-diol (2.11 g, 20 mmol) followed by EDC·HCl (5.75 g, 30 mmol), DMAP (488 mg, 4 mmol) and DIPEA (4.83 mL, 30 mmol). Reaction mixture was stirred at room temperature (RT) for 24 h. The reaction mixture was diluted with water and was the product was extracted with DCM (2×200 mL). The organic layer was separated and evaporated to get the crude. The crude mass was then purified by silica gel (60-120 mesh) column chromatography by eluting with 50% EtOAc in pet-ether to afford compound 5 (3.5 g, 45%). $^1$H NMR (400 MHz, DMSO-d$_6$): δ ppm 4.45 (t, J=5.2 Hz, 2H), 4.10-4.00 (m, 4H), 3.50-3.35 (m, 4H), 2.26 (m, t, J=7.2 Hz, 4H), 1.90-1.75 (m, 1H), 1.60-1.45 (m, 6H), 1.40-1.20 (m, 16H), 0.85 (t, J=6.4 Hz, 3H).

A solution of compound 5 (2.0 g, 5.15 mmol), DMAP (188 mg, 1.54 mmol), and TBDMS-Cl (850 mg, 5.67 mmol) in pyridine (10 mL) was stirred at RT for 3 h. The reaction mixture was diluted with water (20 mL) and the product was extracted with DCM (2×100 mL). The organic layer was separated and evaporated to get the crude. The crude mass was then purified by silica gel (60-120 mesh) chromatography by eluting with 30% EtOAc in pet-ether to obtain compound 6 as a colourless oil (1.2 g, 46%). $^1$H NMR (400 MHz, DMSO-d$_6$): δ ppm 4.51 (t, J=5.2 Hz, 1H), 4.10-3.90 (m, 4H), 3.65-3.50 (m, 2H), 3.45-3.30 (m, 2H), 2.35-2.20 (m, 4H), 1.90-1.80 (m, 1H), 1.60-1.45 (m, 6H), 1.30-1.10 (m, 16H), 0.90-0.75 (m, 12H), 0.10 (s, 6H).

To a solution of compound 7 (375 mg, 3.10 mmol) in CH$_2$Cl$_2$ (13 mL) were added 4-nitrophenyl chloroformate (965 mg, 5.16 mmol) followed by pyridine (0.38 mL, 5.16 mmol) and DMAP (87 mg, 0.77 mmol) and the reaction was continued for 2 h. 6 was added (1.3 g, 2.58 mmol) and the reaction mixture was allowed to stir at 45° C. for 16 h. Reaction mixture was diluted with water (50 mL) and the product was extracted with CH$_2$Cl$_2$ (2×50 mL); the organic layer was separated and evaporated to get the crude mass. The crude mass was purified by silica gel column eluting with 50% EtOAc in pet-ether to get 8 (700 mg, 43%) as yellow oil. $^1$H NMR (400 MHz, DMSO-d$_6$): δ ppm 4.20-3.98 (m, 8H), 3.61 (d, J=5.6 Hz, 2H), 2.50-2.35 (m, 6H), 2.35-2.10 (m, 6H), 1.80-1.70 (m, 2H), 1.60-1.45 (m, 6H), 1.60-1.45 (m, 5H), 1.40-1.20 (m, 16H), 1.00-0.89 (m, 14H), 0.10 (s, 6H).

To a stirred solution of 8 (700 mg, 1.06 mmol) in THF (4 mL) was added TBAF (0.46 mL, 1.593 mmol) at ice temperature and the reaction mixture was stirred at RT for 4 h. The reaction mixture was diluted with water (10 mL) and the product was extracted with CH$_2$Cl$_2$ (2×50 mL); the organic layer was separated and evaporated to get the crude. Crude material was purified by silica gel column eluting with 50% EtOAc in pet-ether yielded 9 (300 mg, 52%) as a colourless gummy liquid.

Compound VL401. To a stirred solution of 9 (200 mg, 0.366 mmol) in CH$_2$Cl$_2$ (2 mL) was added 4-nitrophenyl chloroformate (965 mg, 5.16 mmol) followed by pyridine (0.38 mL, 5.16 mmol) and DMAP (87 mg, 0.77 mmol); the reaction mixture was continued stirring for 2 h and added compound 10 (159 mg, 0.402 mmol) and the reaction mixture was allowed to stir at 90° C. for 16 h. Reaction mixture was diluted with water (50 mL) and the product was extracted with CH$_2$Cl$_2$ (2×50 mL); the organic layer was separated and evaporated to get the crude product. The crude material was purified by silica gel column eluting with 6% MeOH in CH$_2$Cl$_2$ to obtain VL401 (80 mg, 22%) as a gummy liquid. $^1$H NMR (400 MHz, DMSO-d$_6$): δ ppm 7.20-7.10 (m, 1H), 4.85-4.75 (m, 1H), 4.30-4.00 (m, 10H), 3.60-3.30 (m, 5H), 3.00-2.90 (m, 2H), 2.40-2.20 (m, 10H), 1.80-0.80 (m, 75H). Mass [M+H]$^+$ Calcd for 969.7; found 969.6.

Compound VL469. Compound 5A is reacted with 4-nitropehnyl chloroformate in dichloromethane in the presence of pyridine and DMAP. The 4-nitropehnyl carbonate thus formed is then reacted with compound 7 to obtain compound VL469.

Example 2. Synthesis of VL403

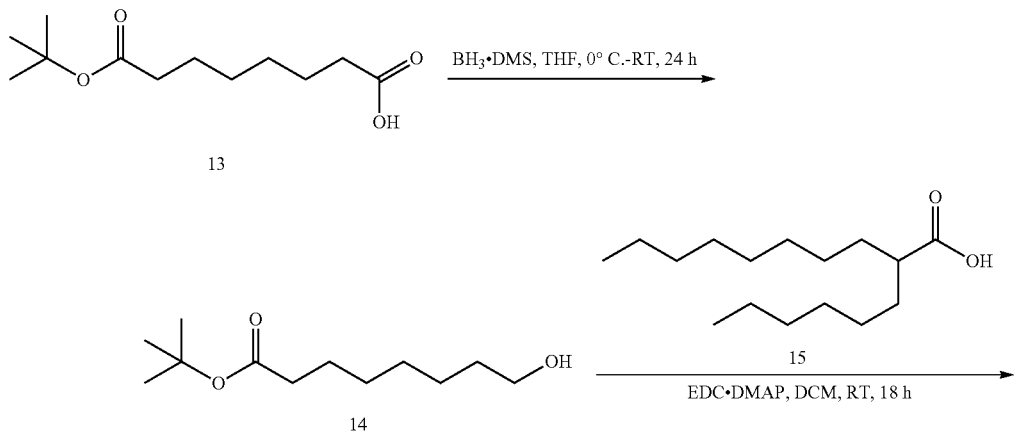

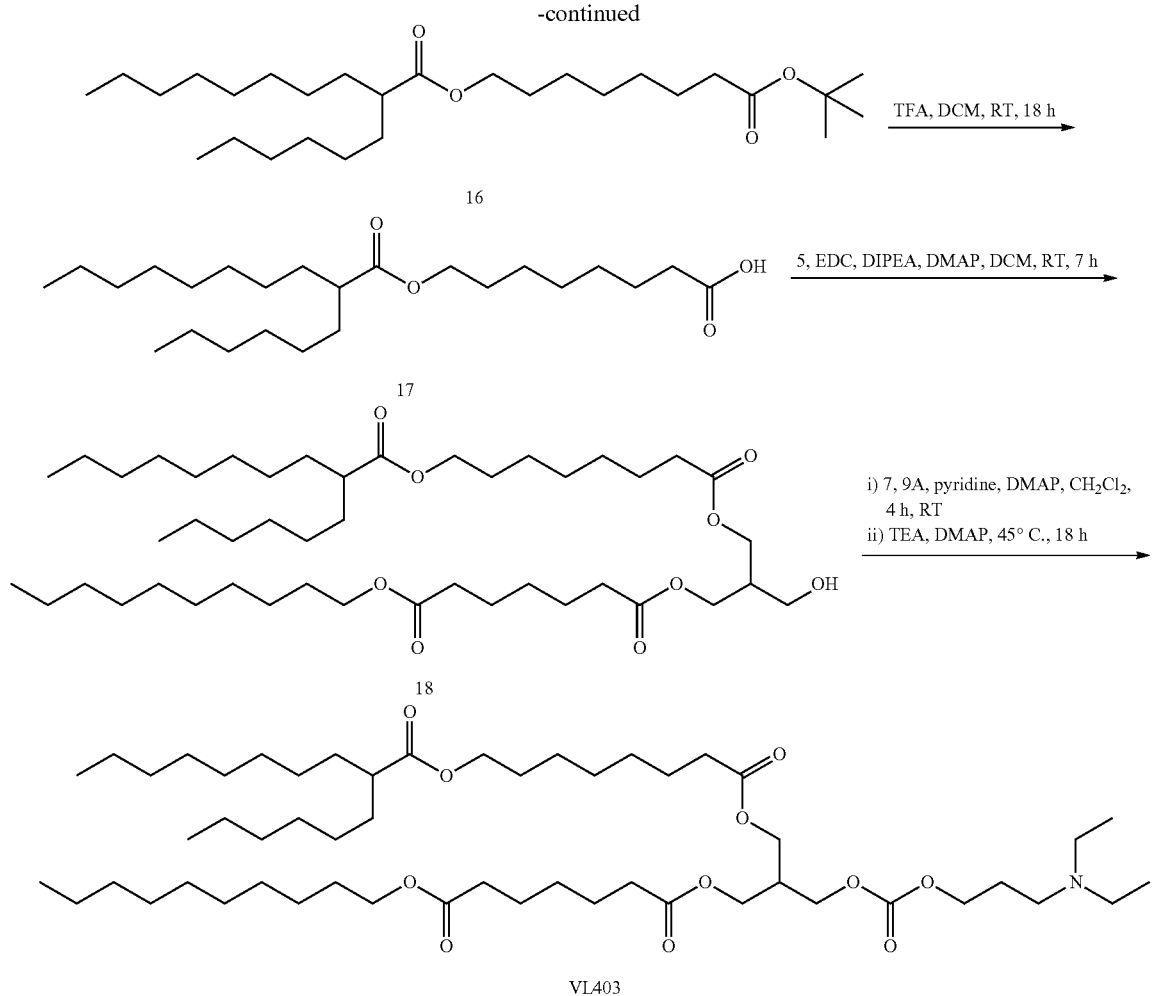

To a solution of commercially available compound 13 (11.5 g, 50 mmol) in THF (50 mL) was added BH$_3$·DMS (2 M in THF, 30 mL) at 0° C. Reaction mixture was stirred at RT for 24 h. The reaction mixture was quenched with MeOH and the organic layer was concentrated under reduce pressure to obtain compound 14 (10 g, 92.5%). $^1$H NMR (400 MHz, CDCl$_3$): δ ppm 3.63 (t, J=6.4 Hz, 2H), 2.20 (t, J=6.4 Hz, 2H), 1.70-1.50 (m, 4H), 1.44 (s, 9H), 1.40-1.30 (m, 7H).

To a stirred solution of compound 14 (4.8 g, 22.2 mmol) in CH$_2$Cl$_2$ (70 mL) was added compound 15 (6.3 g, 24.4 mmol) followed by EDC·HCl (5.5 g, 28.8 mmol), DMAP (1.4 g, 11.1 mmol) and the reaction mixture was stirred for 16 h. The reaction mixture was diluted with water (50 mL) and the product was extracted with CH$_2$Cl$_2$ (2×100 mL); the organic layer was separated and evaporated to get the crude product. The crude product was purified by silica gel column by eluting with 10% EtOAc in pet-ether to obtain compound 16 (5 g, 50%) as a gummy liquid. $^1$H NMR (400 MHz, CDCl$_3$): δ ppm 4.08 (t, J=6.8 Hz, 2H), 2.40-2.20 (m, 3H), 1.70-1.60 (m, 4H), 1.46 (s, 9H), 1.40-1.20 (m, 30H), 0.95-0.85 (m, 6H).

Compound 17. To a stirred solution of compound 16 (1.9 g, 4.18 mmol) in CH$_2$Cl$_2$ (20 mL) was added TFA (2 mL, 12.5 mmol) at 0° C. and the reaction mixture was stirred for 16 h. The reaction mixture was concentrated under reduce pressure to give compound 17 (1.8 g, 99%) as a gummy liquid. $^1$H NMR (400 MHz, CDCl$_3$): δ ppm 4.06 (t, J=6.8 Hz, 2H), 2.40-2.25 (m, 3H), 1.80-1.50 (m, 4H), 1.50-1.20 (m, 30H), 1.00-0.85 (m, 6H).

To a stirred solution of compound 17 (1.5 g, 3.76 mmol) in CH$_2$Cl$_2$ (20 mL) was added compound 5 (2.1 g, 5.65 mmol) followed by EDC·HCl (1.1 g, 5.65 mmol), DIPEA (1 mL, 5.65 mmol) and DMAP (138 mg, 1.13 mmol), and the reaction mixture was stirred for 7 h. The reaction mixture was diluted with water (50 mL) and the product was extracted with CH$_2$Cl$_2$ (2×25 mL); the organic layer was separated and evaporated to get the crude product. The crude mass was purified by silica gel column by eluting with 20% EtOAc in pet-ether to obtain compound 18 (0.6 g, 21%) as a yellow oil. $^1$H NMR (400 MHz, CDCl$_3$): δ ppm 4.25-4.10 (m, 4H), 4.10-4.00 (m, 4H), 3.70-3.60 (m, 2H), 2.60-2.50 (m, 7H), 2.40-2.30 (m, 7H), 1.80-1.50 (m, 10H), 1.50-1.20 (m, 41H), 0.95-0.85 (m, 9H).

To a solution of compound 7 (204 mg, 1.56 mmol) in CH$_2$Cl$_2$ (6 mL) were added 4-nitrophenyl chloroformate (470 mg, 2.34 mmol) followed by pyridine (0.1 mL, 1.17 mmol) and DMAP (14 mg, 0.11 mmol), and the reaction was stirred for 4 h; added compound 18 (300 mg, 0.39 mmol) and the reaction mixture was allowed to stirred at 45° C. for 18 h. Reaction mixture was diluted with water (20 mL) and the product was extracted with CH$_2$Cl$_2$ (2×50 mL); the organic layer was separated and evaporated to get the crude product. The crude mass was purified by silica gel column eluting with 50% EtOAc in pet-ether to get VL403 (130 mg, 35%) as a yellow oil. $^1$H NMR (400 MHz, CDCl$_3$): δ ppm 4.25-4.10 (m, 8H), 4.10-4.00 (m, 4H), 2.60-2.50 (m, 7H), 2.40-2.25 (m, 7H), 1.85-1.75 (m, 2H), 1.70-1.60 (m, 10H), 1.50-1.20 (m, 46H), 1.10-0.95 (m, 6H), 0.95-0.85 (m, 9H). m/z: [M+H]$^+$ Calcd for 926.7; found 926.6.

Example 3. Synthesis of VL404

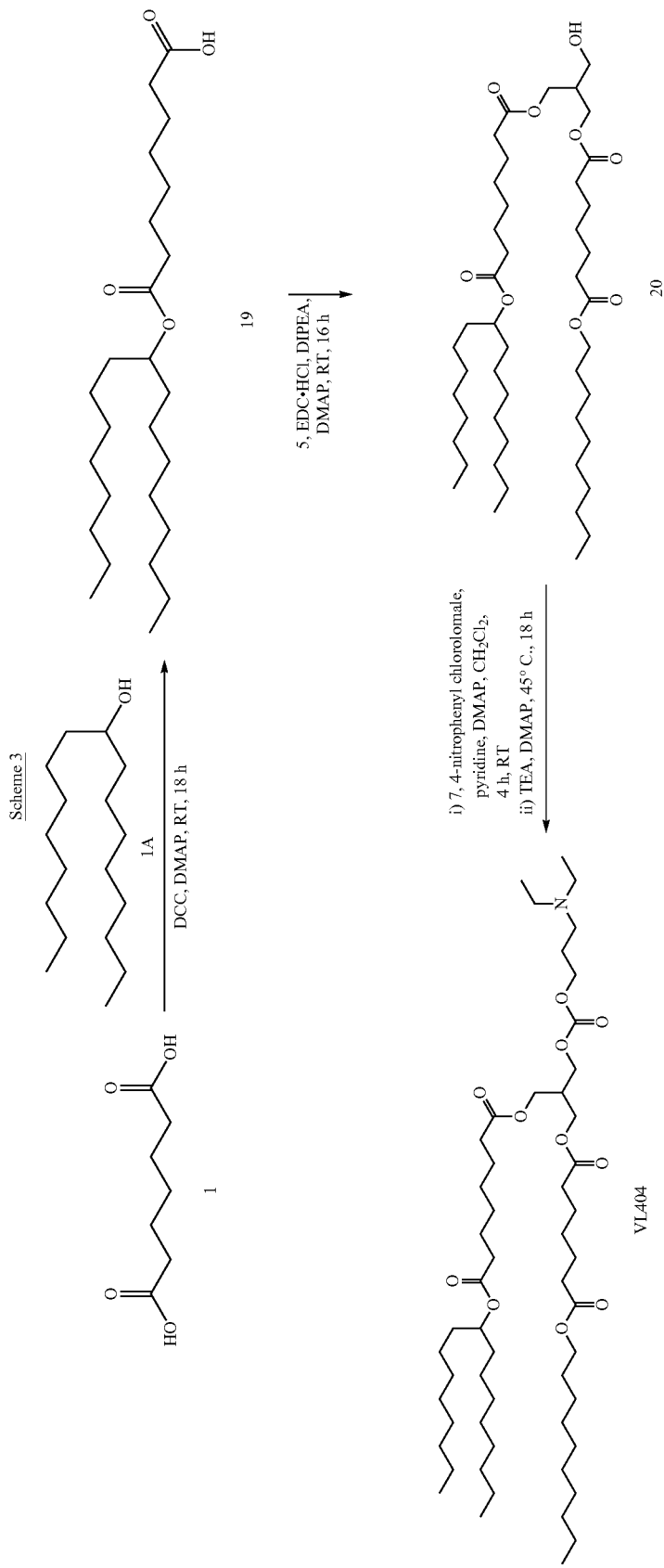

To a stirred solution of compound 1 (9.6 g, 54.68 mmol) in CH$_2$Cl=2 (100 mL) was added compound 1A (10 g, 39.06 mmol) followed by DCC (8.85 g, 42.96 mmol) and DMAP (2.38 g, 19.52 mmol). The reaction mixture was stirred at RT for 18 h. After complete disappearance of compound 1 by TLC, the reaction mixture was diluted with water (100 mL) and the product was extracted into CH$_2$Cl$_2$ (2×100 mL). The organic layer was separated, evaporated in vacuo, and the crude product obtained was purified by silica gel column, eluting with 50% EtOAc in pet-ether to obtain compound 19 (6 g, 26%) as a gummy solid. $^1$H NMR (400 MHz, DMSO-d$_6$): δ ppm 4.90-4.80 (m, 1H), 2.35 (t, J=5.2 Hz, 2H), 2.26 (t, J=5.2 Hz, 2H), 1.80-1.20 (m, 36H), 0.95-0.85 (m, 6H).

To a stirred solution of compound 19 (4.99 g, 9.99 mmol) in CH$_2$Cl$_2$ (20 mL) was added compound 5 (2.0 g, 6.666 mmol) followed by EDC·HCl (1.916 g, 9.99 mmol), DIPEA (3.48 mL, 19.99 mmol), DMAP (244 mg, 1.99 mmol) and the reaction mixture was stirred for 16 h. After complete disappearance of compound 6 by TLC, reaction mixture was diluted with water (50 mL) and the product was extracted with CH$_2$Cl$_2$ (2×50 mL); the organic layer was separated and evaporated to get the crude product. The crude mass was purified by silica gel column by eluting with 50% EtOAc in pet-ether to yield compound 20 (2.1 g, 52%) as a gummy liquid. H NMR (400 MHz, DMSO-d$_6$): δ ppm 4.90-4.70 (i, 2H), 4.20-3.95 (m, 6H), 3.42 (t, J=5.6 Hz, 2H), 2.40-2.20 (m, 8H), 2.10-2.00 (m, 1H), 1.60-1.40 (m, 14H), 1.40-1.10 (m, 44H), 0.85 (t, J=6.4 Hz, 9H).

Compound VL404. To a solution of compound 7 (672 mg, 5.12 mmol) in CH$_2$Cl$_2$ (20 mL) were added 4-nitrophenyl chloroformate (1.53 g, 7.62 mmol) followed by pyridine (0.5 mL, 6.38 mmol) and DMAP (50 mg, 0.384 mmol) and the reaction was stirred for 5 h. After 5 h, added compound 20 (1.0 g, 1.28 mmol) and the reaction mixture was allowed to stir at 45° C. for 18 h. Reaction mixture was diluted with water (20 mL) and the product was extracted with CH$_2$Cl$_2$ (2×50 mL); the organic layer was separated and evaporated to get the crude product. The crude mass was purified by silica gel column eluting with 50% EtOAc in pet-ether to obtain VL404 (510 mg, 42%) as a gummy liquid. $^1$H NMR (400 MHz, CDCl$_3$): δ ppm 4.90-4.80 (m, 1H), 4.25-4.00 (m, 10H), 2.60-2.50 (m, 7H), 2.40-2.25 (m, 8H), 1.85-1.75 (m, 2H), 1.70-1.60 (m, 8H) (1.60-1.45 (m, 4H), 1.40-1.15 (m, 46H), 1.00 (t, J=6.8 Hz, 6H), 0.95-0.85 (m, 9H). ELSD-MS m/z calc. 939.74; found: 940.6.

Example 4. Synthesis of VL406 and VL422

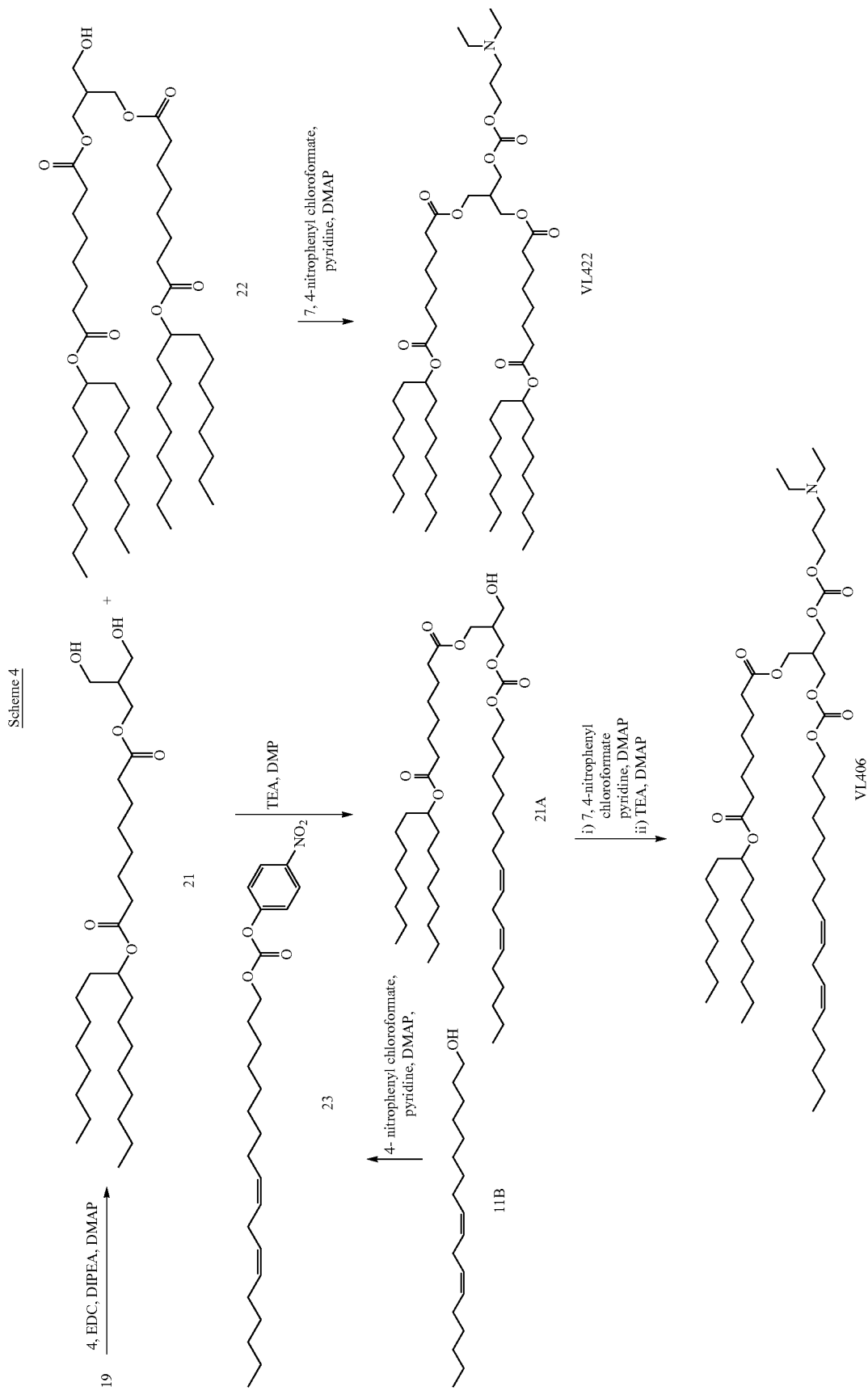

To a solution of compound 11B (5 g, 18.76 mmol) in CH$_2$Cl$_2$ (50 mL) were added 4-nitrophenyl chloroformate (11.37 mg, 56.29 mmol) followed by pyridine (4.53 mL, 56.29 mmol) and DMAP (687 mg, 5.62 mmol) and the reaction was stirred for 16 h. Reaction mixture was then filtered and the white coloured solid was discarded. The filtrate was evaporated and triturated with pet-ether to yield 23 (6 g, 74%) as a gummy liquid. $^1$H NMR (400 MHz, CDCl$_3$): δ ppm 8.27 (d, J=7.2 Hz, 2H), 7.37 (d, J=7.2 Hz, 2H), 5.50-5.30 (m, 4H), 4.28 (t, J=6.4 Hz, 2H), 2.77 (t, J=6.4 Hz, 2H), 2.10-2.00 (m, 4H), 1.85-1.70 (m, 2H), 1.50-1.20 (m, 18H), 0.89 (t, J=7.2 Hz, 3H).

To a solution of 19 (3.0 g, 7.28 mmol) in CH$_2$Cl$_2$ (30 mL) was added compound 4 (772 mg, 7.28 mmol) followed by EDC·HCl (2.0 g, 10.9 mmol), DMAP (173 mg, 1.45 mmol) and DIPEA (3.8 mL, 21.8 mmol). Reaction mixture was stirred at RT for 5 h. The reaction mixture was diluted with water and the product was extracted with CH$_2$Cl$_2$ (2×50 mL). The organic layer was separated and evaporated to get the crude. The crude mass was purified by silica gel (60-120 mesh) column chromatography by eluting with EtOAc in pet-ether to obtain pure compounds 21 and 22. $^1$H NMR (21, 400 MHz, DMSO-d$_6$): δ ppm 4.90-4.80 (m, 1H), 4.46 (t, J=5.2 Hz, 2H), 4.00 (d, J=6.4 Hz, 2H), 3.50-3.30 (m, 4H), 2.30-2.20 (m, 4H), 1.90-1.80 (m, 1H), 1.60-1.40 (m, 8H), 1.40-1.20 (m, 29H), 0.85 (t, J=6.4 Hz, 6H). $^1$H NMR of 22 (400 MHz, CDCl$_3$): δ ppm 4.90-4.80 (m, 2H), 4.20-4.10 (m, 4H), 3.70-3.60 (m, 2H), 2.50-2.20 (m, 10H), 1.80-1.20 (m, 70H), 1.10-1.00 (m, 2H), 1.00-0.90 (m, 12H).

Compound 21A. To a solution of compound 21 (1.0 g, 1.99 mmol) in CH$_2$Cl$_2$ (10 mL) were added compound 23 (517.4 mg, 1.19 mmol) followed by TEA (2.8 mL, 19.98 mmol) and DMAP (244 mg, 1.98 mmol) and the reaction mixture was stirred at RT for 18 h. After completion, the reaction mixture was diluted with water (20 mL) and the product was extracted with CH$_2$Cl$_2$ (2×50 mL), washed with brine (20 mL) and dried over Na$_2$SO$_4$. The crude product was purified on silica column by eluting with 50% EtOAc in pet-ether to obtain 21A (220 mg, 14%) as a gummy liquid.

To a solution of compound 7 (99.15 mg, 0.756 mmol) in CH$_2$Cl$_2$ (3 mL) were added 4-nitrophenyl chloroformate (229 mg, 1.13 mmol) followed by pyridine (0.1 mL, 1.13 mmol) and DMAP (7 mg, 0.05 mmol) and the reaction was stirred for 4 h. 21A was added (150 mg, 0.18 mmol) and the reaction mixture was allowed to stir at 45° C. for 18 h. Reaction mixture was diluted with water (10 mL); the product was extracted with CH$_2$Cl$_2$ (2×50 mL); the organic layer was separated and evaporated to get the crude mass. The crude mass was purified by silica gel column eluting with 50% EtOAc in pet-ether to get VL406 (122 mg, 68%) as a gummy liquid. $^1$H NMR (400 MHz, CDCl$_3$): δ ppm 5.45-5.30 (m, 4H), 4.90-4.80 (m, 1H), 4.25-4.10 (m, 10H), 2.77 (t, J=6.4 Hz, 2H), 2.60-2.40 (m, 6H), 2.35-2.25 (m, 4H), 2.10-2.00 (m, 4H), 1.90-1.80 (m, 2H), 1.70-1.40 (m, 8H), 1.40-1.20 (m, 47H), 1.01 (t, J=7.2 Hz, 6H), 0.95-0.80 (m, 9H). m/z: [M+H]$^+$ Calcd for 950.7, found 950.6.

To a solution of compound 7 (1.7 g, 13.2 mmol) in CH$_2$Cl$_2$ (20 mL) were added 4-nitrophenyl chloroformate (898 mg, 4.46 mmol) followed by pyridine (0.4 mL, 2.23 mmol) and DMAP (54 mg, 0.44 mmol); the reaction was stirred for 30 min. 22 was added and (2.0 g, 2.2 mmol); the reaction mixture was allowed to stir at RT for 16 h. Reaction mixture was diluted with water (10 mL) and extracted with CH$_2$Cl$_2$ (2×50 mL) and then the organic layer was separated and evaporated to a crude mass. The crude mass was purified by silica gel column eluting with 50% EtOAc in pet-ether to get VL422 (770 mg, 33%) as a gummy liquid. $^1$H NMR (400 MHz, CDCl$_3$): δ ppm 4.90-4.80 (m, 2H), 4.20-4.10 (m, 8H), 2.60-2.50 (m, 5H), 2.50-2.40 (m, 1H), 2.35-2.25 (m, 8H), 1.90-1.75 (m, 2H), 1.70-1.55 (m, 8H), 1.55-1.45 (m, 8H), 1.40-1.20 (m, 58H), 1.01 (t, J=7.2 Hz, 6H), 0.87 (t, J=7.2 Hz, 12H). Mass: [M+H]$^+$ calcd. for 1052.8; found 1052.6.

Example 5. Synthesis of VL447, VL448, VL449 and VL451

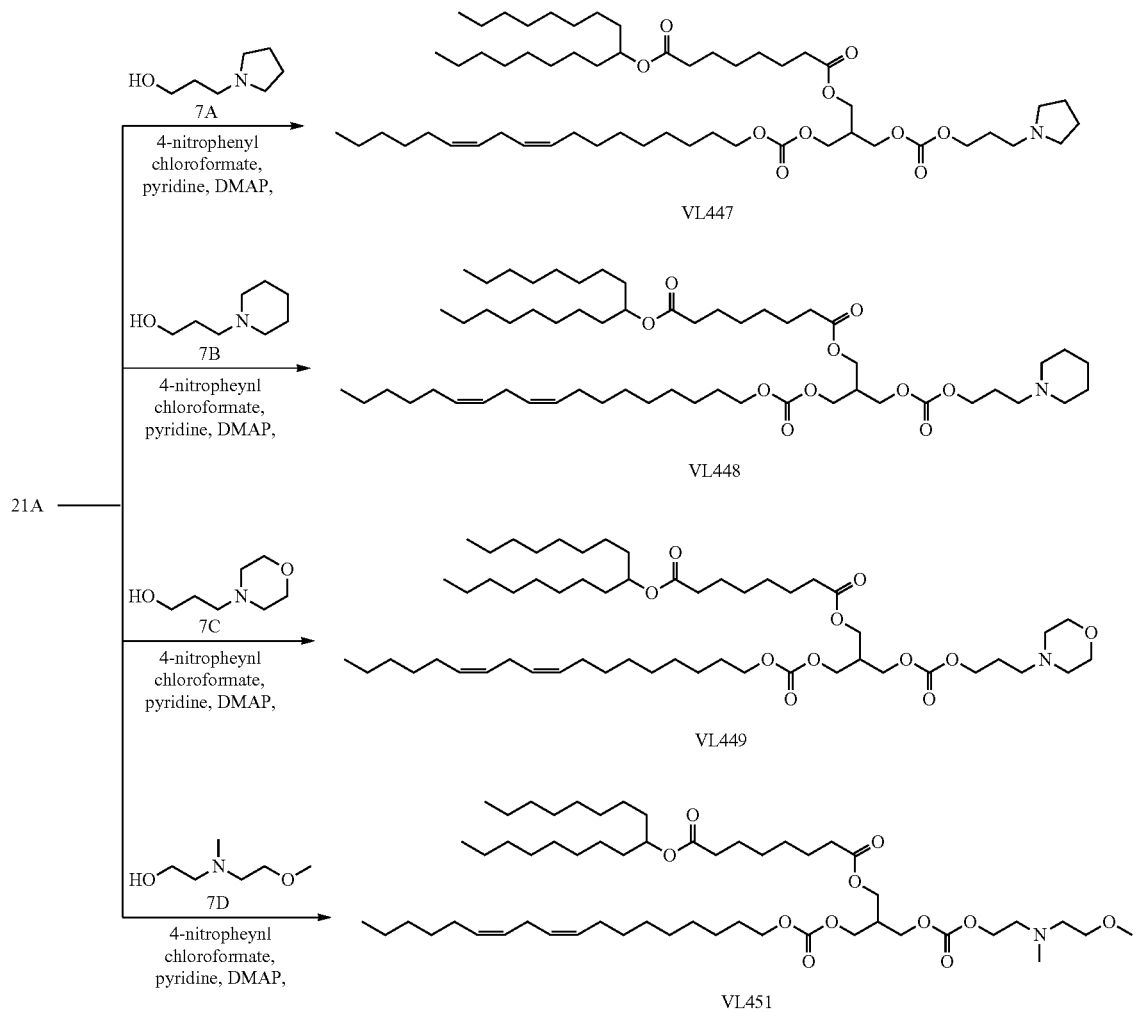

To a solution of compound 7A (195.2 mg, 1.512 mmol) in CH$_2$Cl$_2$ (6 mL) were added 4-nitrophenyl chloroformate (458 mg, 2.268 mmol) followed by pyridine (0.18 mL, 2.268 mmol) and DMAP (14 mg, 0.1134 mmol) and the reaction was stirred for 4 h. Compound 21A (300 mg, 0.378 mmol) followed by TEA (0.51 mg, 3.78 mmol) and DMAP (13.91 mg, 0.1134 mmol); the reaction mixture was allowed to stir at 45° C. for 18 h. Reaction mixture was diluted with water (10 mL) and the product was extracted with CH$_2$Cl$_2$ (2×50 mL); the organic layer was separated and evaporated to a crude mass. The crude mass was purified by silica gel column eluting with 50% EtOAc in pet-ether to obtain VL447 (41 mg, 11%) as a gummy liquid. $^1$H NMR (400 MHz, CDCl$_3$): δ ppm 5.45-5.30 (m, 4H), 4.90-4.80 (m, 1H), 4.30-4.10 (m, 10H), 2.77 (t, J=6.4 Hz, 2H), 2.60-2.40 (m, 7H), 2.40-2.25 (m, 4H), 2.10-2.00 (m, 4H), 1.95-1.85 (m, 2H), 1.80-1.70 (m, 4H), 1.70-1.40 (m, 8H), 1.40-1.20 (m, 46H), 0.95-0.85 (m, 9H). m/z: [M+H]$^+$ Calcd for 948.74; found 948.78.

Compound VL448 was afforded (102 mg, 56%) as a gummy liquid using identical procedure as VL447. $^1$H NMR (400 MHz, DMSO-d$_6$): δ ppm 5.40-5.30 (m, 4H), 4.85-4.75 (m, 1H), 4.20-4.00 (m, 10H), 2.80-2.70 (m, 2H), 2.40-2.20 (m, 11H), 2.10-1.95 (m, 4H), 1.80-1.70 (m, 2H), 1.65-1.40 (m, 14H), 1.40-1.10 (m, 46H), 0.90-0.80 (m, 9H). m/z: [M+H]$^+$ Calcd for 962.76; found 962.9.

Compound VL449 was afforded (110 mg, 60%) as a gummy liquid using identical procedure as VL447. $^1$H NMR (400 MHz, DMSO-d$_6$): δ ppm 5.40-5.30 (m, 4H), 4.85-4.75 (m, 1H), 4.20-4.00 (m, 10H), 3.60-3.50 (m, 4H), 2.80-2.70 (m, 2H), 2.40-2.20 (m, 1H), 2.10-1.95 (m, 4H), 1.80-1.70 (m, 2H), 1.65-1.40 (m, 10H), 1.40-1.10 (m, 44H), 0.90-0.80 (m, 9H). m/z: [M+H]$^+$ Calcd for 964.74; found 962.9.

Compound VL451 was afforded (118 mg, 39%) as a gummy liquid using identical procedure as VL447. $^1$H NMR (400 MHz, DMSO-d$_6$): δ ppm 5.40-5.30 (m, 4H), 4.85-4.75 (m, 1H), 4.20-4.00 (m, 10H), 2.80-2.70 (m, 2H), 2.40-2.20 (m, 11H), 2.10-1.95 (m, 4H), 1.80-1.70 (m, 2H), 1.65-1.40 (m, 14H), 1.40-1.10 (m, 46H), 0.90-0.80 (m, 9H). m/z: [M+H]$^+$ Calcd for 952.74; found 952.6.

Example 6. Synthesis of VL410, VL411, VL421 and VL435

Synthesis of VL410. To a solution of 4E (3 g, 6.97 mmol) in DCM (30 mL) were added 4-nitrophenyl chloroformate (4.17 g, 20.91 mmol), pyridine (1.68 mL, 20.91 mmol) and DMAP (255 mg, 2.09 mmol) and the reaction was stirred for 16 h. The reaction mixture was evaporated completely to get 24 (3.8 g, 92%) as a gummy liquid. $^1$H NMR (400 MHz, CDCl$_3$): δ ppm 8.33 (d, J=7.2 Hz, 2H), 7.50 (d, J=7.2 Hz, 2H), 2.75-2.65 (m, 2H), 2.18 (s, 3H), 2.14 (s, 6H), 1.90-1.80 (m, 2H), 1.50-1.00 (m, 21H), 1.00-0.80 (m, 15H).

To a stirred solution of 5 (500 mg, 1.28 mmol) in CH$_2$Cl$_2$ (10 mL) were added 24 (536 mg, 0.90 mmol) followed by pyridine (0.13 mL, 1.67 mmol) and DMAP (48 mg, 0.3860 mmol) and the reaction was stirred at RT for 16 h. The reaction mixture was diluted with water (20 mL) and extracted with DCM (2×50 mL), washed with brine solution (20 mL) and dried on Na$_2$SO$_4$. The crude was purified on silica column by eluting with 25% EtOAc in pet ether to get 25 (320 mg, 97%) as a gummy liquid. $^1$H NMR (400 MHz, DMSO-d$_6$): δ ppm 4.79 (d, J=5.2 Hz, 1H), 4.40-4.20 (m, 2H), 4.20-3.90 (m, 4H), 3.55-3.45 (m, 2H), 2.60-2.50 (m, 2H), 2.40-2.20 (m, 5H), 2.10-1.90 (m, 8H), 1.90-1.70 (m, 2H), 1.70-1.00 (m, 45H), 1.00-0.89 (t, J=7.2 Hz, 12H).

To a 7 (248 mg, 1.89 mmol) in CH$_2$Cl$_2$ (3 mL) were added 4-nitrophenyl chloroformate (814 mg, 2.83 mmol) followed by pyridine (0.2 mL, 2.83 mmol) and DMAP (17 mg, 0.05 mmol) and the reaction was stirred for 4 h. 25 was added (400 mg, 0.4732 mmol) and the reaction mixture was allowed to stir at 45° C. for 18 h. Reaction mixture was diluted with water (10 mL) and extracted with CH$_2$Cl$_2$ (2×50 mL) and then the organic layer was separated and evaporated to get the crude. Crude material was purified by silica gel column eluting with 50% EtOAc in pet-ether to yield VL-410 (122 mg, 26%) as a gummy liquid. $^1$H NMR (400 MHz, CDCl$_3$): δ ppm 4.33 (d, J=6.0 Hz, 2H), 4.26 (d, J=6.0 Hz, 2H), 4.25-4.15 (m, 4H), 4.05 (t, J=5.6 Hz, 2H), 2.65-2.45 (m, 8H), 2.40-2.25 (m, 4H), 2.08 (s, 3H), 2.05 (s, 3H), 2.02 (s, 3H), 1.80-1.40 (m, 10H), 1.50-1.20 (m, 32H), 1.20-1.00 (m, 12H), 0.90-0.80 (m, 18H). HRMS m/z: [M+H]$^+$ Calcd for 1002.75; found 1002.83.

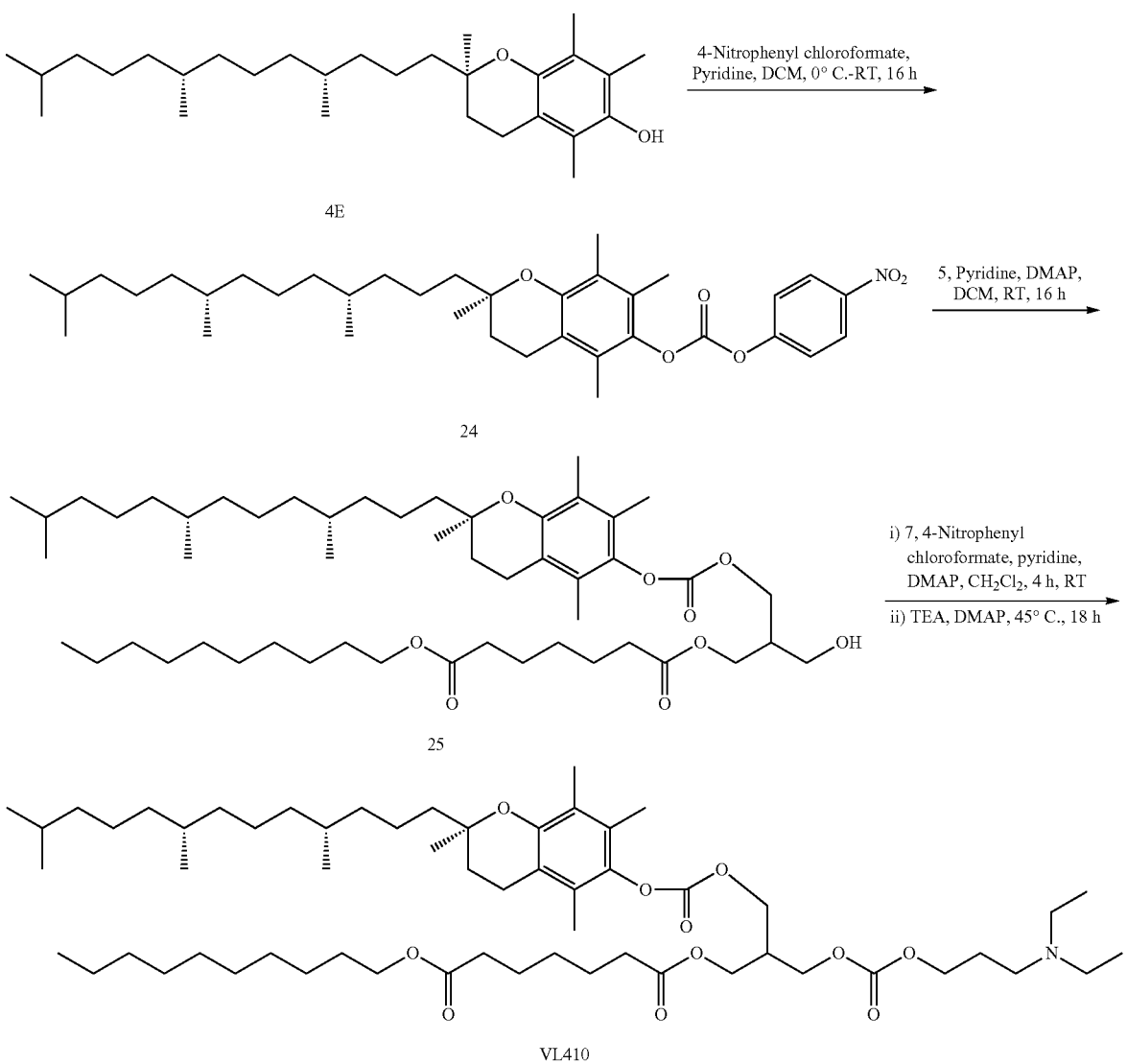

Scheme 6

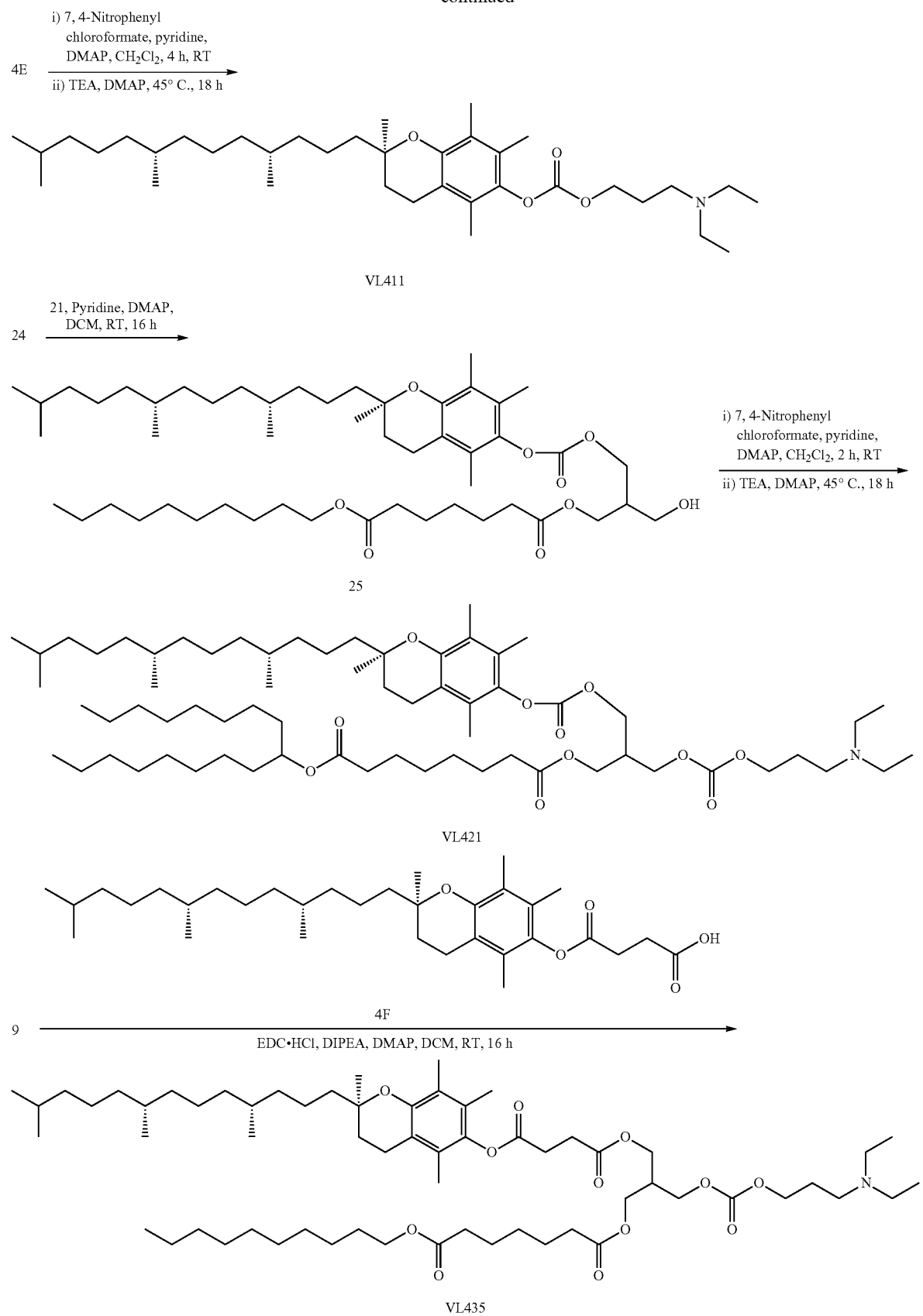

Synthesis of VL411. To a solution of compound 4E (1.3 g, 3.02 mmol) in $CH_2Cl_2$ (15 mL) were added 4-nitrophenyl chloroformate (1.21 g, 6.04 mmol) followed by pyridine (0.5 mL, 6.04 mmol) and DMAP (110 mg, 0.9 mmol) and the reaction was continued stirring for 1 h. After 1 h added compound 7 (2.37 g, 18.1 mmol) and the reaction mixture was allowed to stir at RT for 17 h. Reaction mixture was diluted with water (50 mL); the product was extracted with $CH_2Cl_2$ (2×50 mL) and the organic layer was separated and evaporated to get a crude mass. The crude mass was purified by silica gel column eluting with 50% EtOAc and pet-ether to obtain VL411 (420 mg, 24%) as a gummy liquid. $^1$H NMR (400 MHz, $CDCl_3$): δ ppm 4.30 (t, J=6.4 Hz, 2H), 2.70-2.50 (m, 8H), 2.08 (s, 3H), 2.07 (s, 3H), 2.03 (s, 3H), 1.95-1.70 (m, 4H), 1.62-0.95 (m, 30H), 0.90-0.80 (m, 12H).

Synthesis of VL421. To a stirred solution of compound 21 (1.0 g, 1.83 mmol) in $CH_2Cl_2$ (10 mL) were added compound 24 (1.09 g, 1.83 mmol) followed by pyridine (0.37 mL, 3.54 mmol) and DMAP (67 mg, 0.55 mmol) and the reaction was stirred at RT for 1 h. Reaction mixture was diluted with water (20 mL) and extracted with DCM (2×50 mL), washed with brine solution (20 mL) and dried on $Na_2SO_4$. The crude was purified on silica column by eluting with 30% EtOAc in pet-ether to get 25 (480 mg, 30%) as a gummy liquid.

To a solution of compound 7 (219 mg, 0.1.6u7 mmol) in $CH_2Cl_2$ (4 mL) were added 4-nitrophenyl chloroformate (506 mg, 2.50 mmol) followed by pyridine (0.26 mL, 2.50 mmol) and DMAP (16 mg, 0.12 mmol) and the reaction was stirred for 4 h. After 4 h added compound 25 (400 mg, 0.41 mmol) and the reaction mixture was allowed to stir at 45° C. for 16 h. Reaction mixture was diluted with water (10 mL); product was extracted with $CH_2Cl_2$ (2×50 mL) and then the organic layer was separated and evaporated to get a crude mass. The crude mass was purified by silica gel column eluting with 55% EtOAc in pet-ether to yield VL-421 (110 mg, 24%) as a gummy liquid. $^1$H NMR (400 MHz, $CDCl_3$): δ ppm 4.40-4.20 (m, 8H), 2.65-2.40 (m, 9H), 2.40-2.25 (m, 4H), 2.08 (s, 3H), 2.06 (s, 3H), 2.02 (s, 3H), 1.40-1.20 (m, 4H), 1.70-1.50 (m, 10H), 1.50-1.00 (m, 56H), 0.90-0.80 (m, 18H). Mass m/z: $[M+H]^+$ Calcd for 1114.88; found 1114.93.

Synthesis of VL435. To a solution of compound 9 (220 mg, 0.403 mmol) in $CH_2Cl_2$ (2 mL) was added compound 4F (214 mg, 0.403 mmol) followed by EDC·HCl (115 mg, 0.604 mmol), DMAP (14 mg, 0.12 mmol) and DIPEA (0.2 mL, 1.21 mmol). Reaction mixture was stirred at RT for 16 h. After complete disappearance of compound 9 by TLC, the reaction mixture was diluted with water and the product was extracted into $CH_2Cl_2$ (2×20 mL). The organic layer was separated and evaporated to get a crude mass. The crude mass was purified by silica gel (60-120 mesh) column chromatography by eluting with 50% EtOAc in pet-ether followed by prep HPLC purification afforded VL435 as a formate salt. Obtained product was washed with 10% $NaHCO_3$ solution and then lyophilized to yield pure VL435 (60 mg, 14%). $^1$H NMR (400 MHz, DMSO-$d_6$): δ ppm 4.20-4.12 (m, 8H), 4.00-3.90 (m, 2H), 2.95-2.85 (m, 2H), 2.70-2.60 (m, 2H), 2.45-2.20 (m, 8H), 2.00 (s, 3H), 1.90 (s, 3H), 1.88 (s, 3H), 1.80-1.60 (m, 5H), 1.60-1.00 (m, 50H), 1.00-0.80 (m, 21H). Mass m/z: $[M+H]^+$ Calcd for 1058.78: found 1058.6.

Example 7. PEG-Lipid Synthesis

Scheme 7A
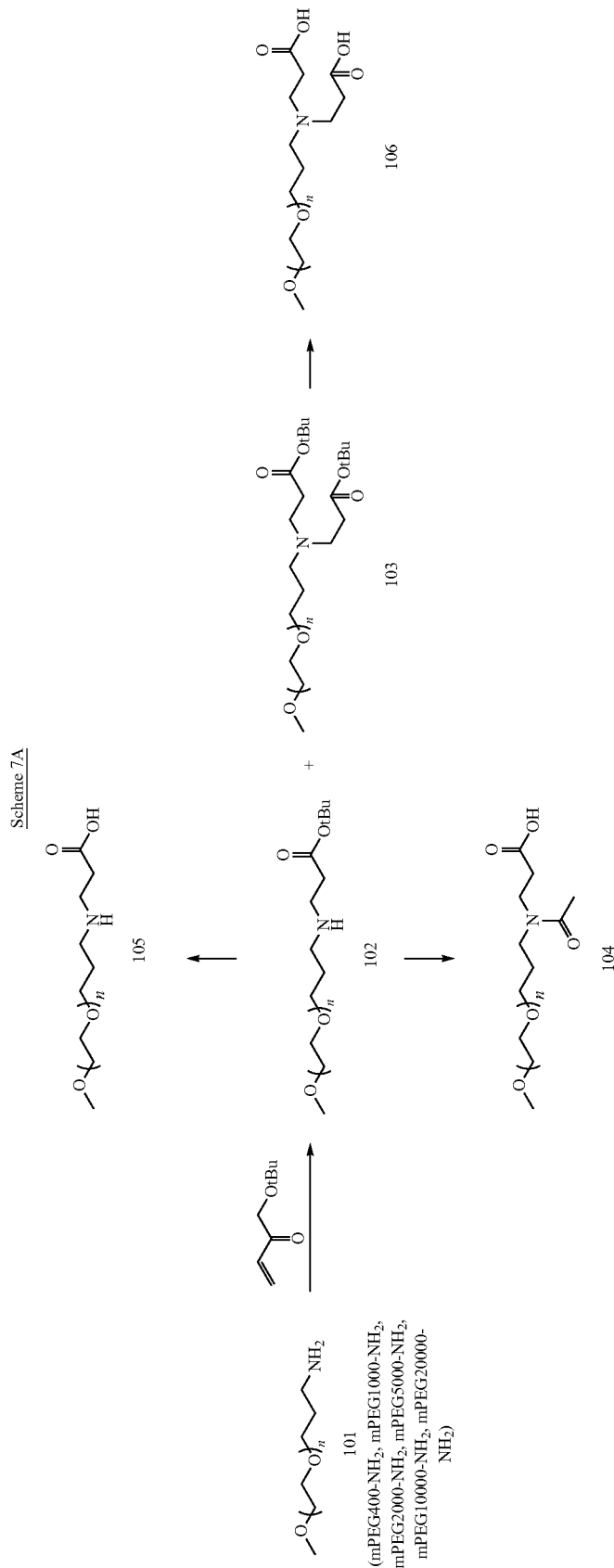

Compound 102 is prepared from desired mPEG-amine 101 by Michael addition of the PEG-amine to tert-butyl acrylate. The mono adduct 102 and diadduct 103 are separated by column chromatography. Acid treatment of 102 affords the acid 105. Acetylation of 102 with acetic anhydride followed by acid treatment affords the carboxylic acid 104. Treatment of 103 with acid affords the dicarboxylic acid 106.

Scheme 7B

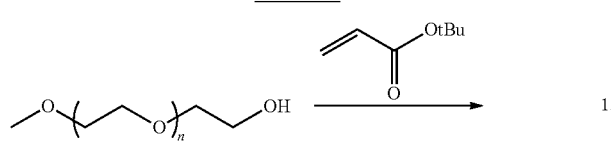

107
(mPEG400-OH, mPEG1000-OH, mPEG2000-OH, mPEG5000-OH, mPEG10000-OH, mPEG20000-OH)

-continued

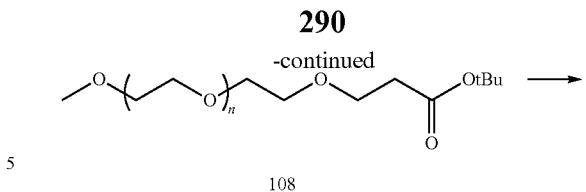

108

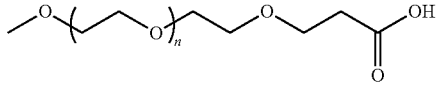

109

Compound 108 is prepared from desired mPEG-OH 107 by Michael addition of the mPEG-OH to tert-butyl acrylate. Treatment of compound 108 with acid affords the carboxylic acid 109.

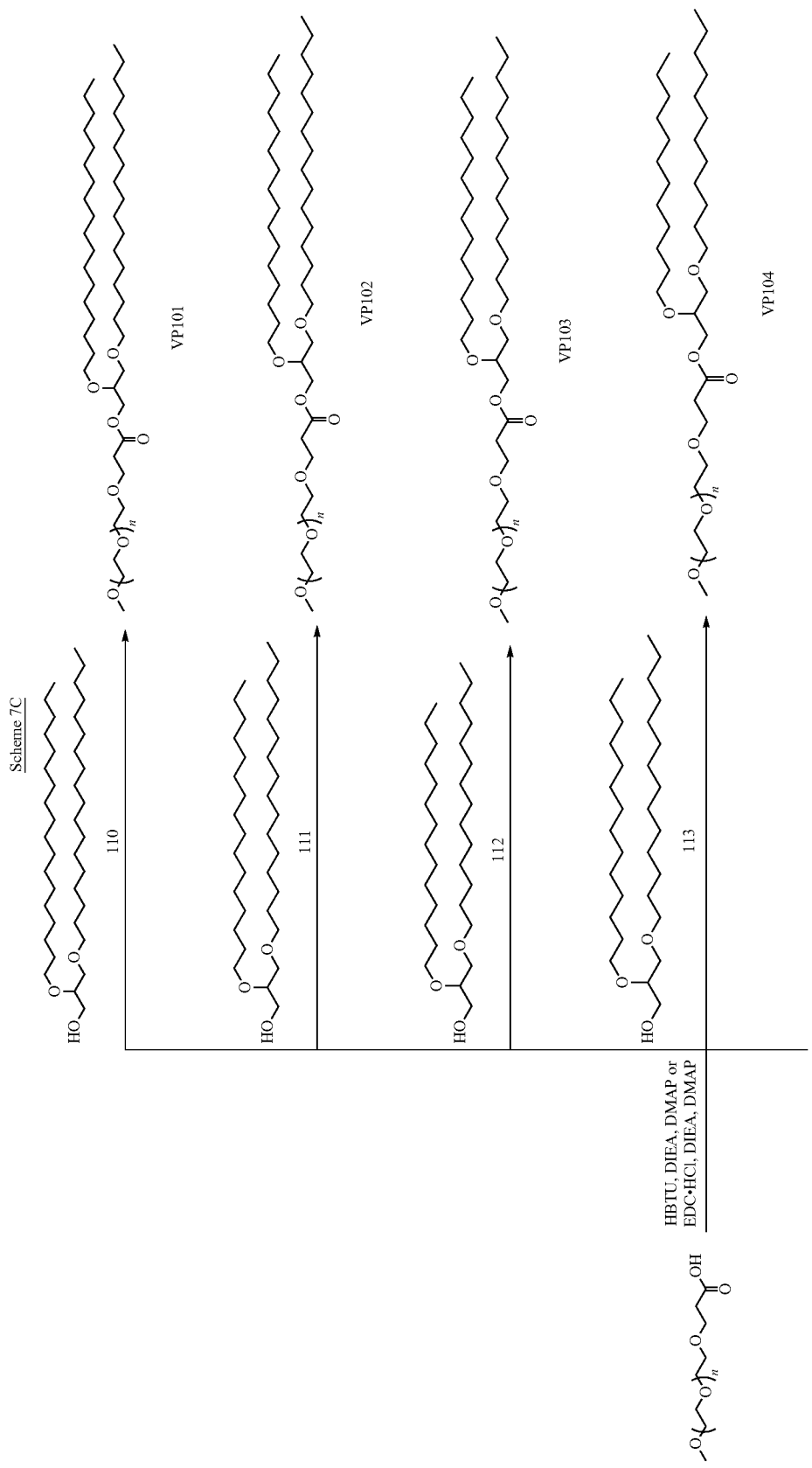

-continued
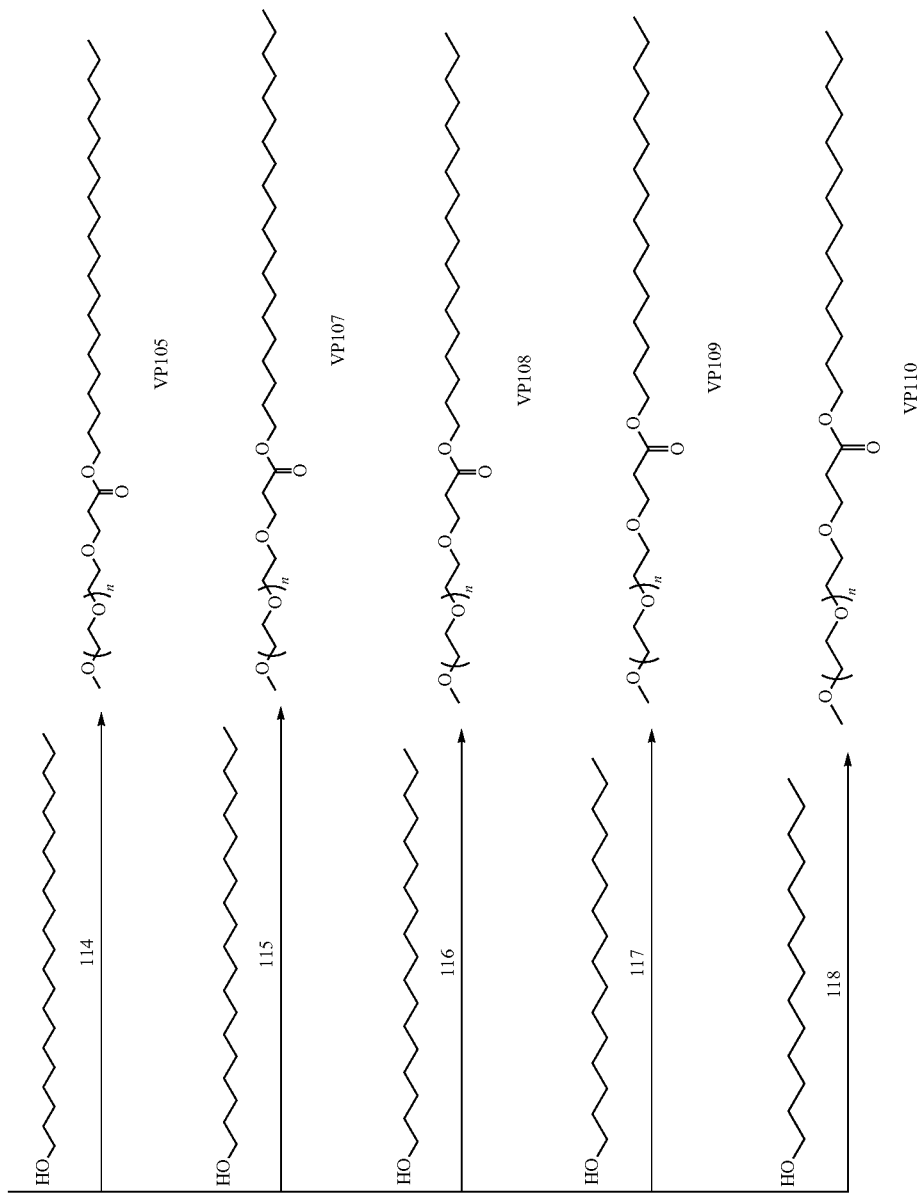

Activation of the carboxylic acid 109 using peptide coupling agent HBTU in the presence of DIEAN and DAMP followed by addition of the alcohol 110 affords the PEG-lipid VP101. Similarly, addition of the alcohols 111-118 to the activated carboxylic acid afford PEG-lipids VP101-VP110.

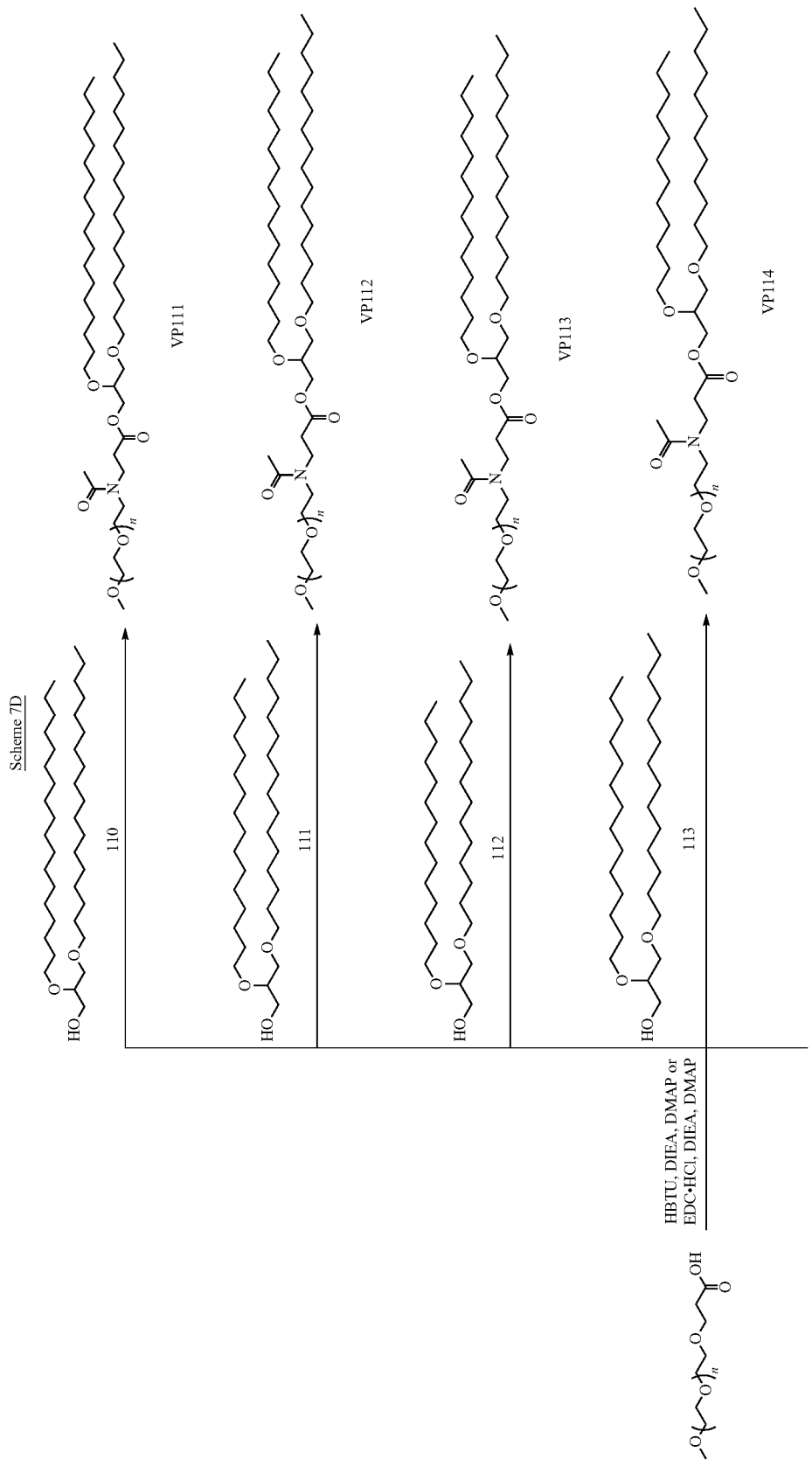

-continued
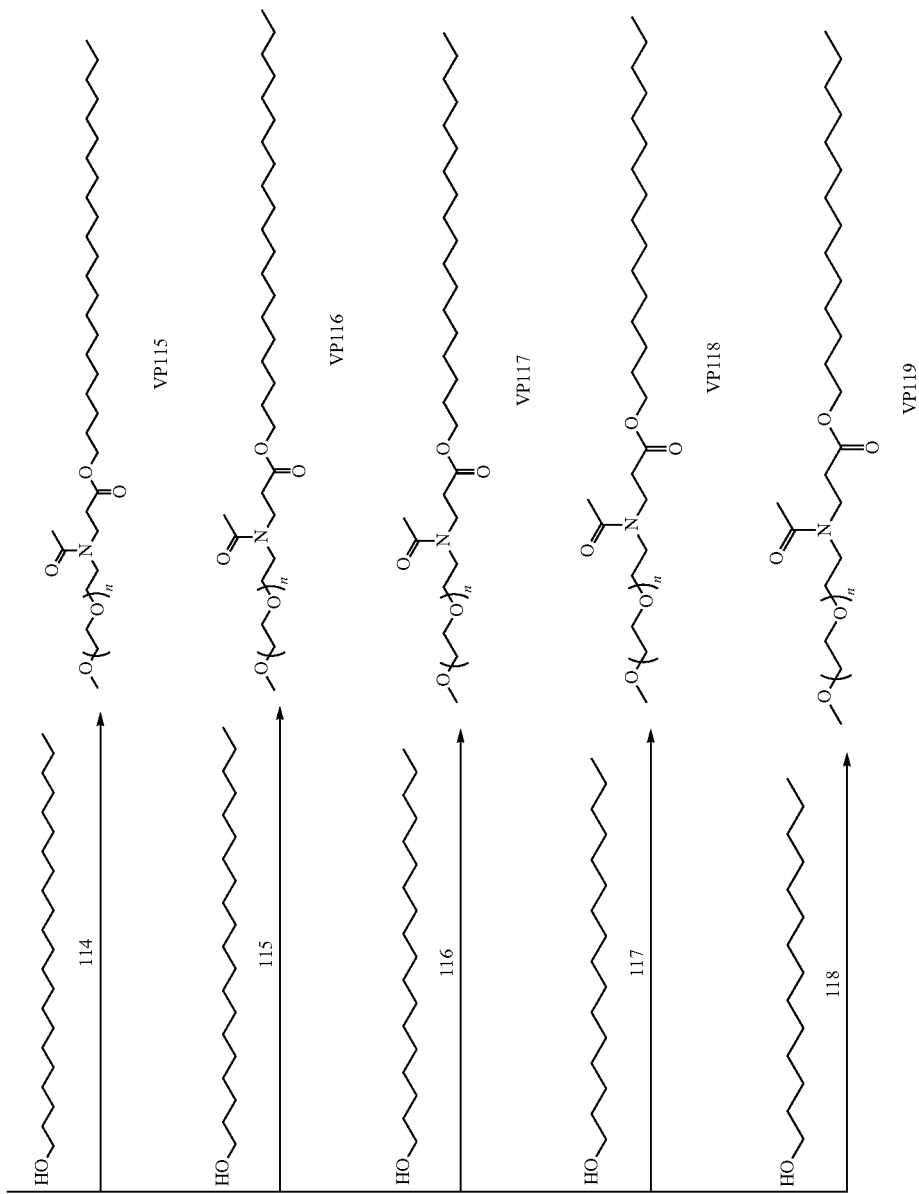

Activation of the carboxylic acid 104 using peptide coupling agent HBTU in the presence of DIEAN and DAMP followed by addition of the alcohol 110 affords the PEG-lipid VP111. Similarly, addition of the alcohols 111-118 to the activated carboxylic acid afford PEG-lipids VP112-VP119.

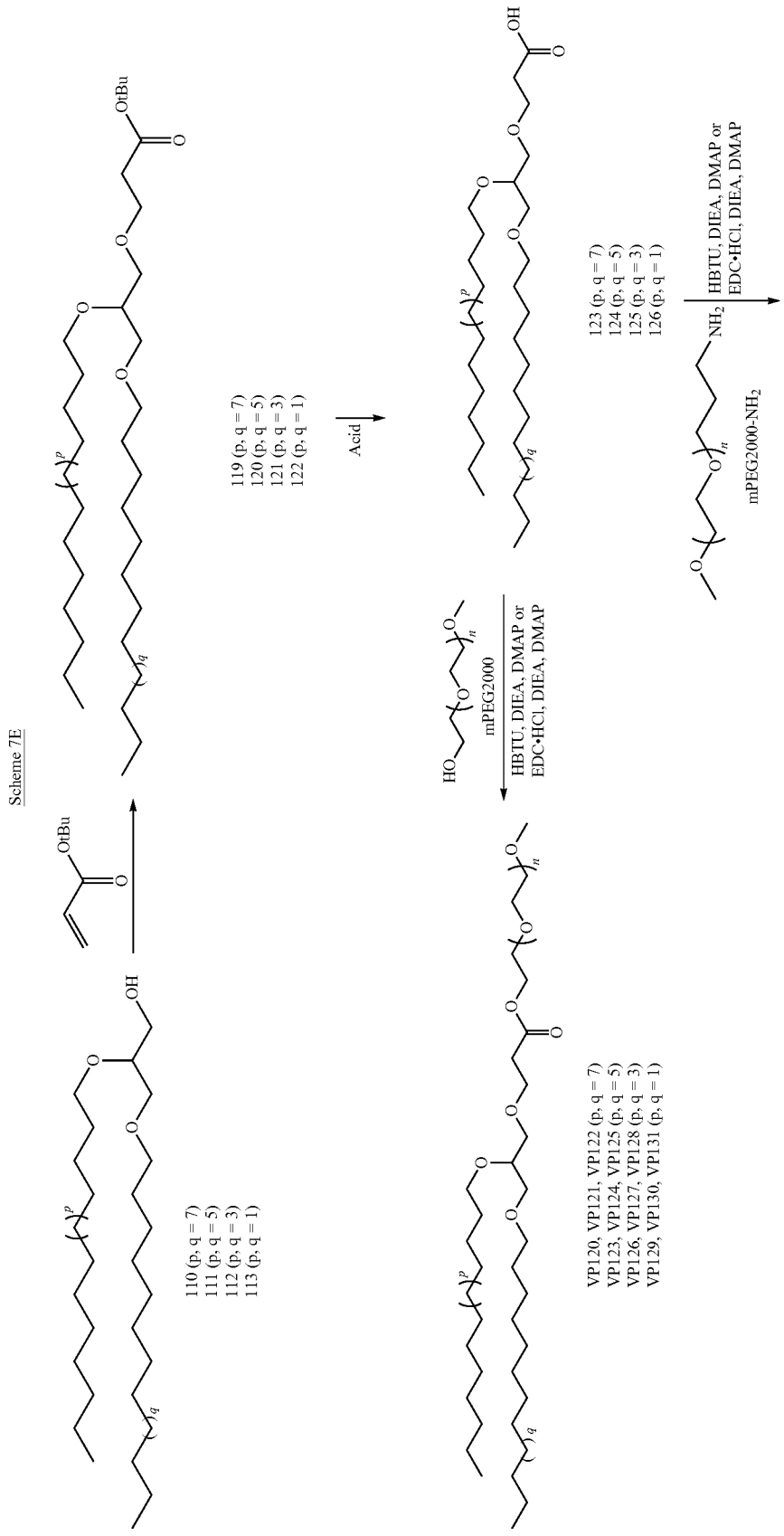

-continued
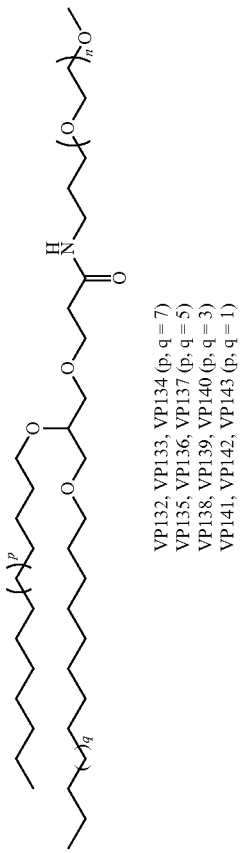
VP132, VP133, VP134 (p, q = 7)
VP135, VP136, VP137 (p, q = 5)
VP138, VP139, VP140 (p, q = 3)
VP141, VP142, VP143 (p, q = 1)

Michael addition of the alcohol 110 to tert-butyl acrylate affords the ester 119. Treatment of the ester 119 with acid affords 123. Activation of the carboxylic acid 123 with peptide coupling agent followed by addition of mPEG2000 affords VP120, the racemic compounds. Similarly, starting with chirally pure 110 affords the enantiomers VP121 and VP122. The PEG-lipids VP123-VP131 are similarly prepared starting from corresponding racemic or chirally pure alcohols 111-113. Activation of the carboxylic acid 123 with peptide coupling agent followed by addition of mPEG2000-$NH_2$ affords VP132, the racemic compounds. Similarly, starting with chirally pure 110 affords the enantiomers VP133 and VP134. The PEG-lipids VP135-VP143 are similarly prepared starting from corresponding racemic or chirally pure alcohols 111-113.

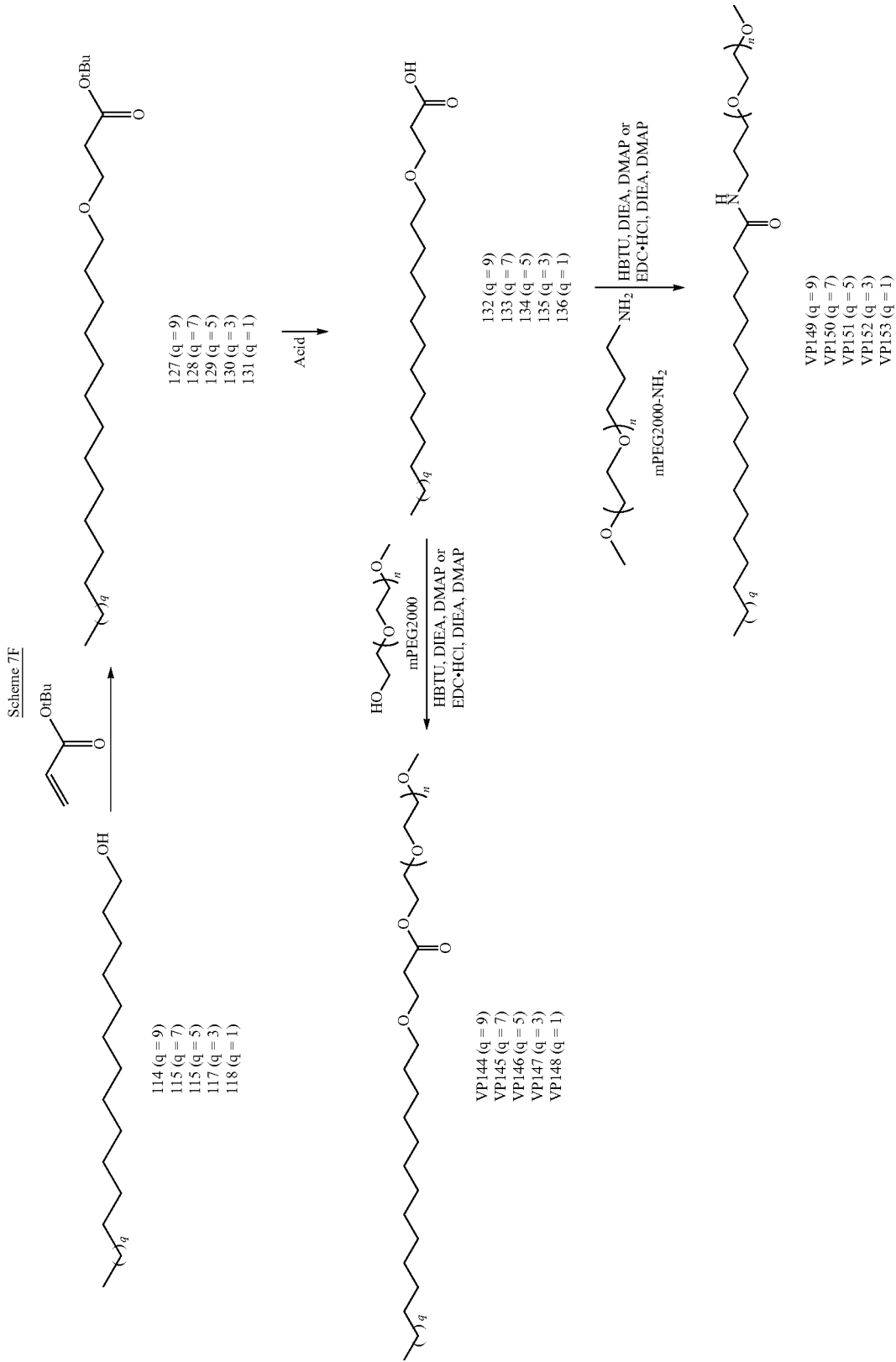

Michael addition of the alcohol 114 to tert-butyl acrylate affords the ester 127. Treatment of the ester 127 with acid affords the carboxylic acid 132. Activation of the carboxylic acid 132 with peptide coupling agent followed by addition of mPEG2000 affords VP144. The PEG-lipids VP145-VP148 are similarly prepared starting from corresponding alcohols 115-118.

Activation of the carboxylic acid 132 with peptide coupling agent followed by addition of mPEG2000-NH$_2$ affords VP149. The PEG-lipids VP150-VP153 are similarly prepared starting from corresponding racemic or chirally pure alcohols 115-118.

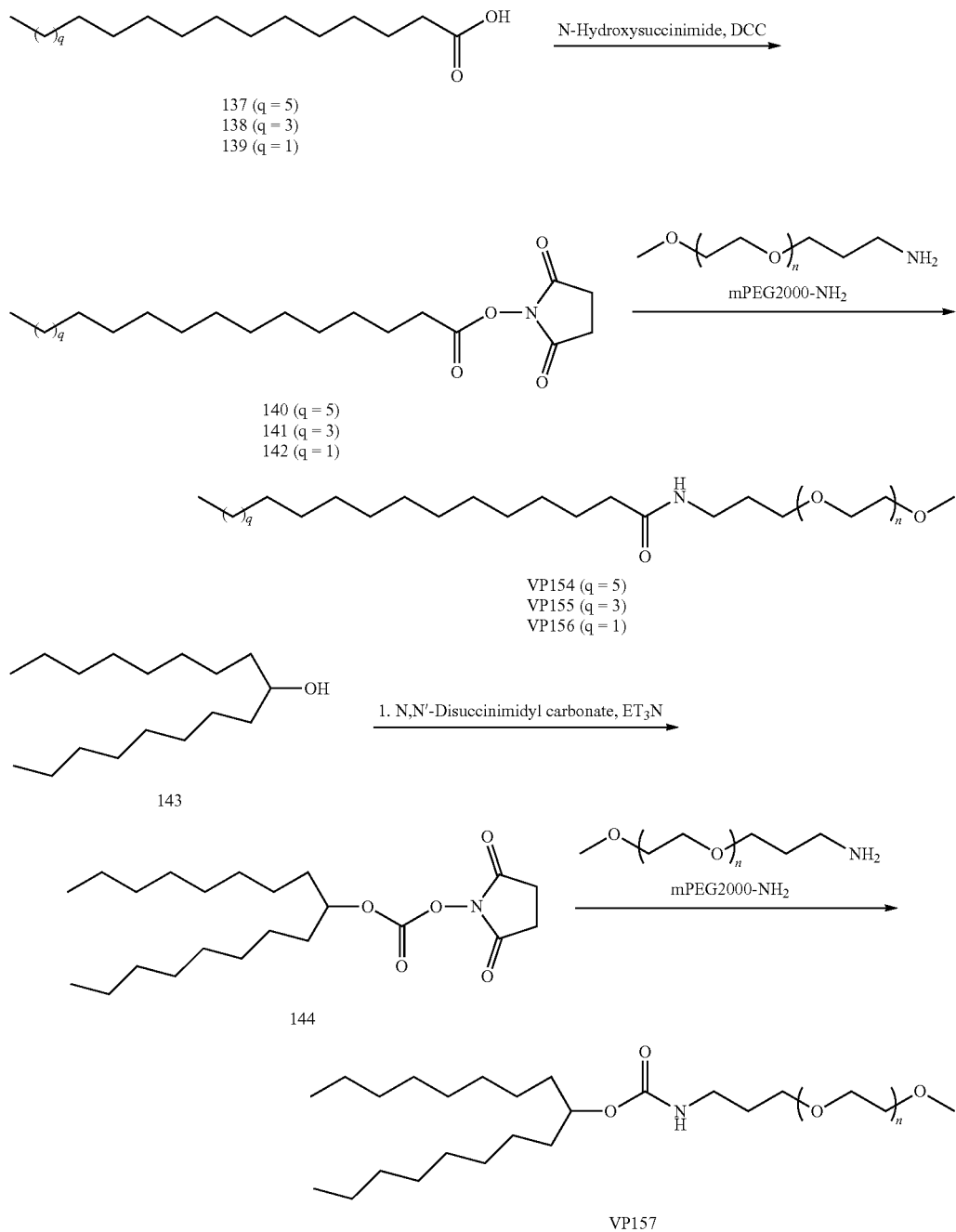

To a stirred solution of the acid 137 (1 g, 3.52 mmol) in THF (10 mL) were added N-hydroxysuccinimide (567 mg, 4.92 mmol) followed by DCC (870 mg, 4.22 mmol) at 0° C. and the reaction mixture was stirred at room temperature for overnight. After completion, solid is filtered and the filtrate was evaporated under reduced pressure to get the crude material. This was recrystallized in isopropyl alcohol, filtered the solid and dried to obtain compound 140 (1 g, 74% yield) as an off white solid. $^1$H NMR (400 MHz, CDCl$_3$): δ 2.83 (s, 4H), 2.61 (t, J=7.2 Hz, 2H), 1.76-1.72 (m, 2H), 1.40-1.38 (m, 2H), 1.29-1.25 (m, 26H), 0.89 (t, J=6.4 Hz, 3H).

To a solution of compound 140 (113 mg, 0.296 mmol) in CH$_2$Cl$_2$ (5 mL) were added mPEG2000-NH$_2$ (500 mg, 0.24 mmol) followed by DIPEA (0.1 mL, 0.73 mmol) at 0° C. and the reaction mixture was stirred at room temperature overnight. The reaction mixture after diluting with dichloromethane (10 mL) was stirred with ice cold water for 15 min. The organic layer was separated, washed with ice cold water, dried over anhydrous Na$_2$SO$_4$ and concentrated under reduced pressure to get the crude product. Silica gel column chromatographic purification (10% MeOH in DCM as an eluent) afforded compound VP154 (160 mg) as an off white solid. $^1$H NMR (400 MHz, DMSO-d$_6$): δ 7.70 (t, 1H), 3.68-3.31 (m, 195H), 3.23 (s, 3H), 3.06 (t, J=6.0 Hz, 2H), 2.03 (t, J=7.6 Hz, 2H), 1.61-1.44 (m, 4H), 1.27-1.23 (m, 28H), 0.87 (t, J=6.8 Hz, 3H). HRMS m/z: [M+H]$^+$ calculated: 2293.3; found: 2294.26.

To a stirred solution of compound 138 (1 g, 3.90 mmol) in THF (10 mL) were added N-hydroxysuccinimide (628 mg, 5.4 mmol) followed by DCC (964 mg, 4.68 mmol) at 0° C. and the reaction mixture was stirred at RT for overnight. Reaction mixture was filtered and the filtrate was evaporated under reduced pressure to get the crude material. This was recrystallized in isopropyl alcohol, filtered the solid and dried to get 141 (1 g, 72% yield) as a white solid. $^1$H NMR (400 MHz, CDCl$_3$): δ 2.83 (s, 4H), 2.61 (t, J=7.6 Hz, 2H), 1.76-1.70 (m, 2H), 1.42-1.25 (m, 24H), 0.89 (t, J=6.8 Hz, 3H).

To a solution of compound 141 (113 mg, 0.29 mmol) in CH$_2$Cl$_2$ (5 mL) were added mPEG2000-NH$_2$ (500 mg, 0.24 mmol) followed by DIPEA (0.1 mL, 0.73 mmol) at 0° C. and the reaction mixture was stirred at room temperature overnight. The progress of the reaction was monitored by TLC. After completion of the reaction, the mixture was diluted with CH$_2$Cl$_2$ (10 mL) and stirred with ice cold water for 15 min. The organic layer was separated, washed with ice cold water, dried over anhydrous Na$_2$SO$_4$ and concentrated under reduced pressure to get the crude product. Silica gel column chromatographic purification using 10% MeOH in CH$_2$Cl$_2$ as an eluent afforded VP155 as an off white solid (0.44 g, 78.5%). $^1$H NMR (400 MHz, DMSO-d$_6$): δ 7.70 (t, 1H), 3.50-3.36 (m, 185H), 3.23 (s, 3H), 3.06 (t, J=6.8 Hz, 1H), 2.03-1.99 (m, 2H), 1.61-1.46 (m, 4H), 1.27-1.23 (m, 24H), 0.87 (t, J=6.8 Hz, 3H). HRMS m/z: [M+H]$^+$ calculated: 2266.8; found: 2266.89.

To a stirred solution of compound 139 (1.6 g, 7.0 mmol) in THF (16 mL) were added N-hydroxysuccinimide (1.12 g, 9.80 mmol) followed by DCC (1.7 g, 8.40 mmol) at 0° C. and the reaction mixture was stirred at RT for overnight. Reaction mixture filtered and the filtrate was evaporated under reduced pressure to get the crude material. The crude was taken in isopropyl alcohol (10 mL) and heated at 80° C. for 45 min and then cooled to 0° C. and the precipitated solid was filtered and dried to get compound 142 (1.6 g, 74% yield) as a white solid. $^1$H NMR (400 MHz, CDCl$_3$): δ 2.83 (s, 4H), 2.61 (t, J=7.2 Hz, 2H), 1.76-1.72 (m, 2H), 1.40-1.25 (m, 20H), 0.89 (t, J=6.4 Hz, 3H).

To a solution of compound 142 (96 mg, 0.296 mmol) in dichloromethane (5 mL) were added mPEG2000-NH$_2$ (500 mg, 0.24 mmol) followed by DIPEA (0.1 mL, 0.73 mmol) at 0° C. and the reaction mixture was stirred at room temperature overnight. The reaction mixture was diluted with dichloromethane (10 mL) and stirred with ice cold water for 15 min. The organic layer was separated, washed with ice cold water, dried over anhydrous Na$_2$SO$_4$ and concentrated under reduced pressure to get the crude product. Silica gel column chromatographic purification using 10% MeOH in DCM as an eluent afforded compound VP156 as an off white solid (0.18 g, 21%). $^1$H NMR (400 MHz, DMSO-d$_6$): δ 7.70 (t, 1H), 3.68-3.34 (m, 189H), 3.23 (s, 3H), 3.06 (q, 2H), 2.03 (t, J=7.2 Hz, 2H), 1.61-1.59 (m, 2H), 1.47-1.46 (m, 2H), 1.46-1.23 (m, 20H), 0.87 (t, J=6.4 Hz, 3H). HRMS m/z: [M+H]$^+$ ca calculated. 2238.9, found: 2238.89.

To a stirred solution of compound 143 (1.0 g, 3.89 mmol) in CH$_2$Cl$_2$ (10 mL) at 0° C. were added N,N'-disuccinimidylcarbonate (1.5 g, 5.84 mmol) followed by triethylamine (1.6 mL, 11.69 mmol) and the reaction mixture was stirred at RT for overnight. To the above reaction mixture, N,N'-disuccinimidylcarbonate (1.5 g, 5.84 mmol) followed by triethylamine (1.6 mL, 11.69 mmol) were added additionally at RT and heated to 40° C. for 3 days. The reaction mixture was diluted with ice-cold water (20 mL) and separated the organic layer. The organic layer was washed with brine (10 mL), dried over anhydrous Na$_2$SO$_4$ and concentrated under reduced pressure. The crude product was purified by flash column chromatography (100-200 mesh Silica gel; eluted with 20% diethyl ether in pet-ether) to afford compound 144 (0.75 g, 1.88 mmol, 48% yield) as a pale-yellow gum. $^1$H NMR (400 MHz, CDCl$_3$): δ 4.82-4.78 (m, 1H), 2.82 (s, 4H), 1.71-1.57 (m, 4H), 1.43-1.22 (m, 24H), 0.91-0.87 (m, 6H).

To a stirred solution of compound mPEG200-NH$_2$ (950 mg, 0.46 mmol) in 10 mL of CH$_2$C$_{12}$ at 0° C. were added pyridine (0.1 mL, 1.40 mmol) followed by compound 144 (279 mg, 0.70 mmol) and stirred at RT for 16 h. The reaction was concentrated completely under reduced pressure mixture. The residue was diluted with CH$_2$Cl$_2$ (10 mL) and stirred with ice cold water for 20 min. The organic layer was separated, washed with ice cold water (10 mL), dried over anhydrous Na$_2$SO$_4$ and concentrated under reduced pressure to get the crude. This was purified by silica gel column using 10% MeOH in CH$_2$Cl$_2$ as an eluent to yield VP157 as an off white solid (0.76 g, 76%). $^1$H NMR (400 MHz, DMSO-d$_6$): δ 6.92 (br t, J=5.6 Hz, 1H), 4.61-4.57 (m, 1H), 3.69-3.67 (m, 1H), 3.59-3.49 (m, 188H), 3.48-3.41 (m, 3H), 3.38-3.333 (m, 2H), 3.24 (s, 3H), 3.02-2.97 (m, 2H), 1.62-1.58 (m, 2H), 1.48-1.39 (m, 4H), 1.31-1.30 (m, 24H), 0.86-0.83 (m, 6H). HRMS m/z: [M+H]$^+$ calculated: 2222.1; found: 2222.4.

Example 8. Guide RNA (gRNA) and mRNA for LNP Evaluation

The guide RNAs (gRNA) shown in Table 3 were synthesized under solid phase oligonucleotide synthesis and deprotection conditions using controlled pore glass support and commercially available phosphoramidite monomers and oligonucleotide synthesis reagents (Methods in Molecular Biology, 1993, 20, 81-114; ACS Chem. Biol. 2015, 10, 1181-1187, incorporated herein by reference in its entirety). The deprotected guide RNAs were purified by HPLC and the integrity of each guide RNA was confirmed by mass spectrometric analysis. The observed mass of each guide RNA was conformed to calculated mass.

TABLE 3

Single guide RNA (gRNA) used in the studies described in Examples 9-23

| Target* | gRNA | SEQ ID NO: | Protospacer (5'-3') | SEQ ID NO: | gRNA sequence (5'-3')# |
|---|---|---|---|---|---|
| PCSK9 | GA055 | 1 | CAGGTTCCATGGGATGCTCT | 7 | csasgsGUUCCAUGGGAUGCUCUgUUUUAGa gcuagaaauagcaaGUUaAaAuAaggcuaGUccGUU |
| PCSK9 | GA010 | 2 | GGCTGATGAGGCCGCACATG | 8 | gsgscsUGAUGAGGCCGCACAUGGUUUUAG AgcuagaaauageAAGUUAAAAUAAGGCUAG UCCGUUAUCAacuugaaaaaguggcaccgagucggug cusususu |
| PCSK9 | GA255 | 3 | CCCATACCTTGGAGCAACGG | 9 | cscscsAUACCUUGGAGCAACGGgUUUUAGa gcuaGaaauagcaaGUUaAaAuAaggCUaGUCcGU UAucAAcuuGaaaaaguGgcaccgAgUCggugcusus usu |
| PCSK9 | GA256 | 3 | CCCATACCTTGGAGCAACGG | 10 | cscscsAUACCUUGGAGCAACGGgUUUUAGa gcuagaaauagcaaGUUaAaAuAaggcuaGUccGUU AucAAcuugaaaaagugGcaccgaguegggugcusususu |
| PCSK9 | GA257 | 3 | CCCATACCTTGGAGCAACGG | 11 | cscscsAUACCUUGGAGCAACGGgUUUUAGa gcuaGaaauagcaaGUUaAaAuAaggcuaGUccGUU AucAAcuugaaaaagugGcaccgagucggugcusususu |
| PCSK9 | GA292 | 3 | CCCATACCTTGGAGCAACGG | 12 | cscscsAUACUUGGAGCAACGGGUUUUAGA GCUAGAAAUAGCAAGUUAAAAUAAGGC UAGUCCGUUAUCAACUUGAAAAAGUGGC ACCGAGUCGGUGCUsususu |
| PCSK9 | GA097 | 4 | CCCGCACCTTGGCGCAGCGG | 13 | cscscsGCACCUUGGCGCAGCGGgUUUUAGa gcuagaaauagcaaGUUaAaAuAaggcuaGUccGUU AucAAcuugaaaaagugGcaccgagucggugcusususu |
| ANGPTL3 | GA258 | | GAGATACCTGAGTAACTTTC | 14 | gsasgsAUACCUGAGUAACUUUCgUUUUAGa gcuaGaaauagcaaGUUaAaAuAaggCUaGUCcGU UAucAAcuuGaaaaaguGgcaccgAgUCggugcusus usu |
| ANGPTL3 | GA259 | 5 | GAGATACCTGAGTAACTTTC | 15 | gsasgsAUACCUGAGUAACUUUCgUUUUAGa gcuagaaauagcaaGUUaAaAuAaggcuaGUccGUU AucAAcuugaaaaagugGcaccgagucggugcusususu |
| ANGPTL3 | GA260 | 5 | GAGATACCTGAGTAACTTTC | 16 | gsasgsAUACCUGAGUAACUUUCgUUUUAGa gcuaGaaauagcaaGUUaAaAuAaggcuaGUccGUU AucAAcuugaaaaagugGcaccgagucggugcusususu |
| ANGPTL3 | GA067 | 6 | AAGATACCTGAATAACTCTC | 17 | asasgsAUACCUGAAUAACUCUCGUUUUAG AgcuagaaauagcAAGUUAAAAUAAGGCUAG UCCGUUAUCAacuugaaaaaguggcaccgagucggug cusususu |
| ANGPTL3 | GA347 | 6 | AAGATACCTGAATAACTCTC | 18 | asasgsAUACCUGAAUAACUCUCgUUUUAGa guaGaaauagcaaGUUaAaAuAaggcuaGUccGUU AucAAcuuGaaaaagug Gcacegagueggugcusususu |

*The gRNAs were designed to target mouse, rat, monkey and human PCSK9 and ANGPTL3 genes.
uppercase and lowercase letters in the guide RNA sequence indicate nucleotides carrying 2'-ribo (2'-OH) and 2'-O-methyl (2'-OMe) ribosugar moiety, respectively, and the letter 's' indicates phosphorothioate (PS) linkage.

The term "protospacer," or "target sequence" and their grammatical equivalents as used herein can refer to a DNA sequence of a target gene. In the native state, a protospacer is adjacent to a PAM (protospacer adjacent motif). The term "spacer" can be the RNA version of the protospacer that binds to the complementary strand of the protospacer. A spacer can be within a guide RNA (gRNA). The site of cleavage by an RNA-guided nuclease is within a protospacer sequence. Please see FIG. 1A for an illustration.

mRNA Encoding SpCas9, CBE, and ABE Proteins mRNA for SpCas9, CBE, and ABE were produced by different methods well known in the art. One of such methods used herein was in vitro transcription (IVT) using T7 polymerase or additional RNA polymerase variants. Typically, IVT of mRNA uses a linearized DNA template that comprises a T7 polymerase promoter, mRNA coding sequence (CDS), 3' and 5' untranslated regions (UTRs), poly A tail, and additional replication and transcription regulatory elements. Prior to IVT, the DNA template was in the form of a plasmid, PCR product, or additional double-stranded DNA construct. A typical IVT reaction includes T7 polymerase, DNA template, RNase inhibitor, cap analog, inorganic pyrophosphatase, and naturally occurring ribonucleotides (rNTPs) such as GTP, ATP, CTP, UTP, or substitutions of natural rNTPs with modified rNTPs such as pseudouridine, N1-methylpseudouridine, 5-methyl cytidine, 5-methoxyuridine, N6-methyl adenosine, and N4-acetylcytidine. The cap analog was a dinucleotide or trinucleotide cap structure with the first initiating nucleotide containing standard 2'-hydroxyl group, 2'-O-methyl group, or additional 2' chemical modification. Cap analog also was added after the IVT reaction using a vaccinia capping enzyme. After IVT, in some cases DNase is added to the transcription mixture to remove DNA template; alternatively, residual DNA was removed by ion exchange column chromatography. Purification and concentration of mRNA were performed with ion exchange chromatography, affinity chromatography, precipitation, ion-pairing reverse-phase chromatography, enzymatic reactions, size exclusion chromatography, and/or tangential flow filtration. Similar IVT and purification process were used to produce mRNA encoding SpCas9, CBE, and ABE; in all cases the DNA template, reaction conditions, and purification parameters were optimized for the specific gene of interest. In some examples, capped and polyadenylated SpCas9 mRNA MS002 was obtained from commercially sources (TriLink, for e.g.). The SpCas9 mRNA MS002 and adenosine base editor (ABE) mRNAs MA002 and MA004 prepared in Verve's laboratory.

The adenosine nucleobase editor mRNA MA002 comprises a fusion protein comprising a polypeptide encoded by the polynucleotide sequence provided below

```
(SEQ ID NO: 19)
ATGAGCGAGGTCGAGTTCTCTCACGAATATTGGATGAGAC

ACGCTCTCACCCTGGCTAAGAGAGCCAGGGACGAAAGAGA

GGTGCCAGTTGGCGCTGTCCTGGTGTTGAACAATCGCGTC

ATCGGAGAAGGATGGAATCGCGCCATTGGCCTGCACGATC

CAACCGCACATGCCGAAATTATGGCTCTGCGGCAAGGCGG

CCTCGTGATGCAAAATTACAGACTGATCGATGCTACCCTC

TACGTCACCTTCGAGCCCTGTGTCATGTGTGCTGGGGCAA

TGATTCACTCCCGGATTGGCCGCGTGGTGTTTGGAGTGCG

GAATGCCAAGACTGGCGCCGCTGGATCTCTGATGGACGTC

CTGCACcatCCTGGGATGAACCACCGGGTCGAGATCACAG

AGGGAATTCTGGCTGACGAGTGCGCTGCCCTGCTGTGCag gTTCTTTAGAATGCCLAGAaggGTGTTCAACGCCCAGAAA

AAAGCTCAGAGCAGCACCGATTCCGGCGGAAGCAGCGGAG

GATCTTCTGGAAGCGAAACCCCAGGCACCAGCGAGTCTGC

CACACCAGAATCATCTGGCGGTAGCTCCGGCGGCAGCGAC

AAGAAGTATTCTATCGGACTGGCCATCGGCACCAACTCTG

TTGGATGGGCCGTGATCACCGACGAGTACAAGGTGCCCAG

CAAGAAATTCAAGGTGCTGGGCAACACCGACAGGCACAGC

ATCAAGAAGAACCTGATCGGCGCACTGCTGTTCGACTCTG

GCGAAACAGCCGAGGCCACCAGACTGAAGAGAACAGCCCG

CAGACGGTACACCAGAAGAAAGAACCGGATCTGCTACCTC

CAAGAGATCTTCAGCAACGAGATGGCCAAGGTGGACGACA

GCTTCTTCCACAGACTGGAAGAGTCCTTCCTGGTGGAAGA
```

GGACAAGAAGCACGAGAGACACCCCATCTTCGGCAACATC

GTGGACGAGGTGGCCTACCACGAGAAGTACCCCACCATCT

ACCACCTGAGAAAGAAACTGGTGGACAGCACCGACAAGGC

CGACCTGAGACTGATCTATCTGGCCCTGGCTCACATGATC

AAGTTCCGGGGCCACTTCCTGATCGAGGGCGACCTGAATC

CTGACAACAGCGACGTGGACAAGCTGTTCATCCAGCTGGT

GCAGACCTACAACCAGCTGTTCGAGGAAAACCCCATCAAC

GCCAGCGGAGTGGATGCCAAGGCCATCCTGTCTGCCAGAC

TGAGCAAGAGCAGACGGCTGGAAAATCTGATCGCCCAGCT

GCCTGGCGAGAAGAAGAATGGCCTGTTCGGCAACCTGATT

GCCCTGAGCCTGGGCCTGACACCTAACTTCAAGAGCAACT

TCGACCTGGCCGAGGACGCCAAACTGCAGCTGAGCAAGGA

CACCTACGACGACGACCTGGACAATCTGCTGGCCCAGATC

GGCGATCAGTACGCCGACTTGTTTCTGGCCGCCAAGAATC

TGAGCGACGCCATCCTGCTGTCCGACATCCTGAGAGTGAA

CACCGAGATCACCAAGGCACCTCTGAGCGCCTCTATGATC

AAGAGATACGACGAGCACCACCAGGATCTGACCCTGCTGA

AGGCCCTCGTTAGACAGCAGCTGCCAGAGAAGTACAAAGA

GATTTTCTTCGACCAGAGCAAGAACGGCTACGCCGGCTAC

ATTGATGGCGGAGCCAGCCAAGAGGAATTCTACAAGTTCA

TCAAGCCCATCCTCGAGAAGATGGACGGCACCGAGGAACT

GCTGGTCAAGCTGAACAGAGAGGACCTGCTGAGAAAGCAG

AGAACCTTCGACAACGGCAGCATCCCTCACCAGATCCACC

TGGGAGAACTGCACGCCATTCTGCGGAGACAAGAGGACTT

TTACCCATTCCTGAAGGACAACCGGGAAAAGATCGAGAAA

ATCCTGACCTTCAGGATCCCCTACTACGTGGGACCACTGG

CCAGAGGCAATAGCAGATTCGCCTGGATGACCAGAAAGAG

CGAGGAAACCATCACTCCCTGGAACTTCGAGGAAGTGGTG

GACAAGGGCGCCAGCGCTCAGTCCTTCATCGAGCGGATGA

CCAACTTCGATAAGAACCTGCCTAACGAGAAGGTGCTGCC

CAAGCACAGCCTGCTGTACGAGTACTTCACCGTGTACAAC

GAGCTGACCAAAGTGAAATACGTGACCGAGGGAATGAGAA

AGCCCGCCTTTCTGAGCGGCGAGCAGAAAAAGGCCATCGT

GGATCTGCTGTTCAAGACCAACCGGAAAGTGACCGTGAAG

CAGCTGAAAGAGGACTACTTCAAGAAAATCGAGTGCTTCG

ACAGCGTCGAGATCTCCGGCGTGGAAGATCGGTTCAATGC

CAGCCTGGGCACATACCACGATCTGCTGAAAATTATCAAG

GACAAGGACTTCCTGGACAACGAAGAGAACGAGGACATCC

TTGAGGACATCGTGCTGACACTGACCCTGTTTGAGGACAG

AGAGATGATCGAGGAACGGCTGAAAACATACGCCCACCTG

-continued

TTCGACGACAAAGTGATGAAGCAACTGAAGCGGCGGAGAT
ACACCGGCTGGGGCAGACTGTCTCGGAAGCTGATCAACGG
CATCCGGGATAAGCAGTCCGGCAAGACCATCCTGGACTTT
CTGAAGTCCGACGGCTTCGCCAACAGAAACTTCATGCAGC
TGATTCACGACGACAGCCTCACCTTCAAAGAGGATATCCA
GAAAGCCCAGGTGTCCGGCCAGGGCGATTCTCTGCATGAG
CACATTGCCAACCTGGCCGGCTCTCCCGCCATTAAGAAAG
GCATCCTGCAGACAGTGAAGGTGGTGGACGAGCTTGTGAA
AGTGATGGGCAGACACAAGCCCGAGAACATCGTGATCGAA
ATGGCCAGAGAGAACCAGACCACACAGAAGGGACAGAAGA
ACAGCCGCGAGAGAATGAAGCGGATCGAAGAGGGCATCAA
AGAGCTGGGCAGCCAGATCCTGAAAGAACACCCCGTGGAA
AACACCCAGCTGCAGAACGAGAAGCTGTACCTGTACTACC
TGCAGAATGGACGGGATATGTACGTGGACCAAGAGCTGGA
CATCAACAGACTGTCCGACTACGATGTGGACCATATCGTG
CCCCAGTCTTTTCTGAAGGACGACTCCATCGACAACAAGG
TCCTGACCAGATCCGACAAGAATCGGGGCAAGAGCGACAA
CGTGCCCTCCGAAGAGGTGGTCAAGAAGATGAAGAACTAC
TGGCGACAGCTGCTGAACGCCAAGCTGATTACCCAGCGGA
AGTTCGACAATCTGACCAAGGCCGAAAGAGGCGGCCTGAG
CGAACTGGATAAGGCCGGCTTCATCAAGAGACAGCTGGTG
GAAACCCGGCAGATCACAAAGCACGTGGCACAGATTCTGG
ACTCTCGGATGAACACTAAGTACGACGAGAACGACAAACT
GATCCGCGAAGTGAAAGTCATCACCCTGAAGTCCAAGCTG
GTGTCCGATTTCCGGAAGGATTTCCAGTTCTACAAAGTGC
GCGAGATCAACAACTACCATCACGCCCACGACGCCTACCT
GAATGCCGTTGTTGGAACAGCCCTGATCAAAAAGTACCCT
AAGCTGGAAAGCGAGTTCGTGTACGGCGACTACAAGGTGT
ACGACGTGCGGAAGATGATCGCCAAGAGCGAGCAAGAGAT
TGGCAAGGCAACCGCCAAGTACTTCTTCTACAGCAACATC
ATGAACTTTTTCAAGACAGAGATCACCCTCGCCAACGGCG
AGATCAGAAAGCGGCCTCTGATCGAGACAAACGGCGAAAC
CGGCGAGATTGTGTGGGATAAGGGCAGAGACTTTGCCACA
GTGCGGAAAGTGCTGAGCATGCCCCAAGTGAATATCGTGA
AGAAAACCGAGGTGCAGACAGGCGGCTTCAGCAAAGAGTC
TATCCTGCCTAAGCGGAACTCCGACAAGCTGATCGCCAGA
AAGAAGGACTGGGACCCCAAGAAGTACGGCGGCTTCGATT
CTCCTACCGTGGCCTATAGCGTGCTGGTGGTGGCCAAAGT
GGAAAAGGGCAAGTCCAAGAAACTCAAGAGCGTGAAAGAG
CTGCTGGGGATCACCATCATGGAAAGAAGCAGCTTCGAGA
AGAATCCGATCGATTTCCTCGAGGCCAAGGGCTACAAAGA

-continued

AGTGAAAAAGGACCTGATCATCAAGCTCCCCAAGTACTCC
CTGTTCGAGCTGGAAAACGGCCGGAAGAGAATGCTGGCCT
CTGCTGGCGAACTGCAGAAGGGAAACGAACTGGCCCTGCC
TAGCAAATATGTGAACTTCCTGTACCTGGCCAGCCACTAT
GAGAAGCTGAAGGGCAGCCCCGAGGACAATGAGCAAAAGC
AGCTGTTTGTGGAACAGCACAAGCACTACCTGGACGAGAT
CATCGAGCAGATCAGCGAGTTTAGCAAGAGAGTGATTCTG
GCCGACGCCAATCTGGACAAAGTGCTGTCCGCCTACAACA
AGCACCGGGACAAGCCTATCAGAGAGCAGGCCGAGAATAT
CATCCACCTGTTTACCCTGACCAACCTGGGAGCCCCTGCC
GCCTTCAAGTACTTTGACACCACCATCGACCGGAAGCGGT
ACACCTCCACCAAAGAGGTGCTGGACGCCACTCTGATCCA
CCAGTCTATCACCGGCCTGTACGAGACACGGATCGACCTG
TCTCAACTCGGAGGCGACGAAGGCGCCGATAAGAGAACCG
CCGATGGCTCTGAGTTCGAGAGCCCCAAGAAAAAGCGCAA
AGTGATGAGCGAGGTCGAGTTCTCTCACGAATATTGGATG
AGACACGCTCTCACCCTGGCTAAGAGAGCCAGGGACGAAA
GAGAGGTGCCAGTTGGCGCTGTCCTGGTGTTGAACAATCG
CGTCATCGGAGAAGGATGGAATCGCGCCATTGGCCTGCAC
GATCCAACCGCACATGCCGAAATTATGGCTCTGCGCCAAG
GCGGCCTCGTGATGCAAAATTACAGACTGATCGATGCTAC
CCTCTACGTCACCTTCGAGCCCTGTGTCATGTGTGCTGGG
GCAATGATTCACTCCCGGATTGGCCGCGTGGTGTTTGGAG
TGCGGAATGCCAAGACTGGCGCCGCTGGATCTCTGATGGA
CGTCCTGCACcatCCTGGGATGAACCACCGGGTCGAGATC
ACAGAGGGAATTCTGGCTGACGAGTGCGCTGCCCTGCTGT
GCaggTTCTTTAGAATGCCtAGAaggGTGTTCAACGCCCA
GAAAAAAGCTCAGAGCAGCACCGATTCCGGCGGAAGCAGC
GGAGGATCTTCTGGAAGCGAAACCCCAGGCACCAGCGAGT
CTGCCACACCAGAATCATCTGGCGGTAGCTCCGGCGGCAG
CGACAAGAAGTATTCTATCGGACTGGCCATCGGCACCAAC
TCTGTTGGATGGGCCGTGATCACCGACGAGTACAAGGTGC
CCAGCAAGAAATTCAAGGTGCTGGGCAACACCGACAGGCA
CAGCATCAAGAAGAACCTGATCGGCGCACTGCTGTTCGAC
TCTGGCGAAACAGCCGAGGCCACCAGACTGAAGAGAACAG
CCCGCAGACGGTACACCAGAAGAAAGAACCGGATCTGCTA
CCTCCAAGAGATCTTCAGCAACGAGATGGCCAAGGTGGAC
GACAGCTTCTTCCACAGACTGGAAGAGTCCTTCCTGGTGG
AAGAGGACAAGAAGCACGAGAGACACCCCATCTTCGGCAA
CATCGTGGACGAGGTGGCCTACCACGAGAAGTACCCCACC -continued
ATCTACCACCTGAGAAAGAAACTGGTGGACAGCACCGACA
AGGCCGACCTGAGACTGATCTATCTGGCCCTGGCTCACAT
GATCAAGTTCCGGGGCCACTTCCTGATCGAGGGCGACCTG
AATCCTGACAACAGCGACGTGGACAAGCTGTTCATCCAGC
TGGTGCAGACCTACAACCAGCTGTTCGAGGAAAACCCCAT
CAACGCCAGCGGAGTGGATGCCAAGGCCATCCTGTCTGCC
AGACTGAGCAAGAGCAGACGGCTGGAAAATCTGATCGCCC
AGCTGCCTGGCGAGAAGAAGAATGGCCTGTTCGGCAACCT
GATTGCCCTGAGCCTGGGCCTGACACCTAACTTCAAGAGC
AACTTCGACCTGGCCGAGGACGCCAAACTGCAGCTGAGCA
AGGACACCTACGACGACGACCTGGACAATCTGCTGGCCCA
GATCGGCGATCAGTACGCCGACTTGTTTCTGGCCGCCAAG
AATCTGAGCGACGCCATCCTGCTGTCCGACATCCTGAGAG
TGAACACCGAGATCACCAAGGCACCTCTGAGCGCCTCTAT
GATCAAGAGATACGACGAGCACCACCAGGATCTGACCCTG
CTGAAGGCCCTCGTTAGACAGCAGCTGCCAGAGAAGTACA
AAGAGATTTTCTTCGACCAGAGCAAGAACGGCTACGCCGG
CTACATTGATGGCGGAGCCAGCCAAGAGGAATTCTACAAG
TTCATCAAGCCCATCCTCGAGAAGATGGACGGCACCGAGG
AACTGCTGGTCAAGCTGAACAGAGAGGACCTGCTGAGAAA
GCAGAGAACCTTCGACAACGGCAGCATCCCTCACCAGATC
CACCTGGGAGAACTGCACGCCATTCTGCGGAGACAAGAGG
ACTTTTACCCATTCCTGAAGGACAACCGGGAAAAGATCGA
GAAAATCCTGACCTTCAGGATCCCCTACTACGTGGGACCA
CTGGCCAGAGGCAATAGCAGATTCGCCTGGATGACCAGAA
AGAGCGAGGAAACCATCACTCCCTGGAACTTCGAGGAAGT
GGTGGACAAGGGCGCCAGCGCTCAGTCCTTCATCGAGCGG
ATGACCAACTTCGATAAGAACCTGCCTAACGAGAAGGTGC
TGCCCAAGCACAGCCTGCTGTACGAGTACTTCACCGTGTA
CAACGAGCTGACCAAAGTGAAATACGTGACCGAGGGAATG
AGAAAGCCCGCCTTTCTGAGCGGCGAGCAGAAAAAGGCCA
TCGTGGATCTGCTGTTCAAGACCAACCGGAAAGTGACCGT
GAAGCAGCTGAAAGAGGACTACTTCAAGAAAATCGAGTGC
TTCGACAGCGTCGAGATCTCCGGCGTGGAAGATCGGTTCA
ATGCCAGCCTGGGCACATACCACGATCTGCTGAAAATTAT
CAAGGACAAGGACTTCCTGGACAACGAAGAGAACGAGGAC
ATCCTTGAGGACATCGTGCTGACACTGACCCTGTTTGAGG
ACAGAGAGATGATCGAGGAACGGCTGAAAACATACGCCCA
CCTGTTCGACGACAAAGTGATGAAGCAACTGAAGCGGCGG
AGATACACCGGCTGGGGCAGACTGTCTCGGAAGCTGATCA
ACGGCATCCGGGATAAGCAGTCCGGCAAGACCATCCTGGA -continued
CTTTCTGAAGTCCGACGGCTTCGCCAACAGAAACTTCATG
CAGCTGATTCACGACGACAGCCTCACCTTCAAAGAGGATA
TCCAGAAAGCCCAGGTGTCCGGCCAGGGCGATTCTCTGCA
TGAGCACATTGCCAACCTGGCCGGCTCTCCCGCCATTAAG
AAAGGCATCCTGCAGACAGTGAAGGTGGTGGACGAGCTTG
TGAAAGTGATGGGCAGACACAAGCCCGAGAACATCGTGAT
CGAAATGGCCAGAGAGAACCAGACCACACAGAAGGGACAG
AAGAACAGCCGCGAGAGAATGAAGCGGATCGAAGAGGGCA
TCAAAGAGCTGGGCAGCCAGATCCTGAAAGAACACCCCGT
GGAAAACACCCAGCTGCAGAACGAGAAGCTGTACCTGTAC
TACCTGCAGAATGGACGGGATATGTACGTGGACCAAGAGC
TGGACATCAACAGACTGTCCGACTACGATGTGGACCATAT
CGTGCCCCAGTCTTTTCTGAAGGACGACTCCATCGACAAC
AAGGTCCTGACCAGATCCGACAAGAATCGGGGCAAGAGCG
ACAACGTGCCCTCCGAAGAGGTGGTCAAGAAGATGAAGAA
CTACTGGCGACAGCTGCTGAACGCCAAGCTGATTACCCAG
CGGAAGTTCGACAATCTGACCAAGGCCGAAAGAGGCGGCC
TGAGCGAACTGGATAAGGCCGGCTTCATCAAGAGACAGCT
GGTGGAAACCCGGCAGATCACAAAGCACGTGGCACAGATT
CTGGACTCTCGGATGAACACTAAGTACGACGAGAACGACA
AACTGATCCGCGAAGTGAAAGTCATCACCCTGAAGTCCAA
GCTGGTGTCCGATTTCCGGAAGGATTTCCAGTTCTACAAA
GTGCGCGAGATCAACAACTACCATCACGCCCACGACGCCT
ACCTGAATGCCGTTGTTGGAACAGCCCTGATCAAAAAGTA
CCCTAAGCTGGAAAGCGAGTTCGTGTACGGCGACTACAAG
GTGTACGACGTGCGGAAGATGATCGCCAAGAGCGAGCAAG
AGATTGGCAAGGCAACCGCCAAGTACTTCTTCTACAGCAA
CATCATGAACTTTTTCAAGACAGAGATCACCCTCGCCAAC
GGCGAGATCAGAAAGCGGCCTCTGATCGAGACAAACGGCG
AAACCGGCGAGATTGTGTGGGATAAGGGCAGAGACTTTGC
CACAGTGCGGAAAGTGCTGAGCATGCCCCAAGTGAATATC
GTGAAGAAAACCGAGGTGCAGACAGGCGGCTTCAGCAAAG
AGTCTATCCTGCCTAAGCGGAACTCCGACAAGCTGATCGC
CAGAAAGAAGGACTGGGACCCCAAGAAGTACGGCGGCTTC
GATTCTCCTACCGTGGCCTATAGCGTGCTGGTGGTGGCCA
AAGTGGAAAAGGGCAAGTCCAAGAAACTCAAGAGCGTGAA
AGAGCTGCTGGGGATCACCATCATGGAAAGAAGCAGCTTC
GAGAAGAATCCGATCGATTTCCTCGAGGCCAAGGGCTACA
AAGAAGTGAAAAAGGACCTGATCATCAAGCTCCCCAAGTA
CTCCCTGTTCGAGCTGGAAAACGGCCGGAAGAGAATGCTG

```
GCCTCTGCTGGCGAACTGCAGAAGGGAAACGAACTGGCCC

TGCCTAGCAAATATGTGAACTTCCTGTACCTGGCCAGCCA

CTATGAGAAGCTGAAGGGCAGCCCCGAGGACAATGAGCAA

AAGCAGCTGTTTGTGGAACAGCACAAGCACTACCTGGACG

AGATCATCGAGCAGATCAGCGAGTTTAGCAAGAGAGTGAT

TCTGGCCGACGCCAATCTGGACAAAGTGCTGTCCGCCTAC

AACAAGCACCGGGACAAGCCTATCAGAGAGCAGGCCGAGA

ATATCATCCACCTGTTTACCCTGACCAACCTGGGAGCCCC

TGCCGCCTTCAAGTACTTTGACACCACCATCGACCGGAAG

CGGTACACCTCCACCAAAGAGGTGCTGGACGCCACTCTGA

TCCACCAGTCTATCACCGGCCTGTACGAGACACGGATCGA

CCTGTCTCAACTCGGAGGCGACGAAGGCGCCGATAAGAGA

ACCGCCGATGGCTCTGAGTTCGAGAGCCCCAAGAAAAAGC

GCAAAGTG
```

The adenosine nucleobase editor mRNA MA004 comprises a fusion protein comprising a polypeptide encoded by the polynucleotide sequence provided below, where u' is N¹-methylpseudouridine.

```
                                              (SEQ ID NO: 20)
AGGAAAu'AAGAGAGAAAAGAAGAGu'AAGAAGAAAu'Au

'AAGAGCCACCAu'GAGCGAGGu'GGAGu'u'CAGCCACG

AGu'ACu'GGAu'GCGGCACGCCCu'GACCCu'GGCCAAG

CGGGCCCGGGACGAGCGGGAGGu'GCCCGu'GGGCGCCGu

'GCu'GGu'GCu'GAACAACCGGGu'GAu'CGGCGAGGGC u'GGAACCGGGCCAu'CGGCCu'GCACGACCCCACCGCCC

ACGCCGAGAu'CAu'GGCCCu'GCGGCAGGGCGGCCu'GG u'GAu'GCAGAACu'ACCGGCu'GAu'CGACGCCACCCu'

Gu'ACGu'GACCu'u'CGAGCCCu'GCGu'GAu'Gu'GCG

CCGGCGCCAu'GAu'CCACAGCCGGAu'CGGCCGGGu'GG u'Gu'u'CGGCGu'GCGGAACGCCAAGACCGGCGCCGCCG

GCAGCCu'GAu'GGACGu'GCu'GCACCACCCCGGCAu'G

AACCACCGGGu'GGAGAu'CACCGAGGGCAu'CCu'GGCC

GACGAGu'GCGCCGCCCu'GCu'Gu'GCCGGu'u'Cu'u'

CCGGAu'GCCCCGGCGGGu'Gu'u'CAACGCCCAGAAGAA

GGCCCAGAGCAGCACCGACAGCGGCGGCAGCAGCGGCGGC

AGCAGCGGCAGCGAGACACCCGGCACCAGCGAGAGCGCCA

CCCCCGAGAGCAGCGGCGGCAGCAGCGGCGGCAGCGACAA

GAAGu'ACAGCAu'CGGCCu'GGCCAu'CGGCACCAACAG

CGu'GGGCu'GGGCCGu'GAu'CACCGACGAGu'ACAAGG u'GCCCAGCAAGAAGa'u'CAAGGu'GCu'GGGCAACACC

GACCGGCACAGCAu'CAAGAAGAACCu'GAu'CGGCGCCC u'GCu'Gu'u'CGACAGCGGCGAGACAGCCGAGGCCACCC
```

```
GGCu'GAAGCGGACCGCCCGGCGGCGGu'ACACCCGGCGG

AAGAACCGGAu'Cu'GCu'ACCu'GCAGGAGAu'Cu'u'C

AGCAACGAGAu'GGCCAAGGu'GGACGACAGCu'u'Cu'u

'CCACCGGCu'GGAGGAGAGCu'u'CCu'GGu'GGAGGAG

GACAAGAAGCACGAGCGGCACCCCAu'Cu'u'CGGCAACA u'CGu'GGACGAGGuGGCCu'ACCACGAGAAGu'ACCCCA

CCAu'CACCACCu'GCGGAAGAAGCu'GGu'GGACAGC

ACCGACAAGGCCGACCu'GCGGCu'GAu'Cu'ACCu'GGC

CCu'GGCCCACAu'GAu'CAAGu'u'CCGGGGCCACu'u'

CCu'GAu'CGAGGGCGACCu'GAACCCCGACAACAGCGAC

Gu'GGACAAGCu'Gu'u'CAu'CCAGCu'GGu'GCAGACC u'ACAACCAGCu'Gu'u'CGAGGAGAACCCCAu'CAACGC

CAGCGGCGu'GGACGCCAAGGCCAu'CCu'GAGCGCCCGG

Cu'GAGCAAGAGCCGGCGGCu'GGAGAACCu'GAu'CGCC

CAGCu'GCCCGGCGAGAAGAAGAACGGCCu'Gu'u'CGGC

AACCu'GAu'CGCCCu'GAGCCu'GGGCCu'GACCCCCAA

Cu'u'CAAGAGCAACu'u'CGACCu'GGCCGAGGACGCCA

AGCa'GCAGCu'GAGCAAGGACACCu'ACGACGACGACCu

'GGACAACCu'GCu'GGCCCAGAu'CGGCGACCAGu'ACG

CCGACCu'Gu'u'CCuGGCCGCCAAGAACCu'GAGCGACG

CCAu'CCu'GCu'GAGCGACAu'CCu'GCGGGu'GAACAC

CGAGAu'CACCAAGGCCCCCCu'GAGCGCCAGCAu'GAu'C

AAGCGGu'ACGACGAGCACCACCAGGACCa'GACCCu'GC u'GAAGGCCCa'GGu'GCGGCAGCAGCu'GCCCGAGAAGu

'ACAAGGAGAu'Cu'u'Cu'u'CGACCAGAGCAAGAACGG

Cu'ACGCCGGCu'ACAu'CGACGGCGGCGCCAGCCAGGAG

GAGu'u'Cu'ACAAGu'u'CAu'CAAGCCCAu'CCu'GGA

GAAGAu'GGACGGCACCGAGGAGCu'GCu'GGu'GAAGCu

'GAACCGGGAGGACCu'GCu'GCGGAAGCAGCGGACCu'u

'CGACAACGGCAGCAu'CCCCCACCAGAu'CCACCu'GGG

CGAGCu'GCACGCCAu'CCu'GCGGCGGCAGGAGGACu'u

'Cu'ACCCCu'u'CCu'GAAGGACAACCGGGAGAAGAu'C

GAGAAGAu'CCu'GACCu'u'CCGGAu CCCCu'ACu'ACG u'GGGCCCCu'GGCCCGGGGCAACAGCCGGu'u'CGCCu

'GGAu'GACCCGCAAGAGCGAGGAGACAAu'CACCCCCu'

GGAACu'u'CGAGGAGGu'GGu'GGACAAGGGCGCCAGCG

CCCAGAGCu'u'CAu'CGAGCGGAu'GACCAACu'u'CGA

CAAGAACCu'GCCCAACGAGAAGGu'GCu'GCCCAAGCAC

AGCCu'GCu'Gu'ACGAGu'ACu'u'CACCGu'GACAA

CGAGCu'GACCAAGGu'GAAGu'ACGu'GACCGAGGGCAu
```

-continued

'GCGGAAGCCCGCCu'u'CCu'GAGCGGCGAGCAGAAGAAGGCCAu'CGuGGACCu'GCu'Gu'u'CAAGACCAACCGGAAGGu'GACCGu'GAAGCAGCu'GAAGGAGGACu'ACu'u'CAAGAAGAu'CGAGu'GCu'u'CGACAGCGu'GGAGAu'CAGCGGCGu'GGAGGACCGGu'u'CAACGCCAGCCu'GGGCACCu'ACCACGACCu'GCu'GAAGAu'CAu'CAAGGACAAGGACu'u'CCu'GGACAACGAGGAGAACGAGGACAu'CCu'GGAGGACAu'CGu'GCu'GACCCu'GACCCu'Gu'u'CGAGGACCGGGAGAu'GAu'CGAGGAGCGGCu'GAAGACCU'ACGCCCACCu'Gu'u'CGACGACAAGGu'GAu'GAAGCAGCu'GAAGCGGCGGCGGu'ACACCGGCu'GGGGCCGGCu'GAGCCGGAAGCu'GAu'CAACGCAu'CCGGGACAAGCAGAGCGGCAAGACCAu'CCu'GGACu'u'CCu'CAAGAGCGACGGCu'u'CGCCAACCGGAACu'u'CAuGCAGCu'GAu'CCACGACGACAGCCu'GACCu'u'CAAGGAGGACAu'CCAGAAGGCCCAGGu'GAGCGGCCAGGGCGACAGCCu'GCACGAGCACAu'CGCCAACCu'GGCCGGCAGCCCCGCCAu'CAAGAAGGGCAu'CCu'GCAGACCGu'GAAGGu'GGu'GGACGAGCu'GGu'GAAGGu'GAu'GGGCCGGCACAAGCCCGAGAACAu'CGu'GAu'CGAGAu'GGCCCGGGAGAACCAGACCACCCAGAAGGGCCAGAAGAACAGCCGGGAGCGGAu'GAAGCGGAu'CGAGGAGGGCAu'CAAGGAGCu'GGGCAGCCAGAu'CCu'GAAGGAGCACCCCGu'GGAGAACACCCAGCu'GCAGAACGAGAAGCu'Gu'ACCu'Gu'ACu'ACCu'GCAGAACGGCCCGGGACAu'Gu'ACGu'GGACCAGGAGCu'GGACAu'CAACCGGCu'GAGCGACu'ACGACGu'GGACCACAu'CGu'GCCCCAGAGCa'u'CCu'GAAGGACGACAGCAu'CGACAACAAGGu'GCu'GACCCGGAGCGACAAGAACCGGGGCAAGAGCGACAACGu'GCCCAGCGAGGAGGu'GGu'GAAGAAGAu'GAAGAACu'ACGGCGGCAGCu'GCu'GAACGCCAAGCu'GAu'CACCCAGCGGAAGu'u'CGACAACCu'GACCAAGGCCGAGCGGGGCGGCCu'GAGCGAGCu'GGACAAGGCCGGCu'u'CAu'CAAGCGGCAGCu'GGu'GGAGACACGGCAGAu'CACCAAGCACGu'GGCCCAGAu'CCu'GGACAGCCGGAu'GAACACCAAGu'ACGACGAGAACGACAAGCu'GAu'CCGGGAGGu'GAAGGu'GAu'CACCCu'CAAGAGCAAGCu'GGu'GAGCGACu'u'CCGGAAGGACu'u'CCAGu'u'Cu'ACAAGGu'GCGGGAGAu'CAACAACu'ACCACCACGCCCACGACGCCu'ACCu'GAACGCCGu'GGu'GGGCACCGCCCu'GAu'CAAGAAGu'ACCCCAAGCu'GGAGAGCGAGu'u'CGu'Gu'ACGGCGACu'ACAAGGu'Gu'ACGACGu'GCGGAAG

-continued

Au'GAu'CGCCAAGAGCGAGCAGGAGAu'CGGCAAGGCCACCGCCAAGu'ACu'u'Cu'u'Cu'ACAGCAACAu'CAu'GAACu'u'Cu'u'CAAGACCGAGAu'CACCCu'GGCCAACGGCGAGAu'CCGGAAGCGGCCCCu'GAu'CGAGACAAACGGCGAGACAGGCGAGAu'CGu'Gu'GGGACAAGGGCCGGGACu'u'CGCCACCGu'GCGGAAGGu'GCu'GAGCAu'GCCCCAGGu'GAACAu'CGu'GAAGAAGACCGAGGu'GCAGACCGGCGGCa'u'CAGCAAGGAGAGCAu'CCu'GCCCAAGCGGAACAGCGACAAGCu'GAuCGCCCGGAAGAAGGACu'GGGACCCCAAGAAGu'ACGGCGGCu'u'CGACAGCCCCACCGu'GGCCu'ACAGCGu'GCu'GGu'GGu'GGCCAAGGu'GGAGAAGGGCAAGAGCAAGAAGCu'CAAGAGCGu'GAAGGAGCu'GCu'GGGCAu'CACCAu'CAu'GGAGCGGAGCAGCu'u'CGAGAAGAACCCCAu'CGACu'u'CCu'GGAGGCCAAGGGCu'ACAAGGAGGu'GAAGAAGGACCu'GAu'CAu'CAAGCu'GCCCAAGu'ACAGCCu'Gu'u'CGAGCu'GGAGAACGGCCGGAAGCGGAu'GCu'GGCCAGCGCCGGCGAGCu'GCAGAAGGGCAACGAGCu'GGCCCu'GCCCAGCAAGu'ACGu'GAACu'u'CCu'Gu'ACCu'GGCCAGCCACu'ACGAGAAGCu'GAAGGGCAGCCCCGAGGACAACGAGCAGAAGCAGCu'Gu'u'CGu'GGAGCAGCACAAGCACa'ACCu'GGACGAGAu'CAu'CGAGCAGAuCAGCGAGu'u'CAGCAAGCGGGu'GAu'CCu'GGCCGACGCCAACCu'GGACAAGGu'GCu'GAGCGCCuACAACAAGCACCGGGACAAGCCCAu'CCGGGAGCAGGCCGAGAACAu'CAu'CCACCu'Gu'u'CACCCu'GACCAACCu'GGGCGCCCCCGCCGCCu'u'CAAGu'ACu'u'CGACACCACCAu'CGACCGGAAGCGGu'ACACCAGCACCAAGGAGGu'GCu'GGACGCCACCCu'GAu'CCACCAGAGCAu'CACCGGCCu'GuACGAGACACGGAu'CGACCu'GAGCCAGCu'GGGCGGCGACGAGGGCGCCGACAAGCGGACCGCCGACGGCAGCGAGu'u'CGAGAGCCCCAAGAAGAAGCGGAAGGu'Gu'GAGCGGCCGCu'u'AAu'u'AAGCu'GCCu'u'Cu'GCGGGGCu'u'GCCu'u'Cu'GGCCAu'GCCCu'u'Cu'u'Cu'Cu'CCCu'u'GCACCu'Gu'ACCuCu'u'GGu'Cu'u'u'GAAu'AAAGCCu'GAGu'AGGAAGu'Cu'AGA

The SpCas9 mRNA MS004 comprises a fusion protein comprising a polypeptide encoded by the polynucleotide sequence provided below, where u' is N1-methylpseudouridine.

(SEQ ID NO: 21)
AGGAAAu'AAGAGAGAAAAGAAGAGu'AAGAAGAAAu'Au
'AAGAGCCACCAu'GGCCCCCAAGAAGAAGCGGAAGGu'G
GGCAu'CCACGGCGu'GCCCGCCGCCGACAAGAAGu'ACA
GCAu'CGGCCu'GGACAu'CGGCACCAACAGCGu'GGGCu
'GGGCCGu'GAu'CACCGACGAGu'ACAAGGu'GCCCAGC
AAGAAGu'u'CAAGGu'Gcu'GGGCAACACCGACCGGCAC
AGCAu'CAAGAAGAACCu'Gau'CGGCGCCCu'Geu'Gu'
u'CGACAGCGGCGAGACGGCCGAGGCCACCCGGCu'GAAG
CGGACCGCCCGGCGGCGGu'ACACCCGGCGGAAGAACCGG
Au'Cu'Gcu'ACCu'GCAGGAGAu'Cu'u'CAGCAACGAG
Au'GGCCAAGGu'GGACGACAGCu'u'Cu'u'CCACCGGC
u'GGAGGAGAGCu'u'Ccu'Ggu'GGAGGAGGACAAGAAG
CACGAGCGGCACCCCAu'Cu'u'CGGCAACAu'Cgu'GGA
CGAGGu'GGCCu'ACCACGAGAAGu'ACCCCACCAu'Cu'
ACCACCu'GCGGAAGAAGCu'Ggu'GGACAGCACCGACAA
GGCCGACCu'GCGGCu'Gau'Cu'ACCu'GGCCCu'GGCC
CACAu'Gau'CAAGu'u'CCGGGGCCACu'u'Ccu'Gau'
CGAGGGCGACCu'GAACCCCGACAACAGCGACGu'GGACA
AGCu'Gu'u'Cau'CCAGCu'Ggu'GCAGACCu'ACAACC
AGCu'Gu'u'CGAGGAGAACCCCAu'CAACGCCAGCGGCG
u'GGACGCCAAGGCCAu'Ceu'GAGCGCCCGGCu'GAGCA
AGAGCCGGCGGCu'GGAGAACCu'Gau'CGCCCAGCu'GC
CCGGCGAGAAGAAGAACGGCCu'Gu'u'CGGCAACCu'Ga
u'CGCCCu'GAGCCu'GGGCCu'GACCCCCAACu'u'CAA
GAGCAACu'u'CGACCu'GGCCGAGGACGCCAAGCu'GCA
GCu'GAGCAAGGACACCu'ACGACGACGACCu'GGACAAC
Cu'Gcu'GGCCCAGAu'CGGCGACCAGu'ACGCCGACCu'
Gu'u'Ccu'GGCCGCCAAGAACCu'GAGCGACGCCAu'Cc
u'Gcu'GAGCGACAu'Ceu'GCGGGu'GAACACCGAGAu'
CACCAAGGCCCCCCu'GAGCGCCAGCAu'Gau'CAAGCGG
u'ACGACGAGCACCACCAGGACCu'GACCCu'Gcu'GAAG
GCCCu'Ggu'GCGGCAGCAGCu'GCCCGAGAAGu'ACAAG
GAGAu'Cu'u'Cu'u'CGACCAGAGCAAGAACGGCu'ACG
CCGGCu'ACAu'CGACGGCGGCGCCAGCCAGGAGGAGu'u
'Cu'ACAAGu'u'Cau'CAAGCCCAu'Ccu'GGAGAAGAu
'GGACGGCACCGAGGAGCu'Gcu'Ggu'GAAGCu'GAACC
GGGAGGACCu'Gcu'GCGGAAGCAGCGGACCu'u'CGACA
ACGGCAGCAu'CCCCCACCAGAu'CCACCu'GGGCGAGCu
'GCACGCCAu'Ccu'GCGGCGGCAGGAGGACu'u'Cu'AC
CCCu'u'Ccu'GAAGGACAACCGGGAGAAGAu'CGAGAAG

-continued

Au'Ccu'GACCu'u'CCGGAu'CCCCu'Acu'ACGu'GGG
CCCCCu'GGCCCGGGGCAACAGCCGGu'u'CGCCu'GGAu
'GACCCGCAAGAGCGAGGAGACGAu'CACCCCCu'GGAAC
u'u'CGAGGAGGu'Ggu'GGACAAGGGCGCCAGCGCCCAG
AGCu'u'Cau'CGAGCGGAu'GACCAACu'u'CGACAAGA
ACCu'GCCCAACGAGAAGGu'Gcu'GCCCAAGCACAGCCu
'Gcu'Gu'ACGAGu'Acu'u'CACCGu'Gu'ACAACGAGC
u'GACCAAGGu'GAAGu'ACGu'GACCGAGGGCAu'GCGG
AAGCCCGCCu'u'Ccu'GAGCGGCGAGCAGAAGAAGGCCA
u'Cgu'GGACCu'Gou'Gu'u'CAAGACCAACCGGAAGGu
'GACCGu'GAAGCAGCu'GAAGGAGGACu'Acu'u'CAAG
AAGAu'CGAGu'Gcu'u'CGACAGCGu'GGAGAu'CAGCG
GCGu'GGAGGACCGGu'u'CAACGCCAGCCu'GGGCACCu
'ACCACGACCu'Gcu'GAAGAu'Cau'CAAGGACAAGGAC
u'u'Ccu'GGACAACGAGGAGAACGAGGACAu'Ccu'GGA
GGACAu'Cgu'Gcu'GACCCu'GACCCu'Gu'u'CGAGGA
CCGGGAGAu'Gau'CGAGGAGCGGCu'GAAGACCu'ACGC
CCACCu'Gu'u'CGACGACAAGGu'Gau'GAAGCAGCu'G
AAGCGGCGGCGGu'ACACCGGCu'GGGGCCGGCu'GAGCC
GGAAGCu'Gau'CAACGGCAu'CCGGGACAAGCAGAGCGG
CAAGACCAu'Ccu'GGACu'u'Ccu'CAAGAGCGACGGCu
'u'CGCCAACCGGAACu'u'Cau'GCAGCu'Gau'CCACG
ACGACAGCCu'GACCu'u'CAAGGAGGACAu'CCAGAAGG
CCCAGGu'GAGCGGCCAGGGCGACAGCCu'GCACGAGCAC
Au'CGCCAACCu'GGCCGGCAGCCCCGCCAu'CAAGAAGG
GCAu'Ccu'GCAGACCGu'GAAGGu'Ggu'GGACGAGCu'
Ggu'GAAGGu'Gau'GGGCCGGCACAAGCCCGAGAACAu'
Cgu'Gau'CGAGAu'GGCCCGGGAGAACCAGACCACCCAG
AAGGGCCAGAAGAACAGCCGGGAGCGGAu'GAAGCGGAu'
CGAGGAGGGCAu'CAAGGAGCu'GGGCAGCCAGAu'Ccu'
GAAGGAGCACCCCGu'GGAGAACACCCAGCu'GCAGAACG
AGAAGCu'Gu'ACCu'Gu'Acu'ACCu'GCAGAACGGCCG
GGACAu'Gu'ACGu'GGACCAGGAGCu'GGACAu'CAACC
GGCu'GAGCGACu'ACGACGu'GGACCACAu'Cgu'GCCC
CAGAGCu'u'Ccu'GAAGGACGACAGCAu'CGACAACAAG
Gu'Gcu'GACCCGGAGCGACAAGAACCGGGGCAAGAGCGA
CAACGu'GCCCAGCGAGGAGGu'Ggu'GAAGAAGAu'GAA
GAACu'Acu'GGCGGCAGCu'Geu'GAACGCCAAGCu'Ga
u'CACCCAGCGGAAGu'u'CGACAACCu'GACCAAGGCCG
AGCGGGGCGGCCu'GAGCGAGCu'GGACAAGGCCGGCu'u
'Cau'CAAGCGGCAGCu'Ggu'GGAGACGCGGCAGAu'CA

-continued

CCAAGCACGu'GGCCCAGAu'Ccu'GGACAGCCGGAu'GA

ACACCAAGu'ACGACGAGAACGACAAGCu'Gau'CCGGGA

GGu'GAAGGu'Gau'CACCCu'CAAGAGCAAGCu'Ggu'G

AGCGACu'u'CCGGAAGGACu'u'CCAGu'u'Cu'ACAAG

Gu'GCGGGAGAu'CAACAACu'ACCACCACGCCCACGACG

CCu'ACCu'GAACGCCGu'Ggu'GGGCACCGCCCu'Gau'

CAAGAAGu'ACCCCAAGCu'GGAGAGCGAGu'u'Cgu'Gu

'ACGGCGACu'ACAAGGu'Gu'ACGACGu'GCGGAAGAu'

Gau'CGCCAAGAGCGAGCAGGAGAu'CGGCAAGGCCACCG

CCAAGu'Acu'u'Cu'u'Cu'ACAGCAACAu'Cau'GAAC u'u'Cu'u'CAAGACCGAGAu'CACCCu'GGCCAACGGCG

AGAu'CCGGAAGCGGCCCCu'Gau'CGAGACGAACGGCGA

GACGGGCGAGAu'Cgu'Gu'GGGACAAGGGCCGGGACu'u

'CGCCACCGu'GCGGAAGGu'Gcu'GAGCAu'GCCCCAGG u'GAACAu'Cgu'GAAGAAGACCGAGGu'GCAGACCGGCG

GCu'u'CAGCAAGGAGAGCAu'Ccu'GCCCAAGCGGAACA

GCGACAAGCu'Gau'CGCCCGGAAGAAGGACu'GGGACCC

CAAGAAGu'ACGGCGGCu'u'CGACAGCCCCACCGu'GGC

Cu'ACAGCGu'Gcu'Ggu'Ggu'GGCCAAGGu'GGAGAAG

GGCAAGAGCAAGAAGCu'CAAGAGCGu'GAAGGAGCu'Gc u'GGGCAu'CACCAu'Cau'GGAGCGGAGCAGCu'u'CGA

GAAGAACCCCAu'CGACu'u'Ccu'GGAGGCCAAGGGCu'

ACAAGGAGGu'GAAGAAGGACCu'Gau'Cau'CAAGCu'G

CCCAAGu'ACAGCCu'Gu'u'CGAGCu'GGAGAACGGCCG

GAAGCGGAu'Gcu'GGCCAGCGCCGGCGAGCu'GCAGAAG

GGCAACGAGCu'GGCCCu'GCCCAGCAAGu'ACGu'GAAC u'u'Ccu'Gu'ACCu'GGCCAGCCACu'ACGAGAAGCu'G

AAGGGCAGCCCCGAGGACAACGAGCAGAAGCAGCu'Gu'u

'Cgu'GGAGCAGCACAAGCACu'ACCu'GGACGAGAu'Ca u'CGAGCAGAu'CAGCGAGu'u'CAGCAAGCGGGu'Gau'

Ccu'GGCCGACGCCAACCu'GGACAAGGu'Gcu'GAGCGC

Cu'ACAACAAGCACCGGGACAAGCCCAu'CCGGGAGCAGG

CCGAGAACAu'Cau'CCACCu'Gu'u'CACCCu'GACCAA

CCu'GGGCGCCCCGCCGCCu'u'CAAGu'Acu'u'CGAC

ACCACCAu'CGACCGGAAGCGGu'ACACCAGCACCAAGGA

GGu'Gcu'GGACGCCACCCu'Gau'CCACCAGAGCAu'CA

CCGGCCu'Gu'ACGAGACGCGGAu'CGACCu'GAGCCAGC u'GGGCGGCGACAGCGGCGGCAAGCGGCCCGCCGCCACCA

AGAAGGCCGGCCAGGCCAAGAAGAAGAAGu'Aau'Gau'A

GGCGGCCGCu'u'Aau'u'AAGCu'GCCu'u'Cu'GCGGG

-continued

GCu'u'GCCu'u'Cu'GGCCAu'GCCCu'u'Cu'u'Cu'C u'CCCu'u'GCACCu'Gu'ACCu'Cu'u'Ggu'Cu'u'u'

GAAu'AAAGCCu'GAGu'AGGAAGu'Cu'AGA.

Example 9. Preparation of Lipid Nanoparticles (LNPs)

The LNPs used as reference in these studies are prepared according to published procedures and are constituted from published LNP excipients and genome editor mRNAs (Miller et al., Angew. Chem. Int. Ed. 2017, 56, 1059-1063; Yin et al., Nature Biotechnology 2016, 34, 328-333) and guide RNAs (Chadwick et al., Arterioscler. Thromb. Vasc. Biol. 2017, 37, 1741-1747; Rossidis et al., Nat. Med 2018, 24, 1513-1518. doi:10.1038/s41591-018-0184-6; Ding et al., Circ Res. 2014, 115, 488-492). The gRNA payload is selected from Table 3 and mRNA payloads MA002, MA004 and MS004 used for constituting these LNPs are prepared as described in Example 8 and the SPcas9 mRMA MS002 was purchased from TriLink BioTechnologies. The reference LNP A1 (Table 4) is constituted from the published lipid 501 (Table 1B), cholesterol (511), DSPC (512) and PEG-lipid (507 or 506) from Table 1B as described in the literature (Angew. Chem. Int. Ed. 2012, 51, 8529-8533). Similarly, the benchmark LNPs B1 and C1 are constituted from lipids 502 (WO 2015/095340 A1) and 503 (Molecular Therapy 2018, 26, 1509-1519) respectively in combination with cholesterol, DSPC and PEG-DMG (506 and 507, Table 1B) as summarized in Table 5. The reported genome editor nuclease mRNA and guide RNAs are used as payload for constituting the reference LNPs. In one approach the LNP formulations A1, B1 and C1 are made by co-formulating mRNA and guide RNA. In this co-formulation method mRNA to guide RNA ratio is varied from 10:1 to 1:10, that result in a series of LNPs for in vitro and in vivo gene editing evaluation. In the second approach: guide RNA and mRNA are formulated separately using same lipid ratios as in Table 6 and then pre-formulated LNPs with guide and mRNA are mixed together at various ratios to obtain a new series of LNPs for gene editing evaluation.

TABLE 4

Exemplary lipid compositions of LNPs A1, B1 and C1

| LNP Formulation | Lipid | Excipients, % mol | | | |
|---|---|---|---|---|---|
| | | Lipid | Cholesterol | DSPC | PEG-DMG |
| A1 | 501 | 50 | 38.5 | 10 | 1.5 |
| B1 | 502 | 45 | 44 | 9 | 2 |
| C1 | 503 | 50 | 38.5 | 9 | 1.5 |

Example 10. Preparation of LNPs F1-F25

The control/benchmark LNP F1 was prepared according to published procedure as described in Molecular Therapy 2018, 26, 1509-1519. An mRNA to guide RNA ratio of 1:1 by weight was used for formulating the LNP. The size and polydispersity index (PDI) of all LNPs were measured by Zeta Sizer Ultra ZSU5700 (Malvern Panalytical Inc.). It should be understood by one of ordinary skill in the art that the size and PDI are subject to the accuracy of the assay employed for the measurement and the standard deviation thereof. Thus, for example, the measured PDI here in is subject to measurement accuracy of +/−10% to the mean value and the LNP mean diameter (size) is subject to measurement accuracy of +/−10% to the mean value. In some instances, for example, the measurement variability may be >10%. Percentage RNA entrapment was measured by RiboGreen assay kit (Quant-iT™ RiboGreen™, Invitrogen). It should be understood by one of ordinary skill in the art that the percentage RNA entrapment is subject to the accuracy of the assay employed for the measurement and the standard deviation thereof. Thus, for example, the measured percentage RNA entrapment in each example is subject to measurement accuracy of +/−10% to the mean value. In some instances, for example, the measurement variability the measurement accuracy may be >10%. The terms 'percentage RNA entrapment', 'percentage total RNA entrapment', 'percentage RNA encapsulation' and 'percentage total RNA encapsulation' are interchangeably used as the measure of the total RNA encapsulated within LNP, after each formulation.

General preparation method of LNPs F2-F5 containing 504 and 513.

Lipids and alcohols were dissolved in ethanol at molar ratios as described in Table 5. N:P ratio was held at 3 to 12. The lipid mixture was combined with a 50 mM sodium citrate buffer (pH 4.8) containing Cas9 mRNA and PCSK9 gRNA (1:1) at an aqueous to ethanol ratio of 3:1 using a microfluidic mixer such a Ignite from Precision Nanosystems. LNPs were collected at a final 16.5% ethanol volume and was held for 1 hr before dialyzed against PBS (pH 7.4) in dialysis cassettes for at least 18 hr. Formulations were concentrated using Amicon ultra centrifugal filters and passed through a 0.2 μm filter to afford LNPs F2-F5 (Table 5). Size and RNA entrapment efficiency of LNPs were determined as described above. In some instances, the mixer is a T mixer. In some instances, it is a cross mixer. In some instances, the aqueous to ethanol ratio is 2:1.

LNP Formulations F6 and F7 were prepared using 505 as described in Table 5 replacing 504 in F2 and F3.

LNP Formulations F8 and F9 were prepared using 519 as described in Table 5 by replacing 504 in F2 and F3.

LNP Formulations F10 and F11 were prepared using 508 as described in Table 5 by replacing 504 in F2 and F3.

LNP Formulations F12 and F13 were prepared using 509 as described in Table 5 by replacing 504 in F2 and F3.

LNP Formulations F14 and F15 were prepared using 510 as described in Table 5 by replacing 504 in F2 and F3.

LNP Formulations F16 and F17 were prepared using 514 as described in Table 5 by replacing 504 in F2 and F3.

LNP Formulations F18 and F19 were prepared using 515 as described in Table 5 by replacing 504 in F2 and F3.

LNP Formulations F20 and F21 were prepared using 516 as described in Table 5 by replacing 504 in F2 and F3.

LNP Formulations F22 and F23 were prepared using 517 as described in Table 5 by replacing 504 in F2 and F3.

LNP Formulations F24 and F25 were prepared using 518 as described in Table 5 by replacing 504 in F2 and F3.

In vivo PCSK9 gene editing of LNPs F1-F5 were evaluated in wild-typeC57BL/6 mice and the results are summarized in Table 5 and in FIG. 1.

TABLE 5

Gene editing in mice hepatocyte by LNPs F1-F5 constituted with amino lipid 501 in the present and in the absence of fatty alcohol as an additional excipient.

| LNP ID | Amino lipid, 501 (mol %) | Cholesterol/ DSPC/PEG-DMG (mol %) | Alcohol (mol %) | | Mean diameter (nm) | % RNA entrapment | % editing in individual animal |
|---|---|---|---|---|---|---|---|
| | | | 504 | 513 | | | |
| F1 | 50 | 38.5/10/1.5 | | | 104 | 98 | 0.29, 0.14, 0.27, 0.26, 0.28 |
| F2 | 50 | 34.65/10/1.5 | 3.85 | | 68.7 | 98 | 1.6, 2.1, 1.6, 0.8, 5 |
| F3 | 50 | 30.8/10/1.5 | 7.7 | | 73.6 | 98 | 5.5, 4.8, 2.9*, 9, 7.8 |
| F4 | 50 | 34.65/10/1.5 | | 3.85 | 72 | 98 | 3.4, 7.1, 1.5, 3.1, 4.2 |
| F5 | 50 | 30.8/10/1.5 | | 7.7 | 78.5 | 98 | 11, 14, 8.8, 16, 4.8* |

*indicate dosing error.

LNPs of Table 5 carrying Cas9 mRNA and PCSK9 gRNA were administered intravenously (tail vein) to wild type C57BL/6 female mice (n=5) at 0.5 mg/kg total RNA dose except LNP F1 (0.75 mg/kg).

Example 11. General Preparation Method of LNPs F27-F43

LNP excipients were dissolved in ethanol at molar ratios as described in Table 5. N:P ratio was held at 3 to 12. The lipid mixture was combined with a buffer (pH 3.0 to 5.8) containing Cas9 mRNA and PCSK9 gRNA GA010 (1:1) using a microfluidic mixer (such as those available from Precision NanoSystems). In some cases, the mixer is a T mixer. In some instances, it is a cross mixer. In some instances, the aqueous to ethanol ratio is 2:1. In some instances, the aqueous to ethanol ratio is 3:1. PEG400 was added to the RNA containing drug substance buffer prior to mixing with lipids, at a certain % as calculated by the weight of PEG400 divided by the weight of the drug substance buffer it is added to. When adding the PEG400 to the drug substance buffer prior to or co-mixed with nucleic acid cargo, the w/w % in the non-RNA containing drug substance buffer is higher than the target w/w % in the final RNA containing drug substance buffer, such that eventual dilution with RNA dilutes the PEG400% to the target w/w %. LNPs were collected and dialyzed against a buffer (pH 6.5 to 8.0) in dialysis cassettes for at least 18 hr, or buffer exchanged via PD-JO columns. Formulations were concentrated and passed through a 0.2 μm filter to afford LNPs F27-F43 (Table 6). The size and polydispersity index of all LNPs were measured by Zeta Sizer Ultra ZSU5700 (Malvern Panalytical Inc.). Percentage RNA entrapment was measured by RiboGreen assay using the kit Quant-iT™ RiboGreen™ from Invitrogen. This data is provided in Table 6 below.

TABLE 6

Summary of composition, physiochemical characteristics of LNPs F27-F43 and % PCSK9 gene editing in C57BL/6 mice liver, after administration of LNPs F27-F40 constituted with PEG400.

| LNP ID | Amino lipid, 502 (mol %) | Cholesterol/ DSPC/PEG-DMG (mol %) | PEG400 (w/w) % | Mean diameter (nm) | % RNA entrapment | % editing in individual animal |
|---|---|---|---|---|---|---|
| F27 | 30-60% | 40-70% | 0 | 98 | 95.9 | 22.8, 23.8, 30.7, 21.5, 23.9 |
| F28 | 30-60% | 40-70% | 0.25 | 96.2 | 95.8 | 23.7, 23.3, 24.0, 29.2, 34.0 |
| F29 | 30-60% | 40-70% | 0.50 | 94.8 | 96.2 | 1.8*, 24, 2*, 30, 32.8 |
| F30 | 30-60% | 40-70% | 0.75 | 95.5 | 95.2 | 31, 29.0 22.0, 27.0, 23.0 |
| F31 | 30-60% | 40-70% | 0 | 97.6 | 96.29 | 49.7, 50.5, 12.3, 51.5, 4.6* |
| F32 | 30-60% | 40-70% | 0.5 | 97.3 | 95.1 | 56.0, 39.2, 57.1, 40.4 3.0* |
| F33 | 30-60% | 40-70% | 5 | 98.4 | 95.92 | 58.1, 39.8 51.2, 46.0, 52.7 |
| F34 | 30-60% | 40-70% | 10 | 97.2 | 96.1 | 46.3, 45.8, 57.7, 4.3* 54.1 |
| F35 | 30-60% | 40-70% | 15 | 101 | 95.2 | 54.3, 53.6 56.1, 53.0, 57.2 |
| F36 | 30-60% | 40-70% | 0 | 93.1 | 92.45 | 44.7, 48.6 47.3, 3.2* 49.2 |
| F37 | 30-60% | 40-70% | 0.5 | 87.8 | 94.09 | 39.3, 18.2 53.9, 40.2, 33.5 |
| F38 | 30-60% | 40-70% | 5 | 92.4 | 93.68 | 50.4, 49.4, 50.2, 48.8, 48.7 |
| F39 | 30-60% | 40-70% | 10 | 88.2 | 94.29 | 7.1*, 44.7, 2.9*, 58.5, 50.1 |
| F40 | 30-60% | 40-70% | 15 | 87.1 | 97.05 | 48.4, 44.0, 38.3, 49.2, 48.8 |
| F41 | 30-60% | 40-70% | 0 | 86.9 | 82.7 | N/A |
| F42 | 30-60% | 40-70% | 0.5 | 85.7 | 85.4 | N/A |
| F43 | 30-60% | 40-70% | 0.5 (in drug product ("DP")) Buffer) | 95.6 | 88.3 | N/A |

*indicates missed injection/incomplete dose. All LNPs of Table 6 were administered to wild type C57BL/6 female mice (n = 5) and the % editing in liver are tabulated. Total RNA dose: 0.5 or 2 mg/kg.

TABLE 7

% of entrapped PEG400 in the LNPs with respect to the amount of PEG400 used for constituting the LNPs selected from Table 6.

| Sample | PEG400 added to the formulation (mg) | Measured % of entrapped PEG400 post formulation |
|---|---|---|
| F27 | 0 | 0 |
| F28 | 0.25 | 20 |
| F29 | 0.5 | 30 |
| F30 | 0.75 | 33 |
| F31 | 0 | 0 |
| F32 | 0.5 | 24 |
| F33 | 5 | 8.9 |
| F34 | 10 | 16.4 |
| F35 | 15 | 25.2 |
| F36 | 0 | 0 |
| F37 | 0.5 | 14 |
| F38 | 5 | 30 |
| F39 | 10 | 26 |
| F40 | 15 | 13.3 |

The % encapsulation of PEG400 of Table 7 was measured by using HPLC. HPLC peak-area of the preformulated and entrapped PEG400 were used to calculate the % encapsulation.

The stability of LNPs formulated with PEG400, especially after storage at 2-8° C. or at −80° C. Addition of PEG400 to payloads increases the encapsulation efficiency and improves LNP stability after freeze-thaw cycles and/or storage. The freezing buffer is a buffer with pH in the range of 6.5-8.5 and a concentration in the range of 10-100 mM. In some instances, it contains 0-50 (w/w) % PEG400. 0-100 freeze thaw cycles are conducted and are described using the following nomenclature: $T_0$ indicates a sample prior to freezing, and $T_x$ is the sample following x number of freeze thaw cycles. In some instances, the number of freeze thaw cycles is 3, indicated by the symbol $T_3$.

TABLE 8

Figure 3:
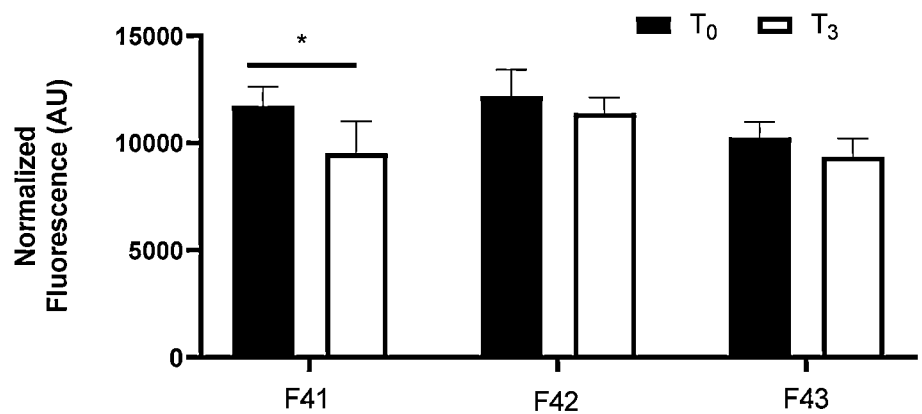
FIG. 3 illustrates the GFP mRNA loaded LNPs (identical in lipid composition and freezing buffer, but differing in the presence and location of PEG400) were applied to HUH7 human liver cell line in both never-frozen and post three freeze/thaw cycle aliquots. GFP fluorescence was measured 72 hours later. PEG400 containing formulations demonstrated no decrease in GFP expression and mRNA delivery efficacy after three freeze/thaw cycles, while the formulation without PEG400 experienced a loss of delivery efficacy.
Figure 4:
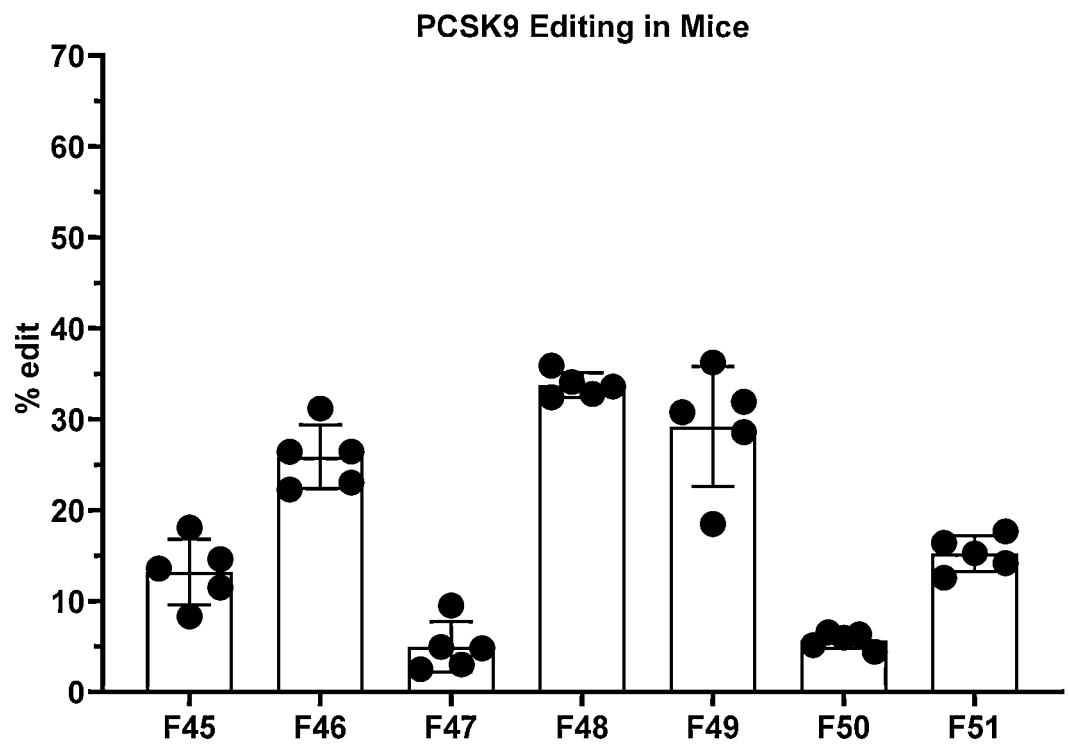
FIG. 4 illustrates PCSK9 gene editing in mouse hepatocytes in wild type C57BL/6 female mice for LNPs F45-F51 (n=5) at doses given in Tables 9 and 10, and described in Example 14.
Figure 5:
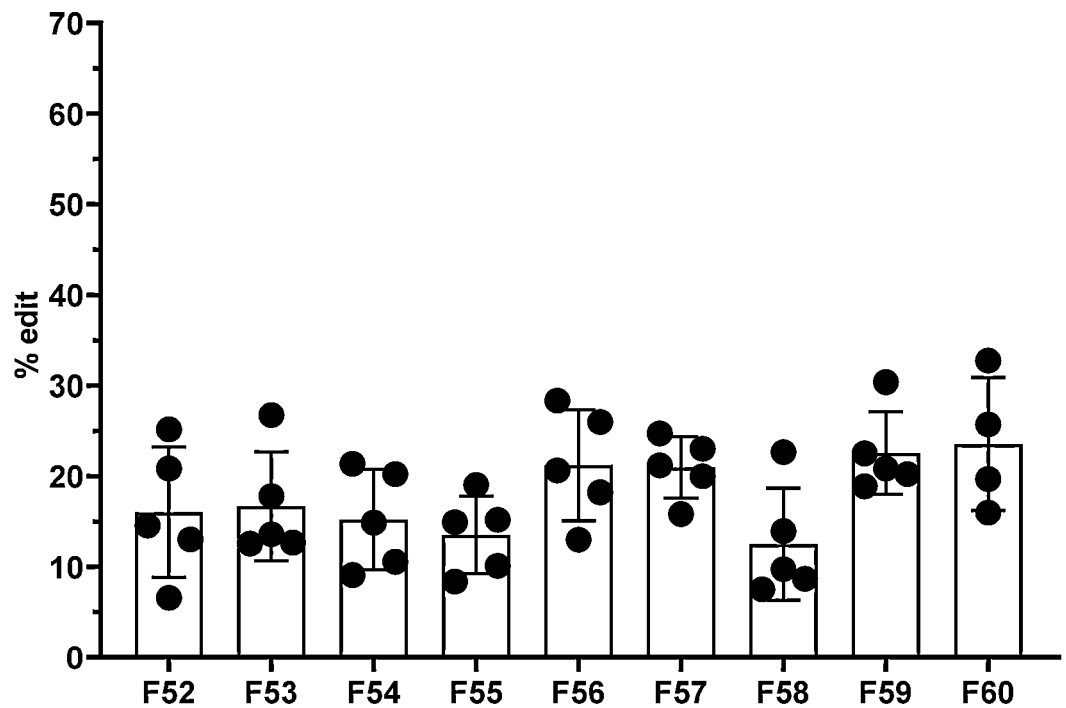
FIG. 5 illustrates PCSK9 gene editing in mouse hepatocytes in wild type C57BL/6 female mice (n=5) for LNPs F52-F60 at doses given in Tables 9 and 10, and described in Example 14. Doses and cargos can be found in those tables.
Figure 6:
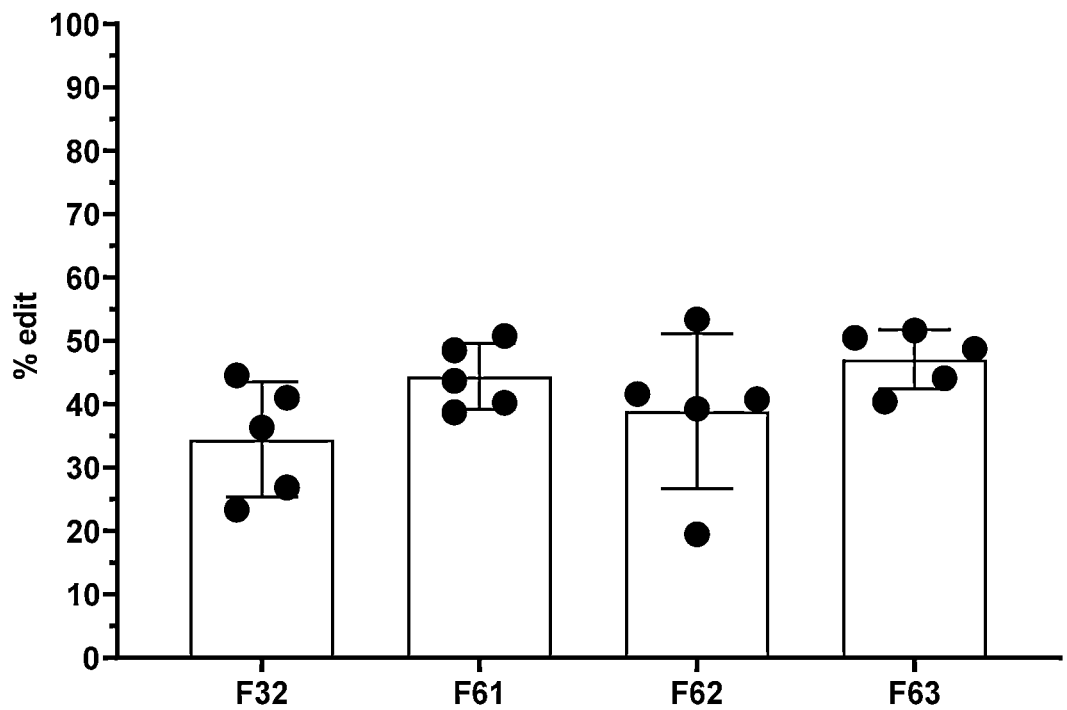
FIG. 6 illustrates PCSK9 gene editing in mouse hepatocytes in wild type C57BL/6 female mice (n=5) for LNPs F32, F61, F62, F63 at doses given in Tables 9 and 10, and described in Example 14. Doses and cargos can be found in those tables.
Figure 7:
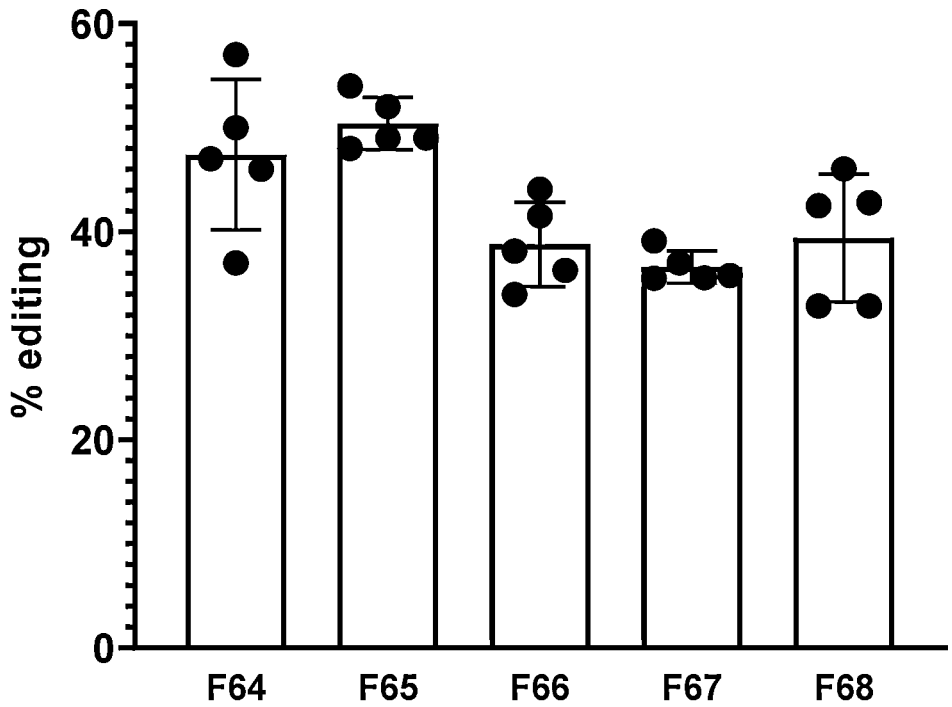
FIG. 7 illustrates PCSK9 gene editing in mouse hepatocytes in wild type C57BL/6 female mice (n=5) for LNPs F64-F68 at doses given in Tables 9 and 10, and described in Example 14. Doses and cargos can be found in those tables
Figure 8:
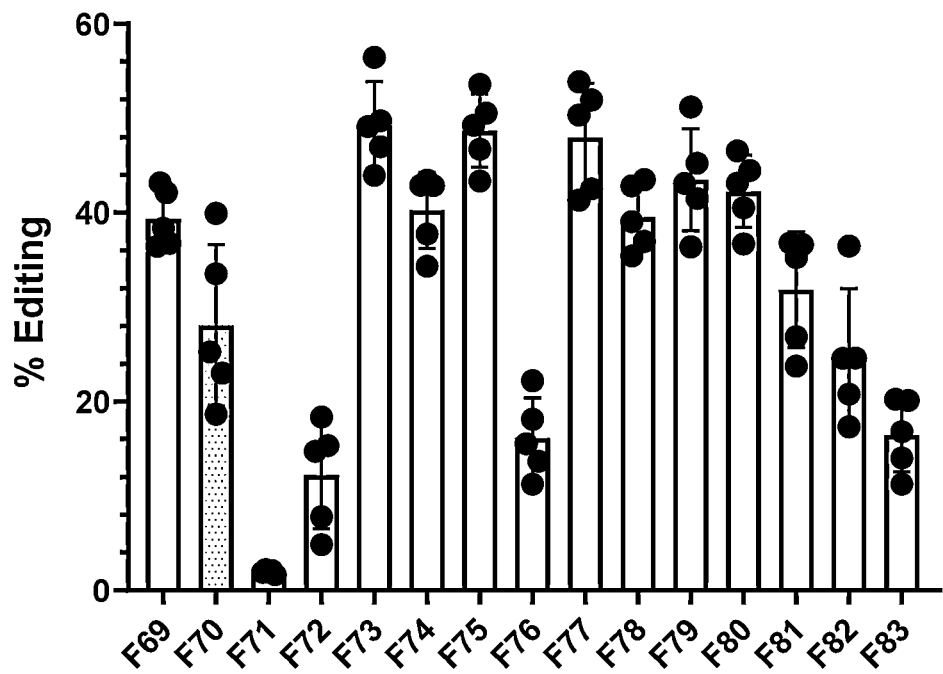
FIG. 8 illustrates PCSK9 gene editing in mouse hepatocytes in wild type C57BL/6 female mice (n=5) for LNPs F69-F83 at doses given in Tables 9 and 10, and described in Example 14. Doses and cargos can be found in those tables. All LNPs were intravenously administered (RO) to wild type C57BL/6 female mice (n=5).
Figure 9:
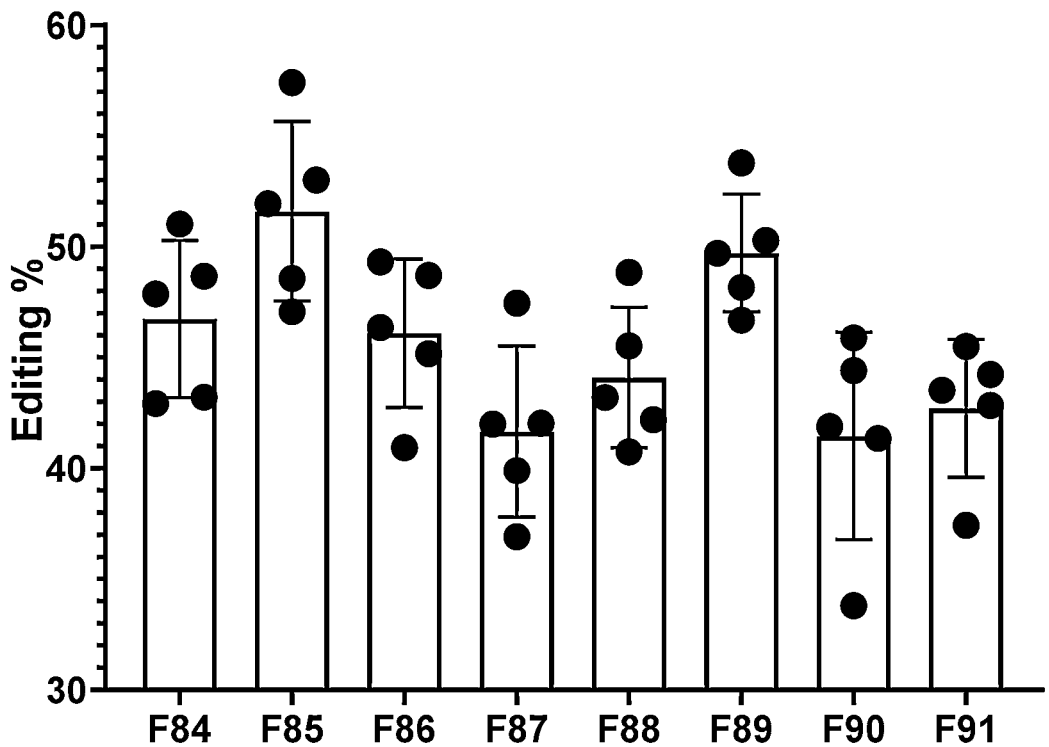
FIG. 9 illustrates PCSK9 gene editing in mouse hepatocytes in wild type C57BL/6 female mice (n=5) for LNPs F84-F91 at doses given in Tables 9 and 10, and described in Example 14.
Figure 10:
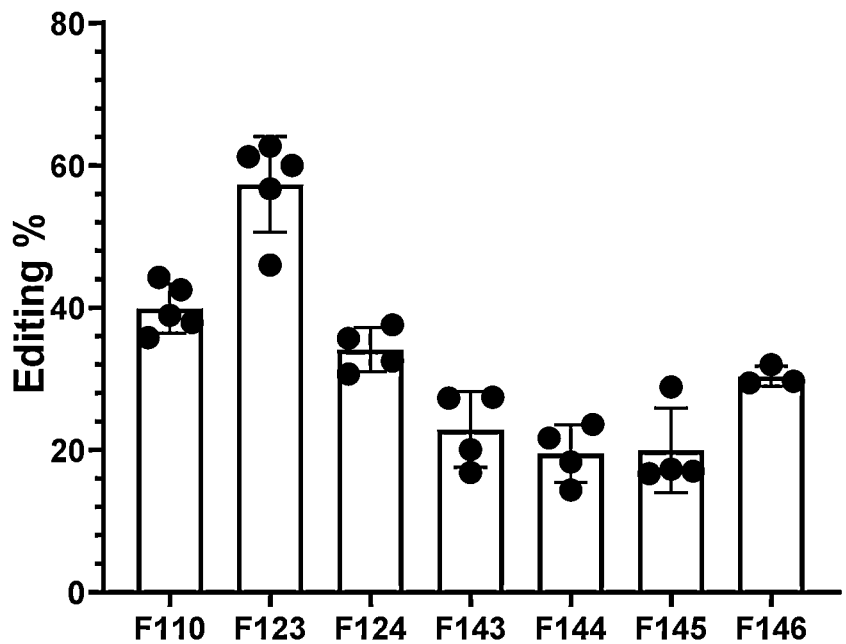
FIG. 10 illustrates PCSK9 gene editing in mouse hepatocytes in wild type C57BL/6 female mice (n=3-5) for F110, F123, F124, and F143-F146 at doses given in Tables 9 and 10, and described in Example 14.
Figure 11:
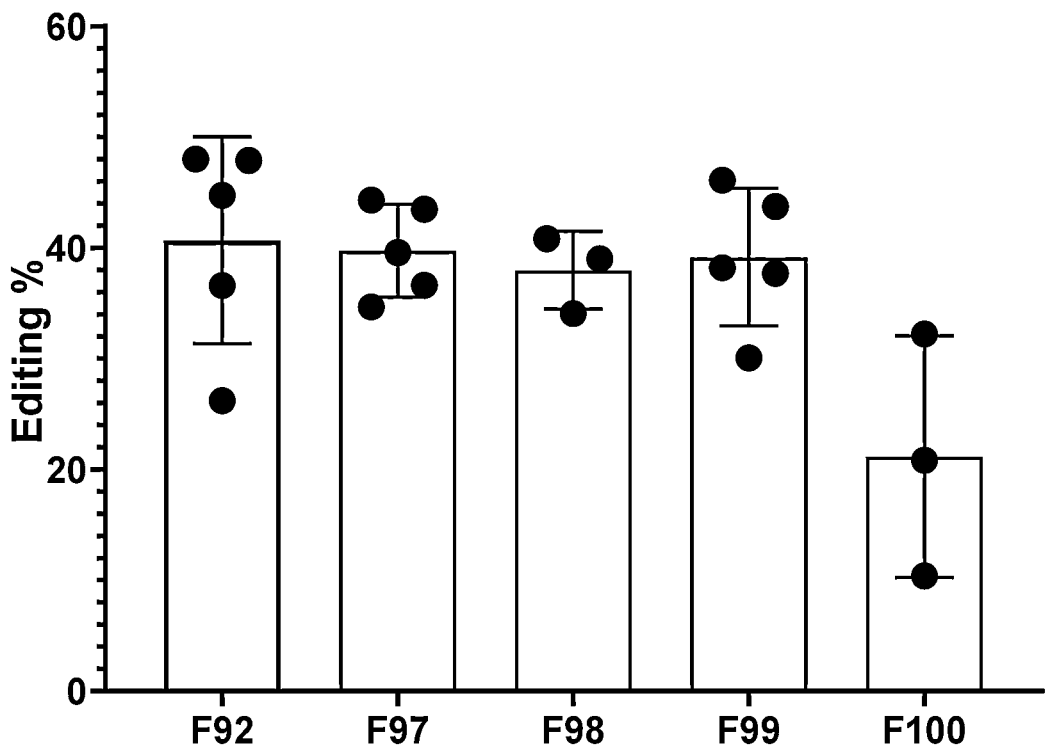
FIG. 11 illustrates PCSK9 gene editing in mouse hepatocytes in wild type C57BL/6 female mice (n=5) for LNPs F92 and F97-F100 at doses given in Table 11 and Example 15.
Figure 12:
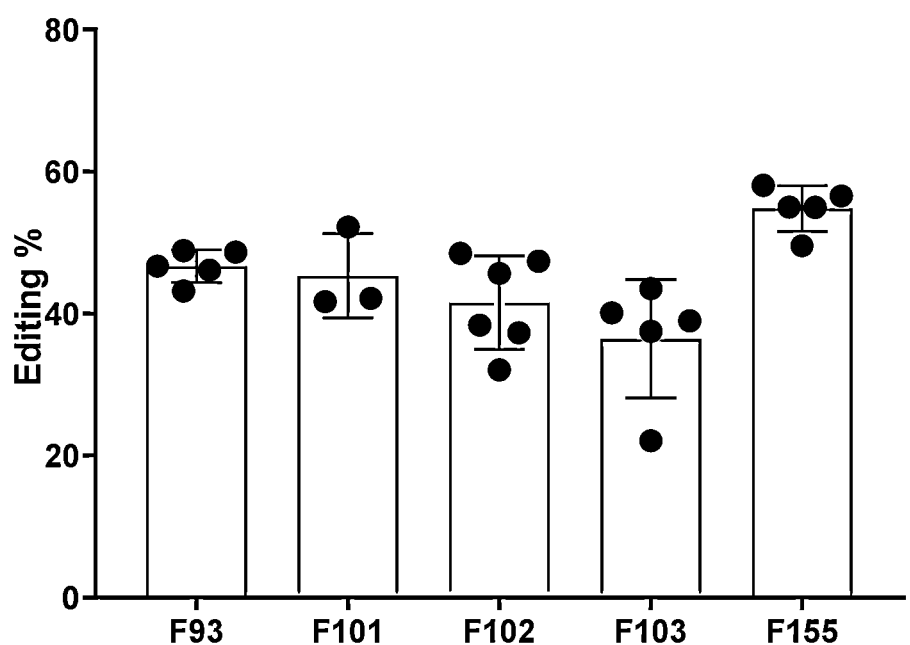
FIG. 12 illustrates PCSK9 gene editing in mouse hepatocytes in wild type C57BL/6 female mice (n=5) for LNPs F93, F101-F103 and F155 at doses given in Table 12 and as described in Example 16. All LNPs were intravenously administered (RO) to wild type C57BL/6 female mice (n=3-5).
Figure 13:
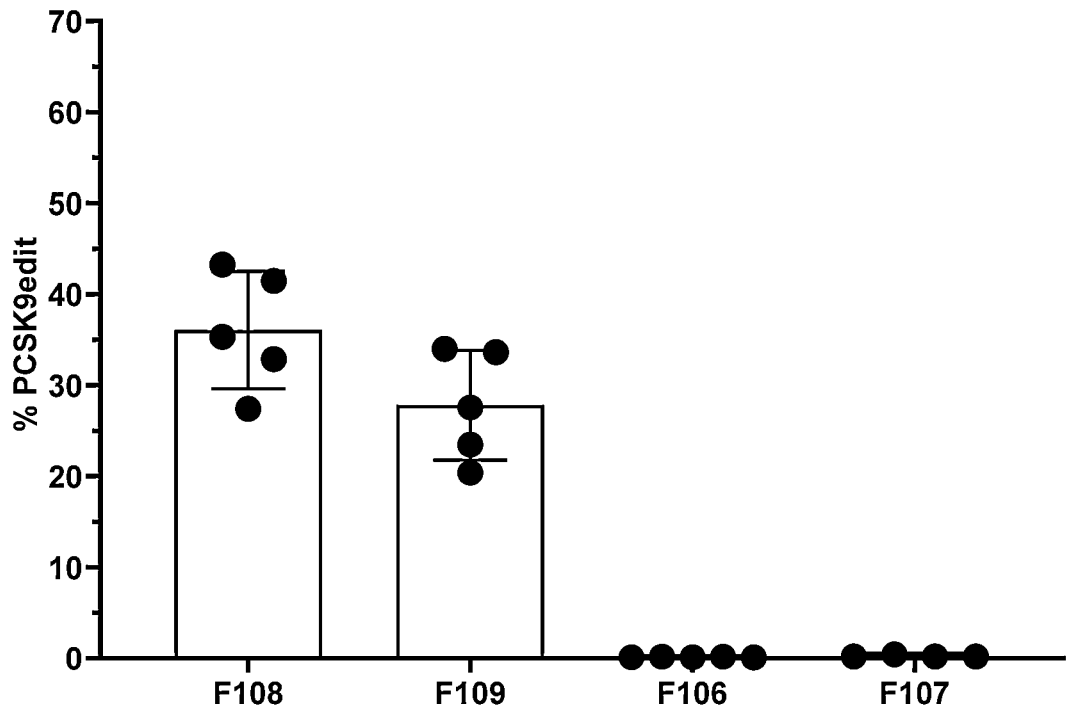
FIG. 13 illustrates PCSK9 gene editing at hepatocytes in wild type C57BL/6 female mice (n=5) at 1 mg/kg total RNA dose for LNPs F106-109 as described in Table 15 and 16. All LNPs were intravenously administered (RO) to wild type C57BL/6 female mice (n=5).
Figure 14:
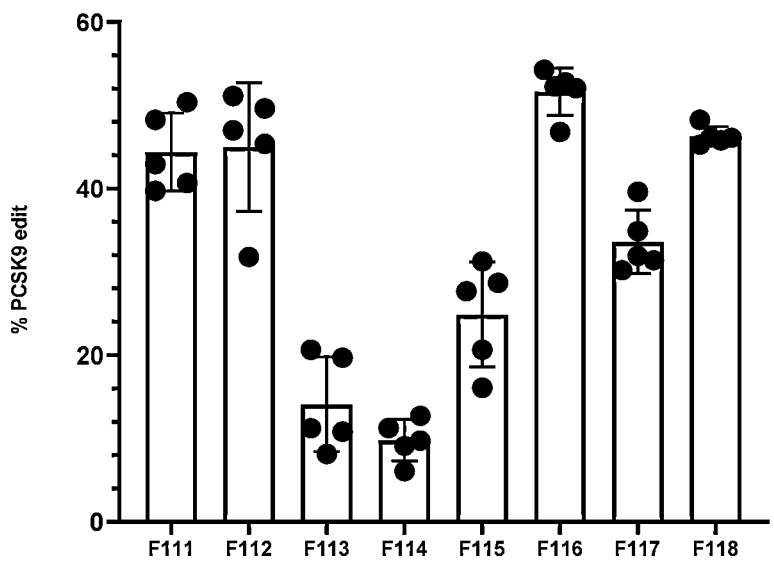
FIG. 14 illustrates PCSK9 gene editing at mouse hepatocytes in wild type C57BL/6 female mice (n=5) at 0.5 mg/kg total RNA dose for LNPs F111-118 as described in Table 15 and 16. All LNPs were intravenously administered (RO) to wild type C57BL/6 female mice (n=5).

Characterization results for LNPs described in Table 6 and FIG. 3 after 0 and 3 freeze/thaw cycles. The LNPs were stored at −80° C..

| | Before Freezing | | | After 3 freeze-thaw cycle | | |
|---|---|---|---|---|---|---|
| LNP | Mean diameter (nm) | PDI* | % RNA entrapment | Mean diameter (nm) | PDI* | % RNA entrapment |
| F41 | 86.9 | 0.0029 | 82.7 | 85 | 0.09 | 81.1 |
| F42 | 85.7 | 0.04 | 85.4 | 88.3 | 0.05 | 82.5 |
| F43 | 95.6 | 0.09 | 88.3 | 95.8 | 0.11 | 82.9 |

*PDI: polydispersity index

The PEG400 in a range of 0-50 w/w % with respect to the weight of the drug substance buffer was mixed with the drug substance (mRNA plus gRNA) in aqueous buffer prior to mixing with lipid excipients in ethanol to constitute the LNPs, and the produced LNPs were divided in to two halves. The first half was stored in a cold room condition (2-8° C.) and the second half was frozen and stored at −80° C. The frozen LNPs were thawed in a range of 0-50 cycles. Z-average size, mRNA encapsulation percentage, RNA degradation through gel electrophoresis, and RNA stability through HPLC methods were measured. The HPLC methods used were an ion-pairing reverse phase high performance liquid chromatography with evaporative light scattering detection (IP-RPLC-HPLC-ELSD) to quantify the % of PEG400 in each sample with respect to the input amount. The LNPs frozen and stored at −80° C. were thawed and intravenously administered to wild-type C57BL/6 female mice to evaluate gene editing. The corresponding LNPs stored at the cold room temperature was used as references for each frozen LNP formulation. The corresponding PEG400 free LNP are used as controls for both −80° C. and cold-room storage.

Example 12. In Vitro Evaluation of LNPs Stored at −80° C.

In vitro editing of efficiency of the LNPs constituted with PEG400 stored at −80° C. after thawing are incubated with both immortalized cell lines and primary cells from mouse, rat, non-human primate, and human in the presence and in the absence of ApoE in the incubating media to evaluate editing efficiency. The corresponding cold-room stored LNPs are used as reference for the study. The % editing were determined using Next Generation Sequencing (NGS) and analysis of editing efficiency as described in Example 13.

In some instances, multiple solutions of identical lipid composition are formulated to obtain the desired LNPs. In some instances, the cargo is mRNA encoding for eGFP. In other instances, the cargo is Cas9 mRNA and guide RNA for gene editing. Some of the LNPs include 0.001-50 (w/w) % PEG400 in the drug substance buffer while at least one other LNP does not include PEG400. The LNP containing PEG400 is split into at least two fractions, which are then buffer exchanged into freezing buffer, freezing buffer containing 0.05-50 w/w % PEG400, or PBS. The LNP without PEG400 is split into at least three fractions, which are then buffer exchanged into freezing buffer, freezing buffer containing 0.05-50 w/w % PEG400, or PBS. Each LNP and buffer combination is split into at least two samples, with one sample held at 2-8° C. ($T_0$) while the other is frozen at −80° C. The samples at −80° C. are thawed and frozen a total of 1-50 times ($T_x$). Cells are then plated at an appropriate density per well in a 96 well plate and a given dose of mRNA encapsulated in each LNP is delivered to cells (N greater than or equal to 3 wells). GFP expression is measured using a plate reader 24-72 hours after cells are dosed with LNPs. We have demonstrated in some instances that although all samples were in a freezing buffer, the LNPs without PEG400 in either the drug substance buffer or the freezing buffer demonstrated a statistically significant loss in GFP expression between the unfrozen $T_0$ samples and the freeze/thaw cycle T3 samples. PEG400 improved RNA stability and functionality by its inclusion in the freezing or drug substance buffers, as those LNPs did not suffer a loss of efficacy between the 3 freeze/thaw cycles.

In Vitro Transfection

Primary hepatocytes. Primary human liver hepatocytes (PHH), primary cynomolgus liver hepatocytes (PCH), or primary mouse liver hepatocytes (PMH) from BioIVT were cultured per the manufacturer's protocol. In brief, the cells were thawed and resuspended in hepatocyte thawing medium followed by centrifugation at 100 g for 10 min at 4° C. The supernatant was discarded, and the pelleted cells resuspended in hepatocyte plating medium. Each vial contains ~5 million cells that were used for plating one 24-well plate. Plated cells were allowed to settle and adhere for 4-6 h in a tissue culture incubator at 37° C. under 5% CO2 atmosphere. After incubation, cells were checked for monolayer formation. The incubating media were then replaced with fresh hepatocyte maintenance media (complete INVITROGRO medium obtained from BioIVT, the cell line provider). The cells thus became ready for transfection. MessengerMAX from Thermo Fisher is used for transfection. Solution A: desired amount of guide RNA is mixed with 1:1 wt ratio of mRNA in OptiMEM. Solution B: Messenger- MAX in OptiMEM. After mixing solutions A and B, the mixture was incubated at rt for 20 min. 60 μL of the incubated solution was added dropwise to each cell wells. The cells were then allowed to remain at 37° C. for 3 days. Cells were harvested and prepared for genomic DNA extraction using Thermo Kingfisher. Extracted genomic DNA was processed by PCR to analyze for gene editing. Amplified PCR product was then subjected to NGS (MiSeq).

gDNA Isolation

Genomic DNA was isolated from approximately 20 mL of monkey liver lysate using a bead-based extraction kit, MagMAX-96 DNA Multi-Sample Kit (Thermo-Fisher Scientific) on the KingFisher Flex automated extraction instrument (Thermo-Fisher Scientific) according to the manufacturer's protocols. Monkey liver was lysed using the FastPrep-24 system (MP Bio) according to the manufacturer's protocol. Livers were loaded into 2 mL lysing matrix tubes (MP Bio) with 0.5 mL of PBS. Extracted genomic DNA was stored at 4° C. until further use or at -80° C. for long term storage.

Example 13: In Vivo Evaluation of LNPs Stored at -80° C. in the Presence and in the Absence of PEG400

In vivo editing efficiency of the LNPs constituted in the presence and in the absence of PEG400 at cold-room temperature and the corresponding LNPs stored at -80° C. were determined as described in the Table 6.

In some instances, C57BL6 and LDLr-/- mice are used, with at least 3 animals per treatment group. Animals are injected via intravenous or retroorbital administration, with doses ranging from 0.05 mg/kg to 2 mg/kg. Mice are then sacrificed after 0-14 days, tissues harvested and processed, and the liver analyzed by Next Generation Sequencing for editing in the target gene. In some instances, LNPs contain commercially or internally produced Cas9 mRNA and relevant guide RNA. In most instances the endpoint of the experiment is liver editing percentage in the target gene.

Identical lipid composition LNPs are formulated with 0-50 (w/w) % PEG400. They are either then buffer exchanged into PBS or into freezing buffer, and then stored at either 2-8° C. or -80° C. LNPs are then injected into mice as described above and the livers are harvested and analyzed for liver editing percentage.

LNPs formulated with 0-50 (w/w) % PEG400 are subjected to 0-50 freeze/thaw cycles. They then are injected into mice and the livers are analyzed for liver editing percentage. The stability of LNPs formulated with 0-50 (w/w) % PEG400 are monitored for RNA degradation and structural integrity from 0 minutes to 52 weeks after formulation at 2-8° C. or -80° C.

Gene editing activity of a number of formulated LNPs from Examples 10-23 were evaluated in wild-type rodent models and in non-human primates.

Mice were treated in accordance with institutional ethical guidelines of animal care, handling, and termination. Mice were kept in a pathogen-free facility, with free access to standard chow and water. Mice were dosed with test articles or PBS as a vehicle by retro-orbital route according to their bodyweight. Relevant tissues were collected post dosed fifth or sixth day. Genomic DNA was extracted, and percent editing of target sequence was evaluated by next-generation sequencing to determine editing efficiency and the results are depicted in FIGS. 4-18.

Genomic DNA Isolation

Genomic DNA was isolated from approximately 20 μL of whole mouse liver lysate using a bead-based extraction kit, MagMAX-96 DNA Multi-Sample Kit (Thermo-Fisher Scientific) on the KingFisher Flex automated extraction instrument (Thermo-Fisher Scientific) according to the manufacturer's protocols. Mouse whole liver was lysed using the FastPrep-24 system (MP Bio) according the to manufacturer's protocol. Livers were loaded into 2 mL lysing matrix tubes (MP Bio) with 0.5 mL of PBS. Extracted genomic DNA was stored at 4° C. until further use or at -80° C. for long term storage.

Next Generation Sequencing (NGS) and Analysis of Editing Efficiency

Next generation sequencing, or deep sequencing, was performed on the region of interest to determine the extent of gene editing. Samples were prepared using the Nextera XT DNA library preparation kit (Illumina) according to the manufacturer's protocol. Briefly, two rounds of PCR were performed first to amplify the region of interest and second to add DNA sequences required for deep sequencing and sample identification to the initial product. The final amplicon was sequenced on the Illumina MiSeq instrument according to the manufacturer's protocol.

Paired-end reads were analyzed with the CRISPResso2 pipeline (https://www.nature.com/articles/s41587-019-0032-3). Briefly, low-quality reads were filtered out, adapter sequences were trimmed from the reads, and the paired-end reads were merged and aligned to the amplicon sequence. The editing percentage was calculated as the number of reads supporting an insertion or a deletion, over the total number of aligned reads. For Cas9, the editing percentage was calculated as the number of reads supporting an insertion or a deletion, over the total number of aligned reads. For ABE, the editing percentage was estimated from the A to G modifications over the editing window.

Paired-End Reads were Analyzed with the CRISPResso2 Pipeline (https://www.nature.com/articles/s41587-019-0032-3).

Briefly, low-quality reads were filtered out, adapter sequences were trimmed from the reads, and the paired-end reads were merged and aligned to the amplicon sequence. The editing percentage was calculated as the number of reads supporting an insertion or a deletion, over the total number of aligned reads. For Cas9, the editing percentage was calculated as the number of reads supporting an insertion or a deletion, over the total number of aligned reads. For ABE, the editing percentage was estimated from the A to G modifications over the editing window.

Next Generation Sequencing (NGS) and Analysis of Editing Efficiency

Next generation sequencing (NGS), or deep sequencing, was performed on the region of interest to determine the extent of gene editing. Samples were prepared using the Nextera XT DNA library preparation kit (Illumina) according to the manufacturer's protocol. Briefly, two rounds of PCR were performed first to amplify the region of interest and second to add DNA sequences required for deep sequencing and sample identification to the initial product. The final amplicon was sequenced on the Illumina MiSeq instrument according to the manufacturer's protocol. Paired-end reads were analyzed with the CRISPResso2 pipeline (see Clement, K., Rees, H., Canver, M. C. et al. CRISPResso2 provides accurate and rapid genome editing sequence analysis. Nat Biotechnol 37, 224-226 (2019). Briefly, low-quality reads were filtered out, adapter sequences were trimmed from the reads, and the paired-end reads were merged and aligned to the amplicon sequence.

The editing percentage was calculated as the number of reads supporting an insertion or a deletion, over the total number of aligned reads. For Cas9, the editing percentage was calculated as the number of reads supporting an insertion or a deletion, over the total number of aligned reads.

Example 14. Preparation of LNPs F45-F91, F94-F96, F110, F123-F125, and F143-F150

General preparation method of LNPs F45-F91, F94-F96, F110, F123-F125, and F143-F150.

Lipids were dissolved in ethanol. The ionizable lipid was included in the LNP at a final molar ratio between 40%-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12.

The lipid mixture was combined with a 0.5% PEG400 (Millipore Sigma) in 50 mM sodium citrate buffer (pH 4.0-6.0) containing SpCas9 mRNA and gRNA (1:1), or ABE mRNA and guide RNA (at ratios 2:1, 3:1, 6:1, 1:1, 1:2, 1:3, or 1:6) at an aqueous to ethanol ratio of 3:1 using a microfluidic mixer. In some instances, the mixer is a Nano-assemblr (Precision Nanosystems). In some cases, the mixer is a T mixer. In some instances, it is a cross mixer. In some instances, the aqueous to ethanol ratio is 2:1.

LNPs were collected at either 8.25% or 16.5% final ethanol volume and were held for 1 hr before being buffer exchanged into PBS or Tris buffer, using PD-10 column (GE Healthcare), dialysis, or Tangential Flow Filtration (TFF) process. In some cases, LNPs were collected at 16.5% ethanol and then diluted to 8.25% ethanol either immediately post formulation or after the 1 hour hold time, before being buffer exchanged. In some instances, formulations were concentrated using Amicon ultra centrifugal filters (100 kDa) and passed through a 0.2 μm filter to afford LNPs. Size and RNA entrapment efficiency of LNPs was done as described in Example D11.

Example LNPs are described in more detail in Table 9 and Table 10. F66-F68, F94, F95, and F123 formulations were made using cross mixing or T mixing. F52-F58 constitute ABE mRNA to guide RNA at ratios 2:1, 3:1, 6:1, 1:1, 1:2, 1:3, or 1:6. F65 was formulated like F64 but with 506 as the stealth-lipid. F69-F83 and F147-F150 constitute a Design of Experiment (DOE) exploring the formulation mol % space. The DoE was designed using JMP software.

LNP liver editing is graphed in FIGS. 4-10 and FIG. 17.

TABLE 9

Composition of LNPs prepred for evaluation.

| LNP | mRNA | gRNA | Dose (mg/kg) | Amino lipid 502 mol % | Structural Lipid (cholesterol) mol % | Helper Lipid (DSPC) mol % | Stealth Lipid* Mol % | N:P | PEG400 w/w % |
|---|---|---|---|---|---|---|---|---|---|
| F45 | MS004 | GA055 | 0.25 | 47.1 | 47.45 | 4.7 | 0.75 | 4.5 | 0.5 |
| F46 | MS004 | GA055 | 0.25 | 47.1 | 46.95 | 4.7 | 1.25 | 4.5 | 0.5 |
| F47 | MS004 | GA055 | 0.25 | 40 | 53.2 | 4.7 | 2.1 | 8 | 0.5 |
| F48 | MS004 | GA055 | 0.25 | 55 | 37.2 | 4.7 | 2.1 | 8 | 0.5 |
| F49 | MS004 | GA055 | 0.25 | 47 | 46.2 | 4.7 | 2.1 | 8 | 0.5 |
| F50 | MS004 | GA055 | 0.25 | 40 | 53.2 | 4.7 | 2.1 | 4.5 | 0.5 |
| F51 | MS004 | GA055 | 0.25 | 55 | 37.2 | 4.2 | 2.1 | 4.5 | 0.5 |
| F52 | MA002 | GA256 | 0.05 | 47.1 | 46.1 | 4.7 | 2.1 | 4.5 | 0.5 |
| F53 | MA002 | GA256 | 0.05 | 47.1 | 46.1 | 4.7 | 2.1 | 4.5 | 0.5 |
| F54 | MA002 | GA256 | 0.05 | 47.1 | 46.1 | 4.7 | 2.1 | 4.5 | 0.5 |
| F55 | MA002 | GA256 | 0.05 | 47.1 | 46.1 | 4.7 | 2.1 | 4.5 | 0.5 |
| F56 | MA002 | GA256 | 0.05 | 47.1 | 46.1 | 4.7 | 2.1 | 4.5 | 0.5 |
| F57 | MA002 | GA256 | 0.05 | 47.1 | 46.1 | 4.7 | 2.1 | 4.5 | 0.5 |
| F58 | MA002 | GA256 | 0.05 | 47.1 | 46.1 | 4.7 | 2.1 | 4.5 | 0.5 |
| F59 | MA002 | GA255 | 0.05 | 47.1 | 46.1 | 4.7 | 2.1 | 4.5 | 0.5 |
| F60 | MA002 | GA257 | 0.05 | 47.1 | 46.1 | 4.7 | 2.1 | 4.5 | 0.5 |
| F32 | MS004 | GA055 | 0.25 | 47.1 | 46.1 | 4.7 | 2.1 | 4.5 | 0.5 |
| F61 | MS004 | GA055 | 0.25 | 55 | 38.2 | 4.7 | 2.1 | 8 | 0.5 |
| F62 | MS004 | GA055 | 0.25 | 55 | 38.2 | 4.7 | 2.1 | 6 | 0.5 |
| F63 | MS004 | GA055 | 0.25 | 47.1 | 46.1 | 4.7 | 2.1 | 6 | 0.5 |
| F64 | MS004 | GA055 | 0.5 | 47.1 | 46.1 | 4.7 | 2.1 | 4.5 | 0.5 |
| F65 | MS004 | GA055 | 0.5 | 47.1 | 46.1 | 4.7 | 2.1 | 4.5 | 0.5 |
| F66 | MS002 | GA010 | 2 | 47.1 | 46.1 | 4.7 | 2.1 | 4.5 | 0.5 |
| F67 | MS002 | GA010 | 2 | 47.1 | 46.1 | 4.7 | 2.1 | 4.5 | 0.5 |
| F68 | MS002 | GA010 | 2 | 47.1 | 46.1 | 4.7 | 2.1 | 4.5 | 0.5 |
| F69 | MS004 | GA055 | 0.25 | 62.9 | 30.3 | 4.7 | 2.1 | 8 | 0.5 |
| F70 | MS004 | GA055 | 0.25 | 47.1 | 46.1 | 4.7 | 2.1 | 8 | 0.5 |
| F71 | MS004 | GA055 | 0.25 | 47.1 | 30.3 | 20.5 | 2.1 | 8 | 0.5 |
| F72 | MS004 | GA055 | 0.25 | 55 | 30.3 | 12.6 | 2.1 | 8 | 0.5 |
| F73 | MS004 | GA055 | 0.25 | 55 | 38.2 | 4.7 | 2.1 | 8 | 0.5 |
| F74 | MS004 | GA055 | 0.25 | 47.1 | 38.2 | 12.6 | 2.1 | 8 | 0.5 |
| F75 | MS004 | GA055 | 0.25 | 52.37 | 35.57 | 9.96 | 2.1 | 8 | 0.5 |
| F76 | MS004 | GA055 | 0.25 | 55 | 30.3 | 12.6 | 2.1 | 6 | 0.5 |
| F77 | MS004 | GA055 | 0.25 | 55 | 38.2 | 4.7 | 2.1 | 6 | 0.5 |
| F78 | MS004 | GA055 | 0.25 | 47.1 | 38.2 | 12.6 | 2.1 | 6 | 0.5 |
| F79 | MS004 | GA055 | 0.25 | 52.37 | 35.57 | 9.96 | 2.1 | 6 | 0.5 |
| F80 | MS004 | GA055 | 0.25 | 55 | 37.3 | 4.7 | 3 | 8 | 0.5 |
| F81 | MS004 | GA055 | 0.25 | 55 | 37.3 | 4.7 | 3 | 6 | |
| F82 | MS004 | GA055 | 0.25 | 55 | 38.2 | 4.7 | 2.1 | 8 | 0.5 |
| F83 | MS004 | GA055 | 0.25 | 47.1 | 46.1 | 4.7 | 2.1 | 8 | 0.5 |
| F84 | MA004 | GA256 | 0.05 | 55 | 38.2 | 4.7 | 2.1 | 8 | 0.5 |
| F85 | MA004 | GA256 | 0.05 | 55 | 38.2 | 4.7 | 2.1 | 8 | 0.5 |

TABLE 9-continued

Composition of LNPs prepred for evaluation.

| LNP | mRNA | gRNA | Dose (mg/kg) | Amino lipid 502 mol % | Structural Lipid (cholesterol) mol % | Helper Lipid (DSPC) mol % | Stealth Lipid* Mol % | N:P | PEG400 w/w % |
|---|---|---|---|---|---|---|---|---|---|
| F86 | MA004 | GA256 | 0.05 | 55 | 38.2 | 4.7 | 2.1 | 8 | 0.5 |
| F87 | MA004 | GA256 | 0.05 | 55 | 38.2 | 4.7 | 2.1 | 8 | 0.5 |
| F88 | MA004 | GA256 | 0.05 | 55 | 37.8 | 4.7 | 2.5 | 8 | 0.5 |
| F89 | MA004 | GA256 | 0.05 | 55 | 37.3 | 4.7 | 3 | 8 | 0.5 |
| F90 | MA004 | GA256 | 0.05 | 55 | 36.8 | 4.7 | 3.5 | 8 | 0.5 |
| F91 | MA004 | GA256 | 0.05 | 55 | 36.3 | 4.7 | 4 | 8 | 0.5 |
| F94 | MS002 | GA055 | 0.5 | 47.1 | 46.1 | 4.7 | 2.1 | 4.5 | 0.5 |
| F95 | MS002 | GA055 | 0.5 | 47.1 | 46.1 | 4.7 | 2.1 | 4.5 | 0.5 |
| F96 | MA004 | GA256 | 0.05 | 55 | 38.2 | 4.7 | 2.1 | 8 | 0.5 |
| F110 | MS004 | GA055 | 0.5 | 47.1 | 46.1 | 4.7 | 2.1 | 4.5 | 0.5 |
| F123 | MS004 | GA055 | 0.5 | 55 | 38.2 | 4.7 | 2.1 | 8 | 0 |
| F124 | MS002 | GA010 | 2 | 47.1 | 46.1 | 4.7 | 2.1 | 4.5 | 0.5 |
| F125 | MA004 | GA256 | 0.05 | 55 | 38.2 | 4.7 | 2.1 | 8 | 0.5 |
| F143 | MS002 | GA010 | 2 | 47.1 | 43.95 | 6.85 | 2.1 | 4.5 | 0.5 |
| F144 | MS002 | GA010 | 2 | 47.1 | 48.45 | 2.35 | 2.1 | 4.5 | 0.5 |
| F145 | MS002 | GA010 | 2 | 47.1 | 46.1 | 4.7 | 2.1 | 6 | 0.5 |
| F146 | MS002 | GA010 | 2 | 47.1 | 46.1 | 4.7 | 2.1 | 8 | 0.5 |
| F147 | MS004 | GA055 | 0.25 | 52.37 | 34.67 | 9.96 | 3 | 8 | 0.5 |
| F148 | MS004 | GA055 | 0.25 | 49 | 39.5 | 9.4 | 2.1 | 8 | 0.5 |
| F149 | MS004 | GA055 | 0.25 | 52 | 38.9 | 7 | 2.1 | 8 | 0.5 |
| F150 | MS004 | GA055 | 0.25 | 50 | 36.9 | 11 | 2.1 | 8 | 0.5 |

Selected LNPs of Table 9 were intravenously administered (tail vein or RO) to wild type C57BL/6 female mice (n=5). Total RNA doses are as given in the table, along with mRNA and guide RNA. The N:P ratio range 3.5-10.0. Liver editing percent data for each LNP is graphed in FIGS. 4-10 and FIG. 17.

TABLE 10

Characterization of LNPs 5 descibed in Table 9 pre and post sterile filtration.

| LNP | Buffer Exchange Process | Concentration Process | DP Buffer | Mean diameter (nm) | Mean diameter post Sterile Filtration (nm) | PDI Post Formulation | PDI Sterile Filtration | % RNA Encapsulation |
|---|---|---|---|---|---|---|---|---|
| F45 | PD-10 | Amicon | PBS | 100 | 146 | 0.0724 | 0.0332 | 98.62 |
| F46 | PD-10 | Amicon | PBS | 98.2 | 126 | 0.0669 | 0.0521 | 97.77 |
| F47 | PD-10 | Amicon | PBS | 70 | 73.8 | 0.122 | 0.05 | 97.42 |
| F48 | PD-10 | Amicon | PBS | 93.8 | 122 | 0.0252 | 0.0382 | 94.63 |
| F49 | PD-10 | Amicon | PBS | 80.7 | 92.6 | 0.0482 | 0.0237 | 97.7 |
| F50 | PD-10 | Amicon | PBS | 66.9 | 86.2 | 0.123 | 0.0436 | 97.81 |
| F51 | PD-10 | Amicon | PBS | 89.4 | 148 | 0.0489 | 0.0797 | 86.33 |
| F52 | PD-10 | Amicon | PBS | 81.3 | 95.6 | 0.0682 | 0.1 | 96.82 |
| F53 | PD-10 | | PBS | 77.4 | 94.3 | 0.03 | 0.0595 | 95.95 |
| F54 | PD-10 | | PBS | 82.6 | 94 | 0.0749 | 0.0561 | 96.38 |
| F55 | PD-10 | | PBS | 81.7 | 94.3 | 0.0774 | 0.0385 | 95.769 |
| F56 | PD-10 | | PBS | 80.3 | 89 | 0.0548 | 0.0648 | 97.61 |
| F57 | PD-10 | | PBS | 80.2 | 87.3 | 0.0878 | 0.0143 | 97.78 |
| F58 | PD-10 | | PBS | 70.8 | 83.2 | 0.0525 | 0.0585 | 98.67 |
| F59 | PD-10 | Amicon | PBS | 79.1 | 92.2 | 0.0781 | 0.0683 | 97.82 |
| F60 | PD-10 | Amicon | PBS | 99.2 | 91.1 | 0.125 | 0.07 | 97.56 |
| F32 | PD-10 | Amicon | PBS | 87.47 | 101.8 | 0.08111 | 0.04155 | 96.54463 |
| F61 | PD-10 | Amicon | PBS | 106.3 | 139.5 | 0.05689 | 0.04 | 91.4516 |
| F62 | PD-10 | Amicon | PBS | 105.7 | 135.1 | 0.0374 | 0.0727 | 90.32308 |
| F63 | PD-10 | Amicon | PBS | 88.687 | 106.1 | 0.09242 | 0.06402 | 97.01425 |
| F64 | PD-10 | Amicon | Tris | 76.3 | 86.5 | 0.0516 | 0.0633 | 89.28 |
| F65 | PD-10 | Amicon | Tris | 79.9 | 95.6 | 0.06 | 0.0461 | 86.82 |
| F66 | PD-10 | Amicon | Tris | 89.2 | 94.8 | 0.11 | 0.0995 | 91.75 |
| F67 | TFF (Regenerated Cellulose) | TFF | Tris | 90.3 | 87.8 | 0.0605 | 0.00292 | 95.5 |
| F68 | TFF (Regenerated Cellulose) | TFF | Tris | 87.5 | 87.2 | 0.0731 | 0.0195 | 97.56 |
| F69 | PD-10 | | Tris | 111 | 141.6907 | 0.065 | 0.07 | 78.4 |
| F70 | PD-10 | | Tris | 86.4 | 83.29661 | 0.0916 | 0.0836 | 88.62 |
| F71 | PD-10 | | Tris | 72.7 | 80.61017 | 0.11 | 0.0186 | 92.09 |

TABLE 10-continued

Characterization of LNPs 5 descibed in Table 9 pre and post sterile filtration.

| LNP | Buffer Exchange Process | Concentration Process | DP Buffer | Mean diameter (nm) | Mean diameter post Sterile Filtration (nm) | PDI Post Formulation | PDI Sterile Filtration | % RNA Encapsulation |
|---|---|---|---|---|---|---|---|---|
| F72 | PD-10 | | Tris | 95.5 | 100.0551 | 0.07 | 0.087 | 88.97 |
| F73 | PD-10 | | Tris | 93.5 | 108.3305 | 0.07 | 0.0526 | 84.67 |
| F74 | PD-10 | | Tris | 79.4 | 80.716 | 0.144 | 0.0533 | 91.3 |
| F75 | PD-10 | | Tris | 86.8 | 96.402 | 0.057 | 0.0221 | 85.7 |
| F76 | PD-10 | | Tris | 101 | 100.9025 | 0.05 | 0.046 | 87.7 |
| F77 | PD-10 | | Tris | 94.2 | 97.62712 | 0.0435 | 0.059667 | 88.5 |
| F78 | PD-10 | | Tris | 81.6 | 97.91102 | 0.078 | 0.0553 | 87.25 |
| F79 | PD-10 | | Tris | 96.2 | 97.1822 | 0.0872 | 0.0536 | 87.39 |
| F80 | PD-10 | | Tris | 84.9 | 91.69068 | 0.07 | 0.022333 | 84.72 |
| F81 | PD-10 | | Tris | 83.6 | 89.73305 | 0.07 | 0.038667 | 80.82 |
| F82 | PD-10 | | Tris | 53.5 | 72.08 | 0.10 | 0.0325 | 91.08 |
| F83 | PD-10 | | Tris | | 76.95 | | 0.05 | 90.81 |
| F84 | Dialysis | | Tris | 107 | 115 | 0.14 | 0.0414 | 91.99 |
| F85 | Dialysis | | Tris | 102 | 116 | 0.0365 | 0.0283 | 93.8 |
| F86 | Dialysis | | Tris | 98.4 | 106 | 0.0595 | 0.0277 | 93.93 |
| F87 | Dialysis | | Tris | 62.1 | 86.9 | 0.156 | 0.0117 | 92.88 |
| F88 | Dialysis | | Tris | 101 | 96.2 | 0.144 | 0.067 | 92.88 |
| F89 | Dialysis | | Tris | 92.5 | 108 | 0.0809 | 0.047 | 93.17 |
| F90 | Dialysis | | Tris | 83 | 96.1 | 0.0267 | 0.0225 | 88.39 |
| F91 | Dialysis | | Tris | 79.8 | 88.5 | 0.0342 | 0.0156 | 90.6 |
| F94 | PD-10 | | Tris | 89 | 92 | 0.05 | 0.07 | 83.94 |
| F95 | PD-10 | | Tris | 83 | 83 | 0.09 | 0.07 | 85.97 |
| F96 | Dialysis | | Tris | 94.8 | 111 | 0.00586 | 0.00686 | 94.89 |
| F110 | TFF (Regenerated Cellulose) | TFF | Tris | | 84.28 | | 0.06117 | |
| F123 | TFF (Regenerated Cellulose) | TFF | Tris | 109 | 116 | 0.105 | 0.00776 | 92.3 |
| F124 | TFF (Regenerated Cellulose) | TFF | Tris | 87.6 | 85.4 | 0.05 | 0.04 | 94.9 |
| F125 | Dialysis | | | 97.1 | 87.2 | 0.0576 | 0.006 | 97.29 |
| F143 | PD-10 | | PBS | 71 | 97.3 | 0.0676 | 0.00411 | 95.92129 |
| F144 | PD-10 | Amicon | PBS | 68.9 | 98.2 | 0.0219 | 0.0284 | 96.17695 |
| F145 | PD-10 | Amicon | PBS | 70.9 | 91.9 | 0.0151 | 0.0118 | 98.22026 |
| F146 | PD-10 | Amicon | PBS | 73.8 | 89.6 | 0.0273 | 0.0141 | 98.50496 |
| F147 | PD-10 | | Tris | 83.7 | 102.58 | 0.108 | 0.036 | 91.24 |
| F148 | PD-10 | | Tris | 85.2 | 119.07 | 0.0789 | 0.017 | 95.16 |
| F149 | PD-10 | | Tris | 93.9 | 137.11 | 0.0759 | 0.067 | 93.95 |
| F150 | PD-10 | | Tris | 88.3 | 117.96 | 0.0728 | 0.01 | 94.69 |

Selected LNPs of Table 10 were intravenously administered (tail vein or RO) to wild type C57BL/6 female mice (n=5). The LNPs were formulated with drug substance buffer with a pH between 4.0 and 6. Total RNA doses are as given in the table, along with mRNA and guide RNA. Liver editing percent data for each LNP is graphed in FIGS. 4-10 and FIG. 17.

Example 15. General Preparation Method of LNPs F92 and F97-F100 Via iLipid N:P Ratio Lipids were dissolved in ethanol. mRNA and guide RNA (ABE mRNA and guide RNA (1:1)) or SpCas9 mRNA and gRNA (1:1) were added to 67 mM citrate buffer containing 0.67 wt %/o PEG400 to make 50 mM citrate buffer containing 0.5% PEG400. Ionizable lipid is added to the RNA containing citrate buffer in an amount to neutralize between 0.1-99% of the "P" (on an N:P basis) of the RNA. The resulting solutions were allowed to incubate for at least 15 minutes at room temperature.

Remaining lipids (the rest of the iLipid+helper lipid+structural lipid+stealth-Lipid) were dissolved in ethanol. The ionizable lipid was included in the LNP at a final molar ratio between 40%-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12.

The lipid mixture was combined with the RNA containing citrate buffer described above in an aqueous to ethanol ratio of 3:1 using a microfluidic mixer. In some instances, the mixer is a Nanoassemblr (Precision Nanosystems). In some cases, the mixer is a T mixer. In some instances, it is a cross mixer. In some instances, the aqueous to ethanol ratio is 2:1.

LNPs were collected at a final 16.5% ethanol volume and were held for 1 hr before being buffer exchanged into PBS or Tris buffer, using PD-10 column (GE Healthcare), dialysis, or Tangential Flow Filtration (TFF) process. In some cases, LNPs are collected at 16.5% ethanol and then diluted to 8.25% ethanol either immediately post formulation or after the 1 hour hold time, before being buffer exchanged. In some instances, formulations are concentrated using Amicon ultra centrifugal filters (100 kDa) and passed through a 0.2 µm filter to afford LNPs. Size and RNA entrapment efficiency of LNPs was done as described in Example 11.

In some instances, citrate buffer constitutes one stream while a portion of the amino lipid sufficient to neutralize 0.1-90% on an N:P basis, all mRNA, and all guide RNA are in the other stream. They are mixed using a mixer (microfluid, T mixer, cross mixer, etc.). The resultant solution is then the aqueous stream in the next mixing event, where the remaining lipids constitute the lipid stream. The two streams are mixed using a mixer. The resulting LNP is then held for an hour, buffer exchanged into Tris or PBS via dialysis, PD-10, or TFF, and then injected into mice.

Example LNPs are described in Table 11. LNP liver editing is graphed in FIG. 11. F92, F97, F98, F99, and F100 had 10%, 15%, 25%, 50%, and 75% neutralization on an NP basis respectively.

TABLE 11

LNP composition and characterization of LNPs F92 and F97-F100 in wild type C57BL/6 mice.

| | mol % | | | | | | | | |
|---|---|---|---|---|---|---|---|---|---|
| | | | | Stealth-Lipid | | Mean diameter (nm) | | PDI | | % |
| | Amino lipid | Structural Lipid | Helper Lipid | (PEG-lipid from | | | | | | |
| LNP | 502 | (Cholesterol) | (DSPC) | Table 1B) | N:P | a | b | a | b | encapsulation |
| F92 | 55 | 38.2 | 4.7 | 2.1 | 8 | 95.7 | 103 | 0.04 | 0.00622 | 93.1 |
| F97 | 55 | 38.2 | 4.7 | 2.1 | 8 | 88.1 | 114 | 0.00695 | 0.023 | 87.53 |
| F98 | 55 | 38.2 | 4.7 | 2.1 | 8 | 87.5 | 113 | 0.0423 | 0.032 | 83.07 |
| F99 | 55 | 38.2 | 4.7 | 2.1 | 8 | 86.3 | 114 | 0.0602 | 0.002 | 70.33 |
| F100 | 55 | 38.2 | 4.7 | 2.1 | 8 | 83.5 | 124 | 0.102 | 0.0583 | 48.25 | a: Post formulation;

b: post sterile filtration.

Stealth Lipid: 507

All LNPs of Table 11 were intravenously administered (RO) to wild type C57BL/6 female mice (n=5), dose 05 mg/kg (total RNA), mRNA: MA004 and gRNA: GA256. Total RNA doses are as given in the table, along with mRNA and guide RNA. Amino lipid 502 was added to the RNA containing citrate buffer (before being mixed with the remaining lipid components) in an amount sufficient to neutralize 10%, 15%, 25%, 50%, and 75% respectively of the "P", (on an N:P basis) of the RNA, to generate F92, F97, F98, F99, F100 respectively. All formulations contain PEG400, 0.5 w/w %. The N:P ratio range 3.5-10.0 Liver editing percent data for each LNP is graphed in FIG. 11.

Example 16. General Preparation Method of LNPs F93, F101-F103, and F155 with Inclusion of Low Molecular Weight Chitosan Lipids were dissolved in ethanol. Low molecular weight chitosan (Sigma Aldrich) was suspended in 67 mM Citrate Buffer containing 0.67 wt % PEG400 at concentrations between 0.1-5 mg/mL. 1 N HCl was added dropwise until chitosan was dissolved in the solution. mRNA and guide RNA (ABE mRNA and guide RNA (1:1) or SpCas9 mRNA and gRNA (1:1)) were added to 67 mM citrate buffer containing 0.67% PEG400 to make 50 mM citrate buffer containing 0.5% PEG400 (pH 4.0-6.0). Chitosan solution is added to the RNA containing citrate buffer in a chitosan to RNA weight ratio of 0.01%-80%.

The ionizable lipid was included in the LNP at a final molar ratio between 40%-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12. The lipid mixture was combined with the RNA/chitosan containing citrate buffer at an aqueous to ethanol ratio of 3:1 using a microfluidic mixer. In some instances, the mixer is a Nanoassemblr (Precision Nanosystems). In some cases, the mixer is a T mixer. In some instances, it is a cross mixer. In some instances, the aqueous to ethanol ratio is 2:1.

LNPs were collected at a final 16.5% ethanol volume and were held for 1 hr before being buffer exchanged into PBS or Tris buffer, using PD-10 column (GE Healthcare), dialysis, or Tangential Flow Filtration (TFF) process. In some cases, LNPs are collected at 16.5% ethanol and then diluted to 8.25% ethanol either immediately post formulation or after the 1 hour hold time, before being buffer exchanged. In some instances, formulations were concentrated using Amicon ultra centrifugal filters (100 kDa) and passed through a 0.2 μm filter to afford LNPs. Size and RNA entrapment efficiency of LNPs was done as described in Example 11.

Example LNPs are described in Table 12. LNP liver editing is graphed in FIG. 12. F93, F101, F102, F103, and F155 included 1%, 0.1%, 0.5%, 5%, and 10% chitosan on an RNA weight ratio basis respectively in the drug substance buffer.

TABLE 12

LNPs F93, F01-F103, and F155 compositions and characterization, and evaluation in wild type C57BL/6 mice.

| | mol % | | | | | Z-avg. (nm) | | PDI | | % |
|---|---|---|---|---|---|---|---|---|---|---|
| | Amino lipid 502 | Structural Lipid | Helper Lipid | Stealth-Lipid | N:P | a | b | a | b | encapsulation |
| F93 | 55 | 38.2 | 4.7 | 2.1 | 8 | 97.7 | 105 | 0.0165 | 0.00976 | 96.7 |
| F101 | 55 | 38.2 | 4.7 | 2.1 | 8 | 94.4 | 114 | 0.0193 | 0.0315 | 94.4 |
| F102 | 55 | 38.2 | 4.7 | 2.1 | 8 | 93 | 115 | 0.0285 | 0.00843 | 94.4 |
| F103 | 55 | 38.2 | 4.7 | 2.1 | 8 | 93.7 | 114 | 0.041 | 0.0786 | 89.0 |
| F155 | 53.5 | 39.5 | 4.9 | 2.2 | 8 | 89.1 | 108.7 | 0.0168 | 0.03483 | 96.2 | a: Post formulation; b: post sterile filtration.

All LNPs of Table 12 were intravenously administered (RO) to wild type C57BL/6 female mice (n=5); dose: 0.05 mg/kg (total RNA); mRNA: MA004 and gRNA: GA256. F155 was GA257. The chitosan citrate solution was added to the RNA containing citrate buffer on a 1%, 0.1%, 0.5%, 5%, and 1% wt ratio basis compared to RNA to generate F93, F101, F102, F103, and F155 respectively. All formulations contain PEG400, 0.5 w/w %. The N:P ratio range 3.5-10.0. Liver editing percent data for each LNP is graphed in FIG. 12.

Example 17. General Preparation Method of LNP F104

Lipids were dissolved in ethanol. Low molecular weight chitosan (Sigma Aldrich) was suspended in 67 mM Citrate Buffer (pH 4.0-6.0) containing 0.67 wt % PEG400 at concentrations between 0.1-5 mg/mL. 1 N HCl was added dropwise until chitosan was dissolved in the solution. mRNA and guide RNA (ABE mRNA and guide RNA (1:1) or SpCas9 mRNA and gRNA (1:1)) were added to 67 mM citrate buffer containing 0.67% PEG400 to make 50 mM citrate buffer containing 0.5% PEG400 (pH 4.0-6.0). Chitosan solution is added to the RNA containing citrate buffer in a chitosan to RNA weight ratio of 0.01%-80%. Ionizable lipid is also added to the RNA containing citrate buffer in an amount to neutralize between 0.5-90% of the "P" (on an N:P basis) of the RNA.

The ionizable lipid was included in the LNP at a final molar ratio between 40%-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12.

The lipid mixture was combined with the RNA containing citrate buffer at an aqueous to ethanol ratio of 3:1 using a microfluidic mixer. In some instances, the mixer is a Nano-assemblr (Precision Nanosystems). In some cases, the mixer is a T mixer. In some instances, it is a cross mixer. In some instances, the aqueous to ethanol ratio is 2:1.

LNPs were collected at a final 16.5% ethanol volume and were held for 1 hr before being buffer exchanged into PBS or Tris buffer, using PD-10 column (GE Healthcare), dialysis, or Tangential Flow Filtration (TFF) process. In some cases, LNPs are collected at 16.5% ethanol and then diluted to 8.25% ethanol either immediately post formulation or after the 1 hour hold time, before being buffer exchanged. In some instances, formulations were concentrated using Amicon ultra centrifugal filters (100 kDa) and passed through a 0.2 μm filter to afford LNPs. Size and RNA entrapment efficiency of LNPs was done as described in Example D11.

Example LNP are described in Table 13. Liver editing % is given in FIG. 16.

TABLE 13

LNP 104 compositions and characterization, and evaluation in wild type C57BL/6 mice.

| | mol % | | | | | Z-avg (nm) | | PDI | | % RNA |
|---|---|---|---|---|---|---|---|---|---|---|
| LNP | Amino lipid 502 | Structural Lipid | Helper Lipid | Stealth-Lipid | N:P | a | b | a | b | encapsulation |
| F104 | 55 | 38.2 | 4.7 | 2.1 | 8 | 89.5 | 109.0 | 0.03 | 0.02 | 88.6 | a: Post Formulation; b: Post sterile filtration.

The LNP of Table 13 was intravenously administered (RO) to wild type C57BL/6 female mice (n=5), dose: 0.05 mg/kg (total RNA); mRNA: MA004 and gRNA: GA256. 1% chitosan on a weight basis to RNA is included in LNP 104. 10% neutralization of NP was performed prior to mixing with the remaining lipids in LNP 104. LNP 104 was formulated with PEG400, 0.5% w/w. The N:P ratio range 3.5-10.0. Liver editing % for LNP 104 is given in FIG. 16.

Example 18. General Preparation Method of LNPs F105, F151, F152

Lipids were dissolved in ethanol. The ionizable lipid was included in the LNP at a final molar ratio between 40%-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12.

In some instances, the LNP only includes SpCas9 guide RNA. In others, the LNP only includes ABE guide RNA. The lipid mixture is combined with a 0.5% PEG400 (Millipore Sigma) in 50 mM sodium citrate buffer (pH 4.0-6.0) containing ABE or SpCas9 guide RNA at an aqueous to ethanol ratio of 3:1 using a microfluidic mixer. In some instances, the mixer is a Nanoassemblr (Precision Nanosystems). In some cases, the mixer is a T mixer. In some instances, it is a cross mixer. In some instances, the aqueous to ethanol ratio is 2:1.

In other instances, the LNP includes either SpCas9 mRNA or ABE mRNA. The lipid mixture is combined with a 0.5% PEG400 (Millipore Sigma) in 50 mM sodium citrate buffer (pH 4.0-6.0) containing ABE or SpCas9 mRNA at an aqueous to ethanol ratio of 3:1 using a microfluidic mixer. In some instances, the mixer is a Nanoassemblr (Precision Nanosystems). In some cases, the mixer is a T mixer. In some instances, it is a cross mixer.

The guide RNA LNPs are formulated separately from the mRNA containing LNPs and the two LNPs are combined post a 1 hour hold time in some instances, post buffer exchange in some instances, or post sterile filtration in other instances.

LNPs were collected at a final 16.5% ethanol volume and were held for 1 hr before being buffer exchanged into PBS or Tris buffer, using PD-10 column (GE Healthcare), dialysis, or Tangential Flow Filtration (TFF) process. In some cases, LNPs are collected at 16.5% ethanol and then diluted to 8.25% ethanol either immediately post formulation or after the 1 hour hold time, before being buffer exchanged. In some instances, formulations were concentrated using Amicon ultra centrifugal filters (100 kDa) and passed through a 0.2 μm filter to afford LNPs. Size and RNA entrapment efficiency of LNPs was done as described in Example D11.

Example LNPs are described in Table 14. Liver editing % is given in FIG. 16.

TABLE 14

LNPs 105. 151, 152 compositions and characterization, and evaluation in wild type C57BL/6 mice.

| LNP | 502 | Mol % | | | N:P Ratio | Mean diameter (nm) | | PDI | | % RNA Encapsulation |
|---|---|---|---|---|---|---|---|---|---|---|
| | | Structural lipid | Helper Lipid | Stealth Lipid | | a | b | a | b | |
| F105 | 55 | 38.2 | 4.7 | 2.1 | 8 | 93.6 | 109 | 0.00879 | 0.0441 | 95.1 |
| F151 | 55 | 38.2 | 4.7 | 2.1 | 8 | 65.9 | | 0.101 | | |
| F152 | 55 | 38.2 | 4.7 | 2.1 | 8 | 90.5 | | 0.0514 | | | a: Post formulation; b: post sterile filtration.

All LNPs of Table 14 were intravenously administered (RO) to wild type C57BL/6 female mice (n=5), dose: 0.05 mg/kg (total RNA, mRNA: MA004, gRNA: GA256). For F151, the lipid mixture was combined with a 0.5% PEG400 in 50 mM sodium citrate buffer (pH 4.2-5.8) containing ABE guide RNA at an aqueous to ethanol ratio of 3:1 using a microfluidic mixer. For F152, the lipid mixture was combined with a 0.5% PEG400 in 50 mM sodium citrate buffer containing ABE mRNA at an aqueous to ethanol ratio of 3:1 using a microfluidic mixer. LNPs were collected at a final 16.5% ethanol volume and were held for 1 h before being combined. This combination of F151 and F152 generated F105. F105 LNPs were dialyzed to Tris buffer via dialysis. The N:P ratio range 3.5-10.0 LNP editing % for F105 is given in FIG. 16.

Example 19. General Preparation Method of F106-F109

F106-F109 were prepared as descried in Example 10. mRNA:gRNA ratio was held at 1:1 in aqueous and Lipid composition is described in Table 15. Mean diameter and % RNA entrapment is described in Table 16.

Example 20. General Preparation Method of F111-F122

Figure 15:
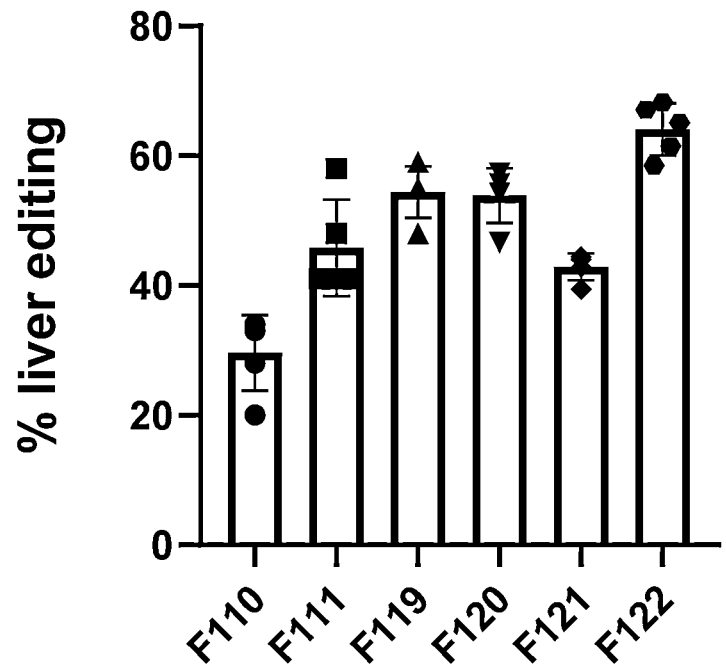
FIG. 15 illustrates PCSK9 gene editing at mouse hepatocytes in wild type C57BL/6 female mice (n=5) at 0.5 mg/kg total RNA dose for LNPs F110, F111, 119, 120, 121 and 122 as described in Table 9, 15 and 16. All LNPs were intravenously administered (RO) to wild type C57BL/6 female mice (n=5).
Figure 16:
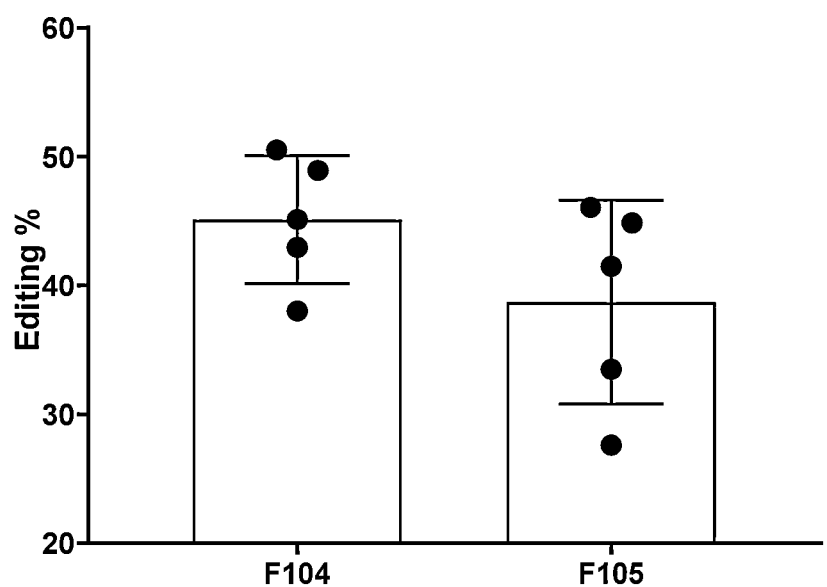
FIG. 16 illustrates PCSK9 liver editing % given for LNPs F104 and F105, as described in Examples 17, 18 and 23 respectively. Formulation composition and characterization data are given in Tables 13 and 14 for F104 and F105 respectively.
Figure 17:
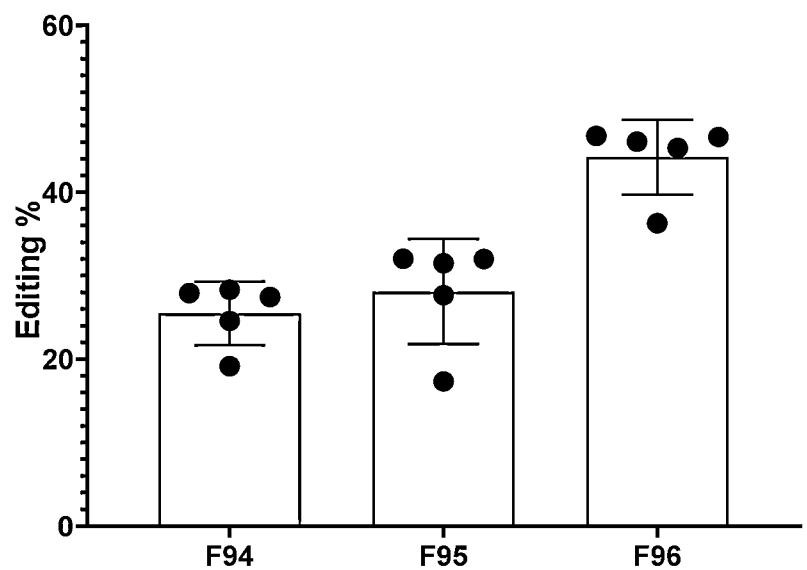
FIG. 17 illustrates PCSK9 editing for LNPs F94-F96 and F147-F150. These are referenced in Example 14 and Tables 9 and 10.
Figure 18:
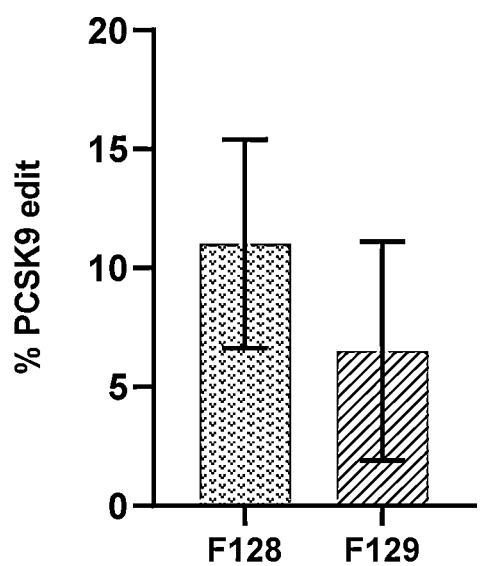
FIG. 18 illustrates PCSK9 gene editing at mouse hepatocytes in wild type C57BL/6 female mice (n=5) at 0.05 mg/kg total RNA dose for LNPs F128 and F129 as described in Table 15 and 16. All LNPs were intravenously administered (RO) to wild type C57BL/6 female mice (n=5).
Figure 19:
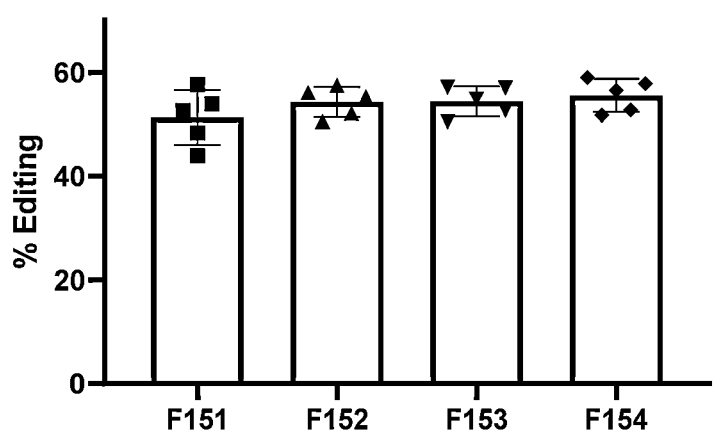
FIG. 19 illustrates the % editing for F151-F154 as described in Example 22 and Table 17.

F111-122 were prepared as descried in Example 10. mRNA:gRNA ratio was held at 1:1 in aqueous and Lipid composition is described in Table 15. Mean diameter and % RNA entrapment is described in Table 16. Liver editing is shown in FIG. 15.

Example 21. General Preparation Method of F126-F142

F121-F142 were prepared as descried in Example 19. mRNA:gRNA ratio was held at 1:1 in aqueous and Lipid composition is described in Table 15. Mean diameter and % RNA entrapment is described in Table 16.

TABLE 15

Composition for LNPs F106-F142. The N:P ratio ranges 3.5-10.0.

| LNP | mRNA | gRNA | Dose (mg/kg) | Amino lipid | Amino mol % | N:P Ratio | Cholesterol (511) mol % | DSPC (512) mol % | PEG-lipid (507) (mol %) |
|---|---|---|---|---|---|---|---|---|---|
| F106 | MS004 | GA055 | 1 | VL411 | 50 | 5.5 | 38.5 | 10 | 1.5 |
| F107 | MS004 | GA055 | 1 | VL404 | 47.1 | 4.5 | 46.1 | 4.7 | 2.1 |
| F108 | MS004 | GA055 | 1 | VL404 | 47.1 | 8 | 46.1 | 4.7 | 2.1 |
| F109 | MS004 | GA055 | 1 | VL404 | 40 | 8 | 53.2 | 4.7 | 2.1 |
| F111 | MS004 | GA055 | 0.5 | VL404 | 47.1 | 6 | 46.1 | 4.7 | 2.1 |
| F112 | MS004 | GA055 | 0.5 | VL404 | 47.1 | 8 | 46.1 | 4.7 | 2.1 |
| F113 | MS004 | GA055 | 0.5 | VL406 | 47.1 | 6 | 46.1 | 4.7 | 2.1 |
| F114 | MS004 | GA055 | 0.5 | VL406 | 47.1 | 8 | 46.1 | 4.7 | 2.1 |
| F115 | MS004 | GA055 | 0.5 | VL401 | 47.1 | 6 | 46.1 | 4.7 | 2.1 |
| F116 | MS004 | GA055 | 0.5 | VL401 | 47.1 | 8 | 46.1 | 4.7 | 2.1 |
| F117 | MS004 | GA055 | 0.5 | VL422 | 47.1 | 6 | 46.1 | 4.7 | 2.1 |
| F118 | MS004 | GA055 | 0.5 | VL422 | 47.1 | 8 | 46.1 | 4.7 | 2.1 |
| F110 | MS004 | GA055 | 0.5 | VL001 | 47.1 | 4.5 | 46.1 | 4.7 | 2.1 |
| F111 | MS004 | GA055 | 0.5 | VL404 | 47.1 | 6 | 46.1 | 4.7 | 2.1 |
| F119 | MS004 | GA055 | 0.5 | VL404 | 55 | 6 | 38.2 | 4.7 | 2.1 |
| F120 | MS004 | GA055 | 0.5 | VL404 | 55 | 6 | 38.2 | 4.7 | 2.1 |
| F121 | MS004 | GA055 | 0.5 | VL422 | 47.1 | 8 | 46.1 | 4.7 | 2.1 |
| F122 | MS004 | GA055 | 0.5 | VL422 | 55 | 8 | 38.2 | 4.7 | 2.1 |
| F126 | MA004 | GA256 | 0.05 | VL410 | 55 | 6 | 38.2 | 4.7 | 2.1 |
| F127 | MA004 | GA256 | 0.05 | VL410 | 55 | 8 | 38.2 | 4.7 | 2.1 |
| F128 | MA004 | GA256 | 0.05 | VL421 | 55 | 6 | 38.2 | 4.7 | 2.1 |
| F129 | MA004 | GA256 | 0.05 | VL421 | 55 | 8 | 38.2 | 4.7 | 2.1 |
| F130 | MA004 | GA256 | 0.05 | VL435 | 55 | 6 | 38.2 | 4.7 | 2.1 |
| F131 | MA004 | GA256 | 0.05 | VL435 | 55 | 8 | 38.2 | 4.7 | 2.1 |
| F132 | MA004 | GA256 | 0.05 | VL404 | 55 | 6 | 38.2 | 4.7 | 2.1 |
| F133 | MA004 | GA256 | 0.05 | VL404 | 55 | 6 | 33.9 | 9 | 2.1 |
| F134 | MA004 | GA256 | 0.05 | VL404 | 52.37 | 6 | 35.57 | 9.96 | 2.1 |
| F135 | MS004 | GA055 | 0.25 | VL447 | 55 | 6 | 38.2 | 4.7 | 2.1 |
| F136 | MS004 | GA055 | 0.25 | VL447 | 55 |  | 38.2 | 4.7 | 2.1 |
| F137 | MS004 | GA055 | 0.25 | VL448 | 55 | 6 | 38.2 | 4.7 | 2.1 |
| F138 | MS004 | GA055 | 0.25 | VL448 | 55 | 8 | 38.2 | 4.7 | 2.1 |
| F139 | MS004 | GA055 | 0.25 | VL449 | 55 | 6 | 38.2 | 4.7 | 2.1 |
| F140 | MS004 | GA055 | 0.25 | VL449 | 55 | 8 | 38.2 | 4.7 | 2.1 |
| F141 | MS004 | GA055 | 0.25 | VL451 | 55 | 6 | 38.2 | 4.7 | 2.1 |
| F142 | MS004 | GA055 | 0.25 | VL451 | 55 | 8 | 38.2 | 4.7 | 2.1 |

TABLE 16

Characterization data for LNPs F106-F142.

| LNP ID | Buffer Exchange Process | Mean diameter (nm) | PDI | % RNA Encapsulation |
|---|---|---|---|---|
| F106 | dialysis | 112 | 0.002 | 91 |
| F107 | dialysis | 75 | 0.15 | 90 |
| F108 | PD-10 | 98.6 | 0.13 | 95 |
| F109 | PD-10 | 107.8 | 0.26 | 91 |
| F111 | Dialysis | 108.5 | 0.00387 | 95.8 |
| F112 | Dialysis | 92.37 | 0.06089 | 96.3 |
| F113 | Dialysis | 74.52 | 0.07232 | 94.3 |
| F114 | Dialysis | 67.19 | 0.1093 | 97.7 |
| F115 | Dialysis | 122.7 | 0.03755 | 93.6 |
| F116 | Dialysis | 115.1 | 0.175 | 96.0 |
| F117 | Dialysis | 64.64 | 0.1397 | 96.9 |
| F118 | Dialysis | 67.38 | 0.1451 | 97.0 |
| F111 | Dialysis | 122 | 0.0419 | 95.8 |
| F119 | Dialysis | 107 | 0.00888 | 96.7 |
| F120 | TFF | 131 | 0.002 | 91.3 |
| F121 | Dialysis | 70.2 | 0.107 | 91.3 |
| F122 | Dialysis | 81 | 0.0156 | 95.8 |
| F126 | Dialysis | 85.9 | 0.0584 | 96.18 |
| F127 | Dialysis | 98.5 | 0.066 | 97.14 |
| F128 | Dialysis | 92.9 | 0.137 | 97.04 |
| F129 | Dialysis | 82 | 0.0388 | 97.22 |
| F130 | Dialysis | 102 | 0.00398 | 96.81 |
| F131 | Dialysis | 72.2 | 0.15 | 95.76 |
| F132 | Dialysis | 86.5 | 0.13 | 94.33 |
| F133 | Dialysis | 118 | 0.0242 | 95.73 |
| F134 | Dialysis | 124 | 0.0138 | 96.22 |
| F135 | Dialysis | 76.7 | 0.0714 | 96.77 |
| F136 | Dialysis | 79.5 | 0.0417 | 97.5 |
| F137 | Dialysis | 66.2 | 0.135 | 93.21 |
| F138 | Dialysis | 73.2 | 0.0825 | 97.97 |
| F139 | Dialysis | 116 | 0.145 | 25.79 |
| F140 | Dialysis | 114 | 0.13 | 25.2 |
| F141 | Dialysis | 123 | 0.138 | 93.51 |
| F142 | Dialysis | 113 | 0.125 | 94.98 |

All LNPs of Table 16 were buffer exchanged into PBS, except F120, which was exchanged into Tris. All LNPs were formulated with drug substance buffer with pH between 4.0 and 6.0.

Example 22. General Preparation Method of F151-F154 with Inclusion of Cetyl Trimethylammonium Bromide (CTAB or 524 in Table 11D)

Lipids were dissolved in ethanol. CTAB (Sigma Aldrich) was mixed with 67 mM Citrate Buffer containing 0.67 wt % PEG400 to form solutions at concentrations between 0.01-5 mg/mL. mRNA and guide RNA (ABE mRNA and guide RNA (1:1) or SpCas9 mRNA and gRNA (1:1)) were added to 67 mM citrate buffer containing 0.67% PEG400 to make 50 mM citrate buffer containing 0.5% PEG400 (pH 4.0-6.0). The 524 solution is added to the RNA containing citrate buffer in a 524 to RNA weight ratio of 0.01%-80%.

The ionizable lipid was included in the LNP at a final molar ratio between 40-70%. The structural lipid was included in the LNP at a final molar ratio between 30% and 60%. The helper lipid was included in the LNP at a final molar ratio between 2% and 25%. The stealth lipid was included in the LNP at a final molar ratio between 0.5% and 5%. N:P ratio was held at 3 to 12. The lipid mixture was combined with the RNA/524 containing citrate buffer at an aqueous to ethanol ratio of 3:1 using a microfluidic mixer. In some instances, the mixer is a Nanoassemblr (Precision Nanosystems). In some cases, the mixer is a T mixer. In some instances, it is a cross mixer. In some instances, the aqueous to ethanol ratio is 2:1.

LNPs were collected at a final 16.5% ethanol volume and were held for 1 hr before being buffer exchanged into PBS or Tris buffer, using PD-10 column (GE Healthcare), dialysis, or Tangential Flow Filtration (TFF) process. In some cases, LNPs are collected at 16.5% ethanol and then diluted to 8.25% ethanol either immediately post formulation or after the 1 hour hold time, before being buffer exchanged. In some instances, formulations were concentrated using Amicon ultra centrifugal filters (100 kDa) and passed through a 0.2-μm filter to afford LNPs. Size and RNA entrapment efficiency of LNPs was done as described in Example 11.

Example LNPs are described in Table 17. F151, F152, F153, and F154 included 0.1%, 0.3%, 0.6%, and 1% 524 (CTAB) on an RNA weight ratio basis respectively in the drug substance buffer.

TABLE 17

LNPs F151-F154 compositions and characterization, and evaluation in wild type C57BL/6 mice.

| | Mol % | | | | | Z average | | PDI | | % RNA |
|---|---|---|---|---|---|---|---|---|---|---|
| LNP | Amino lipid 502 | Structural lipid (Cholesterol) | Helper lipid (DSPC) | Stealth-Lipid (PEG-Lipid from Table 1B) | N:P Ratio | a | b | a | b | Enacapsulation |
| F151 | 55 | 38.2 | 4.7 | 2.1 | 8 | 94.95 | 118.6 | 0.03107 | 0.005914 | 96.31 |
| F152 | 55 | 38.2 | 4.7 | 2.1 | 8 | 95.23 | 117.2 | 0.004556 | 0.0234 | 94.28 |
| F153 | 55 | 38.2 | 4.7 | 2.1 | 8 | 97.66 | 116.1 | 0.008244 | 0.02514 | 96.06 |
| F154 | 55 | 38.2 | 4.7 | 2.1 | 8 | 94.22 | 112.8 | 0.02049 | 0.01147 | 97.29 | a: Post formulation; b: post sterile filtration.

All LNPs of Table 17 were intravenously administered (RO) to wild type C57BL/6 female mice (n=5); dose. 0.05 mg/kg (total RNA); mRNA: MA004 and gRNA: GA257. 524 in citrate solution was added to the RNA containing citrate buffer on a 0.1, 0.3, 0.6, and 1% wt ratio basis compared to RNA to generate F151, F152, F153, and F154 respectively. All formulations contain PEG400, 0.5 w/w %. The N:P ratios range 3.5-10.0.

Example 23

LNP Formulations F159 and F156 were prepared using 521 as described in Table 5 by replacing 504 in F2 and F3, respectively.
LNP Formulations F157 and F158 were prepared using 522 as described in Table 5 by replacing 504 in F2 and F3, respectively.

Example 24

Figure 20:
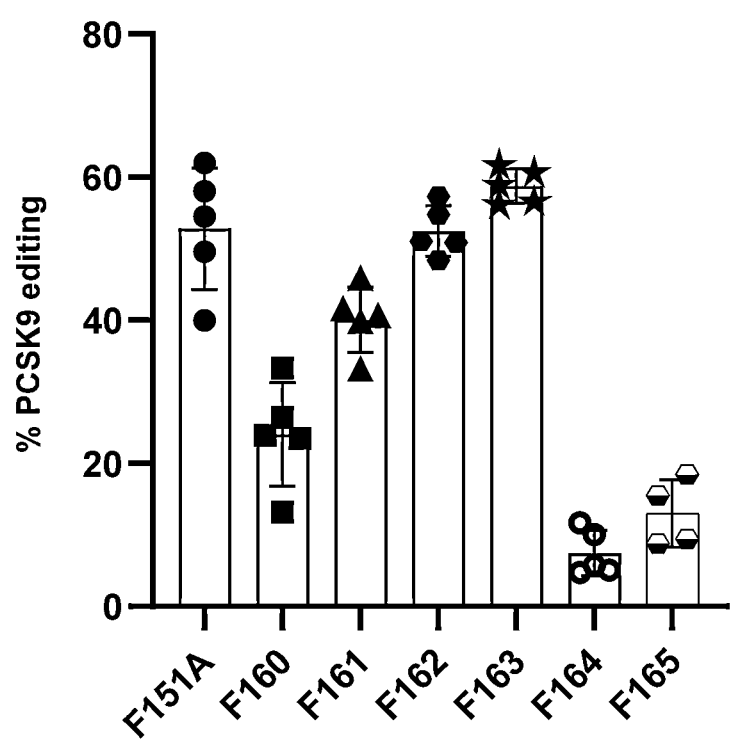
FIG. 20. illustrates the percentage of PCSK9 gene editing achieved in wild type C57BL/6 female mice liver after a single dose administration of LNPs F160-F165 comprising amino lipids VL454, VL459 and VL455 at N to P ratios 6 and 8 as shown in Table 18: (n=5) at 0.125 mg/kg dose, as described in Example 24. F151A is the reference LNP constituted using amino lipid 502.

Lipid excipients were dissolved in ethanol at molar ratios as described in Table 18. Total RNA aqueous mixture was prepared by dissolving mRNA and gRNA (at 1:1 weight ratio) in 50 mM sodium citrate buffer (pH 4.5-6). LNPs F151A and F160-F171 were then formulated by rapid mixing of the aqueous stream with the ethanol stream at a ratio of 3:1 using a microfluidic mixer. N to P ratio was held between 3 to 12. LNPs were collected in an aqueous buffer containing final ethanol concentration of 10-25% by volume and was held for 1 minute to 120 minutes at 4-6° C. before membrane dialysis against DPBS using a dialysis cassettes (10 KDa cut-off membrane) for at least 18 hr. The nanoparticles obtained were analyzed for % entrapped RNAs using Ribogreen quantification assay and average diameter (Z-avg.) was measured by dynamic light scattering (DLS). Percentage entrapment and average particle size (Z-avg.) of LNPs F151A and F160-F171 are tabulated in Table 18. The LNPs F151A and F160-F165, after characterization, were administered by retro-orbital injection to wild type C57BL/6 female mice (n=5) at 0.125 mg/kg total RNA dose and the % PCSK9 gene editing in mice liver was assessed 4 days after dosing, and the editing data is shown in FIG. 20. F151A was administered at the same dose as a reference LNP. The in vivo study and editing analysis were performed as described in Example 13.

TABLE 18

Lipid composition and physiochemical characteristics of LNPs F151A and F160-F171.

| LNP | mRNA | gRNA | Amino lipid | Amino lipid/cholesterol (511)/DSPC (512)/PEG-Lipid (507) mol % | N:P | Z-avg. (nm) | PDI | % RNA Entrapment |
|---|---|---|---|---|---|---|---|---|
| F151A | MA004 | GA256 | 502 | 55/38.2/4.7/2.1 | 8 | 107.1 | 0.04 | 95.6 |
| F160 | MA004 | GA256 | VL454 | 55/38.2/4.7/2.1 | 6 | 72.4 | 0.09 | 91.6 |
| F161 | MA004 | GA256 | VL454 | 55/38.2/4.7/2.1 | 8 | 72.3 | 0.002 | 90.4 |
| F162 | MA004 | GA256 | VL459 | 55/38.2/4.7/2.1 | 6 | 100.6 | 0.009 | 91.7 |
| F163 | MA004 | GA256 | VL459 | 55/38.2/4.7/2.1 | 8 | 105.5 | 0.05 | 92.4 |
| F164 | MA004 | GA256 | VL455 | 55/38.2/4.7/2.1 | 6 | 110.4 | 0.13 | 93.9 |
| F165 | MA004 | GA256 | VL455 | 55/38.2/4.7/2.1 | 8 | 105.7 | 0.05 | 94.1 |
| F166 | MA004 | GA256 | VL460 | 55/38.2/4.7/2.1 | 6 | 151 | 0.1 | 91.1 |
| F167 | MA004 | GA256 | VL460 | 55/38.2/4.7/2.1 | 8 | 90 | 0.12 | 91.9 |
| F168 | MA004 | GA256 | VL471A | 55/38.2/4.7/2.1 | 6 | 86.3 | 0.2 | 94.9 |
| F169 | MA004 | GA256 | VL471A | 55/38.2/4.7/2.1 | 8 | 65.3 | 0.02 | 96.0 |
| F170 | MA004 | GA256 | VL472A | 55/38.2/4.7/2.1 | 6 | 82.2 | 0.1 | 95.3 |
| F171 | MA004 | GA256 | VL472A | 55/38.2/4.7/2.1 | 8 | 80 | 0.12 | 96.5 |

Figure 21:
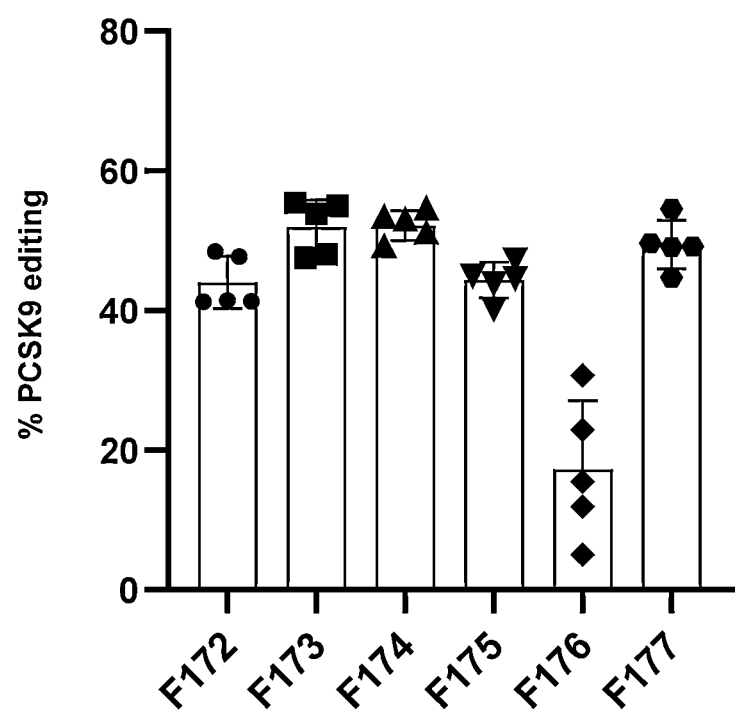
FIG. 21. illustrates the percentage of PCSK9 gene editing in wild type C57BL/6 female mice liver after single dose administration of LNPs F172-F177 (n=5) at 0.1 mg/kg dose of total RNA, as described in Example 24, Table 19. All LNPs administered were constituted using the amino lipid VL422.

The LNP formulations F172-F177 encapsulating mouse PCSK9 gRNA GA256 and ABE mRNA MA004 shown in Table 19 were formulated as descried above (Table 18) and dialyzed against 50 mM Tris at pH 7.5. LNPs F172-F177, after characterization, were administered by retro-orbital injection to wild type C57BL/6 female mice (n=5) at 0.1 mg/kg total RNA dose and the % PCSK9 gene. Editing in mice liver was assessed 4 days after dosing, and the editing data is shown in FIG. 21. The in vivo study and editing analysis were performed as described in Example 13.

TABLE 19

Lipid composition and physiochemical characteristics of LNPs F172-F177.

| LNP | mRNA | gRNA | Amino lipid | Amino lipid/cholesterol (511)/DSPC (512)/PEG-Lipid (507) mol % | N:P | Z-avg (nm) | PDI | % RNA Entrapment |
|---|---|---|---|---|---|---|---|---|
| F172 | MA004 | GA256 | VL422 | 52.4/34.6/9/3 | 6 | 68 | 0.02 | 91.5 |
| F173 | MA004 | GA256 | VL422 | 52.4/34.6/9/3 | 8 | 75 | 0.02 | 92.9 |
| F174 | MA004 | GA256 | VL422 | 50/38/9/3 | 6 | 77 | 0.006 | 92.8 |

TABLE 19-continued

Lipid composition and physiochemical characteristics of LNPs F172-F177.

| LNP | mRNA | gRNA | Amino lipid | Amino lipid/cholesterol (511)/DSPC (512)/PEG-Lipid (507) mol % | N:P | Z-avg (nm) | PDI | % RNA Entrapment |
|---|---|---|---|---|---|---|---|---|
| F175 | MA004 | GA256 | VL422 | 50/38/9/3 | 8 | 71 | 0.04 | 90.4 |
| F176 | MA004 | GA256 | VL422 | 47/41/9/3 | 6 | 57 | 0.01 | 90.7 |
| F177 | MA004 | GA256 | VL422 | 47/41/9/3 | 8 | 73 | 0.05 | 89.4 |

Figure 22:
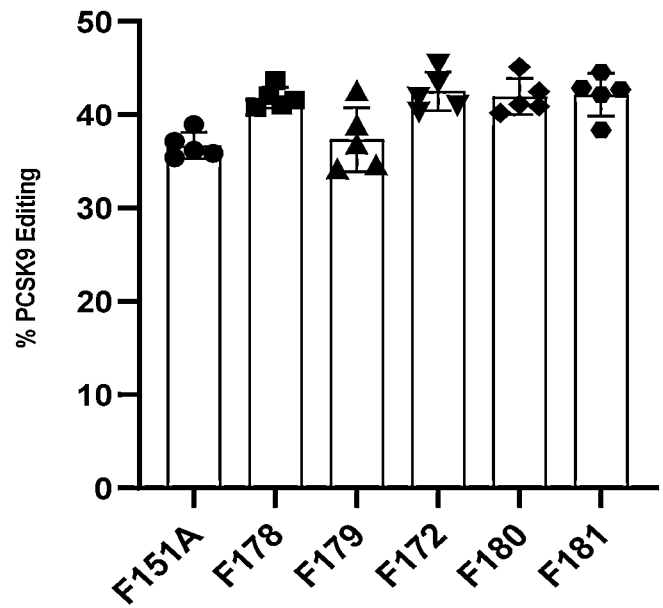
FIG. 22. (A) illustrates the percentage of PCSK9 gene editing in wild type C57BL/6 female mice liver after single dose administration of LNPs F151A, 172 and 178-181 (n=5) at 0.1 mg/kg dose of total RNA, Table 20. F151A is the reference LNP constituted using amino lipid 502. The commercially available PEG-Lipid 507 was replaced with PEG-Lipid VP159 in LNPs F178, F180 and F181. F179-F181 comprising amino lipid VL422.
Figure 22:
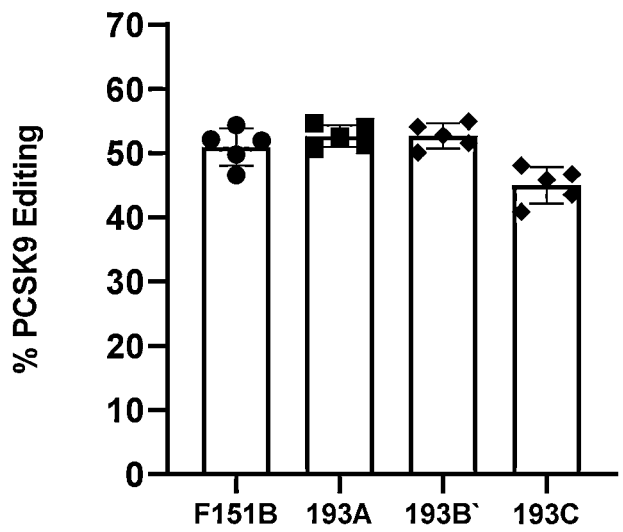

The LNP formulations F151A, and F178-181 encapsulating mouse PCSK9 gRNA GA256 and ABE mRNA MA004 shown in Table 20 were prepared as descried above (Table 18) and were dialyzed against 50 mM Tris at pH 7.5. LNP F179 was made using a X-mixer and mixing ratio of aqueous to ethanolic stream was held at a ratio of 3:1. TFF was used to exchange buffer (50 mM Tris at pH 7.5) of LNP F172. The LNP formulations F151B, and F193A-F193C encapsulating mouse PCSK9 gRNA GA257 and ABE mRNA MA004 shown in Table 20 were prepared as descried above (Table 18) and were dialyzed against 50 mM Tris at pH 7.5. LNP F151B comprises of PEG-Lipid 507 and in LNP F193A the PEG-Lipid 507 is replaced with PEG-Lipid VP177; PEG-Lipid 507 of F193B was replaced with VP177 in LNP F193C. LNP F193B and F193C were formulated amino lipid VL422. After characterization F151A, F151B, F172, F178-F181 and F193A-F193C LNPs were administered by retro-orbital injection to wild type C57BL/6 female mice (n=5) at 0.1 mg/kg total RNA dose and the % PCSK9 editing in mice liver was assessed 4 days after dosing; the editing data is shown in FIG. 22A and FIG. 22B. The in vivo study and editing analysis were performed as described in Example 13. The impact of LNPs comprising PEG-Lipid VP159 on editing in mice was compared with corresponding LNPs constituted with PEG-Lipid 507 with similar excipient compositions and amino lipid as shown in the Table 20.

TABLE 20

Lipid composition and physiochemical characteristics of LNPs F151A, F172 and F178-F181.

| LNP | mRNA | gRNA | Amino lipid | PEG-Lipid | Amino lipid/cholesterol (511)/DSPC (512)/PEG-Lipid mol % | N:P | Z-avg (nm) | PDI | % RNA Entrapment |
|---|---|---|---|---|---|---|---|---|---|
| F151A | MA004 | GA256 | 502 | 507 | 55/38.2/4.7/2.1 | 8 | 107.1 | 0.04 | 95.6 |
| F178 | MA004 | GA256 | 502 | VP159 | 55/38.2/4.7/2.1 | 8 | 111.6 | 0.04 | 94.3 |
| F179 | MA004 | GA256 | VL422 | 507 | 50/38/9/3 | 6 | 67.1 | 0.01 | 93.3 |
| F172 | MA004 | GA256 | VL422 | 507 | 52.4/34.6/10/3 | 6 | 64.3 | 0.02 | 94.3 |
| F180 | MA004 | GA256 | VL422 | VP159 | 50/38/9/3 | 6 | 68.1 | 0.01 | 93.1 |
| F181 | MA004 | GA256 | VL422 | VP159 | 52.4/34.6/10/3 | 6 | 65.8 | 0.01 | 93.3 |
| F151B | MA004 | GA257 | 502 | 507 | 55/38.2/4.7/2.1 | 8 | 108.3 | 0.02 | 91.3 |
| F193A | MA004 | GA257 | 502 | VP177 | 55/38.2/4.7/2.1 | 8 | 113.7 | 0.002 | 89.8 |
| F193B | MA004 | GA257 | VL422 | 507 | 50/38/9/3 | 6 | 74.34 | 0.006 | 88.69 |
| F193C | MA004 | GA257 | VL422 | VP177 | 50/38/9/3 | 6 | 66.8 | 0.02 | 88.2 |

The LNP formulations F182-186 encapsulating mouse PCSK9 gRNA GA256 and ABE mRNA MA004 shown in Table 21 were prepared using amino lipid VL473A as descried above (Table 18) and dialyzed against 50 mM Tris at pH 7.5. After characterization, LNPs F82-F186 were administered by retro-orbital injection to wild type C57BL/6 female mice (n=5) at 0.1 mg/kg total RNA dose and the %4 PCSK9 editing in mice liver was assessed 4 days after dosing and the in vivo study and editing analysis were performed as described in Example 13. The PCSK9 gene editing in livers of individual animal is tabulated in Table 21

TABLE 21

Lipid composition and physiochemical characteristics of LNPs F182-F186.

| LNP | mRNA | gRNA | Amino lipid | Amino lipid/cholesterol (511)/DSPC (512)/PEG-Lipid (507) mol % | N:P | Z-avg (nm) | PDI | % RNA Entrapment | % PCSK9 editing in individual animal |
|---|---|---|---|---|---|---|---|---|---|
| F182 | MA004 | GA256 | VL473A | 55/38.2/4.7/2.1 | 8 | 65.5 | 0.06 | 90.6 | 0.6, 0.9, 0.4, , 0.6, 0.6 |
| F183 | MA004 | GA256 | | 52.4/34.6/10/3 | 6 | 69.9 | 0.14 | 88.6 | 0.6, 0.6, 0.3, 0, .3, 0, .4 |
| F184 | MA004 | GA256 | | 52.4/34.6/10/3 | 8 | 88.4 | 0.06 | 90.1 | 0.3, 0.3, 0.4, 0.4, 0.4 |
| F185 | MA004 | GA256 | | 50/38/9/3 | 6 | 60.8 | 0.12 | 97.9 | 0.3, 0.2, 0.3, 0.3, 0.3 |
| F186 | MA004 | GA256 | | 50/38/9/3 | 8 | 81.9 | 0.003 | 97.3 | 0.2, 0.2, 0.2, 0.3, 0.3 |

The LNP formulations F194-F220, F220A, F220B and F220C shown in Table 22 encapsulating mouse guide RNAs GA256, GA257 and GA010, and mRNAs MA004 and were prepared using amino lipids 502, VL422, VL454, VL455 and L472A and PEG-Lipids 507 and VP154 as descried above. LNPs F209-F220, after characterization, were administered by retro-orbital injection to wild type C57BL/6 female mice (n=5) at 0.1 mg/kg total RNA dose and the % PCSK9 editing in mice liver was assessed 4 days after dosing and the gene editing of individual animal is tabulated in Table 22. The in vivo study and editing analysis were performed as described in Example 13.

TABLE 22

Lipid composition and physiochemical characteristics of LNPs F151 and F194-F220.

| LNP | mRNA | gRNA | Amino lipid/cholesterol/DSPC/PEG-Lipid mol % | Amino lipid | PEG-Lipid | N:P | Z-avg (nm) | PDI | % RNA Entrapment | % PCSK9 editing in individual animal |
|---|---|---|---|---|---|---|---|---|---|---|
| F194 | MS002 | GA010 | 47/42.5/9/1.5 | 502 | VP154 | 6 | 101.4 | 0.05 | 89.8 | * |
| F195 | MS002 | GA010 | 47/41/9/3 | 502 | VP154 | 6 | 67.0 | 0.03 | 87.9 | * |
| F196 | MS002 | GA010 | 47/39/9/5 | 502 | VP154 | 6 | 63.26 | 0.10 | 87.5 | * |
| F197 | MS002 | GA010 | 47/42.5/9/1.5 | 502 | VP154 | 8 | 84.84 | 0.05 | 89.4 | |
| F198 | MS002 | GA010 | 47/41/9/3 | 502 | VP154 | 8 | 63.5 | 0.03 | 91.7 | * |
| F199 | MS002 | GA010 | 47/39/9/5 | 502 | VP154 | 8 | 58.97 | 0.07 | 90.9 | * |
| F201 | MS002 | GA010 | 50/39.5/9/1.5 | 502 | VP154 | 6 | 89.23 | 0.06 | 87.6 | |
| F201 | MS002 | GA010 | 50/38/9/3 | 502 | VP154 | 6 | 68.95 | 0.04 | 81.5 | * |
| F202 | MS002 | GA010 | 50/36/9/5 | 502 | VP154 | 6 | 69.38 | 0.19 | 85.8 | * |
| F203 | MS002 | GA010 | 50/39.5/9/1.5 | 502 | VP154 | 8 | 89.23 | 0.06 | 87.6 | * |
| F204 | MS002 | GA010 | 50/38/9/3 | 502 | VP154 | 8 | 68.95 | 0.04 | 81.5 | |
| F205 | MS002 | GA010 | 50/36/9/5 | 502 | VP154 | 8 | 69.38 | 0.19 | 85.8 | * |
| F206 | MS002 | GA010 | 52.4/33.1/9/1.5 | 502 | VP154 | 8 | 76.51 | 0.01 | 90.8 | * |
| F207 | MS002 | GA010 | 52.4/34.6/9/3 | 502 | VP154 | 8 | 63.92 | 0.14 | 90.8 | * |
| F208 | MS002 | GA010 | 52.4/36.4/9/5 | 502 | VP154 | 8 | 62.02 | 0.13 | 88.5 | ** |
| F209 | MA004 | G256 | 50/38/9/3 | VL422 | VP154 | 6 | 65.36 | 0.07 | 91.5 | 5.9, 12.75, 7.4, 11.6, 5.9 |
| F210 | MA004 | G256 | 47/41/9/3 | VL422 | VP154 | 6 | 61.16 | 0.07 | 92.2 | 12.6, 7.3, 7.8, 19, 14.0 |

TABLE 22-continued

Lipid composition and physiochemical characteristics of LNPs F151 and F194-F220.

| LNP | mRNA | gRNA | Amino lipid/ cholesterol/ DSPC/ PEG-Lipid mol % | Amino lipid | PEG-Lipid | N:P | Z-avg (nm) | PDI | % RNA Entrapment | % PCSK9 editing in individual animal |
|---|---|---|---|---|---|---|---|---|---|---|
| F211 | MA004 | GA256 | 50/38/9/3 | VL454 | 507 | 6 | 70.79 | 0.05 | 90.7 | 13.7, 15.7, 11.9, 21.5 16.3 |
| F212 | MA004 | GA256 | 52.4/35.6/9/3 | VL454 | 507 | 8 | 76.07 | 0.06 | 91.2 | 26.5, 31.2, 31.9, 29.7. 31.0 |
| F213 | MA004 | GA256 | 47/41/9/3 | VL455 | 507 | 5 | 86.42 | 0.01 | 93.6 | 1.5, 9.6, 8.8, 2.4, 4.6 |
| F214 | MA004 | GA256 | 47/41/9/3 | VL455 | 507 | 8 | 83.45 | 0.01 | 94.8 | 0.6, 5.3, 4.7, 5.0, 7.0 |
| F215 | MA004 | GA256 | 50/38/9/3 | VL455 | 507 | 5 | 90.65 | 0.004 | 93.1 | 0.7, 8.3, 6.7, 9.9, 11.2 |
| F216 | MA004 | GA256 | 50/38/9/3 | VL455 | 507 | 8 | 83.36 | 0.05 | 94.1 | 12.2, 5.7, 10.4, 6.9, 4.85 |
| F217 | MA004 | GA256 | 47/41/9/3 | VL472A | 507 | 5 | 77.26 | 0.11 | 95.2 | 3.4, 4.0, 3.9, 6.9, 6.0 |
| F218 | MA004 | GA256 | 47/41/9/3 | VL472A | 507 | 8 | 71 | 0.09 | 96.8 | 0.1, 0.33, 0.09, 0.08, 0.1 |
| F219 | MA004 | GA256 | 50/38/9/3 | VL472A | 507 | 5 | 77.77 | 0.10 | 95.6 | 0.09, 0.1, 0.1, 0.1, 0.09 |
| F220 | MA004 | GA256 | 50/38/9/3 | VL472A | 507 | 8 | 70.88 | 0.07 | 96.8 | 0.2, 0.2, 0.1, 0.2, 0.1 |
| F220A | MA004 | GA257 | 52.4/35.6/9/3 | VL454 | 507 | 8 | 63.88 | 0.11 | 90.3 | 43.7, 42.7, 36.8, 45.9, 36.6 |
| F220B | MA004 | GA257 | 52.4/35.6/9/3 | VL454 | 507 | 6 | 68.59 | 0.11 | 90.4 | 36.7, 40.9, 45.8, 42.0, 38.1 |
| F220C | MA004 | GA257 | 52.4/36.6/9/2 | VL454 | 507 | 6 | 70.3 | 0.009 | 94.8 | 34.9, 42.5, 47.7, 35.3, 36.8 |

* Not evaluated

Example 25

Figure 23:
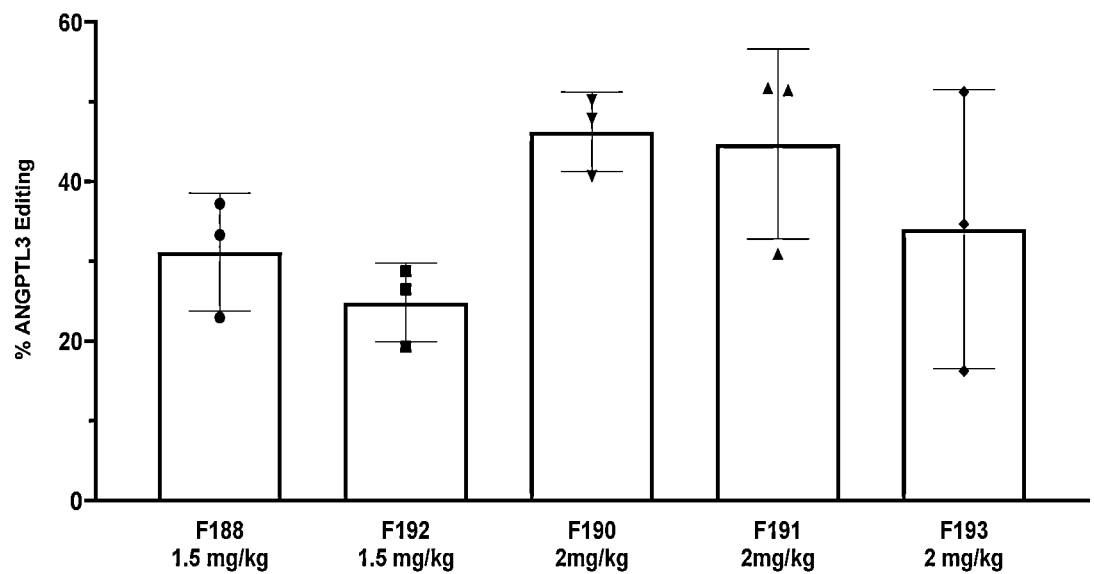
FIG. 23. (A) illustrates the percentage of ANGPTL3 gene editing in the livers of cynomolgus monkeys (n=3) after single dose administration of LNPs F188, F190-F193 as described in Example 25, Table 23. F188 and F192 were dosed at 1.5 mg/kg total RNA dose. F190, F191 and F193 were dosed at 2 mg/kg total RNA dose. F188 is a reference LNP comprising amino lipid 502 and PEG-Lipid 507. The PEG-Lipid 507 of F188 is replaced with PEG-Lipid VP159 in F192. F190, 190A, F191 and F193 comprising of amino lipid VL422 and PEG-Lipid 507.
Figure 23:
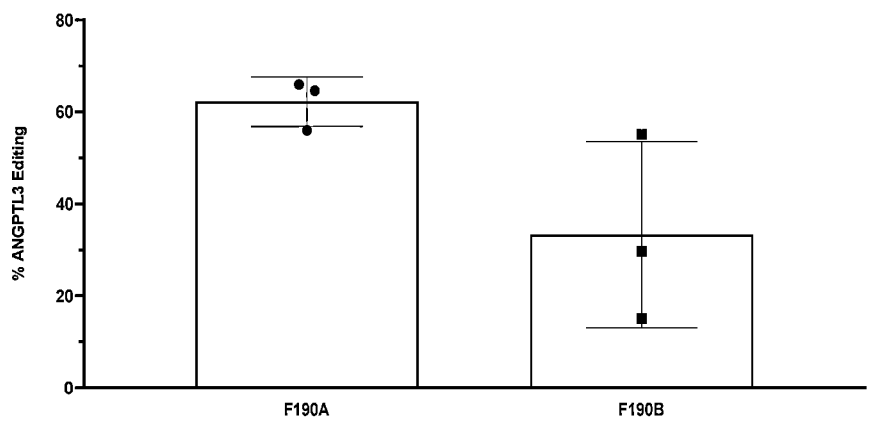

LNPs F188 and F190-F193 were formulated using a X-mixer. TFF was used to exchange buffer (50 mM Tris at pH 7.5). PEG400 was introduced in LNPs F188 and F192 formulations. The LNP formulations F188 and F190-F193 were administered to cynomolgus monkeys (n=3) by intravenous infusion over 1 hour. A 2-week study was performed to evaluate editing of the ANGPTL3 gene in cynomolgus monkeys using guide RNA GA067 and mRNA MA004 through administration of LNPs (FIG. 23A). The MA004/ GA067 LNPs were administered to cynomolgus monkeys via intravenous infusion with the intent of producing targeted adenine base editing of ANGPTL3 gene in the liver. Two weeks after administration of test article, the animals underwent necropsy for collection of liver samples, and the samples were stored at −86 to −60° C. Splice-site editing was analyzed by next generation sequencing, confirming that base change occurred. The LNP formulations F188 and F192 were administered at 1.5 mg/kg (n=3) to evaluate and compare the impact of 3 mol % of the PEG-Lipids 507 and VP159 in NHP (FIG. 23A). The LNP formulations F190 and F191 each comprising amino lipid VL422 showed about 45% adenine base editing at 2 mg/kg dose (n=3). Each LNP differs in excipient composition.

TABLE 23

Lipid composition and physiochemical characteristics of F188, 190-F193, F190A and F190B.

| LNP | mRNA | gRNA | Amino lipid/cholesterol (511)/DSPC (512)/PEG-Lipid mol % | Amino lipid | PEG-Lipid | N:P | Z-avg (nm) | PDI | % RNA Entrapment | % ANGPTL3 editing |
|---|---|---|---|---|---|---|---|---|---|---|
| F188 | MA004 | GA067 | 50/38/9/3 | 502 | 507 | 6 | 63.7 | 0.06 | 93.1 | See FIG. 23A |
| F190 | MA004 | GA067 | 50/38/9/3 | VL422 | 507 | 6 | 68.4 | 0.01 | 94.1 | |
| F191 | MA004 | GA067 | 52.4/34.6/10/3 | VL422 | 507 | 8 | 74.0 | 0.04 | 93.1 | |
| F192 | MA004 | GA067 | 50/38/9/3 | 502 | VP159 | 6 | 77.9 | 0.005 | 93.8 | |
| F193 | MA004 | GA067 | 47/41/9/3 | VL422 | 507 | 6 | 66.8 | 0.05 | 95.4 | |
| F190A | MA004 | GA347 | 50/38/9/3 | VL422 | 507 | 6 | 74.7 | 0.03 | 94.0 | See FIG. 23B |
| F190B | MA004 | GA347 | 50/38/9/3 | VL422 | VP159 | 6 | 72.7 | 0.04 | 94.1 | |

LNP formulations 190A and F190B (Table 23) were prepared from amino lipid VL422, mRNA MA004 and gRNA GA347 using a X-mixer. TFF was used to exchange buffer (50 mM Tris at pH 7.5). F190A and F190B comprise of PEG-Lipids 507 and VP159, respectively. A 2-week study was performed to evaluate editing of the ANGPTL3 gene in cynomolgus monkeys using guide RNA GA347 and mRNA MA004 through administration of LNPs (FIG. 23B) as described above.

Example 26

Figure 24:
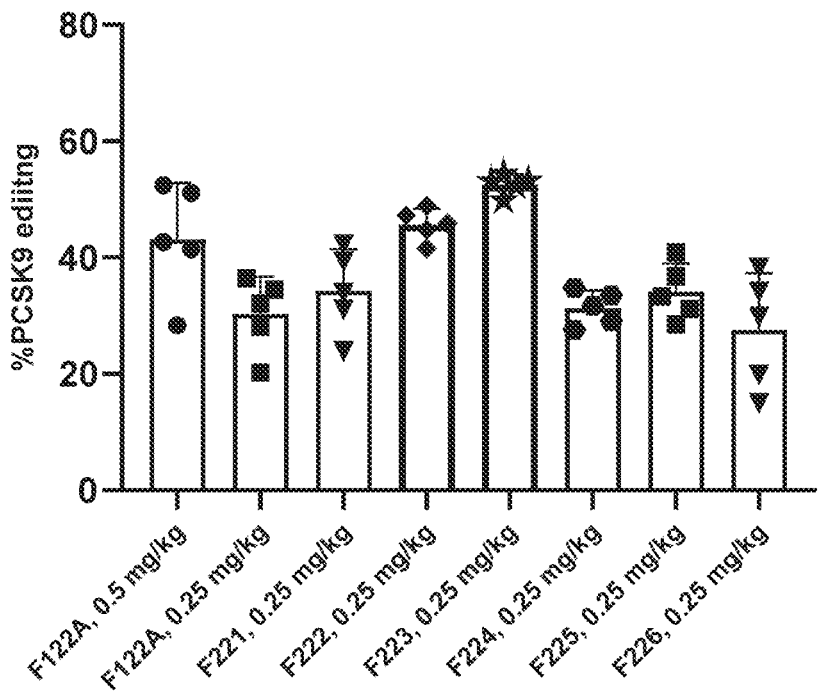
FIG. 24 (A) illustrates the percentage of PCSK9 gene editing in wild type C57BL/6 female mice liver after single dose administration of LNPs F122A and F221-F226 (n=5) at 0.25 mg/kg total RNA dose and FIG. 24 (B) illustrates the percentage of PCSK9 gene editing in wild type C57BL/6 female mice liver after single dose administration of LNPs F122A at 0.5 and 0.25 mg/kg, and F226A-F226C (n=5) at 0.25 mg/kg total RNA dose as described in Example 26, Table 24. Doping of fatty alcohol to LNP comprising amino lipid VL422 improve editing. F223 comprising about 6 mol % of fatty alcohol 504 at 0.25 mg/kg total RNA produced editing equivalent to the corresponding LNP F122A with no fatty alcohol at 0.5 mg/kg. 10 mol % of the alcohol 504 in the LNP composition further improved the editing efficiency. All LNPs evaluated comprise the amino lipid VL422. Formulations F226B and F226C comprising about 6 mol % and 10% of fatty alcohol 513 at 0.25 mg/kg total RNA dose improved the editing efficacy compare to the corresponding LNP F122A with no fatty alcohol at 0.25 mg/kg total RNA dose. All LNPs evaluated comprise the amino lipid VL422.
Figure 24:
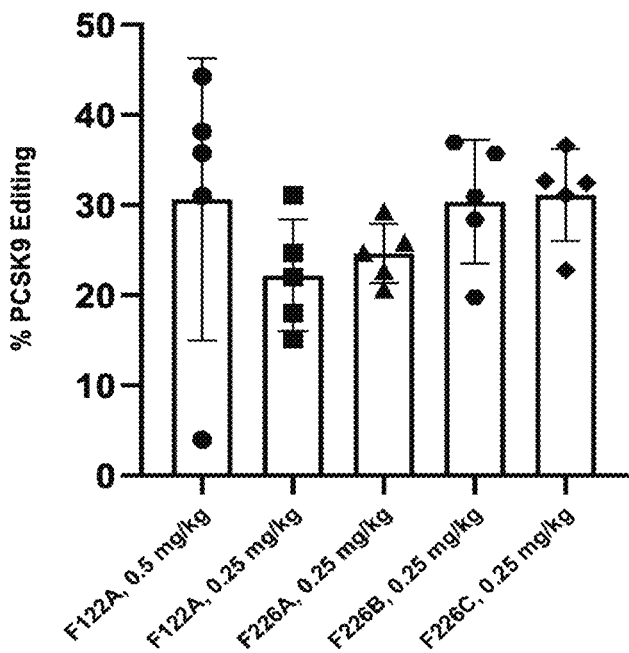

The LNP formulations F122A, F221-F226 and F226A-F226C encapsulating mouse PCSK9 gRNA GA055 and spCAS9 mRNA MS004 shown in Table 24 were prepared by pre-mixing the respective fatty alcohol with the LNP excipients and the formulations were prepared as described in Example 24. Post formulation LNPs F122A and F221-F226 were dialyzed against 50 mM Tris at pH 7.5. The LNPs F122A and F221-F226 after characterization were administered by retro-orbital injection to wild type C57BL/6 female mice (n=5); the percentage PCSK9 editing in mice liver was assessed and the editing data is shown in FIG. 24A. F122A was dosed at 0.5 and 0.25 mg/kg RNA dose, and F221/226 were dosed at 0.25 mg/kg of RNA dose. The in vivo study and editing analysis were performed as described in Example 13. In a separate study LNPs F122A and F226A-F226C were administered by retro-orbital injection to wild type C57BL/6 female mice (n=5); and the percentage PCSK9 editing in mice liver was assessed and the editing data is shown in FIG. 24B.

TABLE 24

Lipid composition and physiochemical characteristics of LNPs F122A, F221-F226 and F226A-F226C.

| LNP ID | VL422 mol % | Cholesterol/DSPC/PEG-DMG (507) mol % | N:P | Fatty alcohol mol % | | | Z-avg. (nm) | PDI | % RNA Entrapment |
|---|---|---|---|---|---|---|---|---|---|
| | | | | 504 | 505 | 513 | | | |
| F122A | 50 | 38/9/3 | 6 | | | | 67.8 | 0.19 | 93.0 |
| F221 | 50 | 36.1/9/3 | | 1.9 | | | 68.2 | 0.002 | 91.9 |
| F222 | 50 | 32.3/9/3 | | 5.7 | | | 76.9 | 0.01 | 92.1 |
| F223 | 50 | 27.6/9/3 | | 10.4 | | | 88.1 | 0.04 | 91.4 |
| F224 | 50 | 36.1/9/3 | | | 1.9 | | 82.3 | 0.21 | 92.0 |
| F225 | 50 | 32.3/9/3 | | | 5.7 | | 68.6 | 0.03 | 91.3 |
| F226 | 50 | 27.6/9/3 | | | 10.4 | | 72.3 | 0.002 | 85.2 |
| F226A | 50 | 27.6/9/3 | | | | 1.9 | 67.1 | 0.07 | 93.6 |
| F226B | 50 | 27.6/9/3 | | | | 5.7 | 70.0 | 0.16 | 92.5 |
| F226C | 50 | 27.6/9/3 | | | | 10.4 | 71.3 | 0.03 | 88.4 |

Example 27. Synthesis of VL454, VL455, VL472A, VL473A, and VL474A
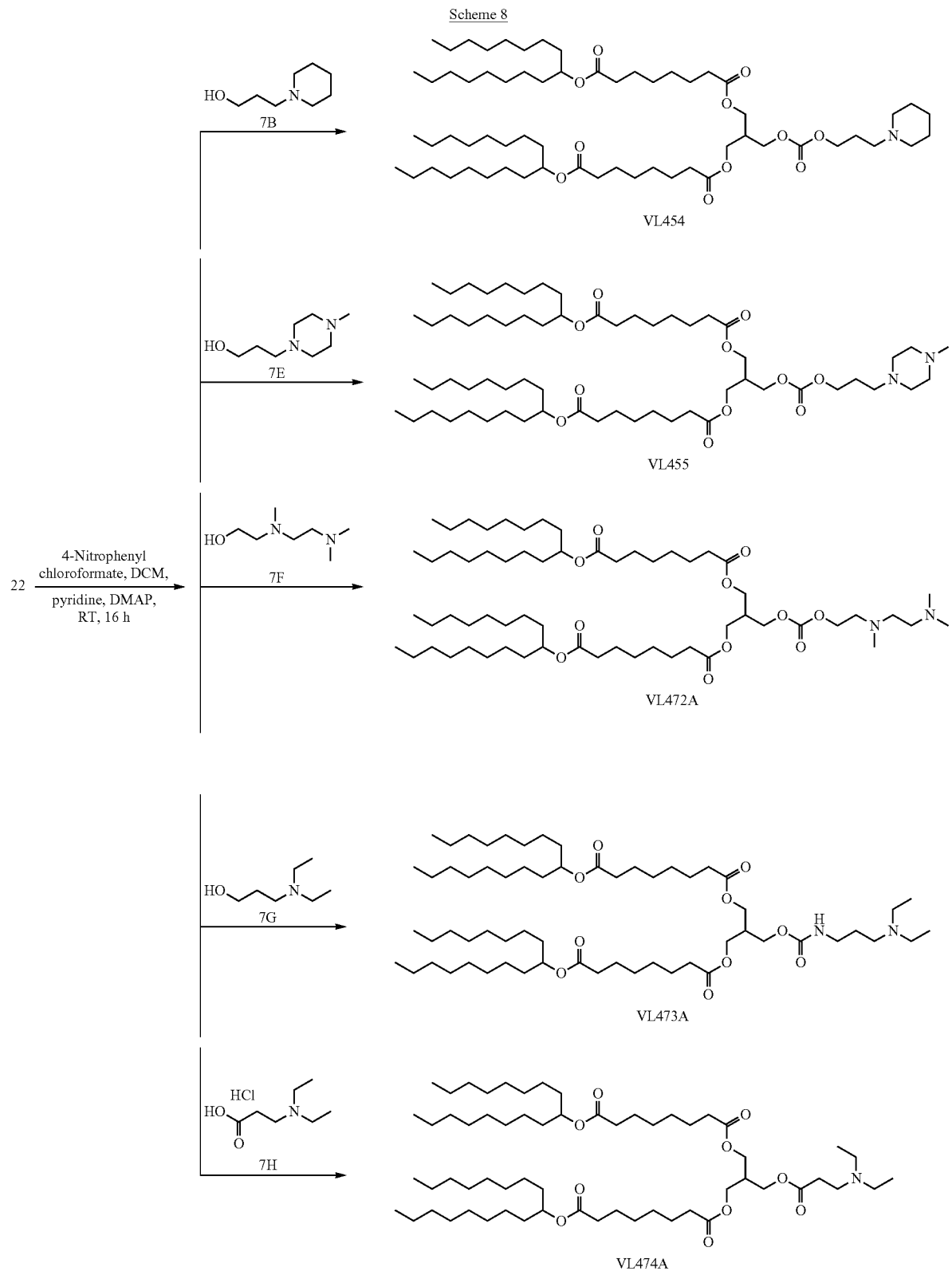

To a stirred solution of Compound 22 (1.0 g, 1.11 mmol) in dichloromethane (DCM, 10 mL), were added 4-nitrophenyl chloroformate (0.67 g, 3.33 mmol) and pyridine (0.26 mL, 3.33 mmol) followed by DMAP (0.067 g, 0.55 mmol) at 25-30° C. The resultant reaction mixture was stirred for 5 h and 7B (0.94 g, 6.66 mmol) was added; allowed to stir at 25°–30° C. for more 16 h. After completion of reaction, the mixture was diluted with water (20 mL) and extracted into DCM (2×50 mL). The organic layer was separated, concentrated under reduced pressure, and the crude was purified by silica gel column using 80% of EtOAc in hexanes as an eluent to afford VL454, as a pale-yellow viscous liquid (Yield: 0.32 g, 26.8%). $^1$H NMR (400 MHz, DMSO-$d_6$): δ ppm 4.90-4.80 (m, 2H), δ 4.199-4.119 (m, 8H), 2.52-2.41 (m, 6H), 2.40-2.31 (m, 8H), 1.98-1.82 (m, 3H), 1.72-1.58 (m, 13H), 1.56-1.45 (m, 10H), 1.41-1.33 (m, 9H), 1.31-1.26 (m, 48H), 0.98-0.85 (t, 12H). MS m/z: [M+H]$^+$ calculated: 1064.8; found: 1065.0.

VL455 was synthesized from compounds 22 and 7E by following VL454 synthetic method to yield a pale-yellow viscous liquid (yield: 0.30 g, 25.4%). $^1$H NMR (400 MHz, DMSO-$d_4$): δ ppm 4.90-4.80 (m, 2H), δ 4.199-4.119 (m, 8H), 2.61-2.48 (m, 5H), 2.50-2.31 (m, 6H), 2.40-2.31 (m, 8H), 1.98-1.82 (m, 2H), 1.72-1.68 (m, 8H), 1.56-1.45 (m, 8H), 1.41-1.33 (m, 10H), 1.31-1.26 (m, 44H), 0.98-0.85 (t, 12H). MS m/z: [M+H]~ calculated: 1079.9; found: 1079.9.

VL472A was synthesized from compounds 22 and 7F by following VL454 synthetic method (as described in scheme 8) to yield a pale-yellow viscous liquid (yield: 0.30 g, 25.4%). $^1$H NMR (400 MHz, CDCl$_3$): δ 4.90-4.80 (m, 2H), δ 4.199-4.119 (m, 8H), 2.71-2.70 (t, 2H), 2.58-2.55 (t, 2H), 2.40-2.31 (m, 3H), 2.32-2.5 (m, 17H), 1.72-1.68 (m, 8H), 1.56-1.45 (m, 8H), 1.41-1.33 (m, 57H), 0.98-0.85 (t, 12H). MS m/z: [M+H]$^+$ calculated: 1067.9; found: 1067.9.

VL473A was synthesized from compounds 22 and 7G by following VL454 synthetic method to yield a pale-yellow viscous liquid (yield: 0.35 g, 30.0%). $^1$H NMR (400 MHz, CDCl$_3$): δ 6.17 (s, 1H), 4.90-4.80 (m, 2H), δ 4.199-4.119 (m, 6H), 3.32-3.26 (t, 2H), 2.66 (s, 6H), 2.41-2.26 (m, 8H), 1.72-1.68 (m, 9H), 1.51-1.45 (m, 9H), 1.41-1.33 (m, 60H), 1.22-1.09 (m, 7H), 0.98-0.85 (t, 12H). MS m/z: [M+H]$^+$ calculated: 1051.9; found: 1051.9.

VL474A was synthesized from compounds 22 and 7H by following VL454 synthetic method to yield a pale-yellow viscous liquid (yield: 0.35 g, 30%). $^1$H NMR (400 MHz, CDCl$_3$): δ 4.90-4.80 (m, 2H), δ 4.199-4.119 (m, 6H), 2.80-2.77 (t, 2H), 2.62-2.48 (m, 6H), 2.41 (m, 1H), 2.31-2.28 (m, 8H), 1.71-1.59 (m, 10H), 1.61-1.41 (m, 9H), 1.41-1.31 (m, 9H), 1.32-1.21 (m, 50H), 1.01-0.99 (t, 6H), 0.98-0.85 (t, 12H). MS m/z: [M+H]$^+$ calculated: 1022.8; found: 1022.8.

Example 28. Synthesis VL459, VL460, VL471A, VL475A and VL476A

VL459, VL460, VL471A, VL475A and VL476A were synthesized as shown in the Scheme 9 and as described in Example 27.

Scheme 9

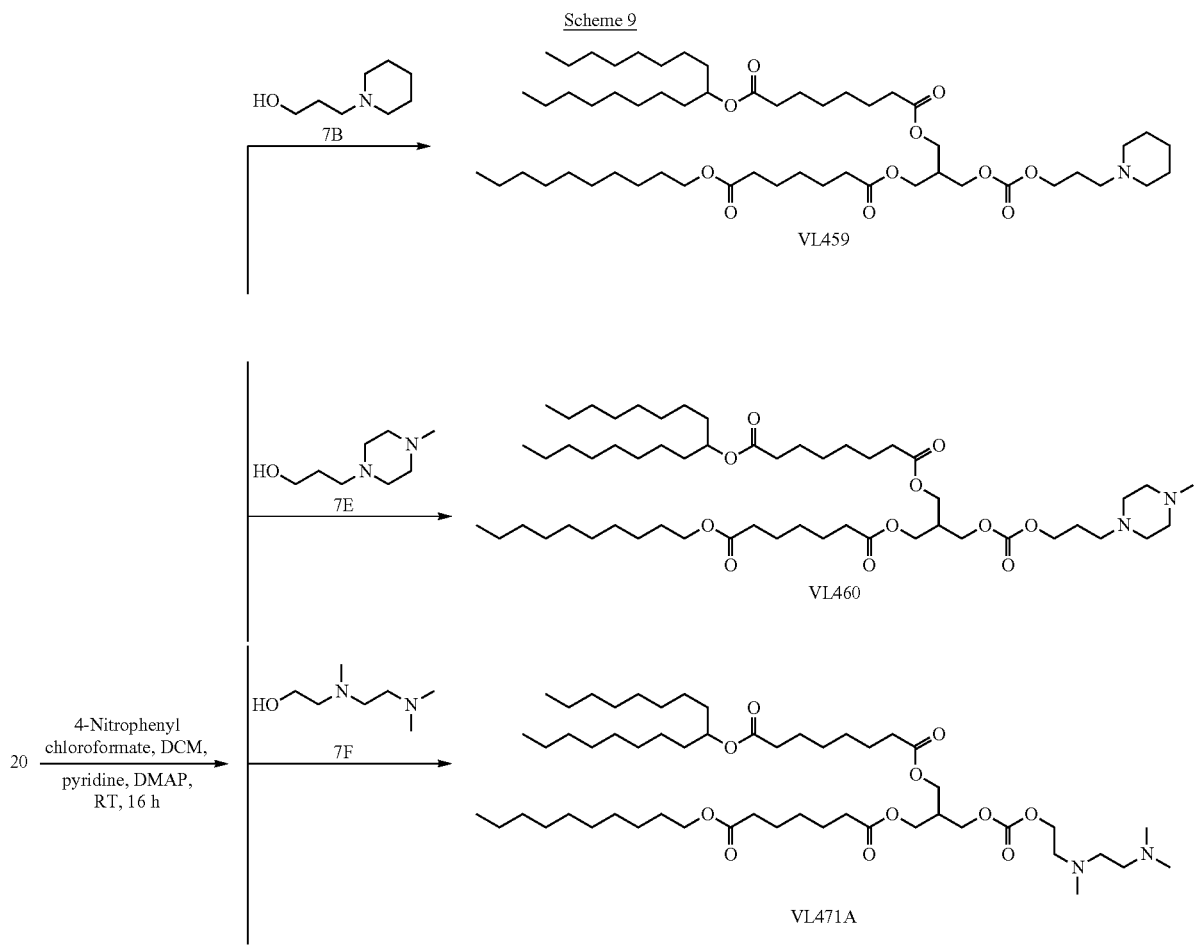

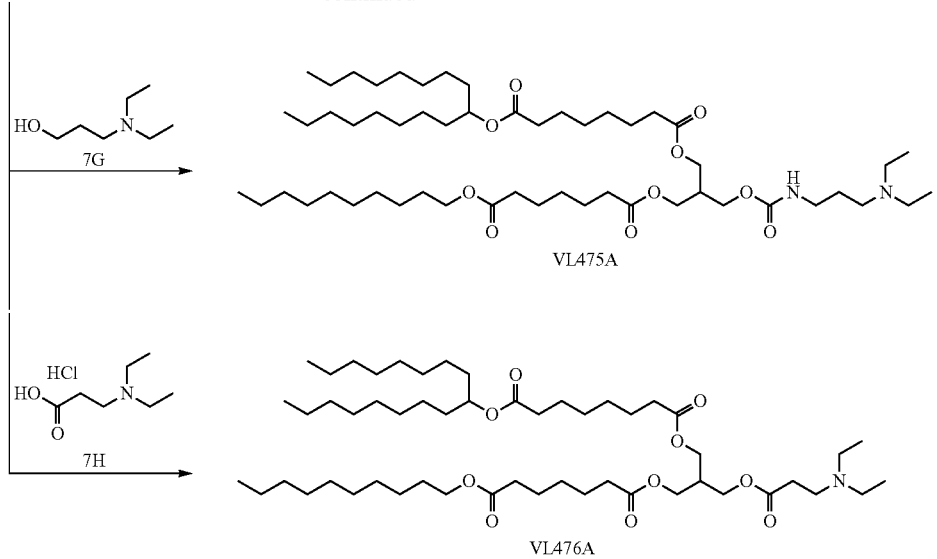

VL459 was prepared from compounds 20 and 7B and was isolated as a pale-yellow viscous liquid (0.26 g, yield: 14.2%). $^1$H NMR (300 MHz, CDCl$_3$): δ 0.84-0.86 (t, 9H), 1.23-1.32 (m, 44H), 1.142-1.59 (m, 6H), 1.62-1.69, (m, 14H), 1.96-2.01 (m, 2H), 2.28-2.31 (m, 8H), 2.31-2.35 (m, 1H), 2.401-2.51 (m, 6H), 4.03-4.08 (t, 2H), 4.13-4.22 (m, 8H), 4.84-4.88 (m, 1H). MS m/z: [M+H]$^+$ calculated: 952.74; found: 952.52.

VL460 was prepared from compounds 20 and 7E and was isolated as a pale-yellow viscous liquid (0.42 g, yield: 22.7%)). $^1$H NMR (300 MHz, CDCl$_3$): δ 0.84-0.86 (t, 9H), 1.23-1.32 (m, 44H), 1.42-1.59 (m, 4H), 1.62-1.69, (m, 10H), 1.83-1.91 (m, 2H), 2.25-2.31 (m, 12H), 2.31-2.34 (m, 2H), 2.40-2.48 (m, 8H), 4.03-4.07 (t, 2H), 4.11-4.21 (m, 8H), 4.81-4.90 (m, 1H). MS m/z: [M+H]$^+$ calculated: 967.7; found: 967.9.

VL471A was prepared from compounds 20 and 7F and was isolated as a pale-yellow liquid pale-yellow viscous liquid (0.21 g, yield: 11%). $^1$H NMR (300 MHz, CDCl$_3$): δ 0.838-0.855 (t, 9H), 1.225-1.317 (m, 44H), 1.416-1.550 (m, 5H), 1.589-1.668, (m, 9H), 2.258-2.418 (m, 18H), 2.535-2.552 (t, 2H), 2.612-2.634 (t, 2H), 2.692-2.731 (t, 2H), 4.0334.078 (t, 2H), 4.128-4.255 (m, 8H), 4.843-4.905 (m, 1H). MS m/z: [M+H]$^+$ calculated: 955.7; found 955.6.

VL475A was prepared from compounds 20 and 7G and was yielded as a pale-yellow viscous liquid (0.42 g, yield: 22.7%). $^1$H NMR (400 MHz, CDCl$_3$): δ 0.84-0.86 (t, 9H), 1.03-1.14, (m, 6H), 1.26-1.34 (m, 44H), 1.42-1.50 (m, 4H), 1.62-1.64, (m, 11H), 1.60-1.78 (m, 2H), 2.26-2.30 (m, 9H), 2.32-2.65 (m, 6H), 3.29 (t, 2H), 4.04-4.12 (m, 8H), 4.85-4.88 (t, 1H), 6.16 (t, 1H). MS m/z: [M+H]$^+$ calculated: 939.7; found: 939.9.

VL476A was prepared from compounds 20 and 7H and was purified as a yield a pale-yellow liquid (0.28 g, yield: 16.3%). $^1$H NMR (400 MHz, CDCl$_3$): δ 0.84-0.86 (t, 9H), 0.87-0.88 (t, 6H), 1.23-1.38 (m, 44H), 1.50-1.60 (m, 4H), 1.61-1.67, (m, 13H), 2.27-2.31 (m, 8H), 2.32-2.35 (m, 1H), 2.47-2.53 (m, 6H), 2.78-2.79 (t, 2H), 4.04-4.08 (t, 2H), 4.13-4.12 (m, 6H), 4.84-4.90 (m, 1H). MS m/z: [M+H]$^+$ calculated: 910.7; found: 910.9.

Example 29. Synthesis of PEG-Lipid VP159

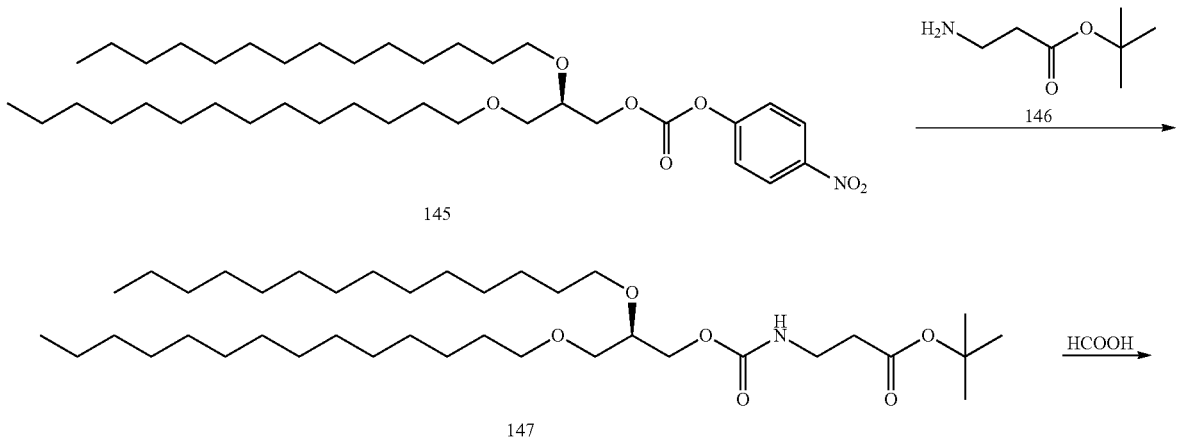

-continued

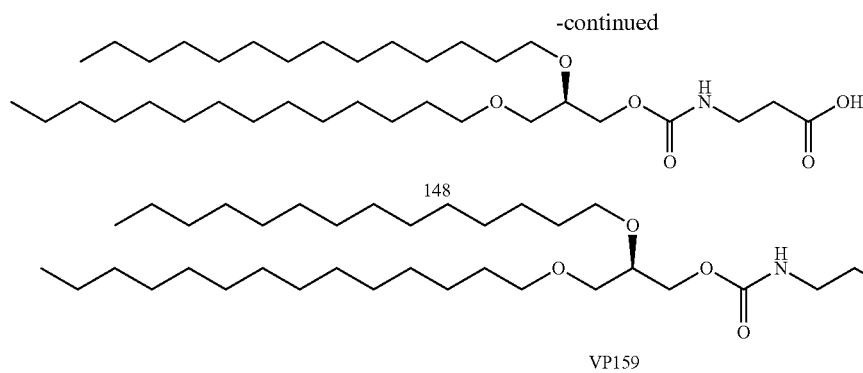 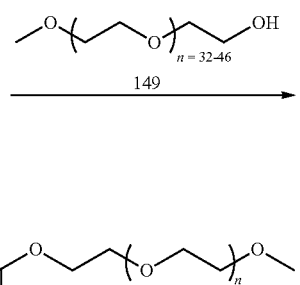

Scheme 10B

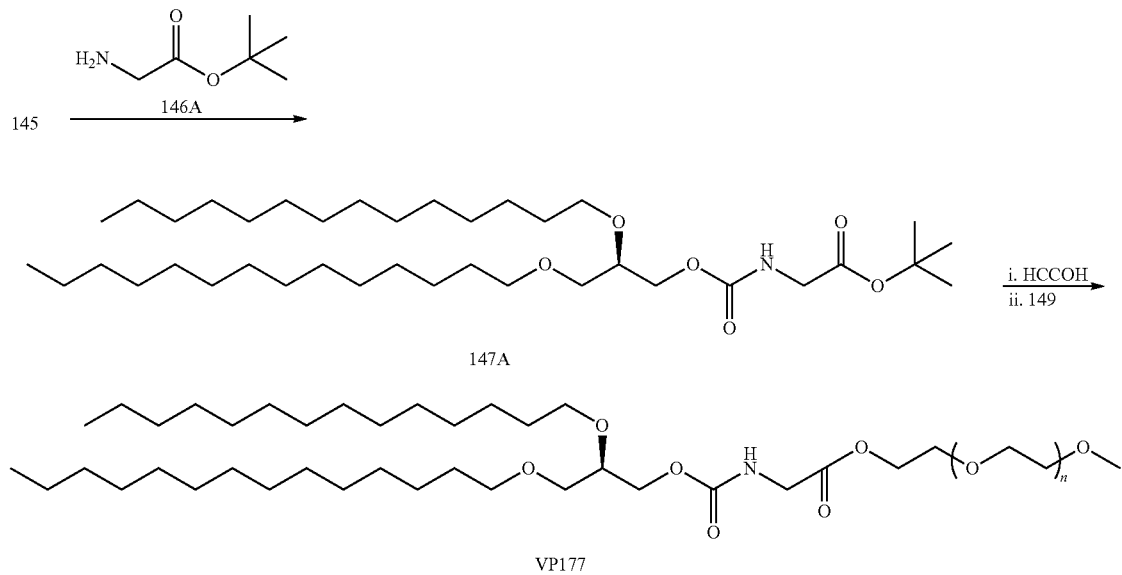

To a stirred solution of compound 145 (6.5 g, 10.77 mmol) in DCM (10 mL) was added pyridine (1.73 mL, 21.54 mmol) dropwise at 20-25° C.; and then compound 146 (7.82 g, 43.08 mmol) was added to the stirring solution. The reaction mixture was stirred for 6 h at room temperature (RT). After completion of the reaction, reaction mixture was concentrated under reduced pressure and the crude was purified by silica gel column chromatography (Combi-flash) using 5% EtOAc in hexane as eluent to afford compound 147 as colorless liquid (5.4 g, 84.60%). $^1$H NMR (400 MHz, CDCl$_3$): δ 5.251-5.22 (m, 1H), δ 4.22-4.12 (m, 1H), 4.10-4.08 (m, 1H), 3.62-3.54 (m, 3H), 3.54-3.39 (m, 6H), 2.46-2.43 (m, 2H), 1.62-1.57 (m, 5H), 1.50 (s, 9H), 1.30 (m, 47H), 0.98-0.85 (m, 6H).

To a stirred solution of compound 147 (5.0 g, 76.21 mmol) in DCM (25 mL) was added formic acid (40 mL) and the reaction mixture was stirred at 20-25° C. for 4 h. The reaction mixture was concentrated to remove formic acid and co-evaporated with toluene under reduced pressure to yield compound 148, which could be used in the next step without further purification. $^1$H NMR (400 MHz, CDCl$_3$): δ 5.33-5.31 (m, 1H), 4.23-4.11 (m, 3H), 3.61-3.56 (m, 4H), 3.49-3.42 (m, 8H), 2.61-2.56 (m, 3H), 1.56 (m, 6H), 1.27 (m, 59H), 0.90-0.87 (m, 6H).

To a stirred solution of compound 148 was added HBTU (1.98 g, 4.999 mmol) at ice cold temperature followed by HOBt hydrate (0.26 g, 0.9984 mmol) in dry DCM (20 mL) under inert atmosphere. The mixture was stirred at ice cold temperature for 10 min, and a solution of compound 149 (7.141 g, 3.328 mmol) in dry DCM over molecular sieves (10 mL) was added followed by dropwise addition of DIPEA (1.73 mL, 9.984 mmol). The resulting mixture was stirred at ice cold temperature for additional 10 min, the cooling bath was removed; the mixture was stirred at RT for 16 h. The reaction mixture was concentrated to get crude product, which was purified by reverse phase column chromatography using Acetonitrile/water as a mobile phase to afford the desired product VP159 as off-white solid (1.5 g, 16%). $^1$H NMR (400 MHz, CDCl$_3$): δ 5.34-5.33 (m, 1H), 4.26-4.20 (m, 2H), 4.19-4.16 (m, 1H), 4.10-4.06 (m, 1H), 3.83-3.80 (m, 1H), 3.74-3.55 (m, 176H), 3.55-3.54 (m, 5H), 3.47-3.41 (m, 7H), 3.38 (s, 3H), 2.58-2.55 (m, 2H), 1.56-1.53 (m, 4H), 1.29-1.25 (m, 44H), 0.89-0.86 (t, 6H). Average mass m/z: [M+Na]$^+$ calculated: 2732.0 found: 2732.1.

Example 30. Synthesis of PEG-Lipids VP161 and VP162

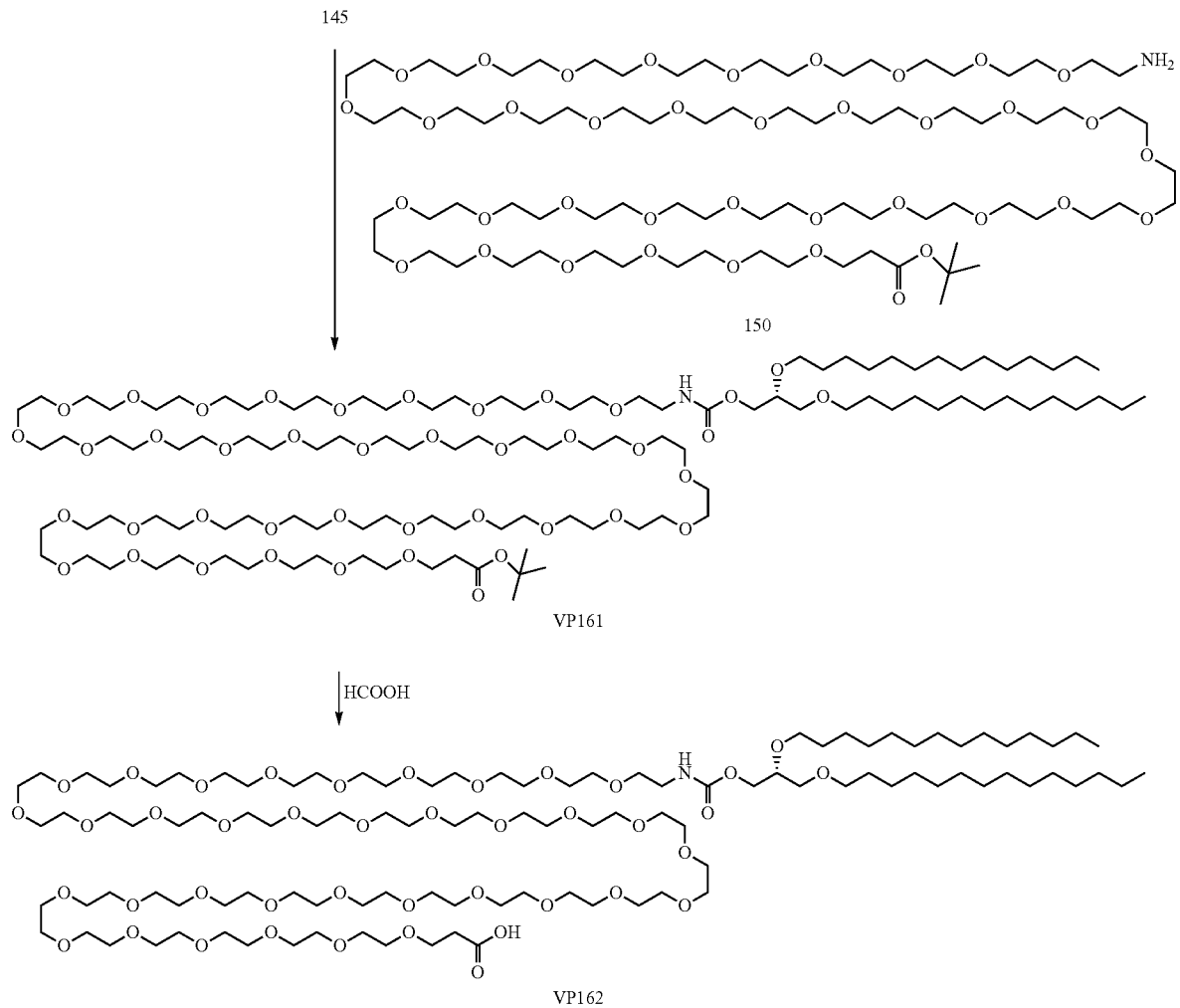

Scheme 11

A stirred solution of compound 145 (3.0 g, 0.0046 mol) in DCM (30 mL) was added pyridine (0.74 mL, 0.0092 mol) at room temperature. To the above solution, compound 150 (11.98 g, 0.0069 mol) was added and continued the stirring for 12 h at 25° C. The reaction mixture was concentrated under reduced pressure and the crude compound was purified by column chromatography (neutral alumina) using 80% EtOAc in hexane as eluent to afford compound VP161 as off-white solid (5.35 g, yield: 51.9%). $^1$H NMR (400 MHz, DMSO-d$_6$): δ 7.13 (t, J=5.6 Hz, 1H), 3.86-3.99 (m, 2H), 3.47-3.57 (m, 4H), 3.30-3.49 (m, 146H), 3.07-3.11 (m, 2H), 2.39-2.49 (m, 2H), 1.45-1.55 (m, 4H), 1.45 (s, 9H), 1.20-1.45 (m, 43H), 0.75-0.85 (m, 6H).

A stirred solution of VP161 (5.0 g, 2.2 mmol) in DCM (10 mL) was added formic acid (35 mL) at ice cold temperature and the resulting reaction mixture was stirred at room temperature for 6 h. The reaction mixture was concentrated to remove formic acid and co-distilled with toluene under reduced pressure to get the desired crude product VP162 as off-white solid (4.28 g, yield: 89.16). $^1$H NMR (400 MHz, CDCl$_3$): δ 5.27 (bs, 1H), 4.06-4.20 (m, 4H), 3.75-3.85 (m, 3H), 3.50-3.70 (m, 144H), 3.30-3.50 (m, 6H), 2.59 (t, J=6 Hz, 2H), 1.53-1.56 (m, 4H), 1.20-1.30 (m, 45H), 0.80-0.90 (m, 6H). MS m/z: [M+H]$^+$ calculated: 2185.4; found: 2185.0.

Example 31. Synthesis of PEG-Lipids VP163, VP164, VP165, VP166, and VP177

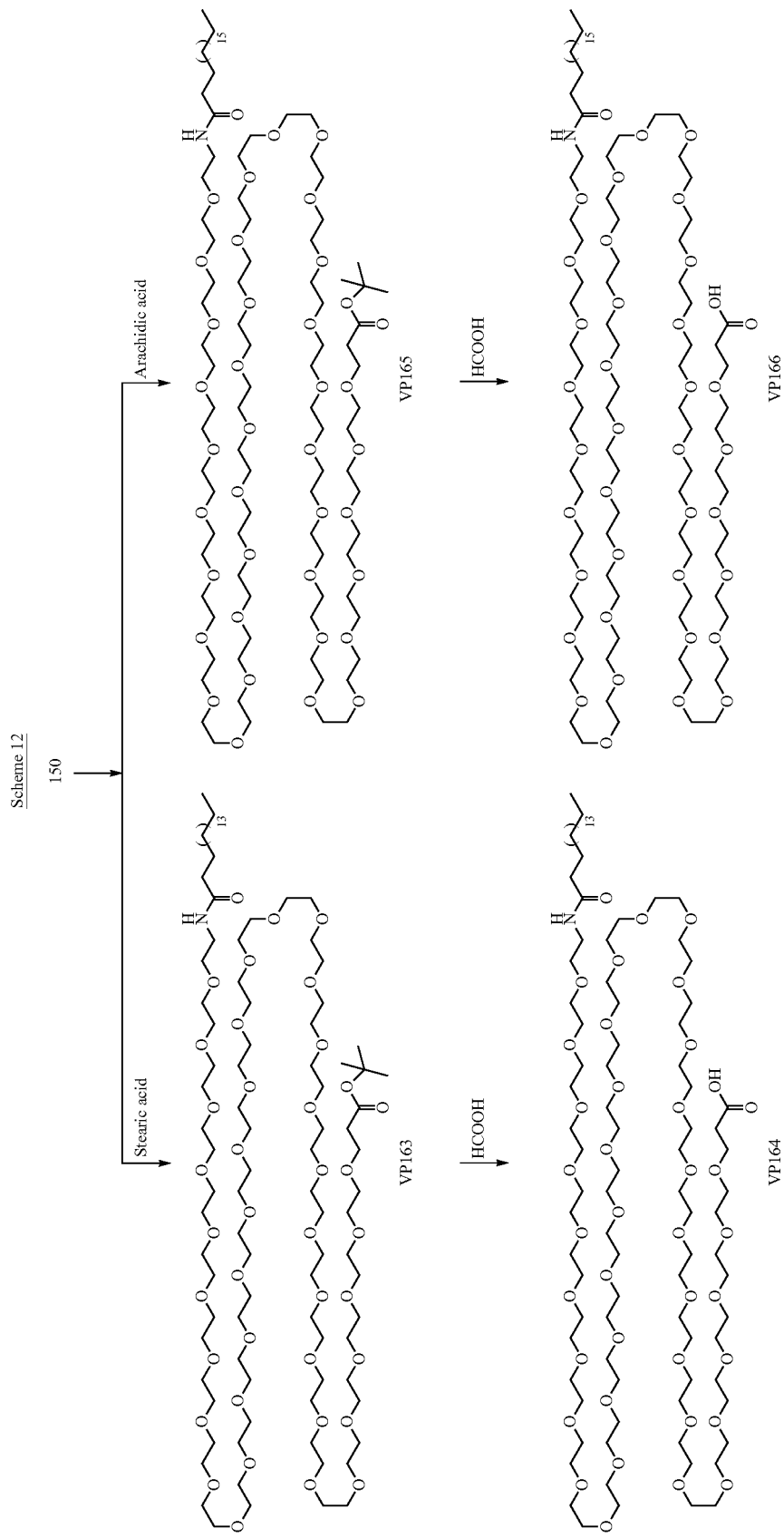

To a stirred solution of stearic acid (430 mg, 1.51 mmol) in DCM (8.6 mL) was added HOBt (20.4 mg, 0.15 mmol) at room temperature. To this reaction mixture was added HBTU (720.5 mg, 1.81 mmol) at ice cold temperature followed by DIPEA (0.78 mL, 4.53 mmol). Then solution of compound 150 (2.61 g, 1.51 mmol) in DCM (2.1 mL, 5 vol) was added at ice cold temperature and the resulting reaction mixture was stirred for 4 h at room temperature. To the reaction mixture was added water (30.0 mL) and extracted with DCM (2×30 mL). The organic layers were washed with brine (30.0 mL), dried over anhydrous sodium sulfate, filtered and the filtrate was evaporated under reduced pressure to get the desired crude. The crude was purified by silica gel column chromatography (CombiFlash) using 10% MeOH in DCM as eluent to afford VP163 as off-white solid (2.31 g, yield: 76.74%). $^1$H NMR (400 MHz, CDCl$_3$): δ 6.30-6.40 (bs, 1H), 3.38-3.72 (m, 151H), 2.68 (bs, 3H), 2.49 (t, 1=8.8 Hz, 2H), 2.19 (t, J=9.6 Hz, 2H), 1.61-1.64 (m, 4H), 1.45 (s, 9H), 1.20-1.45 (m, 29H), 0.80-0.85 (m, 3H). MS m/z: [M+Na]$^+$ calculated: 2019.3; found: 2019.0.

PEG-Lipid VP164 was synthesized following the synthetic method of VP162 (Scheme 11). VP164 was isolated as off-white solid (1.81 g, yield: 88.72%). 6.25 (bs, 1H), 3.54-3.81 (m, 144H), 3.42-3.47 (m, 3H), 2.59 (t, J=6.4 Hz, 2H), 2.17 (t, J=7.6 Hz, 2H), 1.40-1.63 (m, 4H), 1.20-1.45 (m, 27H), 0.80-0.85 (m, 3H). MS m/z: [M+H]~ calculated: 1941.2; found: 1941.0.

PEG-Lipid VP165 was isolated as off-white solid (2.52 g, yield: 89.0%) following the same synthetic method as VP164 by reacting compound 150 and arachidic acid. $^1$H NMR (400 MHz, CDCl$_3$): δ 6.38 (bs, 1H), 3.38-3.72 (m, 132H), 2.47-2.57 (m, 4H), 2.19 (t, J=9.6 Hz, 1H), 1.61-1.64 (m, 1H), 1.43 (s, 9H), 1.20-1.24 (m, 29H), 0.80-0.85 (m, 3H). MS m/z: [M+Na]$^+$ calculated: 2047.3; found: 2047.0.

PEG-Lipid VP166 was isolated as off-white solid (2.52 g, yield: 89.0%) following the same synthetic method as Example VP164. $^1$H NMR (400 MHz, CDCl$_3$): 6.29 (bs, 1H), 5.03 (bs, 3H), 3.54-3.82 (m, 146H), 3.44-3.46 (m, 3H), 2.59 (t, J=6 Hz, 2H), 2.18 (t, J=7.6 Hz, 2H), 1.59-1.63 (m, 2H), 1.25-1.35 (s, 32H), 0.80-0.85 (m, 3H). MS m/z: [M+H]$^+$ calculated: 1969.2; found: 1969.0.

PEG-Lipid VP177 was synthesized as described in Example 33 and according to Scheme 10B. PEG-lipid VP177 isolated as off-white solid. $^1$H NMR (400 MHz, CDCl$_3$): δ 5.345-5.309 (m, 1H), 4.33-4.30 (m, 2H), 4.25-4.21 (m, 1H), 4.15-4.10 (m, 1H), 4.01-4.00 (m, 1H), 3.84 (m, 1H), 3.73-3.70 (m, 3H), 3.67-3.65 (m, 168H), 3.57-3.54 (m, 5H), 3.50-3.42 (m, 8H), 3.39 (s, 3H), 1.57-1.54 (m, 5H), 1.30-1.26 (m, 46H), 0.90-0.87 (t, 6H). MS m/z: [M+H/2]$^+$ calculated: 1227.0; found: 1227.0.

Example 32. Synthesis of Amino Lipids VL509, VL510 and VL511

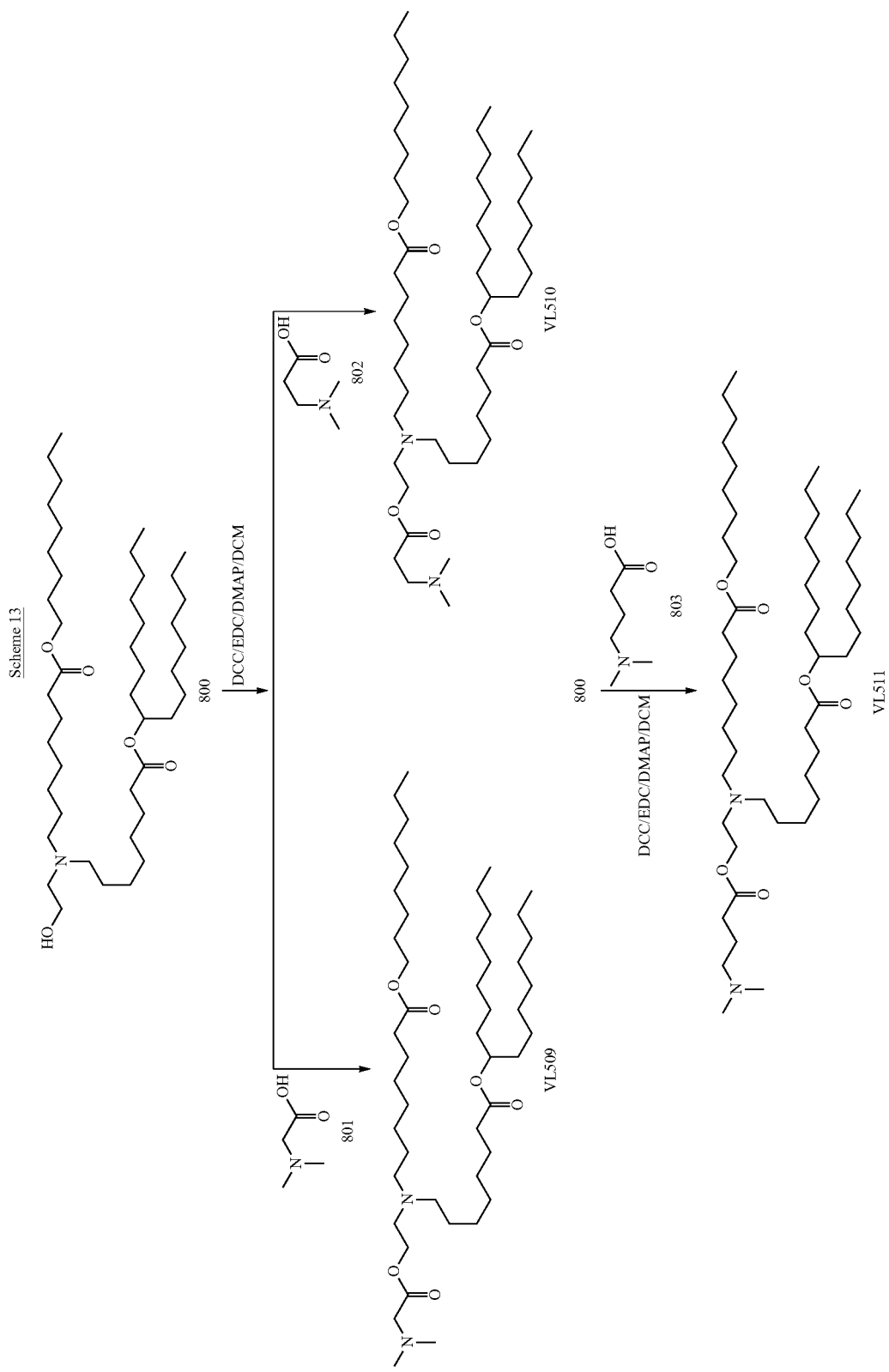

To a stirred solution of 800 (3 g, 4.23 mmol) and 801 (871 mg, 8.46 mmol) in DCM (60 mL) were added EDC·HCl (1.61 g, 8.46 mmol) and DMAP (774 mg, 6.34 mmol). The reaction was allowed to stir at room temperature for 18 h. The reaction was diluted with DCM (100 mL) and washed with water (100 mL). The organic layer was separated and washed with brine, then dried over $Na_2SO_4$, filtered and evaporated under vacuum. The crude product was taken in EtOAc (100 mL) and treated with 1N HCl (50 mL) and then the organic layer was washed with saturated $NaHCO_3$ solution (50 mL) followed by brine, then dried over anhydrous $Na_2SO_4$, filtered and evaporated under vacuum to obtain VL509 (2.32 g, 70% yield) as colourless liquid. $^1$H NMR (400 MHz, $CDCl_3$): δ 4.87-4.84 (m, 1H), 4.23-4.12 (br m, 2H), 4.05 (t, J=6.8 Hz, 2H), 3.17 (s, 2H), 2.52-2.49 (br m, 5H), 2.35 (s, 6H), 2.30-2.25 (m, 4H), 2.05-2.00 (m, 3H), 1.64-1.49 (m, 12H) 1.30-1.25 (m, 48H), 0.89-0.86 (m, 9H). MS m/z: $[M+H]^+$ calculated: 795.71; found: 795.83.

Amino Lipid VL510 was synthesized as a pale yellow liquid from compounds 800 and 802 as described for the synthesis of amino lipid VL509. $^1$H NMR (400 MHz, $CDCl_3$): δ 4.87-4.84 (m, 1H), 4.14 (t, J=6.4 Hz, 2H), 4.05 (t, J=6.8 Hz, 2H), 2.67-2.59 (m, 4H), 2.49-2.41 (m, 6H), 2.30-2.25 (m, 4H), 2.24 (s, 6H), 1.64-1.49 (m, 14H) 1.30-1.25 (m, 48H), 0.89-0.85 (m, 9H). MS m/z: $[M+H]^+$ calculated: 809.73; found: 809.84.

Amino Lipid VL511 was synthesized as a colorless liquid (1.2 g, 52% yield) from compounds 800 and 803 as described for the synthesis of amino lipid VL509. $^1$H NMR (400 MHz, $CDCl_3$): δ 4.87-4.84 (m, 1H), 4.13 (t, 1=6.4 Hz, 2H), 4.07 (t, J=6.8 Hz, 2H), 2.69 (t, J=6.4 Hz, 2H), 2.45-2.30 (m, 8H), 2.30-2.25 (m, 10H), 1.84-1.83 (m, 2H), 1.63-1.30 (m, 14H) 1.30-1.25 (m, 48H), 0.89-0.85 (m, 9H). MS m/z: $[M+H]^+$ calculated: 823.74; found: 823.93.

Example 33. Synthesis of Amino Lipid VL512 and VL513

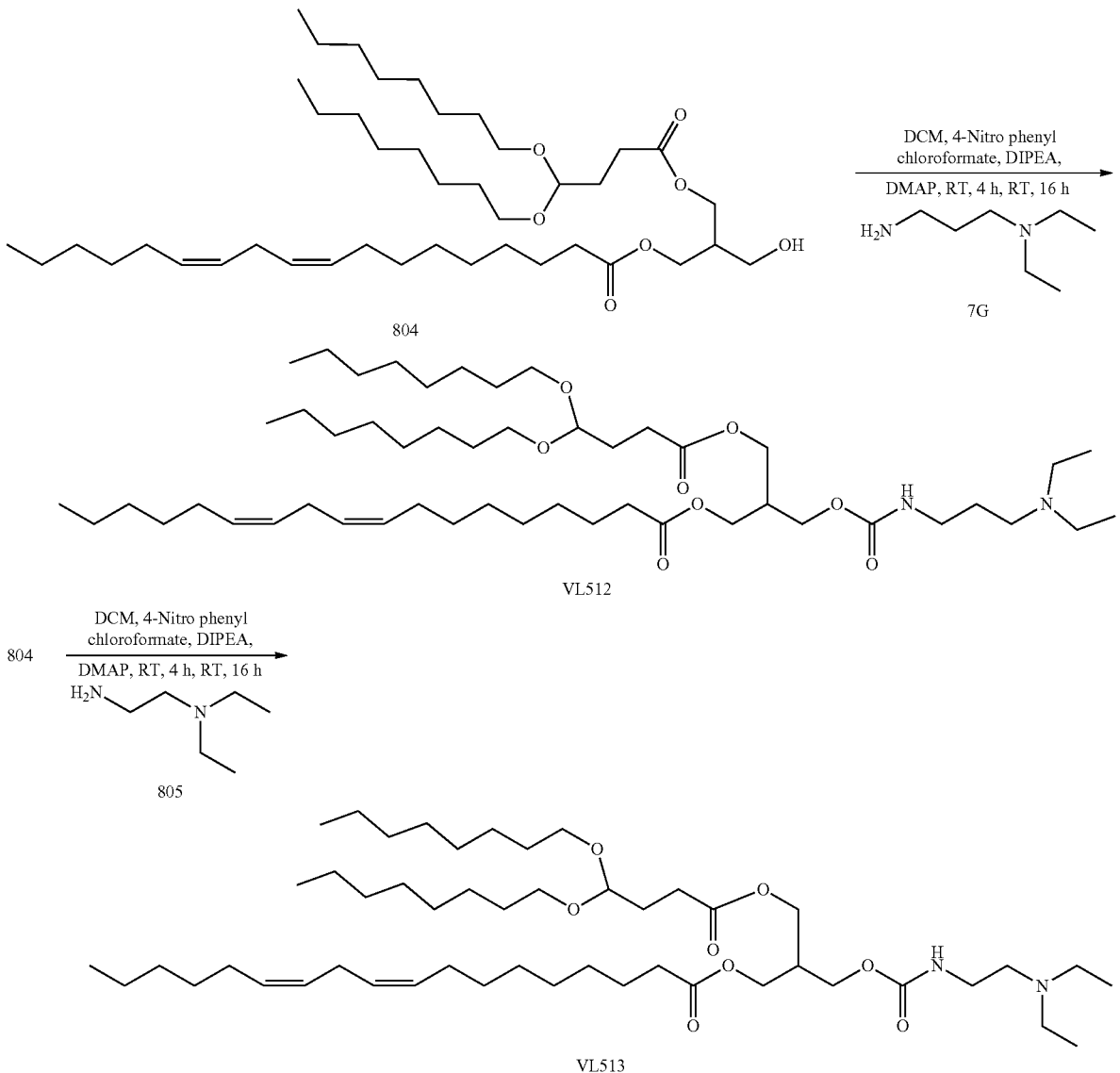

To a solution of compound 804 (1 g, 1.43 mmol) in DCM (10 mL) were added 4-Nitrophenyl chloroformate (578 mg, 2.87 mmol) followed by DIPEA (0.5 mL, 2.87 mmol) and DMAP (35 mg, 0.286 mmol), and the reaction was continued for 4 h. After completion of the reaction, compound 7G (1.1 g, 8.58 mmol) was added. After 16 h, the reaction mixture was diluted with DCM and water: the organic layer was separated and evaporated to get the crude which was purified by silica gel column eluting with 5% EtOAc and pet-ether to get VL512 (320 mg, 26%) as yellow oil. $^1$H NMR (400 MHz, CDCl$_3$): δ 6.2 (bs, 1H), 5.37-5.34 (m, 4H), 4.48 (t, 1H), 4.20-4.13 (m, 6H), 3.57-3.54 (m, 2H), 3.41-3.38 (m, 2H), 3.3-3.26 (m, 2H), 2.76 (t, 2H), 2.75-2.28 (m, 10H), 2.07-2.02 (m, 4H), 1.92-1.91 (m, 2H), 1.6-1.52 (m, 8H), 1.37-1.27 (m, 35H), 1.06 (m, 6H), 0.89-0.86 (m, 9H). MS m/z: [M+H]$^+$ calculated: 851.5; found: 851.5.

Amino Lipid VL513 was synthesized as a colorless liquid ((300 mg, 24.9%) from compounds 804 and 805 as described for the synthesis of amino lipid VL512. $^1$H NMR (400 MHz, CDCl3) δ 5.36-5.34 (m, 4H), 4.48 (t, 1H), 4.20-4.12 (m, 6H), 3.57-3.54 (m, 2H), 3.41-3.38 (m, 2H), 3.25-3.15 (m, 2H), 2.77 (t, 2H), 2.60-2.45 (m, 5H), 2.43-2.34 (m, 3H), 2.30 (t, 2H), 2.1-2.0 (m, 4H), 1.92-1.91 (m, 2H), 1.6-1.52 (m, 8H), 1.37-1.27 (m, 35H), 1.06 (m, 6H), 0.89-0.86 (m, 9H). MS m/z: [M+H]$^+$ calculated: 837.7; found: 837.7.

Example 34. Synthesis of Amino Lipid VL514 and VL515

Scheme 15

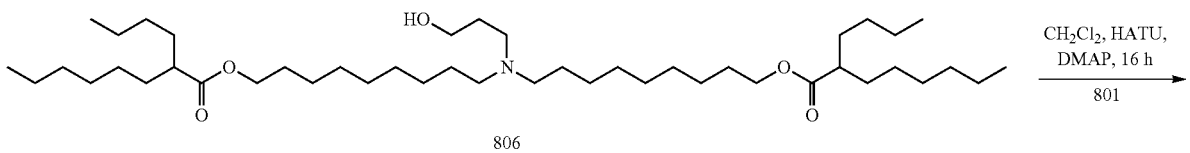

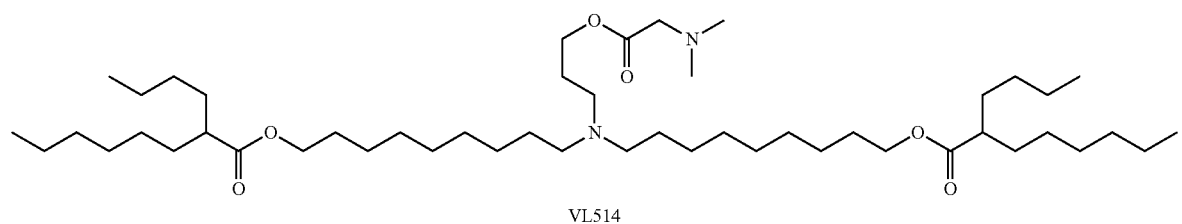

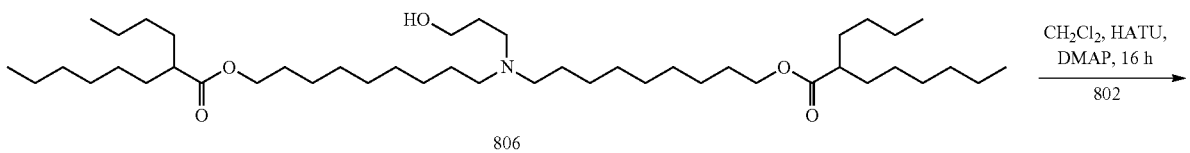

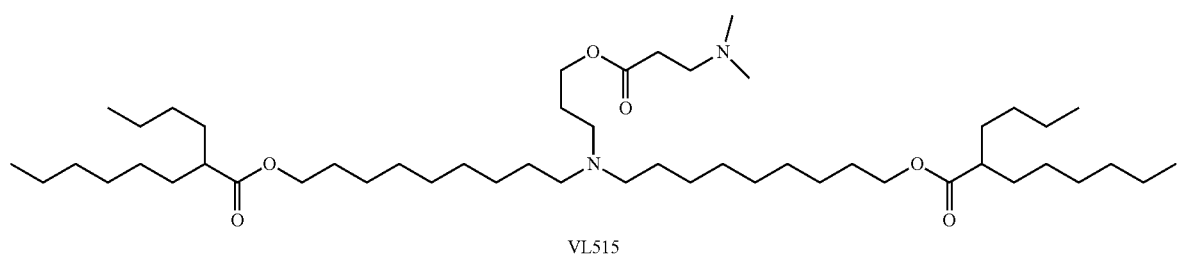

To a stirred solution of compound 806 (0.44 g, 0.28 mmol) in DCM (8 mL) was added 801 (0.06 g, 0.56 mmol) followed by HATU (0.22 g, 0.58 mmol) and DMAP (0.05 g, 0.42 mmol) at RT, and then stirred for 16 h. The reaction mixture was diluted with DCM (50 mL) and washed with water (25 mL), brine (25 mL). The organic layer was dried over anhydrous $Na_2SO_4$, filtered and evaporated to get the crude compound. Obtained crude compound was purified first by silica gel column by eluting with 3% MeOH in DCM and then was further purified by prep HPLC (Mobile phase A: 10 MM Ammonium formate in water Mobile phase B: Acetonitrile/isopropyl alcohol (10:90) to obtain amino lipid VL514 (0.086 g, 19%) as a pale yellow gummy liquid. $^1$H NMR (400 MHz, $CDCl_3$): δ ppm 4.32 (t, 2H), 4.06 (t, 4H), 3.78 (s, 2H), 3.26 (t, 2H), 3.04 (br s, 4H), 2.83 (s, 6H), 2.33-2.25 (m, 4H), 1.73-1.58 (m, 8H), 1.47-1.25 (m, 52H), 0.89-0.88 (m, 12H). MS m/z: $[M+H]^+$ calculated 809.6; found: 809.6.

Amino Lipid VL515 was synthesized as a colorless liquid (0.49 g, 33%) from compounds 806 and 802 as described for the synthesis of amino lipid VL514. $^1$H NMR (400 MHz, $CDCl_3$): δ ppm 4.30 (t, 2H), 4.06 (t, 4H), 3.49 (t, 2H), 3.29 (t, 2H), 3.07 (br s, 4H), 2.95 (s, 8H), 2.32-2.28 (m, 2H), 2.21 (br s, 2H), 1.71-1.54 (m, 12H), 1.47-1.25 (m, 48H), 0.89-0.86 (m, 12H). MS m/z: $[M+H]^+$ calculated: 823.6; found: 823.6.

Example 35. Synthesis of Amino Lipid VL516

To a stirred solution of compound 806 (50 g, 412 mmol) in DCM (1000 mL) was added TBDMS-Cl (224 g, 1480 mmol) and imidazole (210.8 g, 3100 mmol) were added at 0° C. The reaction mixture was warmed to 27° C. and stirred for 16 h. On completion, the reaction mixture was filtered, and the mother liquid was washed with saturated $NaHCO_3$ solution, water and brine. The organic layer was dried over $Na_2SO_4$ filtered and concentrated to get crude compound, which was purified on silica gel (230-400 mesh) column chromatography, eluted with 5% EtOAc in pet-ether. The fractions containing product were collected and concentrated under reduced pressure to afford compound 807 (100 g, yield: 49.6%) as a colorless liquid. To a stirred solution compound 808 (36 g, 215.84 mmol) in DCM (1500 mL) were added DIPEA (113 mL, 647.5 mmol) and HATU (123.2 g, 324.14 mmol) at 0° C. After 10 min, 807 (100 g, 215.84 mmol) was added. Then, the reaction mixture was allowed to warm to 27° C. and stirred for 16 h. On completion, all volatiles removed in vacuo and residue was diluted with EtOAc. The organic layer was washed with saturated $NaHCO_3$ solution, water, brine and dried over $Na_2SO_4$ filtered and concentrated to get desired 809 (108 g, 74%). To a stirred solution of 809 (20 g, 34.72 mmol) in THF (300 mL) was added TBAF (1M solution in THF) (121.5 mL, 121.52 mmol) added at 0° C. The reaction mixture was warmed to 27° C. and stirred for 2 h to get intermediate 809A. To the reaction mixture added EDC·HCl (26.6 g, 138.8 mmol), linoleic acid (38.95 g, 138.88 mmol) and DMAP (850 mg, 6.94 mmol) resulting mixture was stirred at 27° C. for 16 h. On completion, all volatiles were removed in vacuo, and residue was purified on silica gel (230-400 mesh, neutralized with ammonia) column chromatography, eluted with 40-50% EtOAc in pet-ether. The fractions containing product were collected and concentrated under reduced pressure to afford amino lipid VL516 (5.1 g, Yield: 14.4%) as a yellowish thick liquid. MS m/z: $[M+H]^+$ calculated: 1022.61; found: 1022.32.

Scheme 16

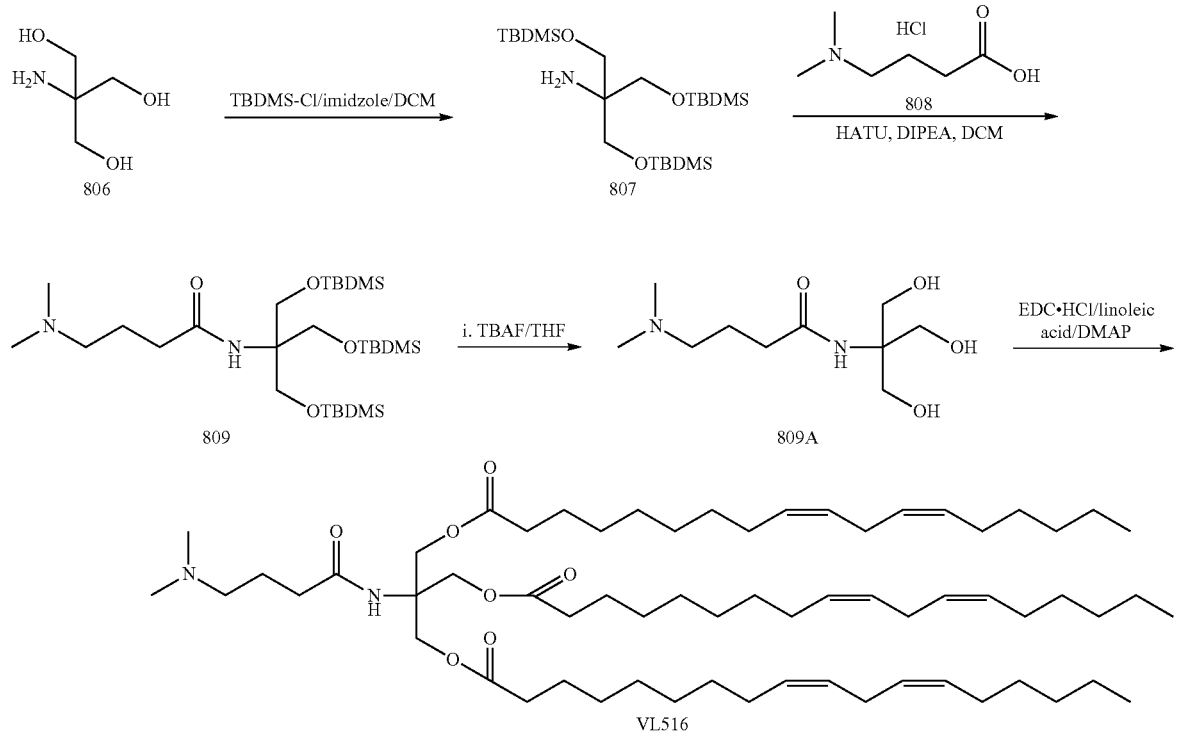

Example 36. Synthesis of Amino Lipid VL517

To a stirred solution of (9Z,12Z)-octadeca-9,12-dien-1-ol (20 g, 75.1 mmol) in DCM (200 mL) were added dihydrofuran-2,5-dione (9 g, 90.2 mmol) and DMAP (11.9 g, 97.7 mmol) at RT and stirred for 2 h. On completion, the reaction mixture was acidified with 1N HCl and extracted into DCM. The organic layer was washed with water, brine and dried over $Na_2SO_4$ filtered and concentrated to get desired compound 810 (20 g, 70%). To a stirred solution of 810 (8 g, 13.9 mmol) in THF (150 mL), EDC·HCl (13.2 g, 69.4 mmol), DMAP (338 mg, 2.7 mmol) and 809A (20.3 g, 55.5 mmol) were added to the reaction mixture, and the resulting mixture was stirred at 27° C. for 16 h. On completion, all volatiles were removed in vacuo and the residue was purified on silica gel (230-400 mesh, neutralized with triethylamine) column chromatography, eluted with 40-50% EtOAc in pet-ether. Then obtained compound was purified by prep HPLC, fractions containing product were collected and concentrated under reduced pressure followed by freeze drying to afford amino lipid VL517 (1.4 g, Yield: 8%) as a yellow liquid. MS m/z: $[M+H]^+$ calculated: 1280.88; found: 1280.05.

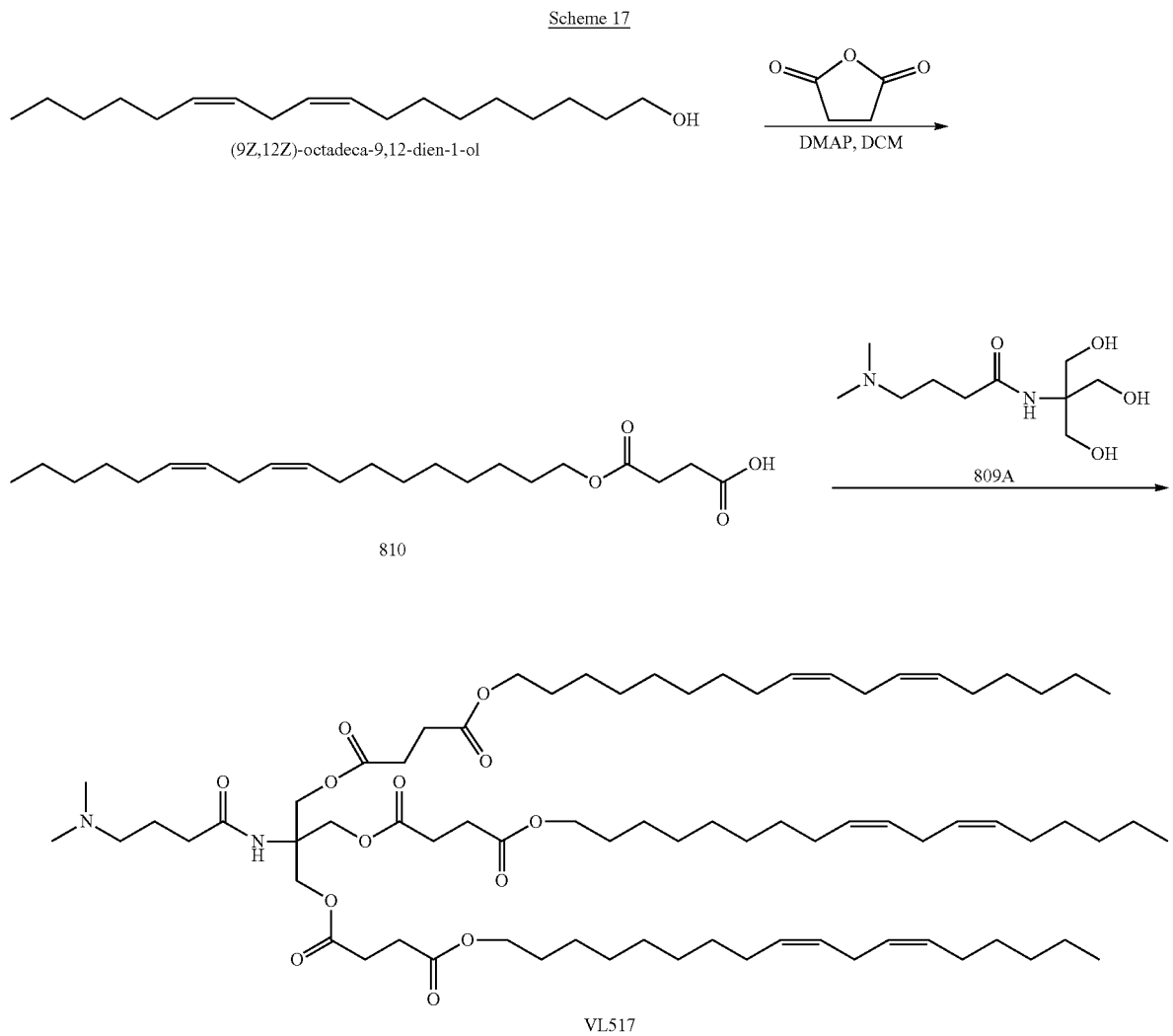

Scheme 17

Example 37. Synthesis of Amino Lipid VL518

To a stirred solution of compound 808 (7.03 g, 41.95 mmol) in THF (60 mL), was added DIPEA (16.6 mL, 95.35 mmol) followed by DCC (15.7 g, 76.28 mmol) at 0° C. Then the reaction mixture was stirred at RT for 15 min. Then was added compound 810A (5 g, 38.14 mmol) at 0° C. The resulting reaction mixture was allowed to stir at RT for 4 h. After completion of the reaction, reaction mixture was filtered, then filtrate was partitioned between Water (150 mL) and DCM (3×150 mL). The organic layer was washed with saturated ammonium chloride solution (2×80 mL) and saturated brine solution (2×80 mL), dried over $Na_2SO_4$, filtered, evaporated to afford compound 811 (crude, as off white thick oily liquid). The crude 811 was directly used in the next step without any further purification. 811 (7 g, 28.66 mmol) and acetic acid (120 mL, 80% in water) was stirred at RT for 16 h. The reaction mixture was evaporated under vacuum. The resulting white solid was dissolved in water (50 ml) and stirred for 15 min at RT and filtered. Resulting filtrate was collected and evaporated under vacuum to afford compound 812 (6 g, crude) as a viscous oil. To a stirred solution of crude 812 (6 g, 29.39 mmol) and linoleic acid (16.47 g, 73.47 mmol) in DCM (80 mL) were added EDC·HCl (11.26 g, 58.78 mmol), DIPEA (12.7 mL, 73.47 mmol) and DMAP (1.79 g, 14.69 mmol) at 0° C. The reaction mixture was allowed to stir at RT for 16 h. The reaction mixture was partitioned between water (100 mL) and DCM (3×150 mL). The organic layer was washed with sat. brine (2×80 mL), dried over sodium sulfate, filtered, evaporated under reduced pressure to get crude, which was further purified by prep-HPLC, to afford amino lipid VL518 as a yellow gum. MS m/z: $[M+H]^+$ calculated: 729.61; found: 729.3.

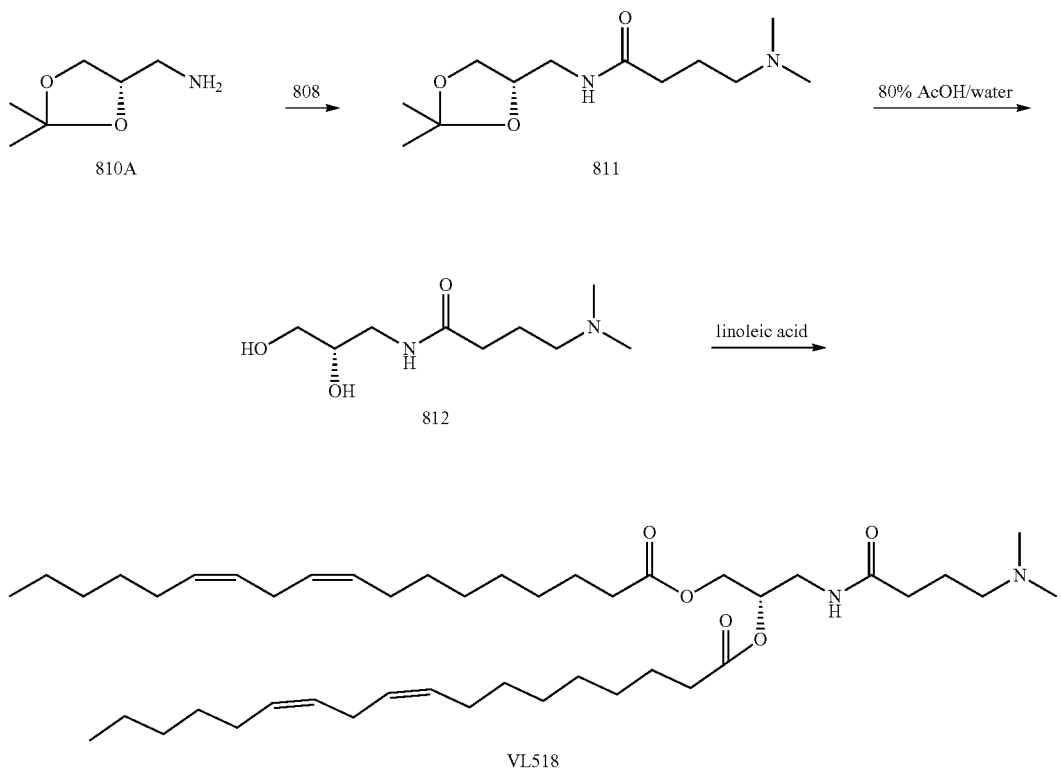

Scheme 18

Example 38. Synthesis of Amino Lipid VL519 and VL520

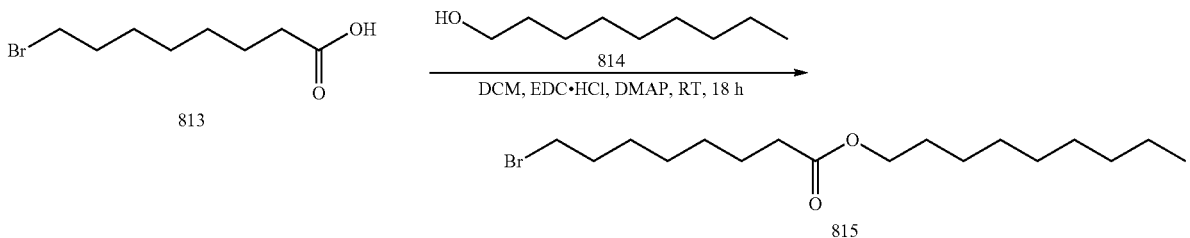

Scheme 19

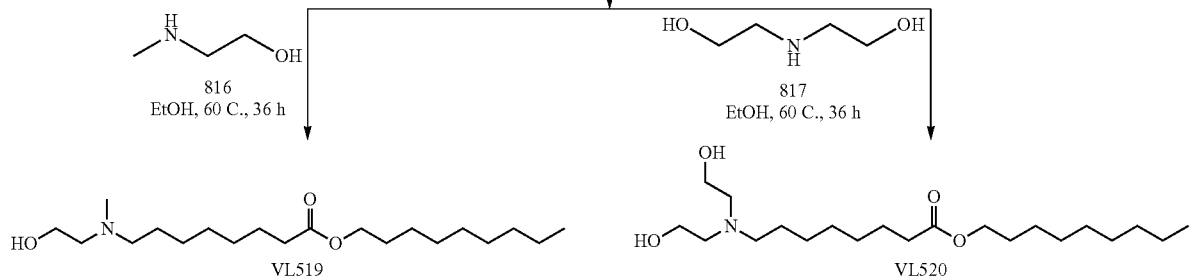

To a stirred solution of compound 813 (5 g, 22 mmol) and compound 814 (6.46 g, 45 mmol) in DCM (100 mL) were added EDC. HCl (4.3 g, 22 mmol) and DMAP (547 mg, 4.5 mmol). The reaction was allowed to stir at room temperature (RT) for 18 h. The reaction was diluted with DCM (100 mL) and extracted with saturated aqueous $NaHCO_3$ solution (50 mL). The organic layer was separated and washed with brine, then dried over $Na_2SO_4$, filtered and evaporated under vacuum. The residue was purified by silica gel column chromatography using 0-10% EtOAc in pet-ether as an eluent to obtain compound 815 (5 g, 64% yield) as a colorless liquid. $^1H$ NMR (400 MHz, $CDCl_3$) δ 4.06 (t, J=6.8 Hz, 2H), 3.40 (t, J=7.2 Hz, 2H), 3.40 (t, J=7.6 Hz, 2H), 2.29 (t, J=7.6 Hz, 2H), 1.85 (m, 2H), 1.72-0.97 (m, 22H), 0.88 (m, J=6.8 Hz, 3H). To a solution of compound 815 (7 g, 20 mmol) in Ethanol (28 mL) was added compound 816 (6.04 g, 80 mmol) and heated at 60° C. for 36 h. After completion, the reaction mixture was diluted with pet-ether (50 mL) and water (50 mL). Then the organic layer was separated and washed with brine solution. Resultant separated organic layer was dried over anhydrous $Na_2SO_4$ and residual solvent was evaporated under high vacuum. The crude product was taken in pentane (25 mL) and cooled to −78° C. the precipitated solid was filtered and washed with cold pentane (2×, 20 mL). The solid was dried under vacuum to get amino lipid VL519 (2.1 g, 30% yield) as an off-white semi solid. $^1H$ NMR (400 MHz, $CDCl_3$) δ 4.07 (t, J=6.8 Hz, 2H), 3.58 (t, J=5.6 Hz, 2H), 2.52 (t, J=5.6 Hz, 2H), 2.40 (t, J=7.2 Hz, 2H), 2.31 (t, J=7.6 Hz, 2H), 2.23 (S, 3H), 1.63-1.58 (m, 4H), 1.49-1.46 (m, 2H), 1.46-1.27 (m, 18H), 0.89 (t, J=6.4 Hz, 3H). MS m/z: $[M+H]^-$ calculated: 344.31; found: 344.36.

Amino lipid VL52 was synthesized as shown in scheme 19 following the same synthetic protocol as VL520. Amino lipid VL520 was isolated (3.5 g, 44 yield) as an off-white semi solid. $^1H$ NMR (400 MHz, $CDCl_3$) 054.07 (t, J=6.8 Hz, 2H), 3.63 (t, J=5.6 Hz, 4H), 2.67 (t, J=5.6 Hz, 4H), 2.54 (t, J=7.2 Hz, 2H), 2.31 (t, J=7.6 Hz, 2H), 1.84-1.83 (m, 4H), 1.59-1.48 (m, 2H), 1.46-1.27 (m, 18H), 0.89 (t, J=6.4 Hz, 3H). MS m/z: $[M+H]^+$ calculated: 374.32; found: 374.37.

Example 39

LNPs F227-F234 were formulated and characterized as described in Example 24. LNPs F227-F230 were formulated using amino lipid 502 and PEG-Lipids VP196-VP199. Formulations F231-F234 were formulated using amino lipid VL422 and PEG-Lipids VP196-VP199. Lipid corn positions of F227-F234 are described in Table 25.

TABLE 25

Lipid composition and physiochemical characteristics of F227-F234.

| LNP | mRNA | gRNA | Amino lipid | PEG-Lipid | Amino lipid/cholesterol (511)/DSPC (512)/PEG-Lipid mol % | N:P | Z-avg (nm) | PDI | % RNA Entrapment |
|---|---|---|---|---|---|---|---|---|---|
| F227 | MA004 | GA260 | 502 | VP196 | 55/38.2/4.7/2.1 | 8 | 98.19 | 0.05 | 90.25 |
| F228 | MA004 | GA260 | 502 | VP197 | 55/38.2/4.7/2.1 | 8 | 99.18 | 0.06 | 90.40 |
| F229 | MA004 | GA260 | 502 | VP198 | 55/38.2/4.7/2.1 | 8 | 109.7 | 0.09 | 82.56 |
| F230 | MA004 | GA260 | 502 | VP199 | 55/38.2/4.7/2.1 | 8 | 107.2 | 0.10 | 84.50 |
| F231 | MA004 | GA260 | VL422 | VP196 | 50/38/9/3 | 6 | 68.1 | 0.01 | 93.1 |
| F232 | MA004 | GA260 | VL422 | VP197 | 50/38/9/3 | 6 | 65.8 | 0.01 | 93.3 |
| F233 | MA004 | GA260 | VL422 | VP198 | 50/38/9/3 | 6 | 108.3 | 0.02 | 91.3 |
| F234 | MA004 | GA260 | VL422 | VP199 | 50/38/9/3 | 6 | 113.7 | 0.002 | 89.8 |

Example 40. Evaluation of LNP Formulations Containing Amino Lipids. 422 and 454 in Non-Human Primate (NHP)

Figure 25:
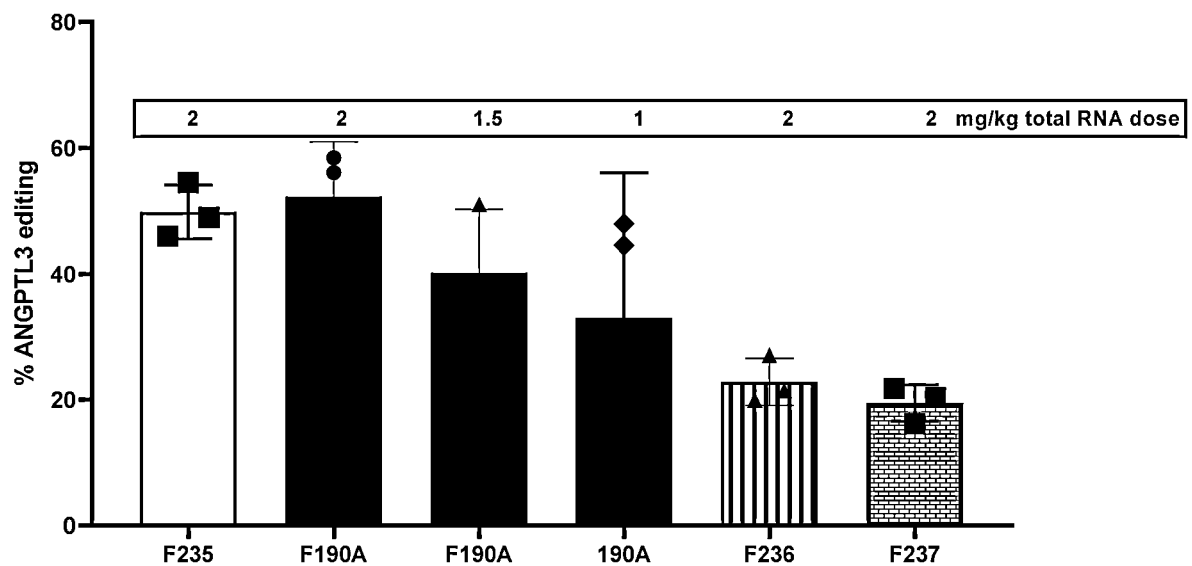
FIG. 25 illustrates the percentage of ANGPTL3 gene editing in the livers of cynomolgus monkeys (n=3) after single dose administration of LNPs F190A, F235-F237 as described in Example 40 (Table 26). LNP F190A was dosed at 2, 1.5 and 1 mg/kg total RNA. F236, F235 and F237 were dosed at 2 mg/kg total RNA.

LNPs F190A and F235-237 shown in Table 26 were formulated using a X-mixer. Buffer exchange (50 mM Tris at pH 7.5) was performed using TFF. F235 was prepared by modifying post mixing ethanol concentration to 8% in aqueous buffer. The LNP formulations F190A and F235-F237 were administered to cynomolgus monkeys (n=3) by intravenous infusion over 1 hour. A 2-week study was performed to evaluate editing of the ANGPTL3 gene in cynomolgus monkeys by administering the LNPs constituted using guide RNA GA347 and mRNA MA004 (FIG. 25). The MA004/GA347 LNPs were administered to cynomolgus monkeys with the intent of producing targeted adenine base editing of ANGPTL3 gene in the liver. The animals underwent necropsy for collection of liver samples, two weeks after administration of test article, and the samples were stored at −86 to −60° C. Splice-site editing was analyzed by next generation sequencing, confirming that base change occurred. The LNP formulation 190A was administered at 2 mg/kg, 1.5 mg/kg and at 1 mg/kg (n=3) total RNA to evaluate the dose response on editing activity of VL422-LNP (FIG. 25) in NHPs. The LNPs F235, F236 and F237 were dosed at 2 mg/kg (Table 26).

All animal studies (mice and monkey) were approved by the respective Institutional Animal Care and Use Committee (IACUC).

TABLE 26

Lipid composition and physiochemical characteristics of F190A and F235-F237.

| LNP | mRNA | gRNA | Amino lipid/cholesterol (511)/DSPC (512)/PEG-Lipid (507) mol % | Amino lipid | N:P | Z-avg (nm) | PDI | % RNA Entrapment | % ANGPTL3 editing |
|---|---|---|---|---|---|---|---|---|---|
| F190A | MA004 | GA347 | 50/38/9/3 | VL422 | 6 | 72.7 | 0.06 | 94.3 | See FIG. 25 |
| F235 | MA004 | GA347 | 50/38/9/3 | VL422 | 6 | 68.7 | 0.03 | 92.5 | |
| F236 | MA004 | GA347 | 50/38/9/3 | VL454 | 6 | 68.6 | 0.02 | 93.8 | |
| F237 | MA004 | GA347 | 52.4/35.6/9/3 | VL454 | 6 | 68.2 | 0.06 | 91.9 | |

Figure 26:
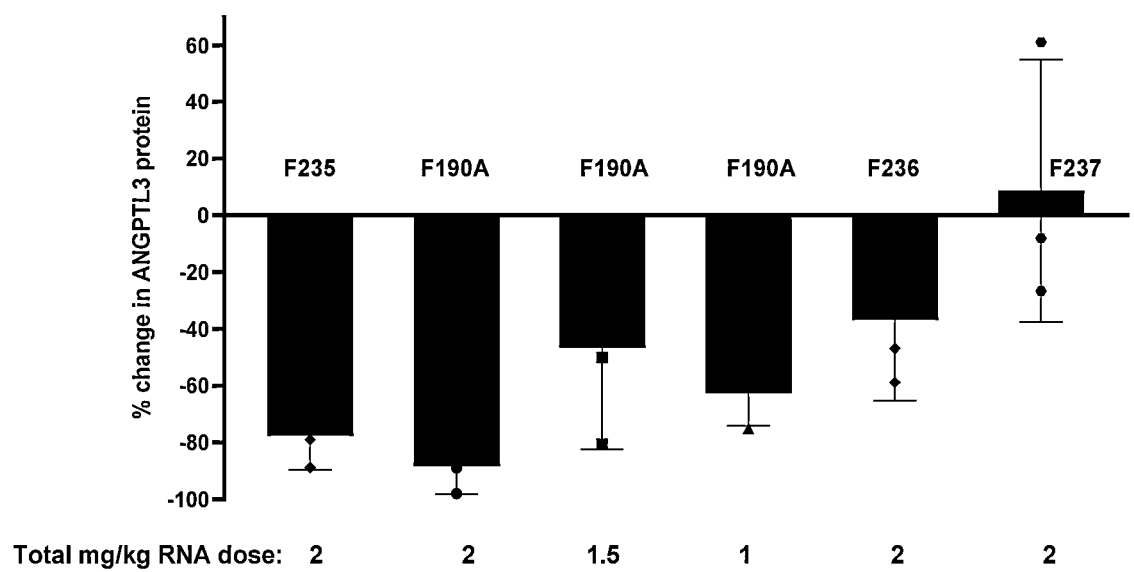
FIG. 26 illustrates the percentage of ANGPTL3 protein knockdown from baseline at day 15 in serum of cynomolgus monkeys (n=3) after single dose administration of LNPs F190A, F235-F237 (Example 40). F190A was dosed at 2, 1.5 and 1 mg/kg RNA respectively. F235, F236 and F237 were dosed at 2 mg/kg RNA.

In addition to liver editing, serum ANGPTL3 protein was measured in NHPs (n=3) post administration of LNP formulations F190A and F235-F237. Whole blood samples were collected for serum ANGPTL3 protein analysis at various time points (at −10, −7 and −5 days) pre-administration and at day 15 post administration of LNPs. Serum samples were isolated from the collected blood samples for ANGTPL3 measurement. For analysis of ANGPT3 protein levels, human ANGPTL3 ELISA kit (DANL30, R&D Systems, Minneapolis, MN) was used with recombinant cynomolgus monkey ANGPTL3 protein (10052-AN, R&D Systems) to analyze pre-dosed serum samples and serum samples collected at day 15, after LNP administration for protein levels (according to the manufacturer's instruction). Percentage change in serum ANGPTL3 level from baseline in treated NHPs at day 15 is shown in FIG. 26.

Example 41

Syntheses of PEG-Lipids VP196, VP197, VP198 and VP199 were accomplished as illustrated in Scheme 20.

Scheme 20

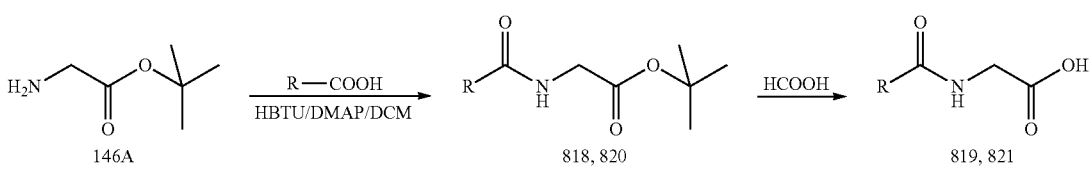

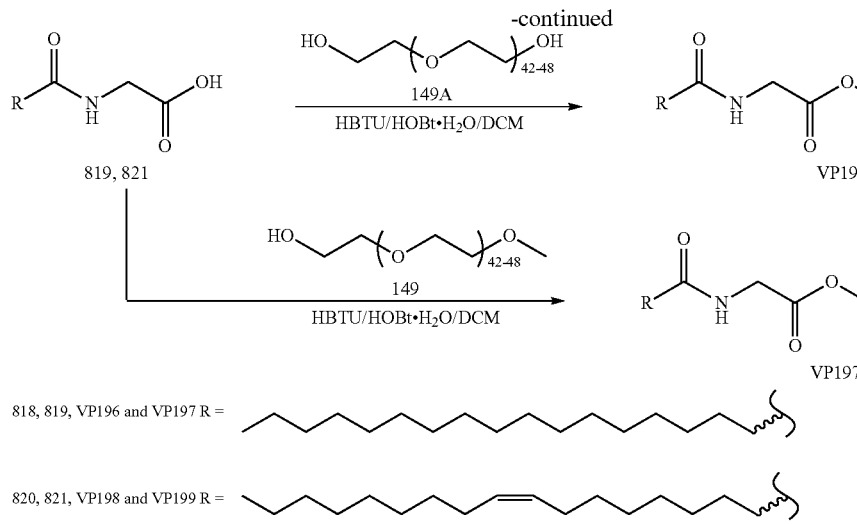

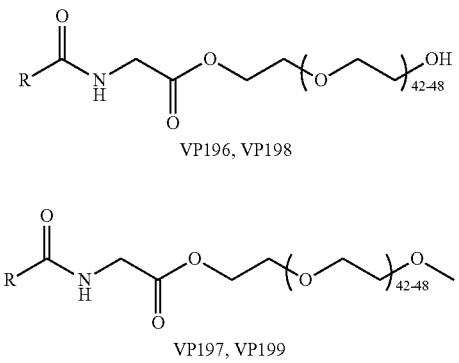

PEG-Lipid VP196:

To a stirred solution of stearic acid (3.0 g, 10.5 mmol, 1.0 eq) in DCM (30 mL), was added HBTU (6.0 g, 15.8 mmol, 1.5 eq.) followed by DMAP (0.26 g, 2.1 mmol, 0.2 eq) under argon atmosphere. The mixture was stirred at 10-15° C. for 30 min, and tert-butyl glycinate (146A, 1.38 g, 10.5 mmol, 1.0 eq) was added followed by dropwise addition of DIPEA (4.68 mL, 26.7 mmol, 2.5 eq). The mixture was stirred at 10-15° C. for additional 10 min, the cooling bath was removed, and the mixture was stirred at room temperature (RT) for 16 h. Upon completion the reaction, the reaction mixture was concentrated under reduced pressure to get crude product, which was purified by column chromatography using 20-25% EtOAc in hexane to afford compound 818 as white solid (3.32 g, 79.2%). $^1$H NMR (400 MHz, CDCl$_3$): δ ppm, 5.91 (s, 1H), δ 3.95-3.94 (d, 2H), 2.24-2.21 (t, 2H), 1.66-1.59 (m, 2H), 1.48 (s, 9H), 1.32-1.25 (m, 30H), 0.90 (m, 3H). To a stirred solution of intermediate 818 (3.3 g, 8.3 mmol) in DCM (18 mL) was added formic acid (29 mL) at RT and was stirred for 16 h, and the mixture was concentrated to remove formic acid; co-evaporated with toluene under reduced pressure to get the crude compound 819 as white solid, which could be used in the next step without further purification. $^1$H NMR (400 MHz, DMSO-d$_6$): δ ppm, 12.46 (s, 1H), δ 8.08-8.05 (m, 1H), 3.70-3.68 (d, 2H), 2.10-2.06 (m, 2H), 1.47-1.44 (m, 2H), 1.38-1.27 (m, 30H), 0.90 (m, 3H). To a stirred solution of compound 819 (0.5 g, 1.46 mmol, 1.0 eq) in dry DCM (5 mL) was added HBTU (0.83 g, 2.19 mmol, 1.5 eq) at 10-15° C. followed by HOBt hydrate (0.06 g, 0.43 mmol, 0.3 eq) under inert atmosphere. The mixture was stirred at 10-15° C. for 30 min, and a solution of 149A (2.92 g, 1.46 mmol, 1.0 eq) in dry DCM (2.5 mL, treated with molecular sieves) was added followed by dropwise addition of DIPEA (0.76 mL, 4.38 mmol, 3.0 eq). The stirring was continued at 10-15° C. for additional 10 min, the cooling bath was removed; the mixture was allowed to stir at RT for 16 h. Upon completion, the reaction mixture was concentrated to get crude product, which was purified by silica gel chromatography using 20-25% MeOH in EtOAc followed by reverse phase column chromatography using 40-50% acetonitrile in water to afford the desired product VP196 as white solid (0.63 g, 18.52%). $^1$H NMR (400 MHz, CDCl$_3$): δ ppm, 6.09 (t, 1H), δ 4.32-4.29 (m, 2H), 4.08-4.07 (d, 2H), 3.83-3.80 (t, 1H), 3.74-3.66 (m, 185H), 3.62-3.60 (t, 1H), 2.78 (s, 1H), 2.25-2.21 (t, 2H), 1.93 (s, 6H), 1.65-1.60 (m, 2H), 1.29 (s, 30H), 0.89-0.86 (t, 3H). MS m/z: [M+H/2]$^+$ calculated: 1250.28; found: 1250.60.

PEG-Lipid VP197:

To a stirred solution of compound 819 (0.5 g, 1.46 mmol, 1.0 eq) in dry DCM (5 mL) was added HBTU (0.83 g, 2.19 mmol, 1.5 eq) at 10-15° C. followed by HOBt hydrate (0.06 g, 0.43 mmol, 0.3 eq) under inert atmosphere. The mixture was stirred at 10-15° C. for 30 min, and a solution of PEG compound 149 (2.92 g, 1.46 mmol, 1.0 eq) in dry DCM (2.5 mL) was added followed by dropwise addition of DIPEA (0.76 mL, 4.38 mmol, 3.0 eq). The mixture was stirred at 10-15° C. for additional 10 min, the cooling bath was removed; the mixture was allowed to stir at RT for 16 h. VP197 was purified and isolated similarly as VP196 to afford as a white solid (0.82 g, 24.11%). $^1$H NMR (400 MHz, CDCl$_3$): δ ppm, 7.27 (t, 1H), δ 4.31-4.29 (m, 2H), 4.08-4.04 (m, 2H), 3.82-3.80 (m, 1H), 3.76-3.69 (m, 4H), 3.65-3.64 (d, 172H), 3.61-3.57 (m, 2H), 3.56-3.45 (m, 1H), 3.38 (s, 3H), 2.25-2.21 (t, 3H), 1.65-1.59 (m, 2H), 1.29-1.24 (m, 29H), 0.89-0.86 (t, 4H). MS m/z: [M+H/2]$^+$ calculated: 1257.29; found: 1257.60.

PEG-Lipid VP198:

To a stirred solution of oleic acid (3.0 g, 10.6 mmol, 1.0 eq) in DCM (30 mL), was added HBTU (6.05 g, 15.9 mmol, 1.5 eq.) followed by DMAP (0.25 g, 2.1 mmol, 0.2 eq) under inert atmosphere. The mixture was stirred at 10-15° C. for 30 min, and tert-butyl glycinate (146A, 1.39 g, 10.6 mmol, 1.0 eq) was added followed by dropwise addition of DIPEA (4.71 mL, 26.5 mmol, 2.5 eq). The mixture was stirred at 10-15° C. for additional 10 min, the cooling bath was removed, and the mixture was allowed to stir at RT for 16 h. Upon completion the reaction mixture was concentrated to get crude product, which was purified by silica gel column chromatography using 20-25% EtOAc in hexane to afford compound 820 as colorless liquid (3.2 g, 76.5%) $^1$H NMR (400 MHz, CDCl$_3$): δ ppm, 5.92 (s, 1H), δ 5.38-5.30 (d, 2H), 3.95-3.93 (d, 2H), 2.24-2.20 (t, 2H), 2.03-1.98 (m, 4H), 1.66-1.60 (m, 3H), 1.48 (s, 9H), 1.30-1.27 (m, 22H), 0.90 (m, 3H). To a stirred solution of intermediate 820 (3.1 g, 7.8 mmol, 1.0 eq.) in DCM (15.5 mL) was added formic acid (25 mL) at 20-25° C. and was stirred for 16 h. The reaction mixture was concentrated to remove formic acid and co-evaporated with toluene under reduced pressure to get the desired compound 821 as a white solid (2.6 g, 97.7%) which could be used in the next step without further purification. To a stirred solution of 821 (0.5 g, 1.47 mmol, 1.0 eq) in dry DCM (5 mL) was added HBTU (0.84 g, 2.2 mmol, 1.5 eq) at 10-15° C. followed by HOBt hydrate (0.06 g, 0.43 mmol, 0.3 eq) under argon atmosphere. The mixture was stirred at 10-15° C. for 30 min, and a solution of PEG compound 149A (2.94 g, 1.47 mmol, 1.0 eq) in dry DCM (2.5 mL) was added followed by dropwise addition of DIPEA (0.77 mL, 4.41 mmol, 3.0 eq). The mixture was stirred at 10-15° C. for additional 10 min, the cooling bath was removed; the mixture was allowed to stir at RT for 16 h. VP198 was purified and isolated in a similar fashion as VP196 to afford as white solid (0.35 g, 10.2%). $^1$H NMR (400 MHz, CDCl$_3$): δ ppm, 6.07 (t, 1H), 6.06 (m, 2H), 5.36-5.32 (m, 2H), 4.32-4.29 (t, 2H), 4.08-4.06 (d, 2H), 3.83-3.80 (t, 1H), 3.74-3.69 (m, 7H), 3.66-3.64 (d, 178H), 3.46-3.45 (d, 1H), 2.25-2.19 (m, 4H), 2.06-1.98 (m, 4H), 1.65-1.60 (m, 2H), 1.30-1.26 (d, 21H), 0.89-0.86 (t, 3H). MS m/z: [M+H/2]$^+$ calculated: 1255.29; found: 1255.7.

PEG-Lipid VP199

To a stirred solution of 821 (0.5 g, 1.47 mmol, 1.0 eq) in dry DCM (5 mL) was added HBTU (0.84 g, 2.2 mmol, 1.5 eq) at 10-15° C. followed by HOBt hydrate (0.0.06 g, 0.43 mmol, 0.3 eq) under argon atmosphere. The mixture was stirred at 10-15° C. for 30 min, and a solution of mPEG compound 149 (2.94 g, 1.47 mmol, 1.0 eq) in dry DCM (2.5 mL) was added followed by dropwise addition of DIPEA (0.77 mL, 4.41 mmol, 3.0 eq). The mixture was stirred at 10-15° C. for additional 10 min, the cooling bath was removed; the mixture was stirred at RT for 16 h. VP199 was purified and isolated in a similar fashion as VP198 (0.680 g, 19.9%). $^1$H NMR (400 MHz, CDCl$_3$): δ ppm, 6.08 (s, 1H), δ 5.35-5.32 (m, 2H), 4.32-4.30 (m, 2H), 4.08-4.07 (d, 2H), 3.83-3.80 (m, 2H), 3.74-3.71 (m, 4H), 3.66-3.64 (d, 182H), 3.56-3.48 (m, 3H), 3.47-3.46 (m, 1H), 3.38 (s, 3H), 2.25-2.21 (t, 2H), 2.06-1.98 (q, 7H), 1.66-1.62 (t, 2H), 1.30-1.26 (d, 22H), 0.89-0.86 (t, 3H). MS m/z: [M+H/2]$^+$ calculated: 1269.2; found: 1255.5.

Example 42

LNPs F238 and F239 shown in Table 27 were formulated using a X-mixer. Buffer exchange (50 mM Tris at pH 8) was performed using TFF. LNP F238 was formulated using VL404 and F239 was formulated using VL422 as amino lipid. LNP F238 constituted from amino lipid VL404 yielded an average particle size of 129.7 nm, and F239 constituted from aminolipid VL422 yielded an average particle size of 75.6 nm while using the same LNP compostions and RNA payloads. The formulations F238 and F239 were administered to cynomolgus monkeys (n=3) by intravenous infusion over 1 hour. A 2-week study was performed to evaluate editing of the ANGPTL3 gene in liver of cynomolgus monkeys by administering the LNPs constituted using guide RNA GA067 and mRNA MA004 (FIG. 27) as described in Example 41. The LNP formulation F238 was administered at 3 mg/kg and F239 was administered at 2.6 mg/kg total RNA respectively. Perentage ANGPTL3 editing liver of NHPs is illustrated in FIG. 27.

TABLE 27

Lipid composition and physiochemical characteristics of F238 and F239.

Figure 27:
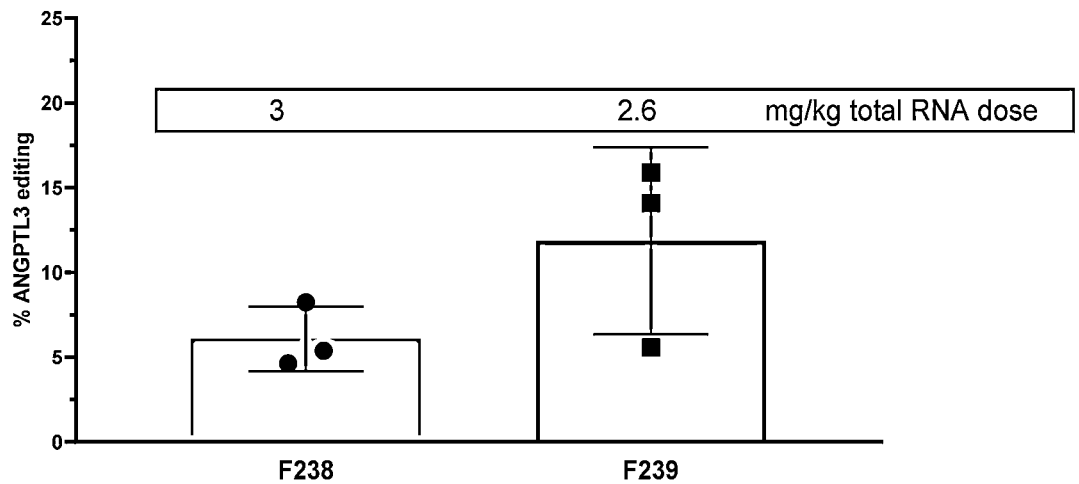
FIG. 27 illustrates the percentage of ANGPTL3 gene editing in the livers of cynomolgus monkeys (n=3) after single dose administration of LNPs F238 and F239 as described in Example 42 (Table 27).
Figure 28:
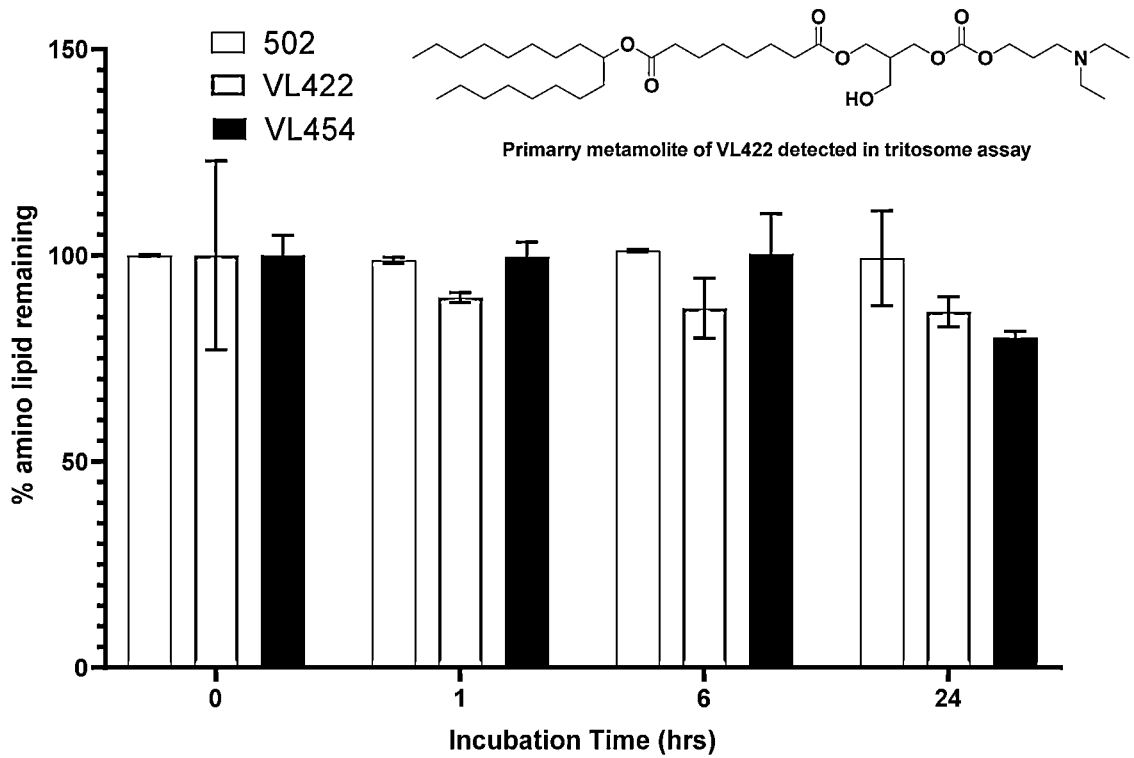
FIG. 28 illustrates the degradation rate of amino lipids 502, VL422 and VL454 in human liver S9 at 0, 1, 6 and 24 hour.
Figure 29:
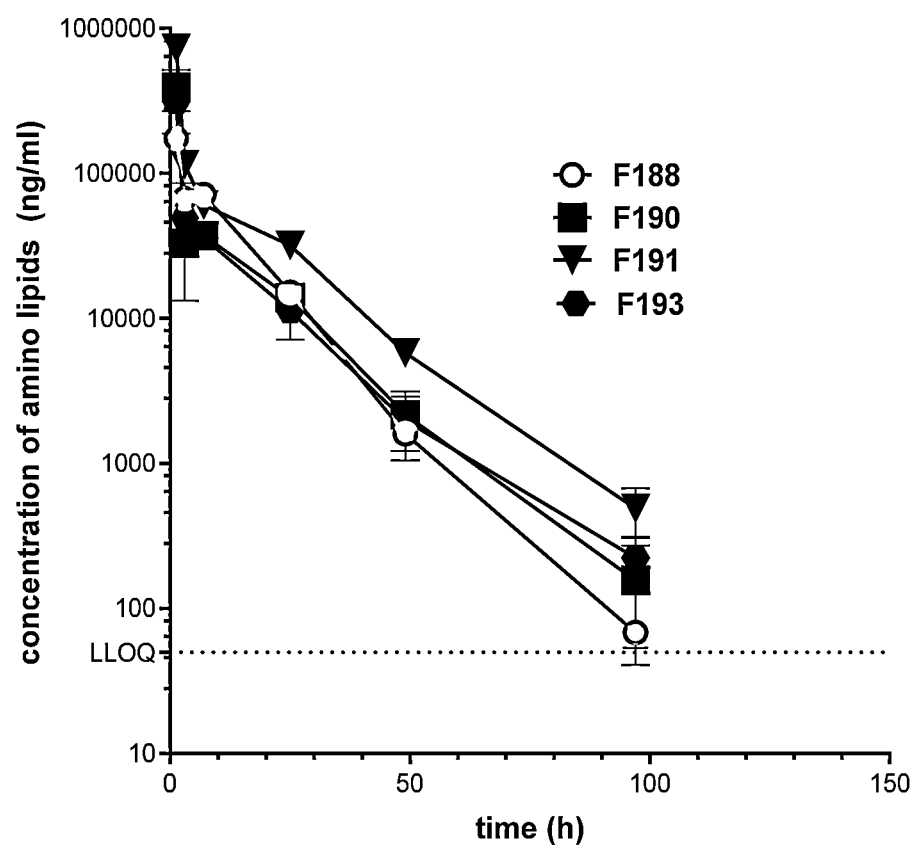
FIG. 29 illustrates amino lipid VL422 exposure profiles in plasma from cynomolgus monkeys after LNP administration. LNPs F188 was dosed at 1.5 mg/kg total RNA dose whereas as F190, F191 and F193 was dosed 2 mg/kg total RNA dose as described in Example 25 and Table 23.

| LNP | mRNA | gRNA | Amino lipid/cholesterol (511)/DSPC (512)/PEG-Lipid (507) mol % | Amino lipid | N:P | Z-avg (nm) | PDI | % RNA Entrapment | % ANGPTL3 editing |
|---|---|---|---|---|---|---|---|---|---|
| F238 | MA004 | GA067 | 55/38.2/4.7/2.1 | VL404 | 6 | 129.7 | 0.009 | 89.1 | See FIG. 27 |
| F239 | MA004 | GA067 | 55/38.2/4.7/2.1 | VL422 | 8 | 75.6 | 0.11 | 95.0 | |

EMBODIMENTS

Non-Limiting Example Embodiments

1. An amino lipid having a structure of Formula (I), or a pharmaceutically acceptable salt or solvate thereof,

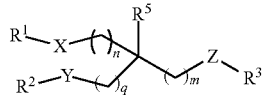

Formula (I)

wherein
each of $R^1$ and $R^2$ is independently $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;
each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, or a bond;
each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)

S—, —SC(=O)—, —OC(=O)S—, —NR⁴C(=O)S—, —SC(=O)NR⁴—, —C(=S)S—, —SC(=S)—, —SC(=S)O—, —NR⁴C(=S)S—, —SC(=S)NR⁴—, —C(=S)S—, —SC(=S)—, —SC(=O)S—, —SC(=S)S—, —NR⁴C(=S)S—, —SC(=S)NR⁴—, —SC(=S)NR⁴—, —O—N=CR⁴—, —CR⁴=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-$NR^7R^8$, —$C_0$-$C_{10}$ alkylene-heterocycloalkyl, or —$C_0$-$C_{10}$ alkylene-heterocycloaryl, wherein the alkylene, heterocycloalkyl and heterocycloaryl is independently substituted or unsubstituted;

each of $R^4$ is independently hydrogen or substituted or unsubstituted $C_1$-$C_6$ alkyl;

$R^5$ is hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl; and each of n, m, and q is independently 0, 1, 2, 3, 4, or 5.

2. An amino lipid having a structure of Formula (I*), or a pharmaceutically acceptable salt or solvate thereof,

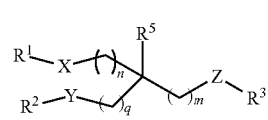

Formula (I*)

wherein $R^1$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

$R^2$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR⁴—, —NR⁴C(=O)—, —C(=O)O—, —OC(=O)—, —OC(=O)O—, —NR⁴C(=O)O—, —OC(=O)NR⁴—, —NR⁴C(=O)NR⁴—, —NRC(=NR⁴)NR⁴—, —C(=S)NR⁴—, —NR⁴C(=S)—, —C(=S)O—, —OC(=S)—, OC(=S)O—, —NR⁴C(=S)O—, —OC(=S)NR⁴—, —NR⁴C(=S)NR⁴—, —C(=O)S—, —SC(=O)—, —OC(=O)S—, —NR⁴C(=O)S—, —SC(=O)NR⁴—, —C(=S)S—, —SC(=S)—, —SC(=S)O—, —NR⁴C(=S)S—, —SC(=S)NR⁴—, —C(=S)S—, —SC(=S)—, —SC(=O)S—, —SC(=S)S—, —NR⁴C(=S)S—, —SC(=S)NR⁴—, —$R^{11}$C(=O)N($R^4$)$R^9$—, —$NR^7$C(=O)$R^9$—, —C(=O)O—, —OC(=O)—, —$R^{11}$C(=O)O$R^9$—, —$R^{11}$OC(=O)$R^9$—, —$R^{11}$OC(=O)O$R^9$—, —$R^{11}$N($R^4$)C(=O)O$R^9$—, —$R^{11}$OC(=O)N($R^4$)$R^9$—, —$R^{11}$(N$R^4$)C(=O)N($R^4$)$R^9$—, —$R^{11}$N($R^4$)C(=N$R^4$)$R^9$—, —$R^{11}$C(=S)N($R^4$)$R^9$—, —$R^{11}$N($R^4$)C(=S)$R^9$—, —$R^{11}$C(=S)O$R^9$—, —$R^{11}$OC(=S)$R^9$—, —$R^{11}$OC(=S)O$R^9$—, —$R^{11}$N($R^4$)C(=S)O$R^9$—, —$R^{11}$OC(=S)N($R^4$)$R^9$—, —$R^{11}$N($R^4$)C(=S)N($R^4$)$R^9$—, —$R^{11}$C(=O)S$R^9$—, —$R^{11}$SC(=O)$R^9$—, —$R^{11}$OC(=O)S$R^9$—, —$R^{11}$N($R^4$)C(=O)S$R^9$—, —$R^{11}$SC(=O)N($R^4$)$R^9$—, —$R^{11}$C(=S)S$R^9$—, —$R^{11}$SC(=S)$R^9$—, —$R^{11}$SC(=S)O$R^9$—, —$R^{11}$N($R^4$)C(=S)S$R^9$—, —$R^{11}$SC(=S)N($R^4$)$R^9$—, —$R^{11}$C(=S)S$R^9$—, —$R^{11}$SC(=S)$R^9$—, —$R^{11}$SC(=O)S$R^9$—, —$R^{11}$SC(=S)S$R^9$—, —$R^{11}$N($R^4$)C(=S)S$R^9$—, —$R^{11}$SC(=S)N($R^4$)$R^9$—, —$R^{11}$O$R^9$—, —$R^{11}$$R^9$—, —O—, —S—, or a bond;

each of L is independently —C(=O)NR⁴—, —NR⁴C(=O)—, —C(=O)O—, —OC(=O)—, —C(=O)—, —OC(=O)O—, —NR⁴C(=O)O—, —OC(=O)NR⁴—, —NR⁴C(=O)NR⁴—, —NR⁴C(=NR⁴)NR⁴—, —C(=S)NR⁴—, —NR⁴C(=S)—, —C(=S)O—, —OC(=S)—, OC(=S)O—, —NR⁴C(=S)O—, —OC(=S)NR⁴—, —NR⁴C(=S)NR⁴—, —C(=O)S—, —SC(=O)—, —OC(=O)S—, —NR⁴C(=O)S—, —SC(=O)NR⁴—, —C(=S)S—, —SC(=S)—, —SC(=S)O—, —NR⁴C(=S)S—, —SC(=S)NR⁴—, —C(=S)S—, —SC(=S)—, —SC(=O)S—, —SC(=S)S—, —NR⁴C(=S)S—, —SC(=S)NR⁴—, —O—N=CR⁴—, —CR⁴=N—O—, —O—, —S—, —$R^{11}$C(=O)N($R^4$)$R^9$—, —$R^{11}$N($R^4$)C(=O)$R^9$—, —$R^{11}$C(=O)O$R^9$—, —$R^{11}$OC(=O)$R^9$—, —$R^{11}$OC(=O)O$R^9$—, —$R^{11}$N($R^4$)C(=O)O$R^9$—, —$R^{11}$OC(=O)N($R^4$)$R^9$—, —$R^{11}$N($R^4$)C(=O)N($R^4$)$R^9$—, —$R^{11}$N($R^4$)C(=N$R^4$)N($R^4$)$R^9$—, —$R^{11}$C(=S)N($R^4$)$R^9$—, —$R^{11}$N($R^4$)C(=S)$R^9$—, —$R^{11}$C(=S)O$R^9$—, —$R^{11}$OC(=S)$R^9$—, —$R^{11}$OC(=S)O$R^9$—, —$R^{11}$N($R^4$)C(=S)O$R^9$—, —$R^{11}$OC(=S)N($R^4$)$R^9$—, —$R^{11}$N($R^4$)C(=S)N($R^4$)$R^9$—, —$R^{11}$C(=O)S$R^9$—, —$R^{11}$SC(=O)$R^9$—, —$R^{11}$OC(=O)S$R^9$—, —$R^{11}$N($R^4$)C(=O)S$R^9$—, —$R^{11}$SC(=O)N($R^4$)$R^9$—, —$R^{11}$C(=S)S$R^9$—, —$R^{11}$SC(=S)$R^9$—, —$R^{11}$SC(=S)O$R^9$—, —$R^{11}$N($R^4$)C(=S)S$R^9$—, —$R^{11}$SC(=S)N($R^4$)$R^9$—, —$R^{11}$C(=S)S$R^9$—, —$R^{11}$SC(=S)$R^9$—, —$R^{11}$SC(=O)S$R^9$—, —$R^{11}$SC(=S)S$R^9$—, —$R^{11}$N($R^4$)C(=S)S$R^9$—, —$R^{11}$SC(=S)N($R^4$)$R^9$—, —$R^{11}$O—N=C$R^9$—, —$R^{11}$C($R^{10}$)=N—O$R^9$—, —$R^{11}$O$R^9$—, —$R^{11}$S$R^9$—, —$C_1$-$C_{10}$ alkylene-C(=O)O—, —$C_1$-$C_{10}$ alkylene-OC(=O)—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-$NR^7R^8$, —$C_0$-$C_{10}$ alkylene-heterocycloalkyl, or —$C_0$-$C_{10}$ alkylene-heterocycloacloaryl, wherein the alkylene, heterocycloalkyl and heterocycloaryl is independently substituted or unsubstituted;

each of $R^4$ is independently hydrogen, substituted or unsubstituted $C_1$-$C_{16}$ alkyl or substituted or unsubstituted $C_1$-$C_{16}$ heteroalkyl;

$R^5$ is hydrogen or substituted or unsubstituted —$C_0$-$C_{10}$ alkylene-L-$R^4$;

each of $R^6$ is independently hydrogen, $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_{16}$ alkyl, substituted or unsubstituted $C_1$-$C_{16}$ heteroalkyl, or $R^7$ and $R^8$ taken together with the nitrogen to which they are attached form a substituted or unsubstituted $C_2$-$C_6$ heterocyclyl; and each of $R^9$ is independently hydrogen or substituted or unsubstituted $C_1$-$C_{16}$ alkylene, or unsubstituted $C_1$-$C_{16}$ heteroalkylene;

each of $R^{10}$ is independently hydrogen or substituted or unsubstituted $C_1$-$C_{16}$ alkylene, or unsubstituted $C_1$-$C_{16}$ heteroalkylene; and each of $R^{10}$ is independently substituted or unsubstituted $C_1$-$C_{16}$ alkylene, or unsubstituted $C_1$-$C_{16}$ heteroalkylene.

each of n, m, and q is independently 0, 1, 2, 3, 4, or 5.

3. The amino lipid of embodiment 1 or 2, or a pharmaceutically acceptable salt or solvate thereof, wherein said amino lipid has a structure of Formula (Ia), or a pharmaceutically acceptable salt or solvate thereof,

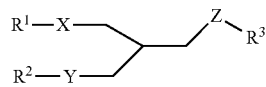

Formula (Ia)

wherein each of $R^1$ and $R^2$ is independently $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)NR$^4$—, —O—, —S—, —$C_1$-$C_{10}$ alkylene-O—, or a bond, wherein the alkylene is substituted or unsubstituted;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—N=CR$^4$—, —CR$^4$=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-NR$^7$R$^8$ or —$C_0$-$C_{10}$ alkylene-heterocycloalkyl, wherein the alkylene and heterocycloalkyl are each independently substituted or unsubstituted;

each of $R^4$ is independently hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl; and each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl.

4. The amino lipid of any one of embodiments 1 to 3, or a pharmaceutically acceptable salt or solvate thereof, wherein X and Y are each independently selected from —C(=O)O— and —OC(=O)—.

5. The amino lipid of any one of embodiments 1 to 3, or a pharmaceutically acceptable salt or solvate thereof, wherein $R^1$ and $R^2$ are each independently selected from substituted or unsubstituted $C_3$-$C_{30}$ alkyl or substituted or unsubstituted $C_3$-$C_{30}$ alkenyl.

6. The amino lipid of any one of embodiments 1 to 3, or a pharmaceutically acceptable salt or solvate thereof, wherein $R^1$ and $R^2$ are each independently selected from —$C_0$-$C_{10}$ alkylene-L-$R^6$.

7. The amino lipid of embodiment 6, or a pharmaceutically acceptable salt or solvate thereof, wherein L is independently —C(=O)O— or —OC(=O)—.

8. The amino lipid of embodiment 6, or a pharmaceutically acceptable salt or solvate thereof, wherein $R^6$ is linear or branched $C_6$-$C_{20}$ alkyl.

9. The amino lipid of embodiment 6, or a pharmaceutically acceptable salt or solvate thereof, wherein $R^6$ is Cy-$C_{3-30}$ alkyl, Cy-$C_{3-30}$ alkenyl, or Cy-$C_{3-30}$ alkynyl.

10. The amino lipid of any one of embodiments 1 to 9, or a pharmaceutically acceptable salt or solvate thereof, wherein $R^1$ and/or $R^2$ comprises an unsymmetrical heteroatom.

11. The amino lipid of any one of embodiments 1 to 10, or a pharmaceutically acceptable salt or solvate thereof, wherein Z is —C(=O)NR⁴—, —NR⁴C(=O)—, —OC(=O)O—, —C(=O)O—, —OC(=O)—, or —O—, and R⁴ is hydrogen or $CH_3$.

12. The amino lipid of any one of embodiments 1 to 10, or a pharmaceutically acceptable salt or solvate thereof, wherein Z is —OC(=O)O—, —C(=O)O— or —OC(=O)—.

13. The amino lipid of any one of embodiments 1 to 12, or a pharmaceutically acceptable salt or solvate thereof, wherein $R^3$ is —$C_1$-$C_6$ alkylene-$NR^7R^8$.

14. The amino lipid of embodiment 13, or a pharmaceutically acceptable salt or solvate thereof, wherein each $R^7$ and $R^8$ is independently substituted or unsubstituted $C_1$-$C_6$ alkyl.

15. The amino lipid of embodiment 13, or a pharmaceutically acceptable salt or solvate thereof, wherein each $R^7$ and $R^8$ is —$CH_2CH_3$.

16. The amino lipid of embodiment 13, or a pharmaceutically acceptable salt or solvate thereof, wherein $R^7$ and $R^8$ are taken together with the nitrogen to which they are attached to form a substituted or unsubstituted 3-7 membered heterocycloalkyl.

17. The amino lipid of any one of embodiments 1 to 12, or a pharmaceutically acceptable salt or solvate thereof, wherein $R^3$ is

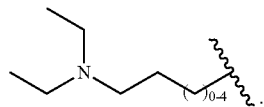

18. The amino lipid of embodiment 1, or a pharmaceutically acceptable salt or solvate thereof, wherein the amino lipid is

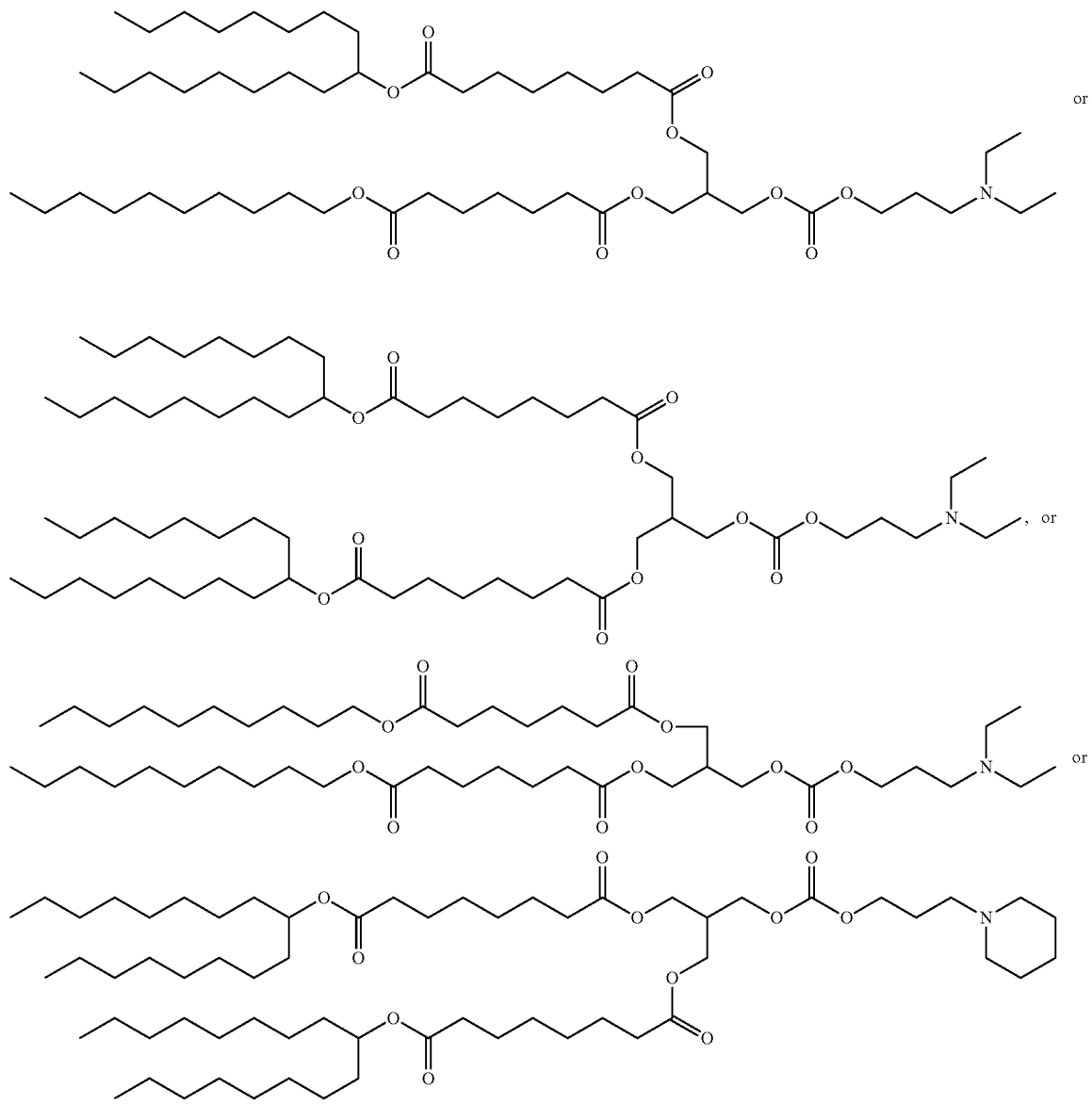

19. An amino lipid having a structure of Formula (II), or a pharmaceutically acceptable salt or solvate thereof,

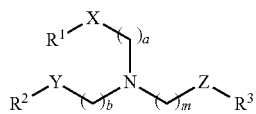

Formula (II)

wherein each of $R^1$ and $R^2$ is independently $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_1$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)S—, —NR$^4$C(=S)S—, —SC(=S)NR$^4$—, —O—N=CR$^4$—, —CR$^4$=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is —$C_0$-$C_{10}$ alkylene-NR$^7R^8$, —$C_0$-$C_{10}$ alkylene-heterocycloalkyl, or —$C_0$-$C_{10}$ alkylene-heterocycloaryl, wherein the alkylene, heterocycloalkyl and heterocycloaryl is independently substituted or unsubstituted;

each of $R^4$ is independently hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{1-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl;

each of a and b is independently 1, 2, 3, 4, 5, 6, 7, 8, 9, or 10; and m is 0, 1, 2, 3, 4, or 5.

20. An amino lipid having a structure of Formula (II*), or a pharmaceutically acceptable salt or solvate thereof,

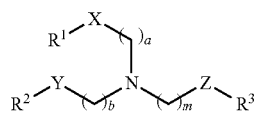

Formula (II*)

wherein each of $R^1$ and $R^2$ is independently hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_1$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —C(=O)—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)S—, —NR$^4$C(=S)S—, —SC(=S)NR$^4$—, —O—N=CR$^4$—, —CR$^4$=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is hydrogen, —$C_1$-$C_6$ alkyl, —$C_0$-$C_{10}$ alkylene-NR$^7R^8$, —$C_0$-$C_{10}$ alkylene-heterocycloalkyl, or —$C_0$-$C_{10}$ alkylene-heterocycloaryl, wherein the alkyl, alkylene, heterocycloalkyl and heterocycloaryl is independently substituted or unsubstituted;

each of $R^4$ is independently hydrogen or substituted or unsubstituted $C_1$-$C_6$ alkyl;

each of R⁶ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R⁷ and R⁸ is independently hydrogen or substituted or unsubstituted $C_1$-$C_6$ alkyl, or R⁷ and R⁸ taken together with the nitrogen to which they are attached form a substituted or unsubstituted $C_2$-$C_6$ heterocyclyl;

each of a and b is independently 1, 2, 3, 4, 5, 6, 7, 8, 9, or 10; and m is 0, 1, 2, 3, 4, or 5.

21. The amino lipid of embodiment 19 or 20, or a pharmaceutically acceptable salt or solvate thereof, wherein each of a and b is independently 3, 4, 5, 6, 7, 8, 9, or 10.

22. The amino lipid of any one of embodiments 19 to 21, or a pharmaceutically acceptable salt or solvate thereof, wherein m is 1, 2, 3, 4, or 5.

23. The amino lipid of any one of embodiments 19 to 22, or a pharmaceutically acceptable salt or solvate thereof, wherein X and Y are each independently selected from —C(=O)O— and —OC(=O)—.

24. The amino lipid of any one of embodiments 19 to 23, or a pharmaceutically acceptable salt or solvate thereof, wherein R¹ and R² are each independently selected from substituted or unsubstituted $C_3$-$C_{30}$ alkyl or substituted or unsubstituted $C_3$-$C_{30}$ alkenyl.

25. The amino lipid of any one of embodiments 19 to 23, or a pharmaceutically acceptable salt or solvate thereof, wherein R¹ and R² are each independently selected from —$C_0$-$C_{10}$ alkylene-L-R⁶.

26. The amino lipid of embodiment 25, or a pharmaceutically acceptable salt or solvate thereof, wherein L is independently —C(=O)O— or —OC(=O)—.

27. The amino lipid of embodiment 25, or a pharmaceutically acceptable salt or solvate thereof, wherein R⁶ is linear or branched $C_6$-$C_{20}$ alkyl.

28. The amino lipid of embodiment 25, or a pharmaceutically acceptable salt or solvate thereof, wherein R⁶ is Cy-$C_{3-30}$ alkyl, Cy-$C_{3-30}$ alkenyl, or Cy-$C_{3-30}$ alkynyl.

29. The amino lipid of any one of embodiments 19 to 28, or a pharmaceutically acceptable salt or solvate thereof, wherein Z is —C(=O)NR⁴—, —NR⁴C(=O)—, —OC(=O)O—, —C(=O)O—, —OC(=O)—, or —O—, and R⁴ is hydrogen or CH₃.

30. The amino lipid of any one of embodiments 19 to 29, or a pharmaceutically acceptable salt or solvate thereof, wherein Z is —OC(=O)O—, —C(=O)O— or —OC(=O)—.

31. The amino lipid of any one of embodiments 19 to 30, or a pharmaceutically acceptable salt or solvate thereof, wherein R³ is —$C_1$-$C_6$ alkylene-NR⁷R⁸

32. The amino lipid of embodiment 31, or a pharmaceutically acceptable salt or solvate thereof, wherein each R⁷ and R⁸ is independently substituted or unsubstituted $C_1$-$C_6$ alkyl.

33. The amino lipid of embodiment 31, or a pharmaceutically acceptable salt or solvate thereof, wherein each R⁷ and R⁸ is —CH₂CH₃.

34. The amino lipid of embodiment 31, or a pharmaceutically acceptable salt or solvate thereof, wherein R⁷ and R⁸ are taken together with the nitrogen to which they are attached to form a substituted or unsubstituted 3-7 membered heterocycloalkyl.

35. The amino lipid of any one of embodiments 19 to 30, or a pharmaceutically acceptable salt or solvate thereof, wherein R³ is

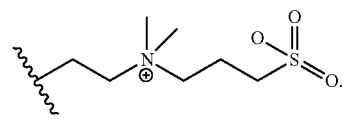 [SMILES: *CC[N+](C)(C)CCCS(=O)(=O)O]

36. A nanoparticle composition that comprises an amino lipid of any one of embodiments 1 to 35, or a pharmaceutically acceptable salt or solvate thereof.

37. An amino lipid having a structure selected from Table 1A, or a pharmaceutically acceptable salt or solvate thereof.

38. A nanoparticle composition that comprises an amino lipid having a structure selected from Table 1A, or a pharmaceutically acceptable salt or solvate thereof.

39. The nanoparticle composition of embodiment 1 or 37, wherein said amino lipid or a pharmaceutically acceptable salt or solvate thereof, comprises from 20 mol % to 80 mol % of a total lipid content present in said nanoparticle composition.

40. The nanoparticle composition of embodiment 1 or 37, wherein said amino lipid or a pharmaceutically acceptable salt or solvate thereof, comprises from 40 mol % to 60 mol % of a total lipid content present in said nanoparticle composition.

41. The nanoparticle composition of embodiment 1 or 37, wherein said amino lipid or a pharmaceutically acceptable salt or solvate thereof, comprises from 50 mol % to 60 mol % of a total lipid content present in said nanoparticle composition.

42. The nanoparticle composition of any one of embodiments 1 or 37 to 40, wherein said amino lipid or a salt or solvate thereof, comprises one or more ionizable nitrogen atoms.

43. The nanoparticle composition of any one of embodiments 1 or 37 to 40, wherein the nanoparticle composition comprises one or more ionizable nitrogen atoms that are from the one or more amino lipids.

44. The nanoparticle composition of any one of embodiments 1 or 37 to 42, wherein said nanoparticle composition comprises only one amino lipid or a salt or solvate thereof.

45. The nanoparticle composition of any one of embodiments 1 or 37 to 43, wherein said nanoparticle composition comprises one or more nucleic acid molecular entities.

46. The nanoparticle composition of embodiment 44, wherein a molar ratio of said ionizable nitrogen atoms to phosphate groups present in said nucleic acid molecular entities (the N to P or N/P ratio) is from about 2 to about 20.

47. The nanoparticle composition of embodiment 45, wherein said N/P ratio is from about 2 to about 15, from about 2 to about 10, from about 2 to about 8, from about 2 to about 6, from about 3 to about 15, from about 3 to about 10, from about 3 to about 8, from about 3 to about 6, from about 4 to about 15, from about 4 to about 10, from about 4 to about 8, or from about 4 to about 6.

48. The nanoparticle composition of embodiment 45, wherein said N/P ratio is from about 3.5 to about 10.
49. The nanoparticle composition of any one of embodiments 1 or 37 to 47, wherein said nanoparticle composition comprises a neutral lipid.
50. The nanoparticle composition of embodiment 48, wherein said neutral lipid comprises from about 1 mol % to about 20 mol % of a total lipid content present in said nanoparticle composition.
51. The nanoparticle composition of embodiment 48 or 49, wherein said neutral lipid comprises from about 2 mol % to about 25 mol % of a total lipid content present in said nanoparticle composition.
52. The nanoparticle composition of embodiment 48 or 49, wherein said neutral lipid comprises from about 5 mol % to about 10 mol % of a total lipid content present in said nanoparticle composition.
53. The nanoparticle composition of any one of embodiments 48 to 51, wherein said neutral lipid is selected from 1,2-distearoyl-sn-glycero-3-phosphocholine (DSPC), 1,2-dipalmitoyl-sn-glycero-3-phosphocholine (DPPC), 1,2-dimyristoyl-sn-glycero-phosphocholine (DMPC), 2-oleoyl-1-palmitoyl-sn-glycero-3-phosphocholine (POPC), 1,2-dioleoyl-sn-glycero-3-phosphoethanolamine (DOPE), and sphingomyelin.
54. The nanoparticle composition of any one of embodiments 48 to 51, wherein said neutral lipid is DSPC.
55. The nanoparticle composition of any one of embodiments 1 or 37 to 53, wherein said nanoparticle composition comprises a structural lipid.
56. The nanoparticle composition of embodiment 54, wherein said structural lipid is sterol or a derivative thereof.
57. The nanoparticle composition of embodiment 54 or 55, wherein said sterol or said derivative thereof is cholesterol or cholesterol derivative.
58. The nanoparticle composition of any one of embodiments 54 to 56, wherein said structural lipid comprises from about 15 mol % to about 65 mol % of a total lipid content present in the nanoparticle composition.
59. The nanoparticle composition of any one of embodiments 54 to 56, wherein said structural lipid comprises from about 30 mol % to about 60 mol % of a total lipid content present in the nanoparticle composition.
60. The nanoparticle composition of any one of embodiments 54 to 56, wherein said structural lipid comprises from about 30 mol % to about 40 mol % of a total lipid content present in the nanoparticle composition.
61. The nanoparticle composition of any one of embodiments 1 or 37 to 59, wherein said nanoparticle composition comprises a PEG lipid.
62. The nanoparticle composition of embodiment 60, wherein said PEG lipid is a PEG-lipid of Table 2.
63. The nanoparticle composition of embodiment 60 or 61, wherein said PEG lipid comprises from about 0.1 mol % to about 6 mol % of a total lipid content present in said nanoparticle composition.
64. The nanoparticle composition of embodiment 60 or 61, wherein said PEG lipid comprises about 2.0 mol % to about 2.5 mol % of a total lipid content present in said nanoparticle composition.
65. The nanoparticle composition of any one of embodiments 60 to 63, wherein a number average molecular weight of said PEG-lipid is from about 200 Da to about 5000 Da.
66. The nanoparticle composition of any one of embodiments 44 to 64, wherein said one or more nucleic acid molecular entities comprise a guide RNA (gRNA) targeting a disease causing gene of interest.
67. The nanoparticle composition of embodiment 65, wherein the guide RNA is a single guide RNA (sgRNA).
68. The nanoparticle composition of embodiment 65 or 66, wherein the disease causing gene of interest is produced in hepatocytes.
69. The nanoparticle composition of any one of embodiments 44 to 67, wherein said one or more nucleic acid molecular entities comprise an mRNA encoding SpCas9, CBE, and/or ABE proteins.
70. The nanoparticle composition of any one of embodiments 1 or 37 to 68, further comprising a nucleic acid stabilizer.
71. A nanoparticle composition comprising:
   (a) one or more nucleic acid molecular entities;
   (b) an amino lipid according to any one of embodiments 1 to 35 or 36, or a salt or solvate thereof,
      wherein said amino lipid or a salt thereof, comprises from 20 mol % to 80 mol % of a total lipid content present in said nanoparticle composition,
      wherein said amino lipid or a salt thereof, comprises one or more ionizable nitrogen atoms, and
      wherein a molar ratio of said ionizable nitrogen atoms to phosphate groups present in said nucleic acid molecular entity is from 2 to 12;
   (c) a neutral lipid, comprising from 2 mol % to 25 mol % of said total lipid content present in said nanoparticle composition;
   (d) a structural lipid, comprising from 30 mol % to 60 mol % of said total lipid content present in said nanoparticle composition; and
   (e) a PEG lipid, comprising from 0.1 mol % to 6 mol % of said total lipid content present in said nanoparticle composition.
72. The nanoparticle composition of any one of embodiments 37 to 70, further comprising a nucleic acid stabilizer.
73. The nanoparticle composition of embodiment 71, wherein the nucleic acid stabilizer comprises polyethylene glycol, cetrimonium bromide, or chitosan.
74. The nanoparticle composition of embodiment 71, wherein the nucleic acid stabilizer comprises polyethylene glycol that has a number average molecular weight of about 120 to about 2000 Da.
75. A nanoparticle composition comprising:
   (a) one or more nucleic acid molecular entities;
   (b) an amino lipid or a salt thereof,
      wherein said amino lipid or a salt thereof, comprises from 20 mol % to 80 mol % of a total lipid content present in said nanoparticle composition,
      wherein said amino lipid or a salt thereof, comprises one or more ionizable nitrogen atoms, and
      wherein a molar ratio of said ionizable nitrogen atoms to phosphate groups present in said nucleic acid molecular entity is from 2 to 12;
   (c) a neutral lipid, comprising from 2 mol % to 25 mol % of said total lipid content present in said nanoparticle composition;
   (d) a structural lipid, comprising from 30 mol % to 60 mol % of said total lipid content present in said nanoparticle composition;
   (e) a PEG lipid, comprising from 0.1 mol % to 6 mol % of said total lipid content present in said nanoparticle composition; and (f) a nucleic acid stabilizer, wherein the nucleic acid stabilizer comprises chitosan, cetrimonium bromide, polyethylene glycol that has a number average molecular weight of about 120 to about 2000 Da, or a combination thereof.

76. The nanoparticle composition of any one of embodiments 71 to 74, wherein the nucleic acid stabilizer comprises PEG 200, PEG 400, or PEG 600.
77. The nanoparticle composition of any one of embodiments 71 to 74, wherein the nucleic acid stabilizer is PEG 400.
78. The nanoparticle composition of any one of embodiments 71 to 76, wherein the nucleic acid stabilizer is present in the nanoparticle composition in an amount of about 0.01% to about 20% by total weight.
79. The nanoparticle composition of any one of embodiments 71 to 76, wherein the nucleic acid stabilizer is present in the nanoparticle composition in an amount of about 0.5% to about 5% by total weight.
80. The nanoparticle composition of any one of embodiments 44 to 78, wherein said one or more nucleic acid molecular entities comprise a PCSK9 gRNA.
81. The nanoparticle composition of any one of embodiments 44 to 78, wherein said one or more nucleic acid molecular entities comprise an mRNA encoding a Cas nuclease.
82. The nanoparticle composition of any one of embodiments 44 to 78, wherein said one or more nucleic acid molecular entities comprise an mRNA, a gRNA, a siRNA, an antisense oligonucleotide, a microRNA, an anti-microRNA, an RNA activator, an aptamer, or a combination thereof.
83. The nanoparticle composition of any one of embodiments 1 or 37 to 81, wherein said nanoparticle composition comprises an antioxidant.
84. The nanoparticle composition of embodiment 82, wherein said antioxidant comprise EDTA.
85. The nanoparticle composition of any one of embodiments 1 or 37 to 83, further comprising a surfactant.
86. The nanoparticle composition of 84, wherein the surfactant is a fatty acid or a fatty alcohol.
87. The nanoparticle composition of 84, wherein the surfactant is a $C_{12}$-$C_{24}$ fatty alcohol.
88. The nanoparticle composition of embodiment 86, wherein the $C_{12}$-$C_{24}$ fatty alcohol is lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, or a combination thereof.
89. The nanoparticle composition of embodiment 86, wherein the $C_{12}$-$C_{24}$ fatty alcohol is oleyl alcohol, stearyl alcohol, or a mixture thereof.
90. The nanoparticle composition of any one of embodiments 84 to 88, wherein the surfactant comprises about 1.0 mol % to about 10 mol % of a total lipid content present in said nanoparticle composition.
91. The nanoparticle composition of any one of embodiments 1 or 37 to 89, wherein a median diameter of the nanoparticle is from about 50 nm to about 150 nm.
92. The nanoparticle composition of any one of embodiments 1 or 37 to 90, wherein a polydispersity index of the nanoparticle is from 0 to 0.15.
93. The nanoparticle composition of any one of embodiments 1 or 37 to 90, wherein a polydispersity index of the nanoparticle is from 0 to 0.05.
94. The nanoparticle composition of any one of embodiments 44 to 92, wherein a nucleic acid entrapment efficiency of the nanoparticle composition is at least 80%, at least 85%, at least 90%, at least 91%, at least 92%, at least 93%, at least 94%, at least 95%, at least 96%, at least 97%, at least 98%, or at least 99%.
95. A PEG lipid having the structure of Formula (III), or a pharmaceutically acceptable salt or solvate thereof,

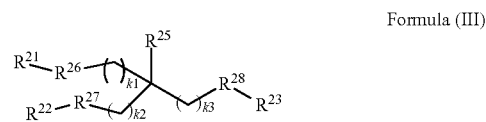

Formula (III)

wherein
each of $R^{21}$ and $R^{22}$ is independently substituted or unsubstituted $C_3$-$C_{30}$ alkyl, substituted or unsubstituted $C_3$-$C_{30}$ alkenyl, or substituted or unsubstituted $C_3$-$C_{30}$ alkynyl;
each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;
each of $R^4$ is independently hydrogen or substituted or unsubstituted $C_1$-$C_6$ alkyl;
$R^{23}$ is —$C_0$-$C_{10}$ alkylene-(CH$_2$—CH$_2$—O)$_{k4}$—$R^{24}$ or —$C_1$-$C_{10}$ heteroalkylene-(CH$_2$—CH$_2$—O)$_{k4}$—$R^{24}$, wherein the alkylene and heteroalkylene are each independently substituted or unsubstituted;
$R^{24}$ is independently hydrogen or substituted or unsubstituted $C_1$-$C_3$ alkyl;
$R^{25}$ is hydrogen or substituted or unsubstituted $C_1$-$C_6$ alkyl;
each of k1, k2, and k3 is independently 0, 1, 2, 3, 4, or 5; and
k4 is an integer selected from 1 to 100.
96. A PEG lipid having the structure of Formula (III*), or a pharmaceutically acceptable salt or solvate thereof,

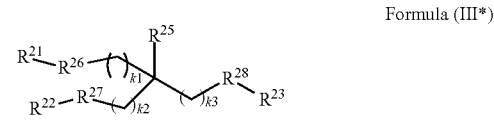

Formula (III*)

wherein
R$^{21}$ is hydrogen, substituted or unsubstituted C$_1$-C$_{30}$ alkyl, substituted or unsubstituted C$_3$-C$_{30}$ alkenyl, or substituted or unsubstituted C$_3$-C$_{30}$ alkynyl;
R$^{22}$ is hydrogen, substituted or unsubstituted C$_1$-C$_{30}$ alkyl, substituted or unsubstituted C$_3$-C$_{30}$ alkenyl, or substituted or unsubstituted C$_3$-C$_{30}$ alkynyl;
each of R$^{26}$, R$^{27}$ and R$^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —N(Ac)—, —OC(O)OCH$_2$C(O)O—, —OC(O)OCH$_2$C(O)NH—, —OC(O)NHCH$_2$C(O)O—, —OC(O)NHCH$_2$C(O)NH—, —OC(O)O(CH$_2$)$_2$C(O)O—, —OC(O)O(CH$_2$)$_2$C(O)NH—, —OC(O)NH(CH$_2$)$_2$C(O)O—, —OC(O)NH(CH$_2$)$_2$C(O)NH—, —OC(O)O(CH$_2$)$_3$C(O)O—, —OC(O)O(CH$_2$)$_3$C(O)NH—, —OC(O)NH(CH$_2$)$_3$C(O)O—, —OC(O)NH(CH$_2$)$_3$C(O)NH—, —C(O)OCH$_2$C(O)NH— —C(O)NHCH$_2$C(O)O—, —C(O)NHCH$_2$C(O)NH—, —C(O)O(CH$_2$)$_2$C(O)O—, —C(O)O(CH$_2$)$_2$C(O)NH—, —C(O)NH(CH$_2$)$_2$C(O)O—, —C(O)NH(CH$_2$)$_2$C(O)NH—, —C(O)O(CH$_2$)$_3$C(O)O—, —C(O)O(CH$_2$)$_3$C(O)NH—, —C(O)NH(CH$_2$)$_3$C(O)O—, —C(O)NH(CH$_2$)$_3$C(O)NH—, —OC(=O)NR$^4$(CH$_2$)$_{1-3}$C(=O)NH—, —OC(=O)NR$^4$(CH$_2$)$_{1-3}$C(=O)O—, —C(=O)NR$^4$(CH$_2$)$_{1-3}$C(=O)NH—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;
each of R$^4$ is independently hydrogen or substituted or unsubstituted C$_1$-C$_6$ alkyl;
R$^{23}$ is —C$_0$-C$_{10}$ alkylene-(CH$_2$—CH$_2$—O)$_{k4}$—R$^{24}$, —C$_1$-C$_{10}$ heteroalkylene-(CH$_2$—CH$_2$—O)$_{k4}$—R$^{24}$, —C$_0$-C$_{10}$ alkylene-(O—CH$_2$—CH$_2$)$_{k4}$—R$^{24}$ or —C$_1$-C$_{10}$ heteroalkylene-(O—CH$_2$—CH$_2$)$_{k4}$—R$^{24}$, wherein the alkylene and heteroalkylene are each independently substituted or unsubstituted;
R$^{24}$ is independently hydrogen, substituted or unsubstituted C$_1$-C$_3$ alkyl, —O—R$^4$, —C(=O)OR$^4$, or —C(=O)R$^4$;
R$^{25}$ is hydrogen or substituted or unsubstituted C$_1$-C$_{22}$ alkyl;
each of k1, k2, and k3 is independently 0, 1, 2, 3, 4, or 5; and
k4 is an integer selected from 1 to 100.

97. The PEG lipid of embodiment 95, or a pharmaceutically acceptable salt or solvate thereof, wherein R$^{21}$ is substituted or unsubstituted C$_3$-C$_{30}$ alkyl, substituted or unsubstituted C$_3$-C$_{30}$ alkenyl, or substituted or unsubstituted C$_3$-C$_{30}$ alkynyl;
R$^{22}$ is hydrogen, substituted or unsubstituted C$_3$-C$_{30}$ alkyl, substituted or unsubstituted C$_3$-C$_{30}$ alkenyl, or substituted or unsubstituted C$_3$-C$_{30}$ alkynyl;
each of R$^{26}$, R$^{27}$ and R$^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —OC(=O)NR$^4$(CH$_2$)$_{1-3}$C(=O)NH—, —OC(=O)NR$^4$(CH$_2$)$_{1-3}$C(=O)O—, —C(=O)NR$^4$(CH$_2$)$_{1-3}$C(=O)NH—, —SC(=O)NR$^4$—, —C(=S)S—, —SC(=S)—, —SC(=S)O—, —NR$^4$C(=S)S—, —SC(=S)NR$^4$—, —C(=S)S—, —SC(=S)—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)— —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O(CH$_2$)$_2$C(NH)NH—, —O—, —S—, or a bond;
each of R$^4$ is independently hydrogen or substituted or unsubstituted C$_1$-C$_6$ alkyl;
R$^{23}$ is —C$_0$-C$_{10}$ alkylene-(CH$_2$—CH$_2$—O)$_{k4}$—R$^{24}$ or —C$_1$-C$_{10}$ heteroalkylene-(CH$_2$—CH$_2$—O)$_{k4}$—R$^{24}$, wherein the alkylene and heteroalkylene are each independently substituted or unsubstituted;
R$^{24}$ is independently hydrogen, substituted or unsubstituted C$_1$-C$_3$ alkyl, —O—R$^4$, —C(=O)OH, or —C(=O)R$^4$;
R$^{25}$ is hydrogen or substituted or unsubstituted C$_1$-C$_6$ alkyl;
each of k1, k2, and k3 is independently 0, 1, 2, 3, 4, or 5; and
k4 is an integer selected from 1 to 100.

98. The PEG lipid of any one of embodiments 94 to 96, or a pharmaceutically acceptable salt or solvate thereof, wherein each of R$^{21}$ and R$^{27}$ is independently unsubstituted, linear C$_{12}$-C$_{25}$ alkyl.

99. The PEG lipid of any one of embodiments 94 to 97, or a pharmaceutically acceptable salt or solvate thereof, each of R$^{26}$, R$^{27}$ and R$^{28}$ is independently selected from —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, NH(CH$_2$)$_2$C(O)N(CH$_3$)—, —NH(CH$_2$)$_2$C(NH)O—, —NH(CH$_2$)$_2$ C(NAc)NH—, —NH(CH$_2$)$_2$C(NH)N(CH$_3$)—, —NH(CH$_2$)$_2$C(NH)NH—, —NH(CH$_2$)$_2$C(NH)N(CH$_3$)—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, and —O(CH$_2$)$_2$C(NH)NH—.

100. The PEG lipid of any one of embodiments 94 to 97, or a pharmaceutically acceptable salt or solvate thereof, wherein each of $R^{26}$ and $R^{27}$ is —O(CH$_2$)$_2$C(O)O— or —O(CH$_2$)$_2$C(O)NH—.

101. The PEG lipid of any one of embodiments 94 to 99, or a pharmaceutically acceptable salt or solvate thereof, wherein $R^{28}$ is —O(CH$_2$)$_2$C(O)O—, or —O(CH$_2$)$_2$C(O)NH—.

102. The PEG lipid of any one of embodiments 94 to 99, or a pharmaceutically acceptable salt or solvate thereof, wherein $R^{28}$ is —O—, —C(=O)O—, or —OC(=O)—.

103. The PEG lipid of any one of embodiments 94 to 101, or a pharmaceutically acceptable salt or solvate thereof, wherein k1 is 0, k2 is 1, and k3 is 1.

104. The PEG lipid of any one of embodiments 94 to 102, or a pharmaceutically acceptable salt or solvate thereof, wherein $R^{23}$ is —C$_0$-C$_3$ alkylene-(CH$_2$—CH$_2$—O)$_{k4}$—$R^{24}$, wherein $R^{24}$ is H or methyl.

105. The PEG lipid of any one of embodiments 94 to 103, or a pharmaceutically acceptable salt or solvate thereof, wherein k4 is 1 to 50.

106. The PEG lipid of any one of embodiments 94 to 104, or a pharmaceutically acceptable salt or solvate thereof, wherein $R^{25}$ is hydrogen.

107. A PEG lipid having the structure selected from Table 2, or a pharmaceutically acceptable salt or solvate thereof.

108. The PEG lipid of embodiment 95, or a pharmaceutically acceptable salt or solvate thereof, wherein the PEG lipid is:

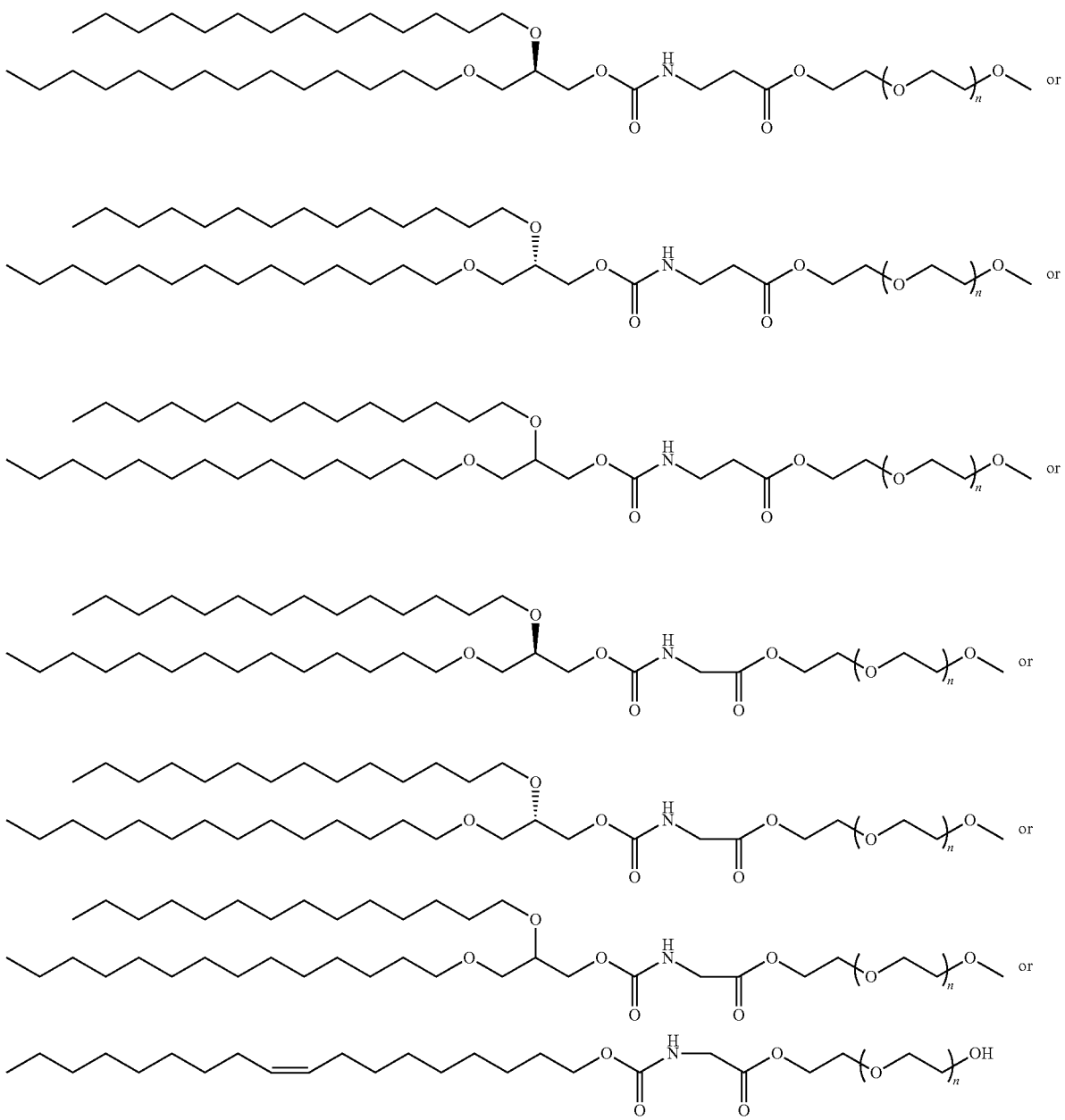

109. A pharmaceutical composition comprising said nanoparticle composition of any one of embodiments 1 or 37 to 93, and an excipient or carrier.
110. The pharmaceutical composition of embodiment 108, wherein said pharmaceutical composition comprises an mRNA encoding a gene editor nuclease.
111. The pharmaceutical composition of embodiment 108 or 109, wherein said pharmaceutical composition comprises one or more guide RNA molecules.
112. The pharmaceutical composition of embodiment 108 or 109, wherein said pharmaceutical composition comprises a PCSK9 guide RNA.
113. The pharmaceutical composition of embodiment 108 or 109, wherein said pharmaceutical composition comprises two or more guide RNA molecules.
114. The pharmaceutical composition of embodiment 112, wherein said two or more guide RNA molecules target two or more genes of interest.
115. The pharmaceutical composition of any one of embodiments 109 to 113, wherein said mRNA encodes Cas9 nuclease.
116. The pharmaceutical composition of any one of embodiments 109 to 113, wherein said mRNA encodes a base editor nuclease.
117. The pharmaceutical composition of any one of embodiments 110 to 115, wherein said mRNA and said one or more guide RNA molecules are present in a same nanoparticle composition.
118. The pharmaceutical composition of any one of embodiments 110 to 115, wherein said mRNA and said one or more guide RNA molecules are present in different nanoparticle compositions.
119. The pharmaceutical composition of any one of embodiments 110 to 117, wherein a ratio of said gRNA molecules to said mRNA in said pharmaceutical composition is from about 0.01 to about 100 by weight or by mole.
120. The pharmaceutical composition of embodiment 118, wherein a ratio of said gRNA molecules to said mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.
121. A pharmaceutical composition comprising:
    (a) a first nanoparticle composition of any one of embodiments 1 or 37 to 93, and
    (b) a second nanoparticle composition of any one of embodiments 1 or 37 to 93.
122. The pharmaceutical composition of embodiment 120, wherein said first nanoparticle composition comprises a gene editor mRNA, and said second nanoparticle composition comprises one or more guide RNA molecules.
123. The pharmaceutical composition 120 or 121, wherein a ratio of guide RNA molecules to mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.
124. The pharmaceutical composition 120 or 121, wherein a ratio of guide RNA to mRNA in said pharmaceutical composition is about 1:1 by weight or by mole.
125. A method of delivering a nucleic acid molecular entity to a cell, the method comprising contacting said cell with a nanoparticle composition of any one of embodiments 1 or 37 to 93 or a pharmaceutical composition of any one of embodiments 108 to 123, whereby said nucleic acid molecular entity is delivered to said cell.
126. The method of embodiment 124, wherein said cell is contacted in vivo, ex vivo, or in intro.
127. A method of producing a polypeptide of interest in a cell, the method comprising contacting said cell with a nanoparticle composition of any one of embodiments 1 or 37 to 93 or a pharmaceutical composition of any one of embodiments 108 to 123, wherein said nanoparticle composition or said pharmaceutical composition comprises a nucleic acid molecular entity, and wherein said nucleic acid molecular entity is translated in the cell thereby producing the polypeptide.
128. A method of making a pharmaceutical composition, comprising combining a first nanoparticle composition of any one of embodiments 1 or 37 to 93, and a second nanoparticle composition of any one of embodiments 1 or 37 to 93.
129. A method of treating a disease or condition in a mammal, the method comprising administering to a mammal a therapeutically effective amount of a pharmaceutical composition of any one of embodiments 108 to 123.
130. A method of editing PCSK9 gene in a cell comprising contacting said cell with a nanoparticle composition of any one of embodiments 1 or 37 to 93 or a pharmaceutical composition of any one of embodiments 108 to 123, wherein said nanoparticle composition or said pharmaceutical composition comprises a PCSK9 guide RNA.
131. A method of producing a stabilized nanoparticle composition of any one of embodiments 71 to 93, comprising combining a nucleic acid stabilizer with a nanoparticle composition that lacks the nucleic acid stabilizer.
132. The method of embodiment 130, wherein the nucleic acid stabilizer is combined with the nanoparticle composition before freezing or storage.
133. The method of embodiment 130, wherein the nucleic acid stabilizer is combined with the nanoparticle composition before, concurrently, or after the addition of the one or more nucleic acid entities.
134. The method of any one of embodiments 130 to 132, wherein the combining comprises mixing the nucleic acid stabilizer with the one or more nucleic acid entities in an aqueous buffer.
135. A method of producing a stabilized nanoparticle composition, comprising
    (a) combining a nucleic acid stabilizer with one or more nucleic acid molecular entities thereby producing a solution comprising the stabilized one or more nucleic acid molecular entities; and
    (b) combining the solution of (a) with a nanoparticle composition that comprises one or more of an amino lipid, a neutral lipid, a structural lipid, and a PEG lipid.

136. The method of embodiment 134, wherein the combining in (a) comprises mixing the nucleic acid stabilizer with the one or more nucleic acid entities in an aqueous buffer.

137. The method of any one of embodiments 130 to 135, further comprising collecting and dialyzing the nanoparticle composition against a buffer with a pH of about 6.5 to about 8.0.

138. The method of any one of embodiments 130 to 136, wherein the nucleic acid stabilizer is polyethylene glycol that has a number average molecular weight of about 120 to about 1000.

139. A method of preparing a formulation comprising lipid nanoparticles, wherein the nanoparticles comprise (i) one or more nucleic acid molecular entities, (ii) an amino lipid, and (iii) one or more lipids selected from a structural lipid, a neutral lipid, and a PEG lipid, the method comprising,
(a) combining a first faction of the amino lipid with the one or more nucleic acid molecular entities in a first solution, wherein the first fraction comprises 0.1 mol % to 99 mol % of the total amino lipid;
(b) combining the remaining of the amino lipid with the one or more lipids selected from a structural lipid, a neutral lipid, and a PEG lipid in a second solution;
(c) mixing the first solution and the second solution, thereby producing the lipid nanoparticles.

140. The method of embodiment 138, wherein the first fraction of the amino lipid is configured to neutralize between 0.1-99% of the phosphate (on an N:P basis) in the one or more nucleic acid molecular entities.

141. The method of embodiment 138, wherein the first fraction of the amino lipid is configured to neutralize between 0.5-90% of the phosphate (on an N:P basis) in the one or more nucleic acid molecular entities.

142. The method of embodiment 138, wherein the first fraction of the amino lipid is configured to neutralize about 10%, 15%, 25%, 50%, or 75% of the phosphate (on an N:P basis) in the one or more nucleic acid molecular entities.

143. The method of any one of embodiments 138 to 141, wherein the first solution is an aqueous buffer solution.

144. The method of any one of embodiments 138 to 142, wherein the first solution further comprises a nucleic acid stabilizer.

145. The method of any one of embodiments 138 to 143, wherein the first solution and the second solution are mixed in an inline mixer.

What is claimed is:

1. An amino lipid having a structure of Formula (I*), or a pharmaceutically acceptable salt or solvate thereof,

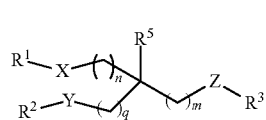

Formula (I*)

wherein $R^1$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

$R^2$ is hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_2$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)$NR^4$—, —$NR^4$C(=O)—, —C(=O)O—, —OC(=O)—, —OC(=O)O—, $NR^4$C(=O)O—, —OC(=O)$NR^4$—, —$NR^4$C(=O)$NR^4$—, —$NR^4$C(=$NR^4$)$NR^4$—, —C(=S)$NR^4$—, —$NR^4$C(=S)—, —C(=S)O—, —OC(=S)—, OC(=S)O—, —$NR^4$C(=S)O—, —OC(=S)$NR^4$—, —$NR^4$C(=S)$NR^4$—, —C(=O)S—, —SC(=O)—, —OC(=O)S—, —$NR^4$C(=O)S—, —SC(=O)$NR^4$—, —C(=S)S—, —SC(=S)—, —SC(=S)O—, —SC(=O)S—, —SC(=S)S—, —$NR^4$C(=S)S—, —SC(=S)$NR^4$—, —$R^{11}$C(=O)N($R^4$)$R^9$—, —$NR^7$C(=O)$R^9$—, —$R^{11}$C(=O)$OR^9$—, —$R^{11}$OC(=O)$R^9$—, —$R^{11}$OC(=O)$OR^9$—, —$R^{11}$N($R^4$)C(=$NR^4$)$R^9$—, $R^{11}$C(=S)N($R^4$)$R^9$—, —$R^{11}$N($R^4$)C(=S)$R^9$—, —$R^{11}$C(=S)$OR^9$—, —$R^{11}$OC(=S)$R^9$—, —$R^{11}$OC(=S)$OR^9$—, —$R^{11}$N($R^4$)C(=S)$OR^9$—, —$R^{11}$OC(=S)N($R^4$)$R^9$—, —$R^{11}$N($R^4$)C(=S)N($R^4$)$R^9$—, —$R^{11}$C(=O)$SR^9$—, —$R^{11}$SC(=O)$R^9$—, —$R^{11}$OC(=O)$SR^9$—, —$R^{11}$N($R^4$)C(=O)$SR^9$—, —$R^{11}$SC(=O)N($R^4$)$R^9$—, —$R^{11}$C(=S)$SR^9$—, —$R^{11}$SC(=S)$R^9$—, —$R^{11}$SC(=S)$OR^9$—, —$R^{11}$SC(=O)$SR^9$—, —$R^{11}$SC(=S)$SR^9$—, —$R^{11}$N($R^4$)C(=S)$SR^9$—, —$R^{11}$SC(=S)N($R^4$)$R^9$—, —$R^{11}$$OR^9$—, —$R^{11}$$SR^9$—, —O—, —S— or a bond;

each of L is independently —C(=O)$NR^4$—, —$NR^4$C(=O)—, —C(=O)O—, —OC(=O)—, —C(=O)—, —OC(=O)O—, —$NR^4$C(=O)O—, —OC(=O)$NR^4$—, —$NR^4$C(=O)$NR^4$—, —$NR^4$(=$NR^4$)$NR^4$—, —C(=S)$NR^4$—, —$NR^4$C(=S)—, —C(=S)O—, —OC(=S)—, —OC(=S)O—, —$NR^4$C(=S)O—, —OC(=S)$NR^4$—, —$NR^4$C(=S)$NR^4$—, —C(=O)S—, —SC(=O)—, —OC(=O)S—, —$NR^4$C(=O)S—, —SC(=O)$NR^4$—, —C(=S)S—, —SC(=S)—, —SC(=S)O—, —SC(=O)S—, —SC(=S)S—, —$NR^4$C(=S)S—, —SC(=S)$NR^4$—, —O—N=$CR^4$—, —$CR^4$=N—O—, —O—, —S—, —$R^{11}$C(=O)N($R^4$)$R^9$—, —$R^{11}$OC(=O)$OR^9$—, —$R^{11}$N($R^4$)C(=O)$R^9$—, —$R^{11}$C(=O)$OR^9$—, —R$^{11}$OC(=O)R$^9$—, —R$^{11}$N(R$^4$)C(=O)OR$^9$—, —R$^{11}$OC(=O)N(R$^4$)R$^9$—, —R$^{11}$N(R$^4$)C(=O)N(R$^4$)R$^9$—, —R$^{11}$N(R$^4$)C(=NR$^4$)N(R$^4$)R$^9$—, —R$^{11}$N(R$^4$)C(=S)R$^9$—, —R$^{11}$C(=S)OR$^9$—, —R$^{11}$OC(=S)R$^9$—, —R$^{11}$OC(=S)OR$^9$—, —R$^{11}$N(R$^4$)C(=S)OR$^9$—, —R$^{11}$OC(=S)N(R$^4$)R$^9$—, —R$^{11}$N(R$^4$)C(=S)N(R$^4$)R$^9$—, —R$^{11}$C(=O)SR$^9$—, —R$^{11}$SC(=O)R$^9$—, —R$^{11}$OC(=O)SR$^9$—, —R$^{11}$N(R$^4$)C(=O)SR$^9$—, —R$^{11}$SC(=O)N(R$^4$)R$^9$—, —R$^{11}$C(=S)SR$^9$—, —R$^{11}$SC(=S)R$^9$—, —R$^{11}$SC(=S)OR$^9$—, —R$^{11}$SC(=O)SR$^9$—, —R$^{11}$SC(=S)SR$^9$—, —R$^{11}$N(R$^4$)C(=S)SR$^9$—, —R$^{11}$SC(=S)N(R$^4$)R$^9$, —R$^{11}$O—N=CR$^9$—, —R$^{11}$C(R$^{10}$)=N—OR$^9$—, —R$^{11}$OR$^9$—, —R$^{11}$SR$^9$—, —C$_1$-C$_{10}$ alkylene-C(=O)O—, —C$_1$-C$_{10}$ alkylene-OC(=O)—, —C$_1$-C$_{10}$ alkylene-O—, or a bond, wherein the alkylene is substituted or unsubstituted;

R$^3$ is —C$_0$-C$_{10}$ alkylene-NR$^7$R$^8$, —C$_0$-C$_{10}$ alkylene-heterocycloalkyl, or —C$_0$-C$_{10}$ alkylene-heteroaryl, wherein the alkylene-heterocycloalkyl and the alkylene-heteroaryl comprises a nitrogen, and wherein the alkylene, heterocycloalkyl and heteroaryl is independently substituted or unsubstituted;

each of R$^4$ is independently hydrogen, substituted or unsubstituted C$_1$-C$_{16}$ alkyl or substituted or unsubstituted C$_1$-C$_{16}$ heteroalkyl;

R$^5$ is hydrogen or substituted or unsubstituted —C$_0$-C$_{10}$ alkylene-L-R$^4$;

each of R$^6$ is independently hydrogen, C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of R$^7$ and R$^8$ is independently hydrogen or substituted or unsubstituted C$_1$-C$_{16}$ alkyl, substituted or unsubstituted C$_1$-C$_{16}$ heteroalkyl, or R$^7$ and R$^8$ taken together with the nitrogen to which they are attached form a substituted or unsubstituted C$_2$-C$_6$ heterocyclyl; and each of R$^9$ is independently hydrogen or substituted or unsubstituted C$_1$-C$_{16}$ alkylene, or unsubstituted C$_1$-C$_{16}$ heteroalkylene;

each of R$^{10}$ is independently hydrogen or substituted or unsubstituted C$_1$-C$_{16}$ alkylene, or unsubstituted C$_1$-C$_{16}$ heteroalkylene; and each of R$^{11}$ is independently substituted or unsubstituted C$_1$-C$_{16}$ alkylene, or unsubstituted C$_1$-C$_{16}$ heteroalkylene;

each of n, m, and q is independently 0, 1, 2, 3, 4, or 5.

2. The amino lipid of claim 1, wherein the amino lipid has a structure of Formula (Ia), or a pharmaceutically acceptable salt or solvate thereof,

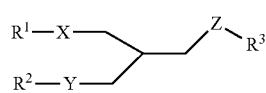

Formula (Ia)

wherein each of R$^1$ and R$^2$ is independently C$_3$-C$_{30}$ alkyl, C$_3$-C$_{30}$ alkenyl, C$_3$-C$_{30}$ alkynyl, C$_3$-C$_{30}$ heteroalkyl, C$_3$-C$_{30}$ heteroalkenyl, C$_3$-C$_{30}$ heteroalkynyl, C$_3$-C$_{10}$ cycloalkyl, —C$_0$-C$_{10}$ alkylene-L-R$^6$, or —C$_2$-C$_{10}$ alkenylene-L-R$^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, —OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —SC(=O)S—, —SC(=S)S—, —NR$^4$C(=S)S—, —SC(=S)NR$^4$—, —O—, —S—, —C$_1$-C$_{10}$ alkylene-O—, or a bond, wherein the alkylene is substituted or unsubstituted;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$, —NR$^4$C(=S)—, —C(=S)O—, —OC(=S)—, —OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, —SC(=S)O—, —SC(=O)S—, —SC(=S)S—, —NR$^4$C(=S)S—, —SC(=S)NR$^4$—, —O—N=CR$^4$—, —CR$^4$=N—O—, —O—, —S—, —C$_1$-C$_{10}$ alkylene-O—, —C$_1$-C$_{10}$ alkylene-C(=O)O—, —C$_1$-C$_{10}$ alkylene-OC(=O)—, or a bond, wherein the alkylene is substituted or unsubstituted;

R$^3$ is —C$_0$-C$_{10}$ alkylene-NR$^7$R$^8$ or —C$_0$-C$_{10}$ alkylene-heterocycloalkyl, wherein the alkylene-heterocycloalkyl comprises a nitrogen, and wherein the alkylene and heterocycloalkyl are each independently substituted or unsubstituted;

each of R$^4$ is independently hydrogen or substituted or unsubstituted C$_1$-C$_6$ alkyl;

each of R$^6$ is independently C$_3$-C$_{30}$ alkyl, C$_3$-C$_{30}$ alkenyl, C$_3$-C$_{30}$ alkynyl, Cy-C$_{3-30}$ alkyl, Cy-C$_{3-30}$ alkenyl, or Cy-C$_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl; and each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl.

3. The amino lipid of claim 1, wherein the amino lipid has a structure of Formula (Ib), or a pharmaceutically acceptable salt or solvate thereof,

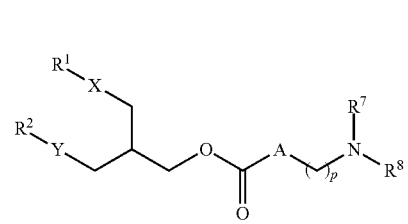

Formula (Ib)

wherein
each of X and Y are the same and are selected from the group consisting of: —OC(=O)—, —OC(=O)O—, —OC(=O)NR$^4$—, —C(=S)O—, —OC(=S)—, —OC(=S)O—, —NR$^4$C(=S)O—, —OC(=S)NR$^4$—, —SC(=O)—, —OC(=O)S—, —SC(=S)O—, —O—, —C$_1$-C$_{10}$ alkylene-O—, and a bond, wherein the alkylene is substituted or unsubstituted R$^1$ and R$^2$ are the same and are selected from the group consisting of: hydrogen, C$_1$-C$_{30}$ alkyl, C$_1$-C$_{30}$ heteroalkyl, and Cy-C$_{3-30}$ alkyl, wherein the alkyl and heteroalkyl are each independently substituted or unsubstituted;

each of R$^4$ is independently hydrogen or substituted or unsubstituted C$_1$-C$_6$ alkyl;

each of Cy is substituted or unsubstituted cycloalkyl, substituted or unsubstituted heterocycloalkyl, substituted or unsubstituted aryl, substituted or unsubstituted heteroaryl; and each of R$^7$ and R$^8$ is independently hydrogen or substituted or unsubstituted C$_1$-C$_6$ alkyl, or R$^7$ and R$^8$ taken together with the nitrogen to which they are attached form a substituted or unsubstituted C$_2$-C$_6$ heterocyclyl,
A is —O—, —CH$_2$—, —S—, or —NR$^{12}$—;

R$^{12}$ is hydrogen, C$_1$-C$_{10}$ alkyl, or C$_1$-C$_{10}$ heteroalkyl, wherein the alkyl and heteroalkyl are each independently substituted or unsubstituted;

Cy is substituted or unsubstituted cycloalkyl, substituted or unsubstituted heterocycloalkyl, substituted or unsubstituted aryl, or substituted or unsubstituted heteroaryl; and p is 1, 2, 3, 4, 5 or 6.

4. The amino lipid of claim 3, wherein each of X and Y are —C(=O)O—, —OC(=O)O—, or —N(H)C(=O)O—.

5. The amino lipid of claim 3, wherein each of R$^1$ and R$^2$ is

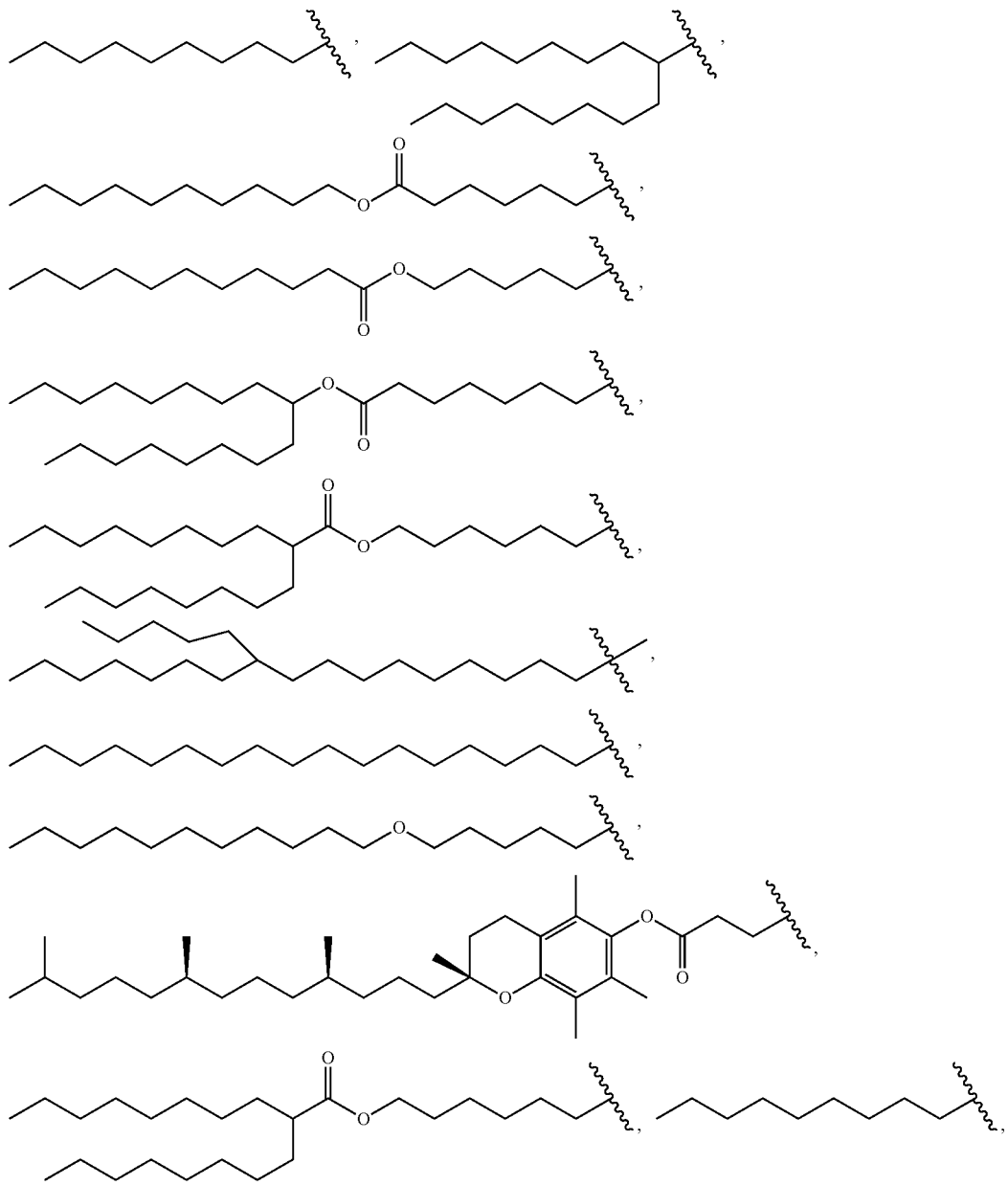

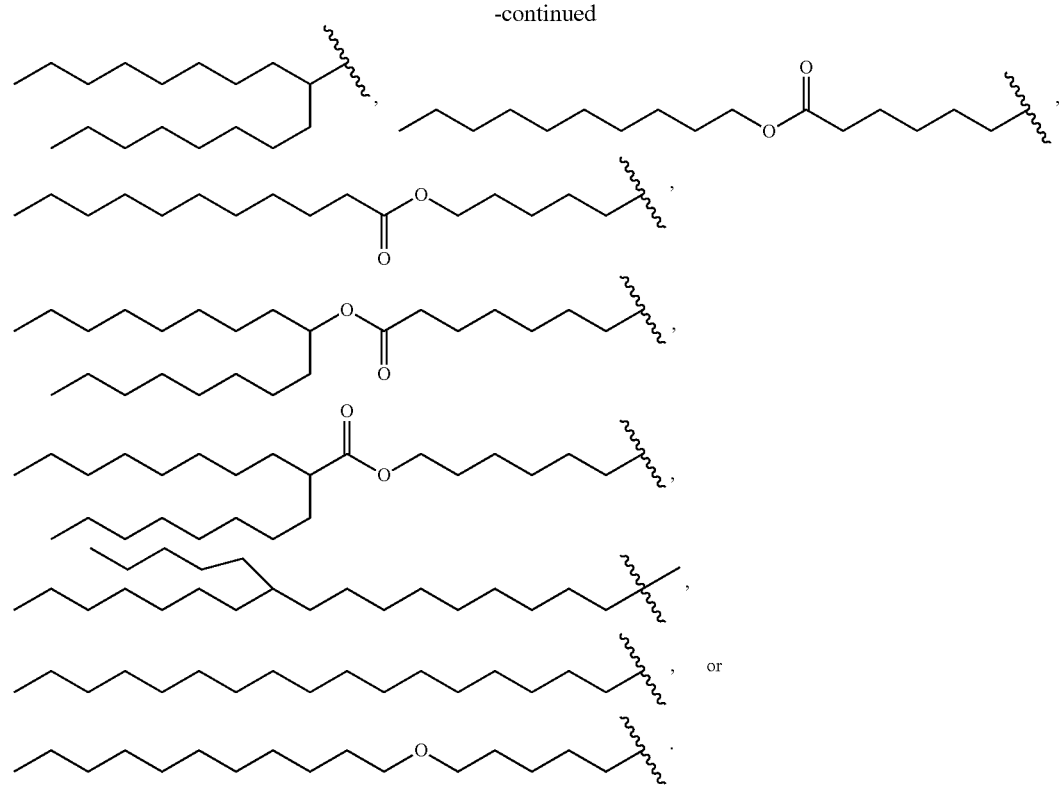
6. The amino lipid of claim 3, wherein the amino lipid is
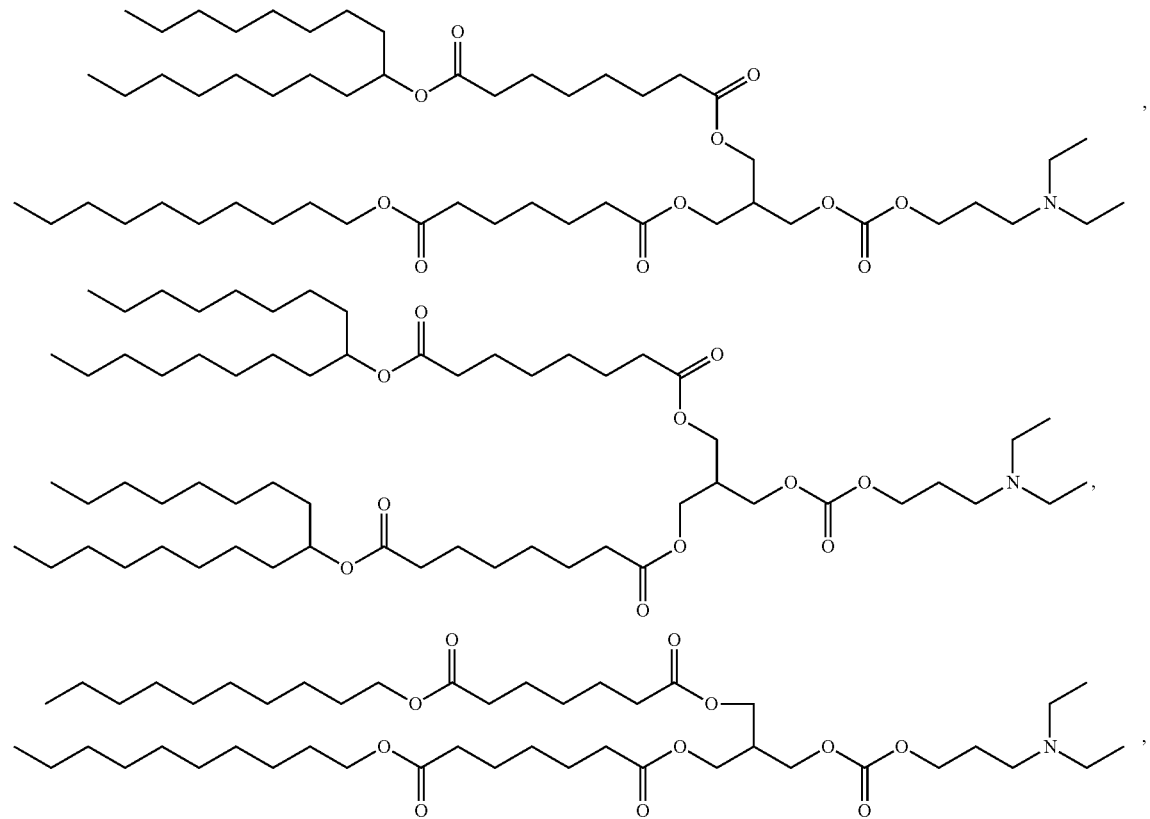

-continued
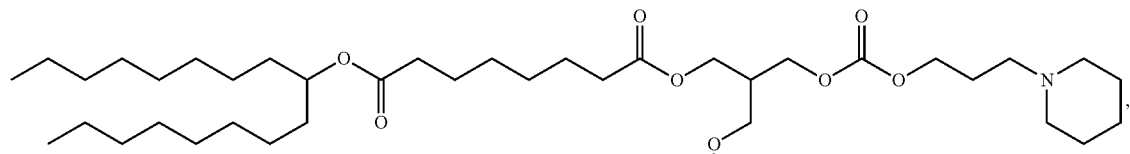
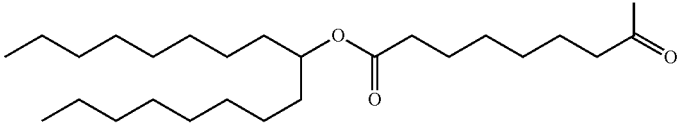
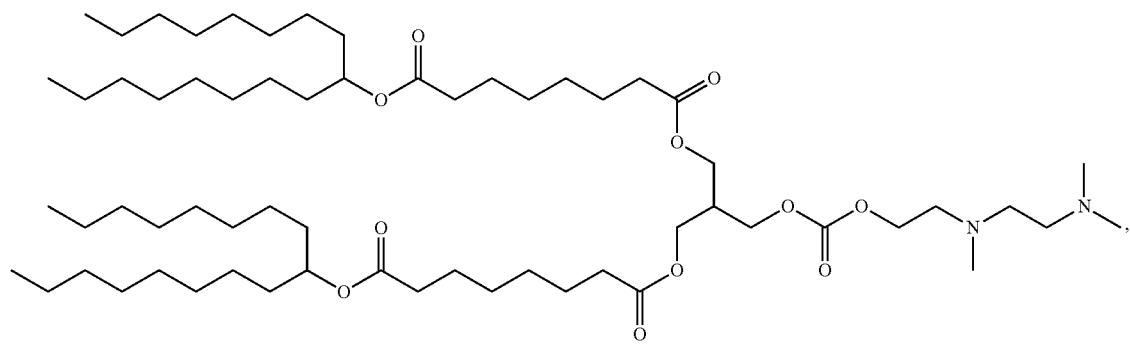
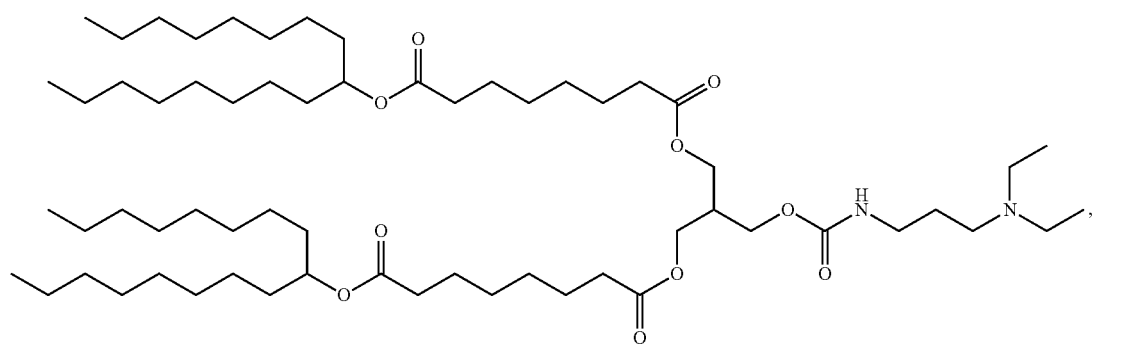
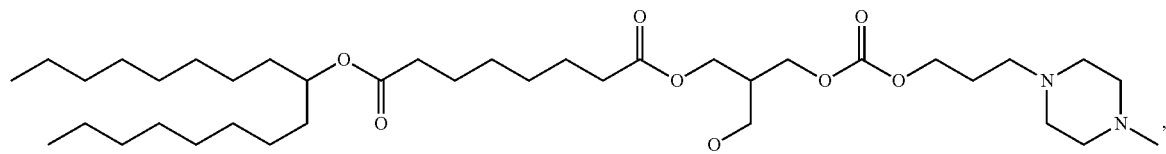
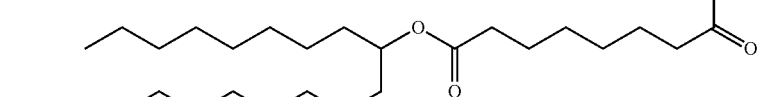
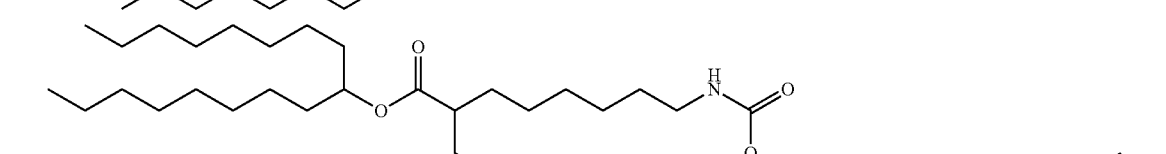
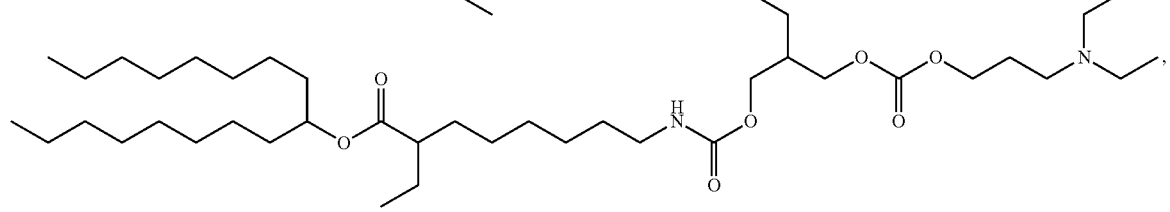

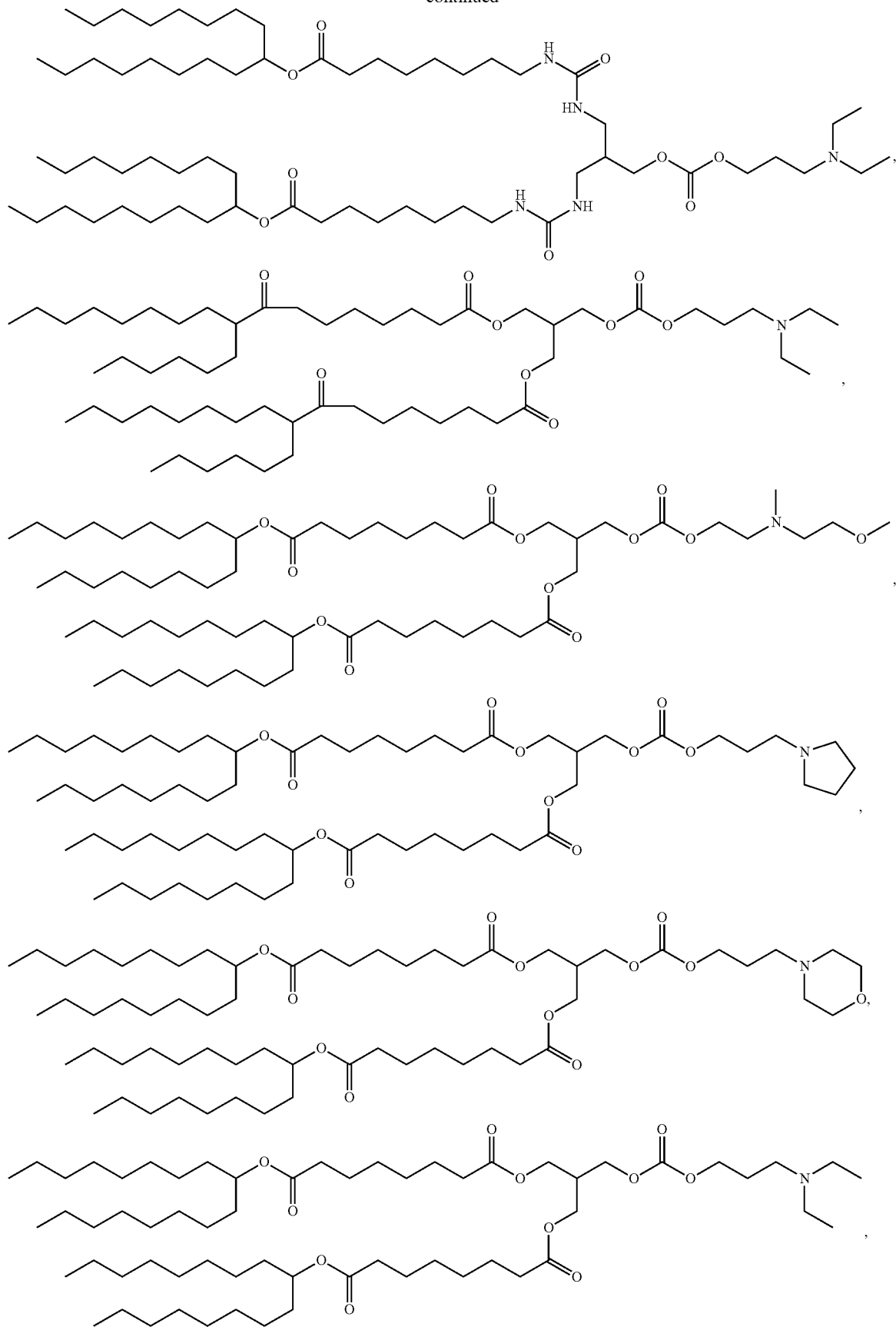

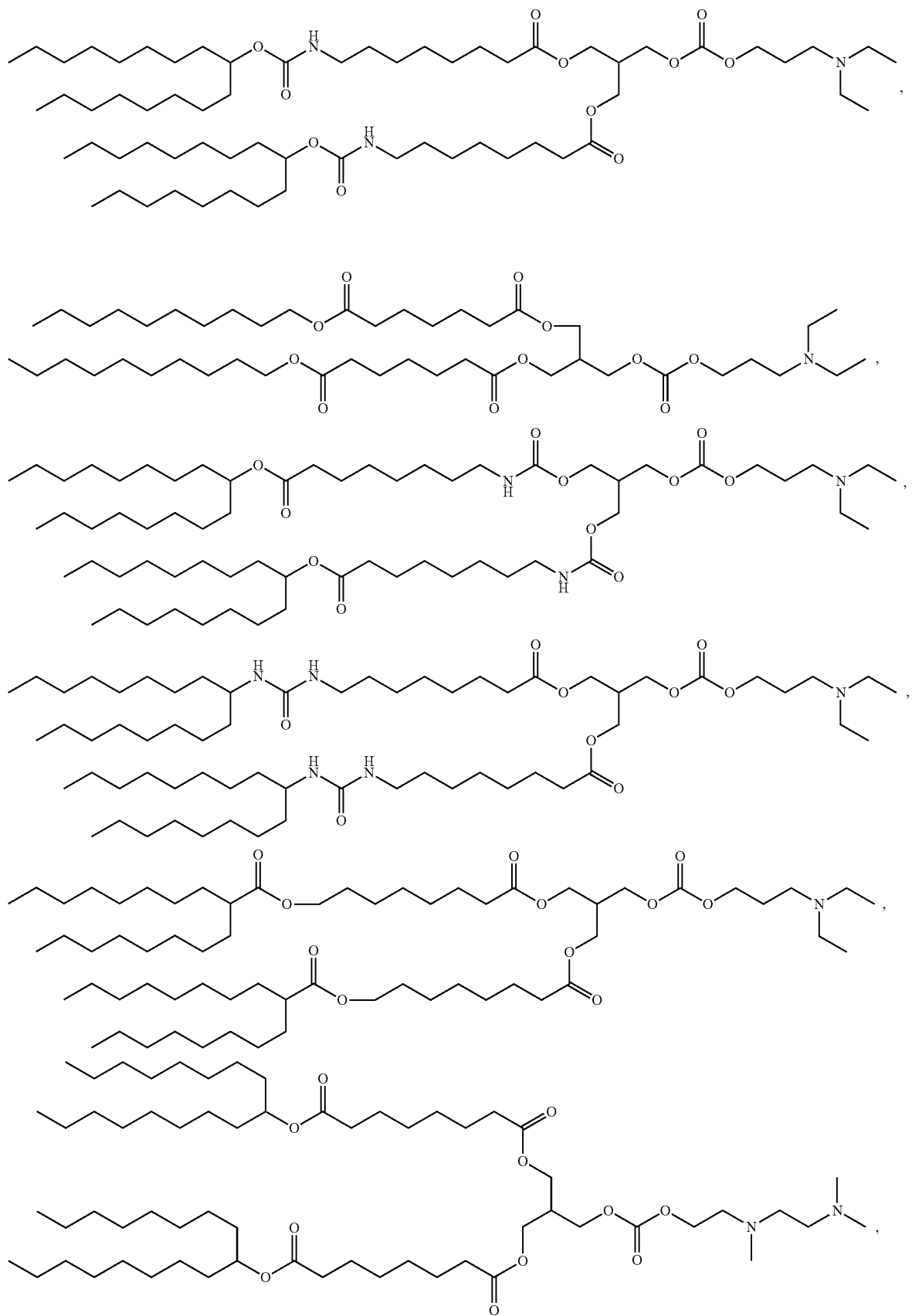

-continued

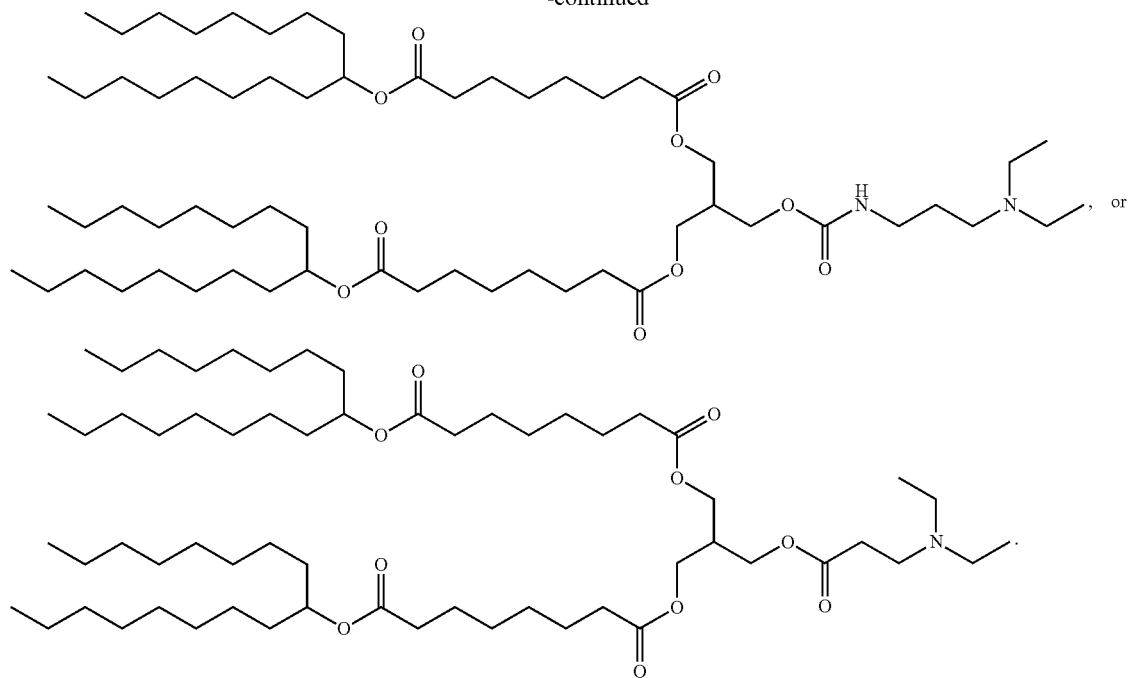

, or

7. The amino lipid of claim 1, wherein $R^1$ and $R^2$ are each independently selected from $-C_0$-$C_{10}$ alkylene-L-$R^6$.

8. The amino lipid of claim 7, wherein L is independently $-C(=O)O-$ or $-OC(=O)-$.

9. The amino lipid of claim 7, wherein $R^6$ is linear or branched $C_6$-$C_{20}$ alkyl.

10. The amino lipid of claim 7, wherein $R^6$ is Cy-$C_{3\text{-}30}$ alkyl, Cy-$C_{3\text{-}30}$ alkenyl, or Cy-$C_{3\text{-}30}$ alkynyl.

11. The amino lipid of claim 1, wherein $R^1$ and/or $R^2$ comprises an unsymmetrical heteroatom.

12. The amino lipid of claim 7, wherein each $R^7$ and $R^8$ is independently substituted or unsubstituted $C_1$-$C_6$ alkyl.

13. The amino lipid of claim 1, wherein $R^3$ is

14. The amino lipid of claim 1, wherein the amino lipid is

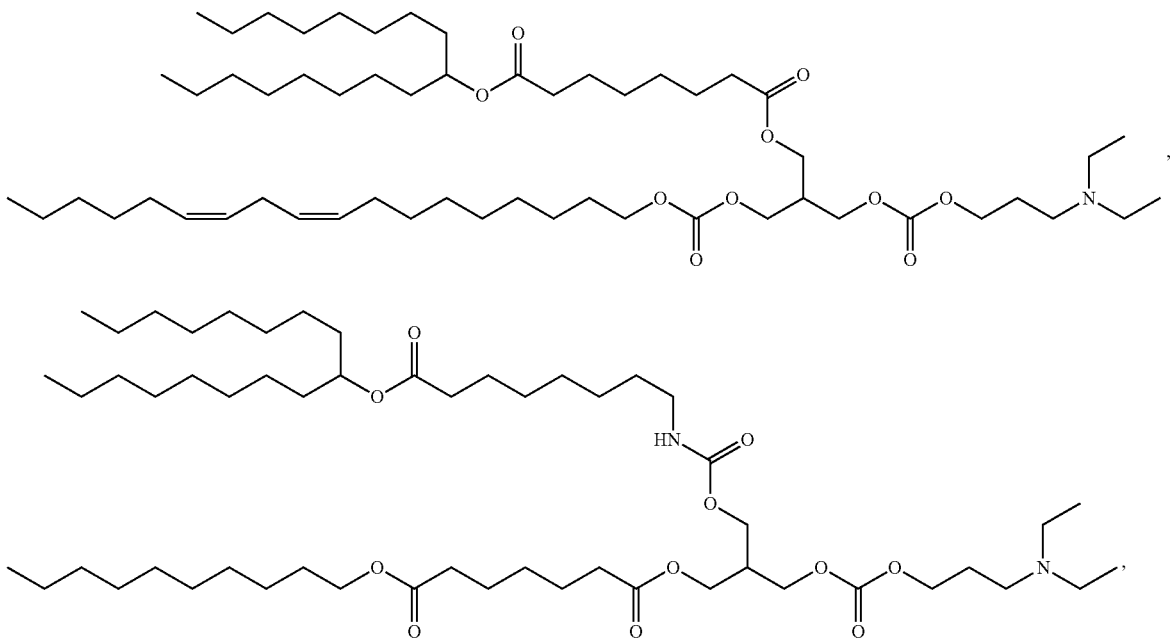

-continued
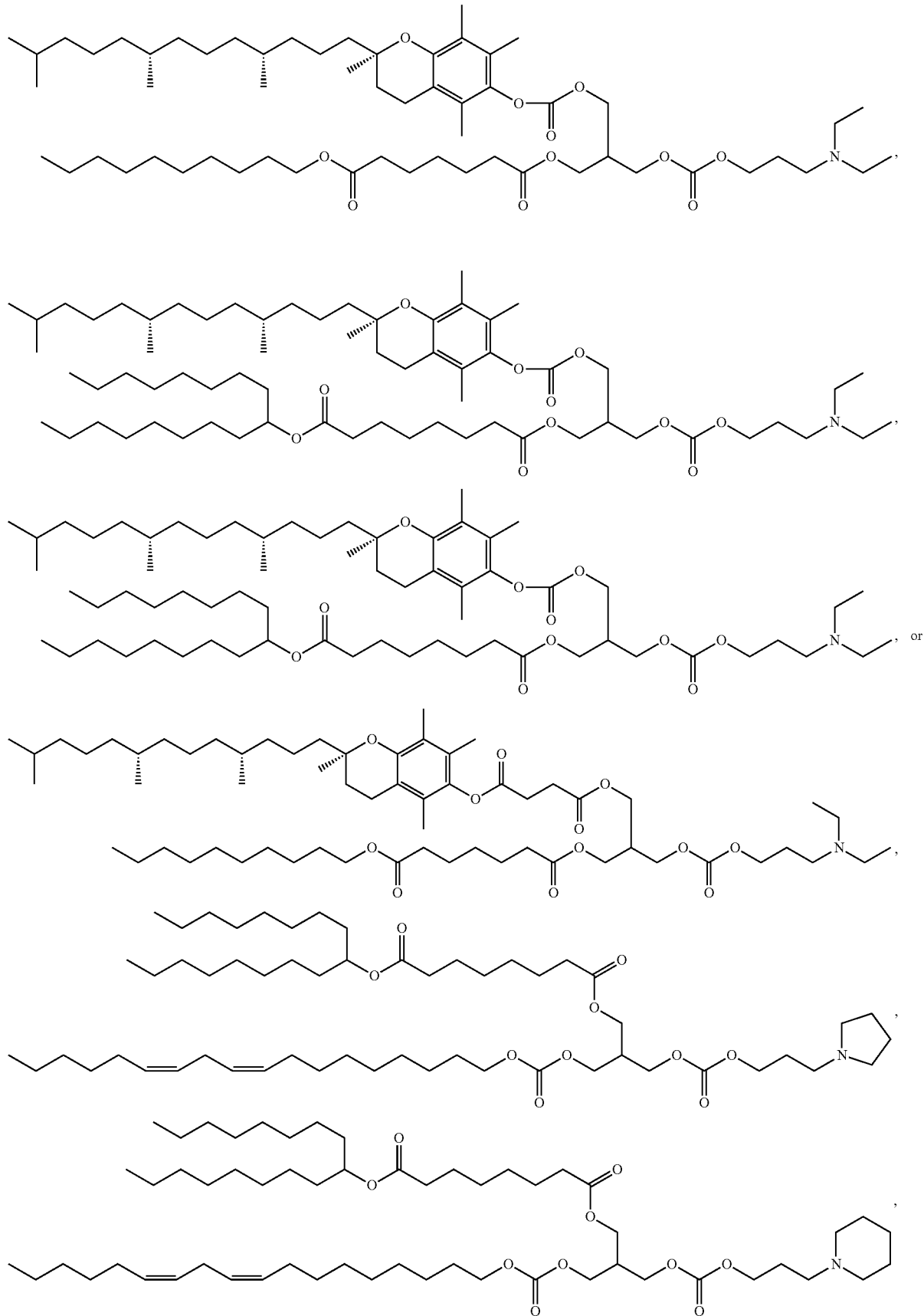

-continued
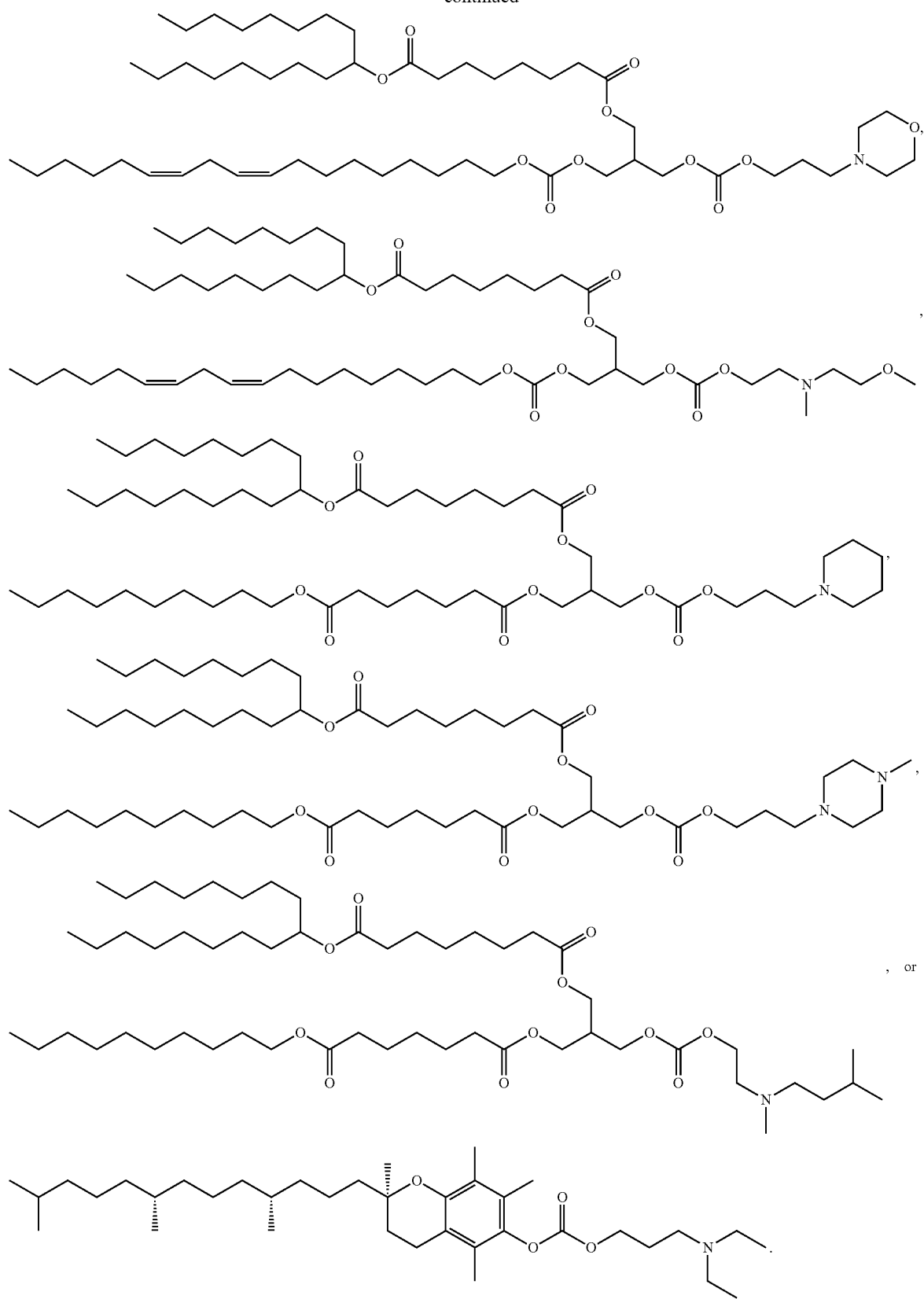

15. An amino lipid having a structure of Formula (II*), or a pharmaceutically acceptable salt or solvate thereof,

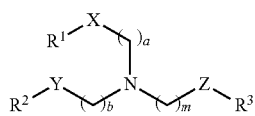

Formula (II*)

wherein
each of $R^1$ and $R^2$ is independently hydrogen, $C_3$-$C_{30}$ alkyl, $C_3$-$C_{30}$ alkenyl, $C_3$-$C_{30}$ alkynyl, $C_3$-$C_{30}$ heteroalkyl, $C_3$-$C_{30}$ heteroalkenyl, $C_3$-$C_{30}$ heteroalkynyl, $C_3$-$C_{10}$ cycloalkyl, —$C_0$-$C_{10}$ alkylene-L-$R^6$, or —$C_1$-$C_{10}$ alkenylene-L-$R^6$, wherein each of the alkyl, alkylene, alkenyl, alkenylene, alkynyl, heteroalkyl, heteroalkenyl, heteroalkynyl, and cycloalkyl is independently substituted or unsubstituted;

each of X, Y, and Z is independently —C(=O)NR$^4$—, —C(=O)—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, —OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, SC(=S)—, —SC(=S)O—, SC(=O)S—, —SC(=S)S—, —NR$^4$C(=S)S—, —SC(=S)NR$^4$—, —O—, —S—, or a bond;

each of L is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, —OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —SC(=O)NR$^4$—, —C(=S)S—, —SC(=S)—, SC(=S)O—, —SC(=O)S—, —SC(=S)S—, —NR$^4$C(=S)S—, —SC(=S)NR$^4$—, —O—N=CR$^4$—, —CR$^4$=N—O—, —O—, —S—, —$C_1$-$C_{10}$ alkylene-O—, —$C_1$-$C_{10}$ alkylene-C(=O)O—, —$C_1$-$C_{10}$ alkylene-OC(=O)—, or a bond, wherein the alkylene is substituted or unsubstituted;

$R^3$ is hydrogen, —$C_1$-$C_6$ alkyl, —$C_0$-$C_{10}$ alkylene-NR$^7$R$^8$, —$C_0$-$C_{10}$ alkylene-heterocycloalkyl, or —$C_0$-$C_{10}$ alkylene-heterocycloaryl, wherein the alkyl, alkylene, heterocycloalkyl and heterocycloaryl is independently substituted or unsubstituted;

each of $R^4$ is independently hydrogen or substituted or unsubstituted $C_1$-$C_6$ alkyl;

each of $R^6$ is independently $C_3$-$C_{30}$ alkyl, $C_3$-$C_{30}$ alkenyl, $C_3$-$C_{30}$ alkynyl, Cy-$C_{3-30}$ alkyl, Cy-$C_{3-30}$ alkenyl, or Cy-$C_{3-30}$ alkynyl, wherein the alkyl, the alkenyl and alkynyl are each independently substituted or unsubstituted;

each of Cy is substituted or unsubstituted cycloalkyl, substituted or unsubstituted heterocycloalkyl, substituted or unsubstituted aryl, substituted or unsubstituted heteroaryl;

each of $R^7$ and $R^8$ is independently hydrogen or substituted or unsubstituted $C_1$-$C_6$ alkyl, or $R^7$ and $R^8$ taken together with the nitrogen to which they are attached form a substituted or unsubstituted $C_2$-$C_6$ heterocyclyl;

each of a and b is independently 1, 2, 3, 4, 5, 6, 7, 8, 9, or 10; and m is 0, 1, 2, 3, 4, or 5.

16. The amino lipid of claim 15, wherein each of a and b is independently 3, 4, 5, 6, 7, 8, 9, or 10, or wherein m is 1, 2, 3, 4, or 5.

17. The amino lipid of claim 15, wherein X and Y are each independently selected from —C(=O)O— and —OC(=O)—.

18. The amino lipid of claim 15, wherein Z is —C(=O)NR$^4$—, —NR$^4$C(=O)—, —OC(=O)O—, —C(=O)O—, —OC(=O)—, or —O—, and $R^4$ is hydrogen or CH$_3$.

19. The amino lipid of claim 1, wherein $R^3$ is —$C_1$-$C_6$ alkylene-NR$^7$R$^8$.

20. A nanoparticle composition that comprises an amino lipid having a structure selected from the following structures, wherein m is 1 through 10:

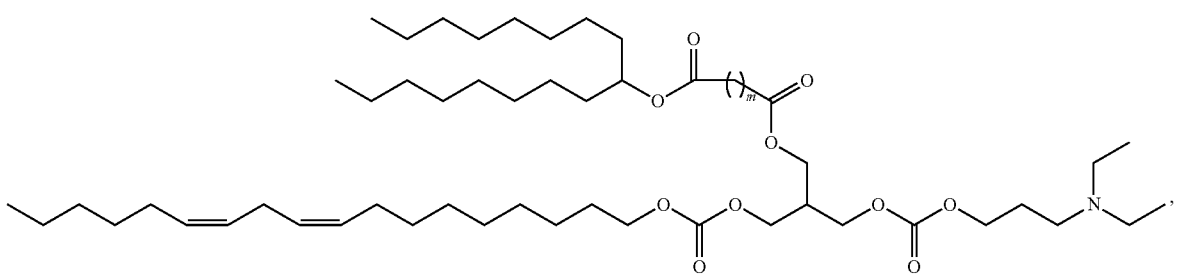

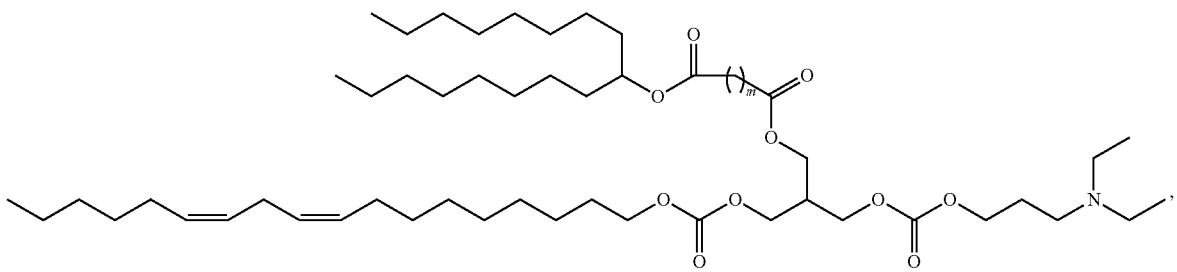

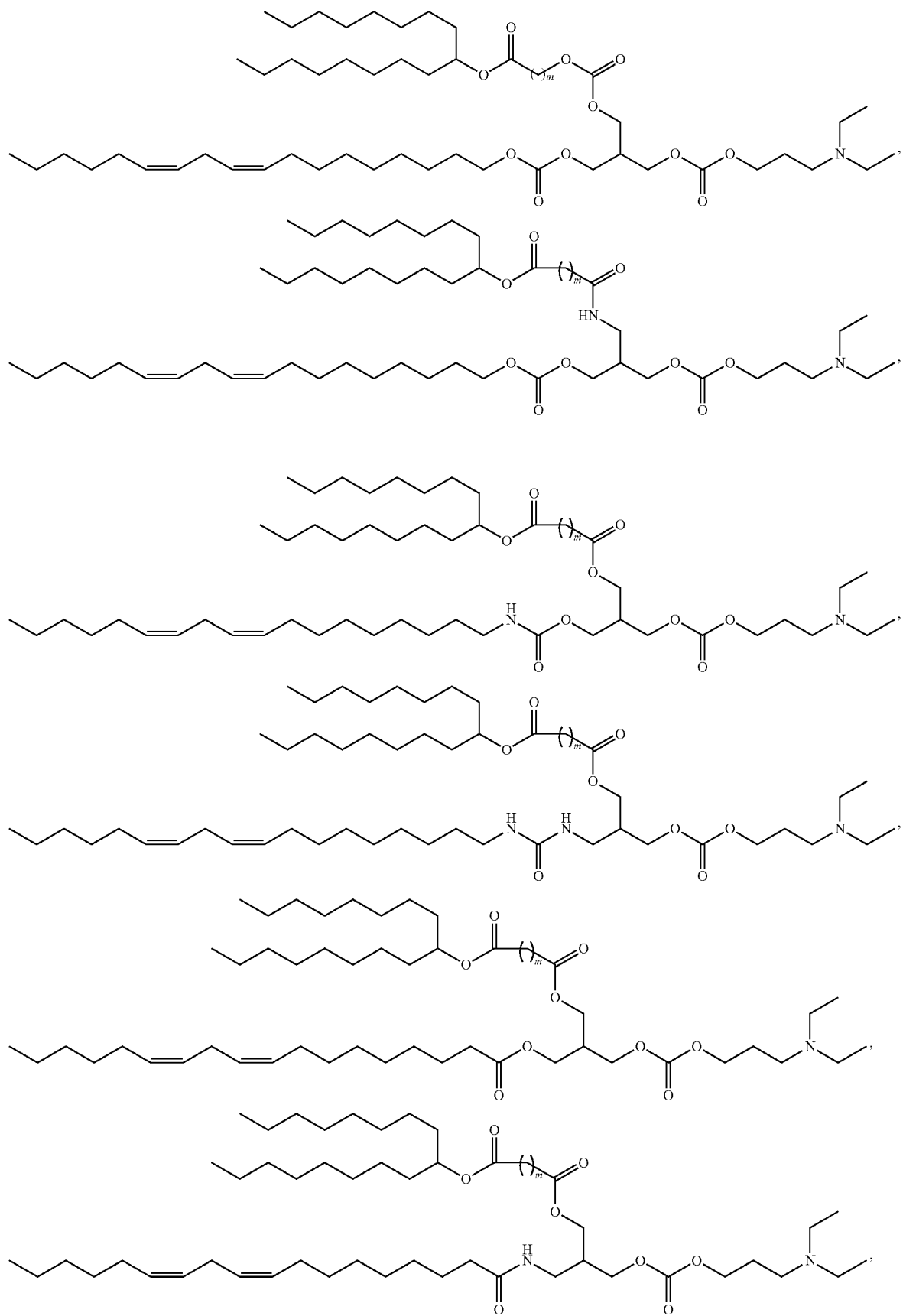

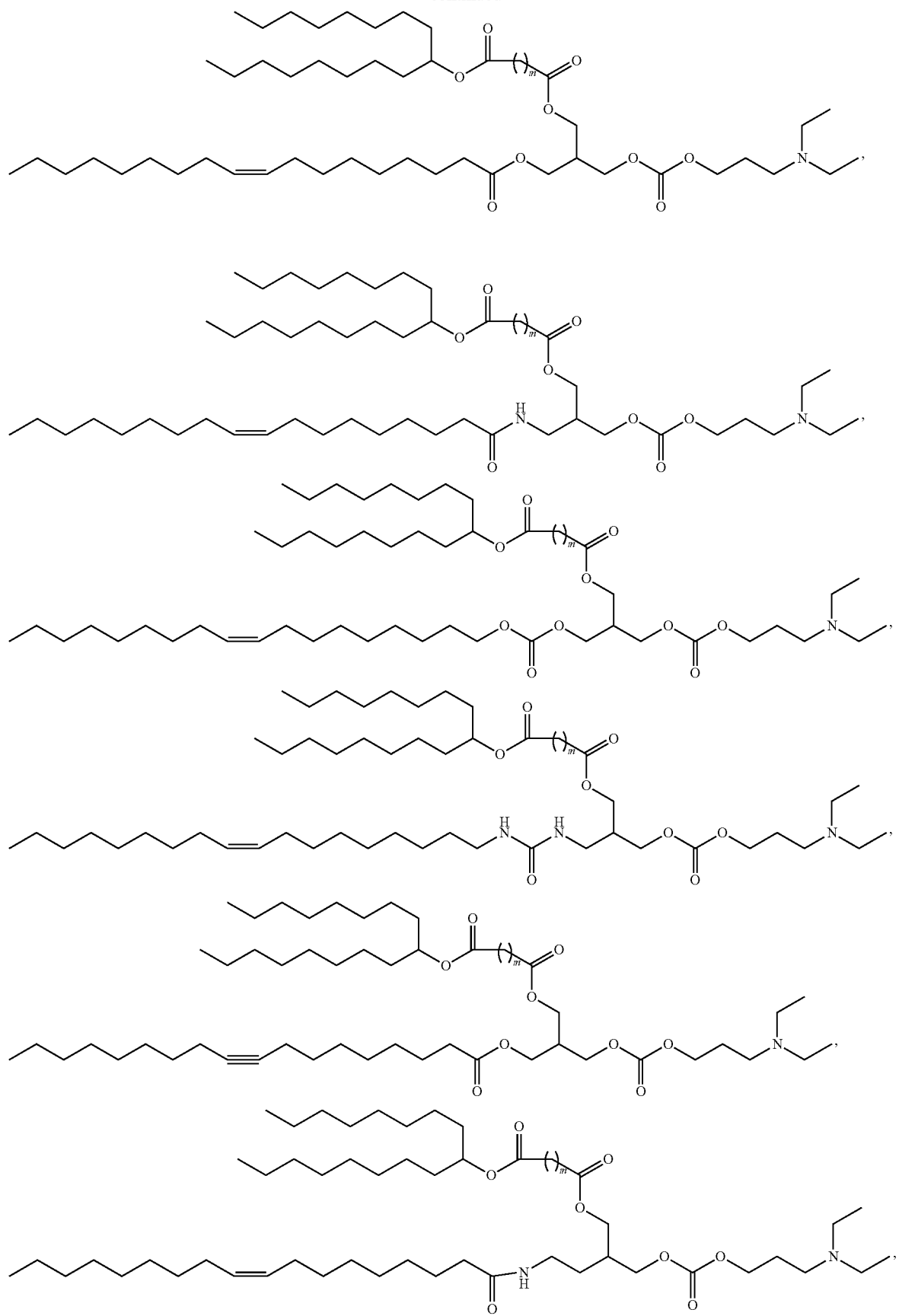

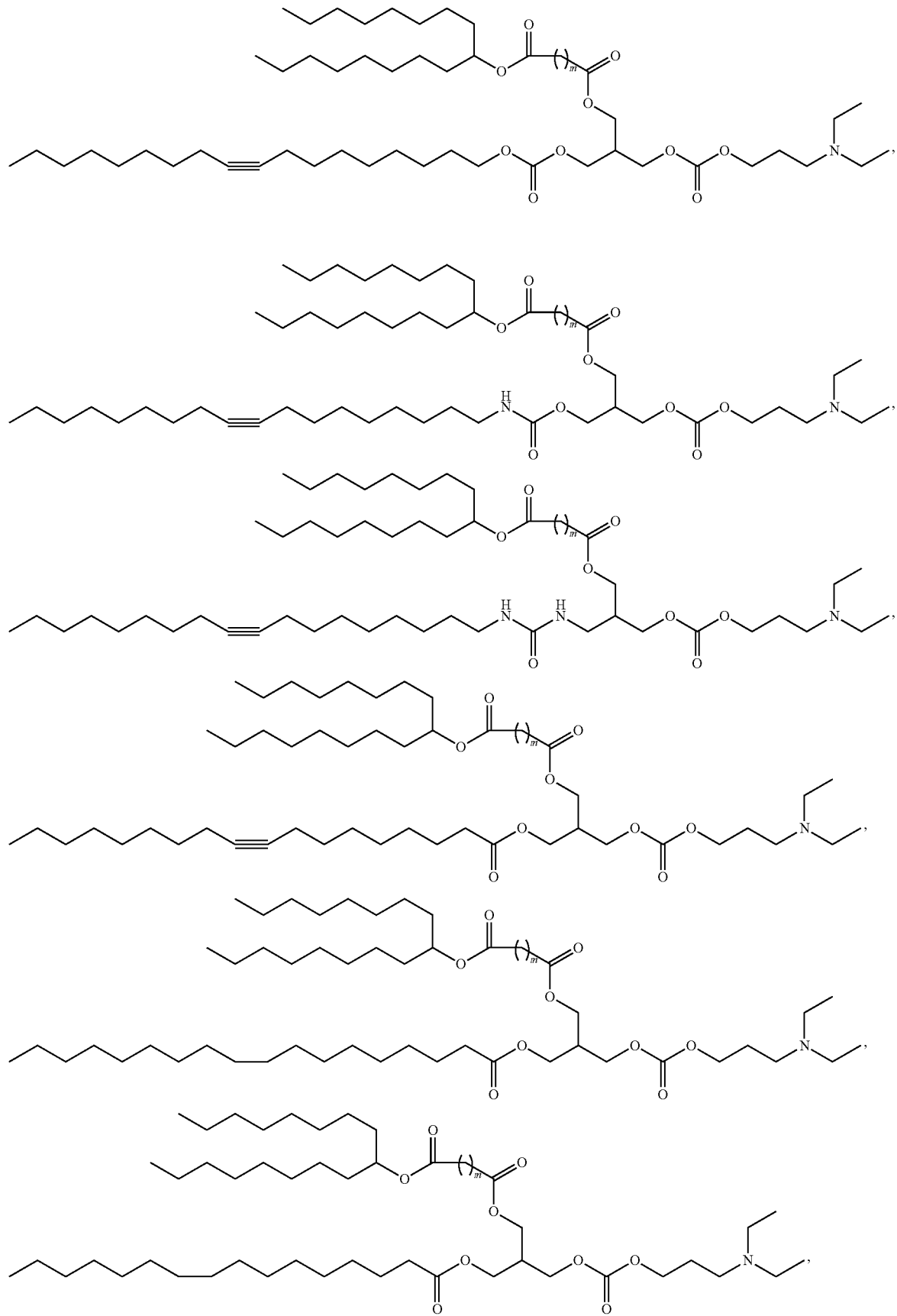

-continued
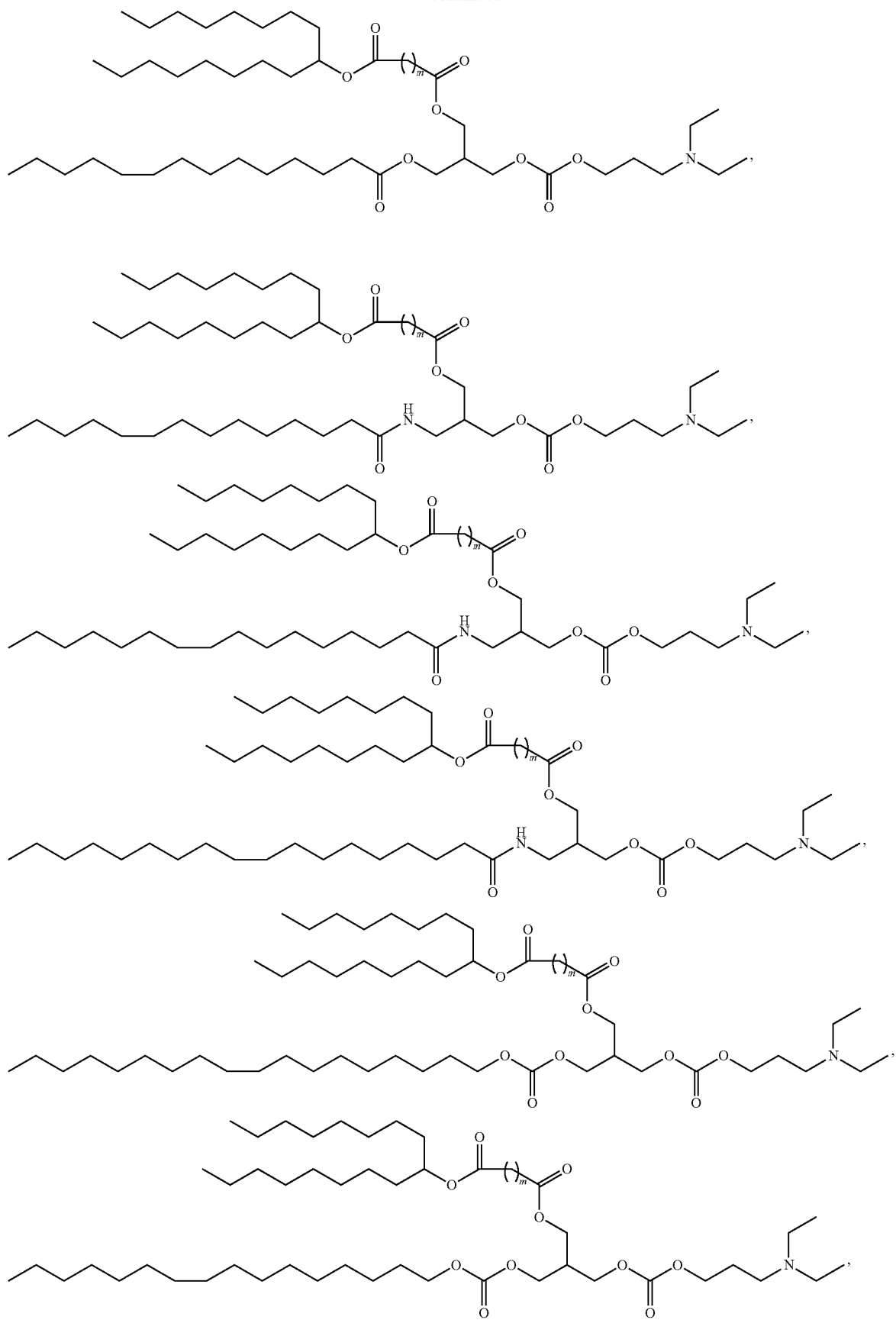

-continued
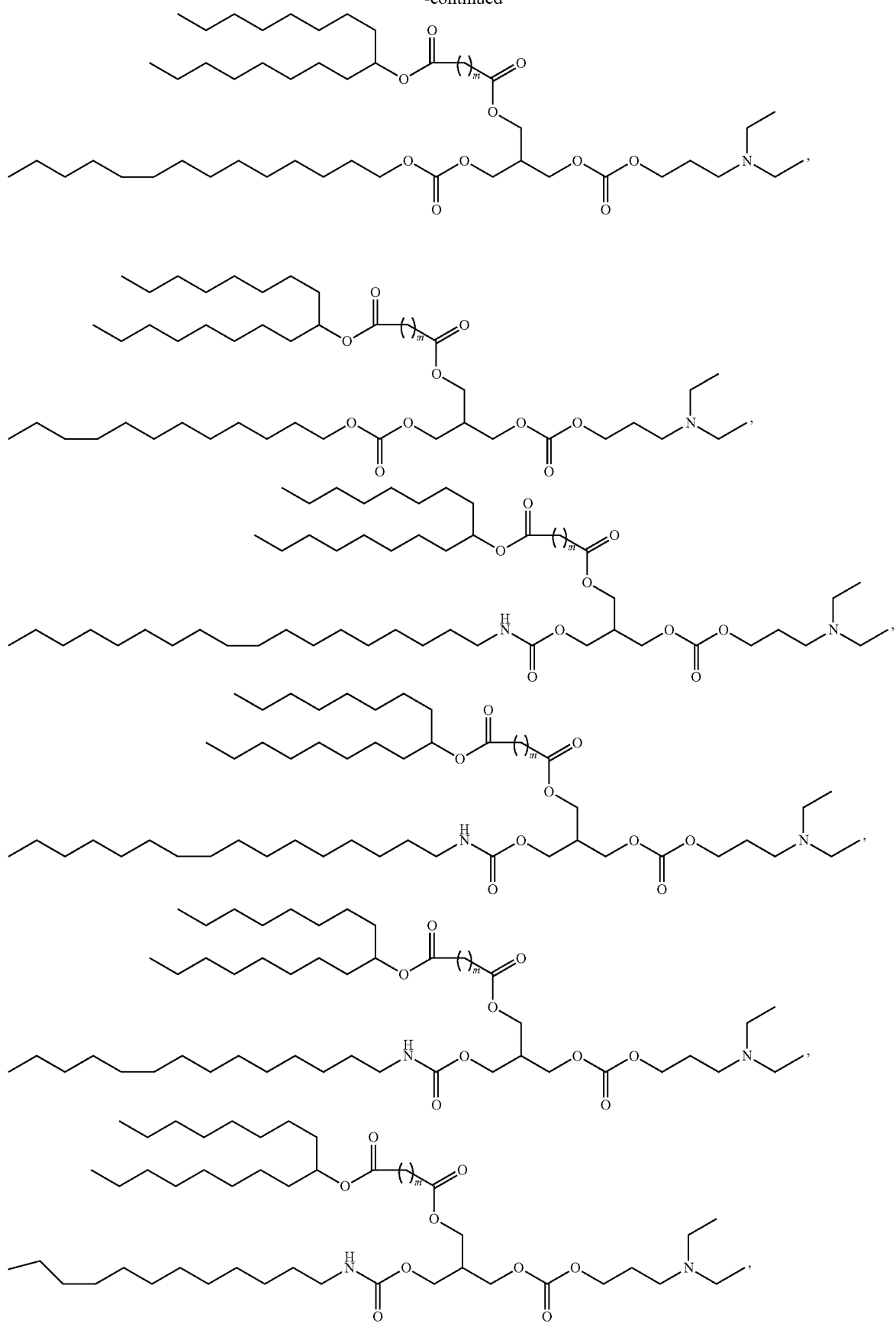

-continued
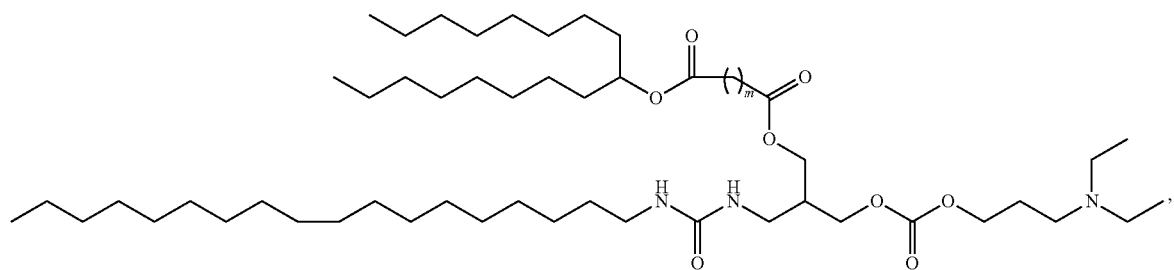
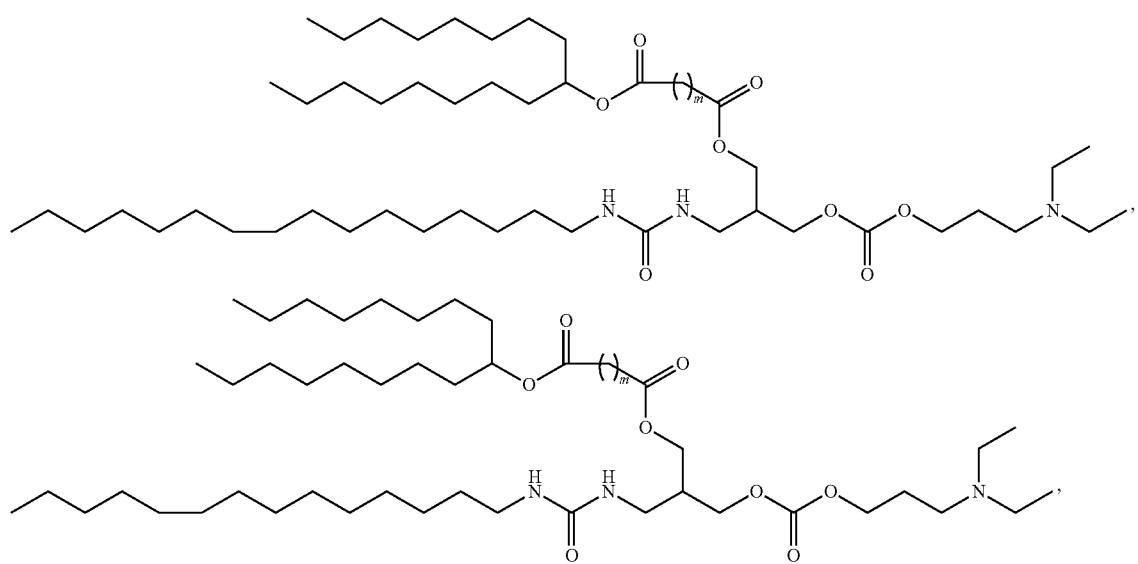
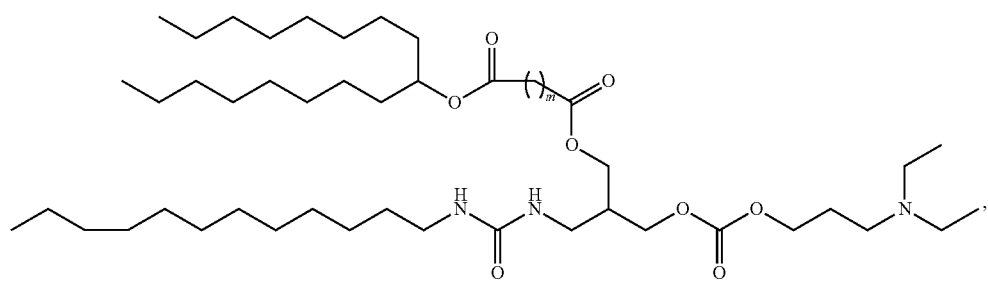
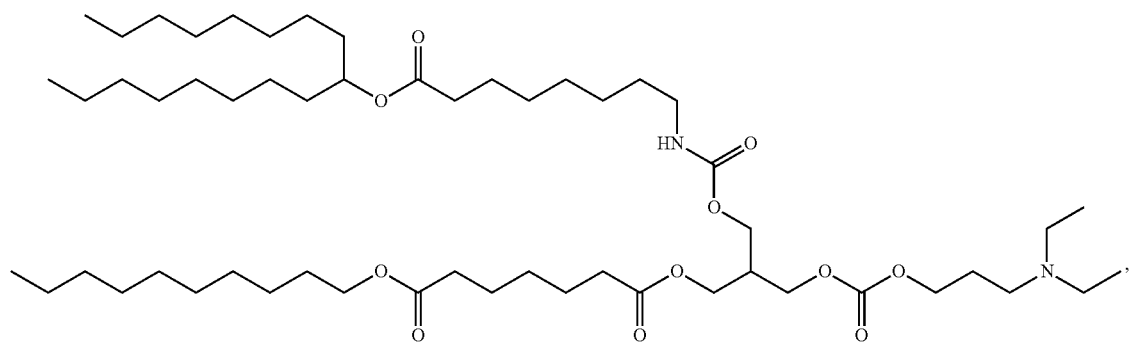

-continued
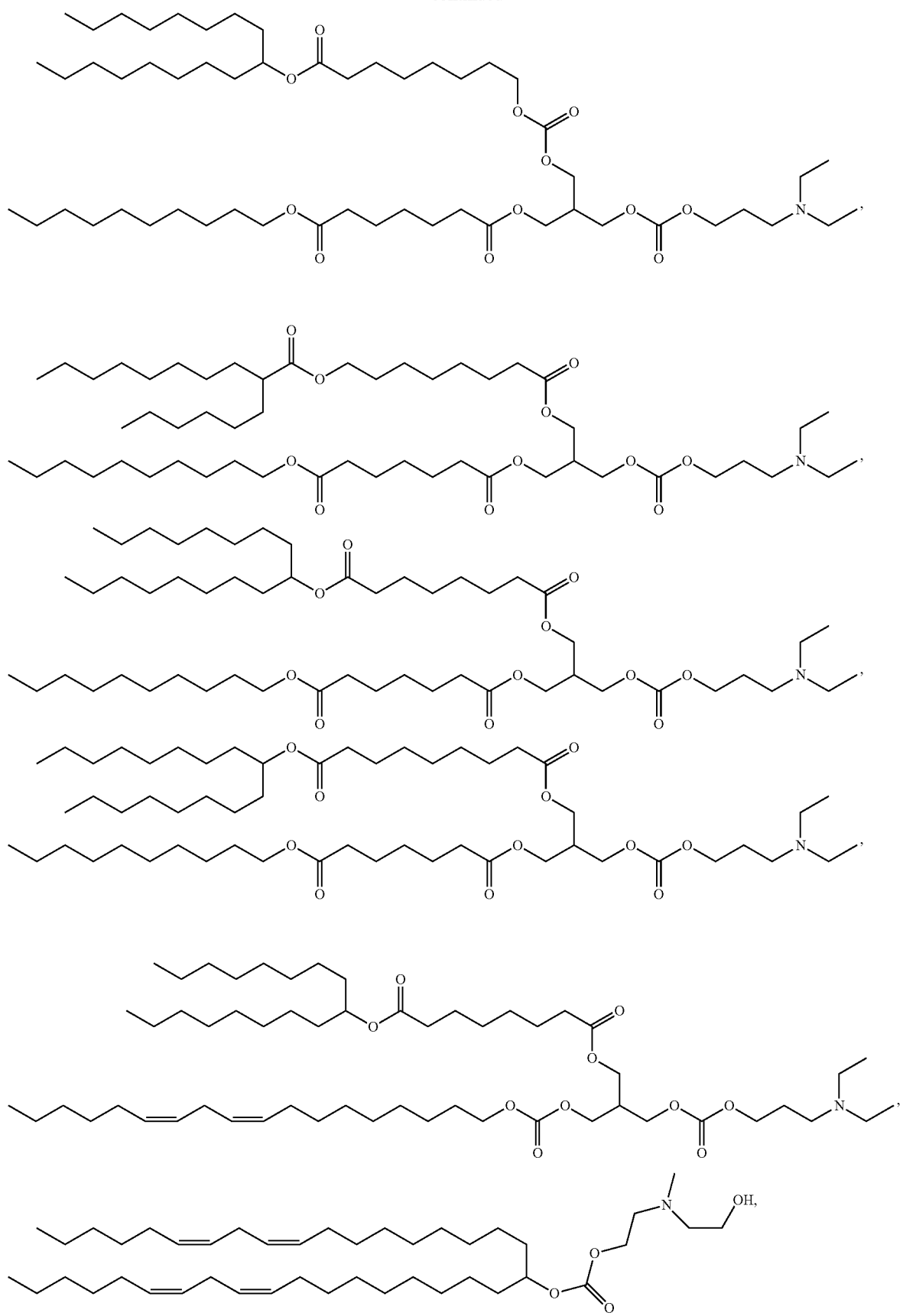

-continued
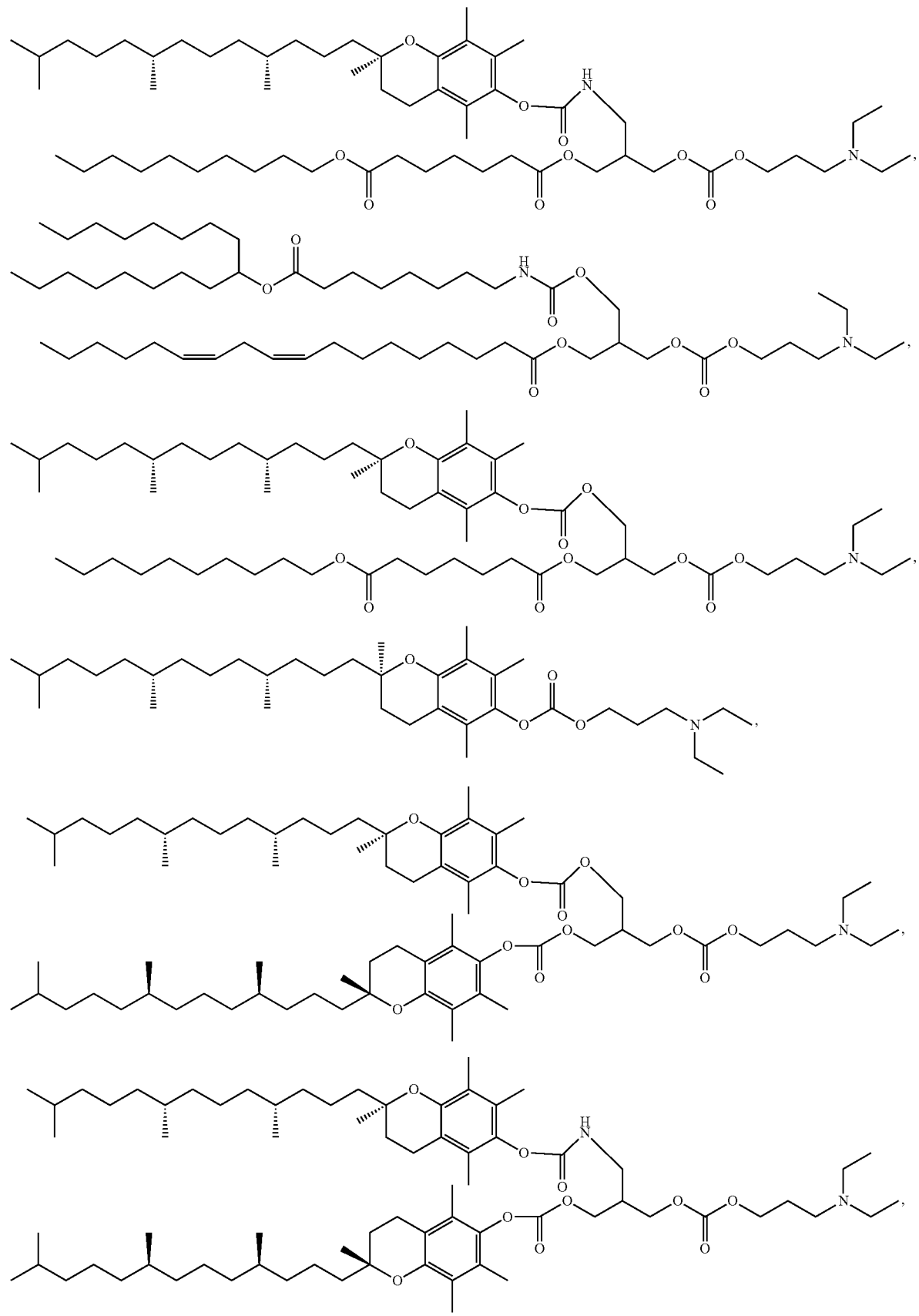

-continued
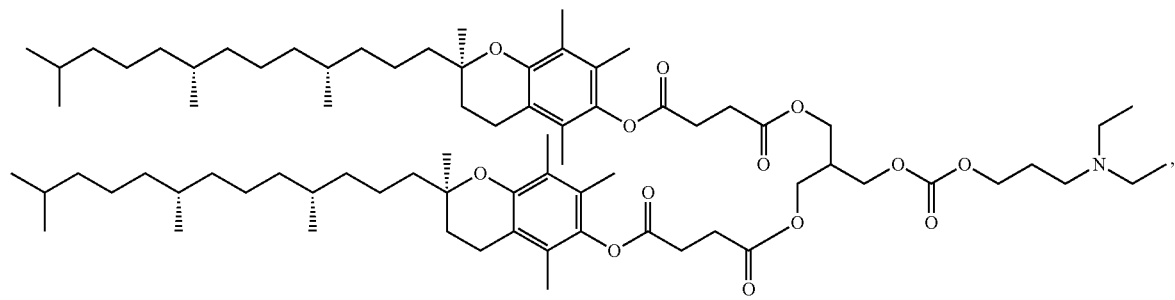
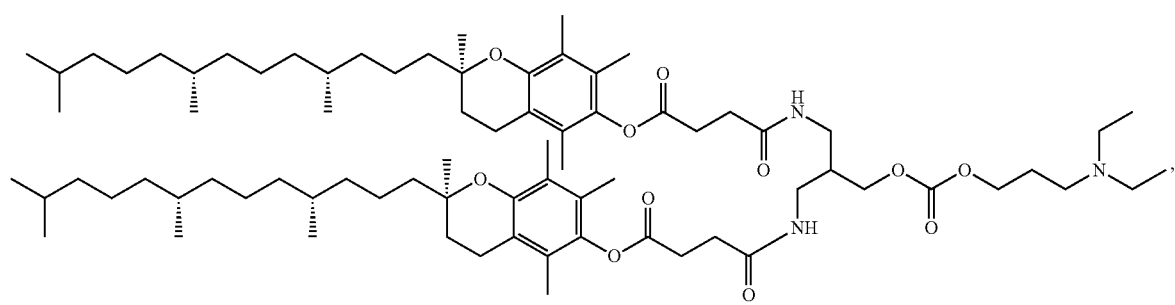
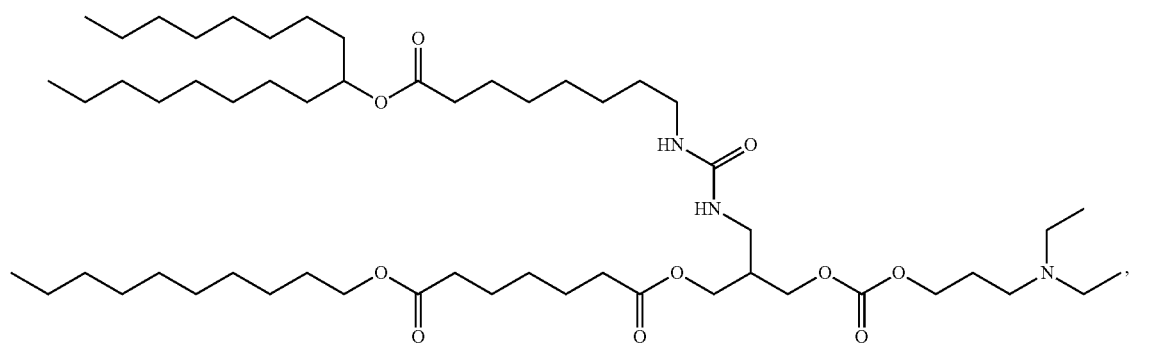
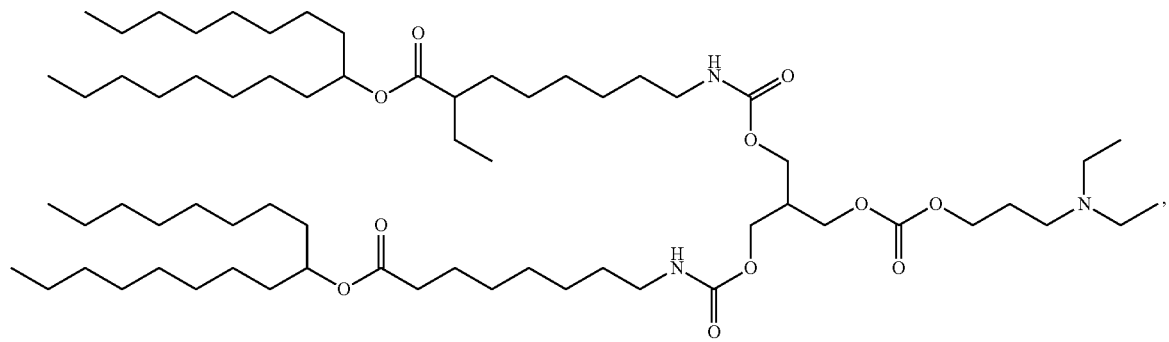
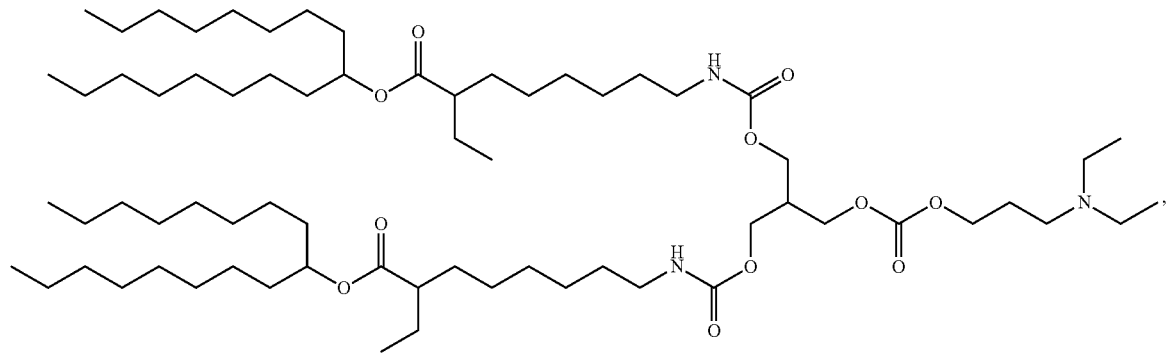

-continued
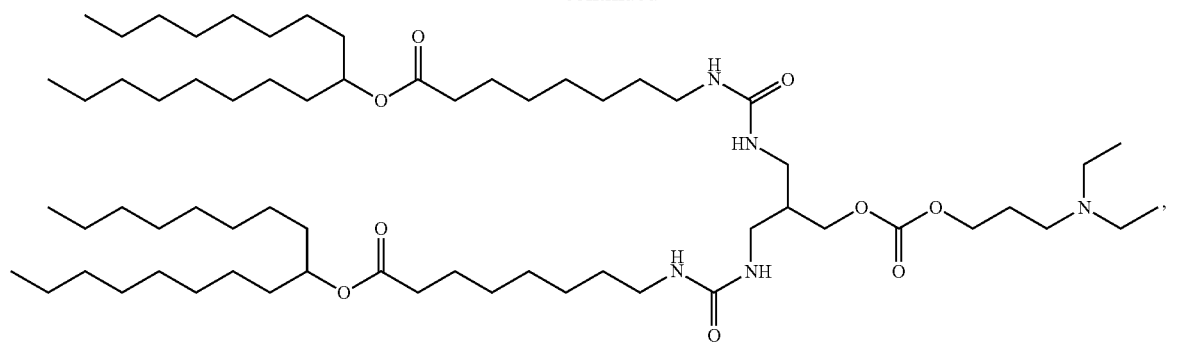
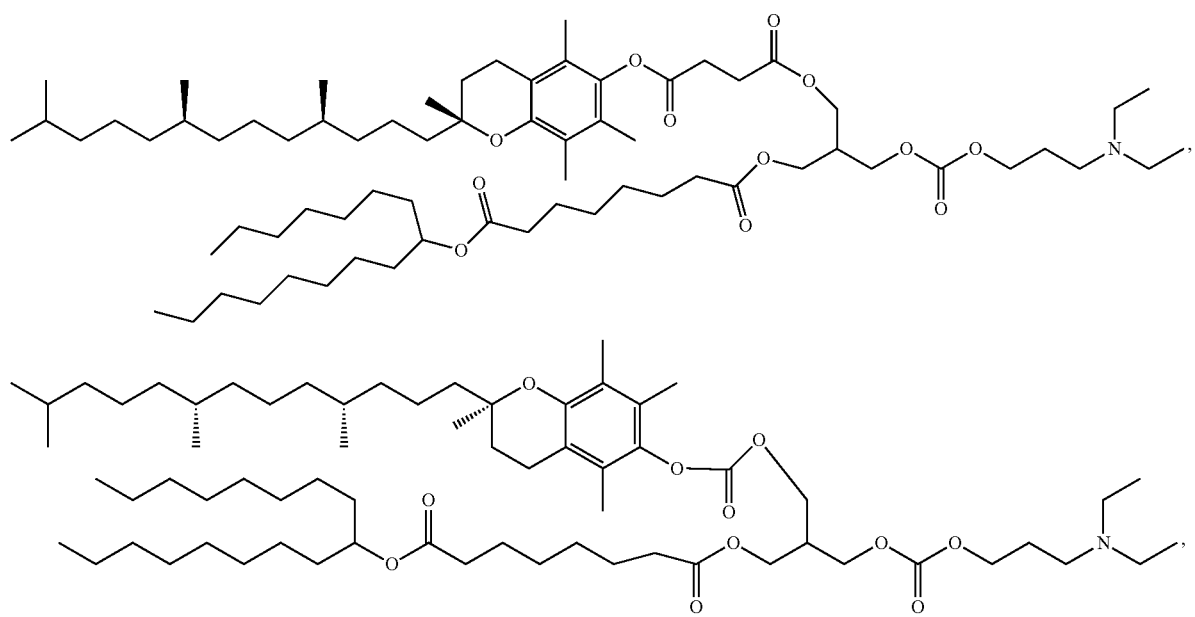
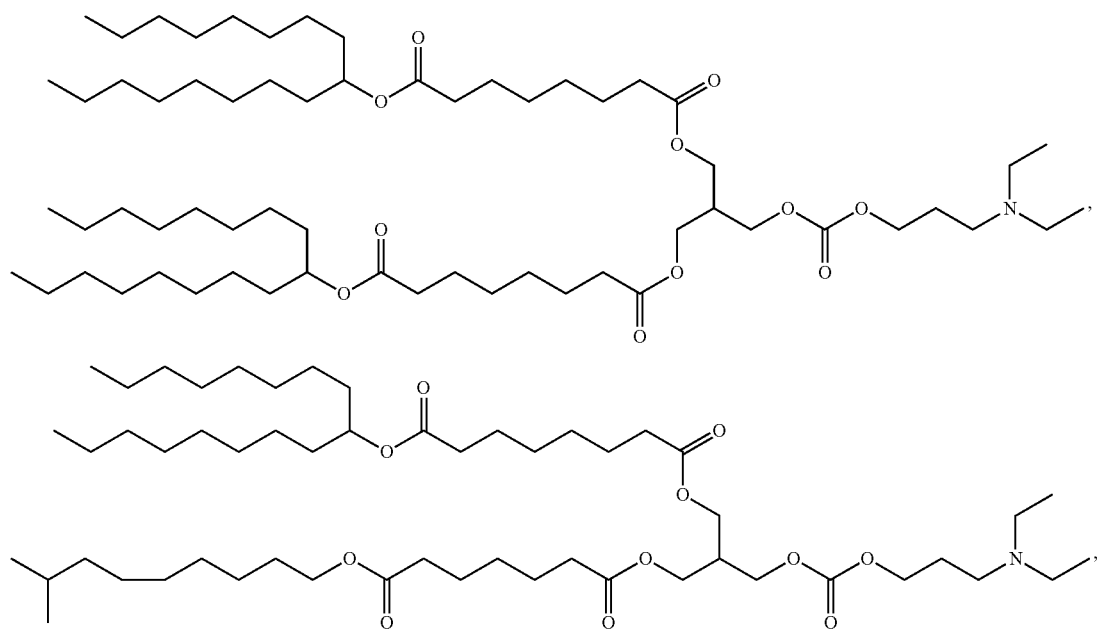

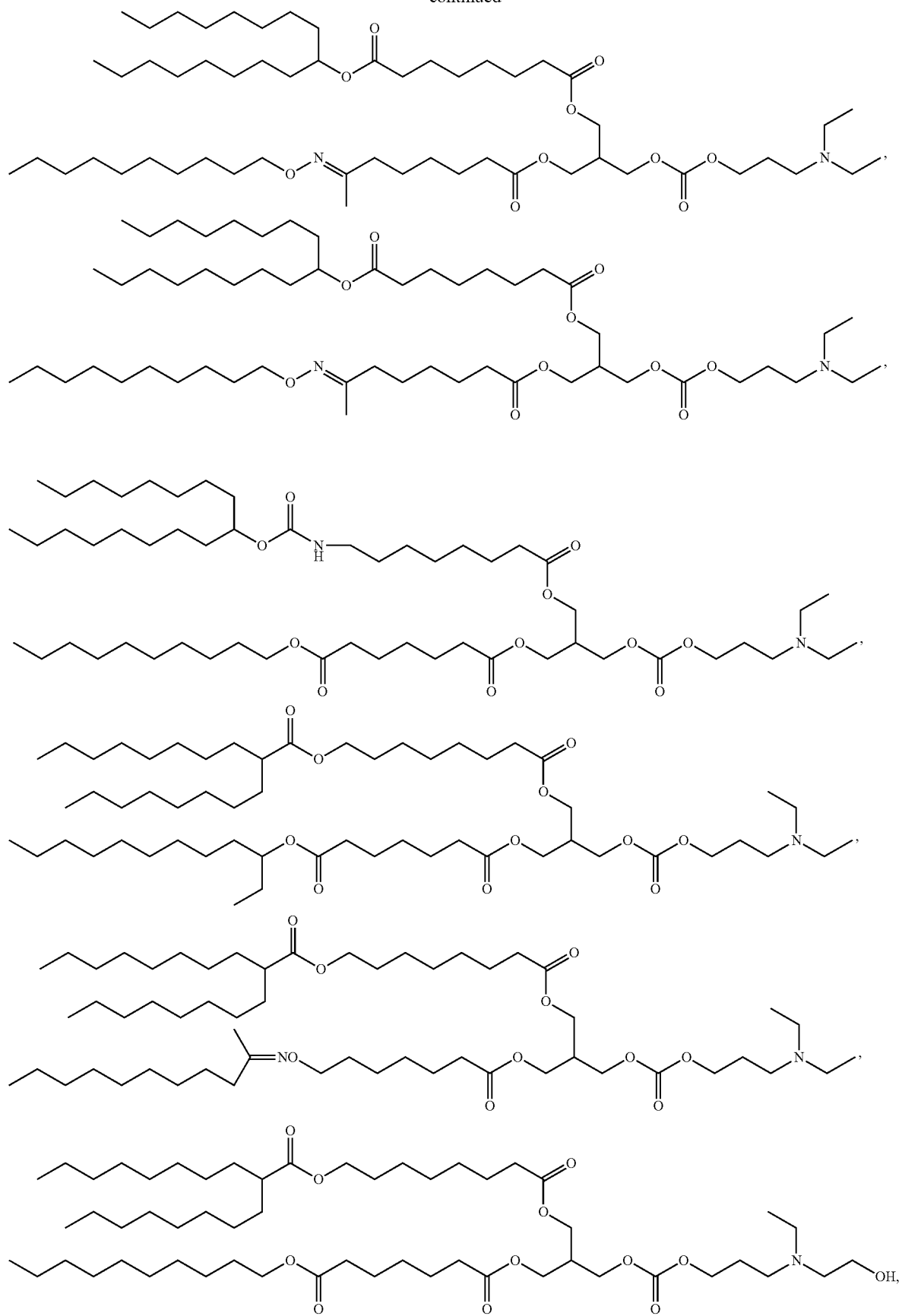

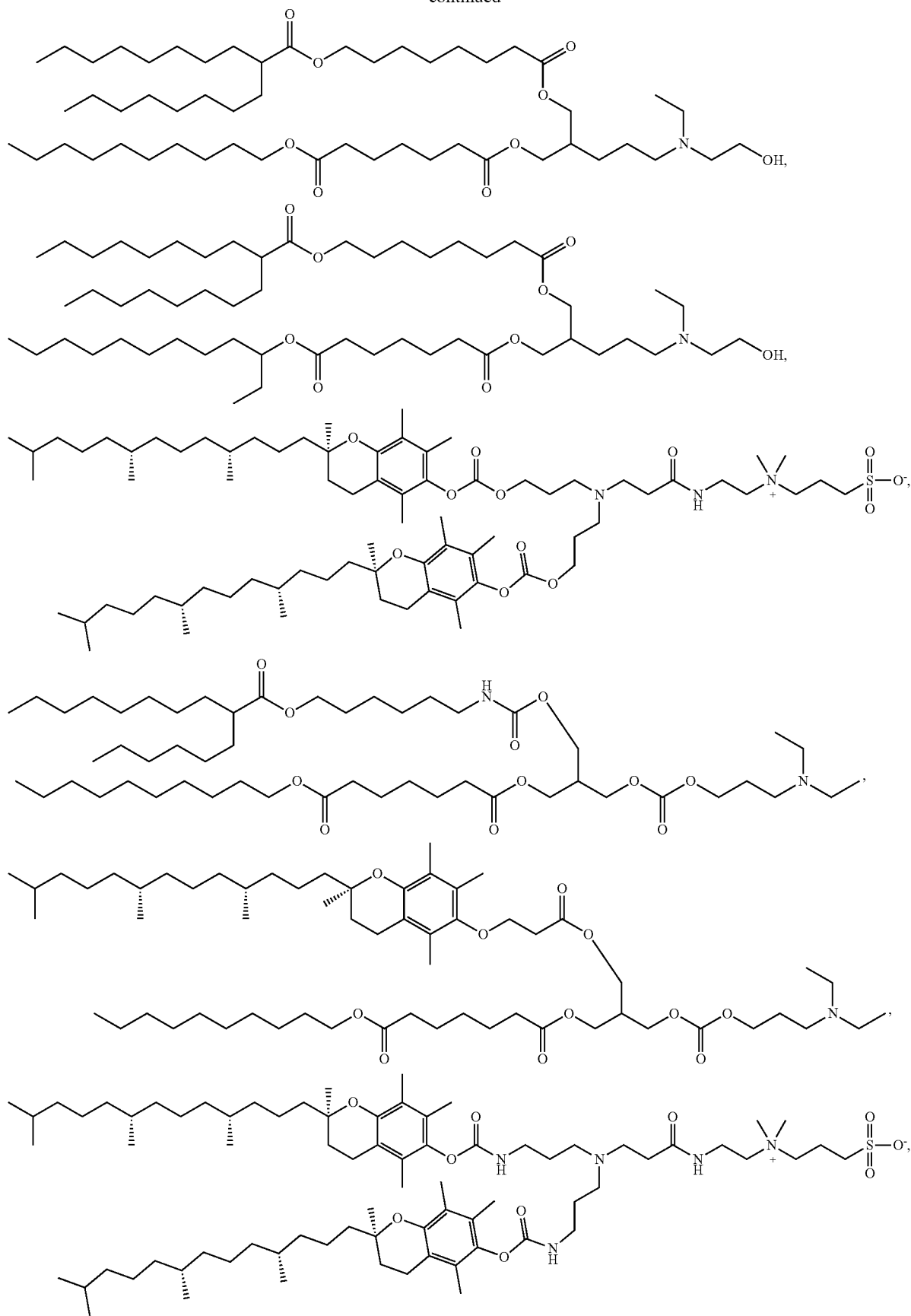

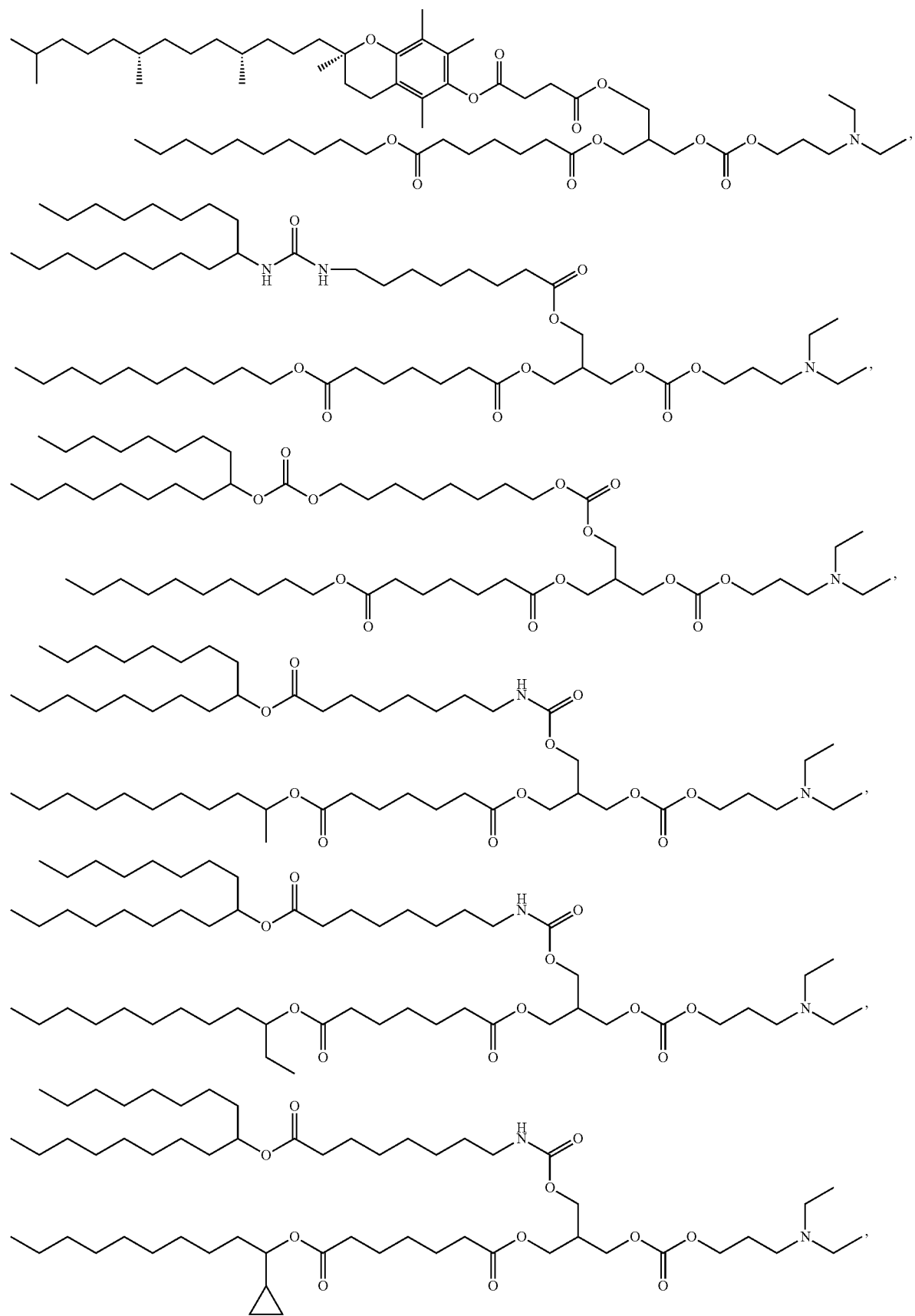

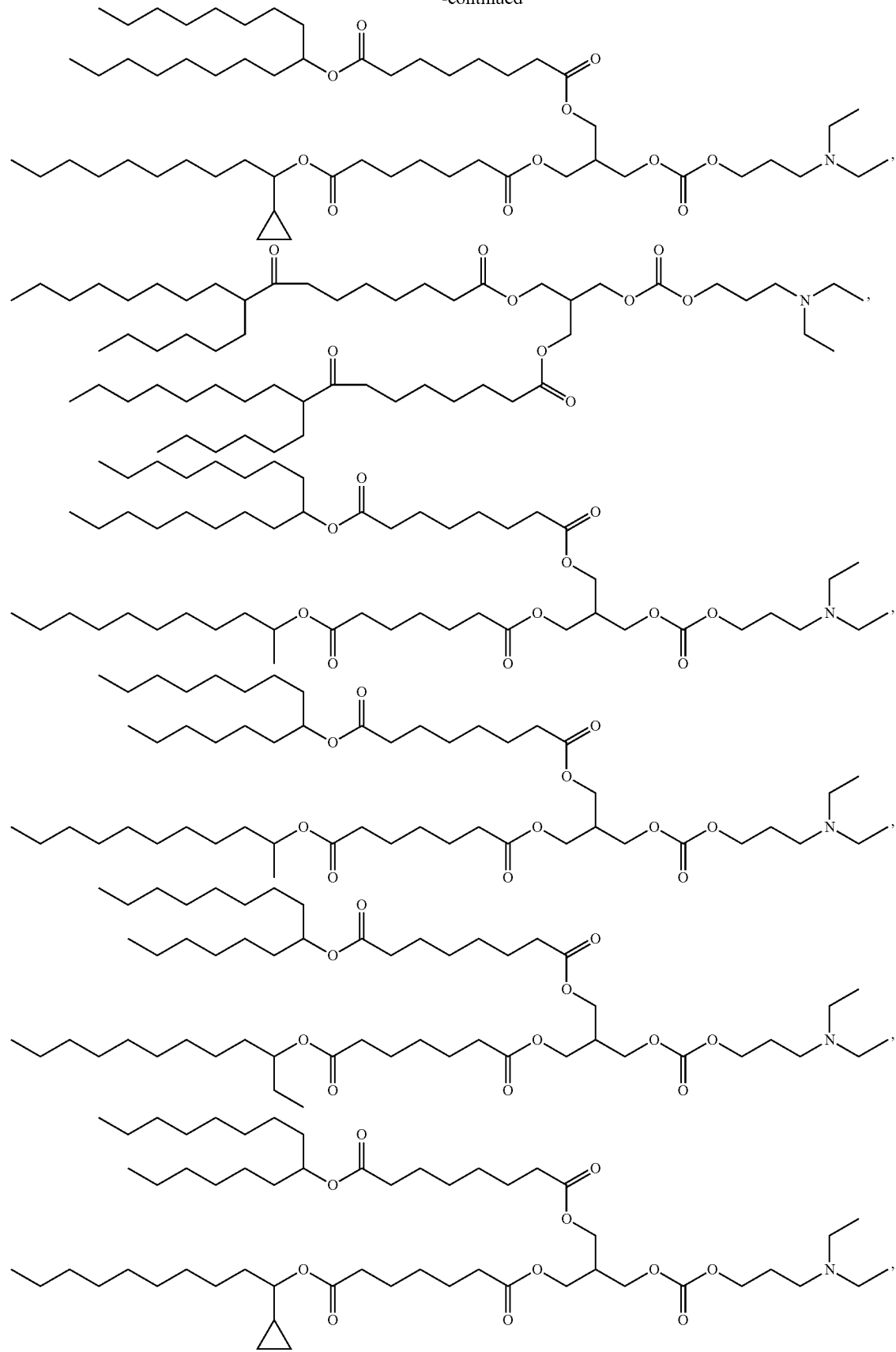

623 624
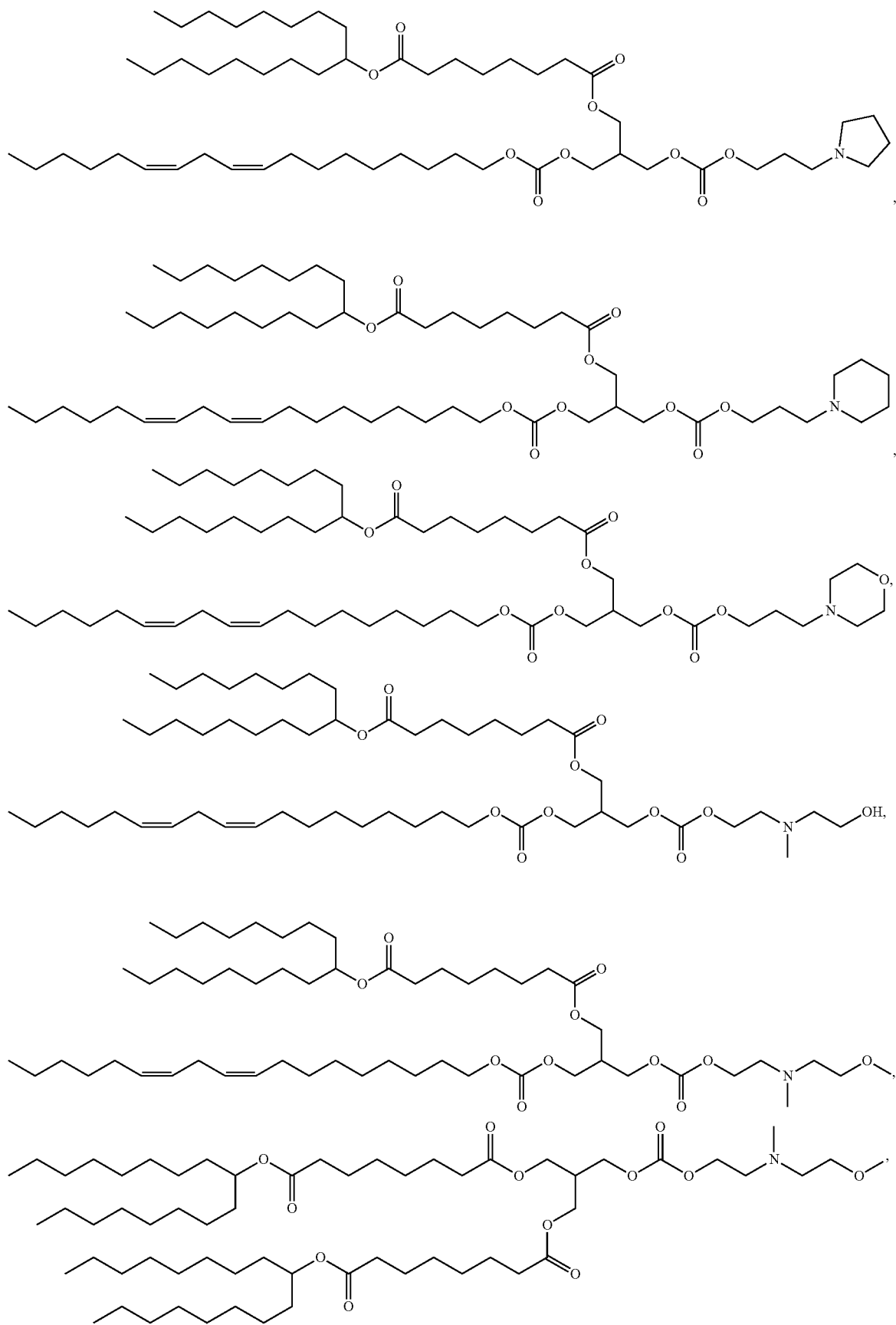

-continued
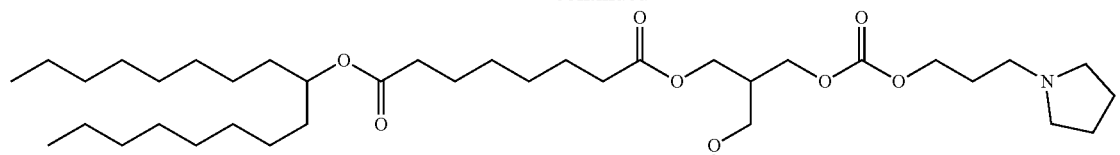
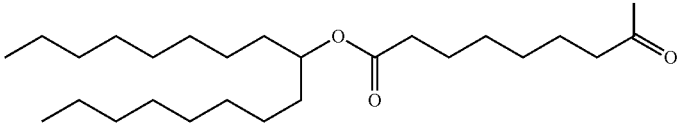
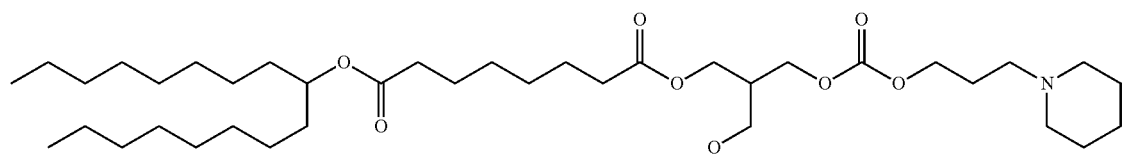
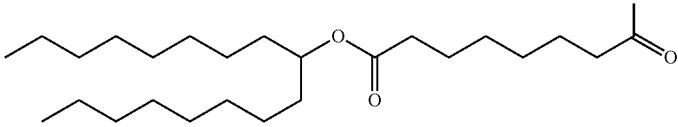
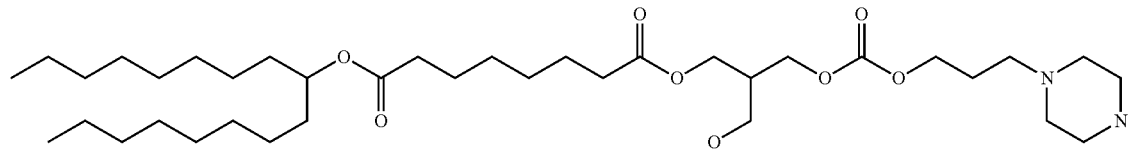
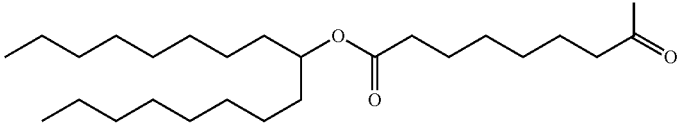
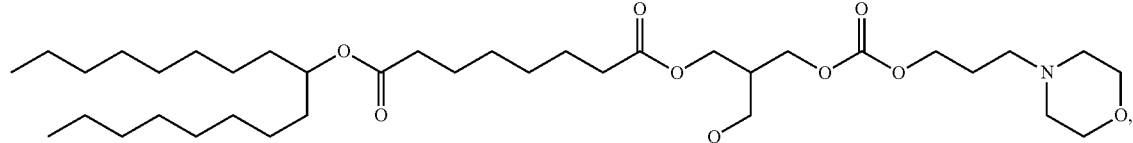
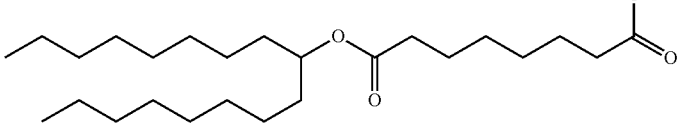
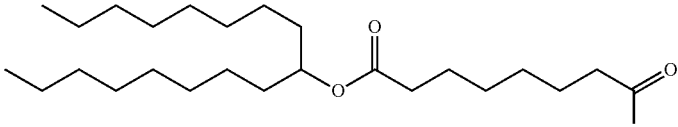
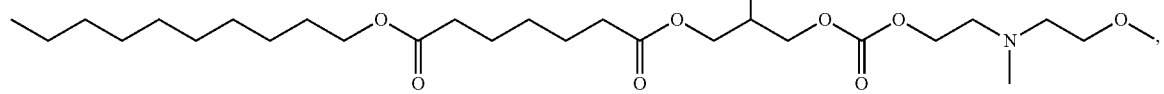
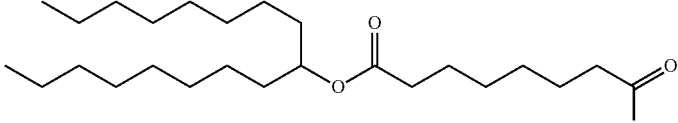
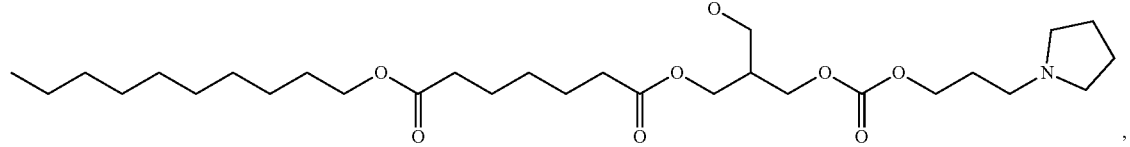

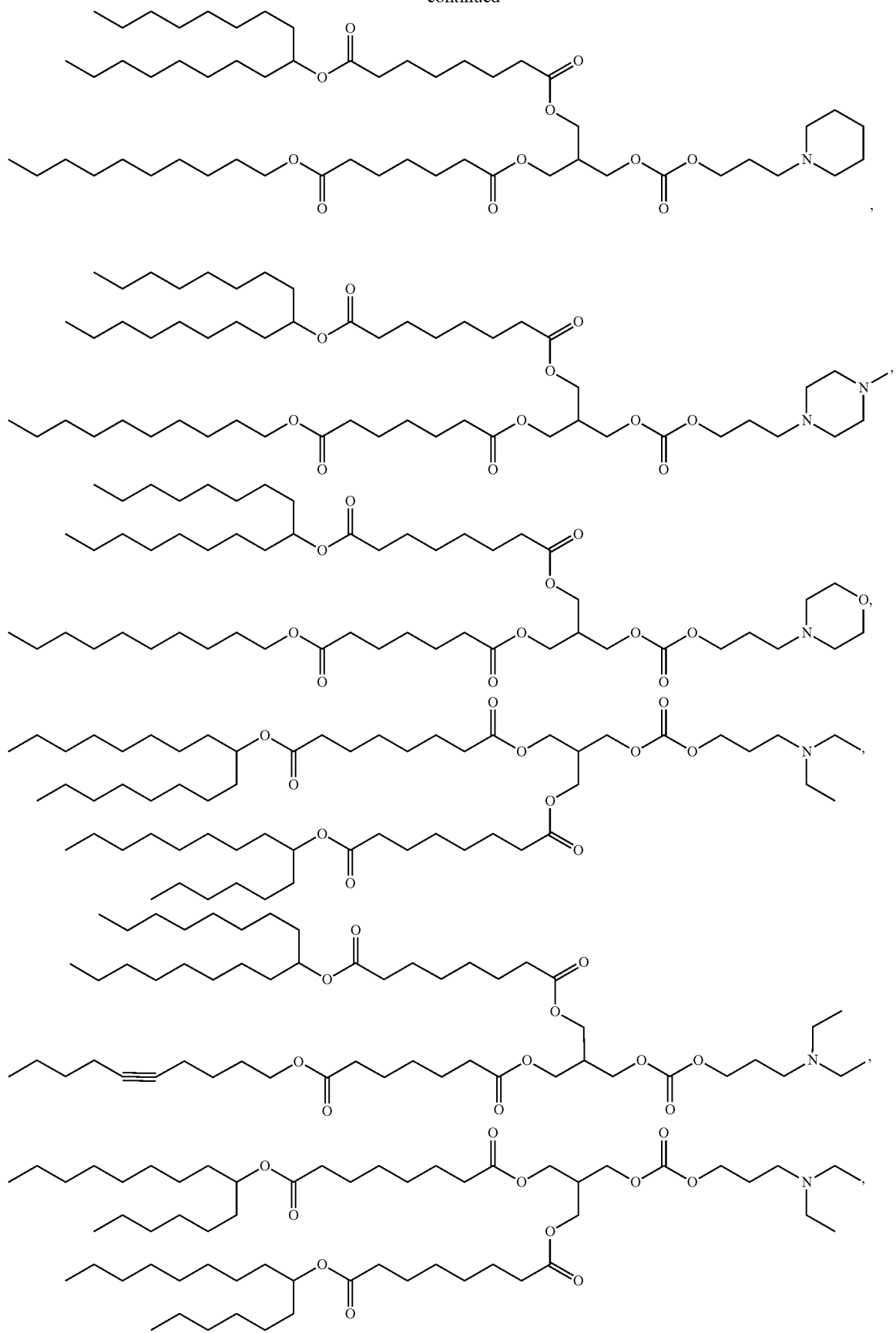

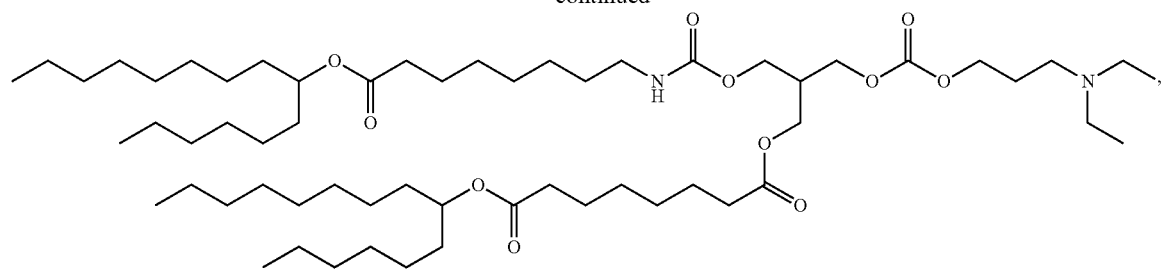
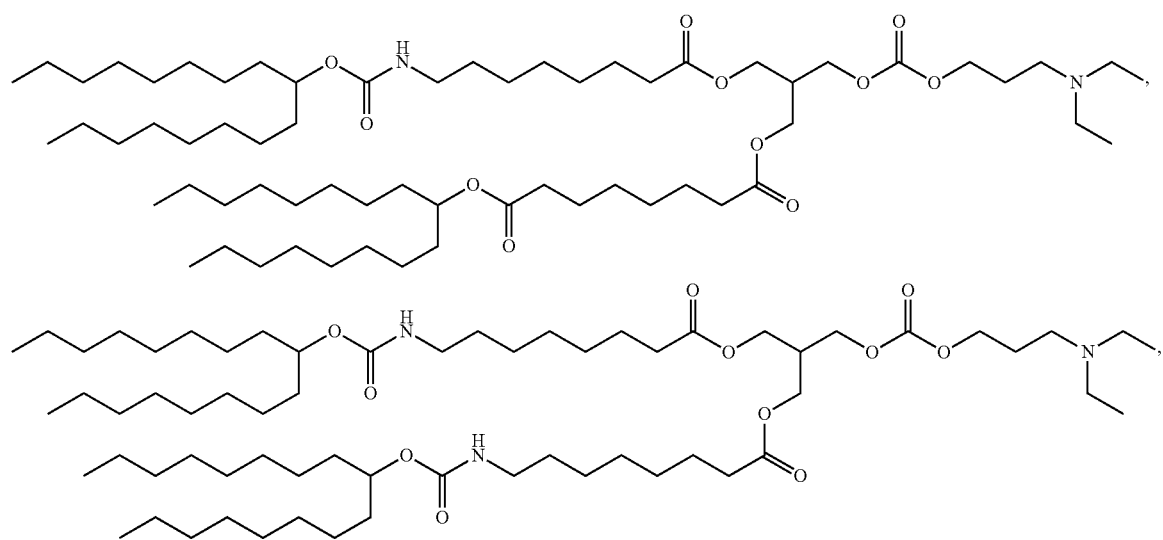
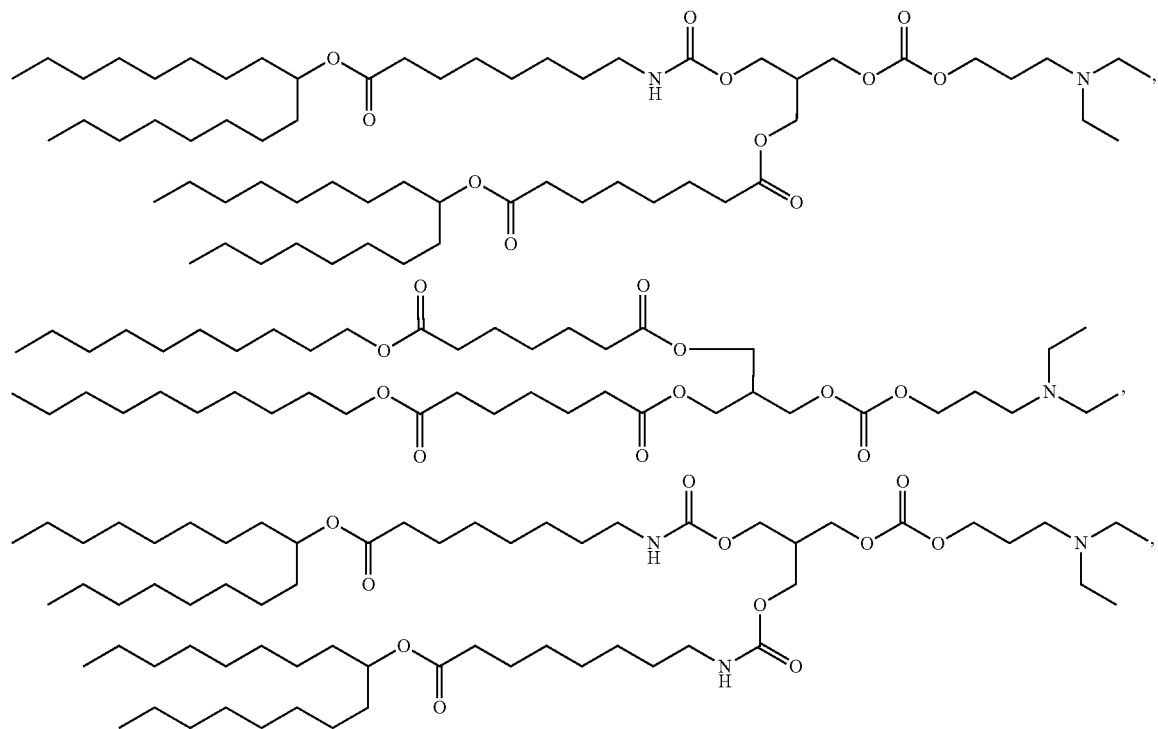

-continued
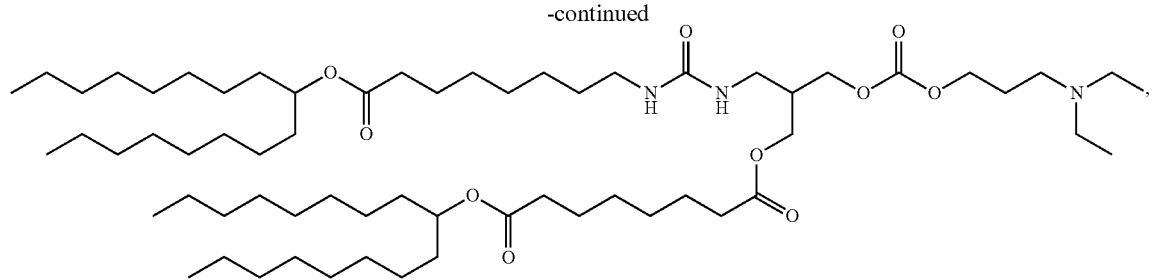
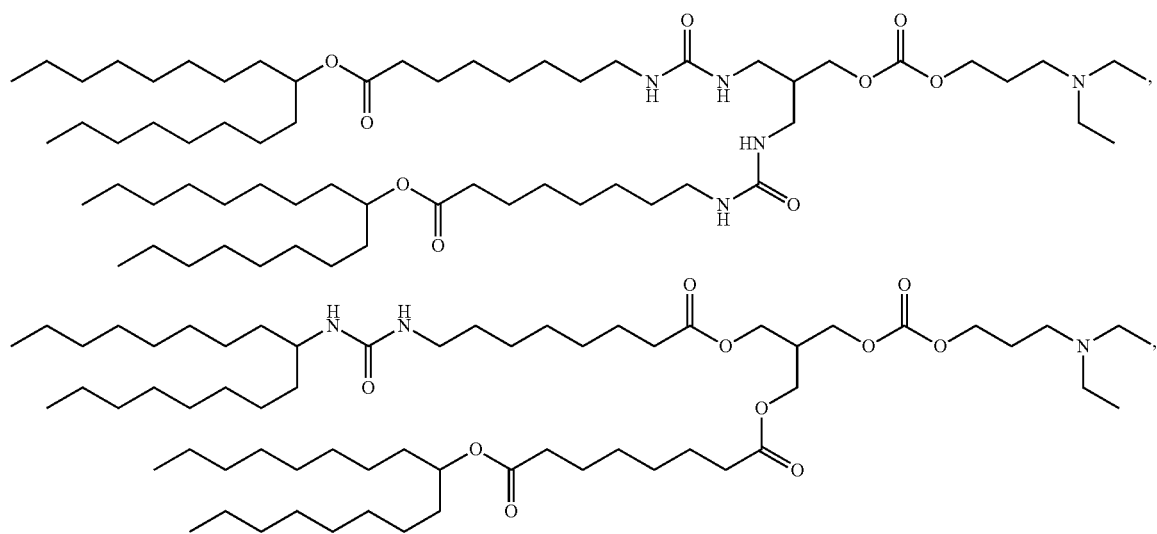
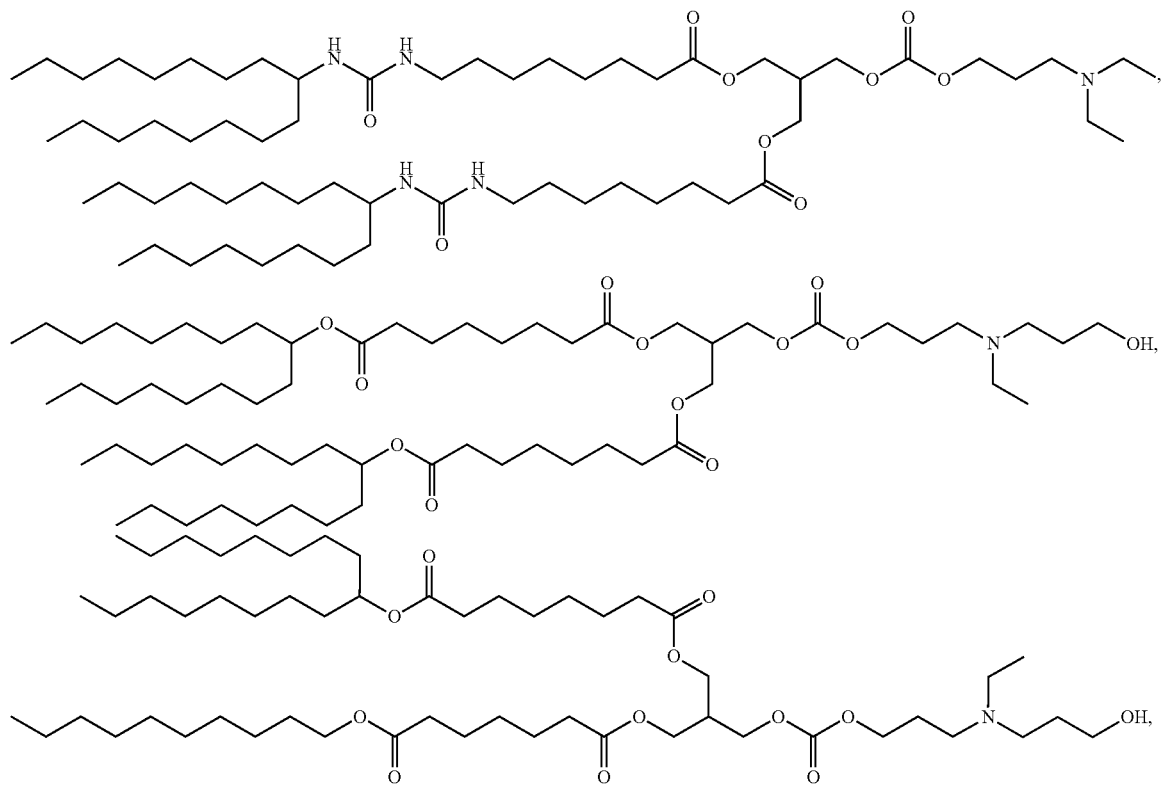

-continued
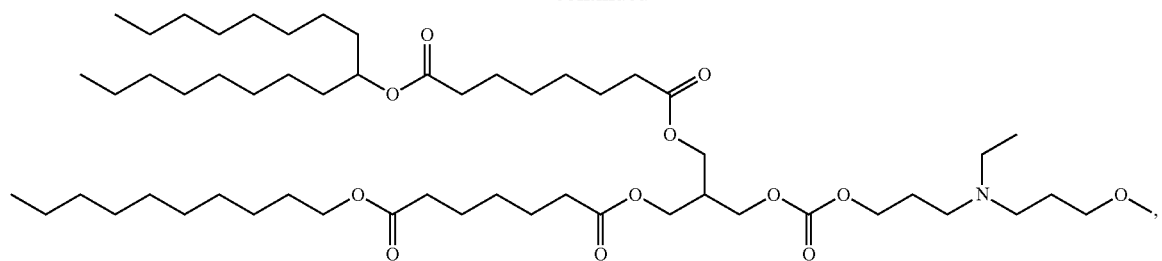
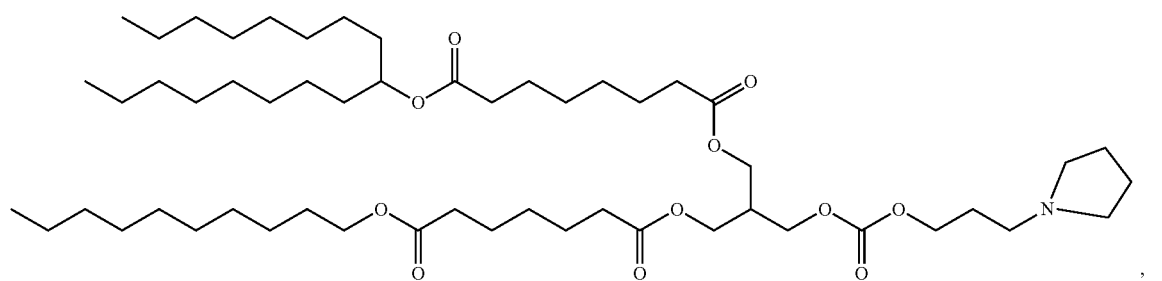
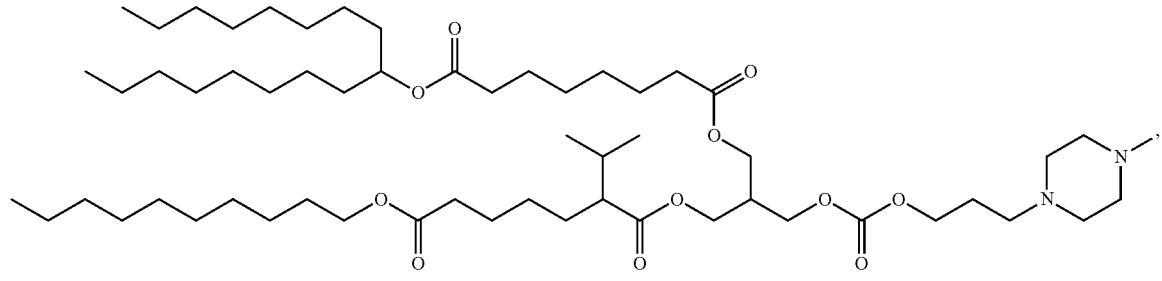
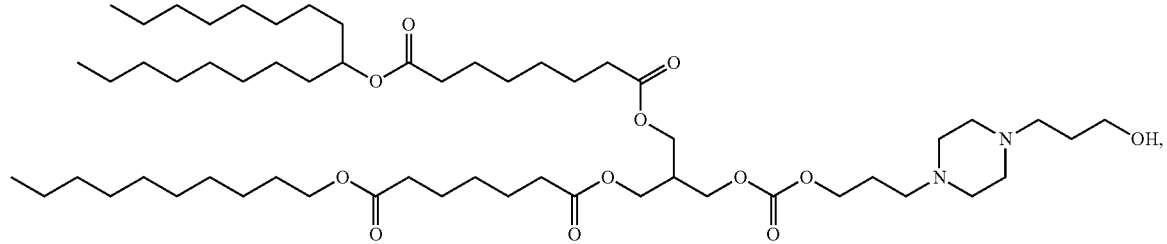
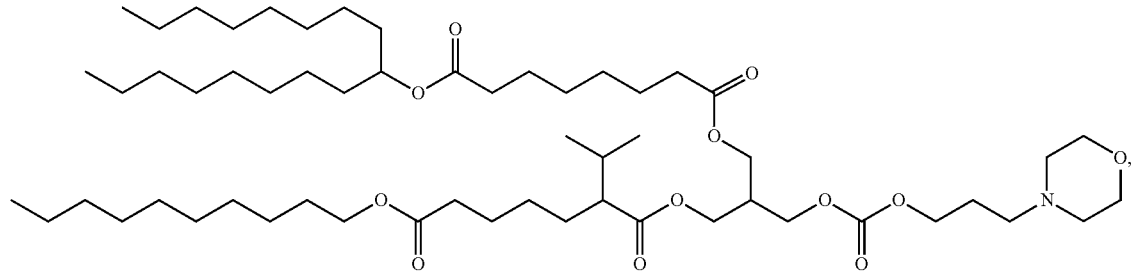
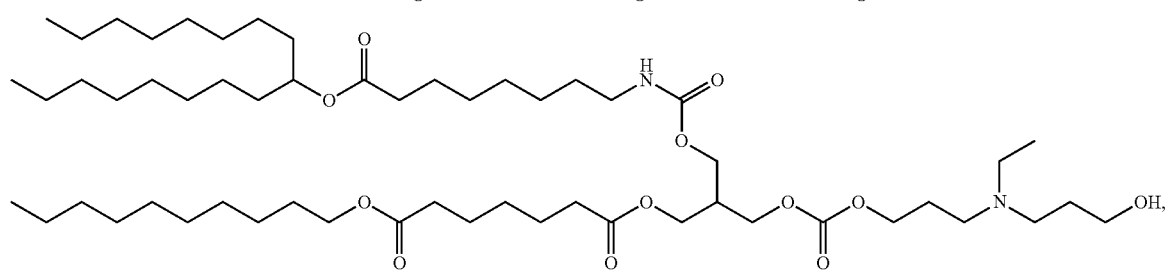

-continued
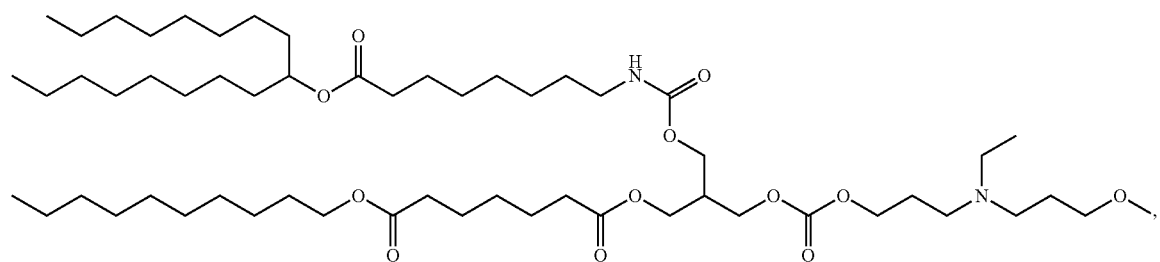
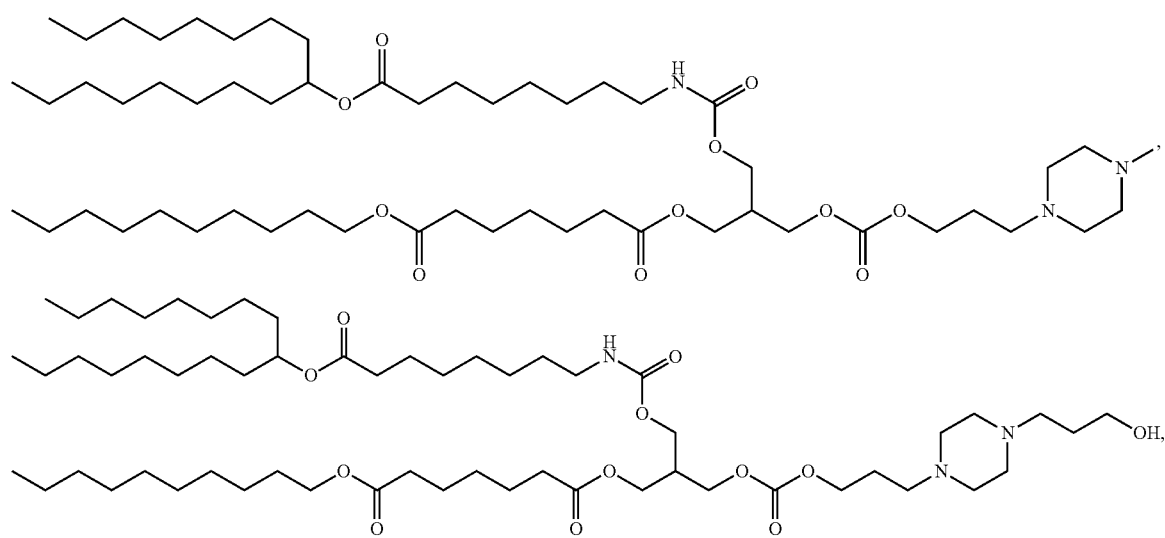
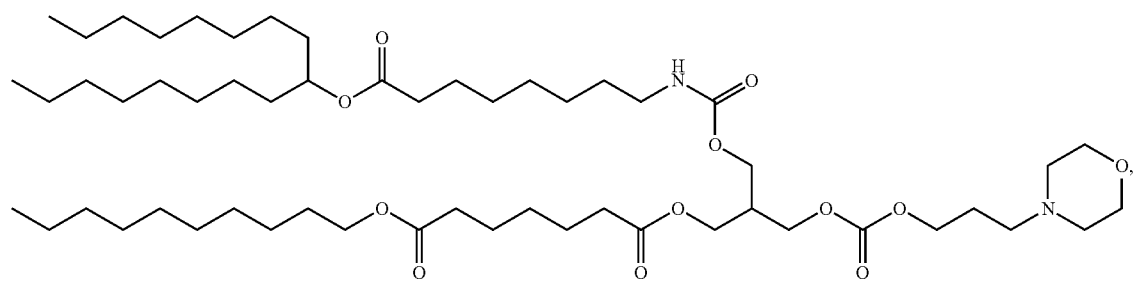
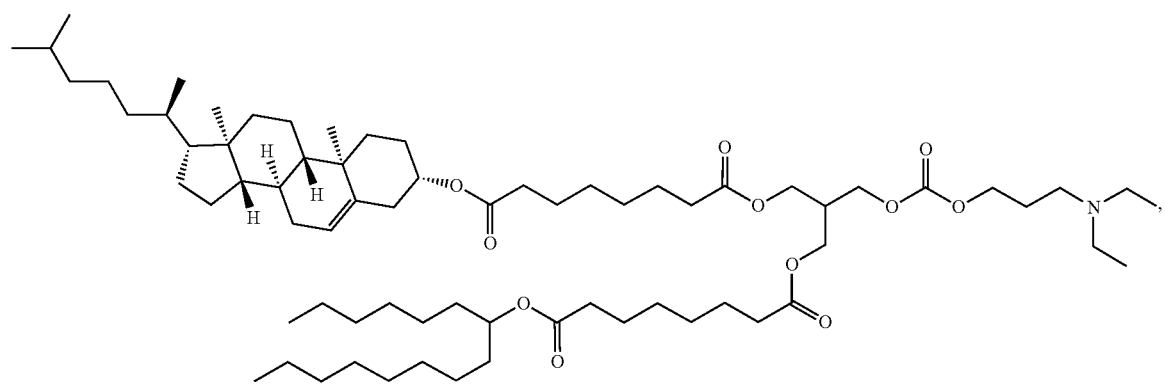

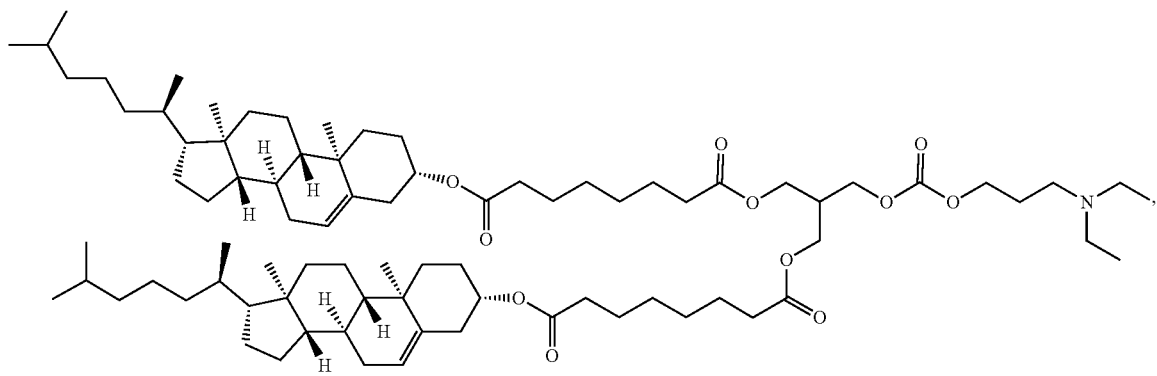
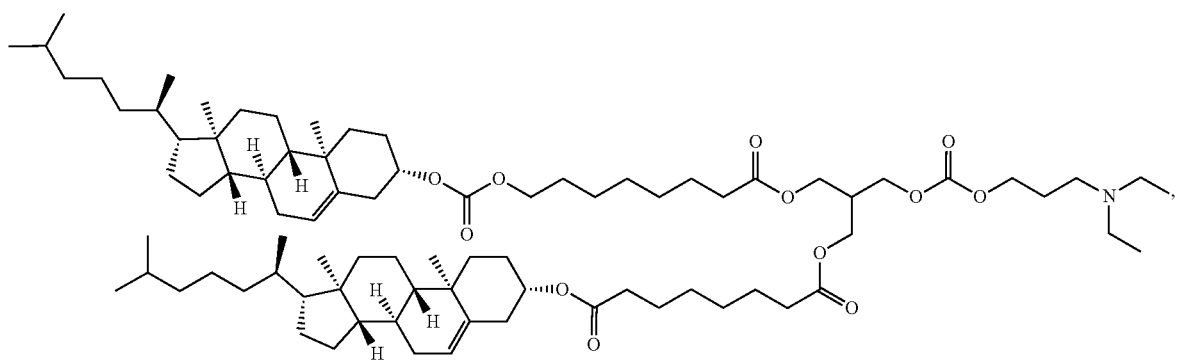
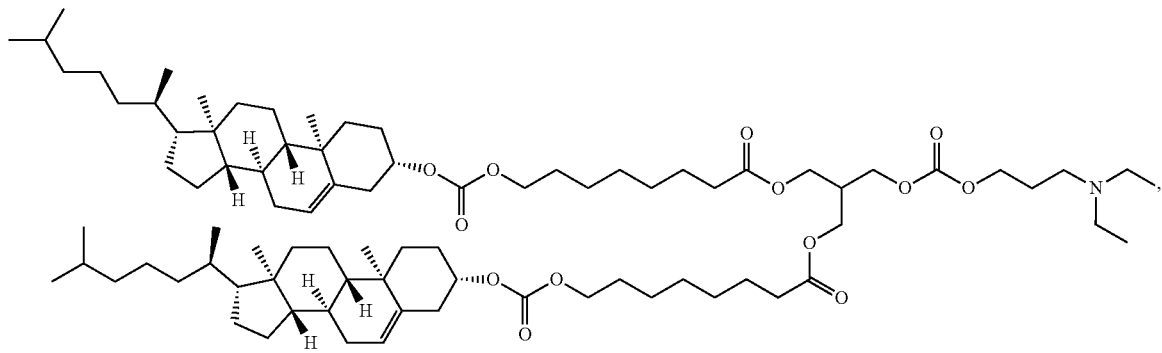
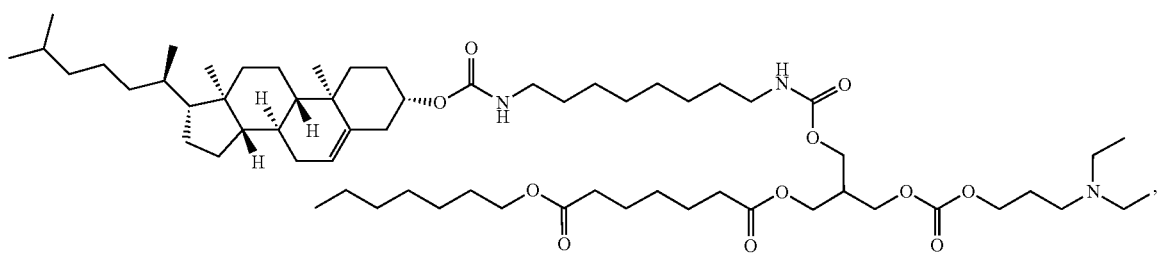
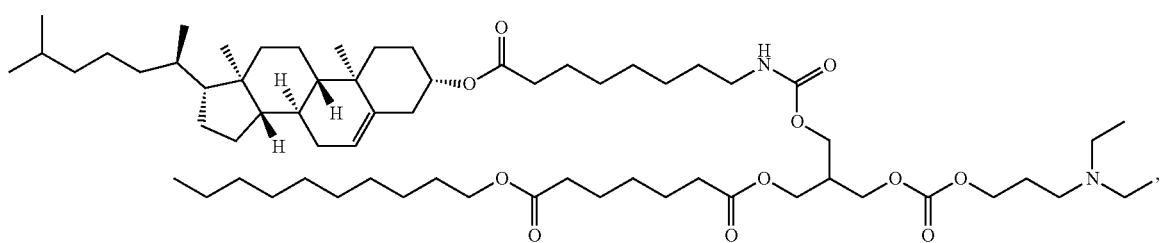

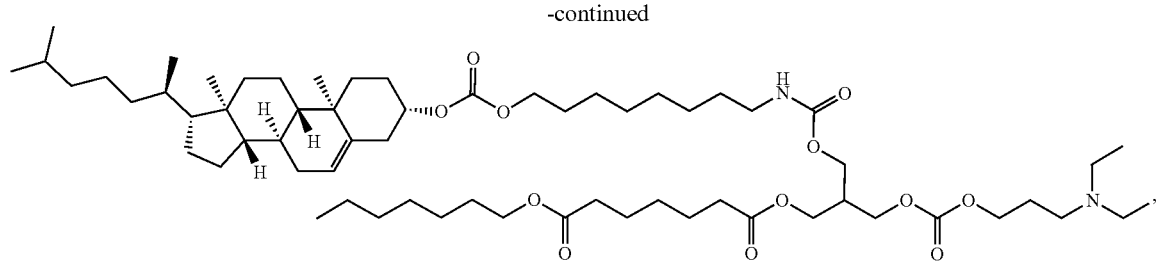,
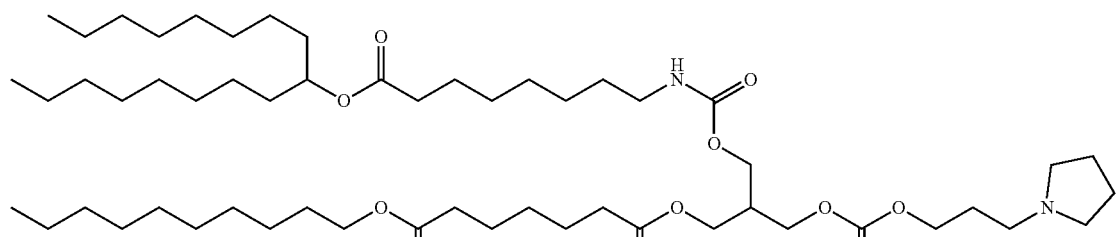,
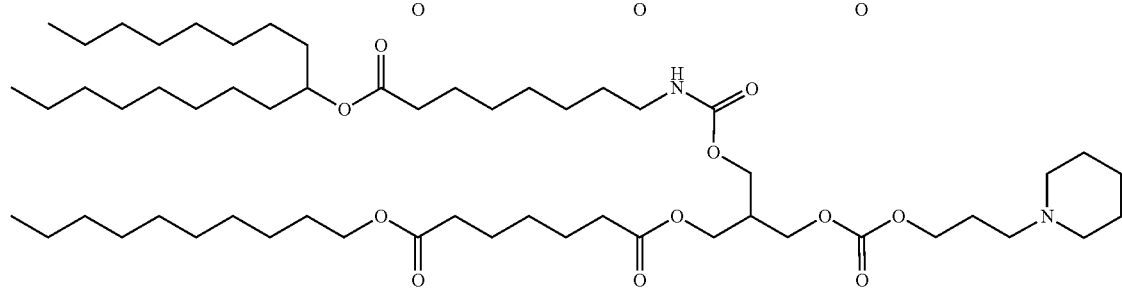,
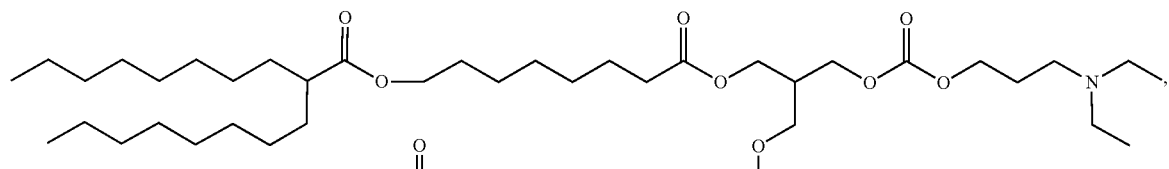,
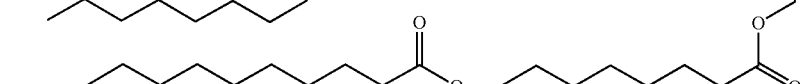
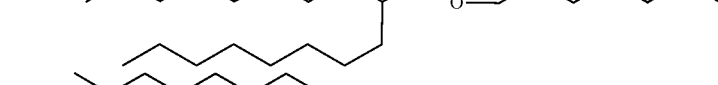
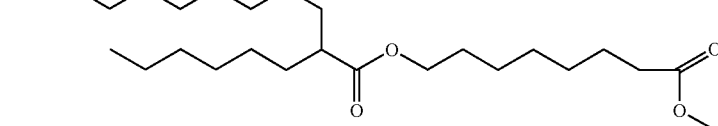,
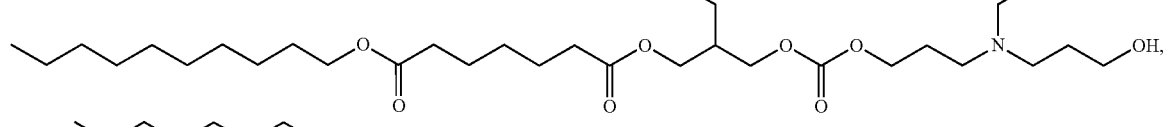
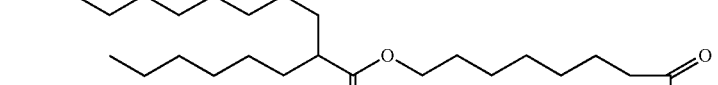
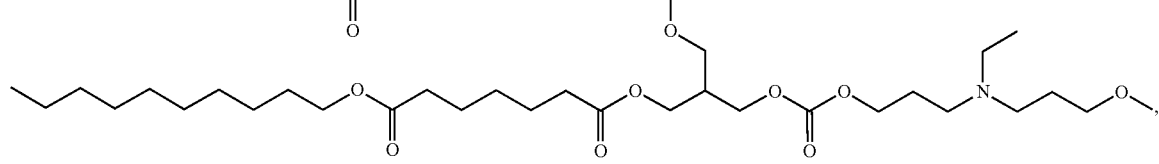, -continued
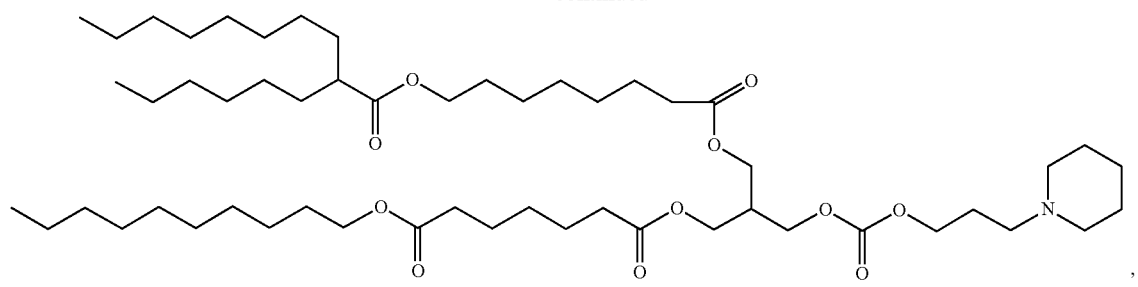
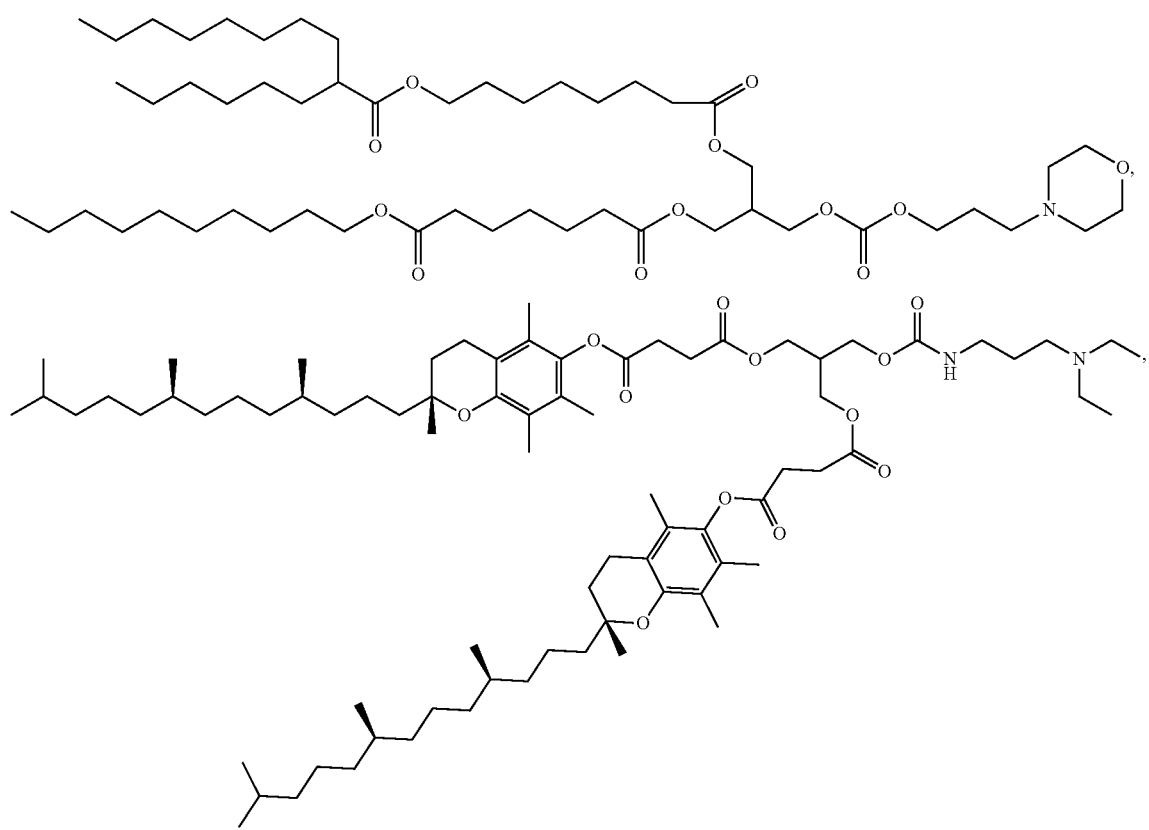
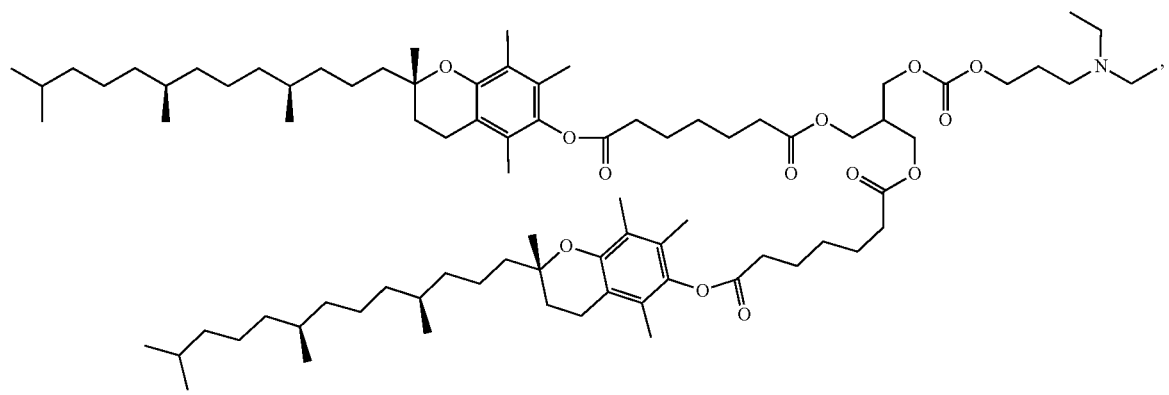

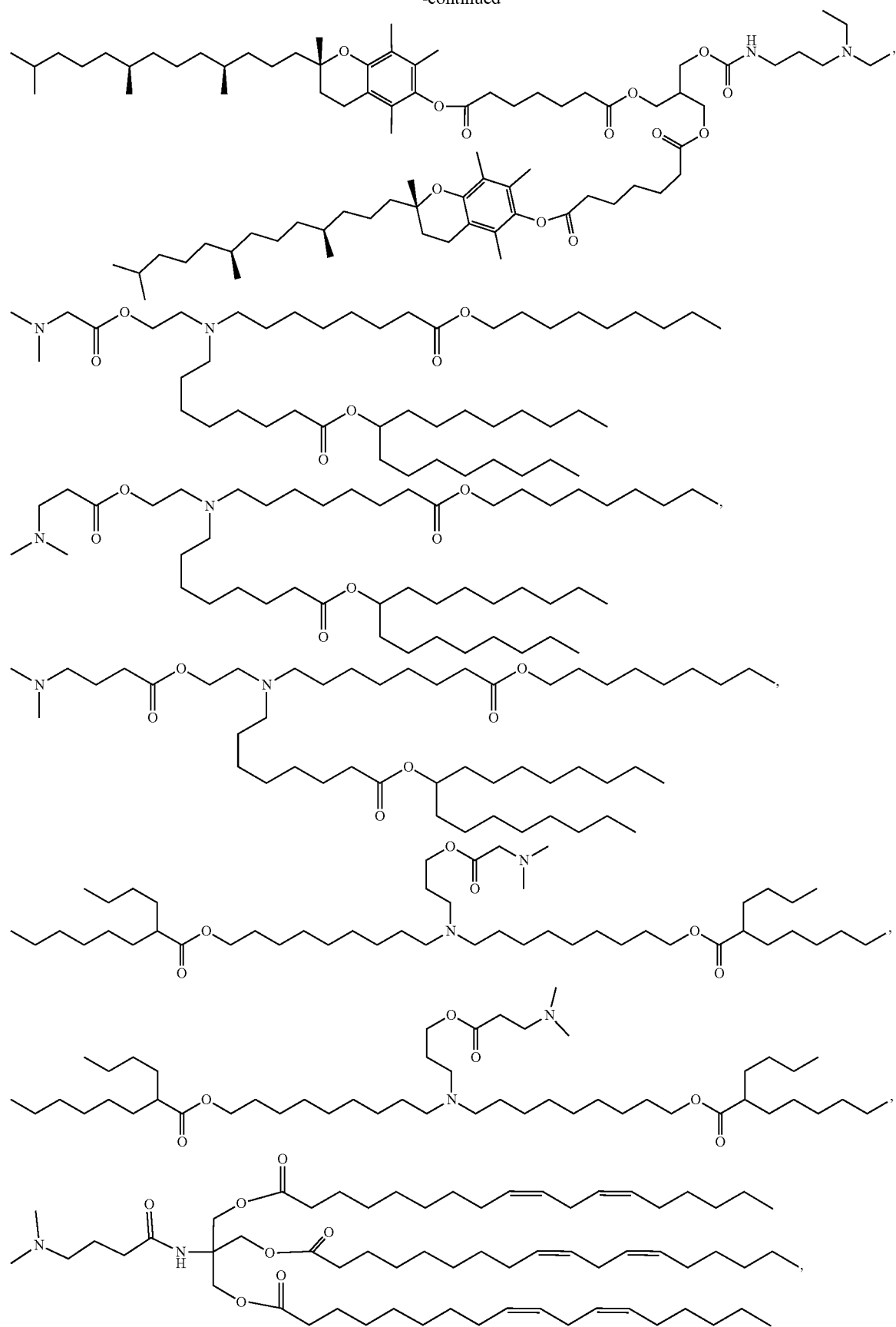

-continued
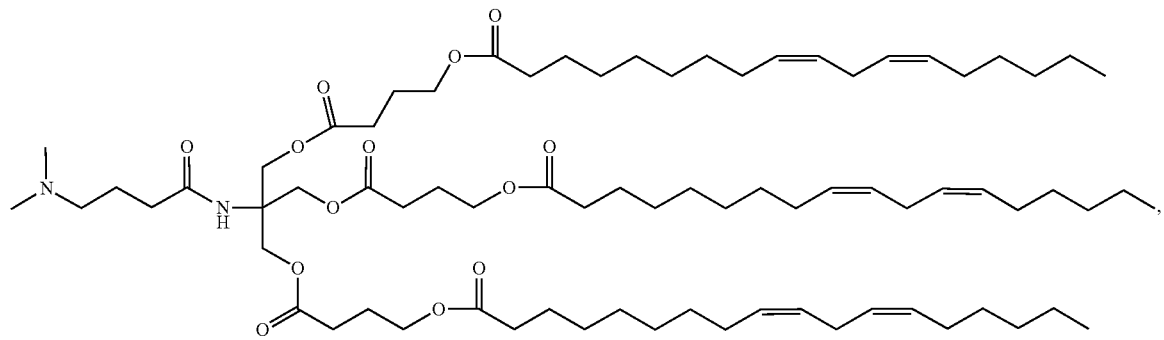
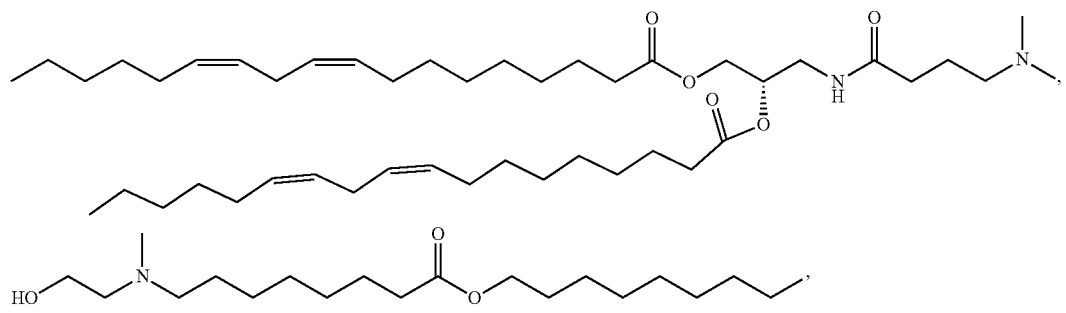
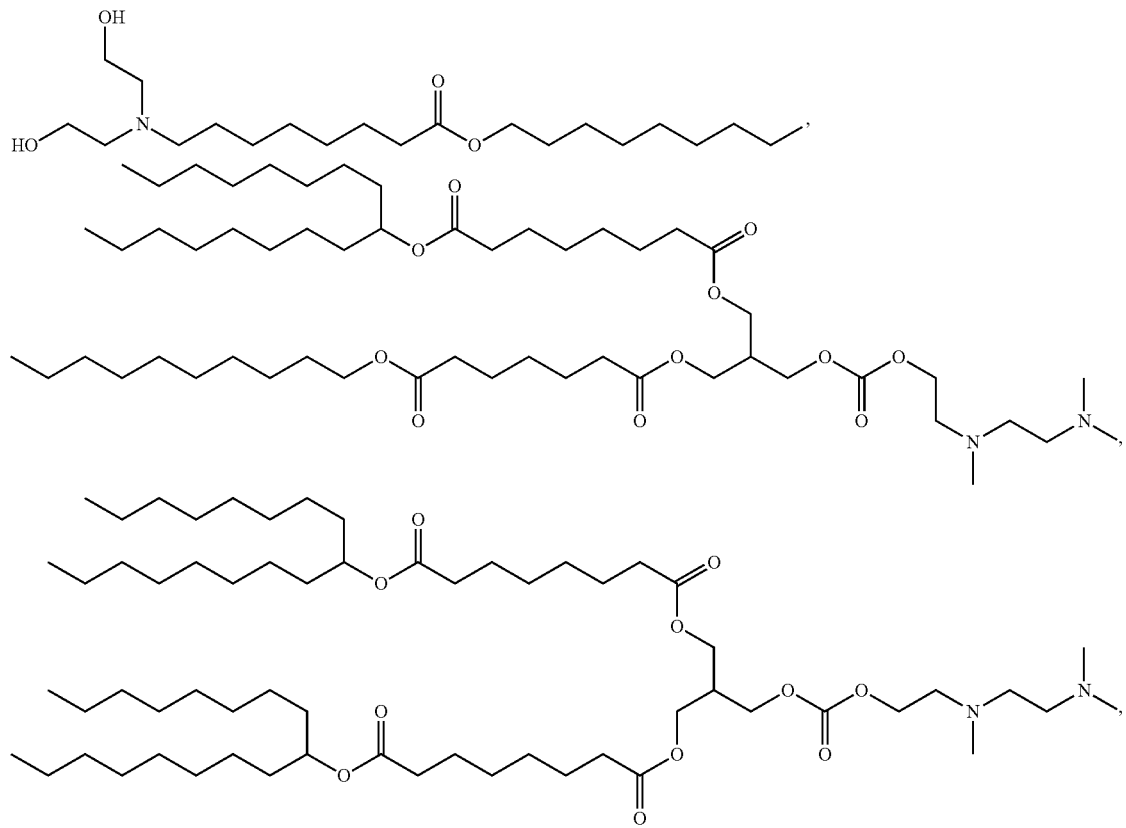

-continued
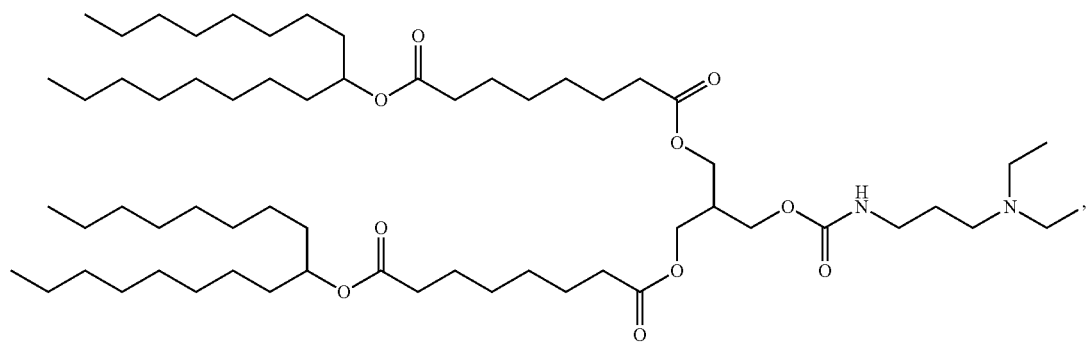
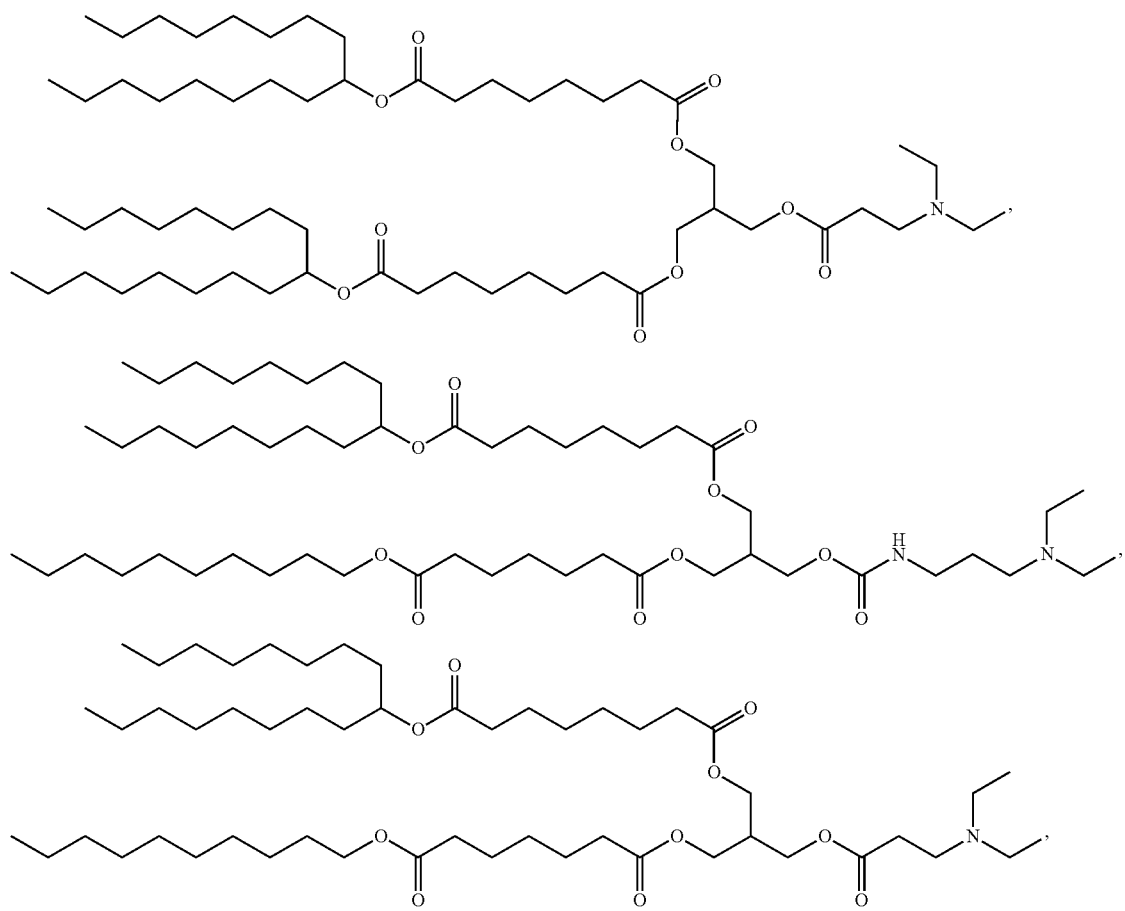
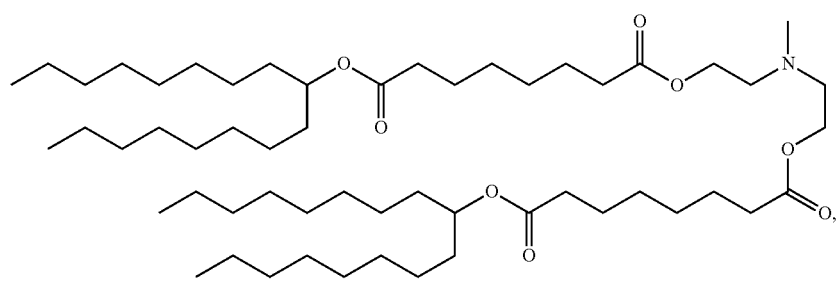

-continued

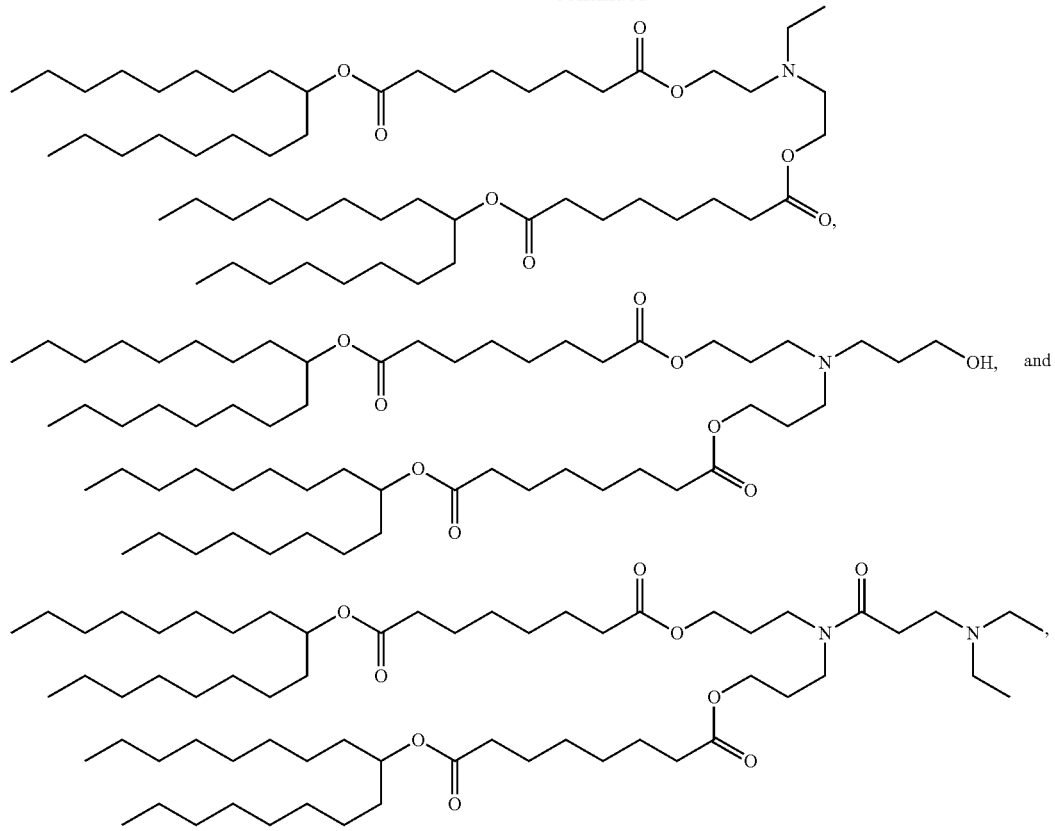

or a pharmaceutically acceptable salt or solvate thereof.

21. A PEG lipid having the structure of Formula (III*), or a pharmaceutically acceptable salt or solvate thereof,

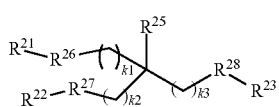

Formula (III*)

wherein
$R^{21}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;
$R^{22}$ is hydrogen, substituted or unsubstituted $C_1$-$C_{30}$ alkyl, substituted or unsubstituted $C_3$-$C_{30}$ alkenyl, or substituted or unsubstituted $C_3$-$C_{30}$ alkynyl;
each of $R^{26}$, $R^{27}$ and $R^{28}$ is independently —C(=O)NR$^4$—, —NR$^4$C(=O)—, —C(=O)O—, —OC(=O)—, —OC(=O)O—, —NR$^4$C(=O)O—, —OC(=O)NR$^4$—, —NR$^4$C(=O)NR$^4$—, —NR$^4$C(=NR$^4$)NR$^4$—, —C(=S)NR$^4$—, —NR$^4$C(=S)—, —C(=S)O—, —OC(=S)—, —OC(=S)O—, —NR$^4$C(=S)O—, —OC(=S)NR$^4$—, —NR$^4$C(=S)NR$^4$—, —C(=O)S—, —SC(=O)—, —OC(=O)S—, —NR$^4$C(=O)S—, —N(Ac)—, —OC(O)OCH$_2$C(O)O—, —OC(O)OCH$_2$C(O)NH—, —OC(O)NHCH$_2$C(O)O—, —OC(O)NHCH$_2$C(O)NH—, —OC(O)(CH$_2$)$_2$C(O)O—, —OC(O)O(CH$_2$)$_2$C(O)NH—, —OC(O)NH(CH$_2$)$_2$C(O)O—, —OC(O)NH(CH$_2$)$_2$C(O)NH—, —OC(O)O(CH$_2$)$_3$C(O)O—, —OC(O)O(CH$_2$)$_3$C(O)NH—, —OC(O)NH(CH$_2$)$_3$C(O)O—, —OC(O)NH(CH$_2$)$_3$C(O)NH—, —C(O)OCH$_2$C(O)NH—, —C(O)NHCH$_2$C(O)O—, —C(O)NHCH$_2$C(O)NH—, —C(O)O(CH$_2$)$_2$C(O)O—, —C(O)O(CH$_2$)$_2$C(O)NH—, —C(O)NH(CH$_2$)$_2$C(O)NH—, —C(O)O(CH$_2$)$_3$C(O)O—, —C(O)NH(CH$_2$)$_2$C(O)O—, —C(O)O(CH$_2$)$_3$C(O)NH—, —C(O)NH(CH$_2$)$_3$C(O)O—, —C(O)NH(CH$_2$)$_3$C(O)NH—, —OC(=O)NR$^4$(CH$_2$)$_{1-3}$C(=O)NH—, —OC(=O)NR$^4$(CH$_2$)$_{1-3}$C(=O)O—, —C(=O)NR$^4$(CH$_2$)$_{1-3}$C(=O)NH—, —SC(=O)NR$^4$—, —C(=S)S—, —SC(=S)—, —SC(=S)O—, —SC(=O)S—, —SC(=S)S—, —NR$^4$C(=S)S—, —SC(=S)NR$^4$—, —O(CH$_2$)$_2$C(O)O—, —O(CH$_2$)$_2$C(O)NH—, —OC(O)(CH$_2$)$_2$O—, —OC(O)(CH$_2$)$_2$NH—, —O(CH$_2$)$_2$C(O)N(CH$_3$)—, —O(CH$_2$)$_2$C(NH)O—, —O(CH$_2$)$_2$C(NAc)NH—, —O(CH$_2$)$_2$C(NH)N(CH$_3$)—, —O(CH$_2$)$_2$C(NH)NH—, —O(CH$_2$)$_2$C(NH)N(CH$_3$)—, —NH(CH$_2$)$_2$C(O)O—, —NH(CH$_2$)$_2$C(O)NH—, —NH(CH$_2$)$_2$C(O)N(CH$_3$)—, —NH(CH$_2$)$_2$C(NH)O—, —NH(CH$_2$)$_2$C(NAc)NH—, —NH(CH$_2$)$_2$C(NH)N(CH$_3$)—, —NH(CH$_2$)$_2$C(NH)NH—, —OC(O)(CH$_2$)$_2$N(CH$_3$)—, —OC(NH)(CH$_2$)$_2$O—, —OC(NMe)(CH$_2$)$_2$NH—, —O$_2$C(NH)(CH$_2$)N(CH$_3$)—, —O—, —S—, or a bond;
each of $R^4$ is independently hydrogen or substituted or unsubstituted $C_1$-$C_6$ alkyl;
$R^{23}$ is —C$_0$-$C_{10}$ alkylene-(CH$_2$—CH$_2$—O)$_{k4}$—R$^{24}$, —C$_1$-$C_{10}$ heteroalkylene-(CH$_2$—CH$_2$—O)$_{k4}$—R$^{24}$, —C$_0$-$C_{10}$ alkylene-(O—CH$_2$—CH$_2$)$_{k4}$—R$^{24}$ or —C$_1$-$C_{10}$ heteroalkylene-(O—CH$_2$—CH$_2$)$_{k4}$—R$^{24}$, wherein the alkylene and heteroalkylene are each independently substituted or unsubstituted;

$R^{24}$ is independently hydrogen, substituted or unsubstituted $C_1$-$C_3$ alkyl, —O—$R^4$, —C(=O)O$R^4$, or —C(=O)$R^4$;

$R^{25}$ is hydrogen or substituted or unsubstituted $C_1$-$C_{22}$ alkyl;

each of k1, k2, and k3 is independently 0, 1, 2, 3, 4, or 5; and k4 is an integer selected from 1 to 100.

22. The PEG lipid of claim 21, wherein $R^{28}$ is —O(CH$_2$)$_2$C(O)O—, —O(CH$_2$)$_2$C(O)NH—, —O—, —C(=O)O—, or —OC(=O)—.

23. The PEG lipid of claim 21, wherein k1 is 0, k2 is 1, and k3 is 1.

24. The PEG lipid of claim 21, wherein $R^{23}$ is —C$_0$-C$_3$ alkylene-(CH$_2$—CH$_2$—O)$_{k4}$—$R^{24}$, wherein $R^{24}$ is H or methyl.

25. The PEG lipid of claim 21, wherein k4 is 1 to 50.

26. The PEG lipid of claim 21, wherein $R^{25}$ is hydrogen.

27. The PEG lipid of claim 21, wherein the PEG lipid has a structure selected from the following structures:

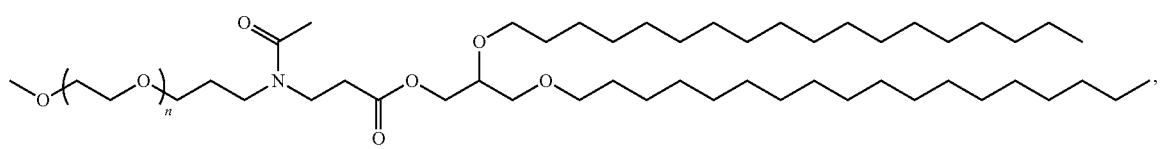

wherein n is 25 to 50;

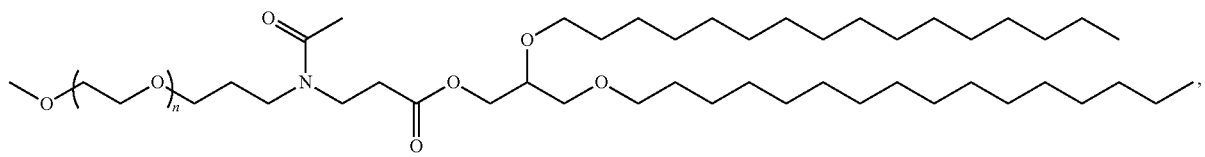

wherein n is 25 to 50;

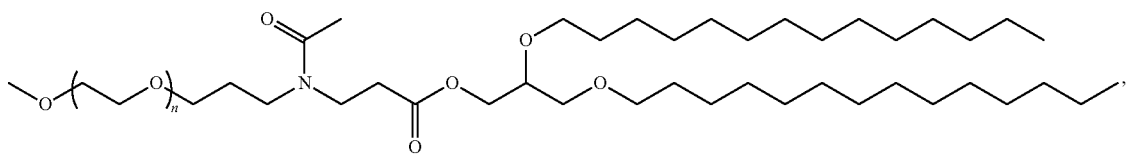

wherein n is 25 to 50;

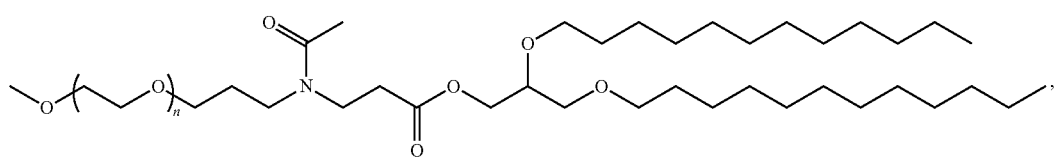

wherein n is 25 to 50;

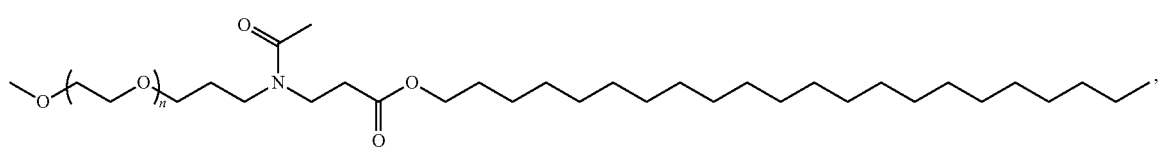

wherein n is 25 to 50;
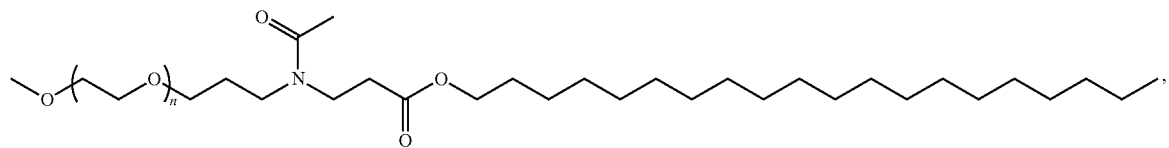
wherein n is 25 to 50;
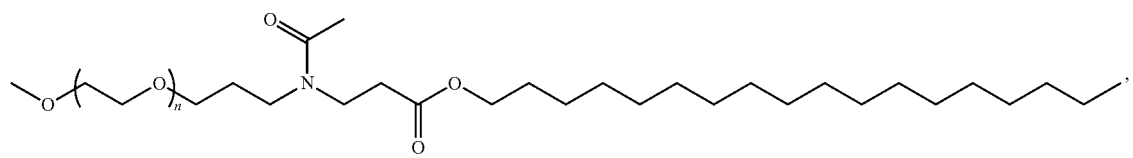
wherein n is 25 to 50;
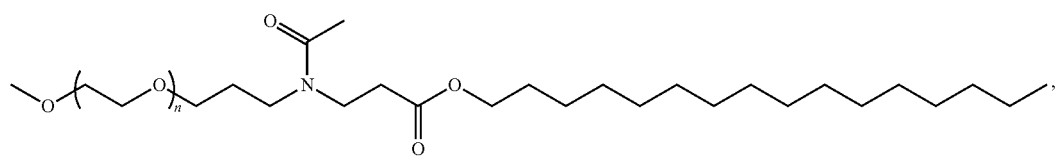
wherein n is 25 to 50;
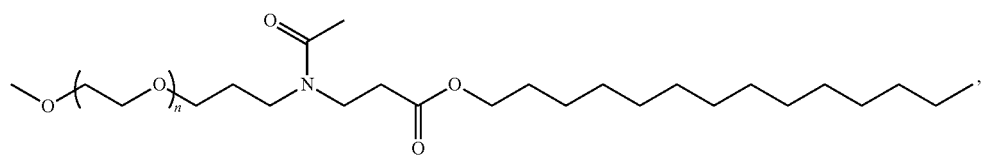
wherein n is from 36 to 48;
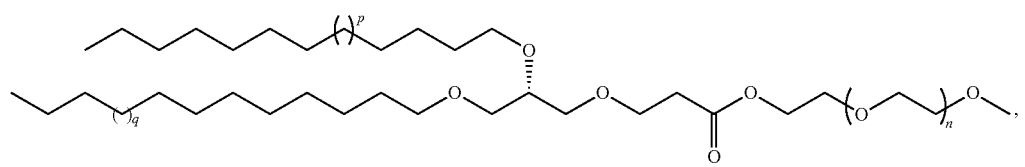
55
wherein p is 7, q is 7, and n is 25 to 50;
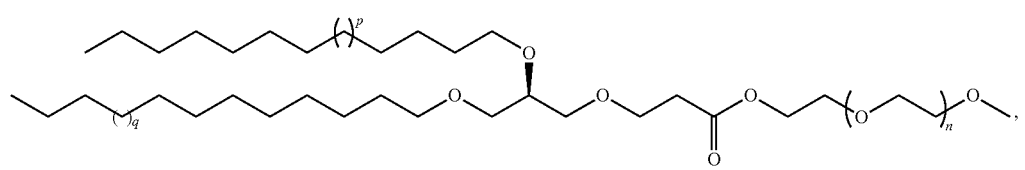

wherein p is 7 and q is 7, and n is 25 to 50;
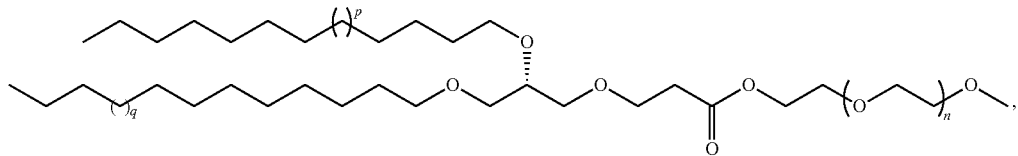
wherein p is 5 and q is 5, and n is 25 to 50;
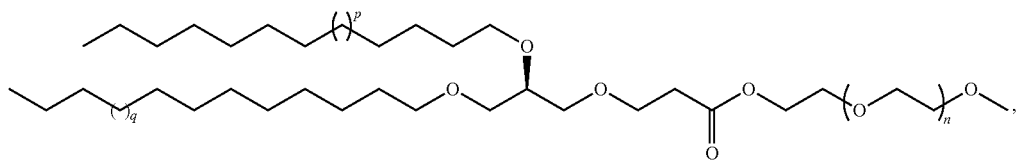
wherein p is 5 and q is 5, and n is 25 to 50;
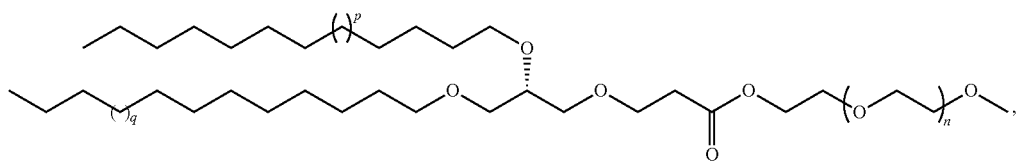
wherein p is 3 and q is 3, and n is 25 to 50;
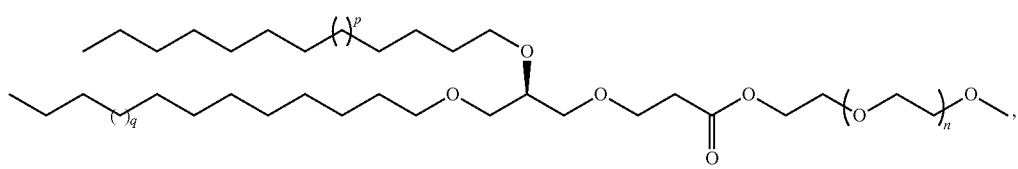
wherein p is 3 and q is 3, and n is 25 to 50;
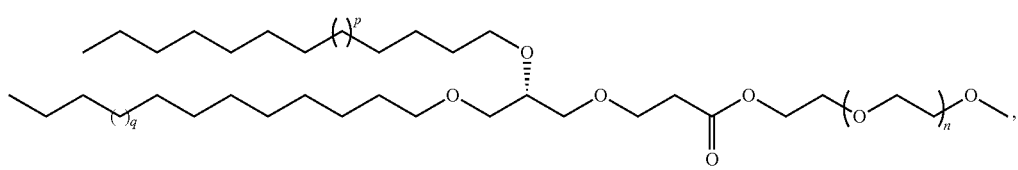
wherein p is 1 and q is 1, and n is 25 to 50;
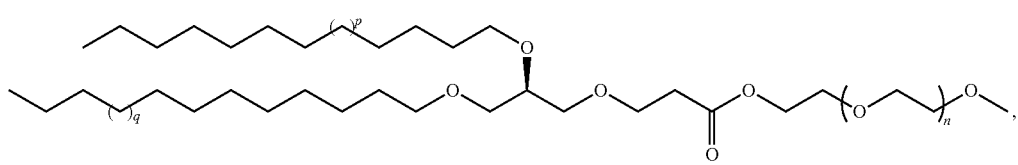

wherein p is 1 and q is 1, and n is 25 to 50;
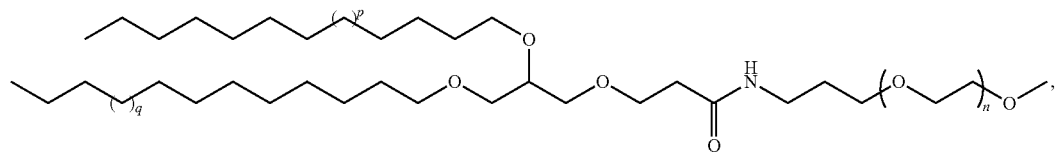
wherein p is 7 and q is 7, and n is 25 to 50;
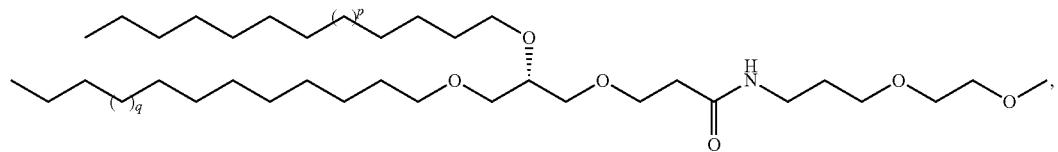
wherein p is 7 and q is 7;
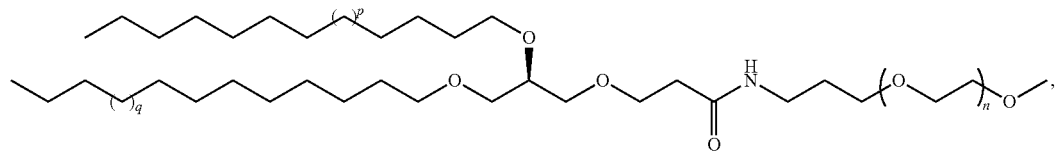
wherein p is 7 and q is 7, and n is 25 to 50;
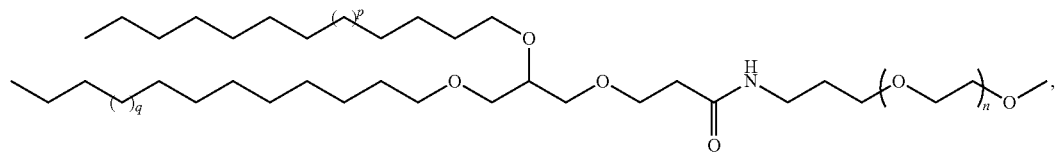
wherein p is 5 and q is 5, and n is 25 to 50;
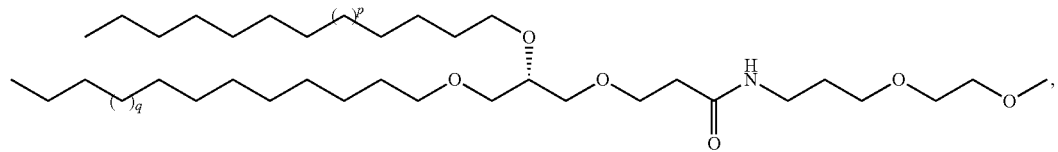
wherein p is 5 and q is 5;
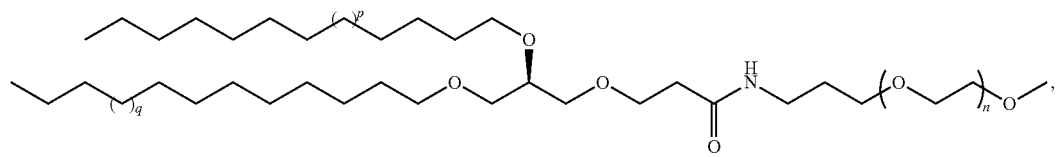

wherein p is 5 and q is 5, and n is 25 to 50;
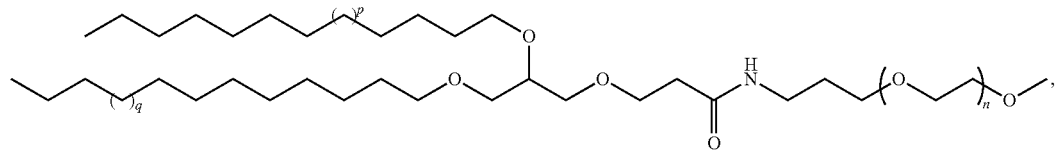
wherein p is 3 and q is 3, and n is 25 to 50;
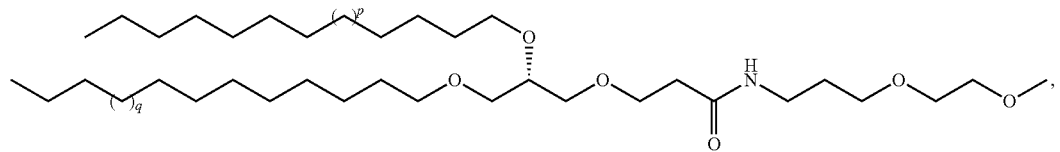
wherein p is 3 and q is 3;
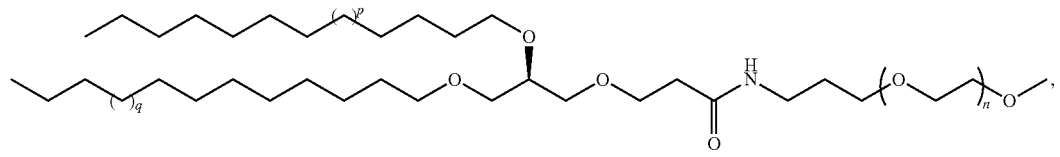
wherein p is 3 and q is 3, and n is 25 to 50;
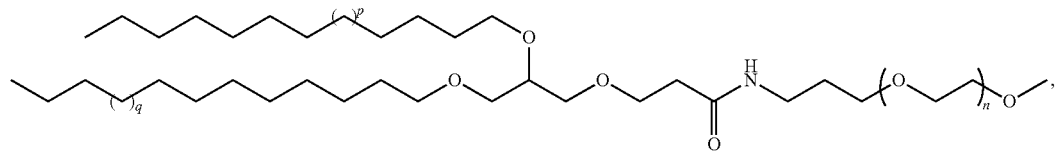
wherein p is 1 and q is 1, and n is 25 to 50;
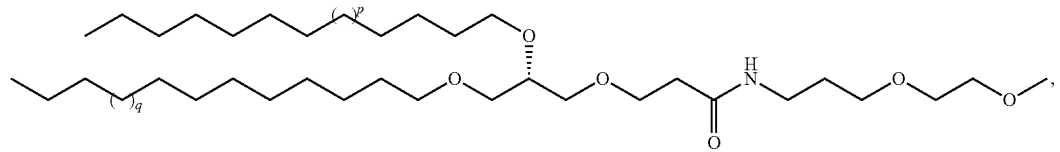
wherein p is 1 and q is 1;
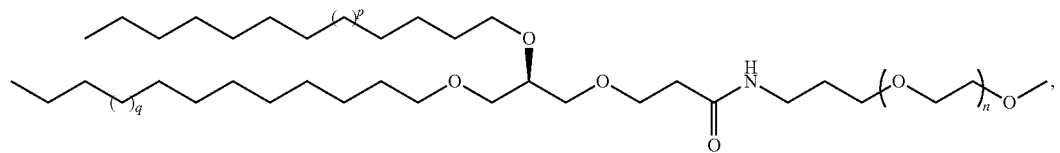

wherein p is 1 and q is 1, and n is 25 to 50;
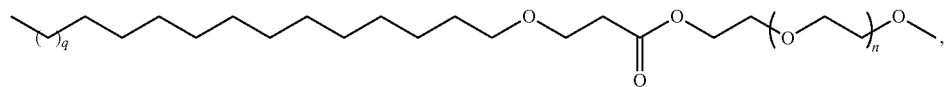
wherein q is 9, and n is 25 to 50;
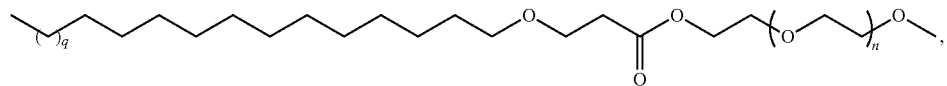
wherein q is 7, and n is 25 to 50;
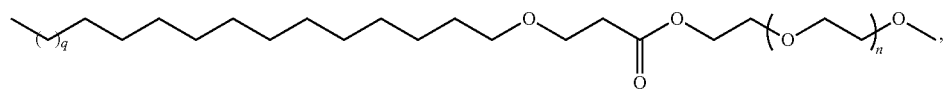
wherein q is 5, and n is 25 to 50;
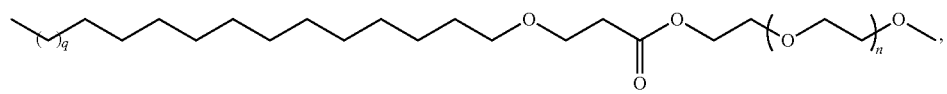
wherein q is 3, and n is 25 to 50;
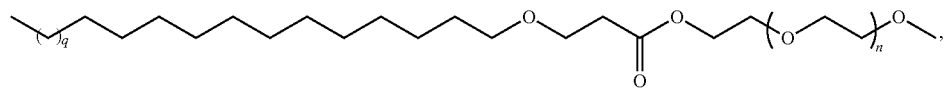
wherein q is 1, and n is 25 to 50;
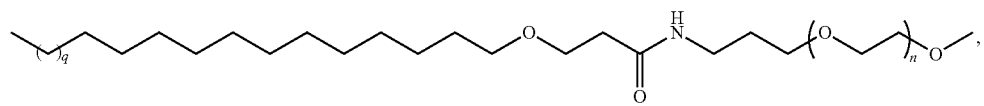
wherein q is 9, and n is 25 to 50;
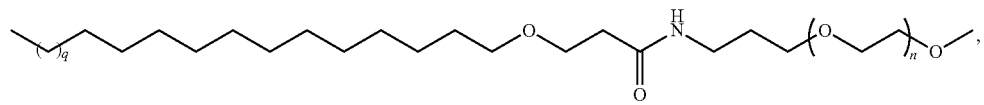
wherein q is 7, and n is 25 to 50;
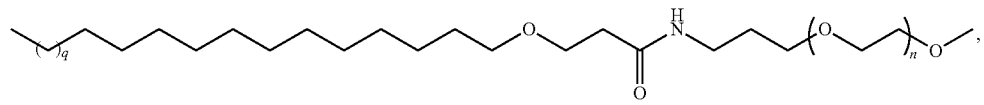

bwherein q is 5, and n is 25 to 50;
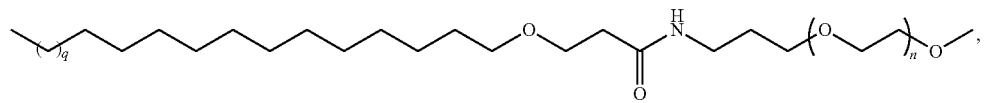
wherein q is 3, and n is 25 to 50;
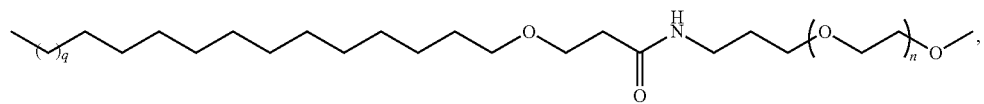
wherein q is 1, and n is 25 to 50;
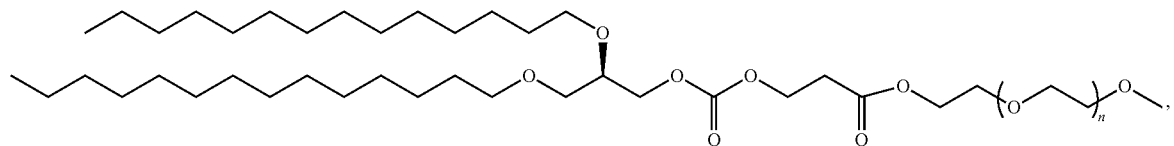
wherein n is from 36 to 48;
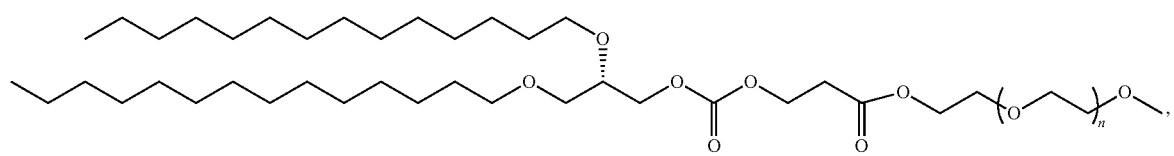
wherein n is from 36 to 48;
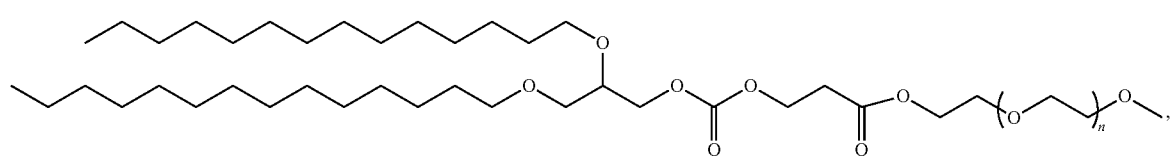
wherein n is from 36 to 48;
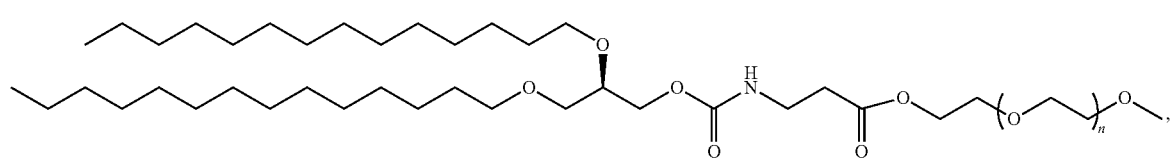

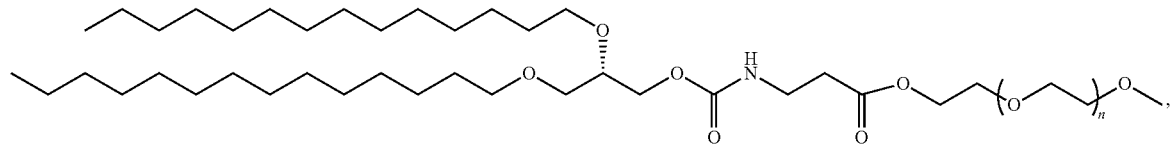
wherein n is from 36 to 48;
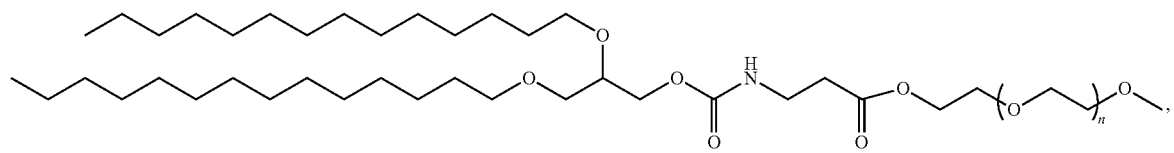
wherein n is from 36 to 48;
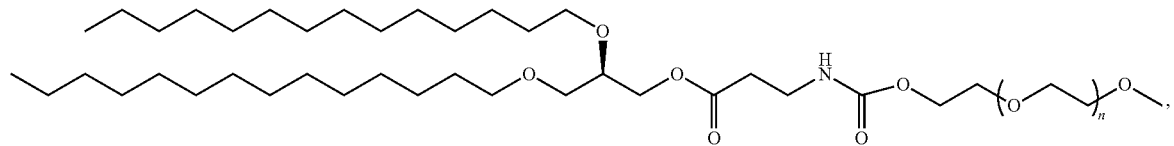
wherein n is from 36 to 48;
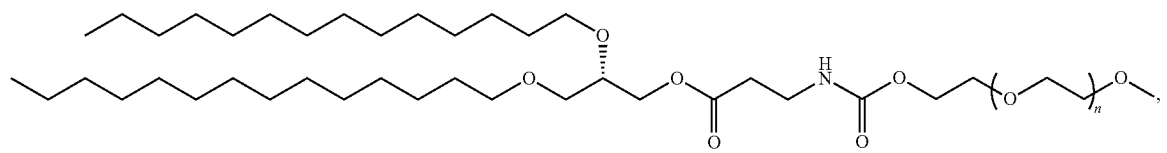
wherein n is from 36 to 48;
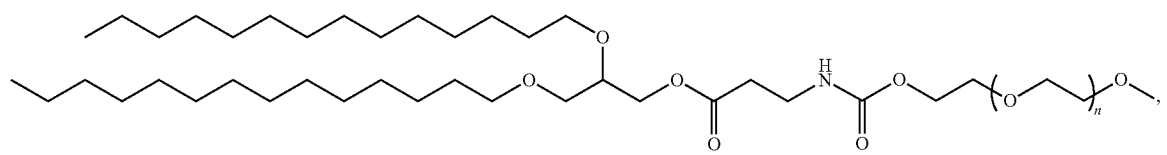

wherein n is from 36 to 48;
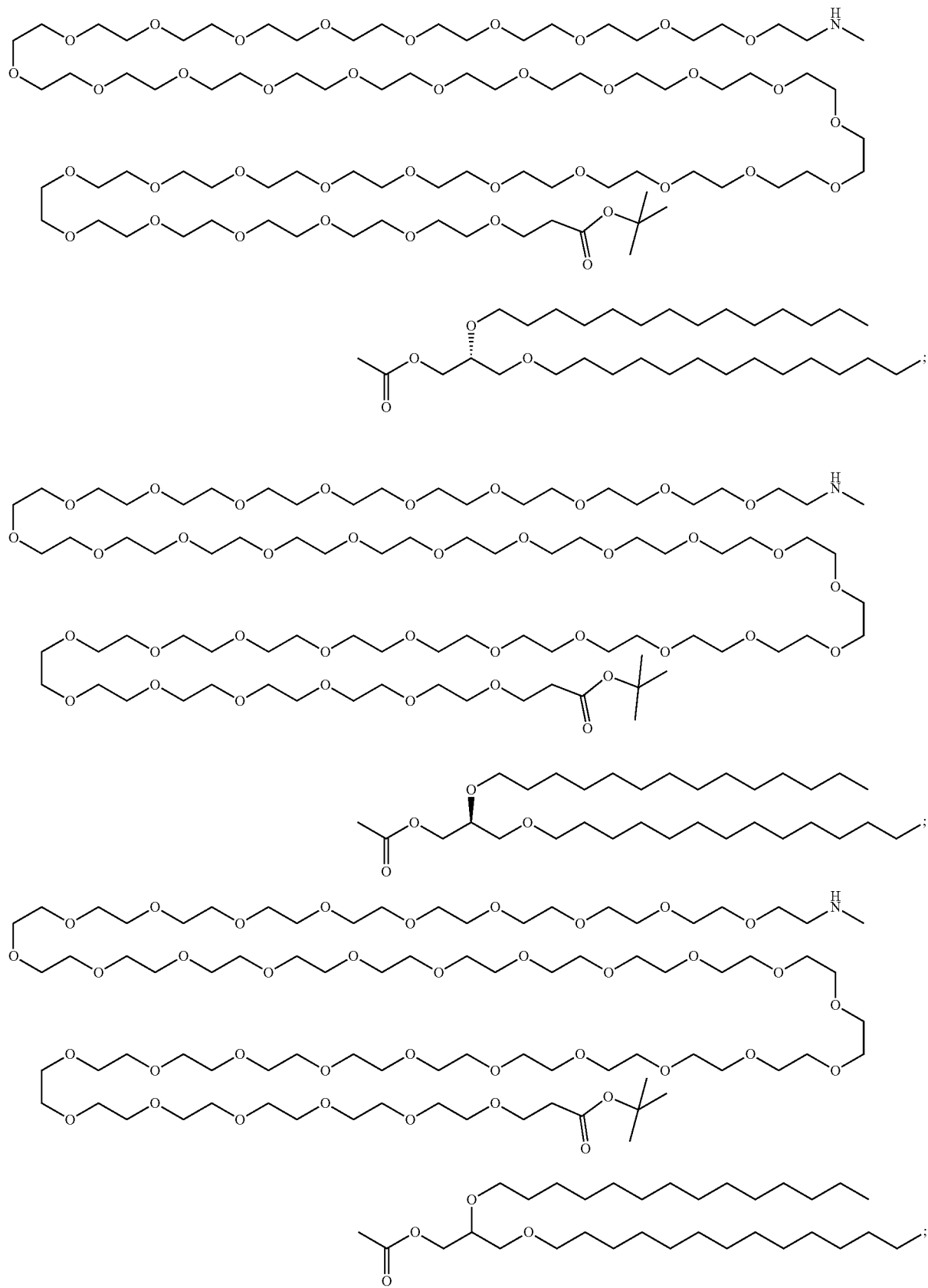

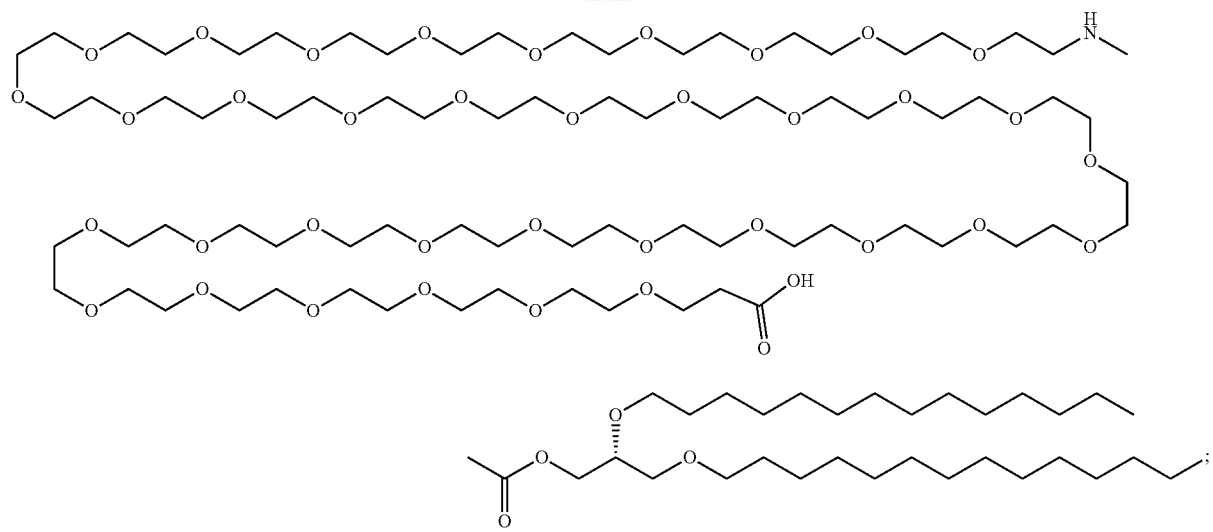
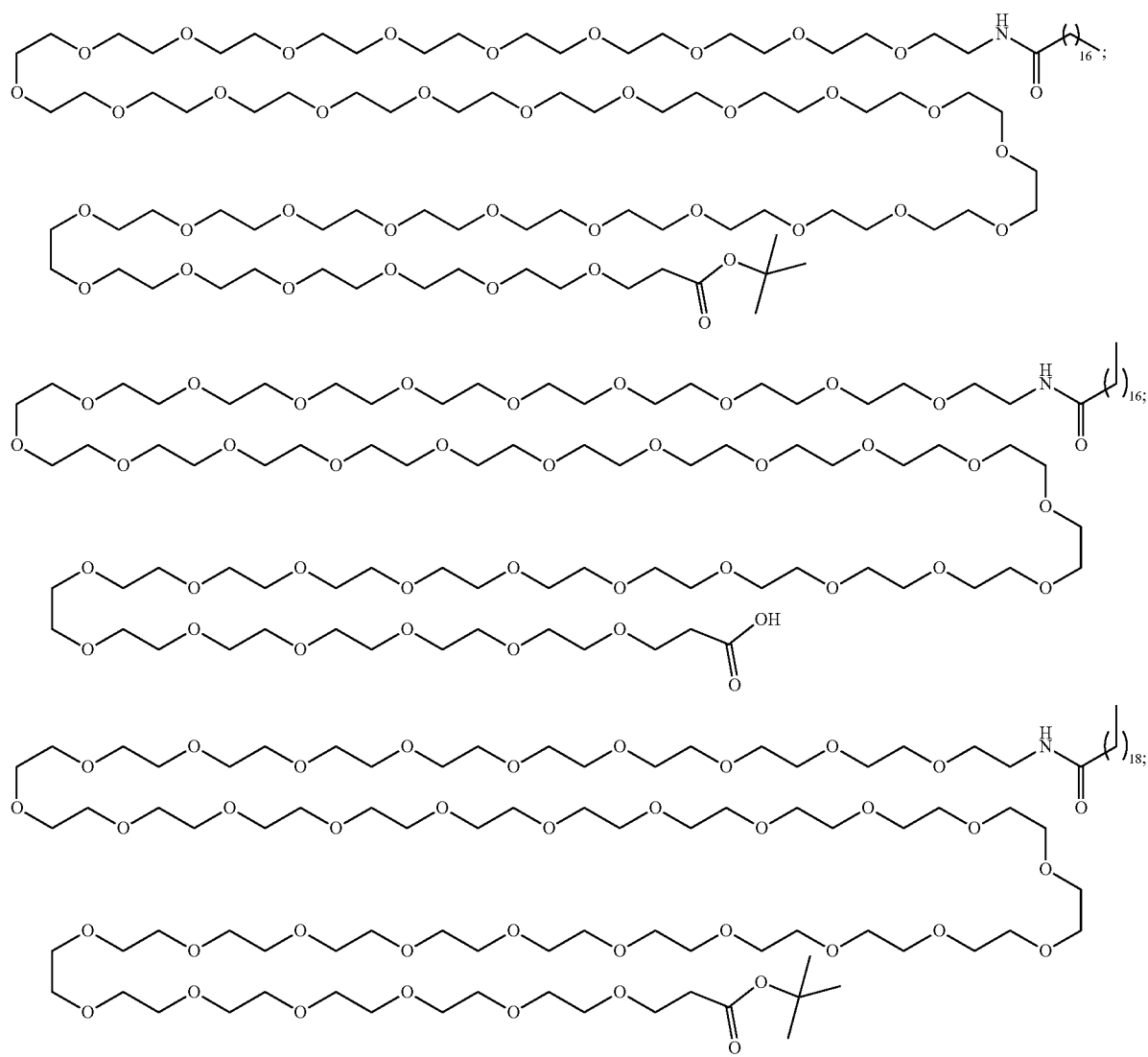

-continued
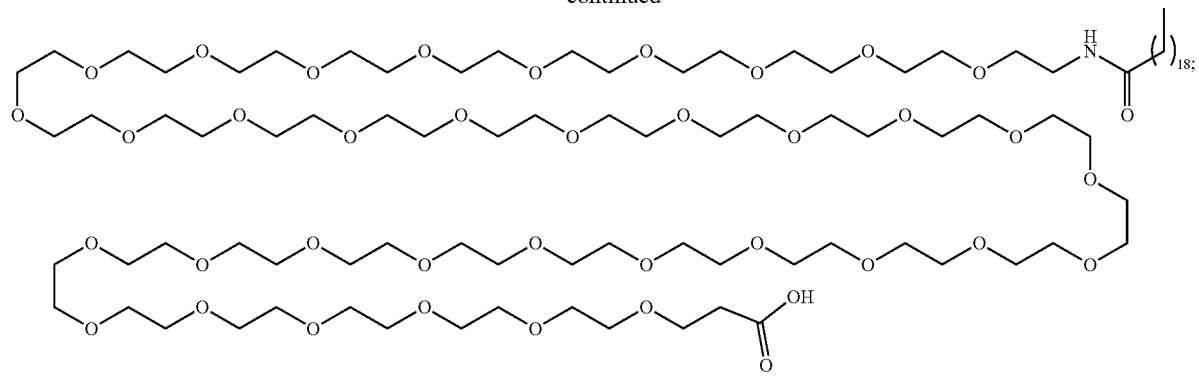
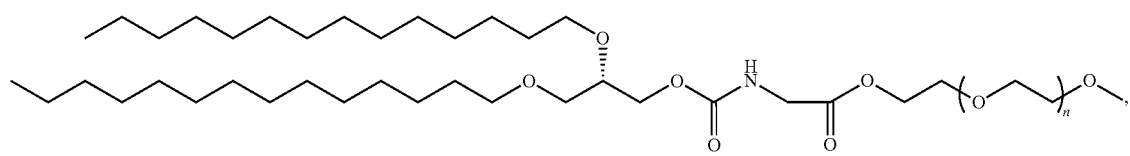
wherein n is from 36 to 48;
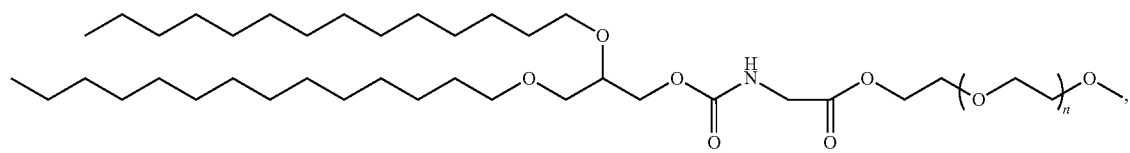
wherein n is from 36 to 48;
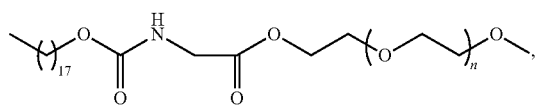
wherein n is from 36 to 48;
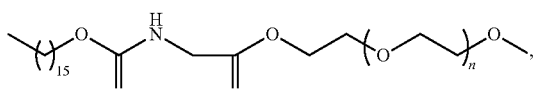
wherein n is from 36 to 48;
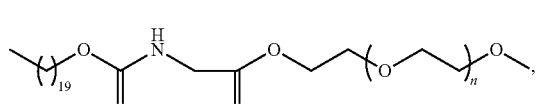
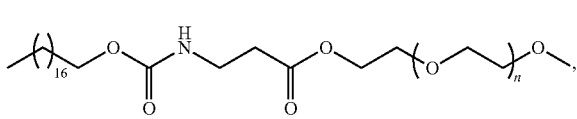

wherein n is from 36 to 48;
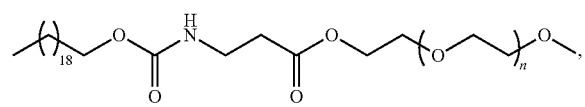
wherein n is from 36 to 48;
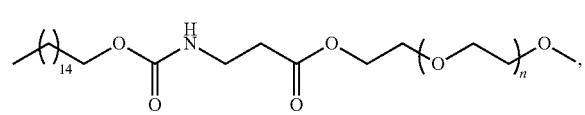
wherein n is from 32 to 48;
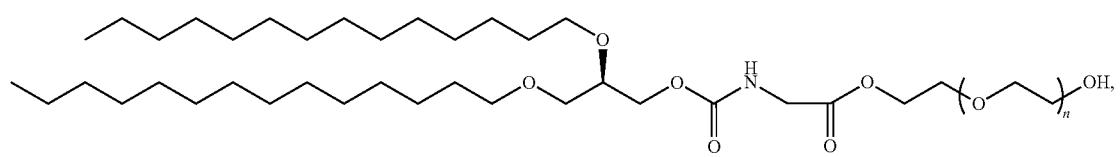
wherein n is from 36 to 48;
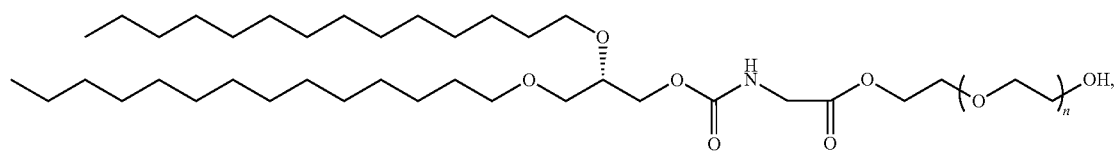
wherein n is from 36 to 48;
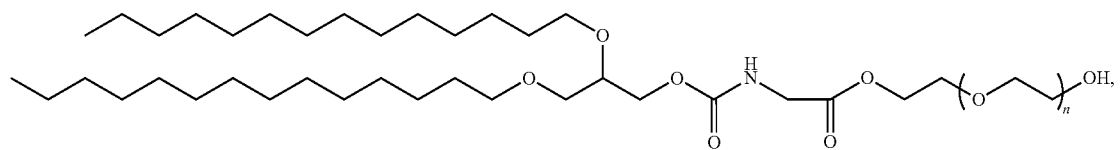
wherein n is from 36 to 48;
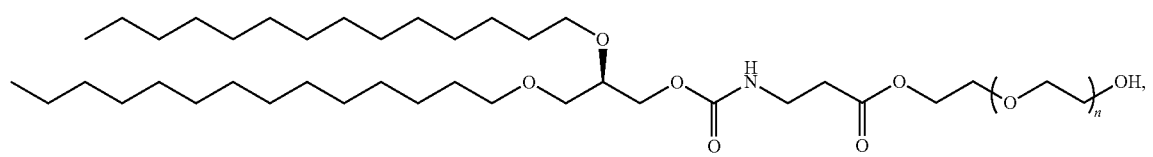
wherein n is from 32 to 48;
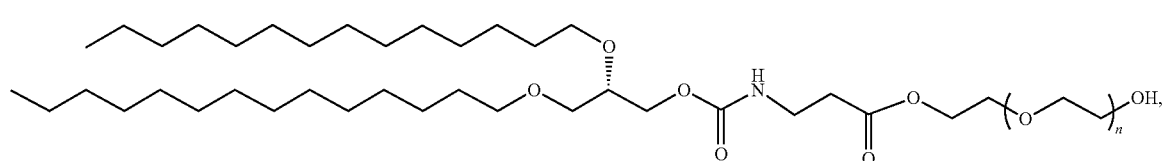

wherein n is from 36 to 48;
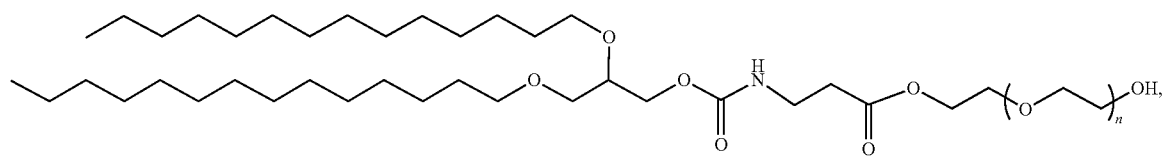
wherein n is from 36 to 48;
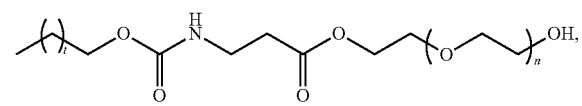
wherein t is 14, 16, or 18, and n is 25 to 50;
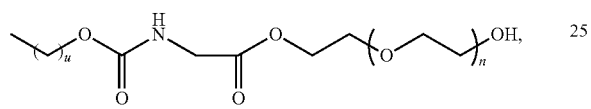
wherein t is 15, 17, or 19, and n is 25 to 50;
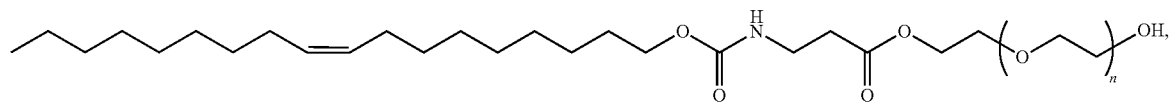
wherein n is 25 to 50;
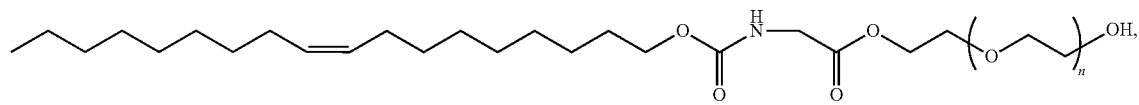
wherein n is 25 to 50;
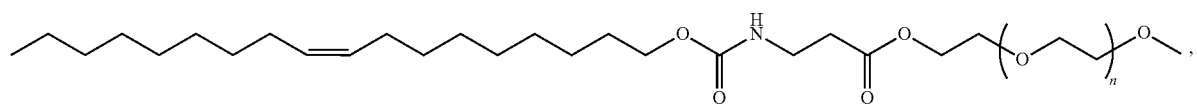
wherein n is 25 to 50;
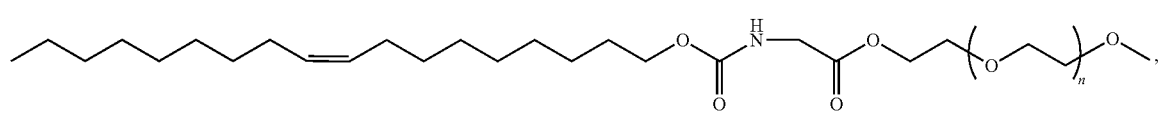

wherein n is 25 to 50;
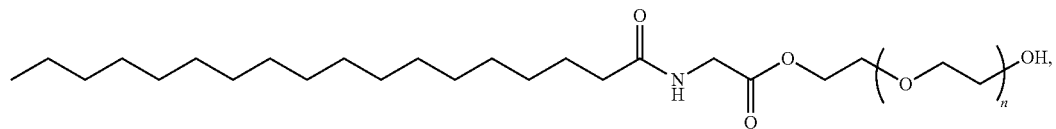
wherein n is 25 to 50;
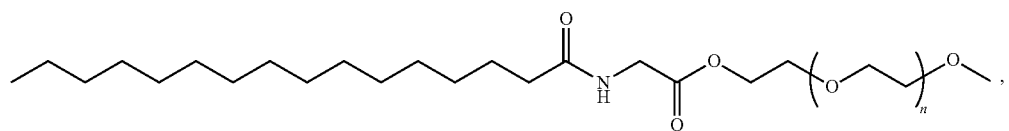
wherein n is 25 to 50;
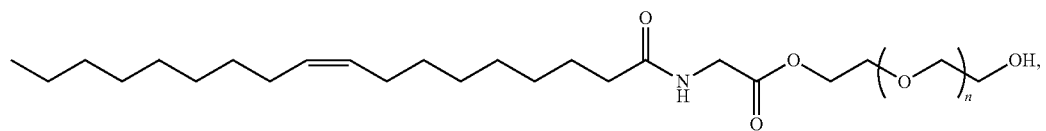
wherein n is 25 to 50;
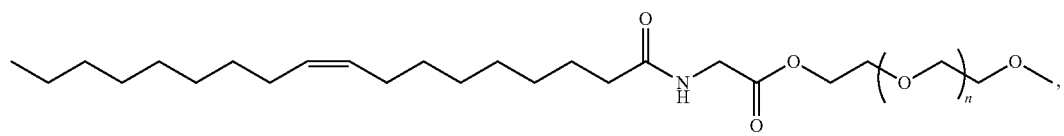
wherein n is 25 to 50;
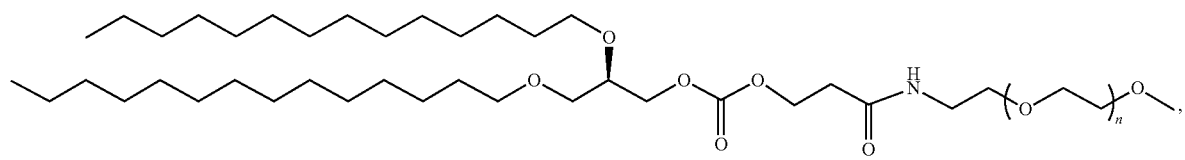
wherein n is from 36 to 48;
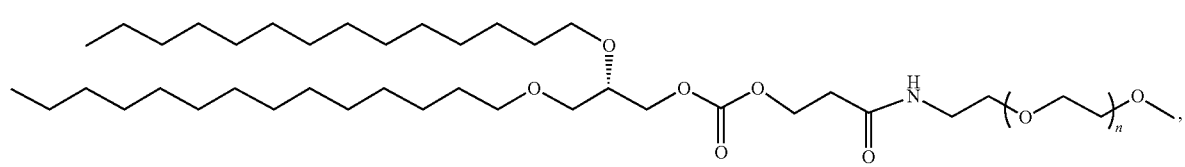

wherein n is from 36 to 48;
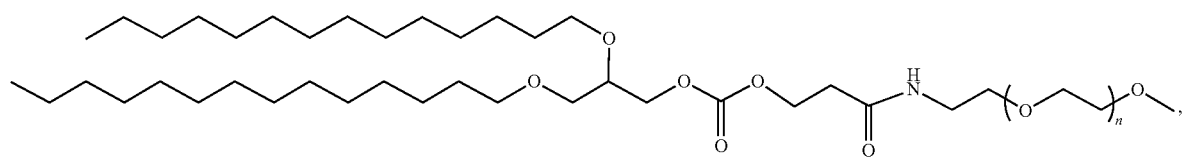
wherein n is from 36 to 48;
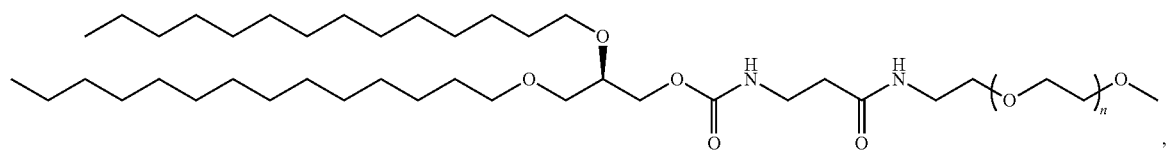
wherein n is from 36 to 48;
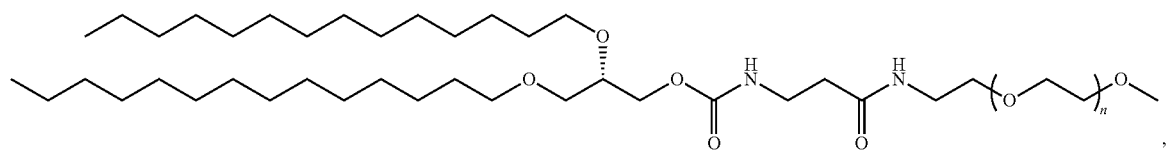
wherein n is from 36 to 48;
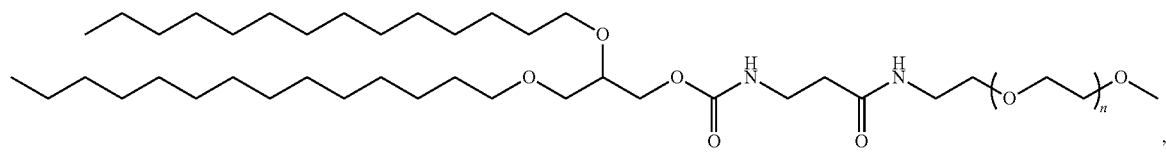
wherein n is from 36 to 48;
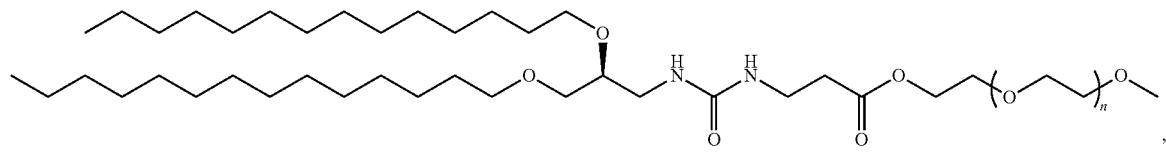
wherein n is from 36 to 48;
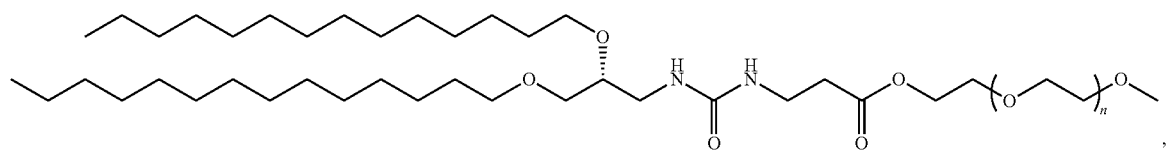

wherein n is from 36 to 48;
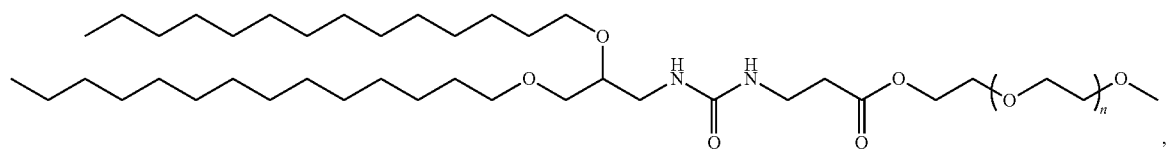
wherein n is from 36 to 48:
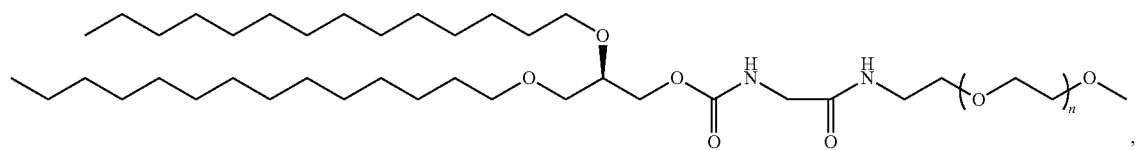
wherein n is from 36 to 48;
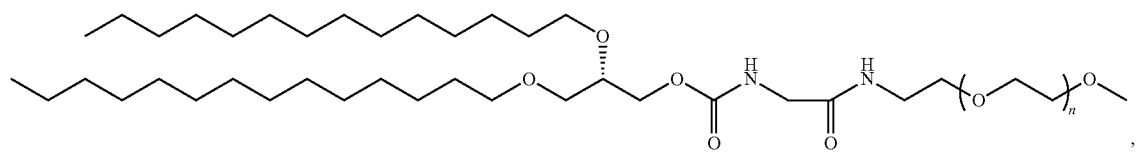
wherein n is from 36 to 48;
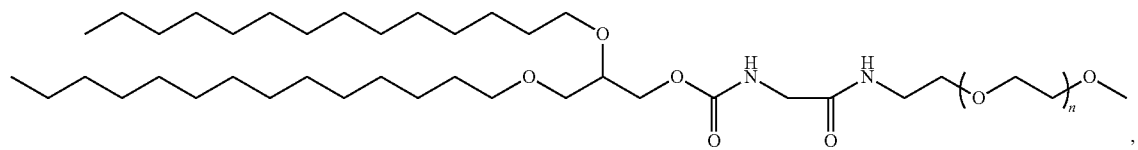
wherein n is from 36 to 48;
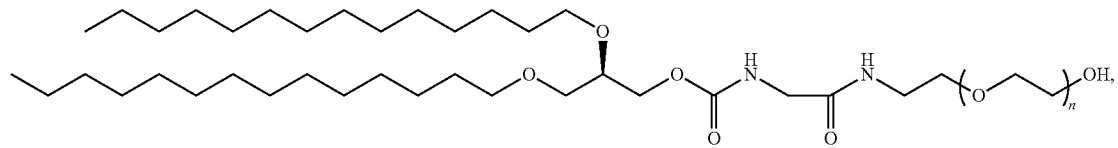
wherein n is from 36 to 48;
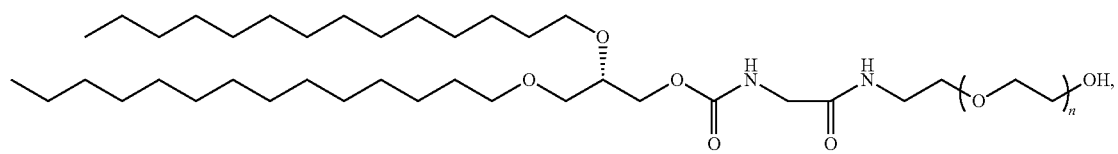

wherein n is from 36 to 48;
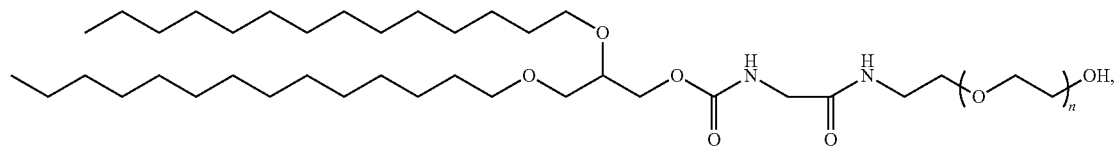
wherein n is from 36 to 48;
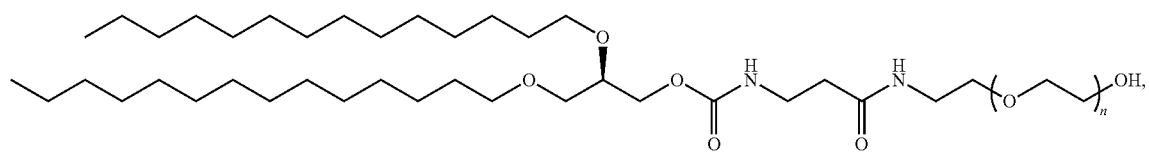
wherein n is from 36 to 48;
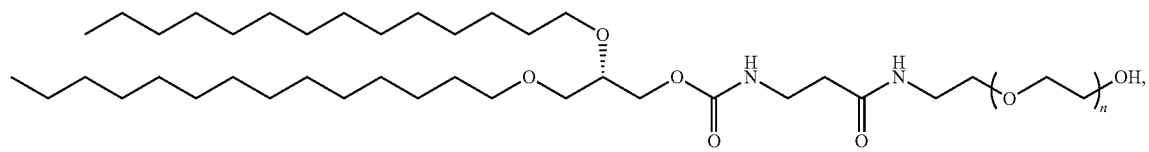
wherein n is from 36 to 48; and
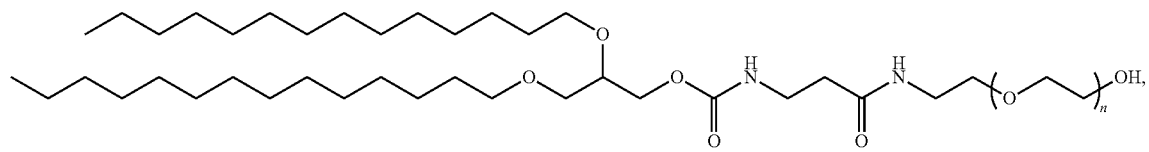
wherein n is from 36 to 48, or a pharmaceutically acceptable salt or solvate thereof.
28. The PEG lipid of claim 21, wherein the PEG lipid is:
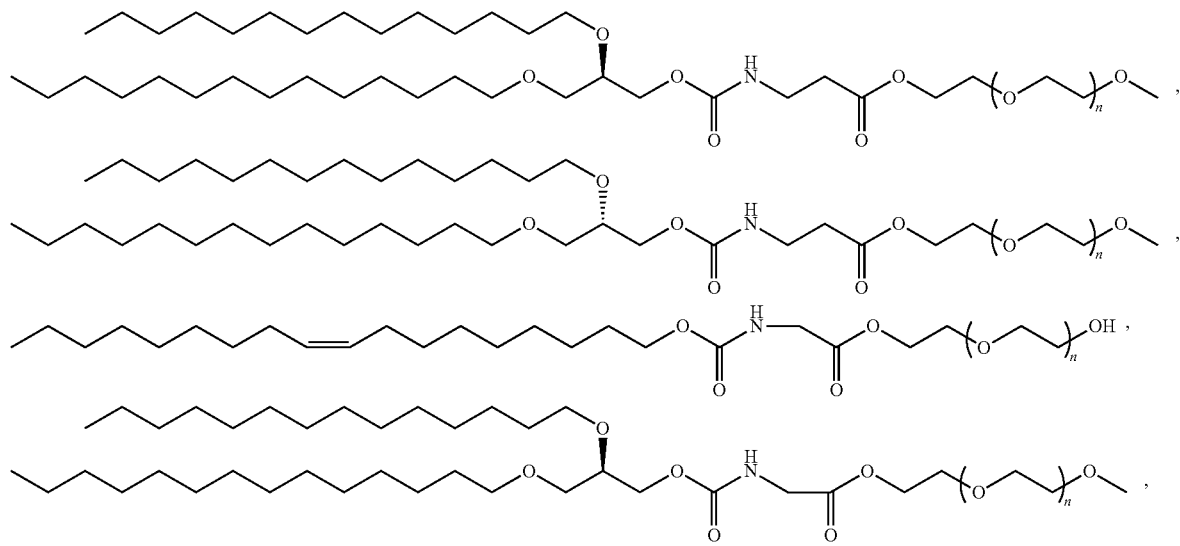

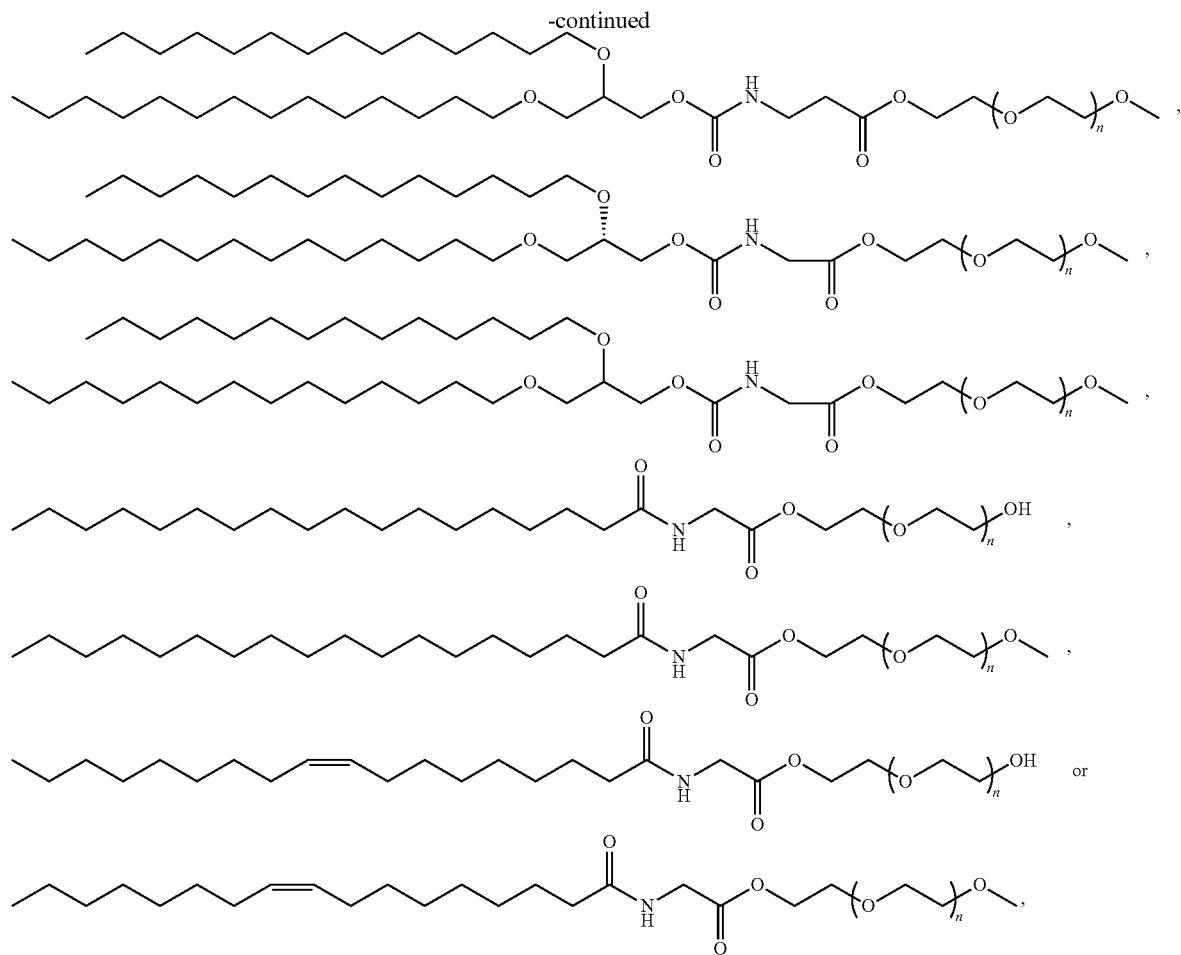
wherein n is from 36 to 48.
29. The amino lipid of claim 1, wherein each of X and Y is —C(=O)O—, —OC(=O)O—, —OC(=O)NR⁴, —N(R⁴)C(=O)O—, or —NR⁴C(=O)NR⁴—.
30. The amino lipid of claim 7, wherein L is —C(=O)O—, —OC(=O)—, —OC(=O)NR⁴, —N(R⁴)C(=O)O—, or —NR⁴C(=O)NR⁴—.
* * * * *

UNITED STATES PATENT AND TRADEMARK OFFICE
CERTIFICATE OF CORRECTION

| | | |
|---|---|---|
| PATENT NO. | : 12,024,484 B2 | Page 1 of 3 |
| APPLICATION NO. | : 18/180306 | |
| DATED | : July 2, 2024 | |
| INVENTOR(S) | : Kallanthottathil G. Rajeev et al. | |

It is certified that error appears in the above-identified patent and that said Letters Patent is hereby corrected as shown below:

On the Title Page

Replace the Title Page with the attached Title Page, showing the corrected number of claims.

In the Claims

Column 573, Line 65:
In Claim 1, replace "$NR^4C(=O)O$-" with -- -$NR^4C(=O)O$- --.

Column 574, Line 34:
In Claim 1, replace "$OC(=S)O$-" with -- -$OC(=S)O$- --

Column 574, Line 43:
In Claim 1, replace "$R^{11}C(=S)N(R^4)R^9$-" with -- -$R^{11}C(=S)N(R^4)R^9$- --

Column 576, Line 21:
In Claim 1, replace "-$C(=S)NR^4$" with -- -$C(=S)NR^4$- --.

Column 576, Line 27:
In Claim 1, replace "$SC(=O)S$-" with -- -$SC(=O)S$- --.

Column 593, Line 30:
In Claim 15, replace "$SC(=S)$-" with -- -$SC(=S)$- --.

Column 593, Line 30:
In Claim 15, replace "$SC(=O)S$-" with -- -$SC(=O)S$- --.

Column 593, Line 42:
In Claim 15, replace "$SC(=S)O$-" with -- -$SC(=S)O$- --.

Signed and Sealed this
Second Day of September, 2025

Coke Morgan Stewart
*Acting Director of the United States Patent and Trademark Office*

Column 594, Line 40:
Delete Claim 20.

Column 685, Line 42:
In Claim 29, replace "-OC(=O)NR$^4$" with -- -OC(=O)NR$^4$- --.

(12) United States Patent
Rajeev et al.

(10) Patent No.: US 12,024,484 B2
(45) Date of Patent: Jul. 2, 2024

(54) LIPID FORMULATIONS FOR GENE EDITING

(71) Applicant: Verve Therapeutics, Inc., Boston, MA (US)

(72) Inventors: Kallanthottathil G. Rajeev, Wayland, MA (US); Souvik Biswas, Woburn, MA (US)

(73) Assignee: VERVE THERAPEUTICS, INC., Boston, MA (US)

( * ) Notice: Subject to any disclaimer, the term of this patent is extended or adjusted under 35 U.S.C. 154(b) by 0 days.

(21) Appl. No.: 18/180,306

(22) Filed: Mar. 8, 2023

(65) Prior Publication Data

US 2024/0010609 A1    Jan. 11, 2024

Related U.S. Application Data

(63) Continuation of application No. PCT/US2021/050511, filed on Sep. 15, 2021.

(60) Provisional application No. 63/078,738, filed on Sep. 15, 2020, provisional application No. 63/220,340, filed on Jul. 9, 2021.

(51) Int. Cl.
*C07C 229/12* (2006.01)
*A61K 47/54* (2017.01)
*C07C 229/24* (2006.01)

(52) U.S. Cl.
CPC .................................. *C07C 229/12* (2013.01)

(58) Field of Classification Search
CPC .... C07C 229/12; C07C 229/24; A61K 47/543
See application file for complete search history.

(56) References Cited

U.S. PATENT DOCUMENTS

| | | |
|---|---|---|
| 5,885,613 A | 3/1999 | Holland et al. |
| 7,371,404 B2 | 5/2008 | Panzner et al. |
| 7,780,983 B2 | 8/2010 | Panzner et al. |
| 7,858,117 B2 | 12/2010 | Panzner et al. |
| 8,021,686 B2 | 9/2011 | Semple et al. |
| 8,236,770 B2 | 8/2012 | Endert et al. |
| 8,492,359 B2 | 7/2013 | Yaworski et al. |
| 9,186,325 B2 | 11/2015 | Manoharan et al. |
| 9,404,127 B2 | 8/2016 | Yaworski et al. |
| 9,415,109 B2 | 8/2016 | Kumar et al. |
| 9,504,651 B2 | 11/2016 | MacLachlan et al. |
| 9,512,073 B2 | 12/2016 | Dong et al. |
| 9,687,448 B2 | 6/2017 | Akinc et al. |
| 9,867,888 B2 | 1/2018 | Benenato |
| 9,868,692 B2 | 1/2018 | Benenato |
| 9,878,042 B2 | 1/2018 | Yaworski et al. |
| 10,059,655 B2 | 8/2018 | Brito et al. |
| 2005/0222064 A1 | 10/2005 | Vargeese et al. |
| 2007/0087045 A1 | 4/2007 | Li et al. |
| 2009/0053142 A1 | 2/2009 | Wynn et al. |
| 2012/0178858 A1 | 7/2012 | Wnuk et al. |
| 2015/0050295 A9 | 2/2015 | Constien et al. |
| 2016/0375134 A1 | 12/2016 | Bancel et al. |
| 2017/0273907 A1 | 9/2017 | Haas et al. |
| 2018/0092848 A1 | 4/2018 | Yaworski et al. |
| 2018/0147298 A1 | 5/2018 | Besin et al. |
| 2018/0148719 A1 | 5/2018 | Lee et al. |
| 2018/0200186 A1 | 7/2018 | Chen et al. |
| 2018/0290965 A1 | 10/2018 | Brito et al. |
| 2018/0353434 A1 | 12/2018 | Hatanaka et al. |
| 2019/0336452 A1 | 11/2019 | Brader |

FOREIGN PATENT DOCUMENTS

| | | |
|---|---|---|
| CN | 101724210 A | 6/2010 |
| CN | 102617364 A | 8/2012 |
| WO | WO-2006007712 A1 | 1/2006 |
| WO | WO-2009122044 A2 | 10/2009 |
| WO | WO-2010006282 A2 | 1/2010 |
| WO | WO-2010054401 A1 | 5/2010 |
| WO | WO-2013063468 A1 | 5/2013 |
| WO | WO-2014136086 A1 | 9/2014 |
| WO | WO-2015095340 A1 | 6/2015 |
| WO | WO-2015096982 A1 | 7/2015 |
| WO | WO-2016126941 A1 | 8/2016 |
| WO | WO-2016153012 A1 | 9/2016 |
| WO | WO-2016197133 A1 | 12/2016 |
| WO | WO-2016207098 A1 | 12/2016 |
| WO | WO-2017173054 A1 | 10/2017 |
| WO | WO-2017196969 A1 | 11/2017 |
| WO | WO-2018062413 A1 | 4/2018 |
| WO | WO-2018119514 A1 | 7/2018 |
| WO | WO-2018170306 A1 | 9/2018 |
| WO | WO-2018185241 A1 | 10/2018 |
| WO | WO-2018191750 A2 | 10/2018 |
| WO | WO-2019027055 A1 | 2/2019 |
| WO | WO-2019046809 A1 | 3/2019 |
| WO | WO-2019067992 A1 | 4/2019 |

(Continued)

OTHER PUBLICATIONS

Annenkov, V.V. et al., "Synthesis of biomimetic polyamines," ARKIVOC, 2009;13:116-130.
Dekmezian, A.H., et al., "An Efficient and Unambiguous Synthesis of 2-Hydroxymethyl-1, 3-Propanediol," Synthetic Communications, 1979;9(5):431-435.
Doherty, D.G. et al., "Synthesis of Aminoalkylisothiuronium Salts and their Conversion to Mercaptoalkylguanidines and Thiazolines2," Journal of the American Chemical Society, 1957;79(21):5667-5671.
Forse, A.C. et al., "Elucidating $CO_2$ Chemisorption in Diamine-Appended Metal-Organic Frameworks," Journal of the American Chemical Society, 2018;140:18016-18031.

(Continued)

*Primary Examiner* — Sikarl A Witherspoon
(74) *Attorney, Agent, or Firm* — Wilson Sonsoni Goodrich & Rosati

(57) ABSTRACT

The present disclosure relates to PEG-lipids, cationic and/or ionizable lipids and nucleic acid-lipid particle compositions comprising the same. The present disclosure also relates to methods of making, using and delivering the described lipids and lipid-containing particles.

29 Claims, 19 Drawing Sheets

Specification includes a Sequence Listing.

SEQUENCE LISTING

```
Sequence total quantity: 21
SEQ ID NO: 1            moltype = DNA  length = 20
FEATURE                 Location/Qualifiers
source                  1..20
                        mol_type = other DNA
                        organism = synthetic construct
SEQUENCE: 1
caggttccat gggatgctct                                                    20

SEQ ID NO: 2            moltype = DNA  length = 20
FEATURE                 Location/Qualifiers
source                  1..20
                        mol_type = other DNA
                        organism = synthetic construct
SEQUENCE: 2
ggctgatgag gccgcacatg                                                    20

SEQ ID NO: 3            moltype = DNA  length = 20
FEATURE                 Location/Qualifiers
source                  1..20
                        mol_type = other DNA
                        organism = synthetic construct
SEQUENCE: 3
cccatacctt ggagcaacgg                                                    20

SEQ ID NO: 4            moltype = DNA  length = 20
FEATURE                 Location/Qualifiers
source                  1..20
                        mol_type = other DNA
                        organism = synthetic construct
SEQUENCE: 4
cccgcacctt ggcgcagcgg                                                    20

SEQ ID NO: 5            moltype = DNA  length = 20
FEATURE                 Location/Qualifiers
source                  1..20
                        mol_type = other DNA
                        organism = synthetic construct
SEQUENCE: 5
gagatacctg agtaactttc                                                    20

SEQ ID NO: 6            moltype = DNA  length = 20
FEATURE                 Location/Qualifiers
source                  1..20
                        mol_type = other DNA
                        organism = synthetic construct
SEQUENCE: 6
```

```
aagatacctg aataactctc                                           20

SEQ ID NO: 7           moltype = RNA   length = 100
FEATURE                Location/Qualifiers
source                 1..100
                       mol_type = other RNA
                       organism = synthetic construct
modified_base          1
                       mod_base = OTHER
                       note = 2'-O-methyl nucleotide with phosphorothioate linkage
modified_base          2
                       mod_base = OTHER
                       note = 2'-O-methyl nucleotide with phosphorothioate linkage
modified_base          3
                       mod_base = OTHER
                       note = 2'-O-methyl nucleotide with phosphorothioate linkage
modified_base          21
                       mod_base = OTHER
                       note = 2'-O-methyl nucleotide
modified_base          28
                       mod_base = OTHER
                       note = 2'-O-methyl nucleotide
modified_base          29
                       mod_base = OTHER
                       note = 2'-O-methyl nucleotide
modified_base          30
                       mod_base = OTHER
                       note = 2'-O-methyl nucleotide
modified_base          31
                       mod_base = OTHER
                       note = 2'-O-methyl nucleotide
modified_base          32
                       mod_base = OTHER
                       note = 2'-O-methyl nucleotide
modified_base          33
                       mod_base = OTHER
                       note = 2'-O-methyl nucleotide
modified_base          34
                       mod_base = OTHER
                       note = 2'-O-methyl nucleotide
modified_base          35
                       mod_base = OTHER
                       note = 2'-O-methyl nucleotide
modified_base          36
                       mod_base = OTHER
                       note = 2'-O-methyl nucleotide
modified_base          37
                       mod_base = OTHER
                       note = 2'-O-methyl nucleotide
modified_base          38
                       mod_base = OTHER
                       note = 2'-O-methyl nucleotide
modified_base          39
                       mod_base = OTHER
                       note = 2'-O-methyl nucleotide
modified_base          40
                       mod_base = OTHER
                       note = 2'-O-methyl nucleotide
modified_base          41
                       mod_base = OTHER
                       note = 2'-O-methyl nucleotide
modified_base          42
                       mod_base = OTHER
                       note = 2'-O-methyl nucleotide
modified_base          46
                       mod_base = OTHER
                       note = 2'-O-methyl nucleotide
modified_base          48
                       mod_base = OTHER
                       note = 2'-O-methyl nucleotide
modified_base          50
                       mod_base = OTHER
                       note = 2'-O-methyl nucleotide
modified_base          52
                       mod_base = OTHER
                       note = 2'-O-methyl nucleotide
modified_base          53
                       mod_base = OTHER
                       note = 2'-O-methyl nucleotide
```

| | |
|---|---|
| modified_base | 54<br>mod_base = OTHER<br>note = 2'-O-methyl nucleotide |
| modified_base | 55<br>mod_base = OTHER<br>note = 2'-O-methyl nucleotide |
| modified_base | 56<br>mod_base = OTHER<br>note = 2'-O-methyl nucleotide |
| modified_base | 57<br>mod_base = OTHER<br>note = 2'-O-methyl nucleotide |
| modified_base | 60<br>mod_base = OTHER<br>note = 2'-O-methyl nucleotide |
| modified_base | 61<br>mod_base = OTHER<br>note = 2'-O-methyl nucleotide |
| modified_base | 66<br>mod_base = OTHER<br>note = 2'-O-methyl nucleotide |
| modified_base | 67<br>mod_base = OTHER<br>note = 2'-O-methyl nucleotide |
| modified_base | 70<br>mod_base = OTHER<br>note = 2'-O-methyl nucleotide |
| modified_base | 71<br>mod_base = OTHER<br>note = 2'-O-methyl nucleotide |
| modified_base | 72<br>mod_base = OTHER<br>note = 2'-O-methyl nucleotide |
| modified_base | 73<br>mod_base = OTHER<br>note = 2'-O-methyl nucleotide |
| modified_base | 74<br>mod_base = OTHER<br>note = 2'-O-methyl nucleotide |
| modified_base | 75<br>mod_base = OTHER<br>note = 2'-O-methyl nucleotide |
| modified_base | 76<br>mod_base = OTHER<br>note = 2'-O-methyl nucleotide |
| modified_base | 77<br>mod_base = OTHER<br>note = 2'-O-methyl nucleotide |
| modified_base | 78<br>mod_base = OTHER<br>note = 2'-O-methyl nucleotide |
| modified_base | 79<br>mod_base = OTHER<br>note = 2'-O-methyl nucleotide |
| modified_base | 80<br>mod_base = OTHER<br>note = 2'-O-methyl nucleotide |
| modified_base | 81<br>mod_base = OTHER<br>note = 2'-O-methyl nucleotide |
| modified_base | 83<br>mod_base = OTHER<br>note = 2'-O-methyl nucleotide |
| modified_base | 84<br>mod_base = OTHER<br>note = 2'-O-methyl nucleotide |
| modified_base | 85<br>mod_base = OTHER<br>note = 2'-O-methyl nucleotide |
| modified_base | 86<br>mod_base = OTHER<br>note = 2'-O-methyl nucleotide |
| modified_base | 87<br>mod_base = OTHER<br>note = 2'-O-methyl nucleotide |
| modified_base | 88<br>mod_base = OTHER<br>note = 2'-O-methyl nucleotide |
| modified_base | 89 |

```
                           mod_base = OTHER
                           note = 2'-O-methyl nucleotide
modified_base              90
                           mod_base = OTHER
                           note = 2'-O-methyl nucleotide
modified_base              91
                           mod_base = OTHER
                           note = 2'-O-methyl nucleotide
modified_base              92
                           mod_base = OTHER
                           note = 2'-O-methyl nucleotide
modified_base              93
                           mod_base = OTHER
                           note = 2'-O-methyl nucleotide
modified_base              94
                           mod_base = OTHER
                           note = 2'-O-methyl nucleotide
modified_base              95
                           mod_base = OTHER
                           note = 2'-O-methyl nucleotide
modified_base              96
                           mod_base = OTHER
                           note = 2'-O-methyl nucleotide
modified_base              97
                           mod_base = OTHER
                           note = 2'-O-methyl nucleotide with phosphorothioate linkage
modified_base              98
                           mod_base = OTHER
                           note = 2'-O-methyl nucleotide with phosphorothioate linkage
modified_base              99
                           mod_base = OTHER
                           note = 2'-O-methyl nucleotide with phosphorothioate linkage
modified_base              100
                           mod_base = OTHER
                           note = 2'-O-methyl nucleotide
SEQUENCE: 7
caggttccat gggatgctct gttttagagc tagaaatagc aagttaaaat aaggctagtc    60
cgttatcaac ttgaaaaagt ggcaccgagt cggtgctttt                         100

SEQ ID NO: 8               moltype = RNA   length = 100
FEATURE                    Location/Qualifiers
source                     1..100
                           mol_type = other RNA
                           organism = synthetic construct
modified_base              1
                           mod_base = OTHER
                           note = 2'-O-methyl nucleotide with phosphorothioate linkage
modified_base              2
                           mod_base = OTHER
                           note = 2'-O-methyl nucleotide with phosphorothioate linkage
modified_base              3
                           mod_base = OTHER
                           note = 2'-O-methyl nucleotide with phosphorothioate linkage
modified_base              29
                           mod_base = OTHER
                           note = 2'-O-methyl nucleotide
modified_base              30
                           mod_base = OTHER
                           note = 2'-O-methyl nucleotide
modified_base              31
                           mod_base = OTHER
                           note = 2'-O-methyl nucleotide
modified_base              32
                           mod_base = OTHER
                           note = 2'-O-methyl nucleotide
modified_base              33
                           mod_base = OTHER
                           note = 2'-O-methyl nucleotide
modified_base              34
                           mod_base = OTHER
                           note = 2'-O-methyl nucleotide
modified_base              35
                           mod_base = OTHER
                           note = 2'-O-methyl nucleotide
modified_base              36
                           mod_base = OTHER
                           note = 2'-O-methyl nucleotide
modified_base              37
                           mod_base = OTHER
```

| | | |
|---|---|---|
| modified_base | 38 | note = 2'-O-methyl nucleotide<br>mod_base = OTHER<br>note = 2'-O-methyl nucleotide |
| modified_base | 39 | mod_base = OTHER<br>note = 2'-O-methyl nucleotide |
| modified_base | 40 | mod_base = OTHER<br>note = 2'-O-methyl nucleotide |
| modified_base | 69 | mod_base = OTHER<br>note = 2'-O-methyl nucleotide |
| modified_base | 70 | mod_base = OTHER<br>note = 2'-O-methyl nucleotide |
| modified_base | 71 | mod_base = OTHER<br>note = 2'-O-methyl nucleotide |
| modified_base | 72 | mod_base = OTHER<br>note = 2'-O-methyl nucleotide |
| modified_base | 73 | mod_base = OTHER<br>note = 2'-O-methyl nucleotide |
| modified_base | 74 | mod_base = OTHER<br>note = 2'-O-methyl nucleotide |
| modified_base | 75 | mod_base = OTHER<br>note = 2'-O-methyl nucleotide |
| modified_base | 76 | mod_base = OTHER<br>note = 2'-O-methyl nucleotide |
| modified_base | 77 | mod_base = OTHER<br>note = 2'-O-methyl nucleotide |
| modified_base | 78 | mod_base = OTHER<br>note = 2'-O-methyl nucleotide |
| modified_base | 79 | mod_base = OTHER<br>note = 2'-O-methyl nucleotide |
| modified_base | 80 | mod_base = OTHER<br>note = 2'-O-methyl nucleotide |
| modified_base | 81 | mod_base = OTHER<br>note = 2'-O-methyl nucleotide |
| modified_base | 82 | mod_base = OTHER<br>note = 2'-O-methyl nucleotide |
| modified_base | 83 | mod_base = OTHER<br>note = 2'-O-methyl nucleotide |
| modified_base | 84 | mod_base = OTHER<br>note = 2'-O-methyl nucleotide |
| modified_base | 85 | mod_base = OTHER<br>note = 2'-O-methyl nucleotide |
| modified_base | 86 | mod_base = OTHER<br>note = 2'-O-methyl nucleotide |
| modified_base | 87 | mod_base = OTHER<br>note = 2'-O-methyl nucleotide |
| modified_base | 88 | mod_base = OTHER<br>note = 2'-O-methyl nucleotide |
| modified_base | 89 | mod_base = OTHER<br>note = 2'-O-methyl nucleotide |
| modified_base | 90 | mod_base = OTHER<br>note = 2'-O-methyl nucleotide |
| modified_base | 91 | mod_base = OTHER<br>note = 2'-O-methyl nucleotide |

```
modified_base        92
                     mod_base = OTHER
                     note = 2'-O-methyl nucleotide
modified_base        93
                     mod_base = OTHER
                     note = 2'-O-methyl nucleotide
modified_base        94
                     mod_base = OTHER
                     note = 2'-O-methyl nucleotide
modified_base        95
                     mod_base = OTHER
                     note = 2'-O-methyl nucleotide
modified_base        96
                     mod_base = OTHER
                     note = 2'-O-methyl nucleotide
modified_base        97
                     mod_base = OTHER
                     note = 2'-O-methyl nucleotide with phosphorothioate linkage
modified_base        98
                     mod_base = OTHER
                     note = 2'-O-methyl nucleotide with phosphorothioate linkage
modified_base        99
                     mod_base = OTHER
                     note = 2'-O-methyl nucleotide with phosphorothioate linkage
modified_base        100
                     mod_base = OTHER
                     note = 2'-O-methyl nucleotide
SEQUENCE: 8
ggctgatgag gccgcacatg gttttagagc tagaaatagc aagttaaaat aaggctagtc   60
cgttatcaac ttgaaaaagt ggcaccgagt cggtgctttt                        100

SEQ ID NO: 9         moltype = RNA   length = 100
FEATURE              Location/Qualifiers
source               1..100
                     mol_type = other RNA
                     organism = synthetic construct
modified_base        1
                     mod_base = OTHER
                     note = 2'-O-methyl nucleotide with phosphorothioate linkage
modified_base        2
                     mod_base = OTHER
                     note = 2'-O-methyl nucleotide with phosphorothioate linkage
modified_base        3
                     mod_base = OTHER
                     note = 2'-O-methyl nucleotide with phosphorothioate linkage
modified_base        21
                     mod_base = OTHER
                     note = 2'-O-methyl nucleotide
modified_base        28
                     mod_base = OTHER
                     note = 2'-O-methyl nucleotide
modified_base        29
                     mod_base = OTHER
                     note = 2'-O-methyl nucleotide
modified_base        30
                     mod_base = OTHER
                     note = 2'-O-methyl nucleotide
modified_base        31
                     mod_base = OTHER
                     note = 2'-O-methyl nucleotide
modified_base        32
                     mod_base = OTHER
                     note = 2'-O-methyl nucleotide
modified_base        34
                     mod_base = OTHER
                     note = 2'-O-methyl nucleotide
modified_base        35
                     mod_base = OTHER
                     note = 2'-O-methyl nucleotide
modified_base        36
                     mod_base = OTHER
                     note = 2'-O-methyl nucleotide
modified_base        37
                     mod_base = OTHER
                     note = 2'-O-methyl nucleotide
modified_base        38
                     mod_base = OTHER
                     note = 2'-O-methyl nucleotide
modified_base        39
```

-continued

```
                              mod_base = OTHER
                              note = 2'-O-methyl nucleotide
modified_base                 40
                              mod_base = OTHER
                              note = 2'-O-methyl nucleotide
modified_base                 41
                              mod_base = OTHER
                              note = 2'-O-methyl nucleotide
modified_base                 42
                              mod_base = OTHER
                              note = 2'-O-methyl nucleotide
modified_base                 46
                              mod_base = OTHER
                              note = 2'-O-methyl nucleotide
modified_base                 48
                              mod_base = OTHER
                              note = 2'-O-methyl nucleotide
modified_base                 50
                              mod_base = OTHER
                              note = 2'-O-methyl nucleotide
modified_base                 52
                              mod_base = OTHER
                              note = 2'-O-methyl nucleotide
modified_base                 53
                              mod_base = OTHER
                              note = 2'-O-methyl nucleotide
modified_base                 54
                              mod_base = OTHER
                              note = 2'-O-methyl nucleotide
modified_base                 57
                              mod_base = OTHER
                              note = 2'-O-methyl nucleotide
modified_base                 61
                              mod_base = OTHER
                              note = 2'-O-methyl nucleotide
modified_base                 66
                              mod_base = OTHER
                              note = 2'-O-methyl nucleotide
modified_base                 67
                              mod_base = OTHER
                              note = 2'-O-methyl nucleotide
modified_base                 70
                              mod_base = OTHER
                              note = 2'-O-methyl nucleotide
modified_base                 71
                              mod_base = OTHER
                              note = 2'-O-methyl nucleotide
modified_base                 72
                              mod_base = OTHER
                              note = 2'-O-methyl nucleotide
modified_base                 74
                              mod_base = OTHER
                              note = 2'-O-methyl nucleotide
modified_base                 75
                              mod_base = OTHER
                              note = 2'-O-methyl nucleotide
modified_base                 76
                              mod_base = OTHER
                              note = 2'-O-methyl nucleotide
modified_base                 77
                              mod_base = OTHER
                              note = 2'-O-methyl nucleotide
modified_base                 78
                              mod_base = OTHER
                              note = 2'-O-methyl nucleotide
modified_base                 79
                              mod_base = OTHER
                              note = 2'-O-methyl nucleotide
modified_base                 80
                              mod_base = OTHER
                              note = 2'-O-methyl nucleotide
modified_base                 82
                              mod_base = OTHER
                              note = 2'-O-methyl nucleotide
modified_base                 83
                              mod_base = OTHER
                              note = 2'-O-methyl nucleotide
modified_base                 84
                              mod_base = OTHER
```

```
                              note = 2'-O-methyl nucleotide
modified_base                 85
                              mod_base = OTHER
                              note = 2'-O-methyl nucleotide
modified_base                 86
                              mod_base = OTHER
                              note = 2'-O-methyl nucleotide
modified_base                 87
                              mod_base = OTHER
                              note = 2'-O-methyl nucleotide
modified_base                 89
                              mod_base = OTHER
                              note = 2'-O-methyl nucleotide
modified_base                 92
                              mod_base = OTHER
                              note = 2'-O-methyl nucleotide
modified_base                 93
                              mod_base = OTHER
                              note = 2'-O-methyl nucleotide
modified_base                 94
                              mod_base = OTHER
                              note = 2'-O-methyl nucleotide
modified_base                 95
                              mod_base = OTHER
                              note = 2'-O-methyl nucleotide
modified_base                 96
                              mod_base = OTHER
                              note = 2'-O-methyl nucleotide
modified_base                 97
                              mod_base = OTHER
                              note = 2'-O-methyl nucleotide with phosphorothioate linkage
modified_base                 98
                              mod_base = OTHER
                              note = 2'-O-methyl nucleotide with phosphorothioate linkage
modified_base                 99
                              mod_base = OTHER
                              note = 2'-O-methyl nucleotide with phosphorothioate linkage
modified_base                 100
                              mod_base = OTHER
                              note = 2'-O-methyl nucleotide
SEQUENCE: 9
cccatacctt ggagcaacgg gtttagagc tagaaatagc aagttaaaat aaggctagtc      60
cgttatcaac ttgaaaaagt ggcaccgagt cggtgctttt                          100

SEQ ID NO: 10                 moltype = RNA   length = 100
FEATURE                       Location/Qualifiers
source                        1..100
                              mol_type = other RNA
                              organism = synthetic construct
modified_base                 1
                              mod_base = OTHER
                              note = 2'-O-methyl nucleotide with phosphorothioate linkage
modified_base                 2
                              mod_base = OTHER
                              note = 2'-O-methyl nucleotide with phosphorothioate linkage
modified_base                 3
                              mod_base = OTHER
                              note = 2'-O-methyl nucleotide with phosphorothioate linkage
modified_base                 21
                              mod_base = OTHER
                              note = 2'-O-methyl nucleotide
modified_base                 28
                              mod_base = OTHER
                              note = 2'-O-methyl nucleotide
modified_base                 29
                              mod_base = OTHER
                              note = 2'-O-methyl nucleotide
modified_base                 30
                              mod_base = OTHER
                              note = 2'-O-methyl nucleotide
modified_base                 31
                              mod_base = OTHER
                              note = 2'-O-methyl nucleotide
modified_base                 32
                              mod_base = OTHER
                              note = 2'-O-methyl nucleotide
modified_base                 33
                              mod_base = OTHER
                              note = 2'-O-methyl nucleotide
```

-continued

```
modified_base     34
                  mod_base = OTHER
                  note = 2'-O-methyl nucleotide
modified_base     35
                  mod_base = OTHER
                  note = 2'-O-methyl nucleotide
modified_base     36
                  mod_base = OTHER
                  note = 2'-O-methyl nucleotide
modified_base     37
                  mod_base = OTHER
                  note = 2'-O-methyl nucleotide
modified_base     38
                  mod_base = OTHER
                  note = 2'-O-methyl nucleotide
modified_base     39
                  mod_base = OTHER
                  note = 2'-O-methyl nucleotide
modified_base     40
                  mod_base = OTHER
                  note = 2'-O-methyl nucleotide
modified_base     41
                  mod_base = OTHER
                  note = 2'-O-methyl nucleotide
modified_base     42
                  mod_base = OTHER
                  note = 2'-O-methyl nucleotide
modified_base     46
                  mod_base = OTHER
                  note = 2'-O-methyl nucleotide
modified_base     48
                  mod_base = OTHER
                  note = 2'-O-methyl nucleotide
modified_base     50
                  mod_base = OTHER
                  note = 2'-O-methyl nucleotide
modified_base     52
                  mod_base = OTHER
                  note = 2'-O-methyl nucleotide
modified_base     53
                  mod_base = OTHER
                  note = 2'-O-methyl nucleotide
modified_base     54
                  mod_base = OTHER
                  note = 2'-O-methyl nucleotide
modified_base     55
                  mod_base = OTHER
                  note = 2'-O-methyl nucleotide
modified_base     56
                  mod_base = OTHER
                  note = 2'-O-methyl nucleotide
modified_base     57
                  mod_base = OTHER
                  note = 2'-O-methyl nucleotide
modified_base     60
                  mod_base = OTHER
                  note = 2'-O-methyl nucleotide
modified_base     61
                  mod_base = OTHER
                  note = 2'-O-methyl nucleotide
modified_base     66
                  mod_base = OTHER
                  note = 2'-O-methyl nucleotide
modified_base     67
                  mod_base = OTHER
                  note = 2'-O-methyl nucleotide
modified_base     70
                  mod_base = OTHER
                  note = 2'-O-methyl nucleotide
modified_base     71
                  mod_base = OTHER
                  note = 2'-O-methyl nucleotide
modified_base     72
                  mod_base = OTHER
                  note = 2'-O-methyl nucleotide
modified_base     73
                  mod_base = OTHER
                  note = 2'-O-methyl nucleotide
modified_base     74
```

|   |   |
|---|---|
| | mod_base = OTHER<br>note = 2'-O-methyl nucleotide |
| modified_base | 75<br>mod_base = OTHER<br>note = 2'-O-methyl nucleotide |
| modified_base | 76<br>mod_base = OTHER<br>note = 2'-O-methyl nucleotide |
| modified_base | 77<br>mod_base = OTHER<br>note = 2'-O-methyl nucleotide |
| modified_base | 78<br>mod_base = OTHER<br>note = 2'-O-methyl nucleotide |
| modified_base | 79<br>mod_base = OTHER<br>note = 2'-O-methyl nucleotide |
| modified_base | 80<br>mod_base = OTHER<br>note = 2'-O-methyl nucleotide |
| modified_base | 81<br>mod_base = OTHER<br>note = 2'-O-methyl nucleotide |
| modified_base | 83<br>mod_base = OTHER<br>note = 2'-O-methyl nucleotide |
| modified_base | 84<br>mod_base = OTHER<br>note = 2'-O-methyl nucleotide |
| modified_base | 85<br>mod_base = OTHER<br>note = 2'-O-methyl nucleotide |
| modified_base | 86<br>mod_base = OTHER<br>note = 2'-O-methyl nucleotide |
| modified_base | 87<br>mod_base = OTHER<br>note = 2'-O-methyl nucleotide |
| modified_base | 88<br>mod_base = OTHER<br>note = 2'-O-methyl nucleotide |
| modified_base | 89<br>mod_base = OTHER<br>note = 2'-O-methyl nucleotide |
| modified_base | 90<br>mod_base = OTHER<br>note = 2'-O-methyl nucleotide |
| modified_base | 91<br>mod_base = OTHER<br>note = 2'-O-methyl nucleotide |
| modified_base | 92<br>mod_base = OTHER<br>note = 2'-O-methyl nucleotide |
| modified_base | 93<br>mod_base = OTHER<br>note = 2'-O-methyl nucleotide |
| modified_base | 94<br>mod_base = OTHER<br>note = 2'-O-methyl nucleotide |
| modified_base | 95<br>mod_base = OTHER<br>note = 2'-O-methyl nucleotide |
| modified_base | 96<br>mod_base = OTHER<br>note = 2'-O-methyl nucleotide |
| modified_base | 97<br>mod_base = OTHER<br>note = 2'-O-methyl nucleotide with phosphorothioate linkage |
| modified_base | 98<br>mod_base = OTHER<br>note = 2'-O-methyl nucleotide with phosphorothioate linkage |
| modified_base | 99<br>mod_base = OTHER<br>note = 2'-O-methyl nucleotide with phosphorothioate linkage |
| modified_base | 100<br>mod_base = OTHER<br>note = 2'-O-methyl nucleotide |

SEQUENCE: 10
cccatacctt ggagcaacgg gttttagagc tagaaatagc aagttaaaat aaggctagtc 60

```
cgttatcaac ttgaaaaagt ggcaccgagt cggtgctttt                                      100
```

| | | |
|---|---|---|
| SEQ ID NO: 11 | moltype = RNA   length = 100 | |
| FEATURE | Location/Qualifiers | |
| source | 1..100 | |
| | mol_type = other RNA | |
| | organism = synthetic construct | |
| modified_base | 1 | |
| | mod_base = OTHER | |
| | note = 2'-O-methyl nucleotide with phosphorothioate linkage | |
| modified_base | 2 | |
| | mod_base = OTHER | |
| | note = 2'-O-methyl nucleotide with phosphorothioate linkage | |
| modified_base | 3 | |
| | mod_base = OTHER | |
| | note = 2'-O-methyl nucleotide with phosphorothioate linkage | |
| modified_base | 21 | |
| | mod_base = OTHER | |
| | note = 2'-O-methyl nucleotide | |
| modified_base | 28 | |
| | mod_base = OTHER | |
| | note = 2'-O-methyl nucleotide | |
| modified_base | 29 | |
| | mod_base = OTHER | |
| | note = 2'-O-methyl nucleotide | |
| modified_base | 30 | |
| | mod_base = OTHER | |
| | note = 2'-O-methyl nucleotide | |
| modified_base | 31 | |
| | mod_base = OTHER | |
| | note = 2'-O-methyl nucleotide | |
| modified_base | 32 | |
| | mod_base = OTHER | |
| | note = 2'-O-methyl nucleotide | |
| modified_base | 34 | |
| | mod_base = OTHER | |
| | note = 2'-O-methyl nucleotide | |
| modified_base | 35 | |
| | mod_base = OTHER | |
| | note = 2'-O-methyl nucleotide | |
| modified_base | 36 | |
| | mod_base = OTHER | |
| | note = 2'-O-methyl nucleotide | |
| modified_base | 37 | |
| | mod_base = OTHER | |
| | note = 2'-O-methyl nucleotide | |
| modified_base | 38 | |
| | mod_base = OTHER | |
| | note = 2'-O-methyl nucleotide | |
| modified_base | 39 | |
| | mod_base = OTHER | |
| | note = 2'-O-methyl nucleotide | |
| modified_base | 40 | |
| | mod_base = OTHER | |
| | note = 2'-O-methyl nucleotide | |
| modified_base | 41 | |
| | mod_base = OTHER | |
| | note = 2'-O-methyl nucleotide | |
| modified_base | 42 | |
| | mod_base = OTHER | |
| | note = 2'-O-methyl nucleotide | |
| modified_base | 46 | |
| | mod_base = OTHER | |
| | note = 2'-O-methyl nucleotide | |
| modified_base | 48 | |
| | mod_base = OTHER | |
| | note = 2'-O-methyl nucleotide | |
| modified_base | 50 | |
| | mod_base = OTHER | |
| | note = 2'-O-methyl nucleotide | |
| modified_base | 52 | |
| | mod_base = OTHER | |
| | note = 2'-O-methyl nucleotide | |
| modified_base | 53 | |
| | mod_base = OTHER | |
| | note = 2'-O-methyl nucleotide | |
| modified_base | 54 | |
| | mod_base = OTHER | |
| | note = 2'-O-methyl nucleotide | |

-continued

```
modified_base    55
                 mod_base = OTHER
                 note = 2'-O-methyl nucleotide
modified_base    56
                 mod_base = OTHER
                 note = 2'-O-methyl nucleotide
modified_base    57
                 mod_base = OTHER
                 note = 2'-O-methyl nucleotide
modified_base    60
                 mod_base = OTHER
                 note = 2'-O-methyl nucleotide
modified_base    61
                 mod_base = OTHER
                 note = 2'-O-methyl nucleotide
modified_base    66
                 mod_base = OTHER
                 note = 2'-O-methyl nucleotide
modified_base    67
                 mod_base = OTHER
                 note = 2'-O-methyl nucleotide
modified_base    70
                 mod_base = OTHER
                 note = 2'-O-methyl nucleotide
modified_base    71
                 mod_base = OTHER
                 note = 2'-O-methyl nucleotide
modified_base    72
                 mod_base = OTHER
                 note = 2'-O-methyl nucleotide
modified_base    74
                 mod_base = OTHER
                 note = 2'-O-methyl nucleotide
modified_base    75
                 mod_base = OTHER
                 note = 2'-O-methyl nucleotide
modified_base    76
                 mod_base = OTHER
                 note = 2'-O-methyl nucleotide
modified_base    77
                 mod_base = OTHER
                 note = 2'-O-methyl nucleotide
modified_base    78
                 mod_base = OTHER
                 note = 2'-O-methyl nucleotide
modified_base    79
                 mod_base = OTHER
                 note = 2'-O-methyl nucleotide
modified_base    80
                 mod_base = OTHER
                 note = 2'-O-methyl nucleotide
modified_base    81
                 mod_base = OTHER
                 note = 2'-O-methyl nucleotide
modified_base    83
                 mod_base = OTHER
                 note = 2'-O-methyl nucleotide
modified_base    84
                 mod_base = OTHER
                 note = 2'-O-methyl nucleotide
modified_base    85
                 mod_base = OTHER
                 note = 2'-O-methyl nucleotide
modified_base    86
                 mod_base = OTHER
                 note = 2'-O-methyl nucleotide
modified_base    87
                 mod_base = OTHER
                 note = 2'-O-methyl nucleotide
modified_base    88
                 mod_base = OTHER
                 note = 2'-O-methyl nucleotide
modified_base    89
                 mod_base = OTHER
                 note = 2'-O-methyl nucleotide
modified_base    90
                 mod_base = OTHER
                 note = 2'-O-methyl nucleotide
modified_base    91
```

```
                        mod_base = OTHER
                        note = 2'-O-methyl nucleotide
modified_base           92
                        mod_base = OTHER
                        note = 2'-O-methyl nucleotide
modified_base           93
                        mod_base = OTHER
                        note = 2'-O-methyl nucleotide
modified_base           94
                        mod_base = OTHER
                        note = 2'-O-methyl nucleotide
modified_base           95
                        mod_base = OTHER
                        note = 2'-O-methyl nucleotide
modified_base           96
                        mod_base = OTHER
                        note = 2'-O-methyl nucleotide
modified_base           97
                        mod_base = OTHER
                        note = 2'-O-methyl nucleotide with phosphorothioate linkage
modified_base           98
                        mod_base = OTHER
                        note = 2'-O-methyl nucleotide with phosphorothioate linkage
modified_base           99
                        mod_base = OTHER
                        note = 2'-O-methyl nucleotide with phosphorothioate linkage
modified_base           100
                        mod_base = OTHER
                        note = 2'-O-methyl nucleotide
SEQUENCE: 11
cccatacctt ggagcaacgg gttttagagc tagaaatagc aagttaaaat aaggctagtc   60
cgttatcaac ttgaaaaagt ggcaccgagt cggtgctttt                        100

SEQ ID NO: 12           moltype = RNA  length = 99
FEATURE                 Location/Qualifiers
source                  1..99
                        mol_type = other RNA
                        organism = synthetic construct
modified_base           1
                        mod_base = OTHER
                        note = 2'-O-methyl nucleotide with phosphorothioate linkage
modified_base           2
                        mod_base = OTHER
                        note = 2'-O-methyl nucleotide with phosphorothioate linkage
modified_base           3
                        mod_base = OTHER
                        note = 2'-O-methyl nucleotide with phosphorothioate linkage
modified_base           96
                        mod_base = OTHER
                        note = nucleotide with phosphorothioate linkage
modified_base           97
                        mod_base = OTHER
                        note = 2'-O-methyl nucleotide with phosphorothioate linkage
modified_base           98
                        mod_base = OTHER
                        note = 2'-O-methyl nucleotide with phosphorothioate linkage
modified_base           99
                        mod_base = OTHER
                        note = 2'-O-methyl nucleotide
SEQUENCE: 12
cccatacttg gagcaacggg ttttagagct agaaatagca agttaaaata aggctagtcc   60
gttatcaact tgaaaaagtg gcaccgagtc ggtgctttt                         99

SEQ ID NO: 13           moltype = RNA  length = 100
FEATURE                 Location/Qualifiers
source                  1..100
                        mol_type = other RNA
                        organism = synthetic construct
modified_base           1
                        mod_base = OTHER
                        note = 2'-O-methyl nucleotide with phosphorothioate linkage
modified_base           2
                        mod_base = OTHER
                        note = 2'-O-methyl nucleotide with phosphorothioate linkage
modified_base           3
                        mod_base = OTHER
                        note = 2'-O-methyl nucleotide with phosphorothioate linkage
modified_base           21
                        mod_base = OTHER
```

```
                      note = 2'-O-methyl nucleotide
modified_base         28
                      mod_base = OTHER
                      note = 2'-O-methyl nucleotide
modified_base         29
                      mod_base = OTHER
                      note = 2'-O-methyl nucleotide
modified_base         30
                      mod_base = OTHER
                      note = 2'-O-methyl nucleotide
modified_base         31
                      mod_base = OTHER
                      note = 2'-O-methyl nucleotide
modified_base         32
                      mod_base = OTHER
                      note = 2'-O-methyl nucleotide
modified_base         33
                      mod_base = OTHER
                      note = 2'-O-methyl nucleotide
modified_base         34
                      mod_base = OTHER
                      note = 2'-O-methyl nucleotide
modified_base         35
                      mod_base = OTHER
                      note = 2'-O-methyl nucleotide
modified_base         36
                      mod_base = OTHER
                      note = 2'-O-methyl nucleotide
modified_base         37
                      mod_base = OTHER
                      note = 2'-O-methyl nucleotide
modified_base         38
                      mod_base = OTHER
                      note = 2'-O-methyl nucleotide
modified_base         39
                      mod_base = OTHER
                      note = 2'-O-methyl nucleotide
modified_base         40
                      mod_base = OTHER
                      note = 2'-O-methyl nucleotide
modified_base         41
                      mod_base = OTHER
                      note = 2'-O-methyl nucleotide
modified_base         42
                      mod_base = OTHER
                      note = 2'-O-methyl nucleotide
modified_base         46
                      mod_base = OTHER
                      note = 2'-O-methyl nucleotide
modified_base         48
                      mod_base = OTHER
                      note = 2'-O-methyl nucleotide
modified_base         50
                      mod_base = OTHER
                      note = 2'-O-methyl nucleotide
modified_base         52
                      mod_base = OTHER
                      note = 2'-O-methyl nucleotide
modified_base         53
                      mod_base = OTHER
                      note = 2'-O-methyl nucleotide
modified_base         54
                      mod_base = OTHER
                      note = 2'-O-methyl nucleotide
modified_base         55
                      mod_base = OTHER
                      note = 2'-O-methyl nucleotide
modified_base         56
                      mod_base = OTHER
                      note = 2'-O-methyl nucleotide
modified_base         57
                      mod_base = OTHER
                      note = 2'-O-methyl nucleotide
modified_base         60
                      mod_base = OTHER
                      note = 2'-O-methyl nucleotide
modified_base         61
                      mod_base = OTHER
                      note = 2'-O-methyl nucleotide
```

-continued

| | |
|---|---|
| modified_base | 66 |
| | mod_base = OTHER |
| | note = 2'-O-methyl nucleotide |
| modified_base | 67 |
| | mod_base = OTHER |
| | note = 2'-O-methyl nucleotide |
| modified_base | 70 |
| | mod_base = OTHER |
| | note = 2'-O-methyl nucleotide |
| modified_base | 71 |
| | mod_base = OTHER |
| | note = 2'-O-methyl nucleotide |
| modified_base | 72 |
| | mod_base = OTHER |
| | note = 2'-O-methyl nucleotide |
| modified_base | 73 |
| | mod_base = OTHER |
| | note = 2'-O-methyl nucleotide |
| modified_base | 74 |
| | mod_base = OTHER |
| | note = 2'-O-methyl nucleotide |
| modified_base | 75 |
| | mod_base = OTHER |
| | note = 2'-O-methyl nucleotide |
| modified_base | 76 |
| | mod_base = OTHER |
| | note = 2'-O-methyl nucleotide |
| modified_base | 77 |
| | mod_base = OTHER |
| | note = 2'-O-methyl nucleotide |
| modified_base | 78 |
| | mod_base = OTHER |
| | note = 2'-O-methyl nucleotide |
| modified_base | 79 |
| | mod_base = OTHER |
| | note = 2'-O-methyl nucleotide |
| modified_base | 80 |
| | mod_base = OTHER |
| | note = 2'-O-methyl nucleotide |
| modified_base | 81 |
| | mod_base = OTHER |
| | note = 2'-O-methyl nucleotide |
| modified_base | 83 |
| | mod_base = OTHER |
| | note = 2'-O-methyl nucleotide |
| modified_base | 84 |
| | mod_base = OTHER |
| | note = 2'-O-methyl nucleotide |
| modified_base | 85 |
| | mod_base = OTHER |
| | note = 2'-O-methyl nucleotide |
| modified_base | 86 |
| | mod_base = OTHER |
| | note = 2'-O-methyl nucleotide |
| modified_base | 87 |
| | mod_base = OTHER |
| | note = 2'-O-methyl nucleotide |
| modified_base | 88 |
| | mod_base = OTHER |
| | note = 2'-O-methyl nucleotide |
| modified_base | 89 |
| | mod_base = OTHER |
| | note = 2'-O-methyl nucleotide |
| modified_base | 90 |
| | mod_base = OTHER |
| | note = 2'-O-methyl nucleotide |
| modified_base | 91 |
| | mod_base = OTHER |
| | note = 2'-O-methyl nucleotide |
| modified_base | 92 |
| | mod_base = OTHER |
| | note = 2'-O-methyl nucleotide |
| modified_base | 93 |
| | mod_base = OTHER |
| | note = 2'-O-methyl nucleotide |
| modified_base | 94 |
| | mod_base = OTHER |
| | note = 2'-O-methyl nucleotide |
| modified_base | 95 |

```
                        mod_base = OTHER
                        note = 2'-O-methyl nucleotide
modified_base           96
                        mod_base = OTHER
                        note = 2'-O-methyl nucleotide
modified_base           97
                        mod_base = OTHER
                        note = 2'-O-methyl nucleotide with phosphorothioate linkage
modified_base           98
                        mod_base = OTHER
                        note = 2'-O-methyl nucleotide with phosphorothioate linkage
modified_base           99
                        mod_base = OTHER
                        note = 2'-O-methyl nucleotide with phosphorothioate linkage
modified_base           100
                        mod_base = OTHER
                        note = 2'-O-methyl nucleotide
SEQUENCE: 13
cccgcacctt ggcgcagcgg gttttagagc tagaaatagc aagttaaaat aaggctagtc   60
cgttatcaac ttgaaaaagt ggcaccgagt cggtgctttt                        100

SEQ ID NO: 14           moltype = RNA   length = 100
FEATURE                 Location/Qualifiers
source                  1..100
                        mol_type = other RNA
                        organism = synthetic construct
modified_base           1
                        mod_base = OTHER
                        note = 2'-O-methyl nucleotide with phosphorothioate linkage
modified_base           2
                        mod_base = OTHER
                        note = 2'-O-methyl nucleotide with phosphorothioate linkage
modified_base           3
                        mod_base = OTHER
                        note = 2'-O-methyl nucleotide with phosphorothioate linkage
modified_base           21
                        mod_base = OTHER
                        note = 2'-O-methyl nucleotide
modified_base           28
                        mod_base = OTHER
                        note = 2'-O-methyl nucleotide
modified_base           29
                        mod_base = OTHER
                        note = 2'-O-methyl nucleotide
modified_base           30
                        mod_base = OTHER
                        note = 2'-O-methyl nucleotide
modified_base           31
                        mod_base = OTHER
                        note = 2'-O-methyl nucleotide
modified_base           32
                        mod_base = OTHER
                        note = 2'-O-methyl nucleotide
modified_base           34
                        mod_base = OTHER
                        note = 2'-O-methyl nucleotide
modified_base           35
                        mod_base = OTHER
                        note = 2'-O-methyl nucleotide
modified_base           36
                        mod_base = OTHER
                        note = 2'-O-methyl nucleotide
modified_base           37
                        mod_base = OTHER
                        note = 2'-O-methyl nucleotide
modified_base           38
                        mod_base = OTHER
                        note = 2'-O-methyl nucleotide
modified_base           39
                        mod_base = OTHER
                        note = 2'-O-methyl nucleotide
modified_base           40
                        mod_base = OTHER
                        note = 2'-O-methyl nucleotide
modified_base           41
                        mod_base = OTHER
                        note = 2'-O-methyl nucleotide
modified_base           42
                        mod_base = OTHER
```

```
                        note = 2'-O-methyl nucleotide
modified_base           46
                        mod_base = OTHER
                        note = 2'-O-methyl nucleotide
modified_base           48
                        mod_base = OTHER
                        note = 2'-O-methyl nucleotide
modified_base           50
                        mod_base = OTHER
                        note = 2'-O-methyl nucleotide
modified_base           52
                        mod_base = OTHER
                        note = 2'-O-methyl nucleotide
modified_base           53
                        mod_base = OTHER
                        note = 2'-O-methyl nucleotide
modified_base           54
                        mod_base = OTHER
                        note = 2'-O-methyl nucleotide
modified_base           57
                        mod_base = OTHER
                        note = 2'-O-methyl nucleotide
modified_base           61
                        mod_base = OTHER
                        note = 2'-O-methyl nucleotide
modified_base           66
                        mod_base = OTHER
                        note = 2'-O-methyl nucleotide
modified_base           67
                        mod_base = OTHER
                        note = 2'-O-methyl nucleotide
modified_base           70
                        mod_base = OTHER
                        note = 2'-O-methyl nucleotide
modified_base           71
                        mod_base = OTHER
                        note = 2'-O-methyl nucleotide
modified_base           72
                        mod_base = OTHER
                        note = 2'-O-methyl nucleotide
modified_base           74
                        mod_base = OTHER
                        note = 2'-O-methyl nucleotide
modified_base           75
                        mod_base = OTHER
                        note = 2'-O-methyl nucleotide
modified_base           76
                        mod_base = OTHER
                        note = 2'-O-methyl nucleotide
modified_base           77
                        mod_base = OTHER
                        note = 2'-O-methyl nucleotide
modified_base           78
                        mod_base = OTHER
                        note = 2'-O-methyl nucleotide
modified_base           79
                        mod_base = OTHER
                        note = 2'-O-methyl nucleotide
modified_base           80
                        mod_base = OTHER
                        note = 2'-O-methyl nucleotide
modified_base           82
                        mod_base = OTHER
                        note = 2'-O-methyl nucleotide
modified_base           83
                        mod_base = OTHER
                        note = 2'-O-methyl nucleotide
modified_base           84
                        mod_base = OTHER
                        note = 2'-O-methyl nucleotide
modified_base           85
                        mod_base = OTHER
                        note = 2'-O-methyl nucleotide
modified_base           86
                        mod_base = OTHER
                        note = 2'-O-methyl nucleotide
modified_base           87
                        mod_base = OTHER
                        note = 2'-O-methyl nucleotide
```

```
modified_base          89
                       mod_base = OTHER
                       note = 2'-O-methyl nucleotide
modified_base          92
                       mod_base = OTHER
                       note = 2'-O-methyl nucleotide
modified_base          93
                       mod_base = OTHER
                       note = 2'-O-methyl nucleotide
modified_base          94
                       mod_base = OTHER
                       note = 2'-O-methyl nucleotide
modified_base          95
                       mod_base = OTHER
                       note = 2'-O-methyl nucleotide
modified_base          96
                       mod_base = OTHER
                       note = 2'-O-methyl nucleotide
modified_base          97
                       mod_base = OTHER
                       note = 2'-O-methyl nucleotide with phosphorothioate linkage
modified_base          98
                       mod_base = OTHER
                       note = 2'-O-methyl nucleotide with phosphorothioate linkage
modified_base          99
                       mod_base = OTHER
                       note = 2'-O-methyl nucleotide with phosphorothioate linkage
modified_base          100
                       mod_base = OTHER
                       note = 2'-O-methyl nucleotide
SEQUENCE: 14
gagatacctg agtaactttc gttttagagc tagaaatagc aagttaaaat aaggctagtc    60
cgttatcaac ttgaaaaagt ggcaccgagt cggtgctttt                         100

SEQ ID NO: 15          moltype = RNA  length = 100
FEATURE                Location/Qualifiers
source                 1..100
                       mol_type = other RNA
                       organism = synthetic construct
modified_base          1
                       mod_base = OTHER
                       note = 2'-O-methyl nucleotide with phosphorothioate linkage
modified_base          2
                       mod_base = OTHER
                       note = 2'-O-methyl nucleotide with phosphorothioate linkage
modified_base          3
                       mod_base = OTHER
                       note = 2'-O-methyl nucleotide with phosphorothioate linkage
modified_base          21
                       mod_base = OTHER
                       note = 2'-O-methyl nucleotide
modified_base          28
                       mod_base = OTHER
                       note = 2'-O-methyl nucleotide
modified_base          29
                       mod_base = OTHER
                       note = 2'-O-methyl nucleotide
modified_base          30
                       mod_base = OTHER
                       note = 2'-O-methyl nucleotide
modified_base          31
                       mod_base = OTHER
                       note = 2'-O-methyl nucleotide
modified_base          32
                       mod_base = OTHER
                       note = 2'-O-methyl nucleotide
modified_base          33
                       mod_base = OTHER
                       note = 2'-O-methyl nucleotide
modified_base          34
                       mod_base = OTHER
                       note = 2'-O-methyl nucleotide
modified_base          35
                       mod_base = OTHER
                       note = 2'-O-methyl nucleotide
modified_base          36
                       mod_base = OTHER
                       note = 2'-O-methyl nucleotide
modified_base          37
```

-continued

```
                        mod_base = OTHER
                        note = 2'-O-methyl nucleotide
modified_base           38
                        mod_base = OTHER
                        note = 2'-O-methyl nucleotide
modified_base           39
                        mod_base = OTHER
                        note = 2'-O-methyl nucleotide
modified_base           40
                        mod_base = OTHER
                        note = 2'-O-methyl nucleotide
modified_base           41
                        mod_base = OTHER
                        note = 2'-O-methyl nucleotide
modified_base           42
                        mod_base = OTHER
                        note = 2'-O-methyl nucleotide
modified_base           46
                        mod_base = OTHER
                        note = 2'-O-methyl nucleotide
modified_base           48
                        mod_base = OTHER
                        note = 2'-O-methyl nucleotide
modified_base           50
                        mod_base = OTHER
                        note = 2'-O-methyl nucleotide
modified_base           52
                        mod_base = OTHER
                        note = 2'-O-methyl nucleotide
modified_base           53
                        mod_base = OTHER
                        note = 2'-O-methyl nucleotide
modified_base           54
                        mod_base = OTHER
                        note = 2'-O-methyl nucleotide
modified_base           55
                        mod_base = OTHER
                        note = 2'-O-methyl nucleotide
modified_base           56
                        mod_base = OTHER
                        note = 2'-O-methyl nucleotide
modified_base           57
                        mod_base = OTHER
                        note = 2'-O-methyl nucleotide
modified_base           60
                        mod_base = OTHER
                        note = 2'-O-methyl nucleotide
modified_base           61
                        mod_base = OTHER
                        note = 2'-O-methyl nucleotide
modified_base           66
                        mod_base = OTHER
                        note = 2'-O-methyl nucleotide
modified_base           67
                        mod_base = OTHER
                        note = 2'-O-methyl nucleotide
modified_base           70
                        mod_base = OTHER
                        note = 2'-O-methyl nucleotide
modified_base           71
                        mod_base = OTHER
                        note = 2'-O-methyl nucleotide
modified_base           72
                        mod_base = OTHER
                        note = 2'-O-methyl nucleotide
modified_base           73
                        mod_base = OTHER
                        note = 2'-O-methyl nucleotide
modified_base           74
                        mod_base = OTHER
                        note = 2'-O-methyl nucleotide
modified_base           75
                        mod_base = OTHER
                        note = 2'-O-methyl nucleotide
modified_base           76
                        mod_base = OTHER
                        note = 2'-O-methyl nucleotide
modified_base           77
                        mod_base = OTHER
```

| | | |
|---|---|---|
| modified_base | 78 | |
| | mod_base = OTHER | |
| | note = 2'-O-methyl nucleotide | |
| modified_base | 79 | |
| | mod_base = OTHER | |
| | note = 2'-O-methyl nucleotide | |
| modified_base | 80 | |
| | mod_base = OTHER | |
| | note = 2'-O-methyl nucleotide | |
| modified_base | 81 | |
| | mod_base = OTHER | |
| | note = 2'-O-methyl nucleotide | |
| modified_base | 83 | |
| | mod_base = OTHER | |
| | note = 2'-O-methyl nucleotide | |
| modified_base | 84 | |
| | mod_base = OTHER | |
| | note = 2'-O-methyl nucleotide | |
| modified_base | 85 | |
| | mod_base = OTHER | |
| | note = 2'-O-methyl nucleotide | |
| modified_base | 86 | |
| | mod_base = OTHER | |
| | note = 2'-O-methyl nucleotide | |
| modified_base | 87 | |
| | mod_base = OTHER | |
| | note = 2'-O-methyl nucleotide | |
| modified_base | 88 | |
| | mod_base = OTHER | |
| | note = 2'-O-methyl nucleotide | |
| modified_base | 89 | |
| | mod_base = OTHER | |
| | note = 2'-O-methyl nucleotide | |
| modified_base | 90 | |
| | mod_base = OTHER | |
| | note = 2'-O-methyl nucleotide | |
| modified_base | 91 | |
| | mod_base = OTHER | |
| | note = 2'-O-methyl nucleotide | |
| modified_base | 92 | |
| | mod_base = OTHER | |
| | note = 2'-O-methyl nucleotide | |
| modified_base | 93 | |
| | mod_base = OTHER | |
| | note = 2'-O-methyl nucleotide | |
| modified_base | 94 | |
| | mod_base = OTHER | |
| | note = 2'-O-methyl nucleotide | |
| modified_base | 95 | |
| | mod_base = OTHER | |
| | note = 2'-O-methyl nucleotide | |
| modified_base | 96 | |
| | mod_base = OTHER | |
| | note = 2'-O-methyl nucleotide | |
| modified_base | 97 | |
| | mod_base = OTHER | |
| | note = 2'-O-methyl nucleotide with phosphorothioate linkage | |
| modified_base | 98 | |
| | mod_base = OTHER | |
| | note = 2'-O-methyl nucleotide with phosphorothioate linkage | |
| modified_base | 99 | |
| | mod_base = OTHER | |
| | note = 2'-O-methyl nucleotide with phosphorothioate linkage | |
| modified_base | 100 | |
| | mod_base = OTHER | |
| | note = 2'-O-methyl nucleotide | |
| SEQUENCE: 15 | | |

```
gagatacctg agtaactttc gttttagagc tagaaatagc aagttaaaat aaggctagtc   60
cgttatcaac ttgaaaaagt ggcaccgagt cggtgctttt                        100
```

| | | |
|---|---|---|
| SEQ ID NO: 16 | moltype = RNA   length = 100 | |
| FEATURE | Location/Qualifiers | |
| source | 1..100 | |
| | mol_type = other RNA | |
| | organism = synthetic construct | |
| modified_base | 1 | |
| | mod_base = OTHER | |
| | note = 2'-O-methyl nucleotide with phosphorothioate linkage | |

```
modified_base      2
                   mod_base = OTHER
                   note = 2'-O-methyl nucleotide with phosphorothioate linkage
modified_base      3
                   mod_base = OTHER
                   note = 2'-O-methyl nucleotide with phosphorothioate linkage
modified_base      21
                   mod_base = OTHER
                   note = 2'-O-methyl nucleotide
modified_base      28
                   mod_base = OTHER
                   note = 2'-O-methyl nucleotide
modified_base      29
                   mod_base = OTHER
                   note = 2'-O-methyl nucleotide
modified_base      30
                   mod_base = OTHER
                   note = 2'-O-methyl nucleotide
modified_base      31
                   mod_base = OTHER
                   note = 2'-O-methyl nucleotide
modified_base      32
                   mod_base = OTHER
                   note = 2'-O-methyl nucleotide
modified_base      34
                   mod_base = OTHER
                   note = 2'-O-methyl nucleotide
modified_base      35
                   mod_base = OTHER
                   note = 2'-O-methyl nucleotide
modified_base      36
                   mod_base = OTHER
                   note = 2'-O-methyl nucleotide
modified_base      37
                   mod_base = OTHER
                   note = 2'-O-methyl nucleotide
modified_base      38
                   mod_base = OTHER
                   note = 2'-O-methyl nucleotide
modified_base      39
                   mod_base = OTHER
                   note = 2'-O-methyl nucleotide
modified_base      40
                   mod_base = OTHER
                   note = 2'-O-methyl nucleotide
modified_base      41
                   mod_base = OTHER
                   note = 2'-O-methyl nucleotide
modified_base      42
                   mod_base = OTHER
                   note = 2'-O-methyl nucleotide
modified_base      46
                   mod_base = OTHER
                   note = 2'-O-methyl nucleotide
modified_base      48
                   mod_base = OTHER
                   note = 2'-O-methyl nucleotide
modified_base      50
                   mod_base = OTHER
                   note = 2'-O-methyl nucleotide
modified_base      52
                   mod_base = OTHER
                   note = 2'-O-methyl nucleotide
modified_base      53
                   mod_base = OTHER
                   note = 2'-O-methyl nucleotide
modified_base      54
                   mod_base = OTHER
                   note = 2'-O-methyl nucleotide
modified_base      55
                   mod_base = OTHER
                   note = 2'-O-methyl nucleotide
modified_base      56
                   mod_base = OTHER
                   note = 2'-O-methyl nucleotide
modified_base      57
                   mod_base = OTHER
                   note = 2'-O-methyl nucleotide
modified_base      60
```

-continued

```
                        mod_base = OTHER
                        note = 2'-O-methyl nucleotide
modified_base           61
                        mod_base = OTHER
                        note = 2'-O-methyl nucleotide
modified_base           66
                        mod_base = OTHER
                        note = 2'-O-methyl nucleotide
modified_base           67
                        mod_base = OTHER
                        note = 2'-O-methyl nucleotide
modified_base           70
                        mod_base = OTHER
                        note = 2'-O-methyl nucleotide
modified_base           71
                        mod_base = OTHER
                        note = 2'-O-methyl nucleotide
modified_base           72
                        mod_base = OTHER
                        note = 2'-O-methyl nucleotide
modified_base           74
                        mod_base = OTHER
                        note = 2'-O-methyl nucleotide
modified_base           75
                        mod_base = OTHER
                        note = 2'-O-methyl nucleotide
modified_base           76
                        mod_base = OTHER
                        note = 2'-O-methyl nucleotide
modified_base           77
                        mod_base = OTHER
                        note = 2'-O-methyl nucleotide
modified_base           78
                        mod_base = OTHER
                        note = 2'-O-methyl nucleotide
modified_base           79
                        mod_base = OTHER
                        note = 2'-O-methyl nucleotide
modified_base           80
                        mod_base = OTHER
                        note = 2'-O-methyl nucleotide
modified_base           81
                        mod_base = OTHER
                        note = 2'-O-methyl nucleotide
modified_base           83
                        mod_base = OTHER
                        note = 2'-O-methyl nucleotide
modified_base           84
                        mod_base = OTHER
                        note = 2'-O-methyl nucleotide
modified_base           85
                        mod_base = OTHER
                        note = 2'-O-methyl nucleotide
modified_base           86
                        mod_base = OTHER
                        note = 2'-O-methyl nucleotide
modified_base           87
                        mod_base = OTHER
                        note = 2'-O-methyl nucleotide
modified_base           88
                        mod_base = OTHER
                        note = 2'-O-methyl nucleotide
modified_base           89
                        mod_base = OTHER
                        note = 2'-O-methyl nucleotide
modified_base           90
                        mod_base = OTHER
                        note = 2'-O-methyl nucleotide
modified_base           91
                        mod_base = OTHER
                        note = 2'-O-methyl nucleotide
modified_base           92
                        mod_base = OTHER
                        note = 2'-O-methyl nucleotide
modified_base           93
                        mod_base = OTHER
                        note = 2'-O-methyl nucleotide
modified_base           94
                        mod_base = OTHER
```

```
                    note = 2'-O-methyl nucleotide
modified_base       95
                    mod_base = OTHER
                    note = 2'-O-methyl nucleotide
modified_base       96
                    mod_base = OTHER
                    note = 2'-O-methyl nucleotide
modified_base       97
                    mod_base = OTHER
                    note = 2'-O-methyl nucleotide with phosphorothioate linkage
modified_base       98
                    mod_base = OTHER
                    note = 2'-O-methyl nucleotide with phosphorothioate linkage
modified_base       99
                    mod_base = OTHER
                    note = 2'-O-methyl nucleotide with phosphorothioate linkage
modified_base       100
                    mod_base = OTHER
                    note = 2'-O-methyl nucleotide
SEQUENCE: 16
gagatacctg agtaactttc gttttagagc tagaaatagc aagttaaaat aaggctagtc   60
cgttatcaac ttgaaaaagt ggcaccgagt cggtgctttt                        100

SEQ ID NO: 17           moltype = RNA  length = 100
FEATURE                 Location/Qualifiers
source                  1..100
                        mol_type = other RNA
                        organism = synthetic construct
modified_base           1
                        mod_base = OTHER
                        note = 2'-O-methyl nucleotide with phosphorothioate linkage
modified_base           2
                        mod_base = OTHER
                        note = 2'-O-methyl nucleotide with phosphorothioate linkage
modified_base           3
                        mod_base = OTHER
                        note = 2'-O-methyl nucleotide with phosphorothioate linkage
modified_base           29
                        mod_base = OTHER
                        note = 2'-O-methyl nucleotide
modified_base           30
                        mod_base = OTHER
                        note = 2'-O-methyl nucleotide
modified_base           31
                        mod_base = OTHER
                        note = 2'-O-methyl nucleotide
modified_base           32
                        mod_base = OTHER
                        note = 2'-O-methyl nucleotide
modified_base           33
                        mod_base = OTHER
                        note = 2'-O-methyl nucleotide
modified_base           34
                        mod_base = OTHER
                        note = 2'-O-methyl nucleotide
modified_base           35
                        mod_base = OTHER
                        note = 2'-O-methyl nucleotide
modified_base           36
                        mod_base = OTHER
                        note = 2'-O-methyl nucleotide
modified_base           37
                        mod_base = OTHER
                        note = 2'-O-methyl nucleotide
modified_base           38
                        mod_base = OTHER
                        note = 2'-O-methyl nucleotide
modified_base           39
                        mod_base = OTHER
                        note = 2'-O-methyl nucleotide
modified_base           40
                        mod_base = OTHER
                        note = 2'-O-methyl nucleotide
modified_base           69
                        mod_base = OTHER
                        note = 2'-O-methyl nucleotide
modified_base           70
                        mod_base = OTHER
                        note = 2'-O-methyl nucleotide
```

| | | |
|---|---|---|
| modified_base | 71 | |
| | mod_base = OTHER | |
| | note = 2'-O-methyl nucleotide | |
| modified_base | 72 | |
| | mod_base = OTHER | |
| | note = 2'-O-methyl nucleotide | |
| modified_base | 73 | |
| | mod_base = OTHER | |
| | note = 2'-O-methyl nucleotide | |
| modified_base | 74 | |
| | mod_base = OTHER | |
| | note = 2'-O-methyl nucleotide | |
| modified_base | 75 | |
| | mod_base = OTHER | |
| | note = 2'-O-methyl nucleotide | |
| modified_base | 76 | |
| | mod_base = OTHER | |
| | note = 2'-O-methyl nucleotide | |
| modified_base | 77 | |
| | mod_base = OTHER | |
| | note = 2'-O-methyl nucleotide | |
| modified_base | 78 | |
| | mod_base = OTHER | |
| | note = 2'-O-methyl nucleotide | |
| modified_base | 79 | |
| | mod_base = OTHER | |
| | note = 2'-O-methyl nucleotide | |
| modified_base | 80 | |
| | mod_base = OTHER | |
| | note = 2'-O-methyl nucleotide | |
| modified_base | 81 | |
| | mod_base = OTHER | |
| | note = 2'-O-methyl nucleotide | |
| modified_base | 82 | |
| | mod_base = OTHER | |
| | note = 2'-O-methyl nucleotide | |
| modified_base | 83 | |
| | mod_base = OTHER | |
| | note = 2'-O-methyl nucleotide | |
| modified_base | 84 | |
| | mod_base = OTHER | |
| | note = 2'-O-methyl nucleotide | |
| modified_base | 85 | |
| | mod_base = OTHER | |
| | note = 2'-O-methyl nucleotide | |
| modified_base | 86 | |
| | mod_base = OTHER | |
| | note = 2'-O-methyl nucleotide | |
| modified_base | 87 | |
| | mod_base = OTHER | |
| | note = 2'-O-methyl nucleotide | |
| modified_base | 88 | |
| | mod_base = OTHER | |
| | note = 2'-O-methyl nucleotide | |
| modified_base | 89 | |
| | mod_base = OTHER | |
| | note = 2'-O-methyl nucleotide | |
| modified_base | 90 | |
| | mod_base = OTHER | |
| | note = 2'-O-methyl nucleotide | |
| modified_base | 91 | |
| | mod_base = OTHER | |
| | note = 2'-O-methyl nucleotide | |
| modified_base | 92 | |
| | mod_base = OTHER | |
| | note = 2'-O-methyl nucleotide | |
| modified_base | 93 | |
| | mod_base = OTHER | |
| | note = 2'-O-methyl nucleotide | |
| modified_base | 94 | |
| | mod_base = OTHER | |
| | note = 2'-O-methyl nucleotide | |
| modified_base | 95 | |
| | mod_base = OTHER | |
| | note = 2'-O-methyl nucleotide | |
| modified_base | 96 | |
| | mod_base = OTHER | |
| | note = 2'-O-methyl nucleotide | |
| modified_base | 97 | |

```
                              mod_base = OTHER
                              note = 2'-O-methyl nucleotide with phosphorothioate linkage
modified_base                 98
                              mod_base = OTHER
                              note = 2'-O-methyl nucleotide with phosphorothioate linkage
modified_base                 99
                              mod_base = OTHER
                              note = 2'-O-methyl nucleotide with phosphorothioate linkage
modified_base                 100
                              mod_base = OTHER
                              note = 2'-O-methyl nucleotide
SEQUENCE: 17
aagatacctg aataactctc gttttagagc tagaaatagc aagttaaaat aaggctagtc    60
cgttatcaac ttgaaaaagt ggcaccgagt cggtgctttt                         100

SEQ ID NO: 18                 moltype = RNA   length = 100
FEATURE                       Location/Qualifiers
source                        1..100
                              mol_type = other RNA
                              organism = synthetic construct
modified_base                 1
                              mod_base = OTHER
                              note = 2'-O-methyl nucleotide with phosphorothioate linkage
modified_base                 2
                              mod_base = OTHER
                              note = 2'-O-methyl nucleotide with phosphorothioate linkage
modified_base                 3
                              mod_base = OTHER
                              note = 2'-O-methyl nucleotide with phosphorothioate linkage
modified_base                 21
                              mod_base = OTHER
                              note = 2'-O-methyl nucleotide
modified_base                 28
                              mod_base = OTHER
                              note = 2'-O-methyl nucleotide
modified_base                 29
                              mod_base = OTHER
                              note = 2'-O-methyl nucleotide
modified_base                 30
                              mod_base = OTHER
                              note = 2'-O-methyl nucleotide
modified_base                 31
                              mod_base = OTHER
                              note = 2'-O-methyl nucleotide
modified_base                 32
                              mod_base = OTHER
                              note = 2'-O-methyl nucleotide
modified_base                 34
                              mod_base = OTHER
                              note = 2'-O-methyl nucleotide
modified_base                 35
                              mod_base = OTHER
                              note = 2'-O-methyl nucleotide
modified_base                 36
                              mod_base = OTHER
                              note = 2'-O-methyl nucleotide
modified_base                 37
                              mod_base = OTHER
                              note = 2'-O-methyl nucleotide
modified_base                 38
                              mod_base = OTHER
                              note = 2'-O-methyl nucleotide
modified_base                 39
                              mod_base = OTHER
                              note = 2'-O-methyl nucleotide
modified_base                 40
                              mod_base = OTHER
                              note = 2'-O-methyl nucleotide
modified_base                 41
                              mod_base = OTHER
                              note = 2'-O-methyl nucleotide
modified_base                 42
                              mod_base = OTHER
                              note = 2'-O-methyl nucleotide
modified_base                 46
                              mod_base = OTHER
                              note = 2'-O-methyl nucleotide
modified_base                 48
                              mod_base = OTHER
```

|  |  |
|---|---|
| modified_base | note = 2'-O-methyl nucleotide 50 |
|  | mod_base = OTHER |
|  | note = 2'-O-methyl nucleotide |
| modified_base | 52 |
|  | mod_base = OTHER |
|  | note = 2'-O-methyl nucleotide |
| modified_base | 53 |
|  | mod_base = OTHER |
|  | note = 2'-O-methyl nucleotide |
| modified_base | 54 |
|  | mod_base = OTHER |
|  | note = 2'-O-methyl nucleotide |
| modified_base | 55 |
|  | mod_base = OTHER |
|  | note = 2'-O-methyl nucleotide |
| modified_base | 56 |
|  | mod_base = OTHER |
|  | note = 2'-O-methyl nucleotide |
| modified_base | 57 |
|  | mod_base = OTHER |
|  | note = 2'-O-methyl nucleotide |
| modified_base | 60 |
|  | mod_base = OTHER |
|  | note = 2'-O-methyl nucleotide |
| modified_base | 61 |
|  | mod_base = OTHER |
|  | note = 2'-O-methyl nucleotide |
| modified_base | 66 |
|  | mod_base = OTHER |
|  | note = 2'-O-methyl nucleotide |
| modified_base | 67 |
|  | mod_base = OTHER |
|  | note = 2'-O-methyl nucleotide |
| modified_base | 70 |
|  | mod_base = OTHER |
|  | note = 2'-O-methyl nucleotide |
| modified_base | 71 |
|  | mod_base = OTHER |
|  | note = 2'-O-methyl nucleotide |
| modified_base | 72 |
|  | mod_base = OTHER |
|  | note = 2'-O-methyl nucleotide |
| modified_base | 74 |
|  | mod_base = OTHER |
|  | note = 2'-O-methyl nucleotide |
| modified_base | 75 |
|  | mod_base = OTHER |
|  | note = 2'-O-methyl nucleotide |
| modified_base | 76 |
|  | mod_base = OTHER |
|  | note = 2'-O-methyl nucleotide |
| modified_base | 77 |
|  | mod_base = OTHER |
|  | note = 2'-O-methyl nucleotide |
| modified_base | 78 |
|  | mod_base = OTHER |
|  | note = 2'-O-methyl nucleotide |
| modified_base | 79 |
|  | mod_base = OTHER |
|  | note = 2'-O-methyl nucleotide |
| modified_base | 80 |
|  | mod_base = OTHER |
|  | note = 2'-O-methyl nucleotide |
| modified_base | 81 |
|  | mod_base = OTHER |
|  | note = 2'-O-methyl nucleotide |
| modified_base | 83 |
|  | mod_base = OTHER |
|  | note = 2'-O-methyl nucleotide |
| modified_base | 84 |
|  | mod_base = OTHER |
|  | note = 2'-O-methyl nucleotide |
| modified_base | 85 |
|  | mod_base = OTHER |
|  | note = 2'-O-methyl nucleotide |
| modified_base | 86 |
|  | mod_base = OTHER |
|  | note = 2'-O-methyl nucleotide |

471 472
-continued

```
modified_base        87
                     mod_base = OTHER
                     note = 2'-O-methyl nucleotide
modified_base        88
                     mod_base = OTHER
                     note = 2'-O-methyl nucleotide
modified_base        89
                     mod_base = OTHER
                     note = 2'-O-methyl nucleotide
modified_base        90
                     mod_base = OTHER
                     note = 2'-O-methyl nucleotide
modified_base        91
                     mod_base = OTHER
                     note = 2'-O-methyl nucleotide
modified_base        92
                     mod_base = OTHER
                     note = 2'-O-methyl nucleotide
modified_base        93
                     mod_base = OTHER
                     note = 2'-O-methyl nucleotide
modified_base        94
                     mod_base = OTHER
                     note = 2'-O-methyl nucleotide
modified_base        95
                     mod_base = OTHER
                     note = 2'-O-methyl nucleotide
modified_base        96
                     mod_base = OTHER
                     note = 2'-O-methyl nucleotide
modified_base        97
                     mod_base = OTHER
                     note = 2'-O-methyl nucleotide with phosphorothioate linkage
modified_base        98
                     mod_base = OTHER
                     note = 2'-O-methyl nucleotide with phosphorothioate linkage
modified_base        99
                     mod_base = OTHER
                     note = 2'-O-methyl nucleotide with phosphorothioate linkage
modified_base        100
                     mod_base = OTHER
                     note = 2'-O-methyl nucleotide
SEQUENCE: 18
aagatacctg aataactctc gttttagagc tagaaatagc aagttaaaat aaggctagtc   60
cgttatcaac ttgaaaaagt ggcaccgagt cggtgctttt                        100

SEQ ID NO: 19        moltype = DNA   length = 9528
FEATURE              Location/Qualifiers
source               1..9528
                     mol_type = other DNA
                     organism = synthetic construct
modified_base        367
                     mod_base = OTHER
                     note = 2'-O-methyl modified nucleotide
modified_base        368
                     mod_base = OTHER
                     note = 2'-O-methyl modified nucleotide
modified_base        369
                     mod_base = OTHER
                     note = 2'-O-methyl modified nucleotide
modified_base        439
                     mod_base = OTHER
                     note = 2'-O-methyl modified nucleotide
modified_base        440
                     mod_base = OTHER
                     note = 2'-O-methyl modified nucleotide
modified_base        441
                     mod_base = OTHER
                     note = 2'-O-methyl modified nucleotide
modified_base        456
                     mod_base = OTHER
                     note = 2'-O-methyl modified nucleotide
modified_base        460
                     mod_base = OTHER
                     note = 2'-O-methyl modified nucleotide
modified_base        461
                     mod_base = OTHER
                     note = 2'-O-methyl modified nucleotide
modified_base        462
```

| | | |
|---|---|---|
| modified_base | | 5131 |
| | mod_base = OTHER | |
| | note = 2'-O-methyl modified nucleotide | |
| modified_base | | 5132 |
| | mod_base = OTHER | |
| | note = 2'-O-methyl modified nucleotide | |
| modified_base | | 5133 |
| | mod_base = OTHER | |
| | note = 2'-O-methyl modified nucleotide | |
| modified_base | | 5203 |
| | mod_base = OTHER | |
| | note = 2'-O-methyl modified nucleotide | |
| modified_base | | 5204 |
| | mod_base = OTHER | |
| | note = 2'-O-methyl modified nucleotide | |
| modified_base | | 5205 |
| | mod_base = OTHER | |
| | note = 2'-O-methyl modified nucleotide | |
| modified_base | | 5220 |
| | mod_base = OTHER | |
| | note = 2'-O-methyl modified nucleotide | |
| modified_base | | 5224 |
| | mod_base = OTHER | |
| | note = 2'-O-methyl modified nucleotide | |
| modified_base | | 5225 |
| | mod_base = OTHER | |
| | note = 2'-O-methyl modified nucleotide | |
| modified_base | | 5226 |
| | mod_base = OTHER | |
| | note = 2'-O-methyl modified nucleotide | |

SEQUENCE: 19

```
atgagcgagg tcgagttctc tcacgaatat tggatgagac acgctctcac cctggctaag    60
agagccaggg acgaaagaga ggtgccagtt ggcgctgtcc tggtgttgaa caatcgcgtc   120
atcggagaag gatggaatcg cgccattggc ctgcacgatc aaccgcaca tgccgaaatt   180
atggctctgc ggcaaggcgg cctcgtgatg caaaattaca gactgatcga tgctaccctc   240
tacgtcacct tcgagccctg tgtcatgtgt gctggggcaa tgattcactc ccggattggc   300
cgcgtggtgt ttggagtgcg gaatgccaag actggcgccg ctggatctct gatgacgtc   360
ctgcaccatc ctgggatgaa ccaccgggtc gagatcacag agggaattct ggctgacgag   420
tgcgctgccc tgctgtgcag gttctttaga atgcctagaa gggtgttcaa cgcccagaaa   480
aaagctcaga gcagcaccga ttccggcgga agcagcggag gatcttctgg aagcgaaacc   540
ccaggcacca gcgagtctgc cacaccagaa tcatctccgg gtagctccgg cggcagcgac   600
aagaagtatt ctatcggact ggccatcggc accaactctg ttggatgggc cgtgatcacc   660
gacgagtaca aggtgcccag caagaaattc aaggtgctgg gcaacaccga caggcacagc   720
atcaagaaga acctgatcgg cgcactgctg ttcgactctg gcgaaacagc cgaggccacc   780
agactgaaga acagcccgc cagacggtac accagaagaa agaaccggat ctgctacctc   840
caagagatct tcagcaacga gatggccaag gtggacgaca gcttcttcca cagactggaa   900
gagtccttcc tggtggaaga ggacaagaag cacgagagac ccccatctt cggcaacatc   960
gtggacgagg tggcctacca cgagaagtac cccaccatct accacctgag aaagaaactg  1020
gtggacagca ccgacaaggc cgacctgaga ctgatctatc tggccctggc tcacatgatc  1080
aagttccggg gccacttcct gatcgaggc gacctgaatc ctgacaacag cgacgtggac  1140
aagctgttca tccagctggt gcagacctac aaccagctgt tcgaggaaaa ccccatcaac  1200
gccagcggag tggatgccaa ggccatcctg tctgccagac tgagcaagag cagacggctg  1260
gaaaatctga tcgcccagct gcctggcgag aagaagaatg gcctgttcgg caacctgatt  1320
gccctgagcc tgggcctgac acctaacttc aagagcaact tcgacctggc cgaggacgcc  1380
aaactgcagc tgagcaagga cacctacgac gacgacctgg acaatctgct ggcccagatc  1440
ggcgatcagt acgccgactt gtttctggcc gccaagaatc tgagcgacgc catcctgctg  1500
tccgacatcc tgagagtgaa caccgagatc accaaggcac ctctgagcgc ctctatgatc  1560
aagagatacg acgagcacca ccaggatctg accctgctga aggccctcgt tagacacag  1620
ctgccagaga agtacaaaga gatttcttc gaccagagca agaacggcta cgccggctac  1680
attgatggcg gagccagcca agaggaattc tacaagttca tcaagcccat cctcgagaag  1740
atggacggca ccgaggaact gctggtcaag ctgaacagag gacctgct gagaaagcag  1800
agaaccttcg acaacggcag catccctcac cagatccacc tgggagaact gcacgccatt  1860
ctgcggagac aagaggactt ttacccattc ctgaaggaca accggggaaa gatcgagaaa  1920
atcctgacct tcaggatccc ctactacgtg ggaccactgg ccagaggcaa tagcagattc  1980
gcctggatga ccagaaagag cgaggaaacc atcactccct ggaacttcga ggaagtggtg  2040
gacaaggcc ccagcgctca gtccttcatc gagcggatga ccaacttcga taagaacctg  2100
cctaacgaga aggtgctgcc caagcacagc ctgctgtacg agtacttcac cgtgtacaac  2160
gagctgacca aagtgaaata cgtgaccgag ggaatgagaa agcccgcctt tctgagcggc  2220
gagcagaaaa aggccatcgt ggatctgctg ttcaagacca ccggaaagt gaccgtgaag  2280
cagctgaaag gactactt caagaaaatc gagtgcttcg acagcgtcga gatctccggc  2340
gtggaagatc ggttcaatgc cagcctgggc acataccacg atctgctgaa aattatcaag  2400
gacaaggact tcctggacaa cgaagagaac gaggacatct tgaggacat cgtgctgaca  2460
ctgaccctgt tgaggacag agagatgatc gaggaacggc tgaaacata cgcccacctg  2520
ttcgacgaca aagtgatgaa gcaactgaag cggcggagat acaccggctg gggcagactg  2580
tctcggaagc tgatcaacgg catccggat aagcagtccg gcaagaccat cctgacttt  2640
ctgaagtccg acggcttcgc caacagaaac ttcatgcagc tgattcacga cgacagcctc  2700
accttcaaag aggatatcca gaaagcccag gtgtccggc agggcgattc tctgcatgag  2760
```

```
cacattgcca acctggccgg ctctcccgcc attaagaaag gcatcctgca gacagtgaag   2820
gtggtggacg agcttgtgaa agtgatgggc agacacaagc ccgagaacat cgtgatcgaa   2880
atggccagag agaaccagac cacacagaag ggacagaaga acagccgcga gagaatgaag   2940
cggatcgaag agggcatcaa agagctgggc agccagatcc tgaaagaaca ccccgtggaa   3000
aacacccagc tgcagaacga gaagctgtac ctgtactacc tgcagaatgg acgggatatg   3060
tacgtggacc aagagctgga catcaacaga ctgtccgact acgatgtgga ccatatcgtg   3120
ccccagtctt ttctgaagga cgactccatc gacaacaagg tcctgaccag atccgacaag   3180
aatcggggca gagcgacaa cgtgccctcc aagaggtgg tcaagaagat gaagaactac   3240
tggcgacgag tgctgaacgc caagctgatt acccagcgga agttcgacaa tctgaccaag   3300
gccgaaagag gcggcctgag cgaactggat aaggccggct tcatcaagag acagctggtg   3360
gaaacccggc agatcacaaa gcacgtggca cagattctgg actctcggat gaacactaag   3420
tacgacgaga acgacaaact gatccgcgaa gtgaaagtca tcaccctgaa gtccaagctg   3480
gtgtccgatt tccggaagga tttccagttc tacaaagtgc gcgagatcaa caactaccct   3540
cacgcccacg acgcctacct gaatgccgtt gttggaacag ccctgatcaa aaagtaccct   3600
aagctggaaa gcgagttcgt gtacggcgac tacaaggtgt acgacgtgcg gaagatgatc   3660
gccaagagcg agcaagagat tggcaaggca accgccaagt acttcttcta cagcaacatc   3720
atgaactttt tcaagacaga gatcaccctc gccaacggcg agatcagaaa gcggcctctg   3780
atcgagacaa acggcgaaac cggcgagatt gtgtgggata agggcagaga cttttgccaca   3840
gtgcggaaag tgctgagcat gccccaagtg aatatcgtga agaaaaccga ggtgcagaca   3900
ggcggcttca gcaaagagtc tatcctgcct aagcggaact ccgacaagct gatcgcccaga   3960
aagaaggact gggaccccaa gaagtacggc ggcttcgatt ctcctaccgt ggcctatagc   4020
gtgctggtgg tggccaaagt ggaaaagggc aagtccaaga actcaagag cgtgaaagag   4080
ctgctgggga tcaccatcat ggaagaagc agcttcgaga agaatccgat cgatttcctc   4140
gaggccaagg gctacaaaga agtgaaaaag gacctgatca tcaagctccc caagtactcc   4200
ctgttcgagc tggaaaacgg ccggaagaga atgctggcct ctgctggcga actgcagaag   4260
ggaaacgaac tggccctgcc tagcaaatat gtgaacttcc tgtacctggc cagccactat   4320
gagaagctga agggcagccc ccggagacaat gagcaaaagc agctgttttgt ggaacagcac   4380
aagcactacc tggacgagat catcgagcag atcagcgagt ttagcaagag agtgattctg   4440
gccgacgcca atctggacaa agtgctgtcc gcctacaaca gcaccggga caagcctatc   4500
agagagcagg ccgagaatat catccacctg tttacccctga ccaacctgga agccctcgg   4560
gccttcaagt actttgacac caccatcgac cggaagcggt acacctccac caaagaggtg   4620
ctggacgcca ctctgatcca ccagtctatc accggcctgt acgagacacg gatcgacctg   4680
tctcaactcg gaggcgacga aggcgccgat aagagaaccg ccgatggctc tgagttcgag   4740
agcccaaga aaaagcgcaa agtgatgagc gaggtcgagt tctctctcacga atattggatg   4800
agacacgctc tcaccctggc taagagagcc agggacgaaa gagaggtgcc agttggcgct   4860
gtcctggtgt tgaacaatcg cgtcatcgga gaaggatgga tcgcgccat ggcctgcac   4920
gatccaaccg cacatgccga aattatggct ctgcggcaag cggcctcgt gatgcaaat   4980
tacagactga tcgatgctac cctctacgtc accttcgagc cctgtgtcat gtgtgctggg   5040
gcaatgatt actcccggat tggccgcgtg gtgtttgaga tgcggaatgc caagactgc   5100
gccgctggat ctctgatgga cgtcctgcac catcctggga tgaaccaccg ggtcgagatc   5160
acagagggaa ttctgctga cgagtgcgct gccctgctgt gcaggttctt tagaatgcct   5220
agaagggtgt tcaacgccca gaaaaaagct cagagcagca ccgattccgg cggaagcagc   5280
ggaggatctt ctggaagcga aaccccaggc accagcagt ctgccacacc agaatcatct   5340
ggcgtagct ccggcggcag cgacaagaag tattctatcg gactggccat cggcaccaac   5400
tctgttggat gggccgtgat caccgacgag tacaaggtgc ccagcaagaa attcaaggtg   5460
ctgggcaaca ccgacaggca cagcatcaag aagaacctga tcggcgcact gctgttcgac   5520
tctggggaaa cagccgaggc caccagactg aagagaacag cccgcagacg gtacaccaga   5580
agaaagaacc ggatctgcta cctccaagag atcttcagca acgagatggc caaggtggac   5640
gacagcttct tccacagact ggaagagtcc ttcctggtgg aagaggacaa gaagcacgag   5700
agacacccca tcttcggcaa catcgtggac gaggtggcct accacgagaa gtaccccacc   5760
atctaccacc tgagaaagaa actggtggac agcaccgaca aggccgacct gagactgatc   5820
tatctggccc tggctcacat gatcaagttc cggggccact tcctgatcga gggcgacctg   5880
aatcctgaca cagcgacgt ggacaagctg ttcatccagc tggtgcagac ctacaaccag   5940
ctgttcgagg aaaaccccat caacgccagc ggagtggatg ccaaggccat cctgtctgcc   6000
agactgagca agagcagacg gctggaaaat ctgatcgccc agctgcctgg cgagaagaag   6060
aatggcctgt tcggcaacct gattgccctg agcctgggcc tgacacctaa cttcaagagc   6120
aacttcgacc tggccgagga cgccaaactg cagctgagca aggacaccta cgacgacgac   6180
ctggacaatc tgctggccca gatcggcgat cagtacgccg acttgtttct ggccgccaag   6240
aatctgagcg acgccatcct gctgtccgac atcctgagag tgaacaccga gatcaccaag   6300
gcacctctga gcgcctctat gatcaagaga tacgacgagc accaccagga tctgaccctg   6360
ctgaaggccc tcgttagaca gcagctgcca gagaagtaca aagagatttt cttcgaccag   6420
agcaagaacg gctacgccgg ctacattgat ggcggagcca gccaagagga attctacaag   6480
ttcatcaagc ccatcctcga gaagatggac ggcaccgagg aactgctggt caagctgaac   6540
agagaggacc tgctgagaaa gcagagaacc ttcgacaacg gcagcatccc tcaccagatc   6600
cacctgggag aactgcacgc cattctgcgc agacaagagg acttttaccc attcctgaag   6660
gacaaccggg aaaagatcga gaaaatcctg accttcagga tccccctacta cgtgggaccca   6720
ctggccagag gcaatagcag attcgcctgg atgaccagaa agagcgagga aaccatcact   6780
ccctggaact tcgaggaagt ggtggacaag ggcgccagcg ctcagtcctt catcgagcgg   6840
atgaccaact tcgataagaa cctgcctaac gagaaggtgc tgcccaagca cagcctgctg   6900
tacgagtact tcaccgtgta caacgagctg accaaagtga aatacgtgac cgagggaatg   6960
agaaagcccg cctttctgag cggcgagcag aaaaaggcca tcgtggatct gctgttcaag   7020
accaaccgga aagtgaccgt gaagcagctg aaagaggact acttcaagaa aatcgagtgc   7080
ttcgacagcg tcgagatctc cggcgtggaa gatcggttca atgccagcct gggcacatac   7140
catgatctgc tgaaaattat caaggacaag gacttcctgg acaacgagga gaacgaggac   7200
atccttgagg acatcgtgct gacactgacc ctgtttgagg acagagagat gatcgaggaa   7260
cggctgaaaa catacgccca cctgttcgac gacaaagtga tgaagcaact gaagcggcgg   7320
agatacaccg gctggggcag actgtctcgg aagctgatca acggcatccg ggataagcag   7380
tccggcaaga ccatcctgga cttttctgaag tccgacggct cgccaacag aaacttcatg   7440
cagctgattc acgacgacag cctcaccttc aaagaggata tccagaaagc ccaggtgtcc   7500
```

```
ggccagggcg attctctgca tgagcacatt gccaacctgg ccggctctcc cgccattaag   7560
aaaggcatcc tgcagacagt gaaggtggtg gacgagcttg tgaaagtgat gggcagacac   7620
aagcccgaga acatcgtgat cgaaatggcc agagagaacc agaccacaca gaagggacag   7680
aagaacagcc gcgagagaat gaagcggatc gaagagggca tcaaagagct gggcagccag   7740
atcctgaaag aacaccccgt ggaaaacacc cagctgcaga agaaagct gtacctgtac   7800
tacctgcaga atggacggga tatgtacgtg gaccaagagc tggacatcaa cagactgtcc   7860
gactacgatg tggaccatat cgtgccccag tcttttctga aggacgactc catcgacaac   7920
aaggtcctga ccagatccga caagaatcgg ggcaagagcg acaacgtgcc ctccgaagag   7980
gtggtcaaga agatgaagaa ctactggcga cagctgctga acgccaagct gattacccag   8040
cggaagttcg acaatctgac caaggccgaa agaggcggcc tgagcgaact ggataaggcc   8100
ggcttcatca agagacagct ggtggaaacc cggcagatca caaagcacgt ggcacagatt   8160
ctggactctc ggatgaacac taagtacgac gagaacgaca aactgatccg cgaagtgaaa   8220
gtcatcaccc tgaagtccaa gctggtgtcc gatttccgga aggatttcca gttctacaaa   8280
gtgcgcgaga tcaacaacta ccatcacgcc cacgacgcct acctgaatgc cgttgttgga   8340
acagccctga tcaaaaagta ccctaagctg gaaagcgagt tcgtgtacgg cgactacaag   8400
gtgtacgacg tgcggaagat gatcgccaag agcgagcaag agattggcaa ggcaaccgcc   8460
aagtacttct tctacagcaa catcatgaac ttttttcaaga cagagatcac cctcgccaac   8520
ggcgagatca gaaagcggcc tctgatcgag acaaacggca aaaccggcga gattgtgtgg   8580
gataagggca gagactttgc cacagtgcgg aaagtgctga gcatgcccca agtgaatatc   8640
gtgaagaaaa ccgaggtgca gacaggcggc ttcagcaaag agtctatcct gcctaagcgg   8700
aactccgaca agctgatcgc cagaaagaag gactgggacc ccaagaagta cggcggcttc   8760
gattctccta ccgtggccta tagcgtgctg gtggtggaaa gggcaagtcc   8820
aagaaactca agagcgtgaa agagctgctg gggatcacca tcatggaaag aagcagcttc   8880
gagaagaatc cgatcgattt cctcgaggcc aagggctaca agaagtgaa aaaggacctg   8940
atcatcaagc tccccaagta ctccctgttc gagctgaaa acggccggaa gagaatgctg   9000
gcctctgctg gcgaactgca gaagggaaac gaactgctga cctgcctagc aa atatgtgaac   9060
ttcctgtacc tggccagcca ctatgagaag ctgaagggca gccccgagga caatgagcaa   9120
aagcagctgt ttgtggaaca gcacaagcac tacctggacg agatcatcga gcagatcagc   9180
gagtttagca agagagtgat tctggccgac gccaatctgg acaaagtgct gtccgcctac   9240
aacaagcacc gggacaagcc tatcagagag caggccagca atatcatcca cctgtttacc   9300
ctgaccaacc tgggagcccc tgccgccttc aagtactttg acaccaccat cgaccggaag   9360
cggtacacct ccaccaaaga ggtgctggac gccactctga tccaccagtc tatcaccggc   9420
ctgtacgaga cacggatcga cctgtctcaa ctcggaggcg acgaaggcgc cgataagaga   9480
accgccgatg gctctgagtt cgagagcccc aagaaaaagc gcaaagtg            9528

SEQ ID NO: 20        moltype = RNA   length = 4929
FEATURE              Location/Qualifiers
source               1..4929
                     mol_type = other RNA
                     organism = synthetic construct
modified_base        7
                     mod_base = OTHER
                     note = N1-methylpseudouridine
modified_base        25
                     mod_base = OTHER
                     note = N1-methylpseudouridine
modified_base        35
                     mod_base = OTHER
                     note = N1-methylpseudouridine
modified_base        37
                     mod_base = OTHER
                     note = N1-methylpseudouridine
modified_base        49
                     mod_base = OTHER
                     note = N1-methylpseudouridine
modified_base        58
                     mod_base = OTHER
                     note = N1-methylpseudouridine
modified_base        63
                     mod_base = OTHER
                     note = N1-methylpseudouridine
modified_base        64
                     mod_base = OTHER
                     note = N1-methylpseudouridine
modified_base        75
                     mod_base = OTHER
                     note = N1-methylpseudouridine
modified_base        78
                     mod_base = OTHER
                     note = N1-methylpseudouridine
modified_base        82
                     mod_base = OTHER
                     note = N1-methylpseudouridine
modified_base        94
                     mod_base = OTHER
                     note = N1-methylpseudouridine
modified_base        100
                     mod_base = OTHER
                     note = N1-methylpseudouridine
```

| | |
|---|---|
| modified_base | 130<br>mod_base = OTHER<br>note = N1-methylpseudouridine |
| modified_base | 136<br>mod_base = OTHER<br>note = N1-methylpseudouridine |
| modified_base | 145<br>mod_base = OTHER<br>note = N1-methylpseudouridine |
| modified_base | 148<br>mod_base = OTHER<br>note = N1-methylpseudouridine |
| modified_base | 151<br>mod_base = OTHER<br>note = N1-methylpseudouridine |
| modified_base | 154<br>mod_base = OTHER<br>note = N1-methylpseudouridine |
| modified_base | 166<br>mod_base = OTHER<br>note = N1-methylpseudouridine |
| modified_base | 169<br>mod_base = OTHER<br>note = N1-methylpseudouridine |
| modified_base | 180<br>mod_base = OTHER<br>note = N1-methylpseudouridine |
| modified_base | 193<br>mod_base = OTHER<br>note = N1-methylpseudouridine |
| modified_base | 199<br>mod_base = OTHER<br>note = N1-methylpseudouridine |
| modified_base | 226<br>mod_base = OTHER<br>note = N1-methylpseudouridine |
| modified_base | 229<br>mod_base = OTHER<br>note = N1-methylpseudouridine |
| modified_base | 235<br>mod_base = OTHER<br>note = N1-methylpseudouridine |
| modified_base | 250<br>mod_base = OTHER<br>note = N1-methylpseudouridine |
| modified_base | 253<br>mod_base = OTHER<br>note = N1-methylpseudouridine |
| modified_base | 256<br>mod_base = OTHER<br>note = N1-methylpseudouridine |
| modified_base | 264<br>mod_base = OTHER<br>note = N1-methylpseudouridine |
| modified_base | 271<br>mod_base = OTHER<br>note = N1-methylpseudouridine |
| modified_base | 274<br>mod_base = OTHER<br>note = N1-methylpseudouridine |
| modified_base | 286<br>mod_base = OTHER<br>note = N1-methylpseudouridine |
| modified_base | 288<br>mod_base = OTHER<br>note = N1-methylpseudouridine |
| modified_base | 292<br>mod_base = OTHER<br>note = N1-methylpseudouridine |
| modified_base | 297<br>mod_base = OTHER<br>note = N1-methylpseudouridine |
| modified_base | 298<br>mod_base = OTHER<br>note = N1-methylpseudouridine |
| modified_base | 306<br>mod_base = OTHER<br>note = N1-methylpseudouridine |
| modified_base | 310 |

|               |                                                              |
|---------------|--------------------------------------------------------------|
|               | mod_base = OTHER<br>note = N1-methylpseudouridine            |
| modified_base | 313<br>mod_base = OTHER<br>note = N1-methylpseudouridine     |
| modified_base | 315<br>mod_base = OTHER<br>note = N1-methylpseudouridine     |
| modified_base | 328<br>mod_base = OTHER<br>note = N1-methylpseudouridine     |
| modified_base | 331<br>mod_base = OTHER<br>note = N1-methylpseudouridine     |
| modified_base | 343<br>mod_base = OTHER<br>note = N1-methylpseudouridine     |
| modified_base | 352<br>mod_base = OTHER<br>note = N1-methylpseudouridine     |
| modified_base | 355<br>mod_base = OTHER<br>note = N1-methylpseudouridine     |
| modified_base | 357<br>mod_base = OTHER<br>note = N1-methylpseudouridine     |
| modified_base | 358<br>mod_base = OTHER<br>note = N1-methylpseudouridine     |
| modified_base | 364<br>mod_base = OTHER<br>note = N1-methylpseudouridine     |
| modified_base | 397<br>mod_base = OTHER<br>note = N1-methylpseudouridine     |
| modified_base | 400<br>mod_base = OTHER<br>note = N1-methylpseudouridine     |
| modified_base | 406<br>mod_base = OTHER<br>note = N1-methylpseudouridine     |
| modified_base | 409<br>mod_base = OTHER<br>note = N1-methylpseudouridine     |
| modified_base | 424<br>mod_base = OTHER<br>note = N1-methylpseudouridine     |
| modified_base | 436<br>mod_base = OTHER<br>note = N1-methylpseudouridine     |
| modified_base | 442<br>mod_base = OTHER<br>note = N1-methylpseudouridine     |
| modified_base | 454<br>mod_base = OTHER<br>note = N1-methylpseudouridine     |
| modified_base | 457<br>mod_base = OTHER<br>note = N1-methylpseudouridine     |
| modified_base | 468<br>mod_base = OTHER<br>note = N1-methylpseudouridine     |
| modified_base | 478<br>mod_base = OTHER<br>note = N1-methylpseudouridine     |
| modified_base | 481<br>mod_base = OTHER<br>note = N1-methylpseudouridine     |
| modified_base | 483<br>mod_base = OTHER<br>note = N1-methylpseudouridine     |
| modified_base | 489<br>mod_base = OTHER<br>note = N1-methylpseudouridine     |
| modified_base | 490<br>mod_base = OTHER<br>note = N1-methylpseudouridine     |
| modified_base | 492<br>mod_base = OTHER                                      |

| | | |
|---|---|---|
| | | note = N1-methylpseudouridine |
| modified_base | 493 | |
| | | mod_base = OTHER |
| | | note = N1-methylpseudouridine |
| modified_base | 499 | |
| | | mod_base = OTHER |
| | | note = N1-methylpseudouridine |
| modified_base | 511 | |
| | | mod_base = OTHER |
| | | note = N1-methylpseudouridine |
| modified_base | 513 | |
| | | mod_base = OTHER |
| | | note = N1-methylpseudouridine |
| modified_base | 514 | |
| | | mod_base = OTHER |
| | | note = N1-methylpseudouridine |
| modified_base | 654 | |
| | | mod_base = OTHER |
| | | note = N1-methylpseudouridine |
| modified_base | 661 | |
| | | mod_base = OTHER |
| | | note = N1-methylpseudouridine |
| modified_base | 667 | |
| | | mod_base = OTHER |
| | | note = N1-methylpseudouridine |
| modified_base | 673 | |
| | | mod_base = OTHER |
| | | note = N1-methylpseudouridine |
| modified_base | 688 | |
| | | mod_base = OTHER |
| | | note = N1-methylpseudouridine |
| modified_base | 693 | |
| | | mod_base = OTHER |
| | | note = N1-methylpseudouridine |
| modified_base | 700 | |
| | | mod_base = OTHER |
| | | note = N1-methylpseudouridine |
| modified_base | 703 | |
| | | mod_base = OTHER |
| | | note = N1-methylpseudouridine |
| modified_base | 714 | |
| | | mod_base = OTHER |
| | | note = N1-methylpseudouridine |
| modified_base | 721 | |
| | | mod_base = OTHER |
| | | note = N1-methylpseudouridine |
| modified_base | 735 | |
| | | mod_base = OTHER |
| | | note = N1-methylpseudouridine |
| modified_base | 736 | |
| | | mod_base = OTHER |
| | | note = N1-methylpseudouridine |
| modified_base | 742 | |
| | | mod_base = OTHER |
| | | note = N1-methylpseudouridine |
| modified_base | 745 | |
| | | mod_base = OTHER |
| | | note = N1-methylpseudouridine |
| modified_base | 769 | |
| | | mod_base = OTHER |
| | | note = N1-methylpseudouridine |
| modified_base | 781 | |
| | | mod_base = OTHER |
| | | note = N1-methylpseudouridine |
| modified_base | 784 | |
| | | mod_base = OTHER |
| | | note = N1-methylpseudouridine |
| modified_base | 793 | |
| | | mod_base = OTHER |
| | | note = N1-methylpseudouridine |
| modified_base | 796 | |
| | | mod_base = OTHER |
| | | note = N1-methylpseudouridine |
| modified_base | 798 | |
| | | mod_base = OTHER |
| | | note = N1-methylpseudouridine |
| modified_base | 799 | |
| | | mod_base = OTHER |
| | | note = N1-methylpseudouridine |

-continued

| | | |
|---|---|---|
| modified_base | 832 | |
| | mod_base = OTHER | |
| | note = N1-methylpseudouridine | |
| modified_base | 855 | |
| | mod_base = OTHER | |
| | note = N1-methylpseudouridine | |
| modified_base | 877 | |
| | mod_base = OTHER | |
| | note = N1-methylpseudouridine | |
| modified_base | 879 | |
| | mod_base = OTHER | |
| | note = N1-methylpseudouridine | |
| modified_base | 882 | |
| | mod_base = OTHER | |
| | note = N1-methylpseudouridine | |
| modified_base | 886 | |
| | mod_base = OTHER | |
| | note = N1-methylpseudouridine | |
| modified_base | 895 | |
| | mod_base = OTHER | |
| | note = N1-methylpseudouridine | |
| modified_base | 897 | |
| | mod_base = OTHER | |
| | note = N1-methylpseudouridine | |
| modified_base | 898 | |
| | mod_base = OTHER | |
| | note = N1-methylpseudouridine | |
| modified_base | 910 | |
| | mod_base = OTHER | |
| | note = N1-methylpseudouridine | |
| modified_base | 919 | |
| | mod_base = OTHER | |
| | note = N1-methylpseudouridine | |
| modified_base | 930 | |
| | mod_base = OTHER | |
| | note = N1-methylpseudouridine | |
| modified_base | 931 | |
| | mod_base = OTHER | |
| | note = N1-methylpseudouridine | |
| modified_base | 933 | |
| | mod_base = OTHER | |
| | note = N1-methylpseudouridine | |
| modified_base | 934 | |
| | mod_base = OTHER | |
| | note = N1-methylpseudouridine | |
| modified_base | 943 | |
| | mod_base = OTHER | |
| | note = N1-methylpseudouridine | |
| modified_base | 954 | |
| | mod_base = OTHER | |
| | note = N1-methylpseudouridine | |
| modified_base | 955 | |
| | mod_base = OTHER | |
| | note = N1-methylpseudouridine | |
| modified_base | 958 | |
| | mod_base = OTHER | |
| | note = N1-methylpseudouridine | |
| modified_base | 961 | |
| | mod_base = OTHER | |
| | note = N1-methylpseudouridine | |
| modified_base | 994 | |
| | mod_base = OTHER | |
| | note = N1-methylpseudouridine | |
| modified_base | 996 | |
| | mod_base = OTHER | |
| | note = N1-methylpseudouridine | |
| modified_base | 997 | |
| | mod_base = OTHER | |
| | note = N1-methylpseudouridine | |
| modified_base | 1006 | |
| | mod_base = OTHER | |
| | note = N1-methylpseudouridine | |
| modified_base | 1009 | |
| | mod_base = OTHER | |
| | note = N1-methylpseudouridine | |
| modified_base | 1018 | |
| | mod_base = OTHER | |
| | note = N1-methylpseudouridine | |
| modified_base | 1023 | |

-continued

|  | mod_base = OTHER<br>note = N1-methylpseudouridine |
| --- | --- |
| modified_base | 1035<br>mod_base = OTHER<br>note = N1-methylpseudouridine |
| modified_base | 1045<br>mod_base = OTHER<br>note = N1-methylpseudouridine |
| modified_base | 1047<br>mod_base = OTHER<br>note = N1-methylpseudouridine |
| modified_base | 1054<br>mod_base = OTHER<br>note = N1-methylpseudouridine |
| modified_base | 1066<br>mod_base = OTHER<br>note = N1-methylpseudouridine |
| modified_base | 1069<br>mod_base = OTHER<br>note = N1-methylpseudouridine |
| modified_base | 1093<br>mod_base = OTHER<br>note = N1-methylpseudouridine |
| modified_base | 1099<br>mod_base = OTHER<br>note = N1-methylpseudouridine |
| modified_base | 1102<br>mod_base = OTHER<br>note = N1-methylpseudouridine |
| modified_base | 1104<br>mod_base = OTHER<br>note = N1-methylpseudouridine |
| modified_base | 1108<br>mod_base = OTHER<br>note = N1-methylpseudouridine |
| modified_base | 1114<br>mod_base = OTHER<br>note = N1-methylpseudouridine |
| modified_base | 1123<br>mod_base = OTHER<br>note = N1-methylpseudouridine |
| modified_base | 1126<br>mod_base = OTHER<br>note = N1-methylpseudouridine |
| modified_base | 1131<br>mod_base = OTHER<br>note = N1-methylpseudouridine |
| modified_base | 1132<br>mod_base = OTHER<br>note = N1-methylpseudouridine |
| modified_base | 1143<br>mod_base = OTHER<br>note = N1-methylpseudouridine |
| modified_base | 1144<br>mod_base = OTHER<br>note = N1-methylpseudouridine |
| modified_base | 1147<br>mod_base = OTHER<br>note = N1-methylpseudouridine |
| modified_base | 1150<br>mod_base = OTHER<br>note = N1-methylpseudouridine |
| modified_base | 1162<br>mod_base = OTHER<br>note = N1-methylpseudouridine |
| modified_base | 1183<br>mod_base = OTHER<br>note = N1-methylpseudouridine |
| modified_base | 1192<br>mod_base = OTHER<br>note = N1-methylpseudouridine |
| modified_base | 1194<br>mod_base = OTHER<br>note = N1-methylpseudouridine |
| modified_base | 1195<br>mod_base = OTHER<br>note = N1-methylpseudouridine |
| modified_base | 1198<br>mod_base = OTHER |

-continued

| | | |
|---|---|---|
| modified_base | 1204 mod_base = OTHER note = N1-methylpseudouridine | |
| modified_base | 1207 mod_base = OTHER note = N1-methylpseudouridine | |
| modified_base | 1215 mod_base = OTHER note = N1-methylpseudouridine | |
| modified_base | 1225 mod_base = OTHER note = N1-methylpseudouridine | |
| modified_base | 1227 mod_base = OTHER note = N1-methylpseudouridine | |
| modified_base | 1228 mod_base = OTHER note = N1-methylpseudouridine | |
| modified_base | 1243 mod_base = OTHER note = N1-methylpseudouridine | |
| modified_base | 1258 mod_base = OTHER note = N1-methylpseudouridine | |
| modified_base | 1273 mod_base = OTHER note = N1-methylpseudouridine | |
| modified_base | 1276 mod_base = OTHER note = N1-methylpseudouridine | |
| modified_base | 1288 mod_base = OTHER note = N1-methylpseudouridine | |
| modified_base | 1306 mod_base = OTHER note = N1-methylpseudouridine | |
| modified_base | 1315 mod_base = OTHER note = N1-methylpseudouridine | |
| modified_base | 1318 mod_base = OTHER note = N1-methylpseudouridine | |
| modified_base | 1327 mod_base = OTHER note = N1-methylpseudouridine | |
| modified_base | 1351 mod_base = OTHER note = N1-methylpseudouridine | |
| modified_base | 1353 mod_base = OTHER note = N1-methylpseudouridine | |
| modified_base | 1354 mod_base = OTHER note = N1-methylpseudouridine | |
| modified_base | 1363 mod_base = OTHER note = N1-methylpseudouridine | |
| modified_base | 1366 mod_base = OTHER note = N1-methylpseudouridine | |
| modified_base | 1372 mod_base = OTHER note = N1-methylpseudouridine | |
| modified_base | 1378 mod_base = OTHER note = N1-methylpseudouridine | |
| modified_base | 1384 mod_base = OTHER note = N1-methylpseudouridine | |
| modified_base | 1395 mod_base = OTHER note = N1-methylpseudouridine | |
| modified_base | 1396 mod_base = OTHER note = N1-methylpseudouridine | |
| modified_base | 1407 mod_base = OTHER note = N1-methylpseudouridine | |

-continued

| | |
|---|---|
| modified_base | 1408<br>mod_base = OTHER<br>note = N1-methylpseudouridine |
| modified_base | 1414<br>mod_base = OTHER<br>note = N1-methylpseudouridine |
| modified_base | 1432<br>mod_base = OTHER<br>note = N1-methylpseudouridine |
| modified_base | 1438<br>mod_base = OTHER<br>note = N1-methylpseudouridine |
| modified_base | 1452<br>mod_base = OTHER<br>note = N1-methylpseudouridine |
| modified_base | 1465<br>mod_base = OTHER<br>note = N1-methylpseudouridine |
| modified_base | 1474<br>mod_base = OTHER<br>note = N1-methylpseudouridine |
| modified_base | 1477<br>mod_base = OTHER<br>note = N1-methylpseudouridine |
| modified_base | 1486<br>mod_base = OTHER<br>note = N1-methylpseudouridine |
| modified_base | 1497<br>mod_base = OTHER<br>note = N1-methylpseudouridine |
| modified_base | 1507<br>mod_base = OTHER<br>note = N1-methylpseudouridine |
| modified_base | 1509<br>mod_base = OTHER<br>note = N1-methylpseudouridine |
| modified_base | 1510<br>mod_base = OTHER<br>note = N1-methylpseudouridine |
| modified_base | 1513<br>mod_base = OTHER<br>note = N1-methylpseudouridine |
| modified_base | 1528<br>mod_base = OTHER<br>note = N1-methylpseudouridine |
| modified_base | 1540<br>mod_base = OTHER<br>note = N1-methylpseudouridine |
| modified_base | 1543<br>mod_base = OTHER<br>note = N1-methylpseudouridine |
| modified_base | 1546<br>mod_base = OTHER<br>note = N1-methylpseudouridine |
| modified_base | 1555<br>mod_base = OTHER<br>note = N1-methylpseudouridine |
| modified_base | 1558<br>mod_base = OTHER<br>note = N1-methylpseudouridine |
| modified_base | 1564<br>mod_base = OTHER<br>note = N1-methylpseudouridine |
| modified_base | 1576<br>mod_base = OTHER<br>note = N1-methylpseudouridine |
| modified_base | 1591<br>mod_base = OTHER<br>note = N1-methylpseudouridine |
| modified_base | 1603<br>mod_base = OTHER<br>note = N1-methylpseudouridine |
| modified_base | 1606<br>mod_base = OTHER<br>note = N1-methylpseudouridine |
| modified_base | 1614<br>mod_base = OTHER<br>note = N1-methylpseudouridine |
| modified_base | 1636 |

| | | |
|---|---|---|
| | | mod_base = OTHER |
| | | note = N1-methylpseudouridine |
| modified_base | 1642 | |
| | | mod_base = OTHER |
| | | note = N1-methylpseudouridine |
| modified_base | 1645 | |
| | | mod_base = OTHER |
| | | note = N1-methylpseudouridine |
| modified_base | 1654 | |
| | | mod_base = OTHER |
| | | note = N1-methylpseudouridine |
| modified_base | 1657 | |
| | | mod_base = OTHER |
| | | note = N1-methylpseudouridine |
| modified_base | 1669 | |
| | | mod_base = OTHER |
| | | note = N1-methylpseudouridine |
| modified_base | 1680 | |
| | | mod_base = OTHER |
| | | note = N1-methylpseudouridine |
| modified_base | 1690 | |
| | | mod_base = OTHER |
| | | note = N1-methylpseudouridine |
| modified_base | 1692 | |
| | | mod_base = OTHER |
| | | note = N1-methylpseudouridine |
| modified_base | 1693 | |
| | | mod_base = OTHER |
| | | note = N1-methylpseudouridine |
| modified_base | 1695 | |
| | | mod_base = OTHER |
| | | note = N1-methylpseudouridine |
| modified_base | 1696 | |
| | | mod_base = OTHER |
| | | note = N1-methylpseudouridine |
| modified_base | 1716 | |
| | | mod_base = OTHER |
| | | note = N1-methylpseudouridine |
| modified_base | 1725 | |
| | | mod_base = OTHER |
| | | note = N1-methylpseudouridine |
| modified_base | 1729 | |
| | | mod_base = OTHER |
| | | note = N1-methylpseudouridine |
| modified_base | 1755 | |
| | | mod_base = OTHER |
| | | note = N1-methylpseudouridine |
| modified_base | 1756 | |
| | | mod_base = OTHER |
| | | note = N1-methylpseudouridine |
| modified_base | 1758 | |
| | | mod_base = OTHER |
| | | note = N1-methylpseudouridine |
| modified_base | 1764 | |
| | | mod_base = OTHER |
| | | note = N1-methylpseudouridine |
| modified_base | 1765 | |
| | | mod_base = OTHER |
| | | note = N1-methylpseudouridine |
| modified_base | 1768 | |
| | | mod_base = OTHER |
| | | note = N1-methylpseudouridine |
| modified_base | 1777 | |
| | | mod_base = OTHER |
| | | note = N1-methylpseudouridine |
| modified_base | 1780 | |
| | | mod_base = OTHER |
| | | note = N1-methylpseudouridine |
| modified_base | 1789 | |
| | | mod_base = OTHER |
| | | note = N1-methylpseudouridine |
| modified_base | 1807 | |
| | | mod_base = OTHER |
| | | note = N1-methylpseudouridine |
| modified_base | 1810 | |
| | | mod_base = OTHER |
| | | note = N1-methylpseudouridine |
| modified_base | 1813 | |
| | | mod_base = OTHER |

-continued

| | | |
|---|---|---|
| modified_base | 1819 | note = N1-methylpseudouridine<br>mod_base = OTHER<br>note = N1-methylpseudouridine |
| modified_base | 1834 | mod_base = OTHER<br>note = N1-methylpseudouridine |
| modified_base | 1837 | mod_base = OTHER<br>note = N1-methylpseudouridine |
| modified_base | 1854 | mod_base = OTHER<br>note = N1-methylpseudouridine |
| modified_base | 1855 | mod_base = OTHER<br>note = N1-methylpseudouridine |
| modified_base | 1870 | mod_base = OTHER<br>note = N1-methylpseudouridine |
| modified_base | 1882 | mod_base = OTHER<br>note = N1-methylpseudouridine |
| modified_base | 1888 | mod_base = OTHER<br>note = N1-methylpseudouridine |
| modified_base | 1897 | mod_base = OTHER<br>note = N1-methylpseudouridine |
| modified_base | 1906 | mod_base = OTHER<br>note = N1-methylpseudouridine |
| modified_base | 1909 | mod_base = OTHER<br>note = N1-methylpseudouridine |
| modified_base | 1926 | mod_base = OTHER<br>note = N1-methylpseudouridine |
| modified_base | 1927 | mod_base = OTHER<br>note = N1-methylpseudouridine |
| modified_base | 1929 | mod_base = OTHER<br>note = N1-methylpseudouridine |
| modified_base | 1935 | mod_base = OTHER<br>note = N1-methylpseudouridine |
| modified_base | 1936 | mod_base = OTHER<br>note = N1-methylpseudouridine |
| modified_base | 1939 | mod_base = OTHER<br>note = N1-methylpseudouridine |
| modified_base | 1960 | mod_base = OTHER<br>note = N1-methylpseudouridine |
| modified_base | 1969 | mod_base = OTHER<br>note = N1-methylpseudouridine |
| modified_base | 1972 | mod_base = OTHER<br>note = N1-methylpseudouridine |
| modified_base | 1977 | mod_base = OTHER<br>note = N1-methylpseudouridine |
| modified_base | 1978 | mod_base = OTHER<br>note = N1-methylpseudouridine |
| modified_base | 1984 | mod_base = OTHER<br>note = N1-methylpseudouridine |
| modified_base | 1989 | mod_base = OTHER<br>note = N1-methylpseudouridine |
| modified_base | 1992 | mod_base = OTHER<br>note = N1-methylpseudouridine |
| modified_base | 1996 | mod_base = OTHER<br>note = N1-methylpseudouridine |

-continued

| | |
|---|---|
| modified_base | 2005<br>mod_base = OTHER<br>note = N1-methylpseudouridine |
| modified_base | 2025<br>mod_base = OTHER<br>note = N1-methylpseudouridine |
| modified_base | 2026<br>mod_base = OTHER<br>note = N1-methylpseudouridine |
| modified_base | 2031<br>mod_base = OTHER<br>note = N1-methylpseudouridine |
| modified_base | 2035<br>mod_base = OTHER<br>note = N1-methylpseudouridine |
| modified_base | 2059<br>mod_base = OTHER<br>note = N1-methylpseudouridine |
| modified_base | 2067<br>mod_base = OTHER<br>note = N1-methylpseudouridine |
| modified_base | 2073<br>mod_base = OTHER<br>note = N1-methylpseudouridine |
| modified_base | 2074<br>mod_base = OTHER<br>note = N1-methylpseudouridine |
| modified_base | 2083<br>mod_base = OTHER<br>note = N1-methylpseudouridine |
| modified_base | 2086<br>mod_base = OTHER<br>note = N1-methylpseudouridine |
| modified_base | 2112<br>mod_base = OTHER<br>note = N1-methylpseudouridine |
| modified_base | 2113<br>mod_base = OTHER<br>note = N1-methylpseudouridine |
| modified_base | 2116<br>mod_base = OTHER<br>note = N1-methylpseudouridine |
| modified_base | 2125<br>mod_base = OTHER<br>note = N1-methylpseudouridine |
| modified_base | 2133<br>mod_base = OTHER<br>note = N1-methylpseudouridine |
| modified_base | 2134<br>mod_base = OTHER<br>note = N1-methylpseudouridine |
| modified_base | 2146<br>mod_base = OTHER<br>note = N1-methylpseudouridine |
| modified_base | 2161<br>mod_base = OTHER<br>note = N1-methylpseudouridine |
| modified_base | 2164<br>mod_base = OTHER<br>note = N1-methylpseudouridine |
| modified_base | 2179<br>mod_base = OTHER<br>note = N1-methylpseudouridine |
| modified_base | 2182<br>mod_base = OTHER<br>note = N1-methylpseudouridine |
| modified_base | 2184<br>mod_base = OTHER<br>note = N1-methylpseudouridine |
| modified_base | 2190<br>mod_base = OTHER<br>note = N1-methylpseudouridine |
| modified_base | 2193<br>mod_base = OTHER<br>note = N1-methylpseudouridine |
| modified_base | 2194<br>mod_base = OTHER<br>note = N1-methylpseudouridine |
| modified_base | 2200 |

|  |  |
|---|---|
|  | mod_base = OTHER |
|  | note = N1-methylpseudouridine |
| modified_base | 2202 |
|  | mod_base = OTHER |
|  | note = N1-methylpseudouridine |
| modified_base | 2212 |
|  | mod_base = OTHER |
|  | note = N1-methylpseudouridine |
| modified_base | 2221 |
|  | mod_base = OTHER |
|  | note = N1-methylpseudouridine |
| modified_base | 2226 |
|  | mod_base = OTHER |
|  | note = N1-methylpseudouridine |
| modified_base | 2230 |
|  | mod_base = OTHER |
|  | note = N1-methylpseudouridine |
| modified_base | 2242 |
|  | mod_base = OTHER |
|  | note = N1-methylpseudouridine |
| modified_base | 2256 |
|  | mod_base = OTHER |
|  | note = N1-methylpseudouridine |
| modified_base | 2257 |
|  | mod_base = OTHER |
|  | note = N1-methylpseudouridine |
| modified_base | 2260 |
|  | mod_base = OTHER |
|  | note = N1-methylpseudouridine |
| modified_base | 2284 |
|  | mod_base = OTHER |
|  | note = N1-methylpseudouridine |
| modified_base | 2287 |
|  | mod_base = OTHER |
|  | note = N1-methylpseudouridine |
| modified_base | 2293 |
|  | mod_base = OTHER |
|  | note = N1-methylpseudouridine |
| modified_base | 2296 |
|  | mod_base = OTHER |
|  | note = N1-methylpseudouridine |
| modified_base | 2298 |
|  | mod_base = OTHER |
|  | note = N1-methylpseudouridine |
| modified_base | 2299 |
|  | mod_base = OTHER |
|  | note = N1-methylpseudouridine |
| modified_base | 2317 |
|  | mod_base = OTHER |
|  | note = N1-methylpseudouridine |
| modified_base | 2323 |
|  | mod_base = OTHER |
|  | note = N1-methylpseudouridine |
| modified_base | 2332 |
|  | mod_base = OTHER |
|  | note = N1-methylpseudouridine |
| modified_base | 2343 |
|  | mod_base = OTHER |
|  | note = N1-methylpseudouridine |
| modified_base | 2346 |
|  | mod_base = OTHER |
|  | note = N1-methylpseudouridine |
| modified_base | 2347 |
|  | mod_base = OTHER |
|  | note = N1-methylpseudouridine |
| modified_base | 2356 |
|  | mod_base = OTHER |
|  | note = N1-methylpseudouridine |
| modified_base | 2361 |
|  | mod_base = OTHER |
|  | note = N1-methylpseudouridine |
| modified_base | 2364 |
|  | mod_base = OTHER |
|  | note = N1-methylpseudouridine |
| modified_base | 2365 |
|  | mod_base = OTHER |
|  | note = N1-methylpseudouridine |
| modified_base | 2374 |
|  | mod_base = OTHER |

-continued

| | | |
|---|---|---|
| modified_base | 2380<br>mod_base = OTHER<br>note = N1-methylpseudouridine | |
| modified_base | 2389<br>mod_base = OTHER<br>note = N1-methylpseudouridine | |
| modified_base | 2400<br>mod_base = OTHER<br>note = N1-methylpseudouridine | |
| modified_base | 2401<br>mod_base = OTHER<br>note = N1-methylpseudouridine | |
| modified_base | 2413<br>mod_base = OTHER<br>note = N1-methylpseudouridine | |
| modified_base | 2421<br>mod_base = OTHER<br>note = N1-methylpseudouridine | |
| modified_base | 2431<br>mod_base = OTHER<br>note = N1-methylpseudouridine | |
| modified_base | 2434<br>mod_base = OTHER<br>note = N1-methylpseudouridine | |
| modified_base | 2440<br>mod_base = OTHER<br>note = N1-methylpseudouridine | |
| modified_base | 2443<br>mod_base = OTHER<br>note = N1-methylpseudouridine | |
| modified_base | 2457<br>mod_base = OTHER<br>note = N1-methylpseudouridine | |
| modified_base | 2458<br>mod_base = OTHER<br>note = N1-methylpseudouridine | |
| modified_base | 2461<br>mod_base = OTHER<br>note = N1-methylpseudouridine | |
| modified_base | 2485<br>mod_base = OTHER<br>note = N1-methylpseudouridine | |
| modified_base | 2488<br>mod_base = OTHER<br>note = N1-methylpseudouridine | |
| modified_base | 2497<br>mod_base = OTHER<br>note = N1-methylpseudouridine | |
| modified_base | 2500<br>mod_base = OTHER<br>note = N1-methylpseudouridine | |
| modified_base | 2503<br>mod_base = OTHER<br>note = N1-methylpseudouridine | |
| modified_base | 2509<br>mod_base = OTHER<br>note = N1-methylpseudouridine | |
| modified_base | 2515<br>mod_base = OTHER<br>note = N1-methylpseudouridine | |
| modified_base | 2517<br>mod_base = OTHER<br>note = N1-methylpseudouridine | |
| modified_base | 2518<br>mod_base = OTHER<br>note = N1-methylpseudouridine | |
| modified_base | 2533<br>mod_base = OTHER<br>note = N1-methylpseudouridine | |
| modified_base | 2536<br>mod_base = OTHER<br>note = N1-methylpseudouridine | |
| modified_base | 2548<br>mod_base = OTHER<br>note = N1-methylpseudouridine | |
| modified_base | 2556<br>mod_base = OTHER<br>note = N1-methylpseudouridine | |

-continued

| | |
|---|---|
| modified_base | 2566<br>mod_base = OTHER<br>note = N1-methylpseudouridine |
| modified_base | 2568<br>mod_base = OTHER<br>note = N1-methylpseudouridine |
| modified_base | 2569<br>mod_base = OTHER<br>note = N1-methylpseudouridine |
| modified_base | 2581<br>mod_base = OTHER<br>note = N1-methylpseudouridine |
| modified_base | 2584<br>mod_base = OTHER<br>note = N1-methylpseudouridine |
| modified_base | 2593<br>mod_base = OTHER<br>note = N1-methylpseudouridine |
| modified_base | 2607<br>mod_base = OTHER<br>note = N1-methylpseudouridine |
| modified_base | 2616<br>mod_base = OTHER<br>note = N1-methylpseudouridine |
| modified_base | 2626<br>mod_base = OTHER<br>note = N1-methylpseudouridine |
| modified_base | 2638<br>mod_base = OTHER<br>note = N1-methylpseudouridine |
| modified_base | 2641<br>mod_base = OTHER<br>note = N1-methylpseudouridine |
| modified_base | 2650<br>mod_base = OTHER<br>note = N1-methylpseudouridine |
| modified_base | 2677<br>mod_base = OTHER<br>note = N1-methylpseudouridine |
| modified_base | 2680<br>mod_base = OTHER<br>note = N1-methylpseudouridine |
| modified_base | 2685<br>mod_base = OTHER<br>note = N1-methylpseudouridine |
| modified_base | 2686<br>mod_base = OTHER<br>note = N1-methylpseudouridine |
| modified_base | 2689<br>mod_base = OTHER<br>note = N1-methylpseudouridine |
| modified_base | 2703<br>mod_base = OTHER<br>note = N1-methylpseudouridine |
| modified_base | 2704<br>mod_base = OTHER<br>note = N1-methylpseudouridine |
| modified_base | 2718<br>mod_base = OTHER<br>note = N1-methylpseudouridine |
| modified_base | 2719<br>mod_base = OTHER<br>note = N1-methylpseudouridine |
| modified_base | 2722<br>mod_base = OTHER<br>note = N1-methylpseudouridine |
| modified_base | 2728<br>mod_base = OTHER<br>note = N1-methylpseudouridine |
| modified_base | 2731<br>mod_base = OTHER<br>note = N1-methylpseudouridine |
| modified_base | 2746<br>mod_base = OTHER<br>note = N1-methylpseudouridine |
| modified_base | 2751<br>mod_base = OTHER<br>note = N1-methylpseudouridine |
| modified_base | 2752 |

| | | |
|---|---|---|
| | | mod_base = OTHER |
| | | note = N1-methylpseudouridine |
| modified_base | 2764 | |
| | | mod_base = OTHER |
| | | note = N1-methylpseudouridine |
| modified_base | 2779 | |
| | | mod_base = OTHER |
| | | note = N1-methylpseudouridine |
| modified_base | 2800 | |
| | | mod_base = OTHER |
| | | note = N1-methylpseudouridine |
| modified_base | 2812 | |
| | | mod_base = OTHER |
| | | note = N1-methylpseudouridine |
| modified_base | 2821 | |
| | | mod_base = OTHER |
| | | note = N1-methylpseudouridine |
| modified_base | 2839 | |
| | | mod_base = OTHER |
| | | note = N1-methylpseudouridine |
| modified_base | 2851 | |
| | | mod_base = OTHER |
| | | note = N1-methylpseudouridine |
| modified_base | 2854 | |
| | | mod_base = OTHER |
| | | note = N1-methylpseudouridine |
| modified_base | 2863 | |
| | | mod_base = OTHER |
| | | note = N1-methylpseudouridine |
| modified_base | 2869 | |
| | | mod_base = OTHER |
| | | note = N1-methylpseudouridine |
| modified_base | 2872 | |
| | | mod_base = OTHER |
| | | note = N1-methylpseudouridine |
| modified_base | 2881 | |
| | | mod_base = OTHER |
| | | note = N1-methylpseudouridine |
| modified_base | 2884 | |
| | | mod_base = OTHER |
| | | note = N1-methylpseudouridine |
| modified_base | 2890 | |
| | | mod_base = OTHER |
| | | note = N1-methylpseudouridine |
| modified_base | 2893 | |
| | | mod_base = OTHER |
| | | note = N1-methylpseudouridine |
| modified_base | 2917 | |
| | | mod_base = OTHER |
| | | note = N1-methylpseudouridine |
| modified_base | 2920 | |
| | | mod_base = OTHER |
| | | note = N1-methylpseudouridine |
| modified_base | 2923 | |
| | | mod_base = OTHER |
| | | note = N1-methylpseudouridine |
| modified_base | 2929 | |
| | | mod_base = OTHER |
| | | note = N1-methylpseudouridine |
| modified_base | 2983 | |
| | | mod_base = OTHER |
| | | note = N1-methylpseudouridine |
| modified_base | 2992 | |
| | | mod_base = OTHER |
| | | note = N1-methylpseudouridine |
| modified_base | 3004 | |
| | | mod_base = OTHER |
| | | note = N1-methylpseudouridine |
| modified_base | 3013 | |
| | | mod_base = OTHER |
| | | note = N1-methylpseudouridine |
| modified_base | 3025 | |
| | | mod_base = OTHER |
| | | note = N1-methylpseudouridine |
| modified_base | 3028 | |
| | | mod_base = OTHER |
| | | note = N1-methylpseudouridine |
| modified_base | 3043 | |
| | | mod_base = OTHER |

| | | |
|---|---|---|
| | | note = N1-methylpseudouridine |
| modified_base | 3058 | |
| | mod_base = OTHER | |
| | note = N1-methylpseudouridine | |
| modified_base | 3073 | |
| | mod_base = OTHER | |
| | note = N1-methylpseudouridine | |
| modified_base | 3075 | |
| | mod_base = OTHER | |
| | note = N1-methylpseudouridine | |
| modified_base | 3079 | |
| | mod_base = OTHER | |
| | note = N1-methylpseudouridine | |
| modified_base | 3081 | |
| | mod_base = OTHER | |
| | note = N1-methylpseudouridine | |
| modified_base | 3084 | |
| | mod_base = OTHER | |
| | note = N1-methylpseudouridine | |
| modified_base | 3088 | |
| | mod_base = OTHER | |
| | note = N1-methylpseudouridine | |
| modified_base | 3106 | |
| | mod_base = OTHER | |
| | note = N1-methylpseudouridine | |
| modified_base | 3108 | |
| | mod_base = OTHER | |
| | note = N1-methylpseudouridine | |
| modified_base | 3112 | |
| | mod_base = OTHER | |
| | note = N1-methylpseudouridine | |
| modified_base | 3124 | |
| | mod_base = OTHER | |
| | note = N1-methylpseudouridine | |
| modified_base | 3130 | |
| | mod_base = OTHER | |
| | note = N1-methylpseudouridine | |
| modified_base | 3139 | |
| | mod_base = OTHER | |
| | note = N1-methylpseudouridine | |
| modified_base | 3147 | |
| | mod_base = OTHER | |
| | note = N1-methylpseudouridine | |
| modified_base | 3154 | |
| | mod_base = OTHER | |
| | note = N1-methylpseudouridine | |
| modified_base | 3163 | |
| | mod_base = OTHER | |
| | note = N1-methylpseudouridine | |
| modified_base | 3166 | |
| | mod_base = OTHER | |
| | note = N1-methylpseudouridine | |
| modified_base | 3177 | |
| | mod_base = OTHER | |
| | note = N1-methylpseudouridine | |
| modified_base | 3178 | |
| | mod_base = OTHER | |
| | note = N1-methylpseudouridine | |
| modified_base | 3181 | |
| | mod_base = OTHER | |
| | note = N1-methylpseudouridine | |
| modified_base | 3196 | |
| | mod_base = OTHER | |
| | note = N1-methylpseudouridine | |
| modified_base | 3208 | |
| | mod_base = OTHER | |
| | note = N1-methylpseudouridine | |
| modified_base | 3211 | |
| | mod_base = OTHER | |
| | note = N1-methylpseudouridine | |
| modified_base | 3250 | |
| | mod_base = OTHER | |
| | note = N1-methylpseudouridine | |
| modified_base | 3265 | |
| | mod_base = OTHER | |
| | note = N1-methylpseudouridine | |
| modified_base | 3268 | |
| | mod_base = OTHER | |
| | note = N1-methylpseudouridine | |

-continued

| | |
|---|---|
| modified_base | 3277<br>mod_base = OTHER<br>note = N1-methylpseudouridine |
| modified_base | 3285<br>mod_base = OTHER<br>note = N1-methylpseudouridine |
| modified_base | 3288<br>mod_base = OTHER<br>note = N1-methylpseudouridine |
| modified_base | 3298<br>mod_base = OTHER<br>note = N1-methylpseudouridine |
| modified_base | 3301<br>mod_base = OTHER<br>note = N1-methylpseudouridine |
| modified_base | 3313<br>mod_base = OTHER<br>note = N1-methylpseudouridine |
| modified_base | 3316<br>mod_base = OTHER<br>note = N1-methylpseudouridine |
| modified_base | 3330<br>mod_base = OTHER<br>note = N1-methylpseudouridine |
| modified_base | 3331<br>mod_base = OTHER<br>note = N1-methylpseudouridine |
| modified_base | 3340<br>mod_base = OTHER<br>note = N1-methylpseudouridine |
| modified_base | 3364<br>mod_base = OTHER<br>note = N1-methylpseudouridine |
| modified_base | 3373<br>mod_base = OTHER<br>note = N1-methylpseudouridine |
| modified_base | 3387<br>mod_base = OTHER<br>note = N1-methylpseudouridine |
| modified_base | 3388<br>mod_base = OTHER<br>note = N1-methylpseudouridine |
| modified_base | 3391<br>mod_base = OTHER<br>note = N1-methylpseudouridine |
| modified_base | 3403<br>mod_base = OTHER<br>note = N1-methylpseudouridine |
| modified_base | 3406<br>mod_base = OTHER<br>note = N1-methylpseudouridine |
| modified_base | 3421<br>mod_base = OTHER<br>note = N1-methylpseudouridine |
| modified_base | 3433<br>mod_base = OTHER<br>note = N1-methylpseudouridine |
| modified_base | 3442<br>mod_base = OTHER<br>note = N1-methylpseudouridine |
| modified_base | 3445<br>mod_base = OTHER<br>note = N1-methylpseudouridine |
| modified_base | 3457<br>mod_base = OTHER<br>note = N1-methylpseudouridine |
| modified_base | 3468<br>mod_base = OTHER<br>note = N1-methylpseudouridine |
| modified_base | 3487<br>mod_base = OTHER<br>note = N1-methylpseudouridine |
| modified_base | 3490<br>mod_base = OTHER<br>note = N1-methylpseudouridine |
| modified_base | 3499<br>mod_base = OTHER<br>note = N1-methylpseudouridine |
| modified_base | 3505 |

-continued

|  |  |
|---|---|
|  | mod_base = OTHER<br>note = N1-methylpseudouridine |
| modified_base | 3508<br>mod_base = OTHER<br>note = N1-methylpseudouridine |
| modified_base | 3514<br>mod_base = OTHER<br>note = N1-methylpseudouridine |
| modified_base | 3526<br>mod_base = OTHER<br>note = N1-methylpseudouridine |
| modified_base | 3529<br>mod_base = OTHER<br>note = N1-methylpseudouridine |
| modified_base | 3537<br>mod_base = OTHER<br>note = N1-methylpseudouridine |
| modified_base | 3538<br>mod_base = OTHER<br>note = N1-methylpseudouridine |
| modified_base | 3549<br>mod_base = OTHER<br>note = N1-methylpseudouridine |
| modified_base | 3550<br>mod_base = OTHER<br>note = N1-methylpseudouridine |
| modified_base | 3555<br>mod_base = OTHER<br>note = N1-methylpseudouridine |
| modified_base | 3556<br>mod_base = OTHER<br>note = N1-methylpseudouridine |
| modified_base | 3558<br>mod_base = OTHER<br>note = N1-methylpseudouridine |
| modified_base | 3565<br>mod_base = OTHER<br>note = N1-methylpseudouridine |
| modified_base | 3574<br>mod_base = OTHER<br>note = N1-methylpseudouridine |
| modified_base | 3582<br>mod_base = OTHER<br>note = N1-methylpseudouridine |
| modified_base | 3603<br>mod_base = OTHER<br>note = N1-methylpseudouridine |
| modified_base | 3607<br>mod_base = OTHER<br>note = N1-methylpseudouridine |
| modified_base | 3616<br>mod_base = OTHER<br>note = N1-methylpseudouridine |
| modified_base | 3619<br>mod_base = OTHER<br>note = N1-methylpseudouridine |
| modified_base | 3631<br>mod_base = OTHER<br>note = N1-methylpseudouridine |
| modified_base | 3634<br>mod_base = OTHER<br>note = N1-methylpseudouridine |
| modified_base | 3642<br>mod_base = OTHER<br>note = N1-methylpseudouridine |
| modified_base | 3652<br>mod_base = OTHER<br>note = N1-methylpseudouridine |
| modified_base | 3663<br>mod_base = OTHER<br>note = N1-methylpseudouridine |
| modified_base | 3664<br>mod_base = OTHER<br>note = N1-methylpseudouridine |
| modified_base | 3667<br>mod_base = OTHER<br>note = N1-methylpseudouridine |
| modified_base | 3669<br>mod_base = OTHER |

-continued

| | | |
|---|---|---|
| modified_base | 3678 | |
| | mod_base = OTHER | |
| | note = N1-methylpseudouridine | |
| modified_base | 3685 | |
| | mod_base = OTHER | |
| | note = N1-methylpseudouridine | |
| modified_base | 3687 | |
| | mod_base = OTHER | |
| | note = N1-methylpseudouridine | |
| modified_base | 3694 | |
| | mod_base = OTHER | |
| | note = N1-methylpseudouridine | |
| modified_base | 3703 | |
| | mod_base = OTHER | |
| | note = N1-methylpseudouridine | |
| modified_base | 3706 | |
| | mod_base = OTHER | |
| | note = N1-methylpseudouridine | |
| modified_base | 3727 | |
| | mod_base = OTHER | |
| | note = N1-methylpseudouridine | |
| modified_base | 3747 | |
| | mod_base = OTHER | |
| | note = N1-methylpseudouridine | |
| modified_base | 3750 | |
| | mod_base = OTHER | |
| | note = N1-methylpseudouridine | |
| modified_base | 3751 | |
| | mod_base = OTHER | |
| | note = N1-methylpseudouridine | |
| modified_base | 3753 | |
| | mod_base = OTHER | |
| | note = N1-methylpseudouridine | |
| modified_base | 3754 | |
| | mod_base = OTHER | |
| | note = N1-methylpseudouridine | |
| modified_base | 3756 | |
| | mod_base = OTHER | |
| | note = N1-methylpseudouridine | |
| modified_base | 3766 | |
| | mod_base = OTHER | |
| | note = N1-methylpseudouridine | |
| modified_base | 3769 | |
| | mod_base = OTHER | |
| | note = N1-methylpseudouridine | |
| modified_base | 3774 | |
| | mod_base = OTHER | |
| | note = N1-methylpseudouridine | |
| modified_base | 3775 | |
| | mod_base = OTHER | |
| | note = N1-methylpseudouridine | |
| modified_base | 3777 | |
| | mod_base = OTHER | |
| | note = N1-methylpseudouridine | |
| modified_base | 3778 | |
| | mod_base = OTHER | |
| | note = N1-methylpseudouridine | |
| modified_base | 3790 | |
| | mod_base = OTHER | |
| | note = N1-methylpseudouridine | |
| modified_base | 3796 | |
| | mod_base = OTHER | |
| | note = N1-methylpseudouridine | |
| modified_base | 3811 | |
| | mod_base = OTHER | |
| | note = N1-methylpseudouridine | |
| modified_base | 3826 | |
| | mod_base = OTHER | |
| | note = N1-methylpseudouridine | |
| modified_base | 3829 | |
| | mod_base = OTHER | |
| | note = N1-methylpseudouridine | |
| modified_base | 3856 | |
| | mod_base = OTHER | |
| | note = N1-methylpseudouridine | |
| modified_base | 3859 | |
| | mod_base = OTHER | |
| | note = N1-methylpseudouridine | |

-continued

| | |
|---|---|
| modified_base | 3861<br>mod_base = OTHER<br>note = N1-methylpseudouridine |
| modified_base | 3879<br>mod_base = OTHER<br>note = N1-methylpseudouridine |
| modified_base | 3880<br>mod_base = OTHER<br>note = N1-methylpseudouridine |
| modified_base | 3889<br>mod_base = OTHER<br>note = N1-methylpseudouridine |
| modified_base | 3898<br>mod_base = OTHER<br>note = N1-methylpseudouridine |
| modified_base | 3901<br>mod_base = OTHER<br>note = N1-methylpseudouridine |
| modified_base | 3907<br>mod_base = OTHER<br>note = N1-methylpseudouridine |
| modified_base | 3916<br>mod_base = OTHER<br>note = N1-methylpseudouridine |
| modified_base | 3922<br>mod_base = OTHER<br>note = N1-methylpseudouridine |
| modified_base | 3925<br>mod_base = OTHER<br>note = N1-methylpseudouridine |
| modified_base | 3940<br>mod_base = OTHER<br>note = N1-methylpseudouridine |
| modified_base | 3954<br>mod_base = OTHER<br>note = N1-methylpseudouridine |
| modified_base | 3955<br>mod_base = OTHER<br>note = N1-methylpseudouridine |
| modified_base | 3970<br>mod_base = OTHER<br>note = N1-methylpseudouridine |
| modified_base | 3973<br>mod_base = OTHER<br>note = N1-methylpseudouridine |
| modified_base | 3997<br>mod_base = OTHER<br>note = N1-methylpseudouridine |
| modified_base | 4000<br>mod_base = OTHER<br>note = N1-methylpseudouridine |
| modified_base | 4017<br>mod_base = OTHER<br>note = N1-methylpseudouridine |
| modified_base | 4032<br>mod_base = OTHER<br>note = N1-methylpseudouridine |
| modified_base | 4041<br>mod_base = OTHER<br>note = N1-methylpseudouridine |
| modified_base | 4042<br>mod_base = OTHER<br>note = N1-methylpseudouridine |
| modified_base | 4057<br>mod_base = OTHER<br>note = N1-methylpseudouridine |
| modified_base | 4062<br>mod_base = OTHER<br>note = N1-methylpseudouridine |
| modified_base | 4069<br>mod_base = OTHER<br>note = N1-methylpseudouridine |
| modified_base | 4072<br>mod_base = OTHER<br>note = N1-methylpseudouridine |
| modified_base | 4075<br>mod_base = OTHER<br>note = N1-methylpseudouridine |
| modified_base | 4078 |

-continued

|  |  |
|---|---|
|  | mod_base = OTHER<br>note = N1-methylpseudouridine |
| modified_base | 4087<br>mod_base = OTHER<br>note = N1-methylpseudouridine |
| modified_base | 4111<br>mod_base = OTHER<br>note = N1-methylpseudouridine |
| modified_base | 4120<br>mod_base = OTHER<br>note = N1-methylpseudouridine |
| modified_base | 4129<br>mod_base = OTHER<br>note = N1-methylpseudouridine |
| modified_base | 4132<br>mod_base = OTHER<br>note = N1-methylpseudouridine |
| modified_base | 4138<br>mod_base = OTHER<br>note = N1-methylpseudouridine |
| modified_base | 4144<br>mod_base = OTHER<br>note = N1-methylpseudouridine |
| modified_base | 4147<br>mod_base = OTHER<br>note = N1-methylpseudouridine |
| modified_base | 4161<br>mod_base = OTHER<br>note = N1-methylpseudouridine |
| modified_base | 4162<br>mod_base = OTHER<br>note = N1-methylpseudouridine |
| modified_base | 4177<br>mod_base = OTHER<br>note = N1-methylpseudouridine |
| modified_base | 4182<br>mod_base = OTHER<br>note = N1-methylpseudouridine |
| modified_base | 4183<br>mod_base = OTHER<br>note = N1-methylpseudouridine |
| modified_base | 4186<br>mod_base = OTHER<br>note = N1-methylpseudouridine |
| modified_base | 4200<br>mod_base = OTHER<br>note = N1-methylpseudouridine |
| modified_base | 4210<br>mod_base = OTHER<br>note = N1-methylpseudouridine |
| modified_base | 4222<br>mod_base = OTHER<br>note = N1-methylpseudouridine |
| modified_base | 4225<br>mod_base = OTHER<br>note = N1-methylpseudouridine |
| modified_base | 4228<br>mod_base = OTHER<br>note = N1-methylpseudouridine |
| modified_base | 4234<br>mod_base = OTHER<br>note = N1-methylpseudouridine |
| modified_base | 4242<br>mod_base = OTHER<br>note = N1-methylpseudouridine |
| modified_base | 4249<br>mod_base = OTHER<br>note = N1-methylpseudouridine |
| modified_base | 4251<br>mod_base = OTHER<br>note = N1-methylpseudouridine |
| modified_base | 4252<br>mod_base = OTHER<br>note = N1-methylpseudouridine |
| modified_base | 4258<br>mod_base = OTHER<br>note = N1-methylpseudouridine |
| modified_base | 4279<br>mod_base = OTHER |

| | | |
|---|---|---|
| | | note = N1-methylpseudouridine |
| modified_base | 4282 | |
| | | mod_base = OTHER |
| | | note = N1-methylpseudouridine |
| modified_base | 4300 | |
| | | mod_base = OTHER |
| | | note = N1-methylpseudouridine |
| modified_base | 4318 | |
| | | mod_base = OTHER |
| | | note = N1-methylpseudouridine |
| modified_base | 4324 | |
| | | mod_base = OTHER |
| | | note = N1-methylpseudouridine |
| modified_base | 4335 | |
| | | mod_base = OTHER |
| | | note = N1-methylpseudouridine |
| modified_base | 4339 | |
| | | mod_base = OTHER |
| | | note = N1-methylpseudouridine |
| modified_base | 4344 | |
| | | mod_base = OTHER |
| | | note = N1-methylpseudouridine |
| modified_base | 4345 | |
| | | mod_base = OTHER |
| | | note = N1-methylpseudouridine |
| modified_base | 4348 | |
| | | mod_base = OTHER |
| | | note = N1-methylpseudouridine |
| modified_base | 4350 | |
| | | mod_base = OTHER |
| | | note = N1-methylpseudouridine |
| modified_base | 4354 | |
| | | mod_base = OTHER |
| | | note = N1-methylpseudouridine |
| modified_base | 4365 | |
| | | mod_base = OTHER |
| | | note = N1-methylpseudouridine |
| modified_base | 4375 | |
| | | mod_base = OTHER |
| | | note = N1-methylpseudouridine |
| modified_base | 4411 | |
| | | mod_base = OTHER |
| | | note = N1-methylpseudouridine |
| modified_base | 4413 | |
| | | mod_base = OTHER |
| | | note = N1-methylpseudouridine |
| modified_base | 4414 | |
| | | mod_base = OTHER |
| | | note = N1-methylpseudouridine |
| modified_base | 4417 | |
| | | mod_base = OTHER |
| | | note = N1-methylpseudouridine |
| modified_base | 4434 | |
| | | mod_base = OTHER |
| | | note = N1-methylpseudouridine |
| modified_base | 4438 | |
| | | mod_base = OTHER |
| | | note = N1-methylpseudouridine |
| modified_base | 4447 | |
| | | mod_base = OTHER |
| | | note = N1-methylpseudouridine |
| modified_base | 4450 | |
| | | mod_base = OTHER |
| | | note = N1-methylpseudouridine |
| modified_base | 4459 | |
| | | mod_base = OTHER |
| | | note = N1-methylpseudouridine |
| modified_base | 4467 | |
| | | mod_base = OTHER |
| | | note = N1-methylpseudouridine |
| modified_base | 4468 | |
| | | mod_base = OTHER |
| | | note = N1-methylpseudouridine |
| modified_base | 4480 | |
| | | mod_base = OTHER |
| | | note = N1-methylpseudouridine |
| modified_base | 4483 | |
| | | mod_base = OTHER |
| | | note = N1-methylpseudouridine |

-continued

| | | |
|---|---|---|
| modified_base | 4486 | |
| | mod_base = OTHER | |
| | note = N1-methylpseudouridine | |
| modified_base | 4501 | |
| | mod_base = OTHER | |
| | note = N1-methylpseudouridine | |
| modified_base | 4510 | |
| | mod_base = OTHER | |
| | note = N1-methylpseudouridine | |
| modified_base | 4513 | |
| | mod_base = OTHER | |
| | note = N1-methylpseudouridine | |
| modified_base | 4521 | |
| | mod_base = OTHER | |
| | note = N1-methylpseudouridine | |
| modified_base | 4546 | |
| | mod_base = OTHER | |
| | note = N1-methylpseudouridine | |
| modified_base | 4567 | |
| | mod_base = OTHER | |
| | note = N1-methylpseudouridine | |
| modified_base | 4570 | |
| | mod_base = OTHER | |
| | note = N1-methylpseudouridine | |
| modified_base | 4576 | |
| | mod_base = OTHER | |
| | note = N1-methylpseudouridine | |
| modified_base | 4578 | |
| | mod_base = OTHER | |
| | note = N1-methylpseudouridine | |
| modified_base | 4579 | |
| | mod_base = OTHER | |
| | note = N1-methylpseudouridine | |
| modified_base | 4585 | |
| | mod_base = OTHER | |
| | note = N1-methylpseudouridine | |
| modified_base | 4594 | |
| | mod_base = OTHER | |
| | note = N1-methylpseudouridine | |
| modified_base | 4611 | |
| | mod_base = OTHER | |
| | note = N1-methylpseudouridine | |
| modified_base | 4612 | |
| | mod_base = OTHER | |
| | note = N1-methylpseudouridine | |
| modified_base | 4617 | |
| | mod_base = OTHER | |
| | note = N1-methylpseudouridine | |
| modified_base | 4620 | |
| | mod_base = OTHER | |
| | note = N1-methylpseudouridine | |
| modified_base | 4621 | |
| | mod_base = OTHER | |
| | note = N1-methylpseudouridine | |
| modified_base | 4633 | |
| | mod_base = OTHER | |
| | note = N1-methylpseudouridine | |
| modified_base | 4647 | |
| | mod_base = OTHER | |
| | note = N1-methylpseudouridine | |
| modified_base | 4666 | |
| | mod_base = OTHER | |
| | note = N1-methylpseudouridine | |
| modified_base | 4669 | |
| | mod_base = OTHER | |
| | note = N1-methylpseudouridine | |
| modified_base | 4681 | |
| | mod_base = OTHER | |
| | note = N1-methylpseudouridine | |
| modified_base | 4684 | |
| | mod_base = OTHER | |
| | note = N1-methylpseudouridine | |
| modified_base | 4696 | |
| | mod_base = OTHER | |
| | note = N1-methylpseudouridine | |
| modified_base | 4705 | |
| | mod_base = OTHER | |
| | note = N1-methylpseudouridine | |
| modified_base | 4707 | |

-continued

|  |  |
|---|---|
| | mod_base = OTHER
note = N1-methylpseudouridine |
| modified_base | 4720
mod_base = OTHER
note = N1-methylpseudouridine |
| modified_base | 4726
mod_base = OTHER
note = N1-methylpseudouridine |
| modified_base | 4735
mod_base = OTHER
note = N1-methylpseudouridine |
| modified_base | 4782
mod_base = OTHER
note = N1-methylpseudouridine |
| modified_base | 4783
mod_base = OTHER
note = N1-methylpseudouridine |
| modified_base | 4810
mod_base = OTHER
note = N1-methylpseudouridine |
| modified_base | 4812
mod_base = OTHER
note = N1-methylpseudouridine |
| modified_base | 4823
mod_base = OTHER
note = N1-methylpseudouridine |
| modified_base | 4824
mod_base = OTHER
note = N1-methylpseudouridine |
| modified_base | 4827
mod_base = OTHER
note = N1-methylpseudouridine |
| modified_base | 4828
mod_base = OTHER
note = N1-methylpseudouridine |
| modified_base | 4833
mod_base = OTHER
note = N1-methylpseudouridine |
| modified_base | 4837
mod_base = OTHER
note = N1-methylpseudouridine |
| modified_base | 4838
mod_base = OTHER
note = N1-methylpseudouridine |
| modified_base | 4840
mod_base = OTHER
note = N1-methylpseudouridine |
| modified_base | 4848
mod_base = OTHER
note = N1-methylpseudouridine |
| modified_base | 4849
mod_base = OTHER
note = N1-methylpseudouridine |
| modified_base | 4853
mod_base = OTHER
note = N1-methylpseudouridine |
| modified_base | 4854
mod_base = OTHER
note = N1-methylpseudouridine |
| modified_base | 4856
mod_base = OTHER
note = N1-methylpseudouridine |
| modified_base | 4862
mod_base = OTHER
note = N1-methylpseudouridine |
| modified_base | 4867
mod_base = OTHER
note = N1-methylpseudouridine |
| modified_base | 4868
mod_base = OTHER
note = N1-methylpseudouridine |
| modified_base | 4870
mod_base = OTHER
note = N1-methylpseudouridine |
| modified_base | 4871
mod_base = OTHER
note = N1-methylpseudouridine |
| modified_base | 4873
mod_base = OTHER |

| | | |
|---|---|---|
| modified_base | 4875 | |
| | mod_base = OTHER | |
| | note = N1-methylpseudouridine | |
| modified_base | 4879 | |
| | mod_base = OTHER | |
| | note = N1-methylpseudouridine | |
| modified_base | 4880 | |
| | mod_base = OTHER | |
| | note = N1-methylpseudouridine | |
| modified_base | 4886 | |
| | mod_base = OTHER | |
| | note = N1-methylpseudouridine | |
| modified_base | 4888 | |
| | mod_base = OTHER | |
| | note = N1-methylpseudouridine | |
| modified_base | 4892 | |
| | mod_base = OTHER | |
| | note = N1-methylpseudouridine | |
| modified_base | 4894 | |
| | mod_base = OTHER | |
| | note = N1-methylpseudouridine | |
| modified_base | 4895 | |
| | mod_base = OTHER | |
| | note = N1-methylpseudouridine | |
| modified_base | 4898 | |
| | mod_base = OTHER | |
| | note = N1-methylpseudouridine | |
| modified_base | 4900 | |
| | mod_base = OTHER | |
| | note = N1-methylpseudouridine | |
| modified_base | 4901 | |
| | mod_base = OTHER | |
| | note = N1-methylpseudouridine | |
| modified_base | 4902 | |
| | mod_base = OTHER | |
| | note = N1-methylpseudouridine | |
| modified_base | 4906 | |
| | mod_base = OTHER | |
| | note = N1-methylpseudouridine | |
| modified_base | 4913 | |
| | mod_base = OTHER | |
| | note = N1-methylpseudouridine | |
| modified_base | 4917 | |
| | mod_base = OTHER | |
| | note = N1-methylpseudouridine | |
| modified_base | 4924 | |
| | mod_base = OTHER | |
| | note = N1-methylpseudouridine | |
| modified_base | 4926 | |
| | mod_base = OTHER | |
| | note = N1-methylpseudouridine | |

SEQUENCE: 20

```
aggaaataag agagaaaaga agagtaagaa gaaatataag agccaccatg agcgaggtgg    60
agttcagcca cgagtactgg atgcggcacg ccctgaccct ggccaagcgg gcccgggacg   120
agcgggaggt gcccgtgggc gccgtgctgg tgctgaacaa cccgggtgat cggcgagggct  180
ggaaccgggc catcggcctg cacgacccca ccgcccacgc cgagatcatg gccctgcggc   240
agggcggcct ggtgatgcag aactaccggc tgatcgacgc caccctgtac gtgaccttcg   300
agccctgcgt gatgtgcgcc ggcgccatga tccacagccg gatcggccgg gtggtgttcg   360
gcgtgcggaa cgccaagacc ggccgccgcc gcagcctgat ggacgtgctg caccacccg    420
gcatgaacca ccgggtggag atcaccgagg gcatcctggc cgacgagtgc gccgccctgc   480
tgtgccggtt cttccggatg ccccggcggg tgttcaacgc ccagaagaag gcccagagca   540
gcaccgacag cggcggcagc agcggcggca gcagcggcag cgagcaccc ggcaccagcg    600
agagcgccac ccccgagagc agcggccgca gcgccgcaag aagtacagca               660
tcggcctggc catcggcacc aacagcgtgg gctgggccgt gatcaccgac gagtacaagg   720
tgcccagcaa gaagttcaag gtgctgggca acaccgaccg gcacagcatc aagaagaacc   780
tgatcggcgc cctgctgttc gacagcggcg agacagccga ggccaccgg ctgaagcgga   840
ccgcccggcg gcggtacacc cggcggaaga accggatctg ctacctgcag gagatcttca   900
gcaacgagat ggccaaggtg gacgacagct tcttccaccg gctggaggag agcttcctgg   960
tggaggagga caagaagcac gagcggcacc ccatcttcgg caacatcgtg gacgaggtgg  1020
cctaccacga gaagtacccc accatctacc acctgcggaa gaagctggtg gacagcaccg  1080
acaaggccga cctgcggctg atctacctgg ccctggccca catgatcaag ttccggggcc  1140
acttcctgat cgagggcgac ctgaacccg acaaacagcg cgtggacaag ctgttcatcc   1200
agctggtgca gacctacaac cagctgttcg aggagaaccc catcaacgcc agcggcgtgg  1260
acgccaaggc catcctgagc gcccggctga gcaagagccg gcgcctggag aacctgatcg  1320
cccagctgcc cggcgagaag aagaacggc tgttcggcaa cctgatcgcc ctgagcctgg   1380
gcctgacccc caacttcaag agcaacttcg acctggccga ggacgccaag ctgcagctga  1440
gcaaggacac ctacgacgac gacctggaca acctgctggc ccagatcggc gaccagtacg  1500
ccgacctgtt cctggccgcc aagaacctga gcgacgccat cctgctgagc gacatcctgc  1560
```

-continued

```
gggtgaacac cgagatcacc aaggcccccc tgagcgccag catgatcaag cggtacgacg   1620
agcaccacca ggacctgacc ctgctgaagg ccctggtgcg gcagcagctg cccgagaagt   1680
acaaggagat cttcttcgac cagagcaaga acggctacgc cggctacatc gacggcggcg   1740
ccagccagga ggagttctac aagttcatca agcccatcct ggagaagatg gacggcaccg   1800
aggagctgct ggtgaagctg aaccgggagg acctgctggc gaaggacggg aacttcgaca   1860
acggcagcat cccccaccag atccacctgg cgagctgca cgccatcctg cggcggcagg   1920
aggacttcta ccccttcctg aaggacaacc gggagaagat cgagaagatc ctgaccttcc   1980
ggatcccctg ctacgtgggc cccctggccc ggggcaacag ccggttcgcc tggatgaccc   2040
gcaagagcga ggagacaatc acccccctgga acttcgagga ggtggtggaa agggcgcca   2100
gcgcccagag cttcatcgag cggatgacca acttcgacaa gaacctgccc aacgagaagg   2160
tgctgcccaa gcacagcctg ctgtacgagt acttcaccgt gtacaacgag ctgaccaagg   2220
tgaagtacgt gaccgagggc atgcggaagc ccgccttcct gagcggcgag cagaagaagg   2280
ccatcgtgga cctgctgttc aagaccaacc ggaaggtgac cgtgaagcag ctgaaggagg   2340
actacttcaa gaagatcgag tgcttcgaca cgtggagat cagcggcgtg gaggaccggt   2400
tcaacgccag cctgggcacc taccacgacc tgctgaagat catcaaggac aaggacttcc   2460
tggacaacga ggagaacgag gacatcctgg aggacatcgt gctgaccctg accctgttcg   2520
aggaccggga gatgatcgag gagcggctga agacctacgc ccacctgttc gacgacaagg   2580
tgatgaagca gctgaagcgg cggcgatcca ccggctgagc cggaagctga   2640
tcaacggcat ccgggacaag cagagcggca gaccatcct ggacttcctc aagagcgacg   2700
gcttcgccaa ccggaacttc atgcagctga tccacgacga cagcctgacc ttcaaggagg   2760
acatccgaga ggcccaggtg agcggccagg gcgacagcct gcacgagcac atcgccaacc   2820
tggccgagca ccccgccatc aagaagggca tcctgcagac cgtgaaggtg gtggacgagt   2880
tggtgaaggt gatgggccgg cacaagcccg agaacatcgt gatcgagatg gcccgggaga   2940
accagaccac ccagaagggc cagaagaaca gccgggagcg gatgaagcgg atcgaggagg   3000
gcatcaagga gctgggcagc cagatcctga aggagcaccc cgtggagaac cccagctgc   3060
agaacgagaa gctgtacctg tactacctgc agaacgggcg cgacatgtac gtggaccagg   3120
agctggacat caaccggctg agcgactacg acgtggacca catcgtgccc cagagcttcc   3180
tgaaggacga cagcatcgac aacaaggtgc tgacccggag cgacaagaac cggggcaaga   3240
gcgacaacgt gcccagcgag gaggtggtga agaagatgaa gaactactgg cggcagctgc   3300
tgaacgccaa gctgatcacc cagcggaagt tcgacaacct gaccaaggcc gacttcggc   3360
gcctgagcga gctggacaag gccggcttca tcaagcggca gctggtggag acacgcagaa   3420
tcaccaagca cgtggcccag atcctggaca gccggatgaa caccaagtac gacgagaacg   3480
acaagctgat ccgggaggtg aaggtgatca ccctcaagag caagctggtg agcgacttcc   3540
ggaaggactt ccagttctac aaggtgcggg agatcaaaca ctaccaccac gcccacgacg   3600
cctacctgaa cgccgtggtg ggcaccgccc tgatcaagaa gtaccccaag ctggagagcg   3660
agttcgtgta cggcgactac aaggtgtacg acgtgcggaa gatgatcgcc aagagcgagc   3720
aggagatcgg caaggccacc gccaagtact tcttctacag caacatcatg aacttcttca   3780
agaccgagat caccctggcc aacggcgaga tccggaagcg gcccctgatc gagacaaacg   3840
gcgagacagg cgagatcgtg tgggacaagg ccgggacttc cgccaccgtg cggaagtgc   3900
tgagcatgcc ccaggtgaac atcgtgaaga gaccgaggt gcagaccggc ggcttcagca   3960
aggagagcat cctgcccaag cggaacacg acaagctgat cgcccggaag aaggactggg   4020
accccaagaa gtacggcggc ttcgacagcc ccaccgtggc ctacagcgtg ctggtggtgg   4080
ccaaggtgga gaagggcaag agcaagaagc tcaagagcgt gaaggagctg ctgggcatca   4140
ccatcatgga gcggagcagc ttcgagaaga ccccatcga cttcctggag gccaagggct   4200
acaaggaggt gaagaaggac ctgatcatca agctgcccaa gtacagcctg ttcgagctgg   4260
agaacggccg gaagcggatg ctggccagcg ccggcgagct gcagaagggc aacgagctgg   4320
ccctgcccag caagtacgtg aacttcctgt acctggccag ccactacgag aagctgaagg   4380
gcagccccga ggacaacgag cagaagcagc tgttcgtgga gcagcacaag cactacctgg   4440
acgagatcat cgagcagatc agcgagttca gcaagcgggt gatcctggcc gacgccaacc   4500
tggacaaggt gctgagcgcc tacaacaagc accgggacaa gcccatccgg gagcaggccg   4560
agaacatcat ccacctgttc accctgacca acctgggcgc ccccgccgcc ttcaagtact   4620
tcgacaccac catcgaccgg aagcggtaca ccagcaccaa ggaggtgctg gacgccaccc   4680
tgatccacca gagcatcacc ggcctgtacg agacacggat cgacctgagc cagctgggcg   4740
gcgacgaggg cgccgacaag cggaccgccg acggcagcga gttcgagagc cccaagaaga   4800
agcggaaggt gtgagcggcc gcttaattaa gctgccttct gcgggcttg ccttctggcc   4860
atgcccttct tctctccctt gcacctgtac ctcttggtct ttgaataaag cctgagtagg   4920
aagtctaga                                                          4929
```

SEQ ID NO: 21          moltype = RNA   length = 4380
FEATURE                Location/Qualifiers
source                 1..4380
                       mol_type = other RNA
                       organism = synthetic construct
modified_base          7
                       mod_base = OTHER
                       note = N1-methylpseudouridine
modified_base          25
                       mod_base = OTHER
                       note = N1-methylpseudouridine
modified_base          35
                       mod_base = OTHER
                       note = N1-methylpseudouridine
modified_base          37
                       mod_base = OTHER
                       note = N1-methylpseudouridine
modified_base          49
                       mod_base = OTHER
                       note = N1-methylpseudouridine
modified_base          73

|                | | |
|---|---|---|
| | | mod_base = OTHER |
| | | note = N1-methylpseudouridine |
| modified_base | 79 | |
| | | mod_base = OTHER |
| | | note = N1-methylpseudouridine |
| modified_base | 88 | |
| | | mod_base = OTHER |
| | | note = N1-methylpseudouridine |
| modified_base | 108 | |
| | | mod_base = OTHER |
| | | note = N1-methylpseudouridine |
| modified_base | 115 | |
| | | mod_base = OTHER |
| | | note = N1-methylpseudouridine |
| modified_base | 121 | |
| | | mod_base = OTHER |
| | | note = N1-methylpseudouridine |
| modified_base | 127 | |
| | | mod_base = OTHER |
| | | note = N1-methylpseudouridine |
| modified_base | 142 | |
| | | mod_base = OTHER |
| | | note = N1-methylpseudouridine |
| modified_base | 147 | |
| | | mod_base = OTHER |
| | | note = N1-methylpseudouridine |
| modified_base | 154 | |
| | | mod_base = OTHER |
| | | note = N1-methylpseudouridine |
| modified_base | 157 | |
| | | mod_base = OTHER |
| | | note = N1-methylpseudouridine |
| modified_base | 168 | |
| | | mod_base = OTHER |
| | | note = N1-methylpseudouridine |
| modified_base | 175 | |
| | | mod_base = OTHER |
| | | note = N1-methylpseudouridine |
| modified_base | 189 | |
| | | mod_base = OTHER |
| | | note = N1-methylpseudouridine |
| modified_base | 190 | |
| | | mod_base = OTHER |
| | | note = N1-methylpseudouridine |
| modified_base | 196 | |
| | | mod_base = OTHER |
| | | note = N1-methylpseudouridine |
| modified_base | 199 | |
| | | mod_base = OTHER |
| | | note = N1-methylpseudouridine |
| modified_base | 223 | |
| | | mod_base = OTHER |
| | | note = N1-methylpseudouridine |
| modified_base | 235 | |
| | | mod_base = OTHER |
| | | note = N1-methylpseudouridine |
| modified_base | 238 | |
| | | mod_base = OTHER |
| | | note = N1-methylpseudouridine |
| modified_base | 247 | |
| | | mod_base = OTHER |
| | | note = N1-methylpseudouridine |
| modified_base | 250 | |
| | | mod_base = OTHER |
| | | note = N1-methylpseudouridine |
| modified_base | 252 | |
| | | mod_base = OTHER |
| | | note = N1-methylpseudouridine |
| modified_base | 253 | |
| | | mod_base = OTHER |
| | | note = N1-methylpseudouridine |
| modified_base | 286 | |
| | | mod_base = OTHER |
| | | note = N1-methylpseudouridine |
| modified_base | 309 | |
| | | mod_base = OTHER |
| | | note = N1-methylpseudouridine |
| modified_base | 331 | |
| | | mod_base = OTHER |

-continued

| | |
|---|---|
| modified_base | note = N1-methylpseudouridine<br>333<br>mod_base = OTHER<br>note = N1-methylpseudouridine |
| modified_base | 336<br>mod_base = OTHER<br>note = N1-methylpseudouridine |
| modified_base | 340<br>mod_base = OTHER<br>note = N1-methylpseudouridine |
| modified_base | 349<br>mod_base = OTHER<br>note = N1-methylpseudouridine |
| modified_base | 351<br>mod_base = OTHER<br>note = N1-methylpseudouridine |
| modified_base | 352<br>mod_base = OTHER<br>note = N1-methylpseudouridine |
| modified_base | 364<br>mod_base = OTHER<br>note = N1-methylpseudouridine |
| modified_base | 373<br>mod_base = OTHER<br>note = N1-methylpseudouridine |
| modified_base | 384<br>mod_base = OTHER<br>note = N1-methylpseudouridine |
| modified_base | 385<br>mod_base = OTHER<br>note = N1-methylpseudouridine |
| modified_base | 387<br>mod_base = OTHER<br>note = N1-methylpseudouridine |
| modified_base | 388<br>mod_base = OTHER<br>note = N1-methylpseudouridine |
| modified_base | 397<br>mod_base = OTHER<br>note = N1-methylpseudouridine |
| modified_base | 408<br>mod_base = OTHER<br>note = N1-methylpseudouridine |
| modified_base | 409<br>mod_base = OTHER<br>note = N1-methylpseudouridine |
| modified_base | 412<br>mod_base = OTHER<br>note = N1-methylpseudouridine |
| modified_base | 415<br>mod_base = OTHER<br>note = N1-methylpseudouridine |
| modified_base | 448<br>mod_base = OTHER<br>note = N1-methylpseudouridine |
| modified_base | 450<br>mod_base = OTHER<br>note = N1-methylpseudouridine |
| modified_base | 451<br>mod_base = OTHER<br>note = N1-methylpseudouridine |
| modified_base | 460<br>mod_base = OTHER<br>note = N1-methylpseudouridine |
| modified_base | 463<br>mod_base = OTHER<br>note = N1-methylpseudouridine |
| modified_base | 472<br>mod_base = OTHER<br>note = N1-methylpseudouridine |
| modified_base | 477<br>mod_base = OTHER<br>note = N1-methylpseudouridine |
| modified_base | 489<br>mod_base = OTHER<br>note = N1-methylpseudouridine |
| modified_base | 499<br>mod_base = OTHER<br>note = N1-methylpseudouridine |

-continued

| | |
|---|---|
| modified_base | 501<br>mod_base = OTHER<br>note = N1-methylpseudouridine |
| modified_base | 508<br>mod_base = OTHER<br>note = N1-methylpseudouridine |
| modified_base | 520<br>mod_base = OTHER<br>note = N1-methylpseudouridine |
| modified_base | 523<br>mod_base = OTHER<br>note = N1-methylpseudouridine |
| modified_base | 547<br>mod_base = OTHER<br>note = N1-methylpseudouridine |
| modified_base | 553<br>mod_base = OTHER<br>note = N1-methylpseudouridine |
| modified_base | 556<br>mod_base = OTHER<br>note = N1-methylpseudouridine |
| modified_base | 558<br>mod_base = OTHER<br>note = N1-methylpseudouridine |
| modified_base | 562<br>mod_base = OTHER<br>note = N1-methylpseudouridine |
| modified_base | 568<br>mod_base = OTHER<br>note = N1-methylpseudouridine |
| modified_base | 577<br>mod_base = OTHER<br>note = N1-methylpseudouridine |
| modified_base | 580<br>mod_base = OTHER<br>note = N1-methylpseudouridine |
| modified_base | 585<br>mod_base = OTHER<br>note = N1-methylpseudouridine |
| modified_base | 586<br>mod_base = OTHER<br>note = N1-methylpseudouridine |
| modified_base | 597<br>mod_base = OTHER<br>note = N1-methylpseudouridine |
| modified_base | 598<br>mod_base = OTHER<br>note = N1-methylpseudouridine |
| modified_base | 601<br>mod_base = OTHER<br>note = N1-methylpseudouridine |
| modified_base | 604<br>mod_base = OTHER<br>note = N1-methylpseudouridine |
| modified_base | 616<br>mod_base = OTHER<br>note = N1-methylpseudouridine |
| modified_base | 637<br>mod_base = OTHER<br>note = N1-methylpseudouridine |
| modified_base | 646<br>mod_base = OTHER<br>note = N1-methylpseudouridine |
| modified_base | 648<br>mod_base = OTHER<br>note = N1-methylpseudouridine |
| modified_base | 649<br>mod_base = OTHER<br>note = N1-methylpseudouridine |
| modified_base | 652<br>mod_base = OTHER<br>note = N1-methylpseudouridine |
| modified_base | 658<br>mod_base = OTHER<br>note = N1-methylpseudouridine |
| modified_base | 661<br>mod_base = OTHER<br>note = N1-methylpseudouridine |
| modified_base | 669 |

-continued

```
                               mod_base = OTHER
                               note = N1-methylpseudouridine
modified_base                  679
                               mod_base = OTHER
                               note = N1-methylpseudouridine
modified_base                  681
                               mod_base = OTHER
                               note = N1-methylpseudouridine
modified_base                  682
                               mod_base = OTHER
                               note = N1-methylpseudouridine
modified_base                  697
                               mod_base = OTHER
                               note = N1-methylpseudouridine
modified_base                  712
                               mod_base = OTHER
                               note = N1-methylpseudouridine
modified_base                  727
                               mod_base = OTHER
                               note = N1-methylpseudouridine
modified_base                  730
                               mod_base = OTHER
                               note = N1-methylpseudouridine
modified_base                  742
                               mod_base = OTHER
                               note = N1-methylpseudouridine
modified_base                  760
                               mod_base = OTHER
                               note = N1-methylpseudouridine
modified_base                  769
                               mod_base = OTHER
                               note = N1-methylpseudouridine
modified_base                  772
                               mod_base = OTHER
                               note = N1-methylpseudouridine
modified_base                  781
                               mod_base = OTHER
                               note = N1-methylpseudouridine
modified_base                  805
                               mod_base = OTHER
                               note = N1-methylpseudouridine
modified_base                  807
                               mod_base = OTHER
                               note = N1-methylpseudouridine
modified_base                  808
                               mod_base = OTHER
                               note = N1-methylpseudouridine
modified_base                  817
                               mod_base = OTHER
                               note = N1-methylpseudouridine
modified_base                  820
                               mod_base = OTHER
                               note = N1-methylpseudouridine
modified_base                  826
                               mod_base = OTHER
                               note = N1-methylpseudouridine
modified_base                  832
                               mod_base = OTHER
                               note = N1-methylpseudouridine
modified_base                  838
                               mod_base = OTHER
                               note = N1-methylpseudouridine
modified_base                  849
                               mod_base = OTHER
                               note = N1-methylpseudouridine
modified_base                  850
                               mod_base = OTHER
                               note = N1-methylpseudouridine
modified_base                  861
                               mod_base = OTHER
                               note = N1-methylpseudouridine
modified_base                  862
                               mod_base = OTHER
                               note = N1-methylpseudouridine
modified_base                  868
                               mod_base = OTHER
                               note = N1-methylpseudouridine
modified_base                  886
                               mod_base = OTHER
```

-continued

| | | |
|---|---|---|
| modified_base | 892 | note = N1-methylpseudouridine |
| | | mod_base = OTHER |
| | | note = N1-methylpseudouridine |
| modified_base | 906 | |
| | | mod_base = OTHER |
| | | note = N1-methylpseudouridine |
| modified_base | 919 | |
| | | mod_base = OTHER |
| | | note = N1-methylpseudouridine |
| modified_base | 928 | |
| | | mod_base = OTHER |
| | | note = N1-methylpseudouridine |
| modified_base | 931 | |
| | | mod_base = OTHER |
| | | note = N1-methylpseudouridine |
| modified_base | 940 | |
| | | mod_base = OTHER |
| | | note = N1-methylpseudouridine |
| modified_base | 951 | |
| | | mod_base = OTHER |
| | | note = N1-methylpseudouridine |
| modified_base | 961 | |
| | | mod_base = OTHER |
| | | note = N1-methylpseudouridine |
| modified_base | 963 | |
| | | mod_base = OTHER |
| | | note = N1-methylpseudouridine |
| modified_base | 964 | |
| | | mod_base = OTHER |
| | | note = N1-methylpseudouridine |
| modified_base | 967 | |
| | | mod_base = OTHER |
| | | note = N1-methylpseudouridine |
| modified_base | 982 | |
| | | mod_base = OTHER |
| | | note = N1-methylpseudouridine |
| modified_base | 994 | |
| | | mod_base = OTHER |
| | | note = N1-methylpseudouridine |
| modified_base | 997 | |
| | | mod_base = OTHER |
| | | note = N1-methylpseudouridine |
| modified_base | 1000 | |
| | | mod_base = OTHER |
| | | note = N1-methylpseudouridine |
| modified_base | 1009 | |
| | | mod_base = OTHER |
| | | note = N1-methylpseudouridine |
| modified_base | 1012 | |
| | | mod_base = OTHER |
| | | note = N1-methylpseudouridine |
| modified_base | 1018 | |
| | | mod_base = OTHER |
| | | note = N1-methylpseudouridine |
| modified_base | 1030 | |
| | | mod_base = OTHER |
| | | note = N1-methylpseudouridine |
| modified_base | 1045 | |
| | | mod_base = OTHER |
| | | note = N1-methylpseudouridine |
| modified_base | 1057 | |
| | | mod_base = OTHER |
| | | note = N1-methylpseudouridine |
| modified_base | 1060 | |
| | | mod_base = OTHER |
| | | note = N1-methylpseudouridine |
| modified_base | 1068 | |
| | | mod_base = OTHER |
| | | note = N1-methylpseudouridine |
| modified_base | 1090 | |
| | | mod_base = OTHER |
| | | note = N1-methylpseudouridine |
| modified_base | 1096 | |
| | | mod_base = OTHER |
| | | note = N1-methylpseudouridine |
| modified_base | 1099 | |
| | | mod_base = OTHER |
| | | note = N1-methylpseudouridine |

-continued

| | |
|---|---|
| modified_base | 1108<br>mod_base = OTHER<br>note = N1-methylpseudouridine |
| modified_base | 1111<br>mod_base = OTHER<br>note = N1-methylpseudouridine |
| modified_base | 1123<br>mod_base = OTHER<br>note = N1-methylpseudouridine |
| modified_base | 1134<br>mod_base = OTHER<br>note = N1-methylpseudouridine |
| modified_base | 1144<br>mod_base = OTHER<br>note = N1-methylpseudouridine |
| modified_base | 1146<br>mod_base = OTHER<br>note = N1-methylpseudouridine |
| modified_base | 1147<br>mod_base = OTHER<br>note = N1-methylpseudouridine |
| modified_base | 1149<br>mod_base = OTHER<br>note = N1-methylpseudouridine |
| modified_base | 1150<br>mod_base = OTHER<br>note = N1-methylpseudouridine |
| modified_base | 1170<br>mod_base = OTHER<br>note = N1-methylpseudouridine |
| modified_base | 1179<br>mod_base = OTHER<br>note = N1-methylpseudouridine |
| modified_base | 1183<br>mod_base = OTHER<br>note = N1-methylpseudouridine |
| modified_base | 1209<br>mod_base = OTHER<br>note = N1-methylpseudouridine |
| modified_base | 1210<br>mod_base = OTHER<br>note = N1-methylpseudouridine |
| modified_base | 1212<br>mod_base = OTHER<br>note = N1-methylpseudouridine |
| modified_base | 1218<br>mod_base = OTHER<br>note = N1-methylpseudouridine |
| modified_base | 1219<br>mod_base = OTHER<br>note = N1-methylpseudouridine |
| modified_base | 1222<br>mod_base = OTHER<br>note = N1-methylpseudouridine |
| modified_base | 1231<br>mod_base = OTHER<br>note = N1-methylpseudouridine |
| modified_base | 1234<br>mod_base = OTHER<br>note = N1-methylpseudouridine |
| modified_base | 1243<br>mod_base = OTHER<br>note = N1-methylpseudouridine |
| modified_base | 1261<br>mod_base = OTHER<br>note = N1-methylpseudouridine |
| modified_base | 1264<br>mod_base = OTHER<br>note = N1-methylpseudouridine |
| modified_base | 1267<br>mod_base = OTHER<br>note = N1-methylpseudouridine |
| modified_base | 1273<br>mod_base = OTHER<br>note = N1-methylpseudouridine |
| modified_base | 1288<br>mod_base = OTHER<br>note = N1-methylpseudouridine |
| modified_base | 1291 |

-continued

| | |
|---|---|
| | mod_base = OTHER |
| | note = N1-methylpseudouridine |
| modified_base | 1308 |
| | mod_base = OTHER |
| | note = N1-methylpseudouridine |
| modified_base | 1309 |
| | mod_base = OTHER |
| | note = N1-methylpseudouridine |
| modified_base | 1324 |
| | mod_base = OTHER |
| | note = N1-methylpseudouridine |
| modified_base | 1336 |
| | mod_base = OTHER |
| | note = N1-methylpseudouridine |
| modified_base | 1342 |
| | mod_base = OTHER |
| | note = N1-methylpseudouridine |
| modified_base | 1351 |
| | mod_base = OTHER |
| | note = N1-methylpseudouridine |
| modified_base | 1360 |
| | mod_base = OTHER |
| | note = N1-methylpseudouridine |
| modified_base | 1363 |
| | mod_base = OTHER |
| | note = N1-methylpseudouridine |
| modified_base | 1380 |
| | mod_base = OTHER |
| | note = N1-methylpseudouridine |
| modified_base | 1381 |
| | mod_base = OTHER |
| | note = N1-methylpseudouridine |
| modified_base | 1383 |
| | mod_base = OTHER |
| | note = N1-methylpseudouridine |
| modified_base | 1389 |
| | mod_base = OTHER |
| | note = N1-methylpseudouridine |
| modified_base | 1390 |
| | mod_base = OTHER |
| | note = N1-methylpseudouridine |
| modified_base | 1393 |
| | mod_base = OTHER |
| | note = N1-methylpseudouridine |
| modified_base | 1414 |
| | mod_base = OTHER |
| | note = N1-methylpseudouridine |
| modified_base | 1423 |
| | mod_base = OTHER |
| | note = N1-methylpseudouridine |
| modified_base | 1426 |
| | mod_base = OTHER |
| | note = N1-methylpseudouridine |
| modified_base | 1431 |
| | mod_base = OTHER |
| | note = N1-methylpseudouridine |
| modified_base | 1432 |
| | mod_base = OTHER |
| | note = N1-methylpseudouridine |
| modified_base | 1438 |
| | mod_base = OTHER |
| | note = N1-methylpseudouridine |
| modified_base | 1443 |
| | mod_base = OTHER |
| | note = N1-methylpseudouridine |
| modified_base | 1446 |
| | mod_base = OTHER |
| | note = N1-methylpseudouridine |
| modified_base | 1450 |
| | mod_base = OTHER |
| | note = N1-methylpseudouridine |
| modified_base | 1459 |
| | mod_base = OTHER |
| | note = N1-methylpseudouridine |
| modified_base | 1479 |
| | mod_base = OTHER |
| | note = N1-methylpseudouridine |
| modified_base | 1480 |
| | mod_base = OTHER |

-continued

| | | |
|---|---|---|
| modified_base | 1485 | note = N1-methylpseudouridine |
| | mod_base = OTHER | |
| | note = N1-methylpseudouridine | |
| modified_base | 1489 | |
| | mod_base = OTHER | |
| | note = N1-methylpseudouridine | |
| modified_base | 1513 | |
| | mod_base = OTHER | |
| | note = N1-methylpseudouridine | |
| modified_base | 1521 | |
| | mod_base = OTHER | |
| | note = N1-methylpseudouridine | |
| modified_base | 1527 | |
| | mod_base = OTHER | |
| | note = N1-methylpseudouridine | |
| modified_base | 1528 | |
| | mod_base = OTHER | |
| | note = N1-methylpseudouridine | |
| modified_base | 1537 | |
| | mod_base = OTHER | |
| | note = N1-methylpseudouridine | |
| modified_base | 1540 | |
| | mod_base = OTHER | |
| | note = N1-methylpseudouridine | |
| modified_base | 1566 | |
| | mod_base = OTHER | |
| | note = N1-methylpseudouridine | |
| modified_base | 1567 | |
| | mod_base = OTHER | |
| | note = N1-methylpseudouridine | |
| modified_base | 1570 | |
| | mod_base = OTHER | |
| | note = N1-methylpseudouridine | |
| modified_base | 1579 | |
| | mod_base = OTHER | |
| | note = N1-methylpseudouridine | |
| modified_base | 1587 | |
| | mod_base = OTHER | |
| | note = N1-methylpseudouridine | |
| modified_base | 1588 | |
| | mod_base = OTHER | |
| | note = N1-methylpseudouridine | |
| modified_base | 1600 | |
| | mod_base = OTHER | |
| | note = N1-methylpseudouridine | |
| modified_base | 1615 | |
| | mod_base = OTHER | |
| | note = N1-methylpseudouridine | |
| modified_base | 1618 | |
| | mod_base = OTHER | |
| | note = N1-methylpseudouridine | |
| modified_base | 1633 | |
| | mod_base = OTHER | |
| | note = N1-methylpseudouridine | |
| modified_base | 1636 | |
| | mod_base = OTHER | |
| | note = N1-methylpseudouridine | |
| modified_base | 1638 | |
| | mod_base = OTHER | |
| | note = N1-methylpseudouridine | |
| modified_base | 1644 | |
| | mod_base = OTHER | |
| | note = N1-methylpseudouridine | |
| modified_base | 1647 | |
| | mod_base = OTHER | |
| | note = N1-methylpseudouridine | |
| modified_base | 1648 | |
| | mod_base = OTHER | |
| | note = N1-methylpseudouridine | |
| modified_base | 1654 | |
| | mod_base = OTHER | |
| | note = N1-methylpseudouridine | |
| modified_base | 1656 | |
| | mod_base = OTHER | |
| | note = N1-methylpseudouridine | |
| modified_base | 1666 | |
| | mod_base = OTHER | |
| | note = N1-methylpseudouridine | |

| | |
|---|---|
| modified_base | 1675<br>mod_base = OTHER<br>note = N1-methylpseudouridine |
| modified_base | 1680<br>mod_base = OTHER<br>note = N1-methylpseudouridine |
| modified_base | 1684<br>mod_base = OTHER<br>note = N1-methylpseudouridine |
| modified_base | 1696<br>mod_base = OTHER<br>note = N1-methylpseudouridine |
| modified_base | 1710<br>mod_base = OTHER<br>note = N1-methylpseudouridine |
| modified_base | 1711<br>mod_base = OTHER<br>note = N1-methylpseudouridine |
| modified_base | 1714<br>mod_base = OTHER<br>note = N1-methylpseudouridine |
| modified_base | 1738<br>mod_base = OTHER<br>note = N1-methylpseudouridine |
| modified_base | 1741<br>mod_base = OTHER<br>note = N1-methylpseudouridine |
| modified_base | 1747<br>mod_base = OTHER<br>note = N1-methylpseudouridine |
| modified_base | 1750<br>mod_base = OTHER<br>note = N1-methylpseudouridine |
| modified_base | 1752<br>mod_base = OTHER<br>note = N1-methylpseudouridine |
| modified_base | 1753<br>mod_base = OTHER<br>note = N1-methylpseudouridine |
| modified_base | 1771<br>mod_base = OTHER<br>note = N1-methylpseudouridine |
| modified_base | 1777<br>mod_base = OTHER<br>note = N1-methylpseudouridine |
| modified_base | 1786<br>mod_base = OTHER<br>note = N1-methylpseudouridine |
| modified_base | 1797<br>mod_base = OTHER<br>note = N1-methylpseudouridine |
| modified_base | 1800<br>mod_base = OTHER<br>note = N1-methylpseudouridine |
| modified_base | 1801<br>mod_base = OTHER<br>note = N1-methylpseudouridine |
| modified_base | 1810<br>mod_base = OTHER<br>note = N1-methylpseudouridine |
| modified_base | 1815<br>mod_base = OTHER<br>note = N1-methylpseudouridine |
| modified_base | 1818<br>mod_base = OTHER<br>note = N1-methylpseudouridine |
| modified_base | 1819<br>mod_base = OTHER<br>note = N1-methylpseudouridine |
| modified_base | 1828<br>mod_base = OTHER<br>note = N1-methylpseudouridine |
| modified_base | 1834<br>mod_base = OTHER<br>note = N1-methylpseudouridine |
| modified_base | 1843<br>mod_base = OTHER<br>note = N1-methylpseudouridine |
| modified_base | 1854 |

| | | |
|---|---|---|
| | | mod_base = OTHER
note = N1-methylpseudouridine |
| modified_base | 1855 | |
| | | mod_base = OTHER
note = N1-methylpseudouridine |
| modified_base | 1867 | |
| | | mod_base = OTHER
note = N1-methylpseudouridine |
| modified_base | 1875 | |
| | | mod_base = OTHER
note = N1-methylpseudouridine |
| modified_base | 1885 | |
| | | mod_base = OTHER
note = N1-methylpseudouridine |
| modified_base | 1888 | |
| | | mod_base = OTHER
note = N1-methylpseudouridine |
| modified_base | 1894 | |
| | | mod_base = OTHER
note = N1-methylpseudouridine |
| modified_base | 1897 | |
| | | mod_base = OTHER
note = N1-methylpseudouridine |
| modified_base | 1911 | |
| | | mod_base = OTHER
note = N1-methylpseudouridine |
| modified_base | 1912 | |
| | | mod_base = OTHER
note = N1-methylpseudouridine |
| modified_base | 1915 | |
| | | mod_base = OTHER
note = N1-methylpseudouridine |
| modified_base | 1939 | |
| | | mod_base = OTHER
note = N1-methylpseudouridine |
| modified_base | 1942 | |
| | | mod_base = OTHER
note = N1-methylpseudouridine |
| modified_base | 1951 | |
| | | mod_base = OTHER
note = N1-methylpseudouridine |
| modified_base | 1954 | |
| | | mod_base = OTHER
note = N1-methylpseudouridine |
| modified_base | 1957 | |
| | | mod_base = OTHER
note = N1-methylpseudouridine |
| modified_base | 1963 | |
| | | mod_base = OTHER
note = N1-methylpseudouridine |
| modified_base | 1969 | |
| | | mod_base = OTHER
note = N1-methylpseudouridine |
| modified_base | 1971 | |
| | | mod_base = OTHER
note = N1-methylpseudouridine |
| modified_base | 1972 | |
| | | mod_base = OTHER
note = N1-methylpseudouridine |
| modified_base | 1987 | |
| | | mod_base = OTHER
note = N1-methylpseudouridine |
| modified_base | 1990 | |
| | | mod_base = OTHER
note = N1-methylpseudouridine |
| modified_base | 2002 | |
| | | mod_base = OTHER
note = N1-methylpseudouridine |
| modified_base | 2010 | |
| | | mod_base = OTHER
note = N1-methylpseudouridine |
| modified_base | 2020 | |
| | | mod_base = OTHER
note = N1-methylpseudouridine |
| modified_base | 2022 | |
| | | mod_base = OTHER
note = N1-methylpseudouridine |
| modified_base | 2023 | |
| | | mod_base = OTHER |

|  |  |
|---|---|
| modified_base | note = N1-methylpseudouridine |
|  | 2035 |
|  | mod_base = OTHER |
|  | note = N1-methylpseudouridine |
| modified_base | 2038 |
|  | mod_base = OTHER |
|  | note = N1-methylpseudouridine |
| modified_base | 2047 |
|  | mod_base = OTHER |
|  | note = N1-methylpseudouridine |
| modified_base | 2061 |
|  | mod_base = OTHER |
|  | note = N1-methylpseudouridine |
| modified_base | 2070 |
|  | mod_base = OTHER |
|  | note = N1-methylpseudouridine |
| modified_base | 2080 |
|  | mod_base = OTHER |
|  | note = N1-methylpseudouridine |
| modified_base | 2092 |
|  | mod_base = OTHER |
|  | note = N1-methylpseudouridine |
| modified_base | 2095 |
|  | mod_base = OTHER |
|  | note = N1-methylpseudouridine |
| modified_base | 2104 |
|  | mod_base = OTHER |
|  | note = N1-methylpseudouridine |
| modified_base | 2131 |
|  | mod_base = OTHER |
|  | note = N1-methylpseudouridine |
| modified_base | 2134 |
|  | mod_base = OTHER |
|  | note = N1-methylpseudouridine |
| modified_base | 2139 |
|  | mod_base = OTHER |
|  | note = N1-methylpseudouridine |
| modified_base | 2140 |
|  | mod_base = OTHER |
|  | note = N1-methylpseudouridine |
| modified_base | 2143 |
|  | mod_base = OTHER |
|  | note = N1-methylpseudouridine |
| modified_base | 2157 |
|  | mod_base = OTHER |
|  | note = N1-methylpseudouridine |
| modified_base | 2158 |
|  | mod_base = OTHER |
|  | note = N1-methylpseudouridine |
| modified_base | 2172 |
|  | mod_base = OTHER |
|  | note = N1-methylpseudouridine |
| modified_base | 2173 |
|  | mod_base = OTHER |
|  | note = N1-methylpseudouridine |
| modified_base | 2176 |
|  | mod_base = OTHER |
|  | note = N1-methylpseudouridine |
| modified_base | 2182 |
|  | mod_base = OTHER |
|  | note = N1-methylpseudouridine |
| modified_base | 2185 |
|  | mod_base = OTHER |
|  | note = N1-methylpseudouridine |
| modified_base | 2200 |
|  | mod_base = OTHER |
|  | note = N1-methylpseudouridine |
| modified_base | 2205 |
|  | mod_base = OTHER |
|  | note = N1-methylpseudouridine |
| modified_base | 2206 |
|  | mod_base = OTHER |
|  | note = N1-methylpseudouridine |
| modified_base | 2218 |
|  | mod_base = OTHER |
|  | note = N1-methylpseudouridine |
| modified_base | 2233 |
|  | mod_base = OTHER |
|  | note = N1-methylpseudouridine |

-continued

| | |
|---|---|
| modified_base | 2254<br>mod_base = OTHER<br>note = N1-methylpseudouridine |
| modified_base | 2266<br>mod_base = OTHER<br>note = N1-methylpseudouridine |
| modified_base | 2275<br>mod_base = OTHER<br>note = N1-methylpseudouridine |
| modified_base | 2293<br>mod_base = OTHER<br>note = N1-methylpseudouridine |
| modified_base | 2305<br>mod_base = OTHER<br>note = N1-methylpseudouridine |
| modified_base | 2308<br>mod_base = OTHER<br>note = N1-methylpseudouridine |
| modified_base | 2317<br>mod_base = OTHER<br>note = N1-methylpseudouridine |
| modified_base | 2323<br>mod_base = OTHER<br>note = N1-methylpseudouridine |
| modified_base | 2326<br>mod_base = OTHER<br>note = N1-methylpseudouridine |
| modified_base | 2335<br>mod_base = OTHER<br>note = N1-methylpseudouridine |
| modified_base | 2338<br>mod_base = OTHER<br>note = N1-methylpseudouridine |
| modified_base | 2344<br>mod_base = OTHER<br>note = N1-methylpseudouridine |
| modified_base | 2347<br>mod_base = OTHER<br>note = N1-methylpseudouridine |
| modified_base | 2371<br>mod_base = OTHER<br>note = N1-methylpseudouridine |
| modified_base | 2374<br>mod_base = OTHER<br>note = N1-methylpseudouridine |
| modified_base | 2377<br>mod_base = OTHER<br>note = N1-methylpseudouridine |
| modified_base | 2383<br>mod_base = OTHER<br>note = N1-methylpseudouridine |
| modified_base | 2437<br>mod_base = OTHER<br>note = N1-methylpseudouridine |
| modified_base | 2446<br>mod_base = OTHER<br>note = N1-methylpseudouridine |
| modified_base | 2458<br>mod_base = OTHER<br>note = N1-methylpseudouridine |
| modified_base | 2467<br>mod_base = OTHER<br>note = N1-methylpseudouridine |
| modified_base | 2479<br>mod_base = OTHER<br>note = N1-methylpseudouridine |
| modified_base | 2482<br>mod_base = OTHER<br>note = N1-methylpseudouridine |
| modified_base | 2497<br>mod_base = OTHER<br>note = N1-methylpseudouridine |
| modified_base | 2512<br>mod_base = OTHER<br>note = N1-methylpseudouridine |
| modified_base | 2527<br>mod_base = OTHER<br>note = N1-methylpseudouridine |
| modified_base | 2529 |

|                |      |
|----------------|------|
| modified_base  | mod_base = OTHER<br>note = N1-methylpseudouridine<br>2533 |
| modified_base  | mod_base = OTHER<br>note = N1-methylpseudouridine<br>2535 |
| modified_base  | mod_base = OTHER<br>note = N1-methylpseudouridine<br>2538 |
| modified_base  | mod_base = OTHER<br>note = N1-methylpseudouridine<br>2542 |
| modified_base  | mod_base = OTHER<br>note = N1-methylpseudouridine<br>2560 |
| modified_base  | mod_base = OTHER<br>note = N1-methylpseudouridine<br>2562 |
| modified_base  | mod_base = OTHER<br>note = N1-methylpseudouridine<br>2566 |
| modified_base  | mod_base = OTHER<br>note = N1-methylpseudouridine<br>2578 |
| modified_base  | mod_base = OTHER<br>note = N1-methylpseudouridine<br>2584 |
| modified_base  | mod_base = OTHER<br>note = N1-methylpseudouridine<br>2593 |
| modified_base  | mod_base = OTHER<br>note = N1-methylpseudouridine<br>2601 |
| modified_base  | mod_base = OTHER<br>note = N1-methylpseudouridine<br>2608 |
| modified_base  | mod_base = OTHER<br>note = N1-methylpseudouridine<br>2617 |
| modified_base  | mod_base = OTHER<br>note = N1-methylpseudouridine<br>2620 |
| modified_base  | mod_base = OTHER<br>note = N1-methylpseudouridine<br>2631 |
| modified_base  | mod_base = OTHER<br>note = N1-methylpseudouridine<br>2632 |
| modified_base  | mod_base = OTHER<br>note = N1-methylpseudouridine<br>2635 |
| modified_base  | mod_base = OTHER<br>note = N1-methylpseudouridine<br>2650 |
| modified_base  | mod_base = OTHER<br>note = N1-methylpseudouridine<br>2662 |
| modified_base  | mod_base = OTHER<br>note = N1-methylpseudouridine<br>2665 |
| modified_base  | mod_base = OTHER<br>note = N1-methylpseudouridine<br>2704 |
| modified_base  | mod_base = OTHER<br>note = N1-methylpseudouridine<br>2719 |
| modified_base  | mod_base = OTHER<br>note = N1-methylpseudouridine<br>2722 |
| modified_base  | mod_base = OTHER<br>note = N1-methylpseudouridine<br>2731 |
| modified_base  | mod_base = OTHER<br>note = N1-methylpseudouridine<br>2739 |
| modified_base  | mod_base = OTHER<br>note = N1-methylpseudouridine<br>2742<br>mod_base = OTHER |

-continued

| | | |
|---|---|---|
| modified_base | 2752 mod_base = OTHER note = N1-methylpseudouridine | |
| modified_base | 2755 mod_base = OTHER note = N1-methylpseudouridine | |
| modified_base | 2767 mod_base = OTHER note = N1-methylpseudouridine | |
| modified_base | 2770 mod_base = OTHER note = N1-methylpseudouridine | |
| modified_base | 2784 mod_base = OTHER note = N1-methylpseudouridine | |
| modified_base | 2785 mod_base = OTHER note = N1-methylpseudouridine | |
| modified_base | 2794 mod_base = OTHER note = N1-methylpseudouridine | |
| modified_base | 2818 mod_base = OTHER note = N1-methylpseudouridine | |
| modified_base | 2827 mod_base = OTHER note = N1-methylpseudouridine | |
| modified_base | 2841 mod_base = OTHER note = N1-methylpseudouridine | |
| modified_base | 2842 mod_base = OTHER note = N1-methylpseudouridine | |
| modified_base | 2845 mod_base = OTHER note = N1-methylpseudouridine | |
| modified_base | 2857 mod_base = OTHER note = N1-methylpseudouridine | |
| modified_base | 2860 mod_base = OTHER note = N1-methylpseudouridine | |
| modified_base | 2875 mod_base = OTHER note = N1-methylpseudouridine | |
| modified_base | 2887 mod_base = OTHER note = N1-methylpseudouridine | |
| modified_base | 2896 mod_base = OTHER note = N1-methylpseudouridine | |
| modified_base | 2899 mod_base = OTHER note = N1-methylpseudouridine | |
| modified_base | 2911 mod_base = OTHER note = N1-methylpseudouridine | |
| modified_base | 2922 mod_base = OTHER note = N1-methylpseudouridine | |
| modified_base | 2941 mod_base = OTHER note = N1-methylpseudouridine | |
| modified_base | 2944 mod_base = OTHER note = N1-methylpseudouridine | |
| modified_base | 2953 mod_base = OTHER note = N1-methylpseudouridine | |
| modified_base | 2959 mod_base = OTHER note = N1-methylpseudouridine | |
| modified_base | 2962 mod_base = OTHER note = N1-methylpseudouridine | |
| modified_base | 2968 mod_base = OTHER note = N1-methylpseudouridine | |

-continued

| | | |
|---|---|---|
| modified_base | 2980 | |
| | mod_base = OTHER | |
| | note = N1-methylpseudouridine | |
| modified_base | 2983 | |
| | mod_base = OTHER | |
| | note = N1-methylpseudouridine | |
| modified_base | 2991 | |
| | mod_base = OTHER | |
| | note = N1-methylpseudouridine | |
| modified_base | 2992 | |
| | mod_base = OTHER | |
| | note = N1-methylpseudouridine | |
| modified_base | 3003 | |
| | mod_base = OTHER | |
| | note = N1-methylpseudouridine | |
| modified_base | 3004 | |
| | mod_base = OTHER | |
| | note = N1-methylpseudouridine | |
| modified_base | 3009 | |
| | mod_base = OTHER | |
| | note = N1-methylpseudouridine | |
| modified_base | 3010 | |
| | mod_base = OTHER | |
| | note = N1-methylpseudouridine | |
| modified_base | 3012 | |
| | mod_base = OTHER | |
| | note = N1-methylpseudouridine | |
| modified_base | 3019 | |
| | mod_base = OTHER | |
| | note = N1-methylpseudouridine | |
| modified_base | 3028 | |
| | mod_base = OTHER | |
| | note = N1-methylpseudouridine | |
| modified_base | 3036 | |
| | mod_base = OTHER | |
| | note = N1-methylpseudouridine | |
| modified_base | 3057 | |
| | mod_base = OTHER | |
| | note = N1-methylpseudouridine | |
| modified_base | 3061 | |
| | mod_base = OTHER | |
| | note = N1-methylpseudouridine | |
| modified_base | 3070 | |
| | mod_base = OTHER | |
| | note = N1-methylpseudouridine | |
| modified_base | 3073 | |
| | mod_base = OTHER | |
| | note = N1-methylpseudouridine | |
| modified_base | 3085 | |
| | mod_base = OTHER | |
| | note = N1-methylpseudouridine | |
| modified_base | 3088 | |
| | mod_base = OTHER | |
| | note = N1-methylpseudouridine | |
| modified_base | 3096 | |
| | mod_base = OTHER | |
| | note = N1-methylpseudouridine | |
| modified_base | 3106 | |
| | mod_base = OTHER | |
| | note = N1-methylpseudouridine | |
| modified_base | 3117 | |
| | mod_base = OTHER | |
| | note = N1-methylpseudouridine | |
| modified_base | 3118 | |
| | mod_base = OTHER | |
| | note = N1-methylpseudouridine | |
| modified_base | 3121 | |
| | mod_base = OTHER | |
| | note = N1-methylpseudouridine | |
| modified_base | 3123 | |
| | mod_base = OTHER | |
| | note = N1-methylpseudouridine | |
| modified_base | 3132 | |
| | mod_base = OTHER | |
| | note = N1-methylpseudouridine | |
| modified_base | 3139 | |
| | mod_base = OTHER | |
| | note = N1-methylpseudouridine | |
| modified_base | 3141 | |

-continued

| | | |
|---|---|---|
| | | mod_base = OTHER |
| | | note = N1-methylpseudouridine |
| modified_base | 3148 | |
| | | mod_base = OTHER |
| | | note = N1-methylpseudouridine |
| modified_base | 3157 | |
| | | mod_base = OTHER |
| | | note = N1-methylpseudouridine |
| modified_base | 3160 | |
| | | mod_base = OTHER |
| | | note = N1-methylpseudouridine |
| modified_base | 3181 | |
| | | mod_base = OTHER |
| | | note = N1-methylpseudouridine |
| modified_base | 3201 | |
| | | mod_base = OTHER |
| | | note = N1-methylpseudouridine |
| modified_base | 3204 | |
| | | mod_base = OTHER |
| | | note = N1-methylpseudouridine |
| modified_base | 3205 | |
| | | mod_base = OTHER |
| | | note = N1-methylpseudouridine |
| modified_base | 3207 | |
| | | mod_base = OTHER |
| | | note = N1-methylpseudouridine |
| modified_base | 3208 | |
| | | mod_base = OTHER |
| | | note = N1-methylpseudouridine |
| modified_base | 3210 | |
| | | mod_base = OTHER |
| | | note = N1-methylpseudouridine |
| modified_base | 3220 | |
| | | mod_base = OTHER |
| | | note = N1-methylpseudouridine |
| modified_base | 3223 | |
| | | mod_base = OTHER |
| | | note = N1-methylpseudouridine |
| modified_base | 3228 | |
| | | mod_base = OTHER |
| | | note = N1-methylpseudouridine |
| modified_base | 3229 | |
| | | mod_base = OTHER |
| | | note = N1-methylpseudouridine |
| modified_base | 3231 | |
| | | mod_base = OTHER |
| | | note = N1-methylpseudouridine |
| modified_base | 3232 | |
| | | mod_base = OTHER |
| | | note = N1-methylpseudouridine |
| modified_base | 3244 | |
| | | mod_base = OTHER |
| | | note = N1-methylpseudouridine |
| modified_base | 3250 | |
| | | mod_base = OTHER |
| | | note = N1-methylpseudouridine |
| modified_base | 3265 | |
| | | mod_base = OTHER |
| | | note = N1-methylpseudouridine |
| modified_base | 3280 | |
| | | mod_base = OTHER |
| | | note = N1-methylpseudouridine |
| modified_base | 3283 | |
| | | mod_base = OTHER |
| | | note = N1-methylpseudouridine |
| modified_base | 3310 | |
| | | mod_base = OTHER |
| | | note = N1-methylpseudouridine |
| modified_base | 3313 | |
| | | mod_base = OTHER |
| | | note = N1-methylpseudouridine |
| modified_base | 3315 | |
| | | mod_base = OTHER |
| | | note = N1-methylpseudouridine |
| modified_base | 3333 | |
| | | mod_base = OTHER |
| | | note = N1-methylpseudouridine |
| modified_base | 3334 | |
| | | mod_base = OTHER |

-continued

| | | |
|---|---|---|
| modified_base | 3343 | |
| | mod_base = OTHER | |
| | note = N1-methylpseudouridine | |
| modified_base | 3352 | |
| | mod_base = OTHER | |
| | note = N1-methylpseudouridine | |
| modified_base | 3355 | |
| | mod_base = OTHER | |
| | note = N1-methylpseudouridine | |
| modified_base | 3361 | |
| | mod_base = OTHER | |
| | note = N1-methylpseudouridine | |
| modified_base | 3370 | |
| | mod_base = OTHER | |
| | note = N1-methylpseudouridine | |
| modified_base | 3376 | |
| | mod_base = OTHER | |
| | note = N1-methylpseudouridine | |
| modified_base | 3379 | |
| | mod_base = OTHER | |
| | note = N1-methylpseudouridine | |
| modified_base | 3394 | |
| | mod_base = OTHER | |
| | note = N1-methylpseudouridine | |
| modified_base | 3408 | |
| | mod_base = OTHER | |
| | note = N1-methylpseudouridine | |
| modified_base | 3409 | |
| | mod_base = OTHER | |
| | note = N1-methylpseudouridine | |
| modified_base | 3424 | |
| | mod_base = OTHER | |
| | note = N1-methylpseudouridine | |
| modified_base | 3427 | |
| | mod_base = OTHER | |
| | note = N1-methylpseudouridine | |
| modified_base | 3451 | |
| | mod_base = OTHER | |
| | note = N1-methylpseudouridine | |
| modified_base | 3454 | |
| | mod_base = OTHER | |
| | note = N1-methylpseudouridine | |
| modified_base | 3471 | |
| | mod_base = OTHER | |
| | note = N1-methylpseudouridine | |
| modified_base | 3486 | |
| | mod_base = OTHER | |
| | note = N1-methylpseudouridine | |
| modified_base | 3495 | |
| | mod_base = OTHER | |
| | note = N1-methylpseudouridine | |
| modified_base | 3496 | |
| | mod_base = OTHER | |
| | note = N1-methylpseudouridine | |
| modified_base | 3511 | |
| | mod_base = OTHER | |
| | note = N1-methylpseudouridine | |
| modified_base | 3516 | |
| | mod_base = OTHER | |
| | note = N1-methylpseudouridine | |
| modified_base | 3523 | |
| | mod_base = OTHER | |
| | note = N1-methylpseudouridine | |
| modified_base | 3526 | |
| | mod_base = OTHER | |
| | note = N1-methylpseudouridine | |
| modified_base | 3529 | |
| | mod_base = OTHER | |
| | note = N1-methylpseudouridine | |
| modified_base | 3532 | |
| | mod_base = OTHER | |
| | note = N1-methylpseudouridine | |
| modified_base | 3541 | |
| | mod_base = OTHER | |
| | note = N1-methylpseudouridine | |
| modified_base | 3565 | |
| | mod_base = OTHER | |
| | note = N1-methylpseudouridine | |

-continued

| | | |
|---|---|---|
| modified_base | 3574 | |
| | mod_base = OTHER | |
| | note = N1-methylpseudouridine | |
| modified_base | 3583 | |
| | mod_base = OTHER | |
| | note = N1-methylpseudouridine | |
| modified_base | 3586 | |
| | mod_base = OTHER | |
| | note = N1-methylpseudouridine | |
| modified_base | 3592 | |
| | mod_base = OTHER | |
| | note = N1-methylpseudouridine | |
| modified_base | 3598 | |
| | mod_base = OTHER | |
| | note = N1-methylpseudouridine | |
| modified_base | 3601 | |
| | mod_base = OTHER | |
| | note = N1-methylpseudouridine | |
| modified_base | 3615 | |
| | mod_base = OTHER | |
| | note = N1-methylpseudouridine | |
| modified_base | 3616 | |
| | mod_base = OTHER | |
| | note = N1-methylpseudouridine | |
| modified_base | 3631 | |
| | mod_base = OTHER | |
| | note = N1-methylpseudouridine | |
| modified_base | 3636 | |
| | mod_base = OTHER | |
| | note = N1-methylpseudouridine | |
| modified_base | 3637 | |
| | mod_base = OTHER | |
| | note = N1-methylpseudouridine | |
| modified_base | 3640 | |
| | mod_base = OTHER | |
| | note = N1-methylpseudouridine | |
| modified_base | 3654 | |
| | mod_base = OTHER | |
| | note = N1-methylpseudouridine | |
| modified_base | 3664 | |
| | mod_base = OTHER | |
| | note = N1-methylpseudouridine | |
| modified_base | 3676 | |
| | mod_base = OTHER | |
| | note = N1-methylpseudouridine | |
| modified_base | 3679 | |
| | mod_base = OTHER | |
| | note = N1-methylpseudouridine | |
| modified_base | 3682 | |
| | mod_base = OTHER | |
| | note = N1-methylpseudouridine | |
| modified_base | 3688 | |
| | mod_base = OTHER | |
| | note = N1-methylpseudouridine | |
| modified_base | 3696 | |
| | mod_base = OTHER | |
| | note = N1-methylpseudouridine | |
| modified_base | 3703 | |
| | mod_base = OTHER | |
| | note = N1-methylpseudouridine | |
| modified_base | 3705 | |
| | mod_base = OTHER | |
| | note = N1-methylpseudouridine | |
| modified_base | 3706 | |
| | mod_base = OTHER | |
| | note = N1-methylpseudouridine | |
| modified_base | 3712 | |
| | mod_base = OTHER | |
| | note = N1-methylpseudouridine | |
| modified_base | 3733 | |
| | mod_base = OTHER | |
| | note = N1-methylpseudouridine | |
| modified_base | 3736 | |
| | mod_base = OTHER | |
| | note = N1-methylpseudouridine | |
| modified_base | 3754 | |
| | mod_base = OTHER | |
| | note = N1-methylpseudouridine | |
| modified_base | 3772 | |

-continued

| | |
|---|---|
| | mod_base = OTHER |
| | note = N1-methylpseudouridine |
| modified_base | 3778 |
| | mod_base = OTHER |
| | note = N1-methylpseudouridine |
| modified_base | 3789 |
| | mod_base = OTHER |
| | note = N1-methylpseudouridine |
| modified_base | 3793 |
| | mod_base = OTHER |
| | note = N1-methylpseudouridine |
| modified_base | 3798 |
| | mod_base = OTHER |
| | note = N1-methylpseudouridine |
| modified_base | 3799 |
| | mod_base = OTHER |
| | note = N1-methylpseudouridine |
| modified_base | 3802 |
| | mod_base = OTHER |
| | note = N1-methylpseudouridine |
| modified_base | 3804 |
| | mod_base = OTHER |
| | note = N1-methylpseudouridine |
| modified_base | 3808 |
| | mod_base = OTHER |
| | note = N1-methylpseudouridine |
| modified_base | 3819 |
| | mod_base = OTHER |
| | note = N1-methylpseudouridine |
| modified_base | 3829 |
| | mod_base = OTHER |
| | note = N1-methylpseudouridine |
| modified_base | 3865 |
| | mod_base = OTHER |
| | note = N1-methylpseudouridine |
| modified_base | 3867 |
| | mod_base = OTHER |
| | note = N1-methylpseudouridine |
| modified_base | 3868 |
| | mod_base = OTHER |
| | note = N1-methylpseudouridine |
| modified_base | 3871 |
| | mod_base = OTHER |
| | note = N1-methylpseudouridine |
| modified_base | 3888 |
| | mod_base = OTHER |
| | note = N1-methylpseudouridine |
| modified_base | 3892 |
| | mod_base = OTHER |
| | note = N1-methylpseudouridine |
| modified_base | 3901 |
| | mod_base = OTHER |
| | note = N1-methylpseudouridine |
| modified_base | 3904 |
| | mod_base = OTHER |
| | note = N1-methylpseudouridine |
| modified_base | 3913 |
| | mod_base = OTHER |
| | note = N1-methylpseudouridine |
| modified_base | 3921 |
| | mod_base = OTHER |
| | note = N1-methylpseudouridine |
| modified_base | 3922 |
| | mod_base = OTHER |
| | note = N1-methylpseudouridine |
| modified_base | 3934 |
| | mod_base = OTHER |
| | note = N1-methylpseudouridine |
| modified_base | 3937 |
| | mod_base = OTHER |
| | note = N1-methylpseudouridine |
| modified_base | 3940 |
| | mod_base = OTHER |
| | note = N1-methylpseudouridine |
| modified_base | 3955 |
| | mod_base = OTHER |
| | note = N1-methylpseudouridine |
| modified_base | 3964 |
| | mod_base = OTHER |

-continued

| | |
|---|---|
| modified_base | note = N1-methylpseudouridine<br>3967<br>mod_base = OTHER<br>note = N1-methylpseudouridine |
| modified_base | 3975<br>mod_base = OTHER<br>note = N1-methylpseudouridine |
| modified_base | 4000<br>mod_base = OTHER<br>note = N1-methylpseudouridine |
| modified_base | 4021<br>mod_base = OTHER<br>note = N1-methylpseudouridine |
| modified_base | 4024<br>mod_base = OTHER<br>note = N1-methylpseudouridine |
| modified_base | 4030<br>mod_base = OTHER<br>note = N1-methylpseudouridine |
| modified_base | 4032<br>mod_base = OTHER<br>note = N1-methylpseudouridine |
| modified_base | 4033<br>mod_base = OTHER<br>note = N1-methylpseudouridine |
| modified_base | 4039<br>mod_base = OTHER<br>note = N1-methylpseudouridine |
| modified_base | 4048<br>mod_base = OTHER<br>note = N1-methylpseudouridine |
| modified_base | 4065<br>mod_base = OTHER<br>note = N1-methylpseudouridine |
| modified_base | 4066<br>mod_base = OTHER<br>note = N1-methylpseudouridine |
| modified_base | 4071<br>mod_base = OTHER<br>note = N1-methylpseudouridine |
| modified_base | 4074<br>mod_base = OTHER<br>note = N1-methylpseudouridine |
| modified_base | 4075<br>mod_base = OTHER<br>note = N1-methylpseudouridine |
| modified_base | 4087<br>mod_base = OTHER<br>note = N1-methylpseudouridine |
| modified_base | 4101<br>mod_base = OTHER<br>note = N1-methylpseudouridine |
| modified_base | 4120<br>mod_base = OTHER<br>note = N1-methylpseudouridine |
| modified_base | 4123<br>mod_base = OTHER<br>note = N1-methylpseudouridine |
| modified_base | 4135<br>mod_base = OTHER<br>note = N1-methylpseudouridine |
| modified_base | 4138<br>mod_base = OTHER<br>note = N1-methylpseudouridine |
| modified_base | 4150<br>mod_base = OTHER<br>note = N1-methylpseudouridine |
| modified_base | 4159<br>mod_base = OTHER<br>note = N1-methylpseudouridine |
| modified_base | 4161<br>mod_base = OTHER<br>note = N1-methylpseudouridine |
| modified_base | 4174<br>mod_base = OTHER<br>note = N1-methylpseudouridine |
| modified_base | 4180<br>mod_base = OTHER<br>note = N1-methylpseudouridine |

-continued

| | |
|---|---|
| modified_base | 4189<br>mod_base = OTHER<br>note = N1-methylpseudouridine |
| modified_base | 4257<br>mod_base = OTHER<br>note = N1-methylpseudouridine |
| modified_base | 4260<br>mod_base = OTHER<br>note = N1-methylpseudouridine |
| modified_base | 4263<br>mod_base = OTHER<br>note = N1-methylpseudouridine |
| modified_base | 4274<br>mod_base = OTHER<br>note = N1-methylpseudouridine |
| modified_base | 4275<br>mod_base = OTHER<br>note = N1-methylpseudouridine |
| modified_base | 4278<br>mod_base = OTHER<br>note = N1-methylpseudouridine |
| modified_base | 4279<br>mod_base = OTHER<br>note = N1-methylpseudouridine |
| modified_base | 4284<br>mod_base = OTHER<br>note = N1-methylpseudouridine |
| modified_base | 4288<br>mod_base = OTHER<br>note = N1-methylpseudouridine |
| modified_base | 4289<br>mod_base = OTHER<br>note = N1-methylpseudouridine |
| modified_base | 4291<br>mod_base = OTHER<br>note = N1-methylpseudouridine |
| modified_base | 4299<br>mod_base = OTHER<br>note = N1-methylpseudouridine |
| modified_base | 4300<br>mod_base = OTHER<br>note = N1-methylpseudouridine |
| modified_base | 4304<br>mod_base = OTHER<br>note = N1-methylpseudouridine |
| modified_base | 4305<br>mod_base = OTHER<br>note = N1-methylpseudouridine |
| modified_base | 4307<br>mod_base = OTHER<br>note = N1-methylpseudouridine |
| modified_base | 4313<br>mod_base = OTHER<br>note = N1-methylpseudouridine |
| modified_base | 4318<br>mod_base = OTHER<br>note = N1-methylpseudouridine |
| modified_base | 4319<br>mod_base = OTHER<br>note = N1-methylpseudouridine |
| modified_base | 4321<br>mod_base = OTHER<br>note = N1-methylpseudouridine |
| modified_base | 4322<br>mod_base = OTHER<br>note = N1-methylpseudouridine |
| modified_base | 4324<br>mod_base = OTHER<br>note = N1-methylpseudouridine |
| modified_base | 4326<br>mod_base = OTHER<br>note = N1-methylpseudouridine |
| modified_base | 4330<br>mod_base = OTHER<br>note = N1-methylpseudouridine |
| modified_base | 4331<br>mod_base = OTHER<br>note = N1-methylpseudouridine |
| modified_base | 4337 |

|                | mod_base = OTHER |
|                | note = N1-methylpseudouridine |
| modified_base  | 4339 |
|                | mod_base = OTHER |
|                | note = N1-methylpseudouridine |
| modified_base  | 4343 |
|                | mod_base = OTHER |
|                | note = N1-methylpseudouridine |
| modified_base  | 4345 |
|                | mod_base = OTHER |
|                | note = N1-methylpseudouridine |
| modified_base  | 4346 |
|                | mod_base = OTHER |
|                | note = N1-methylpseudouridine |
| modified_base  | 4349 |
|                | mod_base = OTHER |
|                | note = N1-methylpseudouridine |
| modified_base  | 4351 |
|                | mod_base = OTHER |
|                | note = N1-methylpseudouridine |
| modified_base  | 4352 |
|                | mod_base = OTHER |
|                | note = N1-methylpseudouridine |
| modified_base  | 4353 |
|                | mod_base = OTHER |
|                | note = N1-methylpseudouridine |
| modified_base  | 4357 |
|                | mod_base = OTHER |
|                | note = N1-methylpseudouridine |
| modified_base  | 4364 |
|                | mod_base = OTHER |
|                | note = N1-methylpseudouridine |
| modified_base  | 4368 |
|                | mod_base = OTHER |
|                | note = N1-methylpseudouridine |
| modified_base  | 4375 |
|                | mod_base = OTHER |
|                | note = N1-methylpseudouridine |
| modified_base  | 4377 |
|                | mod_base = OTHER |
|                | note = N1-methylpseudouridine |

SEQUENCE: 21

```
aggaaataag agagaaaaga agagtaagaa gaaatataag agccaccatg gcccccaaga   60
agaagcggaa ggtgggcatc cacggcgtgc ccgccgccga caagaagtac agcatcggcc  120
tggacatcgg caccaacagc gtgggctggg ccgtgatcac cgacgagtac aaggtgccca  180
gcaagaagtt caaggtgctg ggcaacaccg accggcacag catcaagaag aacctgatcg  240
gcgccctgct gttcgacagc ggcgagacgg ccgaggccac ccgcctgaag cggaccgccc  300
ggcggcggta cacccggcgg aagaaccgga tctgctacct gcaggagatc ttcagcaacg  360
agatggccaa ggtggacgac agcttcttcc accggctgga ggagagcttc ctggtggagg  420
aggacaagaa gcacgagcgg caccccatct tcggcaacat cgtggacgag gtggcctacc  480
acgagaagta cccccaccat caccacctgc ggaagaagct ggtggacagc accgacaagg  540
ccgacctgcg gctgatctac ctggcccctg cccacatgat caagttccgg ggccacttcc  600
tgatcgaggg cgacctgaac cccgacaaca gcgacgtgga caagctgttc atccagctgg  660
tgcagaccta caaccagctg ttcgaggaga accccatcaa cgccagcggc gtggacgcca  720
aggccatcct gagcgcccgg ctgagcaaga gccggcggct ggagaacctg atcgcccagc  780
tgcccggcga aaagaagaac ggcctgttcg gcaacctgat cgccctgagc ctgggcctga  840
cccccaactt caagagcaac ttcgacctgg ccgaggacgc caagctgcag ctgagcaagg  900
acacctacga cgacgacctg gacaacctgc tggcccagat cggcgaccag tacgccgacc  960
tgttcctggc cgccaagaac ctgagcgacg ccatcctgct gagcgacatc ctgcgggtga 1020
acaccgagat caccaaggcc cccctgagcg ccagcatgat caagcggtac gacgagcacc 1080
accaggacct gaccctgctg aaggccctgg tgcggcagca gctgcccgag aagtacaagg 1140
agatcttctt cgaccagagc aagaacggct acgccggcta catcgacggc ggcgccagcc 1200
aggaggagtt ctacaagttc atcaagccca tcctggagaa gatggacggc accgaggagc 1260
tgctggtgaa gctgaaccgg gaggacctgc tgcggaagca gaggaccttc gacaacggca 1320
gcatccccca ccagatccac ctgggcgagc tgcacgccat cctgcggcgg caggaggact 1380
tctacccctt cctgaaggac aaccgggaga gatcgagaa gatcctgacc ttccggatcc 1440
cctactacgt gggcccctg gcccggggca cagccggtt cgcctggatg acccgcaaga 1500
gcgaggagac gatcaccccc tggaacttcg aggaggtggt ggacaagggc gccagcgccc 1560
agagcttcat cgagcggatg accaacttcg acaagaacct gcccaacgag aaggtgctgc 1620
ccaagcacag cctgctgtac gagtacttca ccgtgtacaa cgagctgacc aaggtgaagt 1680
acgtgaccga gggcatgcgg aagcccgcct tctgagcgg cgagcagaag aaggccatcg 1740
tggacctgct gttcaagacc aaccggaagg tgaccgtgaa gcagctgaag gaggactact 1800
tcaagaagat cgagtgcttc gacagcgtgg agatcagcgg cgtggaggac cggttcaacg 1860
ccgcctggg cacctaccac gacctgctga agatcatcaa ggacaaggac ttcctggaca 1920
acgaggagaa cgaggacatc ctggaggaca tcgtgctgac cctgaccctg ttcgaggacc 1980
gggagatgat cgaggagcgg ctgaagacct acgcccacct gttcgacgac aaggtgatga 2040
agcagctgaa gcgcggcggg tacaccggct ggggccggct gagccggaag ctgatcaacg 2100
gcatccggga caagcagagc ggcaagacca tcctggactt cctcaagagc gacggcttcg 2160
ccaaccggaa cttcatgcag ctgatccacg acgacagcct gaccttcaag gaggacatcc 2220
```

```
agaaggccca ggtgagcggc cagggcgaca gcctgcacga gcacatcgcc aacctggccg 2280
gcagccccgc catcaagaag ggcatcctgc agaccgtgaa ggtggtggac gagctggtga 2340
aggtgatggg ccggcacaag cccgagaaca tcgtgatcga gatggcccgg gagaaccaga 2400
ccacccagaa gggccagaag aacagccggg agcggatgaa gcggatcgag gagggcatca 2460
aggagctggg cagccagatc ctgaaggagc accccgtgga gaacacccag ctgcagaacg 2520
agaagctgta cctgtactac ctgcagaacg gccgggacat gtacgtggac caggagctgg 2580
acatcaaccg gctgagcgac tacgacgtgg accacatcgt gccccagagc ttcctgaagg 2640
acgacagcat cgacaacaag gtgctgaccc ggagcgacaa gaaccggggc aagagcgaca 2700
acgtgcccag cgaggaggtg gtgaagaaga tgaagaacta ctggcggcag ctgctgaacg 2760
ccaagctgat cacccagcgg aagttcgaca acctgaccaa ggccgagcgg ggcggcctga 2820
gcgagctgga caaggccggc ttcatcaagc ggcagctggt ggagacgcgg cagatcacca 2880
agcacgtggc ccagatcctg gacagccgga tgaacaccaa gtacgacgag aacgacaagc 2940
tgatccggga ggtgaaggtg atcaccctca agagcaagct ggtgagcgac ttccggaagg 3000
acttccagtt ctacaaggtg cgggagatca acaactacca ccacgcccac gacgcctacc 3060
tgaacgccgt ggtgggcacc gccctgatca agaagtaccc caagctggag agcgagttcg 3120
tgtacggcga ctacaaggtg tacgacgtgc ggaagatgat cgccaagagc gagcaggaga 3180
tcggcaaggc caccgccaag tacttcttct acagcaacat catgaacttc ttcaagaccg 3240
agatcaccct ggccaacggc gagatccgga agcggccct gatcgagacg aacggcgaga 3300
cgggcgagat cgtgtgggac aagggccggg acttcgccac cgtgcggaag gtgctgagca 3360
tgccccaggt gaacatcgtg aagaagaccg aggtgcagac cggcggcttc agcaaggaga 3420
gcatcctgcc caagcggaac agcgacaagc tgatcgcccg gaagaaggac tgggacccca 3480
agaagtacgg cggcttcgac agccccaccg tggcctacag cgtgctggtg gtggccaagg 3540
tggagaaggg caagagcaag aagctcaaga gcgtgaagga gctgctgggc atcaccatca 3600
tggagcggag cagcttcgag aagaacccca tcgacttcct ggaggccaag ggctacaagg 3660
aggtgaagaa ggacctgatc atcaagctgc ccaagtacag cctgttcgag ctggagaacg 3720
gccggaagcg gatgctggcc agcgccggcg agctgcagaa gggcaacgag ctggccctgc 3780
ccagcaagta cgtgaacttc ctgtacctgg ccagccacta cgagaagctg aagggcagcc 3840
ccgaggacaa cgagcagaag cagctgttcg tggagcagca caagcactac ctggacgaga 3900
tcatcgagca gatcagcgag ttcagcaagc gggtgatcct ggccgacgcc aacctggaca 3960
aggtgctgag cgcctacaac aagcaccggg acaagcccat ccgggaggag gccgagaaca 4020
tcatccacct gttcaccctg accaacctgg gcgcccccgc cgccttcaag tacttcgaca 4080
ccaccatcga ccggaagcgg tacaccagca ccaaggaggt gctggacgcc accctgatcc 4140
accagagcat caccggcctg tacgagacgc ggatcgacct gagccagctg ggcggcgaca 4200
gcggcggcaa gcggccgcc gccaccaaga aggccggcca ggccaagaag aagaagtaat 4260
gataggcggc cgcttaatta agctgccttc tgcggggctt gccttctggc catgcccttc 4320
ttctctccct tgcacctgta cctcttggtc tttgaataaa gcctgagtag gaagtctaga 4380
```